US012655139B2

(12) United States Patent
Defossa et al.

(10) Patent No.: US 12,655,139 B2
(45) Date of Patent: Jun. 16, 2026

(54) ISOXAZOLIDINES AS RIPK1 INHIBITORS AND USE THEREOF

(71) Applicant: SANOFI, Paris (FR)

(72) Inventors: Elisabeth Defossa, Frankfurt am Main (DE); Heiner Glombik, Frankfurt am Main (DE); Uwe Heinelt, Frankfurt am Main (DE); Hans Matter, Frankfurt am Main (DE); Maria Mendez-Perez, Frankfurt am Main (DE); Nils Rackelmann, Frankfurt am Main (DE); Kurt Ritter, Frankfurt am Main (DE); Lothar Schwink, Frankfurt am Main (DE); Hauke Szillat, Frankfurt am Main (DE); Gernot Zech, Frankfurt am Main (DE)

(73) Assignee: SANOFI, Paris (FR)

( * ) Notice: Subject to any disclaimer, the term of this patent is extended or adjusted under 35 U.S.C. 154(b) by 827 days.

(21) Appl. No.: 17/926,913

(22) PCT Filed: Jun. 1, 2021

(86) PCT No.: PCT/EP2021/064657

§ 371 (c)(1),
(2) Date: Nov. 21, 2022

(87) PCT Pub. No.: WO2021/245070

PCT Pub. Date: Dec. 9, 2021

(65) Prior Publication Data

US 2023/0219937 A1 Jul. 13, 2023

(30) Foreign Application Priority Data

Jun. 2, 2020 (EP) .................................... 20315292

(51) Int. Cl.
*C07D 413/06* (2006.01)

(52) U.S. Cl.
CPC ................................. *C07D 413/06* (2013.01)

(58) Field of Classification Search
CPC .................................................... C07D 413/06
See application file for complete search history.

(56) References Cited

FOREIGN PATENT DOCUMENTS

| | | | |
|---|---|---|---|
| KR | 10-2020-0087922 | A | 7/2020 |
| WO | WO 2014/125444 | A1 | 8/2014 |
| WO | WO 2016/027253 | A1 | 2/2016 |
| WO | WO 2016/101887 | A1 | 6/2016 |
| WO | WO 2016/185423 | A1 | 11/2016 |
| WO | WO 2017/069279 | A1 | 4/2017 |
| WO | WO 2017/096301 | A1 | 6/2017 |
| WO | WO 2017/136727 | A2 | 8/2017 |
| WO | WO 2018/092089 | A1 | 5/2018 |
| WO | WO 2018/213632 | A1 | 11/2018 |
| WO | WO 2019/086494 | A1 | 5/2019 |
| WO | WO 2019/130230 | A1 | 7/2019 |
| WO | WO 2019/204537 | A1 | 10/2019 |
| WO | WO 2020/043173 | A1 | 3/2020 |

OTHER PUBLICATIONS

Dondelinger et al., "NF-κB-Independent Role of IKKα/IKKβin Preventing RIPK1 Kinase-Dependent Apoptotic and Necroptotic Cell Death during TNF Signaling", Molecular Cell, Oct. 1, 2015, 60(1): 63-76.

European Search Report for European Patent Application No. 21315242.4, mailed Apr. 11, 2022.

Fusco et al., "Incontinentia pigmenti: report on data from 2000 to 2013", Orphanet Journal of Rare Diseases, 2014, 9: 93.

International Search Report and Written Opinion for PCT International Patent Application No. PCT/EP2021/064657, mailed Aug. 4, 2021.

Ridder et al., "Brain endothelial TAK1 and NEMO safeguard the neurovascular unit", J Exp Med., Sep. 2015, 212(10): 1529-1549.

Smahi et al., "Genomic rearrangement in NEMO impairs NF-κB activation and is a cause of incontinentia pigmenti. The International Incontinentia Pigmenti (IP) Consortium", Nature, Jun. 2000, 405(6785): 466-472.

Zefirova et al. History of the Origin and Development of the Concept of Bioisosterism Vestn. Mosk. Univ., Ser. 2. Khimiya, 2002, vol. 43, No. 4 and English translation, 15 pages.

Cai et al., "Plasma membrane translocation of trimerized MLKL protein is required for TNF-induced necroptosis", Nat Cell Biol., Jan. 2014, 16(1): 55-65, [ePub Dec. 8, 2013].

Ertl et al., "Fast Calculation of Molecular Polar Surface Area as a Sum of Fragment-Based Contributions and Its Application to the Prediction of Drug Transport Properties", J. Med. Chem., 2000, 43(20): 3714-3717.

Hara et al., "Inhibition of interleukin 1β converting enzyme family proteases reduces ischemic and excitotoxic neuronal damage", Hara et al., "Inhibition of interleukin 1β converting enzyme family proteases reduces ischemic and excitotoxic neuronaldamage", Proc. Natl. Acad. Sci. USA, Mar. 4, 1997, 94(5): 2007-2012., 94(5): 2007-2012.

Harris et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase", J Med Chem., May 23, 2019, 62(10): 5096-5110.

Lawlor et al., "RIPK3 promotes cell death and NLRP3 inflammasome activation in the absence of MLKL", Nature Communications, Feb. 18, 2015, 6: 6282.

Lee et al., "Interferon-gamma regulates inflammatory cell death by targeting necroptosis in experimental autoimmune arthritis", Scientific Reports, Aug. 31, 2017, 7: 10133.

(Continued)

*Primary Examiner* — Kamal A Saeed
(74) *Attorney, Agent, or Firm* — MH2 Technology Law Group, LLP

(57) ABSTRACT

The present invention relates to isoxazolidines of formula I and their use as receptor-interacting protein kinase 1 inhibitors, for example in the treatment of diseases and disorders mediated by RIP kinase (1) such as rheumatoid arthritis (RA), psoriasis, inflammatory bowel disease (IBD), Crohn's disease or ulcerative colitis.

17 Claims, No Drawings

(56) References Cited

OTHER PUBLICATIONS

Orozco et al., "Structural attributes influencing unbound tissue distribution", European Journal of Medicinal Chemistry, Jan. 2020, 185(1): 111813.
U.S. Appl. No. 17/983,883, filed Nov. 9, 2022, Elisabeth Defossa, Isoxazolidines as RIPK1 Inhibitors and Use Thereof.

ISOXAZOLIDINES AS RIPK1 INHIBITORS AND USE THEREOF

RELATED APPLICATIONS

This application is a 35 U.S.C. § 371 filing of International Patent Application No. PCT/EP2021/064657, filed Jun. 1, 2021, which claims priority to European Patent Application No. 20315292.1, filed Jun. 2, 2020, the entire disclosures of which are hereby incorporated herein by reference.

BACKGROUND

Although inflammation can be a protective mechanism in response to harmful stimuli such as invasion of pathogens and tissue damages, chronic inflammation is an important underlying factor in many human diseases such as neurodegeneration, rheumatoid arthritis, autoimmune and inflammatory diseases, and cancer. Similarly, the activation of cell death pathways, such as necrosis and apoptosis which are useful in eliminating infected or damaged cells, is also an important underlying mechanism for human diseases, including acute and chronic neurodegenerative diseases. Receptor-interacting protein kinase 1 (UniProtKB 013546) is a key regulator of inflammation, apoptosis and necroptosis. Receptor-interacting protein kinase 1 has an important role in modulating inflammatory responses mediated by nuclear-factor kappa-light chain enhancer of activated B cells (NF-κB). More recent research has shown that its kinase activity controls necroptosis, a form of necrotic cell death, which was traditionally thought to be passive and unregulated, and is characterized by a unique morphology. Further, receptor-interacting protein kinase 1 is part of a pro-apoptotic complex indicating its activity in regulating apoptosis.

The receptor-interacting protein kinase 1 is subject to complex and intricate regulatory mechanisms, including ubiquitylation, deubiquitylation, and phosphorylation. These regulatory events collectively determine whether a cell will survive and activate an inflammatory response or die through apoptosis or necroptosis. Dysregulation of receptor-interacting protein kinase 1 signaling can lead to excessive inflammation or cell death, and conversely, research has shown that inhibition of receptor interacting protein kinase 1 can be effective therapies for diseases involving inflammation or cell death.

RIPK1 inhibition has been identified as promising principle to address different diseases like rheumatoid arthritis (RA), psoriasis, multiple sclerosis, Alzheimer's disease, inflammatory bowel disease such as Crohn's disease or ulcerative colitis (UC). To treat some of these diseases like multiple sclerosis (MS) and Alzheimer's disease, access to the central nervous system (CNS) is required, while for other diseases like rheumatoid arthritis, psoriasis, inflammatory bowel disease (IBD) such as Crohn's disease or UC access to the CNS is not essentially required.

The most advanced RIPK1 inhibitor, GSK2982772 (oxazepinone derivative disclosed in WO2014/125444), was evaluated for RA, psoriasis and UC in phase II clinical trails. Interestingly, during the toxicological evaluation of GSK2982772 in monkeys central side effects like irregular gait and uncoordinated movement were reported at doses ≥100 mg/kg (GSK2982772; Savage, Published Phase I Protocol Amendment, 2017).

[1-(6-Methoxypyrimidin-4-yl)-4-piperidyl]-[(3S)-3-(3,5-difluorophenyl)isoxazolidin-2-yl]methanone (comparator compound K, see Example section) is a brain permeable, close analogue to the isoxazolidine derivatives claimed in WO2019130230 and WO2020043173, and when applied to cynomolgus monkeys (1 mg/kg, i.v.) severe side effects were observed (hypoactivity followed by decubitus, hyporeactivity, limb stiffness and hypotonic with phases of prostration). Histopathological examination revealed bilateral and symmetrical lesions of brain necrosis (i.e., malacia) located in the basal ganglia (globus pallidus) and the hypothalamic area, consisting of neuronal necrosis, spongiosis, cellular infiltration dominated by a population of macrophages, and reactive neocapillaries.

For this isoxazolidine derivative, comparator compound K, which showed severe CNS related side effects in the monkey as described above, a TPSA of 68 $Å^2$ was attributed. In the mouse 15 min after i.v. application of 3 mg/kg a brain/blood ratio of 2.1 and brain levels of 1.58 μg/ml were observed confirming the good brain permeability of this kind of compounds. 2 h after oral application of 30 mg/kg to the mouse a brain/plasma ratio of 1.6 was determined.

Therefore, to avoid possible CNS-associated side effects this invention relates to RIPK1 inhibitor compounds with reduced ability to cross the blood-brain-barrier. In the literature there are some compound properties described that are correlated with low blood-brain-barrier permeability like the topologic polar surface area (TPSA) and the number of hydrogen bond donors (HBD) (Eur. J. Med. Chem. 185 (2020) 111813). Molecules possessing a TPSA of >75 $Å^2$ are considered to show impaired brain penetration.

Different RIPK1 inhibitors were already described (e.g. WO2014/125444, WO2016/185423), WO2016027253 (GSK), WO2018/092089).

Denali discloses also benzoxapine derivatives in WO2017136727 and WO2018213632. Other chemical classes of RIPK1 inhibitors are bicyclic sulfones and sulfoxides (WO2019086494, Roche), heterocyclic compounds (WO2017069279, Takeda), as well as other benzoxazepinones (WO2019204537, Genetech).

Interestingly, in WO2016/101887 WO 2017/096301, WO2020043173 and WO2019/130230 that are also related to isoxazolidine derivatives as RIPK1 inhibitors, compounds with a TPSA up to 102 $Å^2$ like example 4 in WO2019/130230 (comparator compound D) are described. Although the TPSA of this compound is well above 75 $Å^2$ it, surprisingly, shows still good brain penetration (brain/plasma ratio 1.1 (2 h after oral application of 30 mg/kg in mouse)). Therefore, at least reasonable CNS penetration can be expected for the compounds described in these applications with a TPSA of about/up to 100 $Å^2$.

To increase the probability of obtaining reduced brain levels this invention is related to new isoxazolidine derivatives as RIPK1 inhibitors possessing a TPSA >90 $Å^2$, preferably >105 $Å^2$, most preferable >120 $Å^2$.

To obtain compounds that only poorly penetrate into the CNS polar heterocycles were implemented in the so called deep pocket 1 (DP1). In the literature (J. Med. Chem. 2019, 62, 10, 5096-5110) replacement of highly potent unsubstituted or halogen substituted phenyl derivatives in DP1 by heterocycles like 2-, 3- or 4-pyridyl, pyrazol-3-yl, imidazol-4-yl or 4-oxazolyl derivatives resulted in a significant drop in enzymatic and cellular activity.

Surprisingly, we could identify compounds with heterocyclic groups in DP1 that showed good potency in the enzymatic ADP-glo and the cellular U937 assay with a TPSA >90 $Å^2$ and showed no CNS related side effects in the monkey.

The invention relates to compounds of formula I:

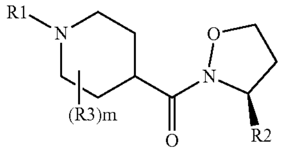

(I)

wherein

R1 represents a 5-6 membered heteroaryl in which 1 to 4 ringatoms are independently selected from —N—, —O— or —S— and wherein R1 is optionally substituted by 1 to 4 substituents independently selected from halogen,
 - —(C1-C4)alkyl,
 - —O(C1-C4)alkyl,
 - —S(C1-C4)alkyl,
 - —S(O)(C1-C4)alkyl,
 - —$S(O)_2$(C1-C4)alkyl,
 - —O(C1-C4)alkyl-R4,
 - —CN,
 - —(CO)OH,
 - —(CO)O(C1-C4)alkyl,
 - —NRaRb,
 - —(CO)NRaRb, and
 - —(CO)NRcRd;

wherein Ra and Rb are independently from each other H or (C1-C4)alkyl; and wherein Rc is H or (C1-C4)alkyl; and wherein Rd is —$(CH_2)_x$—(C3-C7)cycloalkyl or —$(CH_2)_x$—(C3-C7)heterocyclyl, wherein cycloalkyl or heterocyclyl is optionally substituted with 1 to 3 substituents selected from (C1-C4)alkyl, (CO)OH or (CO)O(C1-C4)alkyl;

x is an integer 0, 1, 2 or 3;

R2 is a 5-10 membered heteroaryl or 5 to 6 membered heterocycle, wherein 1 to 4 ring atoms are independently selected from —N—, —O— or —S—, and wherein heteroaryl or heterocycle is optionally substituted by 1 to 4 substituents selected from halogen, CN, —(C1-C4)alkyl, —(C1-C4)alkyl-OH, —(CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo;

R3 is halogen or (C1-C2)alkyl;

m is an integer 0, 1, 2, 3 or 4;

R4 is OH, CN, —(CO)OH, —(CO)NRgRh or —(CO)O(C1-C4)alkyl;

wherein Rg and Rh are independently selected from H or (C1-C4)alkyl;

or a pharmaceutically acceptable salt, solvate, or stereoisomer thereof.

In another aspect provided are methods for making the compounds and intermediates thereof.

In a related aspect, provided herein is a pharmaceutical composition comprising a compound as described herein and a pharmaceutically acceptable excipient.

In another aspect, provided herein is a method of inhibiting receptor-interacting protein kinase 1. Further provided are methods for treating receptor-interacting protein kinase 1-mediated disease or disorder comprising administering a therapeutically effective amount of a compound or a pharmaceutical composition as described herein to a subject in need thereof. The disclosure also provides uses of the compounds or compositions thereof in the manufacture of a medicament for the treatment of a disease, disorder or condition that is mediated by (or mediated, at least in part, by) receptor-interacting protein kinase 1.

DETAILED DESCRIPTION

Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, (C1-4)alkyl includes, but is not limited to, methyl, ethyl, propyl, isopropyl, butyl, isobutyl, sec-butyl, tert-butyl. Alkyl can also refer to alkyl groups having up to 20 carbons atoms, such as, but not limited to heptyl, octyl, nonyl, decyl, etc. Alkyl groups can be substituted or unsubstituted.

As used herein, the term "alkoxy," by itself or as part of another substituent, refers to a group having the formula —OR, wherein R is alkyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated.

Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

As used herein, the term "heteroalkyl," by itself or as part of another substituent, refers to an alkyl group of any suitable length and having from 1 to 3 heteroatoms such as N, O and S, provided that the attachment of the substituent is at a carbon atom. For example, heteroalkyl can include ethers, thioethers and alkyl-amines.

The heteroatoms can be oxidized to form moieties such as, but not limited to, —S(O)— and —$S(O)_2$—. The heteroatom portion of the heteroalkyl can replace a hydrogen of the alkyl group to form a hydroxy, thio, or amino group. Alternatively, the heteroatom portion can be inserted between two carbon atoms.

As used herein, the term "alkenyl" by itself or as part of another substituent, refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5, or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. As used herein, the term "alkynyl," by itself or as part of another substituent refers, to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

As used herein, the terms "halo" and "halogen", by themselves or as part of another substituent, refer to a fluorine, chlorine, bromine, or iodine atom.

As used herein, the term "haloalkyl", by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl", by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$, or $C_{16}$, as well as $C_{5-7}$, $C_{5-10}$, $C_{6-10}$, $C_{6-12}$, or $C_{6-14}$. Aryl groups can be monocyclic, fused to form bicyclic (e.g., benzocyclohexyl), or tricyclic groups, or linked by a bond to form a biaryl group.

Representative aryl groups include phenyl, naphthyl and biphenyl. Other aryl groups include benzyl, having a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more halo, hydroxy, amino, alkylamino, amido, acyl, nitro, cyano, and/or alkoxy groups.

As used herein, the term "heteroaryl", by itself or as part of another substituent, refers to a monocyclic or fused bicyclic or tricyclic aromatic ring assembly containing 5 to 16 ring atoms, where from 1 to 5 of the ring atoms are heteroatoms such as N, O, or S.

The heteroatoms can be oxidized to form moieties such as, but not limited to, —S(O)— and —$S(O)_2$—. Heteroaryl groups can include any number of ring atoms, such as $C_{5-6}$, $C_{3-8}$, $C_{4-8}$, $C_{5-7}$, $C_{5-8}$, $C_{6-8}$, $C_{3-9}$, $C_{3-10}$, $C_{3-11}$, $C_{5-10}$, or $C_{3-12}$, wherein at least one of the carbon atoms is replaced by a heteroatom. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5.

For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O, or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein the term "heterocyclyl," by itself or as part of another substituent, refers to a saturated ring system having from 3 to 12 ring members and from 1 to 4 heteroatoms of N, O and S. The heteroatoms can be oxidized to form moieties such as, but not limited to, —S(O)— and —$S(O)_2$—. Heterocyclyl groups can include any number of ring atoms, such as, $C_{3-6}$, $C_{4-6}$, $C_{5-6}$, $C_{3-6}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more halo, hydroxy, amino, oxo (=O), alkylamino, amido, acyl, nitro, cyano, and/or alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —$NR_2$, wherein each R group is H or alkyl. An amino moiety can be ionized to form the corresponding ammonium cation.

"Dialkylamino" refers to an amino moiety wherein each R group is alkyl. As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or —(C1-C4)alkyl.

As used herein, the term "nitro" refers to the moiety —$NO_2$.

As used herein, the term "oxo" refers to an oxygen atom that is double-bonded to a compound (i.e., O=). As used herein, the term "pharmaceutically acceptable excipient" refers to a substance that aids the administration of an active agent to a subject. By "pharmaceutically acceptable", it is meant that the excipient is compatible with the other ingredients of the formulation and is not deleterious to the recipient thereof. Pharmaceutical excipients useful in the present disclosure include, but are not limited to, binders, fillers, disintegrants, lubricants, glidants, coatings, sweeteners, flavors and colors.

As used herein, the term "salt" refers to acid or base salts of the compounds of the disclosed herein. Illustrative examples of pharmaceutically acceptable salts are mineral acid salts, organic acid salts, quaternary ammonium salts. It is understood that the pharmaceutically acceptable salts are non-toxic.

Pharmaceutically acceptable salts of the acidic compounds disclosed herein are salts formed with bases, namely cationic salts such as alkali and alkaline earth metal salts.

Similarly, acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure. In addition to salt forms, described herein are compounds which are in a prodrug form.

Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop.

Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The invention relates to compounds of formula I:

(I)

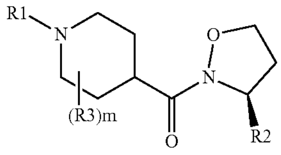

wherein

R1 represents a 5-6 membered heteroaryl in which 1 to 4 ringatoms are independently selected from —N—, —O— or —S— and wherein R1 is optionally substituted by 1 to 4 substituents independently selected from
- halogen,
- —(C1-C4)alkyl,
- —O(C1-C4)alkyl,
- —S(C1-C4)alkyl,
- —S(O)(C1-C4)alkyl,
- —$S(O)_2$(C1-C4)alkyl,
- —O(C1-C4)alkyl-R4,
- —(CO)OH,
- —CN,
- —(CO)O(C1-C4)alkyl,
- —NRaRb,
- —(CO)NRaRb, and
- —(CO)NRcRd;

wherein Ra and Rb are independently from each other H or (C1-C4)alkyl;

and wherein Rc is H or (C1-C4)alkyl; and wherein Rd is —$(CH_2)_x$—(C3-C7)cycloalkyl or —$(CH_2)_x$—(C3-C7)heterocyclyl, wherein cycloalkyl or heterocyclyl is optionally substituted with 1 to 3 substituents selected from (C1-C4)alkyl, (CO)OH or (CO)O(C1-C4)alkyl;

x is an integer 0, 1, 2 or 3;

R2 is a 5-10 membered heteroaryl or 5 to 6 membered heterocycle, wherein 1 to 4 ring atoms are independently selected from —N—, —O— or —S—, and wherein heteroaryl or heterocycle is optionally substituted by 1 to 4 substituents selected from halogen, CN, —(C1-C4)alkyl, —(C1-C4)alkyl-OH, —(CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo;

R3 is Halogen or (C1-C2)alkyl;

m is an integer 0, 1, 2, 3 or 4;

R4 is OH, CN, —(CO)OH, —(CO)NRgRh or —(CO)O(C1-C4)alkyl;

wherein Rg and Rh are independently selected from H or (C1-C4)alkyl;

or a pharmaceutically acceptable salt, solvate, or stereoisomer thereof.

According to another embodiment the compounds of the invention of the formula I is a compound wherein R1 represents a 5-6 membered heteroaryl in which 1 to 2 ringatoms are —N— atoms and wherein R1 is optionally substituted by 1 to 3 substituents independently selected from
- halogen,
- —(C1-C4)alkyl,
- —O(C1-C4)alkyl,
- —S(C1-C4)alkyl,
- —S(O)(C1-C4)alkyl,
- —$S(O)_2$(C1-C4)alkyl,
- —O(C1-C4)alkyl-R4,
- —(CO)OH,
- —CN,
- —(CO)O(C1-C4)alkyl,
- —NRaRb,
- —(CO)NRaRb, and
- —(CO)NRcRd;

wherein Ra, Rb are independently from each other H or (C1-C4)alkyl; and wherein Rc is H or (C1-C4)alkyl; and wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, COOH or COO(C1-C4)alkyl;

x is an integer 0, 1, 2 or 3;

or a pharmaceutically acceptable salt, solvate, or stereoisomer thereof.

According to another embodiment the compounds of the invention of the formula I is a compound wherein R1 is pyridyl, pyrazinyl or pyrimidinyl and wherein R1 is optionally substituted by 1 to 2 substituents independently selected from
- halogen,
- —(C1-C4)alkyl,
- —O(C1-C4)alkyl, —S(C1-C4)alkyl,
—S(O)(C1-C4)alkyl,
—$S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra, Rb are independently from each other H or (C1-C4)alkyl; and
wherein Rc is H or (C1-C4)alkyl; and
wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, (CO)OH or (CO)O(C1-C4)alkyl;
x is an integer 0, 1, 2 or 3;
or a pharmaceutically acceptable salt, solvate, or stereoisomer thereof.

According to another embodiment the compounds of the invention of the formula I is a compound wherein
R1 is pyridyl, pyrazinyl or pyrimidinyl and wherein R1 is optionally substituted by 1 to 2 substituents independently selected from
F, Cl,
methyl,
—O-methyl,
—S methyl,
—S(O) methyl,
—$S(O)_2$ methyl,
—O—$CH_2$—R4,
—(CO)OH,
—CN,
—(CO)O—$CH_3$, —(CO)O—$CH_2$—$CH_3$,
—$NH_2$,
—(CO)$NH_2$, (CO)$NHCH_3$, and
—(CO)NRcRd;
wherein Rc is H or methyl; and
wherein Rd is —($CH_2$)-cycloalkyl or —($CH_2$)-heterocyclyl, wherein cycloalkyl or heterocyclyl is optionally substituted with methyl, ethyl, (CO)OH or (CO)O(C1-C4)alkyl;
or a pharmaceutically acceptable salt, solvate, or stereoisomer thereof.

According to another embodiment the compounds of the invention of the formula I is a compound wherein
R1 is pyridyl, pyrazinyl or pyrimidinyl and wherein R1 is substituted by —(CO)NRcRd;
wherein Rc is H or methyl; and
wherein Rd is —($CH_2$)-cycloalkyl or —($CH_2$)-heterocyclyl,
wherein cycloalkyl is selected from cycloprpopyl, cyclobutyl, cyclopentyl and cyclohexyl,
and wherein heterocyclyl is selected from azirine, azetidine, pyrrolidine and piperidine, and
wherein cycloalkyl or heterocyclyl, is optionally substituted with methyl, ethyl, (CO)OH or (CO)O(C1-C4)alkyl;
or a pharmaceutically acceptable salt, solvate, or stereoisomer thereof.

According to another embodiment the compounds of the invention of the formula I is a compound wherein R1 is pyridyl, pyrazinyl or pyrimidinyl and wherein R1 is substituted by —(CO)NRcRd
wherein Rc is H; and
wherein Rd is —($CH_2$)-cyclopropyl, —($CH_2$)-azetidine or —($CH_2$)-piperidine,
wherein the cyclic group, is optionally substituted with methyl, ethyl, (CO)OH or (CO)O(C1-C4)alkyl;
or a pharmaceutically acceptable salt, solvate, or stereoisomer thereof.

According to another embodiment the compounds of the invention of the formula I is a compound wherein
R1 is selected from 6-yl-pyrimidine-4-carboxamide
2-yl-pyrimidine-4-carboxamide,
6-pyrimidine-4-carbonitrile,
2-pyrimidine-4-carbonitrile,
2-pyrimidine-4-carboxylic acid,
Methyl 2-yl-pyrimidine-4-carboxylate,
Ethyl 2-yl-(5-fluoro-pyrimidin-4-yl-oxyacetate),
4-(Cyanomethoxy)-5-fluoro-pyrimidin-2-yl,
5-fluoro-pyrimidin-4-yl-oxyacetic acid,
5-fluoro-pyrimidin-4-yl-oxyacetamide,
4-Amino-5-fluoro-pyrimidin-2-yl,
4-Cyanopyrimidin-2-yl,
2-yl-5-methyl-pyrimidine-4-carboxamide,
Ethyl 6-yl-5-fluoro-pyrimidine-4-carboxylate,
6-yl-5-fluoro-pyrimidine-4-carboxylic acid,
2-yl-5-fluoro-pyrimidine-4-carboxamide,
5-Fluoro 2-yl-pyrimidin-4-oxyacetonitrile,
5-Fluoro-4-methoxy-pyrimidin-2-yl,
6-yl-5-fluoro-pyrimidine-4-carboxamide,
5-Fluoro-2-yl-pyrimidine-4-carboxamide,
2-yl-N-(1-methylazetidin-3-yl)pyrimidine-4-carboxamide,
2-yl-N-[2-(1-methylcyclo-propyl)ethyl]pyrimidine-4-carboxamide,
tert-butyl 3-yl-pyrimidine-4-carbonylamino azetidine-1-carboxylate,
2-yl-N-[(1-ethyl-4-piperidyl)methyl]pyrimidine-4-carboxamide,
N-(Azetidin-3-yl)-2-yl-pyrimidine-4-carboxamide,
Ethyl 3-yl-pyrimidine-4-carbonyl]amino]azetidine-1-carboxylate,
6-yl-pyrimidine-4-carbonitrile,
5-Methyl-2-yl-pyrimidine-4-carboxamide,
5-Methyl 2-yl-pyrimidine-4-carboxylate,
2-yl-5-fluoro-pyrimidine-4-carboxamide,
2-yl-pyrimidine-4-carboxylic acid,
5-Fluoro-4-methylsulfanyl-pyrimidin-2-yl,
5-Fluoro-4-methylsulfinyl-pyrimidin-2-yl,
5-Fluoro-4-methylsulfonyl-pyrimidin-2-yl,
2-pyridine-4-carbonitrile,
4-(Cyanomethoxy)-5-fluoro-2-pyridyl,
2-pyridine-4-carboxamide,
5-pyrazine-2-carbonitrile,
6-pyrazine-2-carbonitrile,
6-pyrazine-2-carboxamide, and
5-pyrazine-2-carboxamide,
or a pharmaceutically acceptable salt, solvate, or stereoisomer thereof.

According to another embodiment the compounds of the invention of the formula I is a compound wherein
R2
is a 5-10 membered heteroaryl or 5 to 6 membered heterocycle, wherein 1 to 3 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo;

or a pharmaceutically acceptable salt, solvate, or stereoisomer thereof.

According to another embodiment the compounds of the invention of the formula I is a compound wherein

R2 is a 5-10 membered heteroaryl wherein 1 to 3 ring atoms are independently selected from —N—, or —S—, or a 5 to 6 membered heterocycle, wherein 1 to 2 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

According to another embodiment the compounds of the invention of the formula I is a compound wherein

R2 is a 5-10 membered heteroaryl, wherein 1 to 2 ring atoms are —N—, and additionally up to 1 ring atom is —S—; or a 5 to 6 membered heterocycle, wherein 1 to 2 ring atoms are —O—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

According to another embodiment the compounds of the invention of the formula I is a compound wherein

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

According to another embodiment the compounds of the invention of the formula I is a compound wherein

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from F, Cl, Br, CN, -methyl, —$(CH)_2$—OH, $NH_2$, NH(C1-C4)alkyl, NH(CO)—(C1-C4)alkyl, $(CO)NH_2$, —(CO)NH(C1-C4)alkyl, —(CO)NH(CO)—(C1-C4)alkyl, 1-oxo-azirinyl, 1-oxo-azetidinyl, 1-oxo-pyrrolidinyl and 1-oxo-piperidinyl;

or a pharmaceutically acceptable salt, solvate, or stereoisomer thereof.

According to another embodiment the compounds of the invention of the formula I is a compound wherein

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from F, Cl, Br, CN, -methyl, —$(CH)_2$—OH, $NH_2$, $NHCH_3$, —$(CO)NH_2$, —$(CO)NHCH_3$, —$(CO)NH(CO)CH_3$, 1-oxo-azirinyl, 1-oxo-azetidinyl, 1-oxo-pyrrolidinyl and 1-oxo-piperidinyl;

or a pharmaceutically acceptable salt, solvate, or stereoisomer thereof.

According to another embodiment the compounds of the invention of the formula I is a compound wherein R2 is selected from 5-Cyano-3-pyridyl,
5-pyridine-3-carbonitrile,
5-(Hydroxymethyl)-3-pyridyl,
5-carbamoyl-3-pyridyl,
5-(Hydroxymethyl)-3-pyridyl,
6-Amino-3-pyridyl,
5-pyridine-3-carbonitrile,
5-yl-(Methylcarbamoyl)-3-pyridyl,
5-yl-N-methyl-pyridine-3-carboxamide,
5-Acetamido-3-pyridyl,
5-Fluoro-3-pyridyl,
5-(2-oxoazetidin-1-yl)-3-pyridyl,
5-(2-Oxopyrrolidin-1-yl)-3-pyridyl,
5-Cyano-3-pyridyl,
5-fluoro-3-pyridyl,
5-Cyano-6-methyl-3-pyridyl,
5-Cyano-6-methyl-3-pyridyl,
5-Fluoro-3-pyridyl,
5-Carbamoyl-3-pyridyl,
5-yl-pyridine-3-carbonitrile,
5-Cyano-2-pyridyl,
5-Chloro-2-pyridyl,
5-Pyrimidyl,
1-Methylpyrazol-3-yl,
3-Imidazo[1,2-a]pyridin-6-yl,
3-Tetrahydropyranyl,
1-Methylpyrazol-4-yl,
Pyrazin-2-yl,
6-methylpyrazin-2-yl,
5-Methylpyrazin-2-yl, and
5-Methyl-1,3,4-thiadiazol-2-yl, or a pharmaceutically acceptable salt, solvate, or stereoisomer thereof.

According to another embodiment the compounds of the invention of the formula I is a compound wherein R3 is F, Cl, methyl or ethyl;

m is an integer 0, 1, 2 or 3.

According to another embodiment the compounds of the invention of the formula I is a compound wherein R3 is F or methyl;

m is an integer 0 or 1.

According to another embodiment the compounds of the invention of the formula I is a compound wherein R3 is F or methyl.

According to another embodiment the compounds of the invention of the formula I is a compound wherein m is an integer 0, 1 or 2.

According to another embodiment the compounds of the invention of the formula I is a compound wherein m is an integer 0.

According to another embodiment the compounds of the invention of the formula I is a compound wherein m is an integer 1.

According to another embodiment the compounds of the invention of the formula I is a compound wherein R3 is F or methyl;

m is an integer 1.

According to another embodiment the compounds of the invention of the formula I is a compound wherein R4 is OH, CN, —(CO)OH, —(CO)$NH_2$, —(CO)$NHCH_3$ or —(CO)O(C1-C4)alkyl;

or a pharmaceutically acceptable salt, solvate, or stereoisomer thereof.

According to another embodiment the compounds of the invention of the formula I is a compound wherein R4 is OH, CN, —(CO)OH, —(CO)$NH_2$, —(CO)$NHCH_3$, —(CO)O—$CH_3$ or —(CO)O—$CH_2$—$CH_3$;

or a pharmaceutically acceptable salt, solvate, or stereoisomer thereof.

According to another embodiment the compounds of the invention of the formula I is a compound wherein R1 represents a 5-6 membered heteroaryl in which 1 to 2 ringatoms are —N—atoms and wherein R1 is optionally substituted by 1 to 3 substituents independently selected from halogen —(C1-C4)alkyl, —O(C1-C4)alkyl, —S(C1-C4)alkyl, —S(O)(C1-C4)alkyl, —$S(O)_2$(C1-C4)alkyl, —O(C1-C4)alkyl-R4,

—(CO)OH,

—CN,

—(CO)O(C1-C4)alkyl,

—NRaRb,

—(CO)NRaRb, and

—(CO)NRcRd;

wherein Ra, Rb are independently from each other H or (C1-C4)alkyl; and wherein Rc is H or (C1-C4)alkyl; and wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, COOH or COO(C1-C4) alkyl;

x is an integer 0, 1, 2 or 3;

R2 is a 5-10 membered heteroaryl or 5 to 6 membered heterocycle, wherein 1 to 3 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO) NReRf and —NReRf, wherein Re and Rf are independently selected from H, (C1-C4)alkyl or —CO(C1-C4) alkyl; or wherein Re and Rf form together with the nitrogen atom to which they are attached a 4 to 6 membered ring, which is optionally substituted with oxo;

R3 is F, Cl, methyl or ethyl;

m is an integer 0, 1 or 2.

R4 is OH, CN, —(CO)OH, —(CO)$NH_2$, —(CO)$NHCH_3$ or —(CO)O(C1-C4)alkyl;

or a pharmaceutically acceptable salt, solvate, or stereoisomer thereof.

According to another embodiment the compounds of the invention of the formula I is a compound wherein R1 is pyridyl, pyrazinyl or pyrimidinyl and wherein R1 is optionally substituted by 1 to 2 substituents independently selected from -halogen, —(C1-C4)alkyl, —O(C1-C4)alkyl, —S(C1-C4)alkyl, —S(O)(C1-C4)alkyl, —$S(O)_2$(C1-C4)alkyl, —O(C1-C4)alkyl-R4,

—(CO)OH,

—CN,

—(CO)O(C1-C4)alkyl,

—NRaRb,

—(CO)NRaRb, and

—(CO)NRcRd;

wherein Ra, Rb are independently from each other H or (C1-C4)alkyl; and wherein Rc is H or (C1-C4)alkyl; and wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, (CO)OH or (CO)O(C1-C4)alkyl;

x is an integer 0, 1, 2 or 3;

R2 is a 5-10 membered heteroaryl wherein 1 to 3 ring atoms are independently selected from —N—, or —S—, or a 5 to 6 membered heterocycle, wherein 1 to 2 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO) NReRf and —NReRf, wherein Re and Rf are independently selected from H, (C1-C4)alkyl or —CO(C1-C4) alkyl; or wherein Re and Rf form together with the nitrogen atom to which they are attached a 4 to 6 membered ring, which is optionally substituted with oxo at the position adjacent to the nitrogen atom;

R3 is F or methyl;

m is an integer 0 or 1;

R4 is OH, CN, —(CO)OH, —(CO)$NH_2$, —(CO)$NHCH_3$ or —(CO)O(C1-C4)alkyl;

or a pharmaceutically acceptable salt, solvate, or stereoisomer thereof.

According to another embodiment the compounds of the invention of the formula I is a compound wherein R1 is pyridyl, pyrazinyl or pyrimidinyl and wherein R1 is optionally substituted by 1 to 2 substituents independently selected from F, Cl,
methyl,
—O-methyl,
—S methyl,
—S(O) methyl,
—$S(O)_2$ methyl,
—O—$CH_2$—R4,
—(CO)OH,
—CN,
—(CO)O—$CH_3$, —(CO)O—$CH_2$—$CH_3$,
—$NH_2$,
—(CO)$NH_2$, (CO)$NHCH_3$, and
—(CO)NRcRd;
wherein Rc is H or methyl; and
wherein Rd is —($CH_2$)-cycloalkyl or —($CH_2$)-heterocyclyl, wherein cycloalkyl or heterocyclyl is optionally substituted with methyl, ethyl, (CO)OH or (CO)O(C1-C4)alkyl;

R2
is a 5-10 membered heteroaryl, wherein 1 to 2 ring atoms are —N—, and additionally up to 1 ring atom is —S—; or
a 5 to 6 membered heterocycle, wherein 1 to 2 ring atoms are —O—,
and wherein heteroaryl or heterocycle is optionally substituted by 1 to 2 substituents selected from
halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or
wherein Re and Rf form together with the nitrogen atom to which they are attached a 4 to 6 membered ring, which is optionally substituted with oxo at the position adjacent to the nitrogen atom;
R3 is F or methyl;
m is an integer 0 or 1;
R4 is OH, CN, —(CO)OH, —(CO)$NH_2$, —(CO)$NHCH_3$ or —(CO)O(C1-C4)alkyl;
or a pharmaceutically acceptable salt, solvate, or stereoisomer thereof.

According to another embodiment the compounds of the invention of the formula I is a compound wherein
R1 is pyridyl, pyrazinyl or pyrimidinyl and wherein R1 is substituted by
—(CO)NRcRd;
wherein Rc is H or methyl; and
wherein Rd is —($CH_2$)-cycloalkyl or —($CH_2$)-heterocyclyl,
wherein cycloalkyl is selected from cycloprpopyl, cyclobutyl, cyclopentyl and cyclohexyl,
and wherein heterocyclyl is selected from azirine, azetidine, pyrrolidine and piperidine, and
wherein cycloalkyl or heterocyclyl, is optionally substituted with methyl, ethyl, (CO)OH or (CO)O(C1-C4)alkyl;
or a pharmaceutically acceptable salt, solvate, or stereoisomer thereof.

According to another embodiment the compounds of the invention of the formula I is a compound wherein
R1 is pyridyl, pyrazinyl or pyrimidinyl and wherein R1 is substituted by
—(CO)NRcRd
wherein Rc is H; and
wherein Rd is —($CH_2$)-cyclopropyl, —($CH_2$)-azetidine or —($CH_2$)-piperidine,
wherein the cyclic group, is optionally substituted with methyl, ethyl, (CO)OH or (CO)O(C1-C4)alkyl;

or a pharmaceutically acceptable salt, solvate, or stereoisomer thereof.

According to another embodiment the compounds of the invention of the formula I is a compound wherein
R2
is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from
F, Cl, Br, CN, -methyl, —$(CH)_2$—OH, $NH_2$, NH(C1-C4) alkyl, NH(CO)—(C1-C4)alkyl, (CO)$NH_2$, —(CO)NH(C1-C4)alkyl, —(CO)NH(CO)—(C1-C4)alkyl, 1-oxo-azirinyl, 1-oxo-azetidinyl, 1-oxo-pyrrolidinyl and 1-oxo-piperidinyl;
R3 is F or methyl;
m is an integer 0 or 1;
R4 is OH, CN, —(CO)OH, —(CO)$NH_2$, —(CO)$NHCH_3$, —(CO)O—$CH_3$ or —(CO)O—$CH_2$—$CH_3$;
or a pharmaceutically acceptable salt, solvate, or stereoisomer thereof.

Another embodiment are compounds of the formula I as described above, wherein the compounds in which
R1 is not substituted with halogen; and
R2 is unsubstituted or substituted with halogen; and
m is 0 or 1;
are excluded.

In another embodiment of the invention the compound of formula I is selected from
6-[4-[(3S)-3-(5-Cyano-3-pyridyl)isoxazolidine-2-carbonyl]-1-piperidyl]pyrimidine-4-carboxamide
2-[4-[(3S)-3-Pyrimidin-5-ylisoxazolidine-2-carbonyl]-1-piperidyl]pyrimidine-4-carboxamide
2-[4-[(3S)-3-(5-Cyano-3-pyridyl)isoxazolidine-2-carbonyl]-1-piperidyl]pyrimidine-4-carboxamide
6-[4-[(3S)-3-(5-Cyano-3-pyridyl)isoxazolidine-2-carbonyl]-1-piperidyl]pyrimidine-4-carbonitrile
2-[4-[(3S)-3-(5-cyano-3-pyridyl)isoxazolidine-2-carbonyl]-1-piperidyl]pyrimidine-4-carboxylic acid
Methyl 2-[4-[(3S)-3-(5-cyano-3-pyridyl)isoxazolidine-2-carbonyl]-1-piperidyl]pyrimidine-4-carboxylate
2-[4-[(3S)-3-(5-Cyano-3-pyridyl)isoxazolidine-2-carbonyl]-1-piperidyl]pyrimidine-4-carbonitrile
2-[4-[(3S)-3-(5-Cyano-3-pyridyl)isoxazolidine-2-carbonyl]-1-piperidyl]pyridine-4-carbonitrile
5-[(3S)-2-[1-[4-(Cyanomethoxy)-5-fluoro-2-pyridyl]-4-methyl-piperidine-4-carbonyl]isoxazolidin-3-yl]pyridine-3-carbonitrile
2-[4-[(3S)-3-(5-Cyano-3-pyridyl)isoxazolidine-2-carbonyl]-4-methyl-1-piperidyl]pyrimidine-4-carboxamide
Methyl 2-[4-[(3S)-3-(5-cyano-3-pyridyl)isoxazolidine-2-carbonyl]-4-methyl-1-piperidyl]pyrimidine-4-carboxylate
2-[4-[(3S)-3-(5-Cyano-3-pyridyl)isoxazolidine-2-carbonyl]-4-methyl-1-piperidyl]pyrimidine-4-carboxylic acid
2-[4-[(3S)-3-(5-Cyano-3-pyridyl)isoxazolidine-2-carbonyl]-1-piperidyl]pyridine-4-carboxamide
Ethyl 2-[2-[4-[(3S)-3-(5-Cyano-3-pyridyl)isoxazolidine-2-carbonyl]-4-methyl-1-piperidyl]-5-fluoro-pyrimidin-4-yl]oxyacetate
5-[(3S)-2-[1-[4-(Cyanomethoxy)-5-fluoro-pyrimidin-2-yl]piperidine-4-carbonyl]isoxazolidin-3-yl]pyridine-3-carbonitrile
2-[2-[4-[(3S)-3-(5-Cyano-3-pyridyl)isoxazolidine-2-carbonyl]-1-piperidyl]-5-fluoro-pyrimidin-4-yl]oxyacetic acid
2-[2-[4-[(3S)-3-(5-carbamoyl-3-pyridyl)isoxazolidine-2-carbonyl]-1-piperidyl]-5-fluoro-pyrimidin-4-yl]oxyacetic acid 2-[2-[4-[(3S)-3-(5-cyano-3-pyridyl)isoxazolidine-2-carbonyl]-1-piperidyl]-5-fluoro-pyrimidin-4-yl]oxyacetamide 5-[(3S)-2-[1-(4-Amino-5-fluoro-pyrimidin-2-yl)piperidine-4-carbonyl]isoxazolidin-3-yl]pyridine-3-carbonitrile 2-[4-[(3S)-3-(5-Acetamido-3-pyridyl)isoxazolidine-2-carbonyl]-1-piperidyl]pyrimidine-4-carboxamide 2-[4-[(3S)-3-(6-Methylpyrazin-2-yl)isoxazolidine-2-carbonyl]-1-piperidyl]pyrimidine-4-carboxamide 2-[4-[(3S)-3-(6-Methylpyrazin-2-yl)isoxazolidine-2-carbonyl]-1-piperidyl]pyrimidine-4-carbonitrile 2-[4-[(3S)-3-(5-Cyano-3-pyridyl)isoxazolidine-2-carbonyl]-1-piperidyl]-5-methyl-pyrimidine-4-carboxamide 2-[4-[(3S)-3-[5-(2-oxoazetidin-1-yl)-3-pyridyl]isoxazolidine-2-carbonyl]-1-piperidyl]pyrimidine-4-carboxamide 2-[4-[(3S)-3-[5-(2-Oxoazetidin-1-yl)-3-pyridyl]isoxazolidine-2-carbonyl]-1-piperidyl]pyrimidine-4-carbonitrile Ethyl 6-[4-[(3S)-3-(5-cyano-3-pyridyl)isoxazolidine-2-carbonyl]-1-piperidyl]-5-fluoro-pyrimidine-4-carboxylate 6-[4-[(3S)-3-(5-Cyano-3-pyridyl)isoxazolidine-2-carbonyl]-1-piperidyl]-5-fluoro-pyrimidine-4-carboxylic acid 2-[4-[(3S)-3-(5-Cyano-3-pyridyl)isoxazolidine-2-carbonyl]-4-fluoro-1-piperidyl]-5-fluoro-pyrimidine-4-carboxamide 2-[4-[(3S)-3-[5-(2-Oxopyrrolidin-1-yl)-3-pyridyl]isoxazolidine-2-carbonyl]-1-piperidyl]pyrimidine-4-carboxamide 2-[4-Methyl-4-[(3S)-3-pyrimidin-5-ylisoxazolidine-2-carbonyl]-1-piperidyl]pyrimidine-4-carboxamide 2-[5-Fluoro-2-[4-methyl-4-[(3S)-3-pyrimidin-5-ylisoxazolidine-2-carbonyl]-1-piperidyl]pyrimidin-4-yl]oxyacetonitrile 2-[5-Fluoro-2-[4-[(3S)-3-pyrimidin-5-ylisoxazolidine-2-carbonyl]-1-piperidyl]pyrimidin-4-yl]oxyacetonitrile

[1-(5-Fluoro-4-methoxy-pyrimidin-2-yl)-4-piperidyl]-[(3S)-3-pyrimidin-5-ylisoxazolidin-2-yl]methanone 2-[4-[(3S)-3-Pyrimidin-5-ylisoxazolidine-2-carbonyl]-1-piperidyl]pyridine-4-carbonitrile 5-[4-[(3S)-3-(5-Cyano-3-pyridyl)isoxazolidine-2-carbonyl]-1-piperidyl]pyrazine-2-carbonitrile 6-[4-[(3S)-3-(5-Cyano-3-pyridyl)isoxazolidine-2-carbonyl]-1-piperidyl]pyrazine-2-carbonitrile 2-[4-[(3S)-3-(5-Cyano-3-pyridyl)isoxazolidine-2-carbonyl]-1-piperidyl]-5-fluoro-pyrimidine-4-carboxamide 2-[4-[(3S)-3-(5-Fluoro-3-pyridyl)isoxazolidine-2-carbonyl]-1-piperidyl]pyrimidine-4-carboxamide 6-[4-[(3S)-3-(5-Cyano-3-pyridyl)isoxazolidine-2-carbonyl]-1-piperidyl]pyrazine-2-carboxamide 5-[4-[(3S)-3-(5-Cyano-3-pyridyl)isoxazolidine-2-carbonyl]-1-piperidyl]pyrazine-2-carboxamide 6-[4-[(3S)-3-(5-Cyano-3-pyridyl)isoxazolidine-2-carbonyl]-1-piperidyl]-5-fluoro-pyrimidine-4-carboxamide 2-[4-[(3S)-3-Pyrazin-2-ylisoxazolidine-2-carbonyl]-1-piperidyl]pyrimidine-4-carboxamide 5-Fluoro-2-[4-[(3S)-3-pyrazin-2-ylisoxazolidine-2-carbonyl]-1-piperidyl]pyrimidine-4-carboxamide 2-[4-[(3S)-3-(5-Cyano-3-pyridyl)isoxazolidine-2-carbonyl]-1-piperidyl]-N-(1-methylazetidin-3-yl)pyrimidine-4-carboxamide 2-[4-[(3S)-3-(5-cyano-3-pyridyl) isoxazolidine-2-carbonyl]-1-piperidyl]-N-[2-(1-methylcyclo-propyl)ethyl]pyrimidine-4-carboxamide tert-butyl 3-[[2-[4-[(3S)-3-(5-cyano-3-pyridyl)isoxazolidine-2-carbonyl]-1-piperidyl]pyrimidine-4-carbonyl]amino]azetidine-1-carboxylate 2-[4-[(3S)-3-(5-Cyano-3-pyridyl)isoxazolidine-2-carbonyl]-1-piperidyl]-N-[(1-ethyl-4-piperidyl)methyl]pyrimidine-4-carboxamide 5-Fluoro-2-[4-[(3S)-3-(5-fluoro-3-pyridyl)isoxazolidine-2-carbonyl]-1-piperidyl]pyrimidine-4-carboxamide 2-[4-[(3S)-3-(5-Cyano-6-methyl-3-pyridyl)isoxazolidine-2-carbonyl]-1-piperidyl]pyrimidine-4-carboxamide 5-Fluoro-2-[4-[(3S)-3-(6-methylpyrazin-2-yl)isoxazolidine-2-carbonyl]-1-piperidyl]pyrimidine-4-carboxamide 2-[4-[(3S)-3-(5-Chloro-2-pyridyl)isoxazolidine-2-carbonyl]-1-piperidyl]pyrimidine-4-carboxamide 2-[4-[(3S)-3-(5-Chloro-2-pyridyl)isoxazolidine-2-carbonyl]-1-piperidyl]-5-fluoro-pyrimidine-4-carboxamide 2-[4-[(3S)-3-(5-Cyano-6-methyl-3-pyridyl)isoxazolidine-2-carbonyl]-1-piperidyl]-5-fluoro-pyrimidine-4-carboxamide N-(Azetidin-3-yl)-2-[4-[(3S)-3-(5-cyano-3-pyridyl)isoxazolidine-2-carbonyl]-1-piperidyl]pyrimidine-4-carboxamide 2-[4-[(3S)-3-(5-Methylpyrazin-2-yl)isoxazolidine-2-carbonyl]-1-piperidyl]pyrimidine-4-carboxamide Ethyl 3-[[2-[4-[(3S)-3-(5-cyano-3-pyridyl)isoxazolidine-2-carbonyl]-1-piperidyl]pyrimidine-4-carbonyl]amino]azetidine-1-carboxylate 5-fluoro-2-[4-[(3S)-3-(5-methylpyrazin-2-yl)isoxazolidine-2-carbonyl]-1-piperidyl]pyrimidine-4-carboxamide 6-[4-[(3S)-3-(5-methylpyrazin-2-yl)isoxazolidine-2-carbonyl]-1-piperidyl]pyrimidine-4-carbonitrile 2-[(3R,4R)-4-[(3S)-3-(5-Cyano-3-pyridyl)isoxazolidine-2-carbonyl]-3-fluoro-1-piperidyl]pyrimidine-4-carboxamide 2-[(3R,4R)-4-[(3S)-3-(5-Cyano-3-pyridyl)isoxazolidine-2-carbonyl]-3-fluoro-1-piperidyl]pyrimidine-4-carboxamide 2-[(3S,4S)-4-[(3S)-3-(5-Cyano-3-pyridyl)isoxazolidine-2-carbonyl]-3-fluoro-1-piperidyl]pyrimidine-4-carboxamide 2-[(3R,4S)-4-[(3S)-3-(5-Cyano-3-pyridyl)isoxazolidine-2-carbonyl]-3-fluoro-1-piperidyl]pyrimidine-4-carboxamide 2-[(3S,4R)-4-[(3S)-3-(5-cyano-3-pyridyl)isoxazolidine-2-carbonyl]-3-fluoro-1-piperidyl]pyrimidine-4-carboxamide 5-Methyl-2-[4-[(3S)-3-(6-methylpyrazin-2-yl)isoxazolidine-2-carbonyl]-1-piperidyl]pyrimidine-4-carboxamide 2-[4-[(3S)-3-(5-Fluoro-3-pyridyl)isoxazolidine-2-carbonyl]-1-piperidyl]-5-methyl-pyrimidine-4-carboxamide 5-Methyl-2-[4-[(3S)-3-pyrazin-2-ylisoxazolidine-2-carbonyl]-1-piperidyl]pyrimidine-4-carboxamide Methyl 2-[4-[(3S)-3-(5-cyano-3-pyridyl)isoxazolidine-2-carbonyl]-1-piperidyl]pyrimidine-4-carboxylate 2-[4-[(3S)-3-(5-Cyano-3-pyridyl)isoxazolidine-2-carbonyl]-1-piperidyl]pyrimidine-4-carboxylic acid 2-[4-[(3S)-3-(5-Cyano-3-pyridyl)isoxazolidine-2-carbonyl]-1-piperidyl]pyrimidine-4-carboxylic acid 5-[(3S)-2-[1-(5-Fluoro-4-methylsulfanyl-pyrimidin-2-yl)piperidine-4-carbonyl]isoxazolidin-3-yl]pyridine-3-carbonitrile 5-[(3S)-2-[1-(5-Fluoro-4-methylsulfinyl-pyrimidin-2-yl)piperidine-4-carbonyl]isoxazolidin-3-yl]pyridine-3-carbonitrile 5-[(3S)-2-[1-(5-Fluoro-4-methylsulfonyl-pyrimidin-2-yl)piperidine-4-carbonyl]isoxazolidin-3-yl]pyridine-3-carbonitrile 2-[4-[(3S)-3-(5-Cyano-2-pyridyl)isoxazolidine-2-carbonyl]-1-piperidyl]-5-fluoro-pyrimidine-4-carboxamide 6-[4-[(3S)-3-(5-Cyano-2-pyridyl)isoxazolidine-2-carbonyl]-1-piperidyl]pyrimidine-4-carboxamide 2-[4-[(3S)-3-(5-Cyano-2-pyridyl)isoxazolidine-2-carbonyl]-1-piperidyl]pyrimidine-4-carboxamide (S)-6-(4-(3-(5-Methylfuran-3-yl)isoxazolidine-2-carbonyl) piperidin-1-yl)pyrimidine-4-carboxamide (S)-2-(4-(3-(5-methylfuran-3-yl)isoxazolidine-2-carbonyl) piperidin-1-yl)pyrimidine-4-carboxamide 2-[4-[(3S)-3-(5-Cyano-3-pyridyl)isoxazolidine-2-carbonyl]-1-piperidyl]-5-fluoro-pyrimidine-4-carbonitrile 2-[4-[(3S)-3-(5-cyano-2-pyridyl)isoxazolidine-2-carbonyl]-1-piperidyl]-5-fluoro-pyrimidine-4-carbonitrile 5-[(3S)-2-[1-(3-Methyl-1,2,4-thiadiazol-5-yl)piperidine-4-carbonyl]isoxazolidin-3-yl]pyridine-3-carbonitrile 5-[(3S)-2-[1-(5-Fluoro-4-methoxy-pyrimidin-2-yl)piperidine-4-carbonyl]isoxazolidin-3-yl]pyridine-3-carbonitrile 2-[4-[(3S)-3-(5-Cyano-3-pyridyl)isoxazolidine-2-carbonyl]-3,3,4-trifluoro-1-piperidyl]pyrimidine-4-carboxamide

[1-(5-Fluoro-4-methoxy-pyrimidin-2-yl)-4-piperidyl]-[(3S)-3-(6-methylpyrazin-2-yl)isoxazolidin-2-yl]methanone 6-[(3S)-2-[1-(5-fluoro-4-methoxy-pyrimidin-2-yl)piperidine-4-carbonyl]isoxazolidin-3-yl]pyridine-3-carbonitrile 2-[4-[(3S)-3-(6-Cyanopyrazin-2-yl)isoxazolidine-2-carbonyl]-1-piperidyl]pyrimidine-4-carboxamide 6-[(3S)-2-[1-(5-fluoro-4-methoxy-pyrimidin-2-yl)piperidine-4-carbonyl]isoxazolidin-3-yl]pyridine-3-carbonitrile 5-Fluoro-2-[4-[(3S)-3-pyrazin-2-ylisoxazolidine-2-carbonyl]-1-piperidyl]pyrimidine-4-carbonitrile 2-Chloro-5-[4-[(3S)-3-(5-cyano-3-pyridyl)isoxazolidine-2-carbonyl]-1-piperidyl]pyrimidine-4-carboxylic acid 2-[3,3,4-trifluoro-4-[(3S)-3-pyrazin-2-ylisoxazolidine-2-carbonyl]-1-piperidyl]pyrimidine-4-carboxamide 2-[4-[(3S)-3-(5-cyano-3-pyridyl)isoxazolidine-2-carbonyl]-3,3,4-trifluoro-1-piperidyl]pyrimidine-4-carbonitrile 2-[3,3,4-trifluoro-4-[(3S)-3-pyrazin-2-ylisoxazolidine-2-carbonyl]-1-piperidyl]pyrimidine-4-carbonitrile 5-[(3S)-2-[1-(5-fluoro-4-hydroxy-pyrimidin-2-yl)piperidine-4-carbonyl]isoxazolidin-3-yl]pyridine-3-carbonitrile (S)-5-fluoro-2-(4-fluoro-4-(3-(5-fluoropyridin-3-yl)isoxazolidine-2-carbonyl)piperidin-1-yl)pyrimidine-4-carboxamide (S)-2-(4-(3-(6-methylpyridin-3-yl)isoxazolidine-2-carbonyl)piperidin-1-yl)pyrimidine-4-carbonitrile (S)-6-(4-(3-(6-methylpyridin-3-yl)isoxazolidine-2-carbonyl)piperidin-1-yl)pyrimidine-4-carbonitrile (S)-2-(4-(3-(6-methylpyridin-3-yl)isoxazolidine-2-carbonyl)piperidin-1-yl)pyrimidine-4-carboxamide 5-[(3S)-2-[1-(2-chloro-5-fluoro-pyrimidin-4-yl)piperidine-4-carbonyl]isoxazolidin-3-yl]pyridine-3-carbonitrile (S)-2-(4-(3-(5-methylpyridin-3-yl)isoxazolidine-2-carbonyl)piperidin-1-yl)pyrimidine-4-carbonitrile (S)-2-(4-(3-(5-methylpyridin-3-yl)isoxazolidine-2-carbonyl)piperidin-1-yl)pyrimidine-4-carboxamide (S)-6-(4-(3-(5-methylpyridin-3-yl)isoxazolidine-2-carbonyl)piperidin-1-yl)pyrimidine-4-carbonitrile (S)-6-(4-(3-(5-methylpyridin-3-yl)isoxazolidine-2-carbonyl)piperidin-1-yl)pyrimidine-4-carboxamide (S)-6-(4-(3-(6-methylpyridin-3-yl)isoxazolidine-2-carbonyl)piperidin-1-yl)pyrimidine-4-carboxamide (S)-2-(4-(3-(5-fluoro-6-methylpyridin-3-yl)isoxazolidine-2-carbonyl)piperidin-1-yl)pyrimidine-4-carbonitrile 2-[4-[(3S)-3-(5-fluoro-6-methyl-3-pyridyl)isoxazolidine-2-carbonyl]-1-piperidyl]pyrimidine-4-carboxamide (S)-6-(4-(3-(5-fluoro-6-methylpyridin-3-yl)isoxazolidine-2-carbonyl)piperidin-1-yl)pyrimidine-4-carbonitrile 6-[4-[(3S)-3-(5-fluoro-6-methyl-3-pyridyl)isoxazolidine-2-carbonyl]-1-piperidyl]pyrimidine-4-carboxamide (S)-2-(4-(3-(5-fluoro-4-methylpyridin-3-yl)isoxazolidine-2-carbonyl)piperidin-1-yl)pyrimidine-4-carbonitrile (S)-2-(4-(3-(5-fluoro-4-methylpyridin-3-yl)isoxazolidine-2-carbonyl)piperidin-1-yl)pyrimidine-4-carboxamide (S)-6-(4-(3-(5-fluoro-4-methylpyridin-3-yl)isoxazolidine-2-carbonyl)piperidin-1-yl)pyrimidine-4-carboxamide (S)-6-(4-(3-(5-fluoro-4-methylpyridin-3-yl)isoxazolidine-2-carbonyl)piperidin-1-yl)pyrimidine-4-carbonitrile 5-[(3S)-2-[1-(2-methoxypyrimidin-4-yl)piperidine-4-carbonyl]isoxazolidin-3-yl]pyridine-3-carbonitrile 4-[4-[(3S)-3-(5-cyano-3-pyridyl)isoxazolidine-2-carbonyl]-1-piperidyl]pyrimidine-2-carbonitrile 5-[(3S)-2-[1-(2-methylsulfanylpyrimidin-4-yl)piperidine-4-carbonyl]isoxazolidin-3-yl]pyridine-3-carbonitrile 5-[(3S)-2-[1-(2-chloropyrimidin-4-yl)piperidine-4-carbonyl]isoxazolidin-3-yl]pyridine-3-carbonitrile 5-[(3S)-2-[1-(2-aminopyrimidin-4-yl)piperidine-4-carbonyl]isoxazolidin-3-yl]pyridine-3-carbonitrile ethyl 4-[4-[(3S)-3-(5-cyano-3-pyridyl)isoxazolidine-2-carbonyl]-1-piperidyl]pyrimidine-2-carboxylate (S)-2-(4-(3-(4-methylfuran-2-yl)isoxazolidine-2-carbonyl) piperidin-1-yl)pyrimidine-4-carbonitrile (S)-2-(4-(3-(4-methylfuran-2-yl)isoxazolidine-2-carbonyl) piperidin-1-yl)pyrimidine-4-carboxamide (S)-6-(4-(3-(4-methylfuran-2-yl)isoxazolidine-2-carbonyl) piperidin-1-yl)pyrimidine-4-carbonitrile (S)-6-(4-(3-(4-methylfuran-2-yl)isoxazolidine-2-carbonyl) piperidin-1-yl)pyrimidine-4-carboxamide 2-[(3R,4R or 3,4S)-4-[(3S)-3-(5-Cyano-3-pyridyl)isoxazolidine-2-carbonyl]-3-fluoro-1-piperidyl]-5-fluoro-pyrimidine-4-carboxamide 2-[(3S,4S or 3R,4R)-4-[(3S)-3-(5-Cyano-3-pyridyl)isoxazolidine-2-carbonyl]-3-fluoro-1-piperidyl]-5-fluoro-pyrimidine-4-carboxamide 4-[4-[(3S)-3-(5-Cyano-3-pyridyl)isoxazolidine-2-carbonyl]-1-piperidyl]pyrimidine-2-carboxamide 5-[(3S)-2-[1-(2-Bromopyrimidin-4-yl)piperidine-4-carbonyl]isoxazolidin-3-yl]pyridine-3-carbonitrile 5-[(3S)-2-[1-(4-chloropyrimidin-2-yl)piperidine-4-carbonyl]isoxazolidin-3-yl]pyridine-3-carbonitrile 5-[(3S)-2-[1-(6-Chloropyrimidin-4-yl)piperidine-4-carbonyl]isoxazolidin-3-yl]pyridine-3-carbonitrile 5-[(3S)-2-[1-(4-Bromopyrimidin-2-yl)piperidine-4-carbonyl]isoxazolidin-3-yl]pyridine-3-carbonitrile (S)-2-(4-(3-(5-methylfuran-3-yl)isoxazolidine-2-carbonyl) piperidin-1-yl)pyrimidine-4-carbonitrile (S)-6-(4-(3-(5-methylfuran-3-yl)isoxazolidine-2-carbonyl) piperidin-1-yl)pyrimidine-4-carbonitrile 2-Chloro-5-[4-[(3S)-3-pyrazin-2-ylisoxazolidine-2-carbonyl]-1-piperidyl]pyrimidine-4-carboxylic acid 5-[(3S)-2-[1-(6-Bromopyrimidin-4-yl)piperidine-4-carbonyl]isoxazolidin-3-yl]pyridine-3-carbonitrile 2-[4-[(3S)-3-(5-Cyano-3-thienyl)isoxazolidine-2-carbonyl]-1-piperidyl]-5-fluoro-pyrimidine-4-carboxamide 2-[4-[(3S)-3-(5-Cyano-3-furyl)isoxazolidine-2-carbonyl]-1-piperidyl]-5-fluoro-pyrimidine-4-carboxamide 2-[4-[(3S)-3-(5-Cyano-3-thienyl)isoxazolidine-2-carbonyl]-1-piperidyl]pyrimidine-4-carboxamide (S)-5-(2-(1-(6-fluoropyrimidin-4-yl)piperidine-4-carbonyl) isoxazolidin-3-yl)nicotinonitrile 5-Fluoro-2-[4-[(3S)-3-(2-methylthiazol-4-yl)isoxazolidine-2-carbonyl]-1-piperidyl]pyrimidine-4-carboxamide 2-[4-[(3S)-3-(5-Cyano-3-furyl)isoxazolidine-2-carbonyl]-1-piperidyl]pyrimidine-4-carboxamide

[1-(4-chloro-1,3,5-triazin-2-yl)-4-piperidyl]-[(3S)-3-pyrazin-2-ylisoxazolidin-2-yl]methanone 5-Fluoro-2-[4-[(3S)-3-(2-pyridyl)isoxazolidine-2-carbonyl]-1-piperidyl]pyrimidine-4-carboxamide 6-[4-[(3S)-3-(5-Methyl-2-thienyl)isoxazolidine-2-carbonyl]-1-piperidyl]pyrimidine-4-carboxamide 2-[4-[(3S)-3-(6-Cyanopyridazin-4-yl)isoxazolidine-2-carbonyl]-1-piperidyl]-5-fluoro-pyrimidine-4-carboxamide 2-[4-[(3S)-3-(6-Cyanopyridazin-4-yl)isoxazolidine-2-carbonyl]-1-piperidyl]pyrimidine-4-carboxamide

[1-(4-Chloro-6-methyl-1,3,5-triazin-2-yl)-4-piperidyl]-[(3S)-3-pyrazin-2-ylisoxazolidin-2-yl]methanone

[1-(4-chloro-6-methoxy-1,3,5-triazin-2-yl)-4-piperidyl]-[(3S)-3-pyrazin-2-ylisoxazolidin-2-yl]methanone 5-methyl-2-[4-[(3S)-3-(5-methyl-2-thienyl)isoxazolidine-2-carbonyl]-1-piperidyl]pyrimidine-4-carboxamide 5-fluoro-2-[4-[(3S)-3-(5-methyl-2-thienyl)isoxazolidine-2-carbonyl]-1-piperidyl]pyrimidine-4-carboxamide

[1-(4-Amino-6-chloro-1,3,5-triazin-2-yl)-4-piperidyl]-[(3S)-3-pyrazin-2-ylisoxazolidin-2-yl]methanone 2-[(3R,4R or 3S,4S)-3-fluoro-4-[(3S)-3-(6-methyl-3-pyridyl)isoxazolidine-2-carbonyl]-1-piperidyl]-5-methyl-pyrimidine-4-carboxamide 2-[(3S,4S or 3R,4R)-3-fluoro-4-[(3S)-3-(6-methyl-3-pyridyl)isoxazolidine-2-carbonyl]-1-piperidyl]-5-methyl-pyrimidine-4-carboxamide 5-fluoro-6-[4-[(3S)-3-(6-methyl-3-pyridyl)isoxazolidine-2-carbonyl]-1-piperidyl]pyrimidine-4-carboxamide; trifluoroacetic acid 2-[4-[(3S)-3-(2-Cyanothiazol-4-yl)isoxazolidine-2-carbonyl]-1-piperidyl]pyrimidine-4-carboxamide and 2-[4-[(3S)-3-(2-Cyanothiazol-4-yl)isoxazolidine-2-carbonyl]-1-piperidyl]-5-fluoro-pyrimidine-4-carboxamide or a pharmaceutically acceptable salt, solvate or stereoisomer thereof.

According to another embodiment the compounds of the invention of the formula I is a compound wherein R1 is pyrimidinyl and wherein R1 is substituted by —$(CO)NH_2$ and optionally additionally by F;

R2 is selected from pyridyl and pyrazinyl, and is optionally substituted by-methyl, m is an integer 0;

or a pharmaceutically acceptable salt, solvate, or stereoisomer thereof.

In another embodiment of the invention the compound of formula I is selected from 2-[4-[(3S)-3-(5-Cyano-3-pyridyl)isoxazolidine-2-carbonyl]-1-piperidyl]pyrimidine-4-carboxamide, 2-[4-[(3S)-3-(5-Cyano-3-pyridyl)isoxazolidine-2-carbonyl]-1-piperidyl]-5-fluoro-pyrimidine-4-carboxamide, 2-[4-[(3S)-3-(6-Methylpyrazin-2-yl)isoxazolidine-2-carbonyl]-1-piperidyl]pyrimidine-4-carboxamide and 5-Fluoro-2-[4-[(3S)-3-pyrazin-2-ylisoxazolidine-2-carbonyl]-1-piperidyl]pyrimidine-4-carboxamide or a pharmaceutically acceptable salt, solvate, or stereoisomer thereof.

In another embodiment of the invention the compound of formula I is selected from 2-[4-[(3S)-3-(5-Cyano-3-pyridyl)isoxazolidine-2-carbonyl]-1-piperidyl]pyrimidine-4-carboxamide, 2-[4-[(3S)-3-(5-Cyano-3-pyridyl)isoxazolidine-2-carbonyl]-1-piperidyl]-5-fluoro-pyrimidine-4-carboxamide and 2-[4-[(3S)-3-(6-Methylpyrazin-2-yl)isoxazolidine-2-carbonyl]-1-piperidyl]pyrimidine-4-carboxamide;

or a pharmaceutically acceptable salt, solvate, or stereoisomer thereof.

A further embodiment are compounds of formula I which show in the ADP Glo assay as described in the examples an $IC_{50}$ value of 200 nM or less;

or a pharmaceutically acceptable salt, solvate or stereoisomer thereof.

A further embodiment are compounds of formula I which show in the ADP Glo assay as described in the examples an $IC_{50}$ value of 50 nM or less;

or a pharmaceutically acceptable salt, solvate or stereoisomer thereof.

A further embodiment are compounds of formula I which show in the ADP Glo assay as described in the examples an $IC_{50}$ value of 20 nM or less;

or a pharmaceutically acceptable salt, solvate or stereoisomer thereof.

A further embodiment are compounds of formula I which a TPSA value as described in the examples of 90 $Å^2$ or more;

or a pharmaceutically acceptable salt, solvate, or stereoisomer thereof.

A further embodiment are compounds of formula I which a TPSA value as described in the examples of 105 $Å^2$ or more;

or a pharmaceutically acceptable salt, solvate, or stereoisomer thereof.

A further embodiment are compounds of formula I which a TPSA value as described in the examples of 120 $Å^2$ or more;

or a pharmaceutically acceptable salt, solvate, or stereoisomer thereof.

Synthesis of Compounds

The compounds may be prepared using the methods disclosed herein and routine modifications thereof, which will be apparent given the disclosure herein and methods well known in the art.

Scheme 1

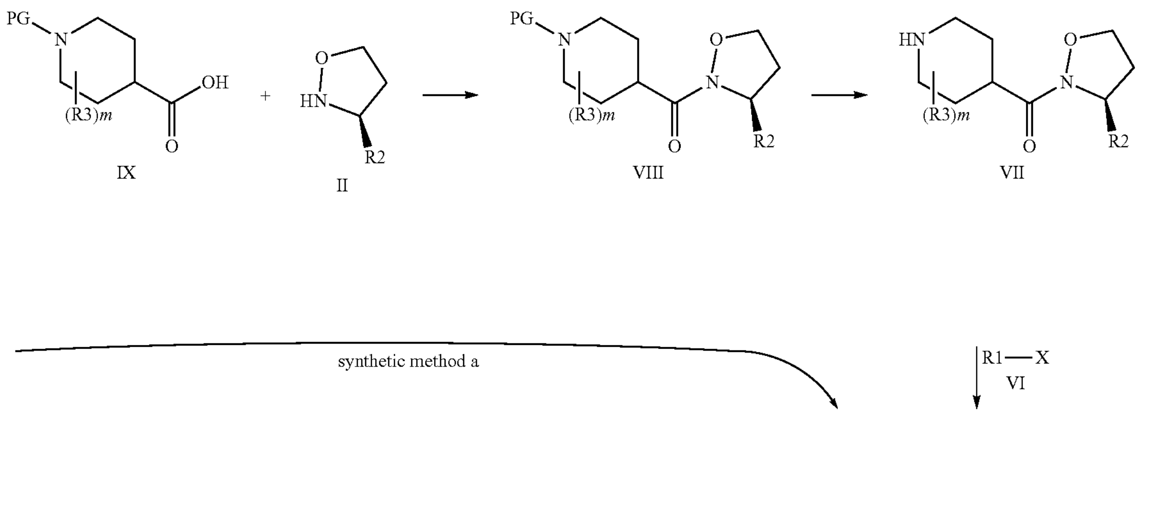

IX II VIII VII

-continued

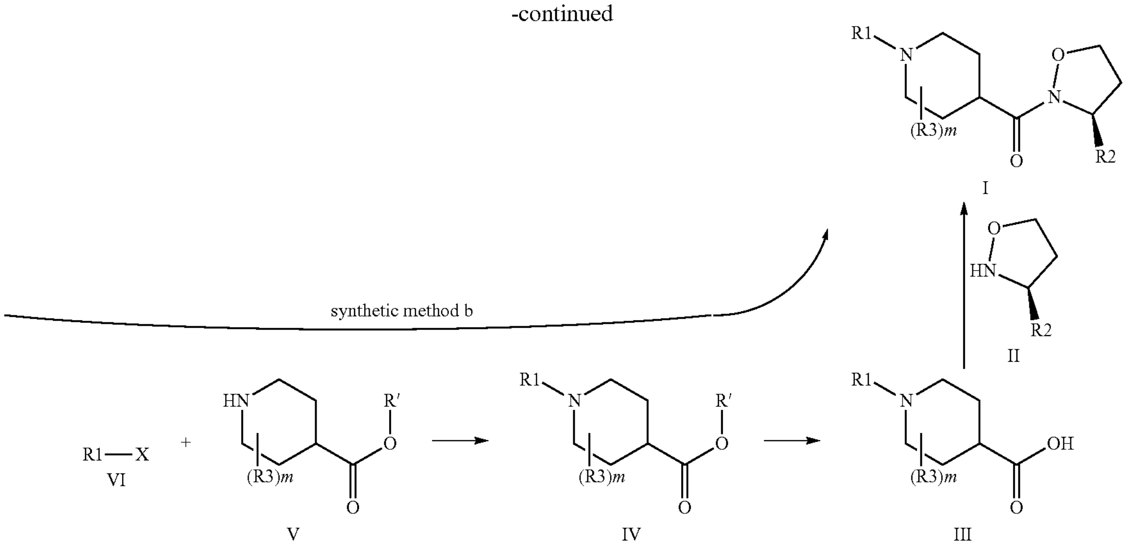

Synthetic Method a:

Isoxazolidines of formula II synthesized by well known procedures from the literature, e.g. Denali WO2017096301 and GSK WO2019130230, are coupled to optionally substituted N-protected 4-piperidyl-carboxylic acids of formula IX optionally substituted with (R3)m, wherein (R3)m is as defined above, using standard acid activation methods like acid chloride, HOBt, HATU, HBTU, PyBOP and 1-propanephosphonic anhydride under basic conditions, e.g. diisopropylethylamine or the like, in aprotic solvents like DMF, DMSO, acetonitrile, or the like to form compounds of formula Vill optionally substituted with (R3)m defined as above. As protecting group (PG) BOC, benzoyl, or benzyl can be used. Cleavage of the protecting group under acidic or hydrogenating conditions leads to compounds of formula VI optionally substituted with (R3)m, which can be reacted with 5-6 membered heterocyclic groups of formula VI, substituted with X representing leaving groups like F, Cl, Br, O-triflate, under e. g. conditions of nucleophilic aromatic substitution or Hartwig-Buchwald coupling to provide compounds of formula I optionally substituted with (R3)m.

Synthetic Method b:

4-Piperidyl-carboxylic esters of formula V optionally substituted with (R3)m can be reacted with 5-6 membered heterocyclic groups of formula VI, substituted with X representing leaving groups like F, Cl, Br, O-triflate, under e. g. conditions of nucleophilic aromatic substitution or Hartwig-Buchwald coupling conditions to provide compounds of formula IV optionally substituted with (R3)m. R' represents methyl, ethyl or tert. butyl. Ester cleavage, methyl and ethyl esters preferably under basic conditions like LiOH, NaOH, tert. butyl esters preferably under acidic conditions like HCl, TFA, p-toluene sulfonic acid yields 4-piperidinyl-carboxylic acids of formula III optionally substituted by (R3)m. Isoxazolidines of formula II synthesized by well known procedures from the literature, e.g. Denali WO2017096301 and GSK WO2019130230, are coupled to 4-piperidyl-carboxylic acids of formula III optionally substituted with (R3)m, wherein (R3)m is as defined above, using standard acid activation methods like acid chloride, HOBt, HATU, HBTU, PyBOP and 1-propanephosphonic anhydride under basic conditions, e.g. diisopropylethylamine or the like, in aprotic solvents like DMF, DMSO, acetonitrile, or the like to form compounds of formula I optionally substituted with (R3)m defined as above.

Functional groups like acids, esters, amides, nitriles, halogens in compounds of formula I can be transformed (functional group interconversion) into other functional groups with standard methods like esterification, saponification, halogenation, Suzuki reaction to yield further compounds of formula I.

The synthesis of typical compounds described herein may be accomplished as described in the following examples. If available, reagents may be purchased commercially, e.g., from Sigma Aldrich or other chemical suppliers. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedure.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis, Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989). The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane, "DCM"), diethyl ether, methanol, pyridine and the like). Unless specified to the contrary, the solvents used in the reactions of the present disclosure are inert organic solvents, and the reactions are carried out under an inert gas, preferably argon.

Pharmaceutical Compositions

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients.

Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical arts.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous, or epidural injection as, for example, a sterile solution or suspension or sustained-release formulation; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically acceptable material, composition or vehicle, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino ($NCH_3$) and are, thus, capable of forming pharmaceutically acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle or the dosage form manufacturing process or by separately reacting a purified compound of the disclosure in its free base form with a suitable organic or inorganic acid and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate and laurylsulphonate salts and the like.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and the like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process or by separately reacting the purified compound in its free acid form with a suitable base, such as the hydroxide, carbonate or bicarbonate of a pharmaceutically-acceptable metal cation, with ammonia or with a pharmaceutically-acceptable organic primary, secondary or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like. Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%. In certain embodiments, a formulation of the present disclosure comprises one or more of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers or finely divided solid carriers or both and then, if necessary, shaping the product. Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin, absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical formulating arts. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure. Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Methods of Treatment

In other embodiments, provided herein is a method of treating a receptor-interacting protein kinase 1-mediated disease or disorder. The method includes administering a therapeutically effective amount of a compound or pharmaceutical composition as described herein to a subject in need thereof. In some embodiments, the receptor-interacting protein kinase 1-mediated disease or disorder is trauma, ischemia, stroke, cardiac infarction, infection, Gaucher's disease, Krabbe disease, sepsis, systemic inflammatory response syndrome (SIRS), Parkinson's disease, Alzheimer's disease, amyotrophic lateral sclerosis, Huntington's disease, HIV-associated dementia, retinal degenerative disease, glaucoma, age-related macular degeneration, rheumatoid arthritis, non-communicable inflammatory skin diseases (ncISD) such as psoriasis or atopic dermatitis, psoriatic arthritis, or inflammatory bowel disease.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo.

"In vivo" means within a living individual, as within an animal or human. In this context, the methods described herein may be used therapeutically in an individual.

"Ex vivo" means outside of a living individual. Examples of ex vivo cell populations include in vitro cell cultures and biological samples including fluid or tissue samples obtained from individuals.

Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor-interacting protein kinase 1 inhibitor, have demonstrated the effectiveness of receptor-interacting protein kinase 1 inhibition in protecting tissues from inflammatory bowel diseases (e.g., ulcerative colitis and Crohn's disease), non-communicable inflammatory skin diseases (ncSD) such as psoriasis or atopic dermatitis, retinal-detachment-induced photoreceptor necrosis, retinitis pigmentosa, cerulein-induced acute pancreatitis, and sepsis/systemic inflammatory response syndrome (SIRS), and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza or SARS-Coronavirus) and lysosomal storage diseases. The receptor-interacting protein kinase 1 inhibitors of the present disclosure are therefore suggesting that both RIPK1 kinase-driven inflammation and cell death are key contributing factors to systemic inflammatory response syndrome (SIRS). There is also rationale that vascular permeability and endothelial dysfunction contribute to SIRS/shock and lethality. The receptor-interacting protein kinase 1 inhibitors of the present disclosure are therefore useful for treating diseases and conditions mediated by receptor-interacting protein kinase 1, including but not limited to inflammatory diseases or disorders, necrotic cell diseases, neurodegenerative diseases, central nervous system (CNS) diseases, ocular diseases, infections, and malignancies. In certain embodiments, the receptor-interacting protein kinase 1 inhibitors described herein can inhibit inflammation, protect tissue or cell from damage or undesired cell death (e.g., necrosis or apoptosis), ameliorate symptoms, and improve immune response or neuronal function in a patient suffering from any of the prescribed diseases or conditions. Moreover, the compounds may be suitable for treatment of immune-mediated disease, such as but not limited to, allergic diseases, autoimmune diseases, and prevention of transplant rejection.

Provided herein are compounds and compositions for use in medicine. In certain embodiments, the compounds and compositions are for use in the treatment of a receptor-interacting protein kinase 1-mediated disease or disorder. Also provided is a method of treating a receptor-interacting protein kinase 1-mediated disease or disorder comprising administering a therapeutically effective amount of a compound or pharmaceutical composition disclosed herein to a subject in need thereof. In certain embodiments, the disease or disorder is an inflammatory disease associated with A20 SNPs.

Various specific diseases and disorders are described below. In certain embodiments, the disease or disorder is necrotizing enterocolitis, tuberous sclerosis, Tangier's Disease, Wohlman's Syndrome, inflammatory bowel disease, Crohn's disease, ulcerative colitis, non-communicable inflammatory skin diseases (ncISD) such as psoriasis or atopic dermatitis, retinal detachment, retinitis pigmentosa, macular degeneration, pancreatitis (e.g., acute pancreatitis), interface dermatitis (e.g. cutaneous lupus erythematosus, lichen planus, lichen planopillaris, toxic epidermal necrolysis (TEN), Stevens-Johnson-Syndrome, Graft versus Host Disease (GvHD), alopecia arreata, vitiligo), atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome (SIRS), cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, bacterial infection, staphylococcus infection, mycobacterium infection, retinitis pigmentosa, influenza, severe acute respiratory syndrome (SARS), middle east respiratory syndrome (MERS), acute respiratory response syndrome (ARDS), transplant rejection, burns or hypoxia. In certain embodiments, the disease or disorder is trauma, ischemia, stroke, cardiac infarction, infection, lysosomal storage disease, Niemann-Pick disease, Gaucher's disease, Krabbe disease, sepsis, systemic inflammatory response syndrome (SIRS), Parkinson's disease, Alzheimer's disease, amyotrophic lateral sclerosis (ALS/Lou Gehrig's Disease), Huntington's disease, HIV-associated dementia, encephalopathy, retinal degenerative disease, glaucoma, age-related macular degeneration, rheumatoid arthritis, non-communicable inflammatory skin diseases (ncISD) such as psoriasis or atopic dermatitis, psoriatic arthritis or inflammatory bowel disease. In certain embodiments, the disease or disorder is Alzheimer's disease, ALS, Friedreich's ataxia, Huntington's disease, Lewy body disease, Parkinson's disease, Huntington's disease, multiple sclerosis, diabetic neuropathy, polyglutamine (polyQ) diseases, stroke, Fahr disease, Menke's disease, Wilson's disease, cerebral ischemia, lysosomal storage disease or a prion disorder. In certain embodiments, the disease is ALS. In certain embodiments, the disease is Alzheimer's disease. In certain embodiments, the disease is lysosomal storage disease. In certain embodiments, the disease is Parkinson's disease. In certain embodiments the disorder is an ischemic disease of organs including but not limited to brain, heart, kidney and liver. In some different embodiments, the disorder is an ocular disorder such as retinal degenerative disease, glaucoma or age-related macular degeneration. In some different embodiments, the disorder is a central nervous system (CNS) disorder.

In certain embodiments, provided is a method of treating rheumatoid arthritis (see Lawlor K E, Nat Commun. 2015, 6282, Lee S H, Sci Rep. 2017, 10133), systemic onset juvenile idiopathic arthritis (SoJIA), spondyloarthritis, osteoarthritis, non-communicable inflammatory skin diseases (ncISD) such as psoriasis or atopic dermatitis, Crohn's disease, ulcerative colitis, or multiple sclerosis, comprising administering a therapeutically effective amount of a compound as provided herein to a subject in need thereof. In certain embodiments, provided is a method of treating autoimmune hepatitis, atherosclerosis, neutrophilic dermatoses, or a rare disease driven by A20, NEMO, and/or LUBAC mutations, comprising administering a therapeutically effective amount of a compound as provided herein to a subject in need thereof.

In certain embodiments, the compounds and compositions are useful for treating non-communicable inflammatory skin diseases (ncISD) such as psoriasis or atopic dermatitis.

In certain embodiments, the disorder is an inflammatory disease of the intestines such as Crohn's disease or ulcerative colitis (both generally known together as inflammatory bowel disease, IBD). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), non-communicable inflammatory skin diseases (ncISD) such as psoriasis or atopic dermatitis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis. In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis. In certain embodiments, the compounds and compositions are useful for treating rheumatoid arthritis (RA). In certain embodiments, the compounds and compositions are useful for treating ulcerative colitis. In certain embodiments, the compounds and compositions are useful for treating non-communicable inflammatory skin diseases (ncISD) such as psoriasis or atopic dermatitis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity.

Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

In another embodiment the receptor interacting protein kinase 1 inhibitors described herein may be used to treat inflammatory diseases and disorders like rheumatoid arthritis (RA), psoriasis, inflammatory bowel disease (IBD) like Crohn's disease or ulcerative colitis.

In another embodiment the receptor interacting protein kinase 1 inhibitors described herein may be used to treat Interface dermatitis like cutaneous lupus erythematosus (CLE), Lichen planus (LP), toxic epidermal necrolysis (TEN) or Stevens-Johnson syndrome (SJS).

In another embodiment the receptor interacting protein kinase 1 inhibitors described herein may be used to treat hyperinflammation during viral infection like corona virus disease-19 (COVID-19), acute respiratory distress syndrome (ARDS), systemic inflammatory response syndrome (SIRS).

In another embodiment the receptor interacting protein kinase 1 inhibitors described herein may be used to treat corona virus disease-19 (COVID-19).

In another embodiment the receptor interacting protein kinase 1 inhibitors described herein may be used to treat Respiratory diseases like Influenza (e.g. swine flu, H7N9), severe acute respiratory syndrome (SARS), Middle East Respiratory Syndrome (MERS), Respiratory-Syncytial-Virus (RSV) or bronchiolitis).

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, systemic inflammatory response syndrome (SIRS), Parkinson's disease, Alzheimer's disease, amyotrophic lateral sclerosis, Huntington's disease, HIV-associated dementia, retinal degenerative disease, glaucoma, age-related macular degeneration, rheumatoid arthritis, non-communicable inflammatory skin diseases (ncISD) such as psoriasis or atopic dermatitis, psoriatic arthritis or inflammatory bowel disease.

The necrotic cell diseases can be acute diseases such as trauma, ischemia, stroke, cardiac infarction, anthrax lethal toxin induced septic shock, sepsis, systemic respiratory response syndrome (SIRS), cell death induced by LPS and HIV induced T-cell death leading to immunodeficiency. In certain embodiments the disorder is an ischemic disease of organs including but not limited to brain, heart, kidney and liver. The necrotic cell diseases also include chronic neurodegenerative diseases, such as Parkinson's disease, Huntington's disease, amyotrophic lateral sclerosis, Alzheimer's disease, infectious encephalopathies, dementia such as HIV associated dementi. In some different embodiments, the disorder is an ocular disorder such as retinal degenerative disease, glaucoma or age-related macular degeneration. In some different embodiments, the disorder is a central nervous system (CNS) disorder.

Neurodegenerative and CNS Diseases

The receptor-interacting protein kinase 1 inhibitors described herein may also be used to treat neurodegenerative diseases. Neurodegenerative diseases can affect many of the body's activities, such as balance, movement, talking, breathing, and heart function. Neurodegenerative diseases can be genetic or caused by medical conditions such as alcoholism, tumors, strokes, toxins, chemicals, and viruses. Non-limiting examples of neurodegenerative diseases include Alzheimer's disease, amyotrophic lateral sclerosis (ALS), Friedreich's ataxia, Huntington's disease, Lewy body disease, Parkinson's disease, and spinal muscular atrophy. In certain embodiments, neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease, and spinal muscular atrophy.

In certain embodiments, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor-interacting protein kinase 1 inhibitors described herein can be used to preserve neuron viability and promote axon growth and nerve functions within the central nervous system (CNS). Accordingly, the compounds may be used to reduce or even reverse the loss of cognitive, motor, and sensory functions associated with a CNS disease or disorder, by preserving neuron viability and/or promoting axon regeneration and/or nerve functions.

The receptor-interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron, and a midbrain neuron. The receptor interacting protein kinase 1 inhibitors described herein can be used in a method for promoting nerve function or preserving the viability following injury to a CNS neuron. In another embodiments, these compounds can be used to promote regeneration of an axon in a CNS neuron that is degenerated in the CNS disease or disorder. The RIP receptor-interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

Non-limiting examples of CNS diseases or disorders include brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabeticneuropathy, polyglutamine (polyQ) diseases, stroke, Fahr disease, Menke's disease, Wilson's disease, cerebral ischemia, and a prion disorder.

In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heartbeat and blood pressure, e.g., an injury to or aneurysm in the brain stem. In certain embodiments, the CNS disease or disorder affects a subject's cognitive ability. In certain embodiments, the CNS disease or disorder affects a subject's movement and/or strength. In certain embodiments, the CNS disease or disorder affects a subject's coordination.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders. In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasaldegeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies. Non-limiting examples of neurodegenerative diseases include Alzheimer's disease, lysosomal storage diseases, amyotrophic lateral sclerosis (ALS), Friedreich's ataxia, Huntington's disease, Lewy body disease, Parkinson's disease, and spinal muscular atrophy.

In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS). In certain embodiments, the compounds and compositions of the present disclosure are useful for treating lysosomal storage diseases.

In certain embodiments, the disorder is a brain disorders, such as, but not limited to, Alzheimer's disease, ALS, frontotemporal dementias, vascular dementia, Huntington's disease, Parkinson's disease, Lewy Body dementia, Progressive Supranuclear Palsy, multiple sclerosis, neuromyelitis optica, ischemic brain damage (stroke), hypoxic brain damage, traumatic brain injury, spinal cord injury, sepsis-induced brain damage, CNS infections, CNS abscesses, glioblastoma multiforme, epilepsy, neuropathic pain, major depression, bipolar depression, schizophrenia, autism, Niemann-Pick disease, neuro-Behçet's disease.

In certain embodiments, provided is a method of treating a CNS disease or disorder, comprising administering a therapeutically effective amount of a compound as provided herein to a subject in need thereof. In certain embodiments, the disease or disorder is Alzheimer's disease or amyotrophic lateral sclerosis (ALS).

Ocular Conditions

The receptor-interacting protein kinase 1 inhibitors described herein can also be used to treat ocular conditions, for example to reduce or prevent the loss of photoreceptor and/or retinal pigment epithelial cell viability.

In certain embodiments, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. AMD may be the neovascular or the dry form of AMD. Retinal detachment may be arhegmatogenous, a serous, and a tractional retinal detachment. In certain embodiments, the ocular condition may be geographic atrophy, glaucoma, or another ischemic eye disease. In certain embodiments, the disclosure provides a method of preserving the viability of retinal pigment epithelial (RPE) cells within the retina of a subject with an ocular condition with administration of a compound of the present disclosure. The subject being treated may have a loss of retinal pigment epithelial cells in the retina of the eye with the condition and the ocular condition may be age-related macular degeneration (AMD), BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), or another uveitis disorder. In certain embodiments, the method comprises administering to the eye of the subject an effective amount of a compound or composition described herein, thereby preserving the viability of the retinal pigment epithelial cells. Provided in another embodiment is a method of preserving the viability of photoreceptor cells disposed within a retina of a subject with age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. Therefore, in certain embodiments, the method comprises administering to the eye an effective amount of a compound or composition described herein, thereby preserving the viability of the photoreceptor cells disposed within the retina of the subject with a condition. Provided in another embodiment is a method of preserving the viability of photoreceptor cells disposed within a retina of a mammalian eye following retinal detachment. The retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma. In certain embodiments, the method comprises administering a compound or composition described herein to the eye in which a region of the retina has been detached in amounts sufficient to preserve the viability of photoreceptor cells disposed within the region of the detached retina. Provided in another embodiment is a method of preserving visual function of an eye of a subject with age-related macular degeneration (AMD), retinosis pigmentosa (RP), macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity, wherein a symptom of the ocular condition is the loss of photoreceptor cells viability in the retina of the eye, wherein the method comprises treating the subject with a compound or composition described herein to the subject. In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments, provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

Non-limiting examples of symptoms associated with the ocular conditions include the loss of retinal ganglion cell viability in the retina of the eye, glaucoma, optic nerve injury, optic neuritis, optic neuropathies, diabetic retinopathy, central retinal artery occlusion, and central retinal vein occlusion. The compounds described herein may also be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial opticneuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with glaucoma, optic nerve injury, optic neuropathies, diabetic retinopathy, central retinal artery occlusion, or central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglioncells disposed within the region of the affected retina. The preserved retinal ganglion cell is capable of supporting axonal regeneration, linear ubiquitin chain assembly complex (LUBAC) deficiency syndrome, hematological and solid organ malignancies, bacterial infections and viral infections (e.g., tuberculosis and influenza or SARS-Coronavirus) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease. In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof. In another embodiment, the present disclosure provides a method of inhibiting receptor-interacting protein kinase 1. The method includes contacting the receptor-interacting protein kinase 1 with an effective amount of a compound as described herein. Inhibiting the receptor-interacting protein kinase 1 generally include contacting the receptor-interacting protein kinase 1 with an amount of the compound sufficient to reduce the activity of the receptor-interacting protein kinase 1 as compared to the receptor-interacting proteinkinase 1 activity in the absence of the compound. For example, contacting the receptor-interacting protein kinase 1 with the compound can result in from about 1% to about 99% receptor-interacting protein kinase 1 inhibition (i.e., the activity of the inhibited enzyme ranges from 99% to 1% of the enzyme activity in the absence of the compound). The level of receptor-interacting protein kinase 1 inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of receptor-interacting protein kinase 1 inhibition can range from about 5% to about 95%, or from about 10% to about 90%, or from about 20% to about 80%, or from about 30% to about 70%, or from about 40% to about 60%. In some embodiments, contacting the receptor-interacting protein kinase 1 with a compound as described herein will result in complete (i.e., 100%) inhibition.

Combination Therapy

In certain embodiments, the compounds described herein may be administered in combination with at least one other therapeutically active agent. The two or more agents can be coadministered, coformulated, or administered separately. In certain embodiments, the other therapeutically active agent is selected from a thrombolytic agent, a tissue plasminogen activator, an anticoagulant, a platelet aggregation inhibitor, an antimicrobial agent (an antibiotic, a broad-spectrum antibiotic, a lactam, an antimycobacterial agent, a bactericidal antibiotic, anti-MRSA therapy), a long acting beta agonist, a combination of an inhaled corticosteroid and a long acting beta agonist, a short acting beta agonist, a leukotriene modifier, an anti-IgE, a methylxanthine bronchodilator, a mast cell inhibitor, a protein tyrosine kinase inhibitor, a CRTH2/D prostanoid receptor antagonist, an epinephrine inhalation aerosol, a phosphodiesterase inhibitor, a combination of a phosphodiesterase-3 inhibitor and a phosphodiesterase-4 inhibitor, a long-acting inhaled anticholinergic, a muscarinic antagonist, a long-acting muscarinic antagonist, a low dose steroid, an inhaled corticosteroid, an oral corticosteroid, a topical corticosteroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor, a cystic fibrosis transmembrane conductance regulator potentiator, a mucolytic agent, pancreatic enzymes, a bronchodilator, an opthalmalic intravitreal injection, an anti-vascular endothelial growth factor inhibitor, a ciliary neurotrophic growth factor agent, a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, inactivated influenza vaccine, a ciliary neurotrophic growth factor, a gene transfer agent, a topical immunomodulator, calcineurin inhibitor, an interferon gamma, an antihistamine, a monoclonal antibody, a polyclonal anti-Tcell antibody, an antithymocyte gamma globulin-equine antibody, an antithymocyte globulin-rabbit antibody, an anti-CD40 antagonist, a JAK inhibitor, and an anti-TCR murine mAb.

Exemplary other therapeutically active agents include heparin, coumadin, clopidrogel, dipyridamole, ticlopidine HCL, eptifibatide, aspirin, vacomycin, cefeprime, a combination of piperacillinand tazobactam, imipenem, meropenem, doripenem, ciprofloxacin, levofloxacin, ofloxacin, moxifloxacin, hydrocortisone, vedolizumab, alicaforsen, remestemcel-L, ixekizumab, tildrakizumab, secukinumab, chlorhexidine, doxycycline, minocycline, fluticasone (fluticasone proprionate, fluticasone furoate), beclomethasone dipropionate, budesonide, trimcinolone acetonide, flunisolide, mometasone fuorate, ciclesonide, arformoterol tartrate, formoterol fumarate, salmeterol xinafoate, albuterol (albuterol sulfate), levalbuterol tartrate, ipratropium bromide, montelukast sodium, zafirlukast, zileuton, omalizumab, theophylline, cromulyn sodium, nedocromil sodium, masitinib, AMG 853, indacaterol, E004, reslizumab, salbutamol, tiotropium bromide, VR506, lebrikizumab, RPL554, afibercept, umeclidinium, indacterol maleate, aclidinium bromide, roflumilast, SCH527123, glycoprronium bromide, olodaterol, a combination of fluticasone furoate and vilanterol vilanterol, a combination of fluticasone propionate and salmeterol, a combination of fluticasone furoate and fluticasone proprionate, a combination of fluticasone propionate and eformoterol fumarate dihydrate, a combination of formoterol and budesonide, a combination of beclomethasone dipropionate and formoterol, a combination of mometasone furoate and formoterol fumarate dihydrate, a combination of umeclidinium and vilanterol, a combination of ipratropium bromide and albuterol sulfate, a combination of glycopyrronium bromide and indacaterol maleate, a combination of glycopyrrolate and formoterol fumarate, a combination of aclidinium and formoterol, isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, delamanid, imatinib, ARG201, tocilizumab, muromonab-CD3, basiliximab, daclizumab, rituximab, prednisolone, anti-thymocyte globulin, FK506 (tacrolimus), methotrexate, cyclosporine, sirolimus, everolimus, mycophenolate sodium, mycophenolate mofetil, cyclophosphamide, azathioprine, thalidomide, chlorambucil, nifedipine, nicardipine, nitroglycerin, lisinopril, diltaizem, fluoxetine, bosentan, epoprostenol, colchicine, para-aminobenzoic acid, dimethyl sulfoxide, D-penicillamine, interferon alpha, interferon gamma (INF-g), omeprazole, metoclopramide, lansoprazole, esomeprazole, pantoprazole, rabeprazole, imatinib, belimumab, ARG201, tocilizumab, ivacaftor, dornase alpha, pancrelipase, tobramycin, aztreonam, colistimethate sodium, cefadroxil monohydrate, cefazolin, cephalexin, cefazolin, moxifloxacin, levofloxacin, gemifloxacin, azithromycin, gentamicin, ceftazidime, a combination of trimethoprim and sulfamethoxazole, chloramphenicol, a combination of ivacftor and lumacaftor, ataluren, NT-501-CNTF, a gene transfer agent encoding myosin VIIA (MY07A), ranibizumab, pegaptanib sodium, NT501, humanized sphingomab, bevacizumab, oseltamivir, zanamivir, rimantadine, amantadine, nafcillin, sulfamethoxazolem, trimethoprim, sulfasalazine, acetyl sulfisoxazole, vancomycin, muromonab-CD3, ASKP-1240, ASP015K, TOL101, pimecrolimus, hydrocortizone, betamethasone, flurandrenolide, triamcinolone, fluocinonide, clobetasol, hydrocortisone, methylprednisolone, prednisolone, a recombinant synthetic type I interferon, interferon alpha-2a, interferon alpha-2b, hydroxyzine, diphenhydramine, flucloxacillin, dicloxacillin, and erythromycin.

A compound described herein may be administered in combination with other anti-inflammatory agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL1 7 biologics, anti-CD22, anti-integrin agents, anti-IFNa, anti-CD20 or CD4 biologics and other cytokine inhibitors or biologics to T-cell or B-cell receptors or interleukins.

In the treatment of ALS, a compound described herein may be administered in combination with riluzole.

In the treatment of Parkinson's disease, a compound described herein may be administered in combination with levodopa, carbodopa or a combination thereof, pramipexole, ropinirole, rotigotine, selegiline, rasagiline, entacapone, tolcapone, benztropine, trihexyphenidyl, or amantadine.

In the treatment of Alzheimer's disease, a compound described herein may be administered in combination with donepezil, galantamine, memantine, rivastigmine, anti-ABeta (amyloid beta) therapies including aducanumab, crenezumab, solanezumab, and gantenerumab, small molecule inhibitors of BACE1 including verubecestat, AZD3293 (LY3314814), elenbecestat (E2609), LY2886721, PF-05297909, JNJ-54861911, TAK-070, VTP-37948, HPP854, CTS-21166, or anti-tau therapies such as LMTM (Leuco-methylthioninium-bis(hydromethanesulfonate®).

In the treatment of rheumatoid arthritis, a compound described herein may be administered in combination with ibuprofen, naproxen, prednisone, methotrexate, leflunomide, hydroxychloroquine, sulfasalazine, abatacept, adalimumab, anakinra, certolizumab, etanercept, golimumab, infliximab, rituximab, tocilizumab or tofacitinib.

In the treatment of CVA, a compound described herein may be administered to in combination with a thrombolytic agent (such as tissue plasminogen activator), an anticoagulant (such as heparin, coumadin, clopidrogel, and a platelet aggregation inhibitor (such as dipyridamole, ticlopidine HCL, eptifibatide, and/or aspirin).

In the treatment of SIRS, a compound described herein may be administered in combination with a broad-spectrum antibiotic (such as vacomycin) or other anti-MRSA therapy (cefeprime, piperacillin/tazobactam, carbapenem (imipenem, meropenem, doripenem), quinolones (ciprofloxacin, levofloxacin, ofloxacin, moxifloxacin, etc.), and low dose steroids such as hydrocortisones.

In the treatment of inflammatory bowel disease (particularly, Crohn's disease and/or ulcerative colitis), a compound of any formula described herein, may be administered in combination with vedolizumab, alicaforsen, or remestemcel-L. Specifically, in the treatment of inflammatory bowel disease (particularly, Crohn's disease and/or ulcerative colitis), a compound described herein may be administered in combination with alicaforsen, or remestemcel-L.

In the treatment of of non-communicable inflammatory skin diseases (ncISD) such as psoriasis or atopic dermatitis, a compound described herein may be administered in combination withixekizumab, tildrakizumab (MK-3222), or secukinumab (AIN457).

Specifically, in the treatment of of non-communicable inflammatory skin diseases (ncISD) such as psoriasis or atopic dermatitis, a compound described herein may be administered in combination with ixekizumab, or tildrakizumab (MK-3222). In the treatment of periodonitis, a compound of any formula described herein may be administered in combination with an antimicrobial agent, (such as chlorhexidine or an antibiotic (such as doxycycline or minocycline.

In the treatment of asthma, a compound of any formula described herein may be administered in combination with an inhaled corticosteroid ((ICS) such as fluticasone proprionate, beclomethasone dipropionate, budesonide (Pulmicort), triamcinolone acetonide, flunisolide, mometasone fuorate, or Ciclesonide, a long acting beta agonist ((LABA) such as formoterol fumarate, salmeterol xinafoate), a combination of an ICS and LABA (such as fluticasone furoate and vilanterol, formoterol/budesonide inhalation, beclomethasone dipropionate/formoterol, and fluticasone propionate/salmeterol, a short acting beta agonist ((SABA) such as albuterol sulfate, levalbuterol tartrate, ipratropium bromide/albuterol, ipratropium bromide, a leukotriene modifier (such as montelukast sodium, zafirlukast, or zileuton, and anti-IgE (such as omalizumab), a methylxanthine bronchodilator (such as theophylline, a mast cell inhibitor (such as cromulyn sodium and nedocromil sodium, a long-acting muscarinic antagonist ((LAMA) such as mometasone furoate/formoterol fumarate dihydrate).

Other agents that may be suitable for use in combination therapy in the treatment of asthma include a protein tyrosine kinase inhibitor (masitinib), CRTH2/D-prostanoid receptorantagonist (AMG 853), indacaterol, an epinephrine inhalation aerosol (E004), fluticasone furoate/fluticasone proprionate, vilanterol inhalation/fluticasone furoate powder, fluticasone propionate/eformoterol fumarate dihydrate, reslizumab, salbutamol dry-powder inhalation, tiotropium bromide, formoterol/budesonide, fluticasone furoate, Vectura's VR506, lebrikizumab (RG3637), a combination phosphodiesterase (PDE)-3 and (PDE)-4 inhibitor (RPL554).

In the treatment of COPD, a compound of any formula described herein, may be administered in combination with a LABA (such as salmeterol xinafoate, umeclidinium/vilanterol, umeclidinium, arformoterol tartrate, formoterol fumarate inhalation powder, indacterol maleate, or fluticasone propionate/eformoterol fumarate dehydrate, a long-acting inhaled anticholinergic (or muscarinic antagonist, such as tiotropium bromide, and aclidinium bromide, a phosphodiesterase (PDE-r) inhibitor (such as roflumilast, Daliresp), a combination ICS/LABA (such as fluticasone furoate and vilanterol, fluticasone propionate/salmeterol, budesonide/formoterol, mometasone/formoterol, ipratropium bromide/albuterol sulfate, albuterol/ipratropium, a SABA (such as ipratropium bromide, and albuterol sulfate, and an ICS (such as budesonide and fluticasone propionate, beclomethasone dipropionate.

Other agents that may be suitable for use in combination therapy in the treatment of COPD include SCH527123 (a CXCR2 antagonist), glycoprronium bromide (NVA237), glycopyrronium bromide and indacaterol maleate (QVA149), glycopyrrolate and formoterol fumarate (PT003), indacaterol maleate (QVA149), olodaterol, tiotropium/olodaterol, and aclidinium/formoterol inhalation.

In the treatment of a mycobacterium infection (tuberculosis), a compound of any formula described herein may be administered in combination with an antimycobacterial agent (such as isoniazid (INH), ehambutol, rifampin, and pyrazinamide a bactericidal antibiotic (such as rifabutin or rifapentine, an aminoglycoside (capreomycin), a fluorquinolone (levofloxacin, moxifloxicin, ofloxacin), thioamide (ehionamide), cyclosporine, para-aminosalicyclic acid, cycloserine, kanamycin, streptomycin, viomycin, capreomycin, bedaquiline fumarate, oxazolidinone, or delamanid (OPC-67683).

Specifically, in the treatment of a mycobacterium infection (tuberculosis), a compound described herein may be administered in combination with an antimycobacterial agent (such as isoniazid (INH), ehambutol, rifampin, and pyrazinamide, a bactericidal antibiotic (such as rifabutin or rifapentine, an aminoglycoside (Capreomycin), a fluorquinolone (levofloxacin, moxifloxicin, ofloxacin), thioamide (ehionamide), cycloserine, kanamycin, streptomycin, viomycin, capreomycin, bedaquiline fumarate, oxazolidinone, or delamanid (OPC-67683).

In the treatment of systemic scleroderma, a compound of any formula described herein may be administered in combination with an oral corticosteroid (such as prednisolone, an immunosuppressive agent (such as methotrexate, cyclosporine, anti-thymocyte globulin, mycophenolate mofetil, cyclophosphamide, FK506 (tacrolimus), thalidomide, chlorambucil, azathioprine, a calcium channel blocker (such as nifedipine or nicardipine, a topical emollient (nitroglycerin ointment), an ACE inhibitor (such as lisinopril), a serotonin reuptake inhibitor (such as fluoxetine, an endothelin-I receptor inhibitor (such as bosentan or epoprostenol an anti-fibrotic agent (such as colchicines, para-aminobenzoic acid (PABA), dimethyl sulfoxide (DMSO), and D-penicillamine, interferon alpha and interferon gamma (INF-g), a proton-pump Inhibitor (such as omeprazole, metoclopramide, lansoprazole, esomeprazole, pantoprazole, rabeprazole or imatinib, ARG201 (arGentis Pharmaceutical), belimumab, tocilizumab.

Specifically, in the treatment of systemic scleroderma, a compound of any formula described herein may be administered in combination with an oral corticosteroid (such as prednisolone), anti-thymocyte globulin, FK506 (tacrolimus), thalidomide, chlorambucil, a calcium channel blocker (such as nifedipine or nicardipine, a topical emollient (nitroglycerin ointment), an ACE inhibitor (such as lisinopril), diltaizem, a serotonin reuptake inhibitor (such as fluoxetine), an endothelin-I receptor inhibitor (such as bosentan or epoprostenol), an anti-fibrotic agent (such as colchicines (Colcrys), para-aminobenzoic acid (PABA), dimethyl sulfoxide (DMSO), and D-penicillamine, interferon alpha and interferon gamma (INF-g), a proton-pump Inhibitor (such as omeprazole, metoclopramide, lansoprazole, esomeprazole, pantoprazole, rabeprazole or imatinib, ARG201 (arGentis Pharmaceutical), or tocilizumab.

In the treatment of cystic fibrosis, a compound as described herein may be administered in combination with a cystic fibrosis transmembrane conductance regulator (CFTR) potentiator (ivacftor, a mucolytic agent (such as dornase alpha), pancreatic enzymes (such as Pancrelipase), a bronchodilator (such as albuterol), an antibiotic (including inhaled, oral or parenteral, such as tobramycin solution for inhalation, aztreonam inhalation, colistimethate sodium, cephalosporins (cefadroxil monohydrate, cefazolin, cephalexin, cefazolin, fluoroquinolones (moxifloxacin, levofloxacin, gemifloxacin, etc), azithromycin, gentamicin, piperacillin/tazobacam, cephalexin, ceftazidime, ciprofloxin, trimethoprim/sulfamethoxazole, or ivacftor/lumacaftor (VX-809), ataluren, or with tiopropium bromide as add on to standard therapy.

In the treatment of retinitis pigmentosa, a compound as described herein may be administered in combination with a ciliary neurotrophic growth factor (NT-501-CNTF) or gene transfer agent, UshStat.

In the treatment of macular degeneration, a compound of any formula described herein, may be administered in combination with opthalmalic intravitreal injections (afibercept) or with an anti-vascular endothelial growth factor (VEGF) inhibitor (such as ranibizumab or pegaptanib sodium, a ciliary neurotrophic growth factor agent (NT501), iSONEP, or bevacizumab.

In the treatment of influenza, a compound as described herein may be administered in combination with a trivalent (IIV3) inactivated influenza vaccine (such as Afluria, Fluarix, Flucelvax, FluLaval, Fluvirin, Fluzone), a quadrivalent (IIV4) inactivated influenza vaccine (such as Fluarix Quadrivalent, Flulaval Quadrivalent, Fluzone Quadrivalent), a trivalent recombinant influenza vaccine (such as FluBlok), a quadrivalent live attenuated influenza vaccine (such as FluMist Quadrivalent), an antiviral agent (such as oseltamivir, zanamivir, rimantadine, or amantadine), or Fluad, Fludase, FluNhance, Preflucel, or VaxiGrip.

In the treatment of a staphylococcus infection, a compound of any formula described herein may be administered in combination with an antibiotic (such as a-Lactam cephalosporin, nafcillin, a sulfonamide (sulfamethoxazole and trimethoprim, sulfasalazine, acetyl sulfisoxazole), or vancomycin.

In the treatment of transplant rejection, a compound of any formula described herein may be administered in combination with a high-dose corticosteroid (such as prednisone, methylprednisolone, a calcineurin inhibitor (such as cyclosporine), tacrolimus, an mTor inhibitor (such as sirolimus or everolimus, an anti-proliferative agent (such as azathioprine, mycophenolate mofetil, or mycophenolate sodium, a monoclonal antibody (such as muromonab-CD3, an interleukine-2 receptor antagonist, daclizumab, or rituximab, a polyclonal anti-T-cell antibody (such as anti-thymocyte gamma globulin-equine, or antithymocyte globulin-rabbit, an anti-CD40 antagonist (ASKP-1240), a JAK inhibitor (ASP015K), or an anti-TCR murine mAb (TOL101).

Specifically, in the treatment of transplant rejection, a compound of any formula described herein may be administered in combination with a monoclonal antibody (such as muromonab-CD3, a polyclonal anti-T-cell antibody (such as anti-thymocyte gamma globulin-equine, or antithymocyte globulin-rabbit, an anti-CD40 antagonist (ASKP-1240), a JAK inhibitor (ASP015K), or an anti-TCR murine mAb (TOL101).

In the treatment of atopic dermatitis, a compound of any formula described herein may be administered in combination with a topical immunomodulator or calcineurin inhibitor (such as pimecrolimus or tacrolimus ointment, a topical corticosteroid (such as hydrocortizone, betamethasone, flurandrenolide, fluticasone, triamcinolone, fluocinonide, and clobetasol, an oral corticosteroid (such as hydrocortisone, methylprednisolone, or prednisolone, an immunosuppressant (such as cyclosporine or interferon gamma (Alferon N, Infergen, Intron A, Roferon-A®), an antihistamine (for itching such as Atarax, Vistaril, Benadryl), an antibiotic (such as penicillin derivatives flucloxacillin or dicloxacillin, erythromycin, a nonsteroidal immunosuppressive agent (such as azathioprine), methotrexate, cyclosporine, or mycophenolate mofetil.

Specifically, in the treatment of atopic dermatitis, a compound of any formula described herein may be administered in combination with a topical immunomodulator or calcineurin inhibitor (such as pimecrolimus) or tacrolimus ointmen, a topical corticosteroid (such as hydrocortizone, betamethasone, flurandrenolide, fluticasone, triamcinolone, fluocinonide, and clobetasol, an oral corticosteroid (such as hydrocortisone, methylprednisolone, or prednisolone, an interferon gamma (Alferon N, Infergen, Intron A, Roferon-A), an antihistamine (for itching such as Atarax, Vistaril, Benadryl), or an antibiotic (such as penicillin derivatives flucloxacillin or dicloxacillin, erythromycin).

In the treatment of burns, e.g. a burn injury or burn shock, a compound of any formula described herein may be administered alone, or in combination with an antimicrobial agent, typically a topical antibiotic (mafenide acetate cream, silver sulfadiazine cream) and/or a analgesic (opioid analgesics, e.g., morphine, oxycodone). Other therapeutic agents that may be useful for the treatment of burns include retinoids and pirfenidone.

In certain embodiments, the at least one other therapeutically active agent is selected from a thrombolytic agent, a tissue plasminogen activator, an anticoagulant, and a platelet aggregation inhibitor.

In certain embodiments, the at least one other therapeutically active agent is selected from heparin, coumadin, clopidrogel, dipyridamole, ticlopidine HCL, eptifibatide, and aspirin. In certain embodiments, the kinase-mediated disease or disorder treated with these agents is a cerebrovascular accident.

In certain embodiments, the at least one other therapeutically active agent is selected from broad-spectrum antibiotic, anti-MRSA therapy and a low dose steroid.

In certain embodiments, the at least one other therapeutically active agent is selected from vacomycin, cefeprime, a combination of piperacillin and tazobactam, imipenem, meropenem, doripenem, ciprofloxacin, levofloxacin, ofloxacin, moxifloxacin, and hydrocortisone. In certain embodiments, the disease or disorder treated with these agents is systemic inflammatory response syndrome.

In certain embodiments, the at least one other therapeutically active agent is alicaforsen or remestemcel-L. In certain embodiments, the disease or disorder treated with these agents is Crohn's disease or ulcerative colitis.

In certain embodiments, the at least one other therapeutically active agent is ixekizumab, or tildrakizumab. In certain embodiments, the kinase-mediated disease or disorder treated with these agents is of non-communicable inflammatory skin diseases (ncISD) such as psoriasis or atopic dermatitis.

In certain embodiments, the at least one other therapeutically active agent is an antimicrobial agent or an antibiotic. In certain embodiments, the at least one other therapeutically active agent is selected from chlorhexidine, doxycycline and minocycline. In certain embodiments, the disease or disorder treated with these agents is periodonitis.

In certain embodiments, the at least one other therapeutically active agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. In certain embodiments, the at least one other therapeutically active agent is selected from fluticasone proprionate, beclomethasone dipropionate, budesonide, trimcinolone acetonide, flunisolide, mometasone fuorate, or ciclesonide, formoterol fumarate, salmeterol xinafoate, a combination of fluticasone furoate and vilanterol, a combination of formoterol and budesonide inhalation, a combination of beclomethasone dipropionate and formoterol, a combination of fluticasone propionate and salmeterol, albuterol sulfate, levalbuterol tartrate, a combination of ipratropium bromide and albuterol, ipratropium bromide, montelukast sodium, zafirlukast, zileuton, omalizumab theophylline, cromulyn sodium, nedocromil sodium, and a combination of mometasone furoate and formoterol fumarate dihydrate.

In certain embodiments, the at least one other therapeutically active agent is selected from protein tyrosine kinase inhibitor, a CRTH2/D-prostanoid receptor antagonist, an epinephrine inhalation aerosol, and a combination of a phosphodiesterase-3 inhibitor and a phosphodiesterase-4 inhibitor. In certain embodiments, the at least one other therapeutically active agent is selected from masitinib, AMG 853, indacaterol, E004, a combination of fluticasone furoate and fluticasone proprionate, a combination of vinanterol fluticasone furoate, a combination of fluticasone propionate and eformoterol fumarate dihydrate, reslizumab, salbutamol, tiotropium bromide, a combination of formoterol and budesonide, fluticasone furoate, VR506, lebrikizumab, and RPL554. In certain embodiments, the kinase-mediated disease or disorder treated with these agents is asthma.

In certain embodiments, the at least one other therapeutically active agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. In certain embodiments, the at least one other therapeutically active agent is selected from salmeterol xinafoate, a combination of umeclidinium and vilanterol, umeclidinium, arformoterol tartrate, formoterol fumarate, indacterol maleate, a combination of fluticasone propionate and eformoterol fumarate dihydrate, tiotropium bromide, aclidinium bromide, roflumilast, a combination of fluticasone furoate and vilanterol, a combination of fluticasone propionate and salmeterol, a combination of budesonide and formoterol, a combination of mometasone and formoterol, a combination of ipratropium bromide and albuterol sulfate, a combination of albuterol and ipratropium, ipratropium bromide, albuterol sulfate, budesonide, fluticasone propionate, and beclometasone dipropionate. In certain embodiments, the at least one other therapeutically active agent is selected from SCH527123, glycoprronium bromide, a combination of glycopyrronium bromide and indacaterol maleate, a combination of glycopyrrolate and formoterol fumarate, indacaterol maleate, olodaterol, tiotropium, olodaterol, and a combination of aclidinium and formoterol. In certain embodiments, the disease or disorder treated with these agents is COPD.

In certain embodiments, the at least one other therapeutically active agent is an antimycobacterial agent or a bactericidal antibiotic. In certain embodiments, the at least one other therapeutically active agent is selected from isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, and delamanid. In certain embodiments, the kinase-mediated disease or disorder treated with these agents is a mycobacterium infection.

In certain embodiments, the at least one other therapeutically active agent is selected from an oral corticosteroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor or imatinib, ARG201, and tocilizumab. In certain embodiments, the at least one active agent is selected from prednisolone, anti-thymocyte globulin, FK506 (tacrolimus), thalidomide, chlorambucil, nifedipine, nicardipine, nitroglycerin ointment, lisinopril, diltaizem, fluoxetine, bosentan, epoprostenol, colchicines, para-aminobenzoic acid, dimethyl sulfoxide, D-penicillamine, interferon alpha, interferon gamma (INF-g), omeprazole, metoclopramide, lansoprazole, esomeprazole, pantoprazole, rabeprazole, imatinib, ARG201, and tocilizumab. In certain embodiments, the disease or disorder treated with these agents is systemic scleroderma.

In certain embodiments, the at least one other therapeutically active agent is selected from a cystic fibrosis transmembrane conductance regulator potentiator, amucolytic agent, pancreatic enzymes, a bronchodilator, an antibiotic, or ivacftor/lumacaftor, ataluren, and tiopropium bromide. In certain embodiments, the at least one other therapeutically active agent is selected from ivacaftor, dornase alpha, pancrelipase, albuterol, tobramycin, aztreonam, colistimethate sodium, cefadroxil monohydrate, cefazolin, cephalexin, cefazolin, moxifloxacin, levofloxacin, gemifloxacin, azithromycin, gentamicin, piperacillin/tazobacam, ceftazidime, ciprofloxin, trimethoprim/sulfamethoxazole, chloramphenicol, or ivacaftor/lumacaftor, ataluren, and tiopropium bromide. In certain embodiments, the disease or disorder treated with these agents is cystic fibrosis.

In certain embodiments, the at least one other therapeutically active agent is a ciliary neurotrophic growth factor or a gene transfer agent. In certain embodiments, the at least one other therapeutically active agent is NT-501-CNTF or a gene transfer agent encoding myosin VIIA (MY07A).

In certain embodiments, the disease or disorder treated with these agents is retinitis pigmentosa.

In certain embodiments, the at least one other therapeutically active agent is selected from opthalmalic intravitreal injections, an anti-vascular endothelial growth factor inhibitor, and a ciliary neurotrophic growth factor agent. In certain embodiments, the at least one other therapeutically active agent is selected from afibercept, ranibizumab, pegaptanib sodium, NT501, humanized sphingomab, and bevacizumab. In certain embodiments, the disease or disorder treated with these agents is macular degeneration.

In certain embodiments, the at least one other therapeutically active agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. In certain embodiments, the at least one other therapeutically active agent is selected from oseltamivir, zanamivir, rimantadine, or amantadine. In certain embodiments, the kinase-mediated disease or disorder treated with these agents is influenza.

In certain embodiments, the at least one other therapeutically active agent is selected from a beta-Lactam, nafcillin, sulfamethoxazolem, trimethoprim, sulfasalazine, acetyl sulfisoxazole, and vancomycin. In certain embodiments, disease or disorder treated with these agents is a staphylococcus infection.

In certain embodiments, the at least one other therapeutically active agent is selected from a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb.

In certain embodiments, the at least one other therapeutically active agent is selected from muromonab-CD3, ASKP-1240, ASP015K, and TOL101. In certain embodiments, the disease or disorder treated with these agents is transplant rejection.

In certain embodiments, the at least one other therapeutically active agent is selected from a topical immunomodulator or calcineurin inhibitor, a topical corticosteroid, an oral corticosteroid, an interferon gamma, an antihistamine, or an antibiotic. In certain embodiments, the at least one other therapeutically active agent is selected from pimecrolimus, tacrolimus, hydrocortizone, betamethasone, flurandrenolide, fluticasone, triamcinolone, fluocinonide, clobetasol, hydrocortisone, methylprednisolone, prednisolone, an interferon alpha protein, a recombinant synthetic type I interferon, interferon alpha-2a, interferon alpha-2b, hydroxyzine, diphenhydramine, flucloxacillin, dicloxacillin, and erythromycin. In certain embodiments, the disease or disorder treated with these agents is atopic dermatitis.

Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration", "administered systemically", "peripheral administration" and "administered peripherally" as used herein mean the administration of a compound, drug or other material other than directly into the central nervous system, such that it enters the patient's system and, thus, is subject to metabolism and other like processes, for example, subcutaneous administration. These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above.

Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight. If desired, the effective daily dose of the active compound may be administered as two, three, four, five, six or more sub-doses administered separately at appropriate intervals throughout the day, optionally, in unit dosage forms. In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar. The compounds of the disclosure can be tested in standard animal models of stroke and standard protocols such as described by Hara, H., et al. *Proc. Natl. Acad. Sci. USA,* 1997.94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day. In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

EXAMPLES

Abbreviations

ACN acetonitrile
aq. aqueous
DEA diethylamine
DIPEA N,N-diisopropylethylamine
DIAD diisopropyl azodicarboxylate
DMF N,N-dimethylformamide
DMSO dimethyl sulfoxide
EA ethyl acetate
eq. equivalent(s)
ESI electro spray ionization
EtOH ethanol
FA formic acid
h hour(s)
HATU 1-[bis(dimethylamino)methylene]-1H-1,2,3-triazolo[4,5-b]pyridinium 3-oxide hexafluorophosphate
HBTU (2-(1H-benzotriazol-1-yl)-1,1,3,3-tetramethyluronium-hexafluorophosphat)
HOBt 1-hydroxybenzotriazole
(RP) HPLC (reversed-phase) high pressure liquid chromatography
IBX 2-iodoxybezoic acid
IPA isopropylamine
(RP) LC (reversed-phase) liquid chromatography
LC/MS liquid chromatography/mass spectrometry
M molar
m/z mass-to-charge ratio
MeOH methanol
min minute(s)
MsCl methanesulfonyl chloride (mesyl chloride)
MTBE methyl-tertiary butylether
N normal
NMR nuclear magnetic resonance
PE petroleum ether
prep. preparative
PyBOP benzotriazol-1-yl-oxytripyrrolidinophosphonium hexafluorophosphate
RT room temperature
sat. saturated
SFC supercritical fluid chromatography
TEA triethylamine
TFA trifluoroacetic acid
TFAA trifluoroacetic anhydride
THF tetrahydrofurane
TLC thin layer chromatography
tR retention time
UV ultraviolet Silica Gel Chromatography Silica gel chromatography was performed using Combi-Flash® Rf (Teledyne ISCO), Biotage Isolera One automated flash purification system or two Büchi systems (C-660, C-605, C-620, C-635 combination and C-660, C-605, C-615, C-630 combination) with pre-packed cartridges.

Preparative RP-HPLC

For preparative reversed phase HPLC an Agilent 1200 preparative HPLC machine, Gilson equipment (GX-271 liquid handler, 331/332-pump, UV/VIS-155) or a Waters Autopurification LC Prep System was used.

Preparative RP-LC

Reversed phase liquid chromatography was performed with a Biotage equipment using C18 columns and a water (0.1% FA)/ACN gradient.

NMR

400 MHz: $^1$H NMR spectra were recorded on a Bruker AVANCE II 400 spectrometer operating at a proton frequency of 400.23 MHz. The instrument was equipped with a 5 mm BBI room temperature probe head. Alternatively, a Bruker AVANCE III HD 400 MHz, or a Bruker AVANCE NEO 400 MHz was used.

600 MHz: $^1$H NMR spectra were recorded on a Bruker AVANCE III 600 spectrometer operating at a proton frequency of 600.05 MHz. The instrument was equipped with a 5 mm BBI room temperature probe head.

Analytical LC/MS Equipment for Method a

Retention time and mass detection were done on a Waters Acquity UHPLC system coupled with a Waters SQD mass detector. The injection volume was 1.0 μl.

Molecular weights are given in gram per mol [g/mol], detected masses in mass per charge [m/z].

Analytical LC/MS Equipment for Method B, C, D

For retention time and mass detection a LC/MS-system from Agilent (LC 1200 Series/MS 6120 quadrupole LC/MS, LC 1260 infinity/MS 6120 quadrupole LC/MS or LC 1260 Infinity II/MSD Infinity Lab) was used. Molecular weights are given in gram per mol [g/mol], detected masses in mass per charge [m/z].

LC/MS-Method a

Gradient: 98% $H_2O$ (0.05% FA)/2% ACN (0.035% FA) for 0.2 min.; then from 98% $H_2O$ (0.05% FA) to 98% ACN (0.035% FA) in 3.6 min, then 98% ACN (0.035% FA) for 0.5 min, flow rate: 1.0 ml/min, column: 2.1×50 mm Waters ACQUITY UPLC BEH C18, 1.7 μm, 55° C.

UV data: retention time ad λ=220 nm given in min

MS data: $ES^+$ ionisation, m/z given as $[M+H]^+$ unless otherwise noted

LC/MS-Method B

Gradient: from 99% $H_2O$ (0.05% TFA)/1% ACN to 7% ACN in 0.3 min; then from 7% ACN to 95% ACN in 1.3 min; flow rate: 1.1 ml/min, column: 2.0×10 mm LunaC18, 3 μm, 30° C., injection volume 0.2 μl UV data: retention time ad λ 220 nm given in min MS data: $ES^+$ ionisation, m/z given as $[M+H]^+$ unless otherwise noted LC/MS-method C Gradient: From 93% $H_2O$ (0.05% TFA)/7% ACN to 95% ACN in 1.45 min; then 5% ACN for 0.05 min; flow rate: 1.1 ml/min, column: 2.0×10 mm LunaC18, 3 μm, 30° C.; injection volume 0.2 μl UV data: retention time ad λ 220 nm given in min MS data: $ES^+$ ionisation, m/z given as $[M+H]^+$ unless otherwise noted LC/MS-method D Gradient: From 96% $H_2O$ (0.05% TFA)/4% ACN to 5% $H_2O$/95% ACN in 2.0 min; then 5% $H_2O$/95% ACN for 0.4 min; flow rate: 1.0 ml/min, column: YMC J'Sphere ODS H80, 20×2.1 mm, 4 μm, 30° C.; injection volume 0.4 μl UV data: retention time ad λ 220 nm given in min MS data: $ES^+$ ionisation, m/z given as [M+H]+ unless otherwise noted LC/MS-method E:

Gradient: From 95% $H_2O$ (0.0375% TFA)/5% ACN (0.01875% TFA) to 5% $H_2O$ (0.0375% TFA)/95% ACN (0.01875% TFA) in 0.8 min; flow rate: 1.5 ml/min, column: Kinetex EVO C18 2.1×30 mm, 5 μm, 50° C.

UV data: retention time ad λ 220 nm given in min

MS data: $ES^+$ ionisation, m/z given as [M+H]+ unless otherwise noted

LC/MS-Method F:

Gradient: From 100% $H_2O$ (0.0375% TFA)/0% ACN (0.01875% TFA) to 40% $H_2O$ (0.0375% TFA)/60% ACN (0.01875% TFA) in 0.8 min; then 40% $H_2O$ (0.0375% TFA)/60% ACN (0.01875% TFA) for 0.4 min; flow rate: 1.5 ml/min, column: Kinetex EVO C18 2.1×30 mm, 5 μm, 50° C.

UV data: retention time ad λ 220 nm given in min

MS data: $ES^+$ ionisation, m/z given as [M+H]+ unless otherwise noted

Analytical Chiral HPLC

SFC: SHIMADZU LC-30AD sf system

LC: Agilent 1100 series system

Salts

In compounds described as HCl—, TFA- or as another salt the exact amount of the respective acid is usually not determined. Therefore, the amount of the acid can range from as low as 0.01 eq. up to 5.0 eq. depending on the chemical structure (e.g. number of basic centres).

Chiral Purity

Compounds are drawn and named as a single enantiomer, if the enantiomeric ratio exceeded 90:10. For enantiomeric ratios below 90:10 the racemic form is used.

Synthetic Methods

Intermediates

I-01: 3-Pyrimidin-5-ylisoxazolidine hydrochloride/TFA Salt

I-01a

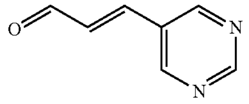

(E)-3-(Pyrimidin-5-yl)acrylaldehyde

A mixture of 5-bromopyrimidine (30 g), prop-2-enal (31.74 g), $Pd(OAc)_2$ (2.12 g), benzyl(triethyl)ammonium chloride (42.98 g), TEA (57.28 g) in DMF (300 ml) was stirred at 80° C. under $N_2$ for 12 h. The mixture was concentrated, the residue was diluted with water (800 ml), extracted with EA (500 ml×4), washed with brine (1.5 l), dried with $Na_2SO_4$, filtered and concentrated. The residue was purified by silica gel chromatography (PE:EA=10:1 to 4:1) and trituration (PE/EA=3:1, 50 mL) to give 4.2 g of the title compound.

$^1H$ NMR (400 MHz, $CDCl_3$): δ ppm 9.78 (1H), 9.26 (1H), 8.95 (2H), 7.45 (1H), 6.86 (1H)

I-01b

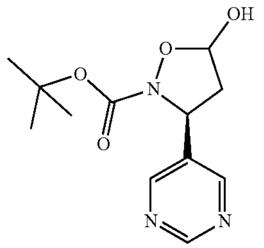

Tert-butyl (3S)-5-hydroxy-3-pyrimidin-5-yl-isoxazolidine-2-carboxylate

To a solution of [diphenyl-[(2S)-pyrrolidin-2-yl]methoxy]-trimethyl-silane (2.28 g) in $CHCl_3$ (50 ml) was added (E)-3-(pyrimidin-5-yl)acrylaldehyde (4.7 g) and tert-butyl N-hydroxycarbamate (5.60 g) at 0° C. The mixture was warmed to 20° C. smoothly and stirred for 12 h. The reaction mixture was concentrated and the residue was purified by prep. RP-LC to yield 6.4 g of the title compound.

I-01c

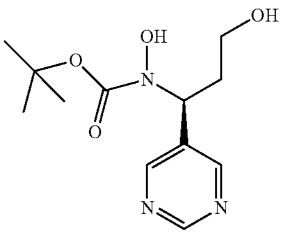

Tert-butyl N-hydroxy-N-[(1S)-3-hydroxy-1-pyrimidin-5-yl-propyl]carbamate

To a solution of tert-butyl (3S)-5-hydroxy-3-pyrimidin-5-yl-isoxazolidine-2-carboxylate (6.1 g) in MeOH (40 ml) was added $NaBH_4$ (1.04 g) at 0° C. The mixture was stirred at 0° C. for 2 h under $N_2$. The mixture was quenched with saturated $NH_4Cl$ solution (200 ml), extracted with EA (200 ml×3), dried with $Na_2SO_4$, filtered and concentrated to yield 5.4 g of the title compound.

$^1H$ NMR (400 MHz, $CDCl_3$): δ ppm 9.14 (1H), 8.81 (2H), 7.18-7.02 (1H), 5.32 (1H), 3.94-3.72 (2H), 2.55-2.39 (1H), 2.31-2.20 (1H), 2.12-2.05 (1H), 1.49 (9H)

I-01d

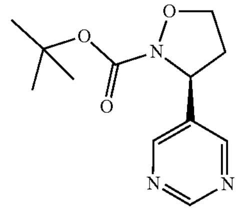

Tert-butyl (3S)-3-pyrimidin-5-ylisoxazolidine-2-carboxylate

To a solution of tert-butyl N-hydroxy-N-[(1S)-3-hydroxy-1-pyrimidin-5-yl-propyl]carbamate (4.9 g) in THF (40 ml) was added tributylphosphane (8.84 g) and DIAD (7.36 g) at 0° C. The mixture was warmed to 20° C. smoothly, stirred for 12 h under $N_2$. The mixture was concentrated and the residue was purified by silica gel chromatography (PE: EA=1:5 to 0:1) followed by prep. RP-LC (flow: 100 ml/min; gradient: from 95% $H_2O$ (0.1% FA)/5% ACN to 71% $H_2O$ (0.1% FA)/29% ACN in 12 min; 71% $H_2O$ (0.1% FA)/29% ACN for 4 min; 71% $H_2O$ (0.1% FA)/29% ACN to 60% $H_2O$ (0.1% FA)/40% ACN in 12 min; column: Agela C18, 20 μm, 100 Å, I.D. 60.6 mm×187 mm) to yield 1.4 g of the title compound.

$^1H$ NMR (400 MHz, $CDCl_3$): δ ppm 9.16 (1H), 8.76 (2H), 5.27 (1H), 4.25 (1H), 3.93 (1H), 2.87 (1H), 2.32 (1H), 1.50 (9H)

Chiral HPLC: tR 1.98 min, 100%; 100% ee (chiralpak AD-3, 50×4.6 mm, 3 μm; phase A: $CO_2$, B: MeOH (0.05% DEA); gradient: MeOH (0.05% DEA) in $CO_2$ from 5 to 40%; flow 3 ml/min; T 35° C., p 100 bar)

I-01

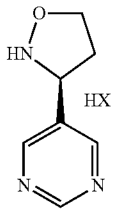

(3S)-3-Pyrimidin-5-ylisoxazolidine HCl/TFA salt

TFA Salt:

Tert-butyl 3-pyrimidin-5-ylisoxazolidine-2-carboxylate (25 mg) was dissolved in a 10 ml round bottomed flask at RT with stirring in dry DCM (2.5 ml). TFA (0.3 ml) was added and the mixture was stirred for 1 h. Then the DCM was removed in vacuo, the residue dissolved in ACN/water and lyophilised overnight. 23 mg of the title compound was obtained as its TFA salt.

LC/MS: m/z=152.2 $[M+H]^+$; tR: 0.37 min (LC/MS-method A)

HCl salt:

Tert-butyl 3-pyrimidin-5-ylisoxazolidine-2-carboxylate (17 mg) was dissolved in dioxane (0.5 ml) and 4 M HCl in dioxane (70 μl) was added at RT with stirring. After 1 h further HCl in dioxane (800 μl) was added and stirring was continued for 3 h. Then the solvent was removed in vacuo, the residue dissolved in ACN/water and lyophilised overnight. 10 mg of the title compound was obtained as its HCl salt.

I-02-1

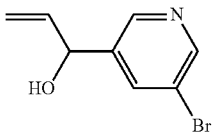

5-[(3S)-Isoxazolidin-3-yl]pyridine-3-carbonitrile
I-02a: 1-(5-Bromo-3-pyridyl)prop-2-en-1-ol Two Reactions Carried Out in Parallel:

A mixture of 5-bromopyridine-3-carbaldehyde (100 g) in THF (500 ml) was degassed and purged with $N_2$ for 3 times. Vinylmagnesiumbromide (1 M, 645 ml) was added dropwise at such a rate to keep the inner temperature below −70° C. The mixture was stirred at −70° C. for 1 h, and then the mixture was stirred at 25° C. for 1 h under $N_2$ atmosphere. Then the two solutions were combined, poured into sat. $NH_4Cl$ (3.00 l) and extracted with MTBE (2.00 l, 1.00 l). The combined organic phase was washed with brine (1.00 l), dried over $Na_2SO_4$, filtered and the filtrate was concentrated under reduced pressure to give the title compound (240 g, crude) as a brown oil.

$^1H$ NMR (400 MHz, $CDCl_3$): δ 8.54 (1H), 8.40 (1H), 7.87 (1H), 5.95-5.97 (1H), 5.36 (1H), 5.25-5.38 (1H), 5.18-5.25 (1H).

I-02b

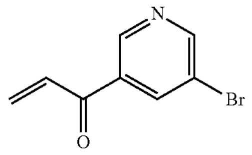

1-(5-Bromo-3-pyridyl)prop-2-en-1-one

Two reactions carried out in parallel.

To a solution of 1-(5-bromo-3-pyridyl)prop-2-en-1-ol (120 g) in ACN (1.20 l) was added IBX (235 g) in portions at 20° C. Then the reaction mixture was heated to 50° C. and stirred for 12 h. The two reaction suspensions were combined and cooled to 25° C., filtered and the filtrate was concentrated under reduced pressure. The title compound (240 g, crude) was obtained as yellow oil and used for the next step without further purification.

$^1H$ NMR (400 MHz, $CDCl_3$): δ 9.02 (1H), 8.86 (1H), 8.36 (1H), 7.07 (1H), 6.49 (1H), 6.06 (1H).

I-02c

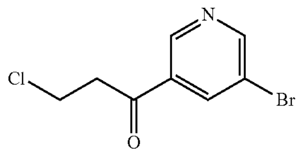

1-(5-Bromo-3-pyridyl)-3-chloro-propan-1-one

To a solution of 1-(5-bromo-3-pyridyl)prop-2-en-1-one (220 g) in DCM (200 ml) was added HCl/dioxane (4 M, 1.04 l) at 0° C. The solution was warmed to 25° C. and stirred for 48 h. The solution was concentrated under reduced pressure to give a brown solid. The solid was diluted with sat. $NaHCO_3$ solution (2.00 l) and extracted with DCM (1.50 l×2). The combined organic layers were washed with brine (1.50 l), dried over $Na_2SO_4$, filtered through a silica gel pad and concentrated under reduced pressure to give a residue. The crude title compound (100 g, crude) was used in the next step without further purification.

I-02d

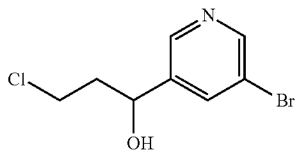

1-(5-Bromo-3-pyridyl)-3-chloro-propan-1-ol

To a solution of 1-(5-bromo-3-pyridyl)-3-chloro-propan-1-one (100 g) in MeOH (500 ml) and THF (250 ml)—degassed and purged with $N_2$ for 3 times—$NaBH_4$ (4.57 g) was added at 0° C. The suspension was stirred at 25° C. for 0.5 h under $N_2$ atmosphere. The reaction solution was combined and poured into sat $NH_4Cl$ (1.00 l) and extracted with EA (2.00 l, 1.00 l). The combined organic layers were washed with brine (1.00 l), dried over $Na_2SO_4$, filtered and concentrated under reduced pressure to give a residue. The residue was dissolved in DCM (600 ml), filtered through a silica gel pad and eluted with MTBE/DCM (v/v=1/1, 1.50 l), the filtrate was concentrated under reduced pressure. The crude title compound (90.0 g) was used in the next step without further purification.

I-02e

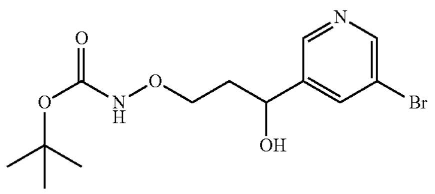

Tert-butyl N-[3-(5-bromo-3-pyridyl)-3-hydroxy-propoxy]carbamate

Two reactions carried out in parallel.

To a solution of tert-butyl N-hydroxycarbamate (47.0 g) in DMF (200 ml) was added NaH (18.0 g, 60%) in portions at 0~5° C. Lots of foam formed. The reaction mixture was stirred for 30 min at 0° C. A solution of 1-(5-bromo-3-pyridyl)-3-chloro-propan-1-ol (45.0 g) in DMF (300 ml) was added drop-wise into the reaction mixture at 0~5° C.

After addition the reaction mixture was warmed to 20° C. and stirred for 12 h. The two reaction solutions were combined and poured into cool sat $NH_4Cl$ (1.50 l) solution and extracted with ethyl acetate (2.00 l, 1.00 l). The combined organic layers were washed with brine (1.00 l), dried over $Na_2SO_4$ and filtered, the filtrate was concentrated in vacuo. The residue was purified by column chromatography ($SiO_2$, PE/EA=100/1 to 0/1). The title compound (50.0 g) was obtained as yellow solid.

$^1H$ NMR (400 MHz, $CDCl_3$): δ 8.56 (1H), 8.52 (1H), 7.97 (1H), 7.32 (1H), 5.09-5.11 (1H), 4.58 (1H), 4.06-4.14 (2H), 2.02-2.08 (1H), 1.88-1.91 (1H), 1.50 (9H).

I-02f

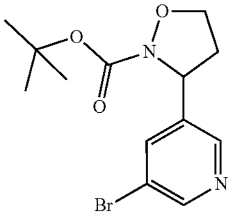

Tert-butyl 3-(5-bromo-3-pyridyl) isoxazolidine-2-carboxylate

Two reactions carried out in parallel.

A suspension of tert-butyl N-[3-(5-bromo-3-pyridyl)-3-hydroxy-propoxy]carbamate (25.0 g) and $Et_3N$ (21.0 g) in DCM (250 ml) was cooled to 0° C. MsCl (9.90 g) was added drop-wise into the reaction mixture which was stirred at 0~5° C. for 1 h. Another portion of $Et_3N$ (14.0 g) was added to the reaction mixture, the solution was warmed to 25° C. and stirred for 16 h. The reaction solution was poured into sat. $NaHCO_3$ solution (100 ml) with stirring. The organic layer was separated and the aqueous layer was extracted with DCM (300 ml, 200 ml). The combined organic layers were washed with brine (100 ml). The organic layer was separated, dried over $Na_2SO_4$, filtered and the filtrate was concentrated under reduced pressure. The two reactions were combined for purification. The residue was purified by column chromatography ($SiO_2$, PE/EA=50/1 to 0/1). The title compound (36.0 g) was obtained as white solid.

$^1H$ NMR (400 MHz, $CDCl_3$): δ 8.58 (1H), 8.50 (1H), 7.87 (1H), 5.21-5.25 (1H), 4.18-4.23 (1H), 3.86-3.92 (1H), 2.81-2.85 (1H), 2.25-2.31 (1H), 1.48 (9H).

I-02g: Tert-butyl 3-(5-cyano-3-pyridyl)isoxazolidine-2-carboxylate

Two reactions carried out in parallel.

To a solution of tert-butyl 3-(5-bromo-3-pyridyl)isoxazolidine-2-carboxylate (15.0 g) in DMF (75.0 ml) was added $Zn(CN)_2$ (8.03 g) and $Pd(PPh_3)_4$ (6.32 g) under $N_2$. The mixture was stirred at 110° C. for 12 h under a nitrogen atmosphere. The 2 reactions were combined for work up. The reaction suspension was poured into water (500 ml) and extracted with EA (500 ml, 300 ml). The combined organic layers were washed with brine (200 ml), dried over $Na_2SO_4$, filtered and the filtrate was concentrated under reduced pressure. The crude product was purified by column chromatography ($SiO_2$, PE/EA=50/1 to 0/1) to give the title compound as a white solid (12 g).

$^1H$ NMR (400 MHz, $CDCl_3$): δ 8.79 (2H), 7.99 (1H), 5.29-5.33 (1H), 4.21-4.24 (1H), 3.87-3.93 (1H), 2.87-2.91 (1H), 2.25-2.30 (1H), 1.50 (9H).

I-02g-1

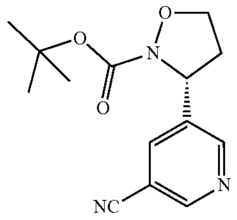

und

I-02g-2

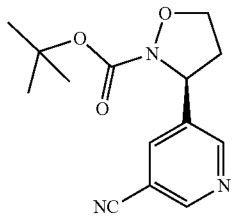

Tert-butyl (3R)-3-(5-cyano-3-pyridyl) isoxazolidine-2-carboxylate and tert-butyl (3S)-3-(5-cyano-3-pyridyl)isoxazolidine-2-carboxylate The two enantiomers were separated by SFC (column: DAICEL CHIRALPAK AD (250×50 mm, 10 μm); mobile phase A: $CO_2$, B: isopropanol (0.1 vol % aqueous $NH_3$ solution (25% w/w)); no gradient, 15% B for 5 min) to furnish the two enantiomers I-02g-1 (5.1 g) and I-02g-2 (5.1 g) as white solids.

I-02g-1: Tert-butyl (3R)-3-(5-cyano-3-pyridyl)isoxazolidine-2-carboxylate $^1$H NMR (400 MHz, $CDCl_3$): δ 8.79 (2H), 8.00 (1H), 5.29-5.33 (1H), 4.20-4.25 (1H), 3.87-3.93 (1H), 2.85-2.92 (1H), 2.25-2.31 (1H), 1.50 (9H).

SFC: tR 1.50 min (Column: Chiralpak AD-3, 100×4.6 mm, I.D., 3 μm, Mobile phase: A $CO_2$, B: isopropanol (0.05% DEA), Gradient: from 5% to 40% in 2 min and hold 40% for 1 min, then from 40% to 5% of B for 1 min, flow rate: 3.4 ml/min, column temp.: 35° C.).

I-02g-2: Tert-butyl (3S)-3-(5-cyano-3-pyridyl)isoxazolidine-2-carboxylate $^1$H NMR (400 MHz, $CDCl_3$): δ 8.79 (2H), 7.99 (1H), 5.29-5.33 (1H), 4.20-4.24 (1H), 3.87-3.93 (1H), 2.87-2.92 (1H), 2.25-2.30 (1H), 1.49 (9H).

SFC: tR 1.72 min (Column: Chiralpak AD-3, 100×4.6 mm, I.D., 3 μm, Mobile phase: A $CO_2$, B: isopropanol (0.05% DEA), Gradient: from 5% to 40% in 2 min and hold 40% for 1 min, then from 40% to 5% of B for 1 min, flow rate: 3.4 ml/min, column temp.: 35° C.).

Alternative Approach to tert-butyl (3S)-3-(5-cyano-3-pyridyl)isoxazolidine-2-carboxylate (I-02g-2)

I-02h

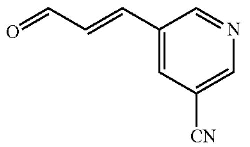

5-[(E)-3-Oxoprop-1-enyl]pyridine-3-carbonitrile

A mixture of 5-bromopyridine-3-carbonitrile (23.4 g), prop-2-enal (21.51 g), $Pd(OAc)_2$ (1.44 g), TEA (38.82 g) and benzyl(triethyl)ammonium chloride (29.12 g) in DMF (230 ml) was degassed and purged with $N_2$ for 3 times, and then the mixture was stirred at 80° C. for 12 h under $N_2$ atmosphere. The mixture was concentrated, diluted with water (500 ml), extracted with EA (300 ml×5), washed with brine (500 ml), dried with $Na_2SO_4$, filtered and concentrated. The residue was purified by flash silica gel chromatography (PE:EA=1:1) to yield 14.5 g of the title compound.

$^1$H NMR (400 MHz, $CDCl_3$) δ=9.79 (1H), 8.99 (1H), 8.92 (1H), 8.14 (1H), 7.48 (1H), 6.84 (1H)

I-02i

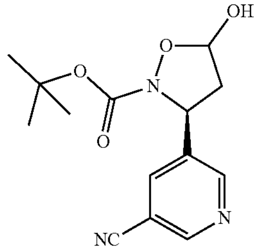

Tert-butyl (3S)-3-(5-cyano-3-pyridyl)-5-hydroxy-isoxazolidine-2-carboxylate

To a solution of (S)-2-(diphenyl((trimethylsilyl)oxy)methyl)pyrrolidine (5.97 g) in $CHCl_3$ (150 ml) was added 5-[(E)-3-oxoprop-1-enyl]pyridine-3-carbonitrile (14.5 g) and tert-butyl N-hydroxycarbamate (13.43 g) at 0° C. The mixture was degassed and purged with $N_2$ for 3 times, then the mixture was warmed to 25° C. gradually, stirred at that temperature for 36 h. The mixture was concentrated and the residue was purified by prep. RP-LC (water (0.1% FA)/ACN) to yield 18.1 g of the title compound.

$^1$H NMR (400 MHz, $CDCl_3$) δ=8.82 (1H), 8.79 (1H), 7.99 (1H), 5.90 (1H), 5.41 (1H), 4.95-4.53 (1H), 2.87 (1H), 2.29-2.20 (1H), 1.47 (9H).

I-02j

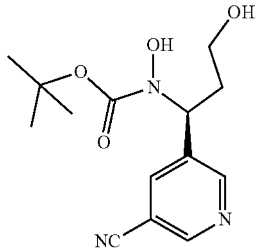

Tert-butyl N-[(1S)-1-(5-cyano-3-pyridyl)-3-hydroxy-propyl]-N-hydroxy-carbamate

To a solution of tert-butyl (38)-3-(5-cyano-3-pyridyl)-5-hydroxy-isoxazolidine-2-carboxylate (18.1 g) in MeOH (150 ml) was added $NaBH_4$ (2.43 g) at 0° C. The mixture was stirred at 0° C. for 2 h. The reaction mixture was quenched with saturated aqueous $NH_4Cl$ solution (10 ml) and diluted with water (500 ml). The resulting solution was extracted with EA (300 ml×4), and the combined organic layers were wash with brine (500 ml) and concentrated. The crude product was purified by RP-LC (flow: 200 ml/min; gradient: from 90% $H_2O$ (0.1% FA)/10% ACN to 65% $H_2O$ (0.1% FA)/35% ACN in 50 min; then 65% $H_2O$ (0.1%

FA)/35% ACN for 17 min; column: Welch Ultimate XB_C18, 20-40 µm, 100 Å, I.D. 95 mm×H 365 mm) to yield 16.4 g of the title compound.

SFC: S-enantiomer: tR 1.03 min (94.7%), R-enantiomer: tR: 1.31 min (5.3%) [Column: Chiralpak AD-3, 50×4.6 mm, I.D., 3 µm, mobile phase: A: $CO_2$, B MeOH (0.05% DEA), Gradient: from 5% to 40% B; flow rate: 3 ml/min, column temp.: 35° C.].

$^1$H NMR (400 MHz, $CDCl_3$) δ=8.82 (2H), 8.11 (1H), 7.12 (1H), 5.35 (1H), 3.94-3.85 (1H), 3.81 (1H), 2.48-2.37 (1H), 2.28 (1H), 2.11-2.01 (1H), 1.52-1.43 (9H).

I-02g-2

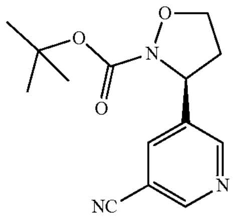

Tert-butyl (3S)-3-(5-cyano-3-pyridyl)isoxazolidine-2-carboxylate

To a solution of tert-butyl N-[(1 S)-1-(5-cyano-3-pyridyl)-3-hydroxy-propyl]-N-hydroxy-carbamate (15.4 g) in THF (160 ml) was added tributylphosphane (17.00 g) dropwise at 0° C. followed by the dropwise addition of DIAD (13.80 g) at 0° C. Then the mixture was warmed to 20° C. gradually and stirred for 16 h. The reaction mixture was concentrated. The crude product was purified by RP-LC (flow: 200 ml/min; gradient: from 90% $H_2O$ (0.1% FA)/10% ACN to 63% $H_2O$ (0.1% FA)/37% ACN in 80 min; then 63% $H_2O$ (0.1% FA)/37% ACN for 30 min; column: Welch Ultimate XB_C18, 20-40 µm, 100 Å, I.D. 95 mm×H 365 mm) and the residue was triturated with PE:EA=5:1 (80 ml) to yield 6.6 g of the title compound (>99.9% ee).

$^1$H NMR (400 MHz, $CDCl_3$) δ=8.84-8.76 (2H), 8.04-7.98 (1H), 5.32 (1H), 4.27-4.20 (1H), 3.95-3.87 (1H), 2.95-2.85 (1H), 2.28 (1H), 1.50 (9H).

SFC: (S) enantiomer tR: 1.89 min (100%) [Column: Chiralpak AD-3, 50×4.6 mm, I.D., 3 µm, Mobile phase: A: $CO_2$, B MeOH (0.05% DEA), Gradient: from 5% to 40%; flow rate: 3 ml/min, column temp.: 35° C.]. For information: (R) enantiomer tR: 1.17 min

I-02-1

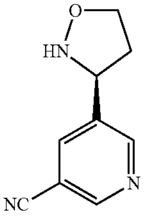

5-[(3S)-Isoxazolidin-3-yl]pyridine-3-carbonitrile

Tert-butyl (3S)-3-(5-cyano-3-pyridyl)isoxazolidine-2-carboxylate (1.25 g) was dissolved in dry DCM (15 ml) at RT with stirring. After adding TFA (5.0 ml) the reaction mixture was stirred for 30 min. Then the solvent was removed in vacuo. Sat. $NaHCO_3$ solution was added to the residue and the aqueous phase was extracted with DCM (3×). The combined organic layers were dried with $Na_2SO_4$, filtered and concentrated in vacuo to yield 790 mg of the title compound which was used directly in the next step without further purification.

LC/MS: m/z=176.2 $[M+H]^+$, tR: 0.71 min (LC/MS-method A).

$^1$H NMR (400.23 MHz, DMSO-$d_6$) δ ppm 8.90 (1H), 8.85 (1H), 8.22 (1H), 7.0-6.3 (1H), 4.58 (1H), 3.95 (1H), 3.70 (1H), 2.64 (1H), 2.18 (1H)

I-02-2

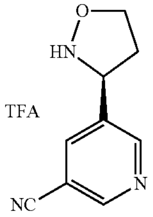

5-[(3S)-Isoxazolidin-3-yl]pyridine-3-carbonitrile trifluoroacetic acid salt

Tert-butyl (S)-3-(5-cyanopyridin-3-yl)isoxazolidine-2-carboxylate (I-02g-2, 250 mg) was dissolved in DCM (5 ml) and trifluoroacetic acid (1.5 ml) was added. After stirring for 0.75 h the solvent was removed in vacuo, the residue was dissolved in ACN/water and lyophilised over night to yield 248 mg of the title compound.

LC/MS: m/z=176.3 $[M+H]^+$; tR: 0.71 min (LC/MS-method A).

$^1$H NMR (400.23 MHz, DMSO-$d_6$) δ ppm 8.93 (1H), 8.87 (1H), 8.26 (1H), 4.70 (1H), 4.07 (1H), 3.80 (1H), 2.69 (1H), 2.28 (1H)

I-02-2(R)

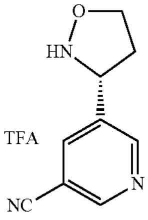

5-[(3R)-Isoxazolidin-3-yl]pyridine-3-carbonitrile TFA salt

Tert-butyl (R)-3-(5-cyanopyridin-3-yl)isoxazolidine-2-carboxylate (I-02g-1, 100 mg) was dissolved in DCM (5 ml) and trifluoroacetic acid (0.27 ml) was added. After stirring for 2 h under Ar the solvent was removed in vacuo and co-evaporated twice with toluene to yield 118 mg of the title compound.

LC/MS: m/z=176.3 $[M+H]^+$; tR: 0.27 min (LC/MS-method D).

I-02-3

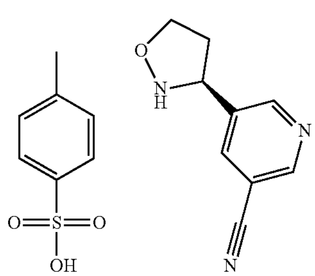

5-[(3S)-Isoxazolidin-3-yl]pyridine-3-carbonitrile (compound with 4-methylbenzenesulfonic acid)

To a mixture of tert-butyl (3S)-3-(5-cyano-3-pyridyl) isoxazolidine-2-carboxylate (I-02g-2, 500 mg) and ethyl acetate (10 ml) at 50° C. was added 4-methylbenzenesulfonic acid (hydrate, 2.1 M in ethyl acetate kept at 35° C., 2.6 ml). After three hours at 55° C., a white precipitate had formed, which was isolated by filtration at room temperature to provide 1.1 g of the title compound.

LC/MS: m/z=175.9 $[M+H]^+$; tR: 0.20 min (LC/MS-method D)

I-03

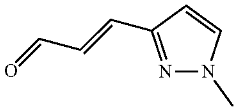

3-(1-Methylpyrazol-3-yl)isoxazolidine TFA salt
I-03a: (E)-3-(1-Methylpyrazol-3-yl)prop-2-enal 1-Methyl-1H-pyrazole-3-carbaldehyde (1.0 g) was dissolved in DCM (15 ml) and (formylmethylene)triphenylphosphorane (3.0 g) was added with stirring. After stirring for 96 h at 40° C. water was added. The aqueous phase was extracted (3×) with DCM, the combined organic phases were dried over magnesium sulphate, filtered and concentrated in vacuo. The residue was purified by flash chromatography on silica gel (90 g; 0% to 20% EA in heptane for 40 min, 20% EA for 70 min). The compound containing fractions were combined and the solvent was removed in vacuo to yield 444.5 mg of the title compound.

LC/MS: m/z=137.2 $[M+H]^+$; tR: 0.59 min (LC/MS-method D).

I-03b

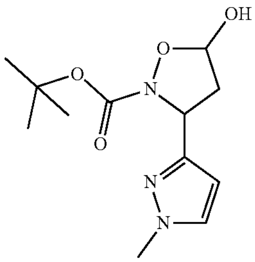

Tert-butyl 5-hydroxy-3-(1-methylpyrazol-3-yl)isoxazolidine-2-carboxylate

[Diphenyl-[(2S)-pyrrolidin-2-yl]methoxy]-trimethyl-silane (219.1 mg) was dissolved in DCM (5 ml) before benzoic acid (79.8 mg), (E)-3-(1-methylpyrazol-3-yl)prop-2-enal (444.5 mg) and tert-butyl N-hydroxycarbamate (532 mg) were added with stirring. After stirring for 4 h further tert-butyl N-hydroxycarbamate (53 mg) was added and the solution stirred for another hour at room temperature. A mixture of DCM and saturated $NH_4Cl$ solution was added. The aqueous phase was extracted once with DCM, the combined organic phases were dried over magnesium sulphate, filtered and concentrated in vacuo. The residue was purified by flash chromatography on silica gel (90 g; 0% to 50% EA in heptane for 30 min, 50% EA for 60 min). The compound containing fractions were combined and the solvent was removed in vacuo to yield 778.5 mg of the title compound which was contaminated with tert-butyl 5-((tert-butoxycarbonyl)(hydroxy)amino)-3-(1-methyl-1H-pyrazol-3-yl)isoxazolidine-2-carboxylate, but was used without further purification in the next step.

LC/MS: m/z=254 $[M-H_2O]^+$; tR: 0.87 min (LC/MS-method D).

$^1$H NMR (400 MHz, DMSO-$d_6$) δ ppm 7.58 (1H), 6.78 (1H), 6.08 (1H), 6.01 (1H), 5.59 (1H), 5.22 (1H), 3.77 (3H), 2.72 (1H), 2.39 (1H), 1.42 (9H).

I-03c

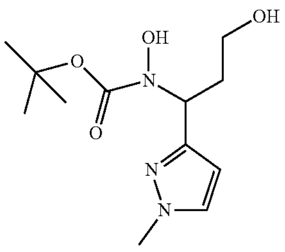

Tert-butyl N-hydroxy-N-[3-hydroxy-1-(1-methylpyrazol-3-yl)propyl]carbamate

Tert-butyl 5-hydroxy-3-(1-methylpyrazol-3-yl)isoxazolidine-2-carboxylate (778.5 mg) was dissolved in methanol (12 ml), cooled to 0° C. and $NaBH_4$ (109.4 mg) was added with stirring. After 24 h saturated $NH_4Cl$ solution was added. The aqueous phase was extracted with DCM (3×), the combined organic phases were dried over magnesium sulphate, filtered and concentrated in vacuo. The residue was further purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure compound containing fractions were combined, the ACN was removed in vacuo and the residue lyophilised overnight to yield 240 mg of the title compound.

LC/MS: m/z=272.3 $[M+H]^+$; tR: 0.75 min (LC/MS-method D)

I-03d

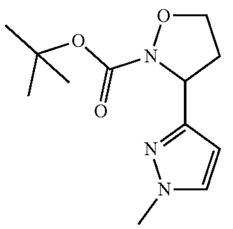

Tert-butyl 3-(1-methylpyrazol-3-yl)isoxazolidine-2-carboxylate

Tert-butyl N-hydroxy-N-[3-hydroxy-1-(1-methylpyrazol-3-yl)propyl]carbamate (240 mg) was dissolved in THF (10 ml) and with stirring under argon triphenylphosphine (563 mg) and DIAD (355 μl) were added at 0° C. After 4 h a further portion of DIAD (88 μl) was added. After stirring for 2 days triphenylphosphine (94.7 mg) and DIAD (53 μl) were added, after 4 h another 53 μl of DIAD were added. After stirring for 3 days triphenylphosphine (142 mg) and DIAD (106 μl) were added and stirred overnight before $H_2O$ was added. The aqueous phase was extracted with DCM (3×), the combined organic phases were dried over magnesium sulphate, filtered and concentrated in vacuo. The residue was further purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure compound containing fractions were combined, the ACN was removed in vacuo and the residue lyophilised overnight. 102.4 mg of the title compound as an 55/45 enantiomeric mixture (Chiralpak AD-H/148, 1 ml/min, 250 mm×4.6 mm, Heptane/EtOH/MeOH 1/1/1) were obtained.

LC/MS: m/z=154 $[M-CO_2tBu+2H]^+$; tR: 1.01 min (LC/MS-method D).

$^1H$ NMR (400 MHz, DMSO-$d_6$) δ ppm 7.58 (1H), 6.10 (1H), 5.15 (1H), 4.09 (1H), 3.78 (3H), 3.71 (1H), 2.58 (1H), 2.42 (1H), 1.41 (9H).

I-03

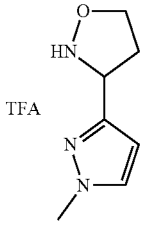

3-(1-Methylpyrazol-3-yl]isoxazolidine TFA salt

Tert-butyl 3-(1-methylpyrazol-3-yl)isoxazolidine-2-carboxylate (102 mg) was dissolved in DCM (3 ml) and TFA (1.5 ml) was added at RT with stirring. After 1.5 h the solvent was removed in vacuo and the residue co-evaporated twice with toluene to yield 121 mg of the title compound.

LC/MS: m/z=154 $[M+H]^+$; tR: 0.09 min (LC/MS-method D).

I-04

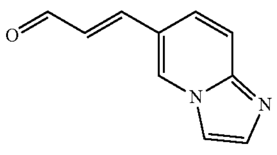

3-Imidazo[1,2-a]pyridin-6-ylisoxazolidine TFA salt
I-04a: (E)-3-Imidazo[1,2-a]pyridin-6-ylprop-2-enal Imidazo[1,2-a]pyridine-6-carbaldehyde (2.0 g) was dissolved in ACN (17 ml) and (formylmethylene)triphenylphosphorane (4.6 g) was added with stirring. After stirring for 24 h at 80° C. water was added. The aqueous phase was extracted with DCM (3×), the combined organic phases were dried over magnesium sulphate, filtered and concentrated in vacuo. The residue was purified by flash chromatography on silica gel (120 g; 0% to 50% EA in heptane for 40 min, 50% EA for 230 min). The compound containing fractions were combined and the solvent was removed in vacuo to yield 1.63 g of the title compound (purity ca. 65%).

LC/MS: m/z=173.2 $[M+H]^+$; tR: 0.09 min (LC/MS-method D).

I-04b

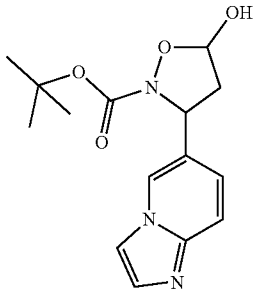

Tert-butyl 5-hydroxy-3-imidazo[1,2-a]pyridin-6-yl-isoxazolidine-2-carboxylate

[Diphenyl-[(2S)-pyrrolidin-2-yl]methoxy]-trimethyl-silane (445.6 mg), benzoic acid (162.2 mg), and (E)-3-imidazo[1,2-a]pyridin-6-ylprop-2-enal (1.63 g) were dissolved in DCM (15 ml) with stirring and cooled to 4° C. After 10 min tert-butyl N-hydroxycarbamate (1.08 g) was added with stirring. After stirring for 24 h at 4° C., a mixture of DCM and saturated $NH_4Cl$ solution was added. The aqueous phase was extracted once with DCM, the combined organic phases were dried over magnesium sulphate, filtered and concentrated in vacuo. The residue was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure compound containing fractions were combined, the ACN was removed in vacuo and the residue lyophilised overnight. 1.20 g of the title compound was obtained (no determination of e.r.).

LC/MS: m/z=306.2 $[M+H]^+$; tR: 0.62 min (LC/MS-method D).

I-04c

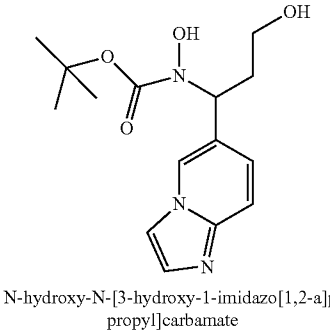

Tert-butyl N-hydroxy-N-[3-hydroxy-1-imidazo[1,2-a]pyridin-6-yl-propyl]carbamate

Tert-butyl 5-hydroxy-3-imidazo[1,2-a]pyridin-6-yl-isoxazolidine-2-carboxylate (1.20 g, possible excess of S enantiomer not determined) was dissolved in methanol (15 ml), cooled to 0° C. and $NaBH_4$ (148.2 mg) was added with stirring. After 48 h saturated $NH_4Cl$ solution was added. The aqueous phase was extracted with DCM (3×), the combined organic phases were dried over magnesium sulphate, filtered and concentrated in vacuo to yield 1.05 g of the title compound which was used without further purification in the next step.

LC/MS: m/z=308.3 $[M+H]^+$; tR: 0.54 min (LC/MS-method D)

I-04d

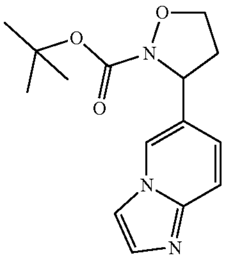

Tert-butyl 3-imidazo[1,2-a]pyridin-6-ylisoxazolidine-2-carboxylate

Tert-butyl N-hydroxy-N-[3-hydroxy-1-imidazo[1,2-a]pyridin-6-yl-propyl]carbamate (1.045 g) was dissolved in THF (20 ml) and with stirring under argon triphenylphosphine (2.17 g) and DIAD (1.37 ml) were added at 0° C. After 24 h $H_2O$ was added. The aqueous phase was extracted with DCM (3×), the combined organic phases were dried over magnesium sulphate, filtered and concentrated in vacuo. The residue was purified by flash chromatography on silica gel (180 g; 0% to 90% EA in heptane for 260 min). The compound containing fractions were combined and the solvent was removed in vacuo to yield 512.5 mg of the title compound.

LC/MS: m/z=290.3 $[M+H]^+$; tR: 0.69 min (LC/MS-method D)

I-04

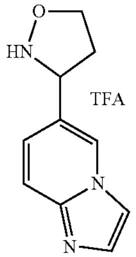

3-Imidazo[1,2-a]pyridin-6-ylisoxazolidine TFA salt

Tert-butyl 3-imidazo[1,2-a]pyridin-6-ylisoxazolidine-2-carboxylate (255 mg) was dissolved in DCM (3 ml) and TFA (3.4 ml) was added at RT with stirring. After 1.5 h the solvent was removed in vacuo and the residue thus obtained co-evaporated twice with toluene to yield 382 mg of the title compound.

LC/MS: m/z=190.1 $[M+H]^+$; tR: 0.10 min (LC/MS-method D)

I-05: 5-(Isoxazolidin-3-yl)pyridin-2-ol HCl salt

I-05a

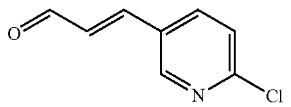

(E)-3-(6-Chloro-3-pyridyl)prop-2-enal

6-Chloronicotinaldehyde (2 g) was dissolved in ACN (50 ml) and (formylmethylene)triphenylphosphorane (4.7 g) was added with stirring. After stirring for 3 h at 80° C. the solution was concentrated in vacuo. The residue was purified by flash chromatography on silica gel (100 g; 0% to 85% EA in heptane in 45 min). The compound containing fractions were combined and the solvent was removed in vacuo to yield 2.07 g of the title compound.

LC/MS: m/z=168.2 $[M+H]^+$; tR: 0.85 min (LC/MS-method D).

$^1H$ NMR (400 MHz, DMSO-$d_6$) δ ppm 9.71 (1H), 8.77 (1H), 8.29 (1H), 7.79 (1H), 7.65 (1H), 7.03 (1H).

I-05b

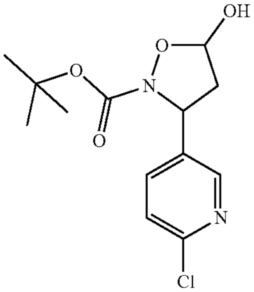

Tert-butyl 3-(6-chloro-3-pyridyl)-5-hydroxy-isoxazolidine-2-carboxylate

[Diphenyl-[(2S)-pyrrolidin-2-yl]methoxy]-trimethyl-silane (869.9 mg), benzoic acid (318.1 mg), and (E)-3-(6-chloro-3-pyridyl)prop-2-enal (2.17 g) were dissolved in DCM (20 ml) under stirring before tert-butyl N-hydroxycarbamate (2.11 g) was added. After stirring for 3 h at RT, saturated $NH_4Cl$ solution was added and the mixture was passed through an Agilent Chem Elut SLE cartridge eluting with DCM. The eluate was concentrated in vacuo and the residue thus obtained was purified by flash chromatography on silica gel (100 g; 0% to 65% EA in 52 min. The compound containing fractions were combined and the solvent was removed in vacuo to yield 3.64 g of the title compound (purity ca. 70%, no determination of e.r.).

LC/MS: m/z=301.1 $[M+H]^+$; tR: 1.14 min (LC/MS-method D).

I-05c

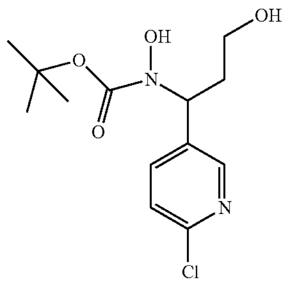

Tert-butyl N-[1-(6-chloro-3-pyridyl)-3-hydroxy-propyl]-N-hydroxy-carbamate

Tert-butyl 3-(6-chloro-3-pyridyl)-5-hydroxy-isoxazolidine-2-carboxylate (3.536 g, possible excess of S enantiomer not determined) was dissolved in methanol (10 ml), cooled to 0° C. and $NaBH_4$ (444.8 mg) was added with stirring. After 2 h at 0° C. saturated $NH_4Cl$ solution was added. The aqueous phase was extracted with DCM (3×), the combined organic phases were dried over magnesium sulphate, filtered and concentrated in vacuo. The residue was purified by flash chromatography on silica gel (50 g; 0% to 90% in 19 min). The compound containing fractions were combined and the solvent was removed in vacuo to yield 2.145 g of the title compound.

LC/MS: m/z=303.2 $[M+H]^+$; tR: 0.96 min (LC/MS-method D)

I-05d

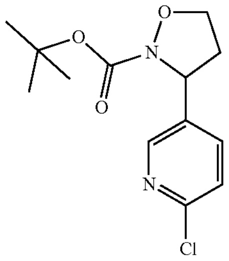

Tert-butyl 3-(6-chloro-3-pyridyl) isoxazolidine-2-carboxylate

Tert-butyl N-[1-(6-chloro-3-pyridyl)-3-hydroxy-propyl]-N-hydroxy-carbamate (2.145 g) was dissolved in THF (100 ml) and with stirring under argon triphenylphosphine (4.51 g) and DIAD (2.85 ml) were added at 0° C. After 24 h a mixture of DCM and $H_2O$ was added and the phases were separated. The aqueous phase was extracted with DCM (3×), the combined organic phases were dried over magnesium sulphate, filtered and concentrated in vacuo. The residue was purified by flash chromatography on silica gel (100 g; 0% to 77% EA in heptane in 24 min. The compound containing fractions were combined and the solvent was removed in vacuo to yield 3.609 g of the title compound as mixture with 110 mol % reduced DIAD.

An analytical pure sample was obtained by preparative HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm) to yield 88 mg of a 60/40 enantiomeric mixture (Chiralpak IC/144, 250×4.6 mm, Heptane/EtOH/MeOH 5/1/1). Preparative chiral HPLC (30 ml/min, heptane/EtOH/MeOH 5/1/1, Chiralpak IC, 250×30 mm, 5 μm) yielded 27 mg and 19 mg of the two enantiomers.

LC/MS: m/z=285.1 $[M+H]^+$; tR: 1.28 min (LC/MS-method D)

$^1H$ NMR (400 MHz, DMSO-$d_6$) δ ppm 8.37 (1H), 7.79 (1H), 7.51 (1H), 5.24 (1H), 4.17 (1H), 3.76 (1H), 2.82 (1H), 2.18 (1H), 1.39 (9H).

I-05

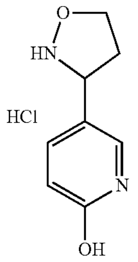

5-(Isoxazolidin-3-yl) pyridin-2-ol HCl salt

Tert-butyl 3-(6-chloro-3-pyridyl)isoxazolidine-2-carboxylate (325 mg) was dissolved in HCl (12.5 ml, 6 M) and heated at 100° C. with stirring. After 120 h the solvent was removed in vacuo and the residue co-evaporated three times with toluene. The residue thus obtained was dissolved in ACN/water and lyophilized to yield 226 mg of the title compound.

LC/MS: m/z=167.2 $[M+H]^+$; tR: 0.09 min (LC/MS-method D)

I-06

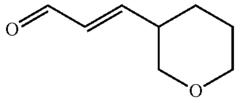

3-Tetrahydropyran-3-ylisoxazolidine TFA salt

I-06a: (E)-3-Tetrahydropyran-3-ylprop-2-enal

Tetrahydro-2H-pyran-3-carbaldehyde (539 mg) was dissolved in toluene (15 ml) and (formylmethylene)triphenylphosphorane (1.56 g) was added with stirring. After stirring for 24 h at 120° C. the solution was concentrated in vacuo. The residue was purified by flash chromatography on silica gel (25 g; 0% to 50% EA in heptane in 7 min). The compound containing fractions were combined and the solvent was removed in vacuo to yield 203 mg of the title compound as mixture with ca. 50% (2E,4E)-5-(tetrahydro-2H-pyran-3-yl)penta-2,4-dienal.

LC/MS: m/z=141.2 $[M+H]^+$; tR: 0.69 min (LC/MS-method D).

I-06b

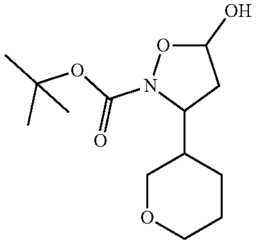

Tert-butyl 5-hydroxy-3-tetrahydropyran-3-yl-isoxazolidine-2-carboxylate

[Diphenyl-[(2S)-pyrrolidin-2-yl]methoxy]-trimethyl-silane (85 mg), benzoic acid (25 mg) and tert-butyl N-hydroxycarbamate (206.6 mg) were dissolved in chloroform (1 ml) with stirring. (E)-3-Tetrahydropyran-3-ylprop-2-enal (203 mg) was dissolved in chloroform (1 ml) and added with stirring at 4° C. After stirring for 24 h at 4° C., the solution was concentrated in vacuo. The residue was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure compound containing fractions were combined, the ACN was removed in vacuo and the residue lyophilised overnight to yield 112 mg of the title compound (no determination of er.).

LC/MS: m/z=174.3 $[M-CO_2tBu+2H]^+$; tR: 0.81 min (LC/MS-method D).

I-06c

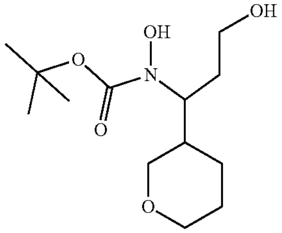

Tert-butyl N-hydroxy-N-[3-hydroxy-1-tetrahydropyran-3-yl-propyl]carbamate

Tert-butyl 5-hydroxy-3-tetrahydropyran-3-yl-isoxazolidine-2-carboxylate (112 mg, possible excess of S enantiomer not determined) was dissolved in methanol (5 ml), cooled to 0° C. and $NaBH_4$ (15.5 mg) was added with stirring. After 45 min at 0° C. saturated $NH_4Cl$ solution was added and the mixture was passed through an Agilent Chem Elut SLE cartridge eluting with DCM. The eluate was concentrated in vacuo to yield 103 mg of the title compound which was used without further purification in the next step.

LC/MS: m/z=176.2 $[M-CO_2tBu+2H]^+$; tR: 0.96 min (LC/MS-method D)

I-06d

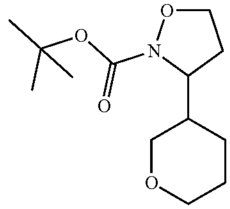

Tert-butyl 3-tetrahydropyran-3-ylisoxazolidine-2-carboxylate

Tert-butyl N-hydroxy-N-[3-hydroxy-1-tetrahydropyran-3-yl-propyl]carbamate (103 mg) was dissolved in THF (5 ml) and with stirring under argon triphenylphosphine (237.9 mg) and DIAD (150.3 μl) were added at 0° C. After 24 h a mixture of DCM and $H_2O$ was added and the phases were separated. The aqueous phase was extracted with DCM (3×), the combined organic phases were dried over magnesium sulphate, filtered and concentrated in vacuo. The residue was purified by flash chromatography on silica gel (10 g; 0% to 50% EA in heptane in 10 min). The compound containing fractions were combined and the solvent was removed in vacuo to yield 254 mg of the title compound as mixture with 200% reduced DIAD.

LC/MS: m/z=158.3 $[M-CO_2tBu+2H]^+$; tR: 1.19 min (LC/MS-method D)

I-06

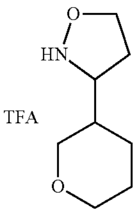

TFA

3-Tetrahydropyran-3-ylisoxazolidine TFA salt

Tert-butyl 3-tetrahydropyran-3-ylisoxazolidine-2-carboxylate (254 mg) was dissolved in DCM (5 ml) and TFA (0.5 ml) was added at RT with stirring. After 1.5 h the solvent was removed in vacuo and the residue co-evaporated twice with toluene to yield 278 mg of the title compound.

LC/MS: m/z=158.2 $[M+H]^+$; tR: 0.17 min (LC/MS-method D, retention time is based on MS trace)

I-07

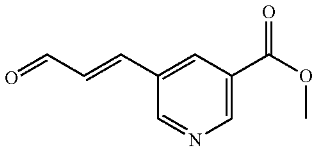

(5-Isoxazolidin-3-yl-3-pyridyl)methanol TFA salt

I-07a: Methyl 5-[(E)-3-oxoprop-1-enyl]pyridine-3-carboxylate

Methyl-5-formylnicotinate (1.0 g) was dissolved in ACN (20 ml) and (formylmethylene)triphenylphosphorane (1.9 g) was added with stirring. After stirring for 14 h at 80° C. the solution was concentrated in vacuo. The residue was purified by flash chromatography on silica gel (90 g; 10% to 35% EA in heptane for 150 min). The compound containing fractions were combined and the solvent was removed in vacuo to yield 520 mg of the title compound.

LC/MS: m/z=192.2 $[M+H]^+$; tR: 0.76 min (LC/MS-method D).

I-07b

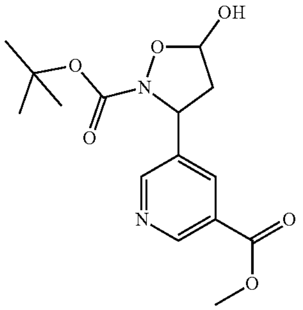

Tert-butyl 5-hydroxy-3-(5-methoxycarbonyl-3-pyridyl)isoxazolidine-2-carboxylate

Methyl 5-[(E)-3-oxoprop-1-enyl]pyridine-3-carboxylate (520 mg), [diphenyl-[(2S)-pyrrolidin-2-yl]methoxy]-trimethyl-silane (182.6 mg) and benzoic acid (66.8 mg) were dissolved in DCM (10 ml) with stirring and tert-butyl N-hydroxycarbamate (443.4 mg) was added with stirring at 4° C. After stirring for 24 h at 4° C., a mixture of DCM and saturated $NH_4Cl$ solution was added and the phases were separated. The aqueous phase was extracted with DCM, the combined organic phases were dried over magnesium sulphate, filtered and concentrated in vacuo. The residue was purified by flash chromatography on silica gel (90 g; 15% to 65% EA in heptane for 140 min). The compound containing fractions were combined and the solvent was removed in vacuo to yield 750 mg of the title compound (no determination of e.r.).

LC/MS: m/z=325.3 $[M+H]^+$; tR: 0.95 min (LC/MS-method D).

I-07c

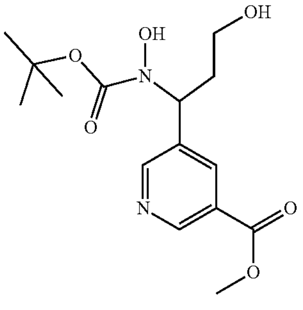

Methyl 5-[1-[tert-butoxycarbonyl(hydroxy)amino]-3-hydroxy-propyl]pyridine-3-carboxylate Tert-butyl 5-hydroxy-3-(5-methoxycarbonyl-3-pyridyl) isoxazolidine-2-carboxylate (750 mg, possible excess of S enantiomer not determined) was dissolved in methanol (25 ml), cooled to 0° C. and $NaBH_4$ (87.5 mg) was added with stirring. After 45 min at 0° C. a mixture of saturated $NH_4Cl$ solution and DCM was added and the phases were separated. The aqueous phase was extracted with DCM (2×), the combined organic phases were dried over magnesium sulphate, filtered and concentrated in vacuo to yield 630 mg of the title compound which was used without further purification in the next step.

LC/MS: m/z=327.3 $[M+H]^+$; tR: 0.80 min (LC/MS-method D)

I-07d

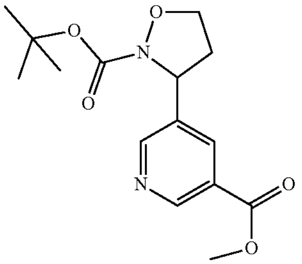

Tert-butyl 3-(5-methoxycarbonyl-3-pyridyl)isoxazolidine-2-carboxylate

Methyl 5-[1-[tert-butoxycarbonyl(hydroxy)amino]-3-hydroxy-propyl]pyridine-3-carboxylate (630 mg) was dissolved in THF (30 ml) and with stirring under argon triphenylphosphine (1.23 g) and DIAD (776 μl) were added at 0° C. After 4.5 h a mixture of DCM and $H_2O$ was added and the phases were separated. The aqueous phase was extracted with DCM (3×), the combined organic phases were dried over magnesium sulphate, filtered and concentrated in vacuo. The residue was purified by flash chromatography on silica gel (90 g; 10% to 35% EA in heptane for 120 min). The compound containing fractions were combined and the solvent was removed in vacuo to yield 310 mg of the title compound. An analytically pure sample was obtained by purifying an aliquot by preparative HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm) to give 47 mg of the title compound after lyophilization.

LC/MS: m/z=309.3 $[M+H]^+$; tR: 1.07 min (LC/MS-method D)

$^1H$ NMR (400 MHz, DMSO-$d_6$) δ ppm 9.00 (1H), 8.79 (1H), 8.20 (1H), 5.35 (1H), 4.19 (1H), 3.77 (1H), 2.87 (1H), 2.23 (1H).

I-07e

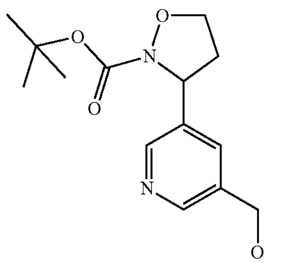

Tert-butyl 3-[5-hydroxymethyl)-3-pyridyl]isoxazolidine-2-carboxylate

Tert-butyl 3-(5-methoxycarbonyl-3-pyridyl)isoxazolidine-2-carboxylate (100 mg) was dissolved in THF (5 ml), lithium aluminum hydride (324 μl, 1 M in THF) was added at −78° C. with stirring under argon and the mixture kept at this temperature. After 3.5 h lithium aluminum hydride (20 μl, 1 M in THF) was added. After 30 min aqueous sodium potassium tartrate solution (10% w/w) was added at −78° C. The mixture was diluted with DCM, the phases separated and the aqueous phase was extracted with DCM (3×), the combined organic phases were dried over magnesium sulphate, filtered and concentrated in vacuo to yield 119 mg of the title compound.

LC/MS: m/z=281.3 $[M+H]^+$; tR: 0.61 min (LC/MS-method D)

I-07

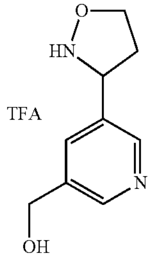

(5-Isoxazolidin-3-yl-3-pyridyl)methanol TFA salt

Tert-butyl 3-[5-(hydroxymethyl)-3-pyridyl]isoxazolidine-2-carboxylate (119 mg) was dissolved in DCM (3 ml) and TFA (1.6 ml) was added at RT with stirring. After 1.5 h the solvent was removed in vacuo and the residue co-evaporated twice with toluene to yield 140 mg of the title compound.

LC/MS: m/z=181.2 $[M+H]^+$; tR: 0.10 min (LC/MS-method D)

I-08: 5-(Isoxazolidin-3-yl)pyridine-3-carboxamide TFA salt

I-08a

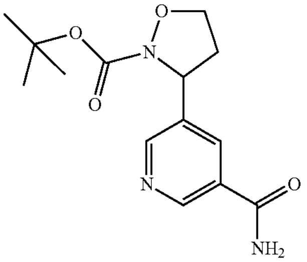

Tert-butyl 3-(5-carbamoyl-3-pyridyl)isoxazolidine-2-carboxylate

Tert-butyl 3-(5-methoxycarbonyl-3-pyridyl)isoxazolidine-2-carboxylate (I-07d, 90 mg) was dissolved in ammonia (1 ml, 7 M in methanol) and the mixture was stirred at 60° C. in an autoclave for 6.5 h. After this ammonia (1 ml, 7 M in methanol) was added. After further 18 h at 60° C. and 48 h at RT, the solution was concentrated in vacuo to yield 89 mg of the title compound which was used without further purification in the next step.

LC/MS: m/z=294.2 $[M+H]^+$; tR: 0.74 min (LC/MS-method D)

I-08

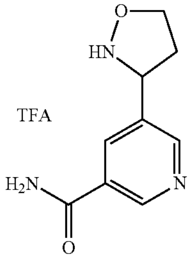

5-(isoxazolidin-3-yl)pyridine-3-carboxamide TFA salt

Tert-butyl 3-(5-carbamoyl-3-pyridyl)isoxazolidine-2-carboxylate (89 mg) was dissolved in DCM (3 ml) and TFA (1.2 ml) was added at RT with stirring. After 1.5 h the solvent was removed in vacuo and the residue co-evaporated twice with toluene to yield 93 mg of the title compound.

LC/MS: m/z=194.2 $[M+H]^+$; tR: 0.092 min (LC/MS-method D)

I-09: 5-(Isoxazolidin-3-yl)pyridin-2-amine TFA salt

I-09a

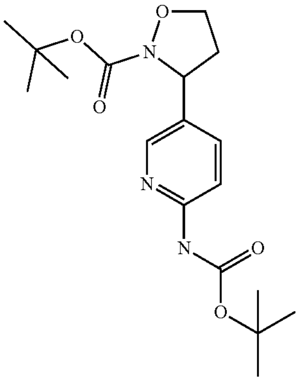

Tert-butyl 3-[6-(tert-butoxycarbonylamino)-3-pyridyl]isoxazolidine-2- carboxylate Tert-butyl 3-(6-chloro-3-pyridyl)isoxazolidine-2-carboxylate (I-05d, 90 mg) was dissolved in THF (4 ml) and with stirring under argon were added $Cs_2CO_3$ (206 mg), tert-butyl carbamate (113.4 mg), $Pd_2(dba)_3$ (11.6 mg) and X-phos (6.2 mg). After 24 h stirring at 80° C. a mixture of $H_2O$ and DCM was added and the phases were separated. The aqueous phase was extracted with DCM (3×), the combined organic phases were dried over magnesium sulphate, filtered and concentrated in vacuo. The residue was purified by flash chromatography on silica gel (5 g; 0% to 50% EA in heptane in 16 min). The compound containing fractions were combined and the solvent was removed in vacuo to yield 104 mg of the title compound.

LC/MS: m/z=366.5 $[M+H]^+$; tR: 2.13 min (LC/MS-method A)

$^1H$ NMR (400 MHz, DMSO-$d_6$) δ ppm 9.73 (1H), 8.17 (1H), 7.76 (1H), 7.67 (1H), 5.13 (1H), 4.16 (1H), 3.75 (1H), 2.77 (1H), 2.18 (1H), 1.47 (9H), 1.39 (9H).

I-09

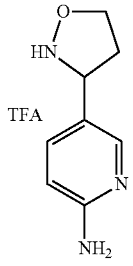

5-(Isoxazolidin-3-yl)
pyridin-2-amine TFA salt

Tert-butyl (3S)-3-[6-(tert-butoxycarbonylamino)-3-pyridyl]isoxazolidine-2-carboxylate (99 mg) was dissolved in DCM (2 ml) and TFA (416 μl) was added at RT with stirring. After 2 h the solvent was removed in vacuo and the residue co-evaporated twice with toluene to yield 115 mg of the title compound.

LC/MS: m/z=166.3 $[M+H]^+$; tR: 0.09 min (LC/MS-method D)

I-10a

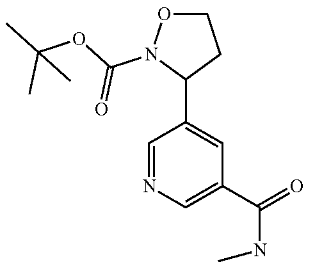

I-10: 5-(Isoxazolidin-3-yl)-N-methyl-pyridine-3-carboxamide TFA salt
Tert-butyl 3-[5-(methylcarbamoyl)-3-pyridyl]isoxazolidine-2-carboxylate Tert-butyl 3-(5-methoxycarbonyl-3-pyridyl)isoxazolidine-2-carboxylate (I-07d, 90 mg) was dissolved in methylamine (1.3 ml, 8 M in ethanol). After 1 h at 100° C. with stirring in a microwave oven the solvent was removed in vacuo and the residue was dried in high vacuo to yield 84 mg of the title compound.

LC/MS: m/z=308.3 $[M+H]^+$; tR: 0.818 min (LC/MS-method D)

I-10

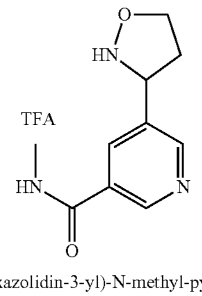

5-(Isoxazolidin-3-yl)-N-methyl-pyridine-
3-carboxamide TFA salt

Tert-butyl 3-[5-(methylcarbamoyl)-3-pyridyl]isoxazolidine-2-carboxylate (84 mg) was dissolved in DCM (3 ml) and TFA (205 μl) was added at RT with stirring. After 1.5 h the conversion was not complete, TFA (100 μl) was added at RT with stirring. After 24 h the solvent was removed in vacuo and the residue co-evaporated twice with toluene to yield 124 mg of the title compound.

LC/MS: m/z=208.2 $[M+H]^+$; tR: 0.096 min (LC/MS-method D)

I-11a

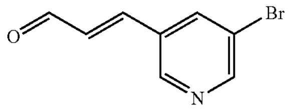

I-11: N-[5-[(3S)-Isoxazolidin-3-yl]-3-pyridyl]acetamide TFA salt
(E)-3-(5-Bromo-3-pyridyl)prop-2-enal 5-Bromonicotinaldehyde (3.0 g) was dissolved in ACN (2 ml) and (formylmethylene)triphenylphosphorane (5.4 g) was added with stirring. After stirring for 13 h at 80° C. the solution was concentrated in vacuo. The residue was purified by flash chromatography on silica gel (190 g; 10% to 22% EA in heptane in 85 min). The compound containing fractions were combined and the solvent was removed in vacuo to yield 2.3 g of the title compound.

LC/MS: m/z=212.1 $[M+H]^+$; tR: 0.89 min (LC/MS-method D)

$^1$H NMR (400 MHz, DMSO-$d_6$): δ ppm 9.70 (1H), 8.91 (1H), 8.81 (1H), 8.53 (1H), 7.75 (1H), 7.08 (1H).

I-11b

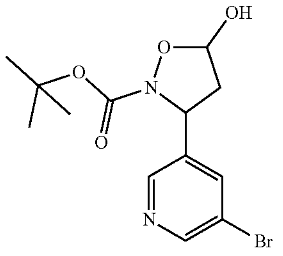

Tert-butyl (3S)-3-(5-bromo-3-pyridyl)-5-hydroxy-isoxazolidine-2-carboxylate (E)-3-(5-bromo-3-pyridyl)prop-2-enal (2.3 g), [diphenyl-[(2S)-pyrrolidin-2-yl]methoxy]-trimethyl-silane (728 mg) and benzoic acid (359.3 mg) were dissolved in DCM (30 ml) with stirring and tert-butyl N-hydroxycarbamate (1.71 g) was added with stirring at 4° C. After stirring for 24 h at 4° C., a mixture of DCM and saturated $NH_4Cl$ solution was added and the phases were separated. The aqueous phase was extracted with DCM, the combined organic phases were dried over magnesium sulphate, filtered and concentrated in vacuo. The residue was purified by flash chromatography on silica gel (180 g; 12% to 35% EA in heptane in 70 min). The compound containing fractions were combined and the solvent was removed in vacuo to yield 2.94 g of the title compound.

LC/MS: m/z=345.2 $[M+H]^+$; tR: 1.12 min (LC/MS-method D).

I-11c

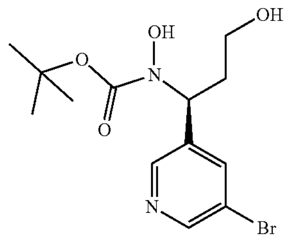

Tert-butyl N-[(1S)-1-(5-bromo-3-pyridyl)-3-hydroxy-propyl]-N-hydroxy-carbamate

Tert-butyl (3S)-3-(5-bromo-3-pyridyl)-5-hydroxy-isoxazolidine-2-carboxylate (2.94 g) was dissolved in methanol (100 ml), cooled to 0° C. and $NaBH_4$ (322.2 mg) was added with stirring. After 90 min at 0° C. a mixture of saturated $NH_4Cl$ solution and DCM was added and the phases were separated. The aqueous phase was extracted with DCM (2×), the combined organic phases were dried over magnesium sulphate, filtered and concentrated in vacuo to yield 2.8 g of the title compound which was used without further purification in the next step.

LC/MS: m/z=347.2 $[M+H]^+$; tR: 0.95 min (LC/MS-method D)

I-11d

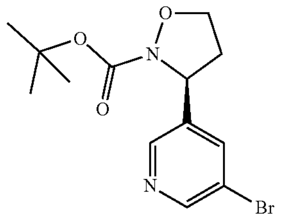

Tert-butyl (3S)-3-(5-bromo-3-pyridyl)isoxazolidine-2-carboxylate

Tert-butyl N-[(1S)-1-(5-bromo-3-pyridyl)-3-hydroxy-propyl]-N-hydroxy-carbamate (1.50 g) was dissolved in THF (50 ml) and with stirring under argon triphenylphosphine (2.75 g) and DIAD (1.74 ml) were added at 0° C. After 2 h a mixture of DCM and $H_2O$ was added and the phases were separated. The aqueous phase was extracted with DCM (3×), the combined organic phases were dried over magnesium sulphate, filtered and concentrated in vacuo. The residue was purified by flash chromatography on silica gel (90 g; 10% to 25% EA in heptane in 75 min). The compound containing fractions were combined and the solvent was removed in vacuo to yield 1.40 g of the title compound as a mixture with reduced DIAD. An analytically pure sample was obtained by purifying an aliquot by preparative HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm) yielding 22 mg after lyophilization.

LC/MS: m/z=329.1 $[M+H]^+$; tR: 1.26 min (LC/MS-method D)

$^1H$ NMR (400 MHz, DMSO-$d_6$) δ ppm 8.63 (1H), 8.54 (1H), 7.95 (1H), 5.24 (1H), 4.18 (1H), 3.77 (1H), 2.82 (1H), 2.23 (1H), 1.39 (9H).

Chiral HPLC (Chiralpak AD-H/148, 250×4.6 mm, EtOH/MeOH 1/1, 1 ml/min): 93/7 er

I-11e

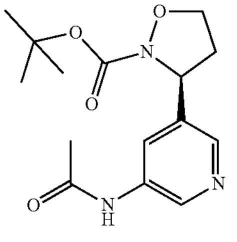

Tert-butyl (3S)-3-(5-acetamido-3-pyridyl)isoxazolidine-2-carboxylate

Tert-butyl (3S)-3-(5-bromo-3-pyridyl)isoxazolidine-2-carboxylate (100 mg) was dissolved in dioxane (10 ml) and under argon acetamide (25.9 mg), cesium carbonate (141.4 mg), 4,5-bis(diphenylphosphino)-9,9-dimethylxanthene (5.6 mg) and tris(dibenzylideneacetone)dipalladium(0) (29.3 mg) were added. After 9.5 h at 100° C. $H_2O$ and EA were added and the phases were separated. The aqueous phase was extracted with EA (3×), washed with brine, the combined organic phases were dried over magnesium sulphate, filtered and concentrated in vacuo. The residue was purified by flash chromatography on silica gel (25 g; 0% to 5% MeOH in DCM over 30 min). The compound containing fractions were combined and the solvent was removed in vacuo to yield 60 mg of the title compound.

LC/MS: m/z=308.37 $[M+H]^+$; tR: 1.13 min (LC/MS-method A)

$^1H$ NMR (400 MHz, DMSO-$d_6$) δ ppm 10.16 (1H), 8.64 (1H), 8.21 (1H), 7.98 (1H), 5.20 (1H), 4.16 (1H), 3.74 (1H), 2.83 (1H), 2.14 (1H), 2.06 (3H), 1.39 (9H).

I-11

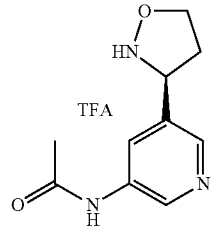

N-[5-[(3S)-Isoxazolidin-3-yl]-3-pyridyl]acetamide TFA salt

Tert-butyl (3S)-3-(5-acetamido-3-pyridyl)isoxazolidine-2-carboxylate (60 mg) was dissolved in DCM (3 ml) and TFA (147 μl) was added at RT with stirring. After 1.5 h the solvent was removed in vacuo and the residue co-evaporated twice with toluene to yield 20 mg of the title compound.

LC/MS: m/z=208.2 $[M+H]^+$; tR: 0.15 min (LC/MS-method D)

I-12a

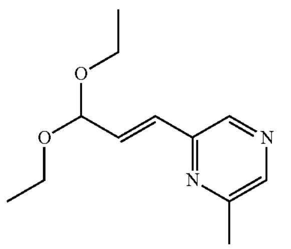

I-12: (3S)-3-(6-Methylpyrazin-2-yl)isoxazolidine hydrochloride salt
2-[(E)-3,3-Diethoxyprop-1-enyl]-6-methyl-pyrazine A mixture of 2-chloro-6-methyl-pyrazine (30 g), 3,3-diethoxyprop-1-ene (243.03 g), $K_2CO_3$ (64.50 g), tetrabutylammonium acetate (140.72 g), KCl (17.40 g) and $Pd(OAc)_2$ (2.62 g) in DMF (300 ml) was stirred at 120° C. for 12 h under $N_2$ atmosphere. The reaction mixture was concentrated. The residue was diluted with EA (500 ml), filtered, the filtrate was diluted with water (500 ml) and extracted with EA (300 ml×3). The combined organic layers were washed with brine (1 l), dried with $Na_2SO_4$, filtered and concentrated. The residue was purified by silica gel column chromatography (PE:EA=10:1 to 3:1) to yield 21.1 g of the title compound.

$^1$H NMR (400 MHz, $CDCl_3$): δ ppm 8.39 (1H), 8.30 (1H), 6.81 (2H), 5.15 (1H), 3.72 (2H), 3.59 (2H), 2.55 (3H), 1.26 (6H)

I-12b

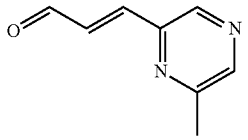

(E)-3-(6-Methylpyrazin-2-yl)prop-2-enal

To a solution of 2-[(E)-3,3-diethoxyprop-1-enyl]-6-methyl-pyrazine (37 g) in acetone (166 ml) was added HCl solution (1 M, 166.45 ml). The mixture was stirred at 25° C. for 1 h. Then the mixture was adjusted with saturated $NaHCO_3$ solution (50 ml) to pH=7, extracted with EE (300 ml×3). The combined organic layers were washed with brine (500 ml×2), dried with $Na_2SO_4$, filtered and concentrated. The residue was purified by silica gel column chromatography (PE:EA=10:1 to 3:1) to yield 22.4 g of the title compound.

I-12c

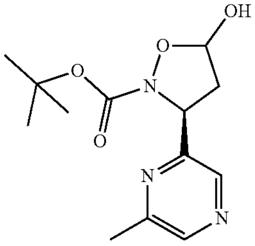

Tert-butyl (3S)-5-hydroxy-3-(6-methylpyrazin-2-yl)isoxazolidine-2-carboxylate

To a solution of [diphenyl-[(2S)-pyrrolidin-2-yl]methoxy]-trimethyl-silane (9.84 g) in $CHCl_3$ (230 ml) were added (E)-3-(6-methylpyrazin-2-yl)prop-2-enal (22.4 g) and tert-butyl N-hydroxycarbamate (24.16 g) at 0° C. The mixture was warmed to 20° C. smoothly and stirred for 12 h. The reaction mixture was concentrated. The residue was purified by RP-LC (flow: 100 ml/min; gradient: from 90% $H_2O$ (0.1% FA)/10% ACN to 55% $H_2O$ (0.1% FA)/45% ACN in 22 min; 55% $H_2O$ (0.1% FA)/45% ACN for 16 min; column: Agela C18, 20 μm, 100 Å, 60.6 mm×187 mm) to yield 23.5 g of the title compound.

I-12d

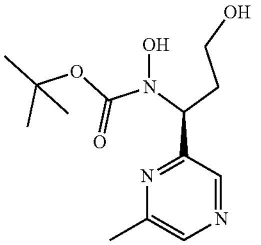

Tert-butyl N-hydroxy-N-[(1S)-3-hydroxy-1-(6-methylpyrazin-2-yl)propyl]carbamate

To a solution of tert-butyl (3S)-5-hydroxy-3-(6-methylpyrazin-2-yl)isoxazolidine-2-carboxylate (23.5 g) in MeOH (235 ml) was added $NaBH_4$ (3.79 g). The mixture was stirred at 0° C. for 2 h. The reaction mixture was quenched by addition of saturated $NH_4Cl$ (50 ml) solution, then diluted with water (800 ml) and extracted with EA (1 l×3). The combined organic layers were washed with brine (1 l), dried over $Na_2SO_4$, filtered and concentrated under reduced pressure to give a residue. The crude product was purified by RP-LC (flow: 200 ml/min; gradient: from 90% $H_2O$ (0.1% FA)/10% ACN to 70% $H_2O$ (0.1% FA)/30% ACN in 12 min; 70% $H_2O$ (0.1% FA)/30% ACN for 10 min; column: Welch Ultimate XB C18, 20-40 μm, 120 Å, 95 mm×365 mm) to yield 21 g of the title compound.

I-12e

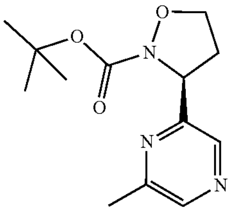

Tert-butyl (3S)-3-(6-methylpyrazin-2-yl)isoxazolidine-2-carboxylate

To a solution of tert-butyl N-hydroxy-N-[(1S)-3-hydroxy-1-(6-methylpyrazin-2-yl)propyl]carbamate (21 g) in THF (210 ml) was added tributylphosphane (23.99 g) and DIAD (19.48 g) at 0° C. The mixture was stirred at 0° C. for 6 h, and then it was stirred at 25° C. for 6 h. The reaction mixture was concentrated under reduced pressure to remove the solvent. The crude product was purified by RP prep-HPLC (flow: 400 ml/min; gradient: from 80% $H_2O$ (0.1% FA)/20% ACN to 56% $H_2O$ (0.1% FA)/44% ACN in 44 min; 56% $H_2O$ (0.1% FA)/44% ACN for 19 min; column: Phenomenex luna C18, 15 μm, 100 Å, 150 mm×400 mm) followed by silica gel column chromatography (PE:EA=10:1 to 0:1) to give three fractions: fraction one 3 g (90.8% e.e.), fraction two 3.5 g (90.4% e.e.) and fraction three 1.5 g (87.5% e.e.). Fraction one and fraction two were combined with to give 6.3 g of the title compound (90.4% ee).

$^1H$ NMR (400 MHz, $CDCl_3$): δ ppm 8.58 (1H), 8.37 (1H), 5.34 (1H), 4.18 (1H), 3.95 (1H), 2.86-2.72 (1H), 2.67-2.57 (1H), 2.56 (3H), 1.50 (9H).

Chiral HPLC:

(chiralpak IC-3, 50×4.6 mm, 3 μm; phase A: $CO_2$, B MeOH (0.05% DEA; gradient: MeOH (0.05% DEA) in $CO_2$ from 5 to 40%; flow 3 ml/min; T 35° C., p 100 bar)

Tert-butyl (3R)-3-(6-methylpyrazin-2-yl)isoxazolidine-2-carboxylate: tR 2.06 min, 4.8%, Tert-butyl (3S)-3-(6-methylpyrazin-2-yl)isoxazolidine-2-carboxylate: tR 1.17 min, 95.2%

I-12

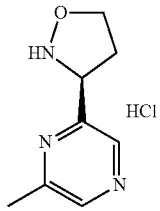

(3S)-3-(6-Methylpyrazin-2-yl)isoxazolidine hydrochloride salt

Tert-butyl (S)-3-(6-methylpyrazin-2-yl)isoxazolidine-2-carboxylate (500 mg) was dissolved in dioxane (6 ml) and HCl (9.42 ml, 4 M in dioxane) was added at RT with stirring. After standing overnight the solvent was removed in vacuo, the residue dissolved in ACN/water and lyophilised overnight to yield 420 mg of the title compound.

LC/MS: m/z=166.2 $[M+H]^+$; tR: 0.70 min (LC/MS-method A).

I-13a

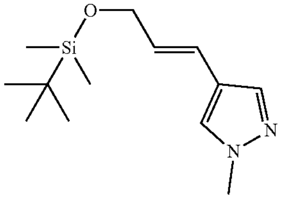

I-13: 3-(1-Methylpyrazol-4-yl)isoxazolidine hydrochloride salt

Tert-butyl-dimethyl-[(E)-3-(1-methylpyrazol-4-yl)allyloxy]silane

4-Bromo-1-methyl-1H-pyrazole (1.05 g), (E)-3-(tert-butyldimethylsilyloxy)propene-1-yl-boronic acid pinacol ester (2.24 ml) and caesium carbonate (4.12 g) were dissolved in a mixture of dioxane (42 ml) and water (10.5 ml). Ar was bubbled through the solution for 5 min. Then chloro(2-dicyclohexylphosphino-2',4',6'-triisopropyl-1,1'-biphenyl)[2-(2'-amino-1,1'-biphenyl]palladium(II) (249 mg) was added, again Ar was bubbled through the solution for 2 min and the mixture was refluxed for 1 h with stirring under Ar. After cooling water and EA were added. The aqueous phase was extracted with EA (2×). The combined organic phases were dried over sodium sulphate, filtered and concentrated in vacuo to yield 1.97 g of the title compound that was directly used in the next step.

I-13b

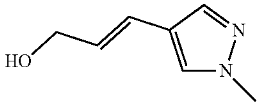

(E)-3-(1-Methylpyrazol-4-yl)prop-2-en-1-ol

At 0° C. tert-butyl-dimethyl-[(E)-3-(1-methylpyrazol-4-yl)allyloxy]silane (1.97 g) was dissolved in THF (40 ml) and tetrabutylammonium fluoride (9.6 ml, 1 M in THF) was added. After 5 h solid $NaHCO_3$ was added with stirring. After 2 h the suspension was filtered and the filtrate concentrated in vacuo. The residue was purified by silica gel chromatography (80 g $SiO_2$, 100% DCM for 5 min; from 100% DCM to 10% ethanol in 40 min; then 10% EtOH for 10 min). The pure product containing fractions were combined and the solvent was removed in vacuo to yield 1.08 g of the title compound.

LC/MS: m/z=139.2 $[M+H]^+$; tR: 0.71 min (LC/MS-method A)

I-13c

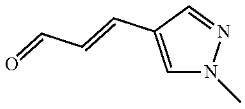

(E)-3-(1-Methylpyrazol-4-yl)prop-2-enal (E)-3-(1-Methyl-1H-pyrazol-4-yl)prop-2-en-1-ol (870 mg) was dissolved in DCM (42 ml) and $MnO_2$ (10.95 g) was added with stirring. After 30 min the mixture was filtered and the filtrate concentrated in vacuo to yield 666 mg of the title compound that was directly used in the next step.

LC/MS: m/z=137.2 $[M+H]^+$; tR: 0.79 min (LC/MS-method A)

I-13d

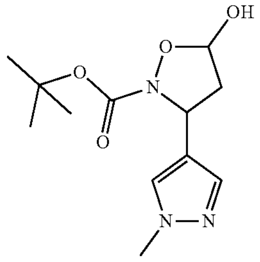

Tert-butyl 5-hydroxy-3-(1-methylpyrazol-4-yl)isoxazolidine-2-carboxylate

At 0° C. [diphenyl-[(2S)-pyrrolidin-2-yl]methoxy]-trimethyl-silane (410 mg) was dissolved in DCM (28 ml). (E)-3-(1-Methyl-1H-pyrazol-4-yl)acrylaldehyde (0.66 g) and tert-butyl N-hydroxycarbamate (0.79 g) were added with stirring. After standing in the refrigerator (4° C.) overnight further silyl ether (0.1 eq.) and carbamate (0.5 eq.) were added and the mixture kept for 24 h in the refrigerator. Then saturated $NH_4Cl$ solution was added. The aqueous phase was extracted (3×) with DCM, the combined organic phases were dried over sodium sulphate, filtered and concentrated in vacuo. The residue was purified by RP prep-HPLC (flow 50 ml/min; 90% $H_2O$/10% ACN to 10%

$H_2O$/90% ACN in 17.5 min; Agilent Prep C18—10 μm, 30×250 mm). The pure product containing fractions were combined, the ACN was removed in vacuo and the aqueous phase was lyophilised to yield 267 mg of the title compound.

LC/MS: m/z=270.3 $[M+H]^+$; tR: 1.21 min (LC/MS-method A).

I-13e

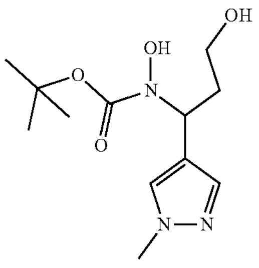

Tert-butyl N-hydroxy-N-[3-hydroxy-1-(1-methylpyrazol-4-yl)propyl]carbamate

Tert-butyl 5-hydroxy-3-(1-methylpyrazol-4-yl)isoxazolidine-2-carboxylate (266 mg) was dissolved in methanol (12 ml), cooled to 0° C. and $NaBH_4$ (37 mg) was added with stirring. After 1 h saturated $NH_4Cl$ solution was added. The aqueous phase was extracted (2×) with DCM, the combined organic phases were dried over sodium sulphate, filtered and concentrated in vacuo. The residue was purified by RP prep-HPLC (flow 50 ml/min, 90% $H_2O$/10% ACN to 10% $H_2O$/90% ACN in 17.5 min; Agilent Prep C18—10 μm, 30×250 mm). The pure product containing fractions were combined, the ACN was removed in vacuo and the aqueous phase was lyophilised to yield 73 mg of the title compound.

LC/MS: m/z=272.3 $[M+H]^+$; tR: 1.06 min (LC/MS-method A)

I-13f

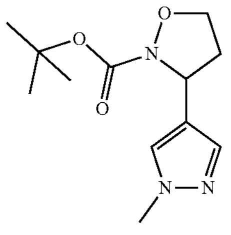

Tert-butyl 3-(1-methylpyrazol-4-yl)isoxazolidine-2-carboxylate

Tert-butyl N-hydroxy-N-[3-hydroxy-1-(1-methylpyrazol-4-yl)propyl]carbamate (72 mg) was dissolved in THF (3 ml) and with stirring triphenylphosphine (101 mg) and DIAD (210 μl) were added. After standing overnight further triphenylphosphine (36 mg) and DIAD (25 μl) were added. After stirring for 5 h the temperature was increased to 50° C. and stirring continued for 1.5 h. Then the solvent was removed in vacuo and the residue was directly separated by RP prep-HPLC (flow 50 ml/min, 97% $H_2O$/3% ACN to 10% $H_2O$/90% ACN in 15 min; Agilent Prep C18—10 μm, 21.2×250 mm). The pure product containing fractions were combined, the ACN was removed in vacuo and the aqueous phase was lyophilised to yield 30 mg of the title compound. 50 mg of the starting material were also recovered.

LC/MS: m/z=254.3 $[M+H]^+$; tR: 1.44 min (LC/MS-method A).

I-13

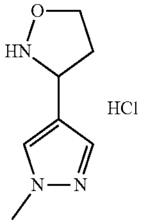

3-(1-Methylpyrazol-4-yl)isoxazolidine hydrochloride salt

Following the procedure described in I-12 77 mg of the title compound was obtained.

LC/MS: m/z=154.1 $[M+H]^+$; tR: 0.05 min (LC/MS-method B).

I-14: 3-(5-Fluoro-3-pyridyl)isoxazolidine HCl/TFA Salt

I 14-1a

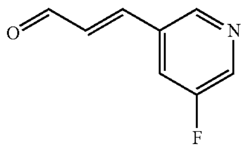

(E)-3-(5-Fluoro-3-pyridyl)prop-2-enal

A mixture of 3-bromo-5-fluoro-pyridine (48 g), prop-2-enal (45.87 g), $Pd(OAc)_2$ (3.06 g), benzyl(triethyl)ammonium chloride (62.12 g) and TEA (82.80 g) in DMF (400 ml) was stirred at 70° C. under $N_2$ atmosphere for 12 h. The mixture was concentrated, diluted with water (800 ml), extracted with ethyl acetate (500 ml×3), washed with brine (1 l), dried with $Na_2SO_4$, filtered and concentrated. The residue was purified by flash silica gel column chromatography (PE:EA=1:1) to yield 26.7 g of the title compound.

$^1H$ NMR (400 MHz, $CDCl_3$): δ ppm 9.77 (1H), 8.62 (1H), 8.55 (1H), 7.60 (1H), 7.50 (1H), 6.78 (1H).

I-14-1b

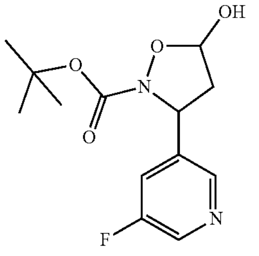

Tert-butyl 3-(5-fluoro-3-pyridyl)-5-hydroxy-isoxazolidine-2-carboxylate (E)-3-(5-Fluoro-3-pyridyl)prop-2-enal (2.5 g) was solved in toluene (30 ml) and cooled to 0° C. [Diphenyl-[(2S)-pyrrolidin-2-yl]methoxy]-trimethyl-silane (1.03 ml) and benzoic acid (404 mg) were added and the mixture was stirred for a few minutes. Tert-butyl hydroxycarbamate (2.64 g) was added. The suspension was stirred for 2 h at 0° C. and stored at 5° C. overnight. The reaction mixture was quenched with saturated sodium bicarbonate solution and extracted three times with ethyl acetate. The combined organic layers were dried with sodium sulfate, filtered and evaporated under reduced pressure. The raw material was purified by silica gel chromatography (330 g $SiO_2$, n-heptane/acetone=100/0 to 40/60 in 33 min). The combined fractions were evaporated under reduced pressure and purified by prep. RP-HPLC in six runs (Column: YMC-Actus Triart Prep C18-S, 250×30, S-10 μm, 12 nm; flow: 70 ml/min; 2 min 95% $H_2O$+0.05% TFA, within 12 min up to 100% ACN, 4 min 100% ACN). The combined fractions were lyophilised and gave 1.034 g of the title compound showing no chiral induction at the 3-pyridyl-isoxazolidine position.

I-14-1c

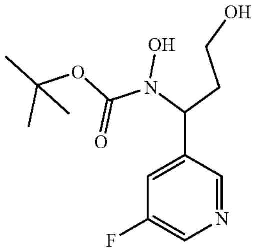

Tert-butyl N-[1-(5-fluoro-3-pyridyl)-3-hydroxy-propyl]-N-hydroxy-carbamate

Tert-butyl 3-(5-fluoro-3-pyridyl)-5-hydroxy-isoxazolidine-2-carboxylate (1.034 g) was solved in methanol (15 ml) and cooled to 0° C. Sodium borohydride (137.6 mg) was added in 2 portions (10 minutes in between) at 0° C. with stirring. The mixture was allowed to warm up to room temperature and stirred for 2 h. The reaction mixture was evaporated under reduced pressure, quenched with saturated sodium bicarbonate solution and extracted three times with ethyl acetate. The combined organic layers were dried with sodium sulfate, filtered and evaporated under reduced pressure to give 856 mg of the title compound.

I-14-1d

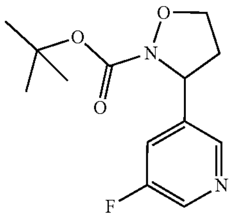

Tert-butyl 3-(5-fluoro-3-pyridyl)isoxazolidine-2-carboxylate

Tert-butyl N-[1-(5-fluoro-3-pyridyl)-3-hydroxy-propyl]-N-hydroxy-carbamate (854 mg) and triphenylphosphine (1.10 g) were solved in THF (20 ml). The solution was cooled to 0° C. and diisopropylazodicarboxylate (696 μl) was added. Stirred for 30 minutes at 0° C. and left standing for 3 days. Then further triphenylphosphine (1.10 g) and diisopropylazodicarboxylate (696 μl) were added and stirred overnight. The reaction mixture was purified by prep. RP-HPLC (Column: Water OBD Sunfire C18 250×50 mm 10 μm; flow rate: 150 ml/min; 4 min 90% $H_2O$, within 25 min up to 90% ACN). The combined fractions were lyophilised and gave 636 mg of the title compound.

I-14-1

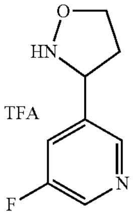

3-(5-Fluoro-3-pyridyl)isoxazolidine TFA salt

Tert-butyl 3-(5-fluoro-3-pyridyl)isoxazolidine-2-carboxylate (174.4 mg) was solved in dichloromethane (5 ml) and trifluoroacetate (0.5 ml) and stirred overnight. The mixture was evaporated under reduced pressure and lyophilised twice to give 158 mg of the title compound.

LC/MS: m/z=169.2 $[M+H]^+$; tR: 0.69 min (LC/MS-method A)

I-14-2: (3S)-3-(5-Fluoro-3-pyridyl)isoxazolidine HCl Salt

I-14-2a

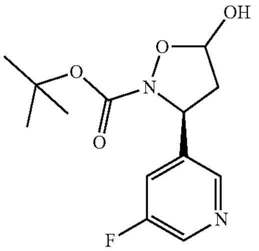

Tert-butyl (3S)-3-(5-fluoro-3-pyridyl)-5-hydroxy-isoxazolidine-2- carboxylate

To a solution of [diphenyl-[(2S)-pyrrolidin-2-yl]methoxy]-trimethyl-silane (11.50 g) in chloroform (260 ml) was added (E)-3-(5-fluoro-3-pyridyl)prop-2-enal (I-14-1a, 26.7 g) and tert-butyl N-hydroxycarbamate (28.23 g) at 0° C. The mixture was warmed to 20° C. smoothly and stirred for 12 h. The reaction mixture was concentrated. The residue was purified by RP-LC (flow: 400 ml/min; gradient: from 90% $H_2O$ (0.1% FA)/10% ACN to 60% $H_2O$ (0.1% FA)/40% ACN in 50 min; 60% $H_2O$ (0.1% FA)/40% ACN for 25 min; column: Phenomenex luna C18.15 μm, 100 Å, I.D. 150 mm×H 400 mm) to yield 25 g of the title compound.

$^1H$ NMR (400 MHz, $CDCl_3$): δ ppm 8.45-8.37 (2), 7.44 (1H), 5.94-5.84 (1H), 5.39 (1H), 2.84 (1H), 2.33-2.20 (1H), 1.47 (9H).

I-14-2b

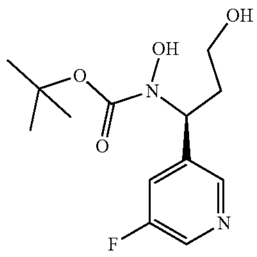

Tert-butyl N-[(1S)-1-(5-fluoro-3-pyridyl)-3-hydroxy-propyl]-N-hydroxy- carbamate To a solution of tert-butyl 3-(5-fluoro-3-pyridyl)-5-hydroxy-isoxazolidine-2-carboxylate (25 g) in methanol (250 ml) was added $NaBH_4$ (3.99 g) at 0° C. The mixture was stirred at 0° C. for 1 h. The reaction mixture was quenched with saturated $NH_4Cl$ solution (50 ml), and then diluted with water (800 ml), extracted with ethyl acetate (1 lx3). The combined organic layers were washed with brine (1 l), dried with $Na_2SO_4$, filtered and concentrated. The crude product was purified by RP-LC (flow: 200 ml/min; gradient: from 90% $H_2O$ (0.1% FA)/10% ACN to 60% $H_2O$ (0.1% FA)/40% ACN in 15 min; 60% $H_2O$ (0.1% FA)/40% ACN for 8 min; column: Welch Ultimate XB_C18, 20-40 μm, 120 Å, I.D. 95 mmxH 365 mm) to yield 23.5 g of the title compound (enantiomeric ratio: 94.7 (S): 5.3 (R)).

$^1$H NMR (400 MHz, $CDCl_3$): δ ppm 8.49-8.30 (2H), 7.66-7.51 (1H), 5.33 (1H), 3.89-3.71 (2H), 2.41 (1H), 2.05 (1H), 1.47 (9H).

Chiral HPLC:

(chiralpak AD-3, 50×4.6 mm, 3 μm; phase A: $CO_2$, B MeOH (0.05% DEA; gradient: MeOH (0.05% DEA) in $CO_2$ from 5 to 40%; flow 3 ml/min; T 35° C., p 100 bar)

Tert-butyl N-[(1S)-1-(5-fluoro-3-pyridyl)-3-hydroxy-propyl]-N-hydroxy-carbamate: tR 0.90 min, 94.7%, Tert-butyl N-[(1R)-1-(5-fluoro-3-pyridyl)-3-hydroxy-propyl]-N-hydroxy-carbamate: tR 0.97 min, 5.3%

I-14-2c

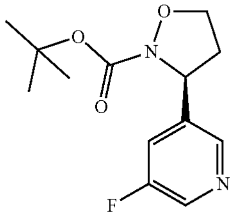

Tert-butyl (3S)-3-(5-fluoro-3-pyridyl)isoxazolidine-2-carboxylate

To a solution of tert-butyl N-[1-(5-fluoro-3-pyridyl)-3-hydroxy-propyl]-N-hydroxy-carbamate (23.5 g) in THF (235 ml) was added tributylphosphane (26.57 g) and DIAD (21.58 g) at 0° C. The mixture was warmed to 25° C. smoothly, stirred for 12 h under $N_2$ atmosphere. Then the reaction mixture was concentrated. The residue was purified by RP HPLC (flow: 400 ml/min; gradient: from 80% $H_2O$ (0.1% FA)/20% ACN to 56% $H_2O$ (0.1% FA)/44% ACN in 44 min; 56% $H_2O$ (0.1% FA)/44% ACN for 19 min; column: Phenomenex luna C18, 15 μm, 100 Å, I.D. 150 mmxH 400 mm) and silica gel column chromatography (PE:EA=10:1 to 0:1) to yield 14.3 g of the title compound.

$^1$H NMR (400 MHz, $CDCl_3$): δ ppm 8.42 (1H), 8.38 (1H), 7.46 (1H), 5.28 (1H), 4.21 (1H), 3.90 (1H), 2.85 (1H), 2.29 (1H), 1.48 (9H).

Chiral HPLC: tR: 5.47 min, (R-enantiomer, 5.3%), 10.18 min (S-enatiomer, 94.7%), (Chiralcel AD-H, 4.6 mmx250 mm, 5 μm; EtOH+0.1% IPA; flow 0.75 ml/min; T 30° C.)

I-14-2

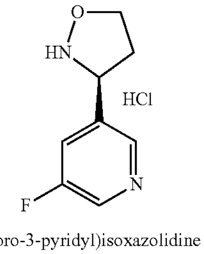

(3S)-3-(5-Fluoro-3-pyridyl)isoxazolidine HCl salt

Following the procedure described in I-12 129 mg of the title compound was obtained.

LC/MS: m/z=169.2 [M+H]$^+$; tR: 0.68 min (LC/MS-method A).

I-15

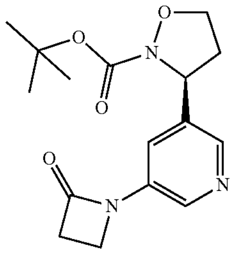

1-[5-[(3S)-Isoxazolidin-3-yl]-3-pyridyl]azetidin-2-one TFA salt

I-15a: Tert-butyl (3S)-3-[5-(2-oxoazetidin-1-yl)-3-pyridyl]isoxazolidine-2-carboxylate Tert-butyl (3S)-3-(5-bromo-3-pyridyl)isoxazolidine-2-carboxylate (I-11d, 100 mg) was dissolved in dioxane (2 ml) and under argon 2-azetidinone (31.2 mg), cesium carbonate (141.4 mg), 45-bis(diphenylphosphino)-9,9-dimethylxanthene (5.6 mg) and tris(dibenzylideneacetone)dipalladium (0) (29.3 mg) were added. After 5 h at 100° C. a mixture of EA and $H_2O$ was added, the phases were separated and the aqueous phase was extracted with EA (3×). The combined organic phases were washed with brine and dried over magnesium sulphate, filtered and concentrated in vacuo. The residue was purified by flash chromatography on silica gel (25 g; 0% to 3% MeOH in DCM over 37 min). The compound containing fractions were combined and the solvent was removed in vacuo to yield 81 mg of the title compound.

LC/MS: m/z=320.4 [M+H]+; tR: 1.38 min (LC/MS-method A) $^1$H NMR (400 MHz, DMSO-$d_6$) δ ppm 8.47 (1H), 8.39 (1H), 7.70 (1H), 5.22 (1H), 4.18 (1H), 3.78-3.65 (3H), 3.14 (1H), 2,84 (1H), 2.17 (1H), 1.40 (9H).

I-15

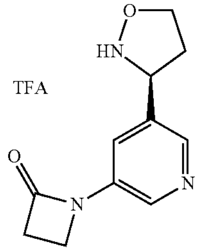

1-[5-[(3S)-Isoxazolidin-3-yl]-3-pyridyl]azetidin-2-one TFA salt

Tert-butyl (3S)-3-[5-(2-oxoazetidin-1-yl)-3-pyridyl] isoxazolidine-2-carboxylate (80 mg) was dissolved in DCM (3 ml) and TFA (188 μl) was added at RT with stirring. After 72 h the conversion was not complete, further TFA (50 μl) was added at RT with stirring. After 1 h the solvent was removed in vacuo and the residue co-evaporated twice with toluene to yield 80 mg of the title compound.

LC/MS: m/z=220.1 $[M+H]^+$; tR: 0.22 min (LC/MS-method D)

I-16

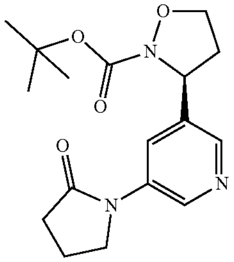

1-[5-[(3S)-isoxazolidin-3-yl]-3-pyridyl]pyrrolidin-2-one
I-16a: Tert-butyl (3S)-3-[5-(2-oxopyrrolidin-1-yl)-3-pyridyl]isoxazolidine-2-carboxylate Tert-butyl (3S)-3-(5-bromo-3-pyridyl)isoxazolidine-2-carboxylate (I 11d, 100 mg) was dissolved in dioxane (3 ml) and under argon 2-pyrrolidinone (35 μl), cesium carbonate (141.4 mg), 4,5-bis(diphenylphosphino)-9,9-dimethylxanthene (5.6 mg) and tris(dibenzylideneacetone)dipalladium (0) (29.3 mg) were added. After 5 h at 100° C. a mixture of EA and $H_2O$ was added, the phases were separated and the aqueous phase was extracted with EA (3×). The combined organic phases were washed with brine and dried over magnesium sulphate, filtered and concentrated in vacuo. The residue was purified by flash chromatography on silica gel (25 g; 0% to 3% MeOH in DCM over 37 min). The compound containing fractions were combined and the solvent was removed in vacuo to yield 21 mg of the title compound.

LC/MS: m/z=334.4 $[M+H]^+$; tR: 1.34 min (LC/MS-method A)

$^1H$ NMR (400 MHz, DMSO-$d_6$) δ ppm 8.71 (1H), 8.30 (1H), 8.10 (1H), 5.23 (1H), 4.17 (t1H), 3.87 (2H), 3.75 (1H), 2.84 (1H), 2.50 (2H), 2.17 (1H), 2.09 (1H), 1.39 (9H).

I-16

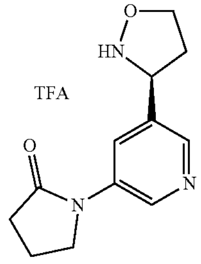

1-[5-[(3S)-Isoxazolidin-3-yl]-3-pyridyl]pyrrolidin-2-one TFA salt

Tert-butyl (3S)-3-[5-(2-oxopyrrolidin-1-yl)-3-pyridyl] isoxazolidine-2-carboxylate (20 mg) was dissolved in DCM (3 ml) and TFA (45 μl) was added at RT with stirring. After 1.5 h the conversion was not complete, further TFA (30 μl) was added at RT with stirring. After 1 h the solvent was removed in vacuo and the residue co-evaporated twice with toluene to yield 20 mg of the title compound.

LC/MS: m/z=234.1 $[M+H]^+$; tR: 0.21 min (LC/MS-method D)

I-17: (3S)-3-Pyrazin-2-ylisoxazolidine hydrochloride Salt

I-17a

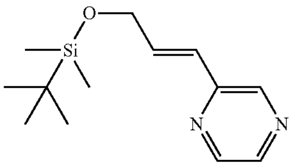

Tert-butyl-dimethyl-[(E)-3-pyrazin-2-ylallyoxy]silane

2-Bromopyrazine (2.5 g), (E)-3-(tert-butyldimethylsilyloxy)propene-1-yl-boronic acid pinacol ester (5.3 ml) and caesium carbonate (9.73 g) were dissolved in a mixture of dioxane (42 ml) and water (10.5 ml). Then Ar was bubbled through the solution for 5 min and chloro(2-dicyclohexylphosphino-2',4',6'-triisopropyl-1,1'-biphenyl)[2-(2'-amino-1,1'-biphenyl]palladium(II) (590 mg) was added. Ar was again bubbled through the solution for 5 min and the mixture was refluxed for 1 h with stirring under Ar. After cooling water and EA were added. The aqueous phase was extracted with EA (2×). The combined organic phases were dried over sodium sulphate, filtered and concentrated in vacuo to yield 6.36 g of the title compound that was directly used in the next step.

I-17b

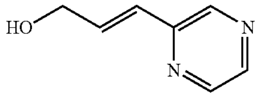

(E)-3-Pyrazin-2-ylprop-2-en-1-ol

Tert-butyl-dimethyl-[(E)-3-pyrazin-2-ylallyloxy]silane (6.36 g) was dissolved in THF (100 ml), the mixture was cooled to 0° C. and tetrabutylammonium fluoride (31.75 ml, 1 M in THF) was added. After 2 h solid $NaHCO_3$ was added with stirring. After 1.5 h the suspension was filtered and the filtrate concentrated in vacuo. The residue was purified by silica gel chromatography (200 g $SiO_2$, 100% DCM for 5 min; from 100% DCM to 10% ethanol in 45 min; then 10% EtOH for 15 min). The pure product containing fractions were combined and the solvent was removed in vacuo to yield 1.82 g of the title compound.

LC/MS: m/z=137.2 $[M+H]^+$; tR: 0.64 min (LC/MS-method A)

I-17c

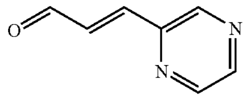

(E)-3-Pyrazin-2-ylprop-2-enal (E-3-Pyrazin-2-ylprop-2-en-1-ol (1.82 ma) was dissolved in DCM (90 ml) and $MnO_2$ (23.24 g) was added with stirring. After 30 min the mixture was filtered and the filtrate concentrated in vacuo to yield 1.12 g of the title compound that was directly used in the next step.

LC/MS: m/z=135.1 $[M+H]^+$; tR: 0.73 min (LC/MS-method A)

I-17d

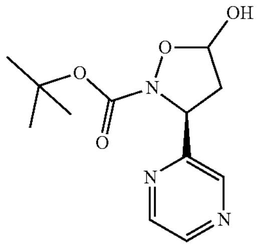

Tert-butyl (3S)-5-hydroxy-3-pyrazin-2-yl-isoxazolidine-2-carboxylate

[Diphenyl-[(2S)-pyrrolidin-2-yl]methoxy]-trimethyl-silane (700 mg) was dissolved in DCM (40 ml) and the mixture was cooled to 0° C. (E)-3-Pyrazin-2-ylprop-2-enal (1.12 g) dissolved in DCM (10 ml) and tert-butyl N-hydroxycarbamate (1.36 g) were added with stirring. After standing in the refrigerator (4° C.) overnight further silyl ether (0.1 eq.) and carbamate (0.5 eq.) were added and the mixture kept for 24 h in the refrigerator. Then saturated $NH_4Cl$ solution was added. The aqueous phase was extracted with DCM (2×), the combined organic phases were dried over sodium sulphate, filtered and concentrated in vacuo. The residue was purified by RP prep-HPLC in 6 runs (flow 75 ml/min, 90% $H_2O$/10% ACN to 10% $H_2O$/90% ACN in 17.5 min; Agilent Prep C18—10 μm, 30×250 mm). The pure product containing fractions were combined, the ACN was removed in vacuo and the aqueous phase was lyophilised to yield 358 mg of the title compound.

LC/MS: m/z=268.3 $[M+H]^+$; tR: 1.19 min (LC/MS-method A).

I-17e

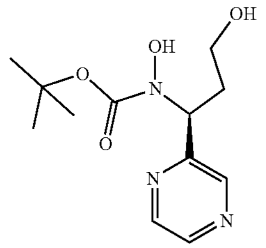

Tert-butyl N-hydroxy-N-[(1S)-3-hydroxy-1-pyrazin-2-yl-propyl]carbamate

Tert-butyl (3S)-5-hydroxy-3-pyrazin-2-yl-isoxazolidine-2-carboxylate (360 mg) was dissolved in methanol (20 ml), cooled to 0° C. and $NaBH_4$ (50 mg) was added with stirring. After 1 h saturated $NH_4Cl$ solution was added. The aqueous phase was extracted with DCM (5×), the combined organic phases were dried over sodium sulphate, filtered and concentrated in vacuo. The residue was purified by RP prep-HPLC (flow 75 ml/min, 90% $H_2O$/10% ACN to 10% $H_2O$/90% ACN in 17.5 min; Agilent Prep C18—10 μm, 30×250 mm). The pure product containing fractions were combined, the ACN was removed in vacuo and the aqueous phase was lyophilised to yield 209 mg of the title compound.

LC/MS: m/z=270.3 $[M+H]^+$; tR: 1.06 min (LC/MS-method A)

I-17f

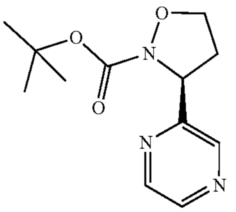

Tert-butyl (3S)-3-pyrazin-2-ylisoxazolidine-2-carboxylate

Tert-butyl N-hydroxy-N-[(1S)-3-hydroxy-1-pyrazin-2-yl-propyl]carbamate (205 mg) was dissolved in THF (5 ml) and with stirring triphenylphosphine (290 mg) and DIAD (210 μl) were added. After stirring for 1 h the solvent was removed in vacuo and the residue was purified by RP prep-HPLC (flow 75 ml/min, 90% $H_2O$/10% ACN to 10% $H_2O$/90% ACN in 15 min; Agilent Prep C18-10 μm, 30×250 mm). The product containing fractions were combined, the ACN was removed in vacuo and the aqueous phase was lyophilised to yield 275 mg of the title compound, which was still containing about 50 mol % of reduced DIAD.

LC/MS: m/z=252.3 $[M+H]^+$; tR: 1.38 min (LC/MS-method A).

I-17

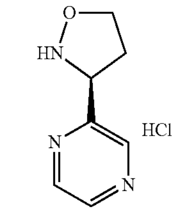

(3S)-3-Pyrazin-2-yl-ylisoxazolidine hydrochloride salt

Following the procedure described in I-12 the title compound (256 mg) was obtained, which was still contaminated with ~50 mol % of reduced DIAD from step I-35f, but this did not interfere with the following step.

LC/MS: m/z=152.2 $[M+H]^+$; tR: 0.46 min (LC/MS-method A).

I-18: 5-[(3S)-Isoxazolidin-3-yl]-2-methyl-pyridine-3-carbonitrile HCl salt

I-18a

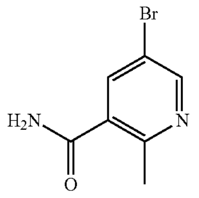

5-Bromo-2-methyl-pyridine-3-carboxamide

To a solution of 5-bromo-2-methyl-pyridine-3-carboxylic acid (15 g), $NH_4Cl$ (11.14 g) and HATU (39.60 g) in DMF (150 ml) was added DIPEA (26.92 g). The mixture was stirred at 20° C. for 12 h. The reaction mixture was diluted with saturated $NaHCO_3$ solution (300 ml), extracted with EA (200 ml×3), washed with brine (200 ml), dried with $Na_2SO_4$, filtered and concentrated to yield 15 g of the title compound which was used directly in the next step.

I-18b

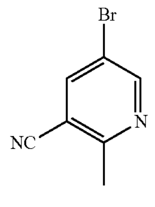

5-Bromo-2-methyl-pyridine-3-carbonitrile

To a solution of 5-bromo-2-methyl-pyridine-3-carboxamide (15 g) in dioxane (300 ml) was added pyridine (55.17 g) and TFAA (73.25 g) and the reaction was stirred at 20° C. for 12 h. Then the mixture was quenched with ice/water (500 ml) and extracted with EA (200 ml×3). The combined organic layers were washed with brine (200 ml), dried with $Na_2SO_4$, filtered and concentrated. The residue was purified by silica gel column chromatography (PE:EA=1:0 to 10:1) to yield 10.2 g of the title compound.

$^1$H NMR (400 MHz, $CDCl_3$) δ ppm 8.75 (1H), 8.02 (1H), 2.75 (3H)

I-18d

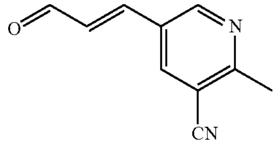

2-Methyl-5-[(E)-3-oxoprop-1-enyl]pyridine-3-carbonitrile

A mixture of 5-bromo-2-methyl-pyridine-3-carbonitrile (13.7 g), prop-2-enal (11.69 g), $Pd(OAc)_2$ (780.53 mg), benzyl(triethyl)ammonium chloride (15.84 g) and TEA (21.11 g) in DMF (130 ml) was stirred at 80° C. under $N_2$ atmosphere for 12 h. The mixture was diluted with water (500 ml), extracted with EA (500 ml×4), washed with brine (250 ml), dried with $Na_2SO_4$, filtered and concentrated. The residue was purified by silica gel column chromatography (PE:EA=10:1 to 2:1) to yield 6.5 g of the title compound.

$^1$H NMR (400 MHz, $CDCl_3$): δ ppm 9.78 (1H), 8.87 (1H), 8.09 (1H), 7.47 (1H), 6.81 (1H), 2.86 (3H)

I-18e

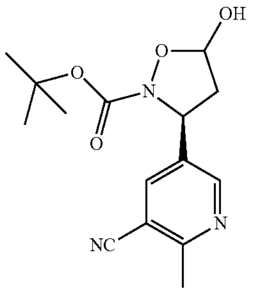

Tert-butyl (3S)-3-(5-cyano-6-methyl-3-pyridyl)-5-hydroxy-isoxazolidine-2-carboxylate To a solution of [diphenyl-[(2S)-pyrrolidin-2-yl]methoxy]-trimethyl-silane (2.50 g) in $CHCl_3$ (70 ml) was added 2-methyl-5-[(E)-3-oxoprop-1-enyl]pyridine-3-carbonitrile (6.6 g) and tert-butyl N-hydroxycarbamate (6.12 g) at 0° C. The mixture was warmed to 25° C. smoothly, stirred for 36 h. The reaction mixture was concentrated. The residue was purified by RP prep-HPLC (0.1% FA condition) to yield 4.9 g of the title compound.

$^1$H NMR (400 MHz, $CDCl_3$): δ ppm 8.65 (1H), 7.91 (1H), 5.87 (1H), 5.36 (1H), 4.61-4.33 (1H), 2.86-2.74 (4H), 2.23 (1H), 1.46 (9H)

I-18f

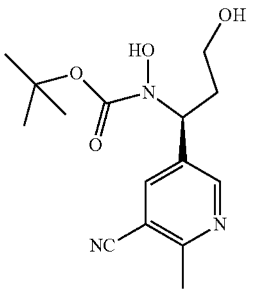

Tert-butyl N-[(1S)-1-(5-cyano-6-methyl-3-pyridyl)-3-hydroxy-propyl]-N-hydroxy-carbamate To a solution of tert-butyl (3S)-3-(5-cyano-6-methyl-3-pyridyl)-5-hydroxy-isoxazolidine-2-carboxylate (4.9 g) in MeOH (50 ml) $NaBH_4$ (728.53 mg) was added at 0° C. The mixture was stirred at 0° C. for 2 h under $N_2$ atmosphere. Then the mixture was quenched with saturated $NH_4Cl$ solution (10 ml), diluted with water (200 ml), extracted with EA (200 ml×2), dried with $Na_2SO_4$, filtered and concentrated. The residue was combined with a former batch, purified by silica gel chromatography (PE:EA=3:1 to 2:1) to yield 3.1 g of the title compound.

$^1H$ NMR (400 MHz, $CDCl_3$): δ ppm 8.69 (1H), 8.03 (1H), 6.72 (1H), 5.31 (1H), 3.92-3.75 (2H), 2.77 (3H), 2.41 (1H), 2.04-1.97 (1H), 1.49 (9H)

I-18g

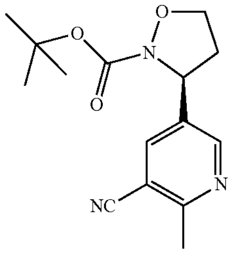

Tert-butyl (3S)-3-(5-cyano-6-methyl-3-pyridyl)-isoxazolidine-2-carboxylate

To a solution of tert-butyl N-[(1 S)-1-(5-cyano-6-methyl-3-pyridyl)-3-hydroxy-propyl]-N-hydroxy-carbamate (3.1 g) in THF (31 ml) tributylphosphane (3.27 g) and DIAD (2.65 g) were added at 0° C. The mixture was warmed to 20° C. smoothly and stirred for 16 h under $N_2$. The mixture was concentrated. The residue was purified by prep. RP-LC (flow: 200 ml/min; gradient: from 85% $H_2O$ (0.1% FA)/15% ACN to 55% $H_2O$ (0.1% FA)/45% ACN in 44 min; 55% $H_2O$ (0.1% FA)/45% ACN for 24 min; column: Welch Ultimate XB C18, 20/40 μm, 100 Å, 95 mm×365 mm) followed by flash silica gel chromatography (PE:EA=1:4) to yield 1.8 g of the title compound (enantiomeric ratio 96 (S): 4 (R)).

$^1H$ NMR (400 MHz, $CDCl_3$): δ ppm 8.66 (1H), 7.92 (1H), 5.27 (1H), 4.22 (1H), 3.90 (1H), 2.86 (1H), 2.77 (3H), 2.26 (1H), 1.50 (9H)

Chiral HPLC:

(chiralpak AD-3, 50×4.6 mm, 3 μm; phase A: $CO_2$, B: MeOH (0.05% DEA; gradient: MeOH (0.05% DEA) in $CO_2$ from 5 to 40%; flow 3 ml/min; T 35° C., p 100 bar)

Tert-butyl (3R)-3-(5-cyano-6-methyl-3-pyridyl)isoxazolidine-2-carboxylate: tR 0.70 min, 4.3%, Tert-butyl (3S)-3-(5-cyano-6-methyl-3-pyridyl)isoxazolidine-2-carboxylate: tR 1.91 min, 95.7%

I-18

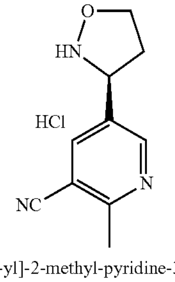

5-[(3S)-Isoxazolidin-3-yl]-2-methyl-pyridine-3-carbonitrile HCl salt

Following the procedure described in I-12 314 mg of the title compound was obtained.

LC/MS: m/z=190.2 $[M+H]^+$; tR: 0.88 min (LC/MS-method A).

$^1H$ NMR (600.05 MHz, DMSO-$d_6$) δ ppm 8.83 (1H), 8.39 (1H), 5.04 (1H), 4.43 (1H), 4.18 (1H), 2.83 (1H), 2.70 (3H), 2.58 (1H)

I-19: (3S)-3-(5-Chloro-2-pyridyl)isoxazolidine TFA Salt

I-19a

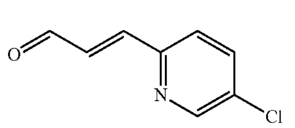

(E)-3-(5-Chloro-2-pyridyl)prop-2-enal

A mixture of 5-chloropyridine-2-carbaldehyde (27 g) and 2-(triphenyl-lambda5-phosphanylidene)acetaldehyde (58.05 g) in THF (250 ml) was stirred at 70° C. for 12 h. The reaction mixture was concentrated. The residue was purified by silica gel column chromatography (PE:EA=1:0 to 0:1) to yield 5.3 g of the title compound.

$^1H$ NMR (400 MHz, $CDCl_3$): δ ppm 9.81 (1H), 8.66 (1H), 7.75 (1H), 7.55-7.44 (2 H), 7.07 (1H).

I-19b

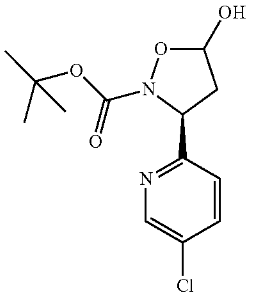

Tert-butyl (3S)-3-(5-Chloro-2-pyridyl)-5-hydroxy-isoxazolidine-2-carboxylate

To a solution of [diphenyl-[(2S)-pyrrolidin-2-yl] methoxy]-trimethyl-silane (2.06 g) in $CHCl_3$ (53 ml) was added (E)-3-(5-chloro-2-pyridyl)prop-2-enal (5.3 g) at 0° C. The mixture was stirred at 0° C. for 15 min, tert-butyl N-hydroxycarbamate (5.05 g) was added. The mixture was warmed to 25° C. smoothly and stirred for 12 h. The reaction mixture was concentrated. The residue was purified by RP prep-HPLC (0.1% FA condition) to yield 4.93 g of the title compound.

I-19c

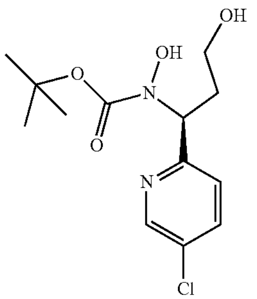

Tert-butyl N-[(1S)-1-(5-chloro-2-pyridyl)-3-hydroxy-propyl]-N-hydroxy-carbamate

To a solution of tert-butyl (3S)-3-(5-chloro-2-pyridyl)-5-hydroxy-isoxazolidine-2-carboxylate (4.9 g) in MeOH (49 ml) was added $NaBH_4$ (308.21 mg) at 0° C. The mixture was stirred at 0° C. for 1 h. The reaction mixture was quenched with saturated $NH_4Cl$ solution (30 ml), diluted with water (200 ml), extracted with EA (200 ml×3). The combined organic layers were washed with brine (300 ml), dried over $Na_2SO_4$, filtered and concentrated. The residue was purified by RP prep-HPLC (0.1% FA condition) to yield 3.7 g of the title compound.

$^1$H NMR (400 MHz, $CDCl_3$): δ ppm 8.45 (1H), 7.69 (1H), 7.29 (1H), 5.44 (1H), 3.87-3.77 (2H), 2.33 (1H), 2.18-2.07 (1H), 1.43 (9H)

I-19d

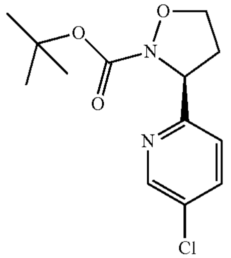

Tert-butyl (3S)-3-(5-chloro-2-pyridyl)isoxazolidine-2-carboxylate

To a solution of tert-butyl N-[(1 S)-1-(5-chloro-2-pyridyl)-3-hydroxy-propyl]-N-hydroxy-carbamate (3.7 g) in THF (37 ml) was added tributylphosphane (3.96 g) and DIAD (3.21 g) at 0° C. The mixture was warmed to 25° C. smoothly and stirred for 12 h under $N_2$. Additional tributylphosphane (989 mg) and DIAD (988 mg) were added at 0° C. The reaction mixture was warmed to 25° C. smoothly and stirred for 12 h. The reaction mixture was concentrated. The residue was purified by RP prep-HPLC (0.1% FA condition) and silica gel column chromatography (PE:EA=10/1 to 0/1) to yield 2.3 g of the title compound (enantiomeric ratio 95 (S): 5 (R)).

$^1$H NMR (400 MHz, $CDCl_3$): δ ppm 8.51 (1H), 7.65 (1H), 7.48 (1H), 5.33 (1H), 4.14 (1H), 3.92 (1H), 2.85-2.74 (1H), 2.62-2.49 (1H), 1.49 (9H)

Chiral HPLC:

(chiralpak AD-3, 50×4.6 mm, 3 μm; phase A: $CO_2$, B: MeOH (0.05% DEA; gradient: MeOH (0.05% DEA) in $CO_2$ from 5 to 40%; flow 3 ml/min; T 35° C., p 100 bar)

Tert-butyl (3R)-3-(5-cyano-6-methyl-3-pyridyl)isoxazolidine-2-carboxylate: tR 0.68 min, 4.9%, Tert-butyl (3S)-3-(5-cyano-6-methyl-3-pyridyl)isoxazolidine-2-carboxylate: tR 1.42 min, 95.1%

I-19

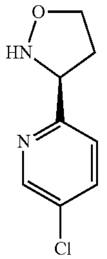

TFA (3S)-3-(5-Chloro-2-pyridyl)isoxazolidine TFA salt

Tert-butyl (3S)-3-(5-chloro-2-pyridyl)isoxazolidine-2-carboxylate (60 mg) was dissolved in DCM (1.5 ml) and trifluoroacetic acid (1.0 ml) was added. After stirring for 2.5 h further TFA (0.2 ml) was added. After standing overnight the solvent was removed in vacuo. The residue was dissolved in ACN/water and lyophilised to yield 60 mg of the title compound.

LC/MS: m/z=185.1 $[M+H]^+$; tR: 1.00 min (LC/MS-method A).

I-20: (3S)-3-(5-Methylpyrazin-2-yl)isoxazolidine HCl salt

I-20a

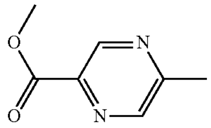

Methyl 5-methylpyrazine-2-carboxylate

To a solution of 5-methylpyrazine-2-carboxylic acid (24 g) in MeOH (240 ml) was added $H_2SO_4$ (852.09 mg). The mixture was stirred at 80° C. for 12 h. The reaction mixture was adjusted to pH=7~8 with saturated $NaHCO_3$ (300 ml) solution, extracted with EA (500 mL×3). The combined organic layers were washed with brine (500 ml), dried over $Na_2SO_4$, filtered and concentrated under reduced pressure to yield 25.65 g of the title compound.

$^1$H NMR (400 MHz, $CDCl_3$): δ ppm 9.20 (1H), 8.58 (1H), 4.04 (3H), 2.68 (3H)

I-20b

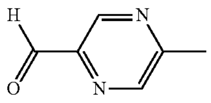

5-Methylpyrazine-2-carbaldehyde

To a solution of methyl 5-methylpyrazine-2-carboxylate (41.3 g) in THF (600 ml) was added LiAlH4 (1 M, 135.72 ml) at −78° C. The mixture was stirred at −78° C. for 0.3 h. The reaction mixture was quenched with AcOH (40 ml) at −78° C. The resulting mixture was warmed to 25° C. and concentrated. The residue was dissolved in HCl (1.5 M, 400 ml) and extracted with DCM (800 ml×3). The organic layers were combined, washed with saturated $NaHCO_3$ solution (200 ml), dried over $Na_2SO_4$, filtered and concentrated under reduced pressure to give a residue. The residue was purified by silica gel column chromatography (PE:EA=1/0~0/1) to yield 21.5 g of the title compound.

$^1$H NMR (400 MHz, $CDCl_3$): δ ppm 10.13 (1H), 9.07 (1H), 8.63 (1H), 2.70 (3H)

I-20c

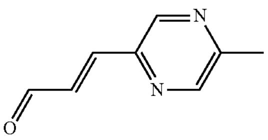

(E)-3-(5-Methylpyrazin-2-yl)prop-2-enal

A mixture of 5-methylpyrazine-2-carbaldehyde (24.9 g) and (formylmethylene)triphenyl-phosphorane (62.05 g) in THF (250 ml) was stirred at 70° C. for 12 h under $N_2$ atmosphere. The reaction mixture was concentrated under reduced pressure to remove solvent, and then triturated with PE/EA (1:1, 1 1), filtered. The filtrate was concentrated, the residue was purified by silica gel column chromatography (PE:EA=1/0~0/1) to yield 17.9 g of the title compound.

$^1$H NMR (400 MHz, $CDCl_3$): δ ppm 9.82 (1H), 8.65 (1H), 8.55 (1H), 7.52 (1H), 7.17 (1H), 2.64 (3H).

I-20d

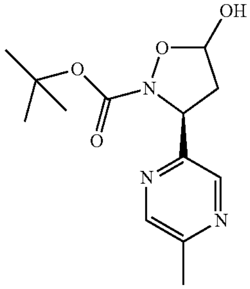

Tert-butyl (3S)-5-hydroxy-3-(5-methylpyrazin-2-yl)isoxazolidine-2-carboxylate

To a solution of [diphenyl-[(2S)-pyrrolidin-2-yl] methoxy]-trimethyl-silane (3.95 g) in $CHCl_3$ (89 ml) was added (E)-3-(5-methylpyrazin-2-yl)prop-2-enal (9 g) at 0° C. The mixture was stirred at 0° C. for 15 min. Then tert-butyl N-hydroxycarbamate (9.71 g) was added. The mixture was stirred at 0° C. for 2 h, warmed to and then was stirred at 25° C. for 10 h. The reaction mixture was concentrated under reduced pressure to remove solvent. The residue was purified by prep. RP-LC (flow: 400 mL/min; gradient: from 80% $H_2O$ (0.1% FA)/20% ACN to 70% $H_2O$ (0.1% FA)/30% ACN in 45 min; 70% $H_2O$ (0.1% FA)/30% ACN for 28 min; column: Phenomenex luna C18, 15 μm, 100 Å, 150 mm×400 mm) to yield 7.75 g of the title compound.

I-20e

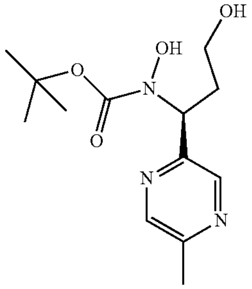

Tert-butyl N-hydroxy-N-[(1S)-3-hydroxy-1-(5-methylpyrazin-2-yl)propyl]carbamate

To a solution of tert-butyl (3S)-5-hydroxy-3-(5-methylpyrazin-2-yl)isoxazolidine-2-carboxylate (15.5 g) in MeOH (150 ml) was added $NaBH_4$ (1.04 g) at 0° C. The mixture was stirred at 0° C. for 1 h. The reaction mixture was quenched with saturated $NH_4Cl$ solution (50 ml), diluted with water (800 ml), extracted with EA (500 ml×3). The combined organic layers were washed with brine (1000 ml), dried over $Na_2SO_4$, filtered and concentrated. The crude product was purified by prep. RP-LC (flow: 100 ml/min; gradient: from 90% $H_2O$ (0.1% FA)/10% ACN to 71% $H_2O$ (0.1% FA)/29% ACN in 9 min; 71% $H_2O$ (0.1% FA)/29% ACN for 12 min; column: Agela C18, 20 μm, 100 Å, 60.6 m×187 mm) to yield 14.1 g of the title compound.

$^1$H NMR (400 MHz, $CDCl_3$): δ ppm=8.54 (1H), 8.34 (1H), 7.62 (1H), 5.50 (1H), 3.83 (2H), 2.57 (3H), 2.47 (1H), 2.37 (1H), 2.16 (1H), 1.48 (9H)

I-20f

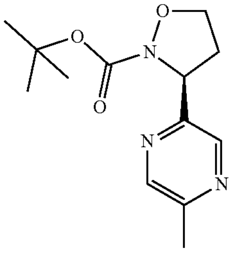

Tert-butyl (3S)-3-(5-methylpyrazin-2-yl)isoxazolidine-2-carboxylate

To a solution of tert-butyl N-hydroxy-N-[(1 S)-3-hydroxy-1-(5-methylpyrazin-2-yl)propyl]carbamate (14.1 g) in THF (141 ml) was added tributylphosphane (16.11 g) and DIAD (13.08 g) at 0° C. The mixture was stirred at 0° C. for 2 h, warmed to 25° C. smoothly, stirred for 10 h under $N_2$. The reaction mixture was concentrated under reduced pressure to remove the solvent. The crude product was purified by prep. RP-LC (flow: 400 ml/min; gradient: from 85% $H_2O$ (0.1% FA)/15% ACN to 50% $H_2O$ (0.1% FA)/50% ACN in 40 min; 50% $H_2O$ (0.1% FA)/50% ACN for 19 min; column: Phenomenex luna C18, 15 μm, 100 Å, 150 mm×400 mm) and silica gel column chromatography (PE:EA=10/1~0/1) to yield 8 g of crude material (89% ee) as a yellow oil. This was triturated with PE/EA (10:1, 50 ml) to yield 5.8 g of the title compound as the filter cake (99.0% e.e.).

$^1$H NMR (400 MHz, $CDCl_3$): δ ppm 8.64 (1H), 8.40 (1H), 5.35 (1H), 4.19 (1H), 3.95 (1H), 2.84-2.72 (1H), 2.67-2.59 (1H), 2.59-2.55 (3H), 1.50 (9H)

Chiral HPLC:

(chiralpak AD-3, 50×4.6 mm, 3 μm; phase A: $CO_2$, B MeOH (0.05% DEA; gradient: MeOH (0.05% DEA) in $CO_2$ from 5 to 40%; flow 3 ml/min; T 35° C., p 100 bar)

Tert-butyl (3R)-3-(5-methylpyrazin-2-yl)isoxazolidine-2-carboxylate: tR 0.97 min, 0.5%, Tert-butyl (3S)-3-(5-methylpyrazin-2-yl)isoxazolidine-2-carboxylate: tR 2.40 min, 99.5%

I-20

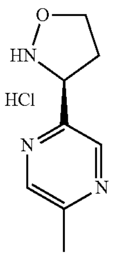

(3 S)-3-(5-Methylpyrazin-2-yl)isoxazolidine HCl salt

Tert-butyl (3S)-3-(5-methylpyrazin-2-yl)isoxazolidine-2-carboxylate (75 mg) was dissolved in dioxane (3 ml). HCl solution (4 N in dioxane, 1.4 ml) was added with stirring followed by further HCl solution (4 N in dioxane, 1.4 ml) 24 h later. After 1 h the mixture was concentrated in vacuo, dissolved in ACN/water and lyophilised overnight to yield 60 mg of the title compound.

LC/MS: m/z=166.2 $[M+H]^+$; tR: 0.68 min (LC/MS-method A).

I-21: 3-(5-Methyl-1,3,4-thiadiazol-2-yl)isoxazolidine TFA salt

I-21a

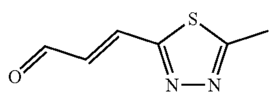

(E)-3-(5-Methyl-1,3,4-thiadiazol-2-yl)prop-2-enal

5-Methyl-1,3,4-thiadiazole-2-carbaldehyde (700 g) was dissolved in ACN (10 ml) and (formylmethylene)triphenylphosphorane (1.8 g) was added with stirring. After stirring for 24 h at RT the solution was concentrated in vacuo. The residue was purified by flash chromatography on silica gel (25 g; 0% to 100% EA in heptane in 8 min). The compound containing fractions were combined and the solvent was removed in vacuo to yield 293 mg of the title compound containing some residual triphenylphosphine oxide (13%).

LC/MS: m/z=155.1 $[M+H]^+$; tR: 0.52 min (LC/MS-method D).

1H N MR (600 MHz, DMSO-$d_6$) δ ppm 9.77 (1H), 8.05 (1H), 6.92 (1H), 2.80 (3H).

I-21b

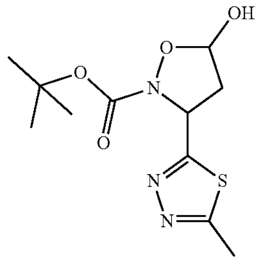

Tert-butyl 5-hydroxy-3-(5-methyl-1,3,4-thiadiazol-2-yl)isoxazolidine-2-carboxylate (E)-3-(5-Methyl-1,3,4-thiadiazol-2-yl)prop-2-enal (273 mg), [diphenyl-[(2S)-pyrrolidin-2-yl]methoxy]-trimethyl-silane (118.4 mg), benzoic acid (43.5 mg) and tert-butyl N-hydroxycarbamate (288.7 mg) were dissolved in DCM (10 ml) and stirred at −20° C. After stirring for 48 h at this temperature a mixture of DCM and saturated $NH_4Cl$ solution was added and the phases were separated. The aqueous phase was extracted with DCM, the combined organic phases were dried over magnesium sulphate, filtered and concentrated in vacuo. The residue was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure compound containing fractions were combined, the ACN was removed in vacuo and the residue lyophilised overnight and 183 mg of the title compound were obtained (no determination of er.).

LC/MS: m/z=288.1 $[M+H]^+$; tR: 0.97 min (LC/MS-method D).

I-21c

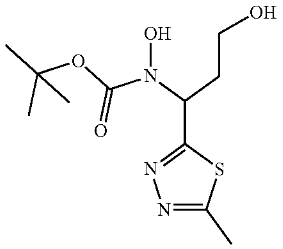

Tert-butyl N-hydroxy-N-[3-hydroxy-1-(5-methyl-1,3,4-thiadiazol-2-yl)propyl]carbamate Tert-butyl 5-hydroxy-3-(5-methyl-1,3,4-thiadiazol-2-yl) isoxazolidine-2-carboxylate (163 mg, possible excess of S enantiomer not determined) was dissolved in methanol (1 ml), cooled to 0° C. and $NaBH_4$ (21.5 mg) was added with stirring. After 45 min at 0° C. saturated $NH_4Cl$ solution was added and the mixture was passed through an Agilent Chem Elut SLE cartridge eluting with DCM. The eluate was concentrated in vacuo to yield 103 mg of the title compound which was used without further purification in the next step.

LC/MS: m/z=290.1 $[M+H]^+$; tR: 0.77 min (LC/MS-method D)

I-21d

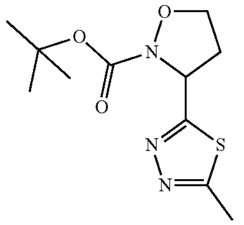

Tert-butyl 3-(5-methyl-1,3,4-thiadiazol-2-yl)isoxazolidine-2-carboxylate

Tert-butyl N-hydroxy-N-[3-hydroxy-1-(5-methyl-1,3,4-thiadiazol-2-yl)propyl]carbamate (155 mg) was dissolved in THF (3 ml) and with stirring under argon triphenylphosphine (340.2 mg) and DIAD (215 μl) were added at 0° C. After 24 h $H_2O$ was added and the mixture was passed through an an Agilent Chem Elut SLE cartridge eluting with DCM. The eluate was concentrated in vacuo and the residue was purified by flash chromatography on silica gel (10 g; 0% to 100% EA in heptane in 12 min). The compound containing fractions were combined and the solvent was removed in vacuo to yield 34 mg of the title compound.

LC/MS: m/z=272.2 $[M+H]^+$; tR: 1.01 min (LC/MS-method D)

$^1H$ NMR (600 MHz, DMSO-$d_6$) δ ppm 5.59 (1H), 4.16 (1H), 3.77 (1H), 2.83 (1H), 2.69 (3H), 2.59 (1H), 1.44 (9H).

I-21

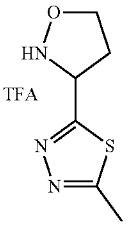

3-(5-Methyl-1,3,4-thiadiazol-2-yl)isoxazolidine TFA salt

Tert-butyl 3-(5-methyl-1,3,4-thiadiazol-2-yl)isoxazolidine-2-carboxylate (34 mg) was dissolved in DCM (5 ml) and TFA (0.2 ml) was added at RT with stirring. After 2 h the solvent was removed in vacuo and the residue was co-evaporated twice with toluene to yield 34 mg of the title compound.

LC/MS: m/z=172.2 $[M+H]^+$; tR: 0.21 min (LC/MS-method D)

I-22

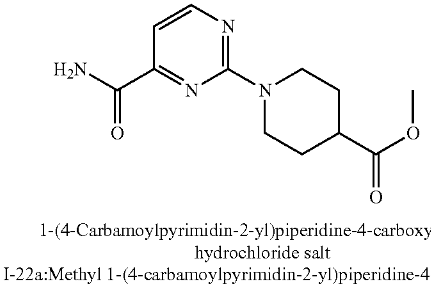

1-(4-Carbamoylpyrimidin-2-yl)piperidine-4-carboxylic acid hydrochloride salt
I-22a:Methyl 1-(4-carbamoylpyrimidin-2-yl)piperidine-4-carboxylate Methyl piperidine-4-carboxylate (600 mg) and 2-chloropyrimidine-4-carboxamide (615 mg) were dissolved in dry ACN (10 ml) in a microwave vessel (10 -20 ml). After DIPEA (2.59 ml) was added the mixture was heated at 150° C. in a microwave oven for 1 h. After cooling the solvent was removed in vacuo. The residue was purified by silica gel chromatography (40 g $SiO_2$, n-heptane 100% to 100% EA in 40 min). The pure compound containing fractions were combined and concentrated in vacuo to yield 834 mg of the title compound that was directly used in the next step.

I-22

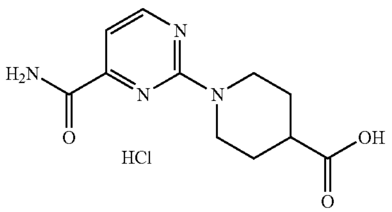

1-(4-Carbamoylpyrimidin-2-yl)piperidine-4-carboxylic acid hydrochloride salt

Methyl 1-(4-carbamoylpyrimidin-2-yl)piperidine-4-carboxylatearboxylate (834 mg) was dissolved in THF (15 ml). Then lithium hydroxide (166 mg) was added with stirring followed by water (3 ml). After standing overnight the solvent was removed in vacuo. HCl (1 N), water and ACN were added to the residue. The precipitate formed was sucked off and dried in a vacuum oven to yield 663 mg of the title compound.

LC/MS: m/z=251.3 $[M+H]^+$; tR: 1.04 min (LC/MS-method A)

I-22-1

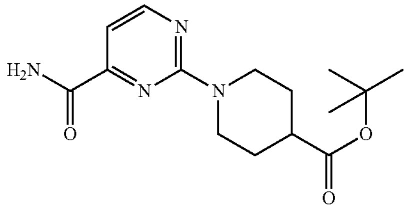

1-(4-Carbamoylpyrimidin-2-yl)piperidine-4-carboxylic acid
I-22-1a: Tert-butyl 1-(4-carbamoylpyrimidin-2-yl)piperidine-4-carboxylate Tert-butyl piperidine-4-carboxylate hydrochloride (1.000 g) was dissolved in dry ACN (10 ml). At RT DIPEA (3.7 ml) and 2-chloropyrimidine-4-carboxamide (695.9 mg) were added and the mixture was heated at 120° C. for 2.5 h under argon. After cooling the solvent was removed in vacuo. The residue thus obtained was dissolved in a mixture of water and DCM, the phases were separated and the aqueous phase was extracted with DCM (3×). The combined organic phases were dried over magnesium sulphate, filtered and concentrated in vacuo. The residue was purified by flash chromatography on silica gel (25 g; 0% to 50% EA in heptane in 12 min). The compound containing fractions were combined and the solvent was removed in vacuo to yield 1.024 g of the title compound.

LC/MS: m/z=307.3 $[M+H]^+$; tR: 1.28 min (LC/MS-method D)

I-22-1

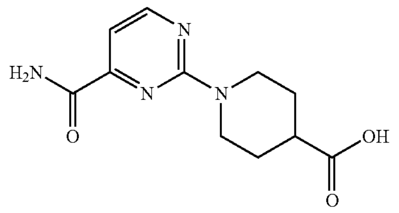

1-(4-Carbamoylpyrimidin-2-yl)piperidine-4-carboxylic acid

Tert-butyl 1-(4-carbamoylpyrimidin-2-yl)piperidine-4-carboxylate (1.024 g) was dissolved in DCM (10 ml) and TFA (6.6 ml) was added at RT with stirring. After 2 h the solvent was removed in vacuo and the residue co-evaporated twice with toluene. The residue thus obtained was dissolved in ACN, the precipitate was filtered, washed with heptane and dried in vacuo to yield 780 mg of the title compound LC/MS: m/z=251.2 $[M+H]^+$; tR: 0.70 min (LC/MS-method D)

I-22-2

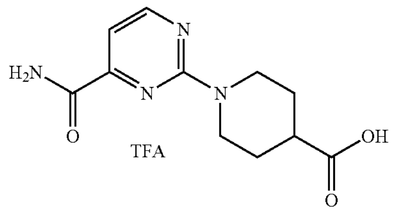

1-(4-Carbamoylpyrimidin-2-yl)piperidine-4-carboxylic acid TFA salt

Crude tert-butyl 1-(4-carbamoylpyrimidin-2-yl)piperidine-4-carboxylate (I-22-1a, 425 mg) was dissolved in DCM (12 ml) and TFA (1.22 ml) was added at RT with stirring. After standing overnight toluene (10 ml) was added and then the solvent was removed in vacuo. The residue was lyophilised to yield 350 mg of the title compound.

LC/MS: m/z=251.3 $[M+H]^+$; tR: 1.04 min (LC/MS-method A)

I-23: 1-(4-Cyanopyrimidin-2-yl)piperidine-4-carboxylic acid

I-23a

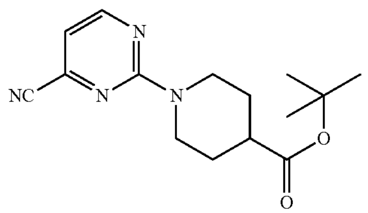

Tert-butyl 1-(4-cyanopyrimidin-2-yl)piperidine-4-carboxylate

Tert-butyl piperidine-4-carboxylate hydrochloride (1.000 g) was dissolved in dry ACN (10 ml). At RT DIPEA (3.7 ml) and 2-chloropyrimidine-4-carbonitrile (629.4 mg) were added and the mixture was heated at 120° C. for 2.5 h under argon. After cooling the solvent was removed in vacuo. The residue thus obtained was dissolved in a mixture of water and DCM and the aqueous phase was extracted with DCM (3×). The combined organic phases were dried over magnesium sulphate, filtered and concentrated in vacuo. The residue was purified by flash chromatography on silica gel (25 g; 0% to 50% EA in heptane in 13 min). The compound containing fractions were combined and the solvent was removed in vacuo to yield 879 mg of the title compound.

LC/MS: m/z=289.3 $[M+H]^+$; tR: 1.69 min (LC/MS-method D)

I-23

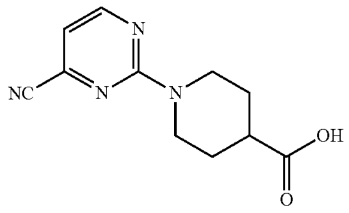

1-(4-Cyanopyrimidin-2-yl)piperidine-4-carboxylate acid

Tert-butyl 1-(4-cyanopyrimidin-2-yl)piperidine-4-carboxylate (879 mg) was dissolved in DCM (10 ml) and TFA (5 ml) was added at RT with stirring. After 2 h the solvent was removed in vacuo and the residue co-evaporated twice with toluene. The residue was dissolved in ACN/heptane, the precipitate was filtered, washed with heptane and dried in vacuo to yield 790 mg of the title compound.

LC/MS: m/z=233.1 $[M+H]^+$; tR: 1.05 min (LC/MS-method D)

I-23-1

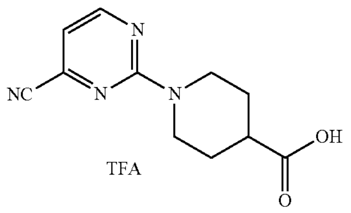

1-(4-Cyanopyrimidin-2-yl)piperidine-4-carboxylate acid TFA salt

Crude tert-butyl 1-(4-cyanopyrimidin-2-yl)piperidine-4-carboxylate (I-23a, 448 mg) was dissolved in DCM (12 ml) and TFA (1.22 ml) was added at RT with stirring. After standing overnight toluene (10 ml) was added and then the solvent was removed in vacuo. The residue was lyophilised to yield 380 mg of the title compound.

LC/MS: m/z=233.2 $[M+H]^+$; tR: 1.47 min (LC/MS-method A)

I-24 I-24a

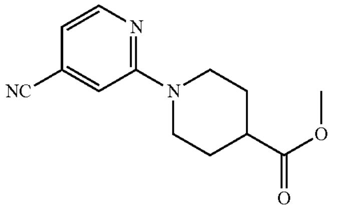

1-(4-Cyano-2-pyridyl)piperidine-4-carboxylic acid trifluoroacetic acid salt
Methyl 1-(4-cyano-2-pyridyl)piperidine-4-carboxylate Methyl piperidine-4-carboxylate (800 mg) was dissolved in dry ACN (12 ml) in a microwave vessel (10 –20 ml). After DIPEA (3.9 ml) and 4-cyano-2-fluoropyridine (790 mg) were added the mixture was heated at 150° C. in a microwave oven for 1 h. After cooling the solvent was removed in vacuo. The residue was purified by silica gel chromatography (40 g $SiO_2$, n-heptane 100% for 5 min, then 100% heptane to 40% n-heptane/60% EA for 45 min.). The pure compound containing fractions were combined and concentrated in vacuo. The residue was dissolved in ACN/$H_2O$ and lyophilised overnight to yield 896 mg of the title compound.

LC/MS: m/z=246.4 $[M+H]^+$; tR: 1.77 min (LC/MS-method A)

I-24

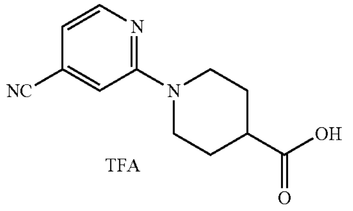

1-(4-Cyano-2-pyridyl)piperidine-4-carboxylic acid trifluoroacetic acid salt

Methyl 1-(4-cyanopyridin-2-yl)piperidine-4-carboxylate (225 mg) was dissolved in THF (10 ml). Then LiOH (33 mg) and water (2 ml) were added with stirring. After standing overnight further LiOH (16 mg) and water (1 ml) were added with stirring. After stirring for 2.5 h the THF was removed in vacuo. Water was added to the residue and the mixture was acidified with HCl (1 N in water). After lyophilisation overnight the residue was dissolved in ACN/water and purified by RP prep-HPLC (flow 25 ml/min; 95% $H_2O$+0.05% TFA/5% ACN in 45 min to 5% $H_2O$+0.05% TFA/95% ACN; column Purosphere® STAR-RP18, 25×250 mm, 10 μm). The pure compound containing fractions were combined, the ACN was removed in vacuo and the residue lyophilised overnight to yield 207 mg of the title compound.

LC/MS: m/z=232.3 $[M+H]^+$; tR: 1.33 min (LC/MS-method A).

I 25: 5-[(3S)-2-(4-Methylpiperidine-4-carbonyl)isoxazolidin-3-yl]pyridine-3-carbonitrile trifluoro acetic acid salt I-25a

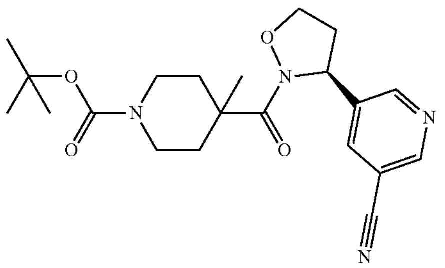

Tert-butyl 4-[(3S)-3-(5-Cyano-3-pyridyl)isoxazolidine-2-carbonyl]-4-methyl- piperidine-1-carboxylate 1-Tert-butoxycarbonyl-4-methyl-piperidine-4-carboxylic acid (100 mg) was dissolved in dry DCM (4.5 ml) under Ar. A catalytic amount of dry DMF (~2 drops) was added and the mixture cooled to 0° C. Then thionyl chloride (60 μl) dissolved in dry DCM (0.5 ml) was added with stirring. After 1.5 h further thionyl chloride (25 μl in 0.3 ml dry DCM) was added. After 1 h the mixture was concentrated in vacuo and the residue was dissolved in dry DCM (5 ml). This solution was added to a mixture of 5-[(3S)-isoxazolidin-3-yl]pyridine-3-carbonitrile trifluoroacetic acid salt (I-02-2, 115 mg) and DIPEA (280 μl) dissolved in dry DCM (1.5 ml) under Ar with stirring at 0° C. After the addition the ice bath was removed and stirring continued for 1 h. Then sat. $NaHCO_3$ solution was added and the aqueous phase was extracted with DCM (3×). The combined organic phases were dried over sodium sulphate, filtered and concentrated in vacuo. The residue was purified by silica gel chromatography (12 g $SiO_2$, 100% DCM to 80% DCM/20% EtOH in 25 min). The pure compound containing fractions were combined, concentrated in vacuo, the residue dissolved in ACN/water and lyophilised overnight to yield 121 mg of the title compound.

LC/MS: m/z=301.4 $[M-CO_2tBu+2H]^+$; tR: 2.12 min (LC/MS-method A).

I-25

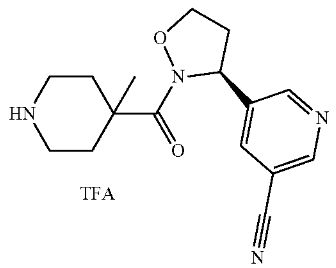

5-[(3S)-2-(4-Methylpiperidine-4-carbonyl)isoxazolidin-S-yl]pyridine-3-carbonitrile trifluoro acetic acid salt TFA (0.5 ml) was added to a solution of tert-butyl 4-[(3S)-3-(5-cyano-3-pyridyl)isoxazolidine-2-carbonyl]-4-methyl-piperidine-1-carboxylate (118 mg) in dry DCM (2 ml) under Ar with stirring. After 1.5 h the mixture was concentrated in vacuo, the residue dissolved in water and then purified by RP prep-HPLC (flow 25 mi/min; from 95% $H_2O$+0.05% TFA/5% ACN to 5% $H_2O$+0.05% TFA/95% ACN in 45 min.; Purosphere® STAR-RP18, 25×250 mm, 10 μm). The pure product containing fractions were combined and the ACN was removed in vacuo. The aqueous solution was lyophilised to yield 82 mg of the title compound.

LC/MS: m/z=301.3 $[M+H]^+$; tR: 0.78 min (LC/MS-method A)

I-26

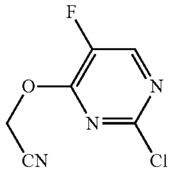

2-(2-Chloro-5-fluoro-pyrimidin-4-yl) oxyacetonitrile 2,4-Dichloro-5-fluoropyrimidine (1 g) was dissolved in ACN (80 ml). Glyconitrile (431 μl, 70% in water) and caesium carbonate (1.85 g) were added with stirring. After stirring for 2.5 h the mixture was filtered and the filtrate concentrated in vacuo. The residue was purified by silica gel chromatography (24 g $SiO_2$, 100% n-heptane for 5 min, 100% n-heptane to 75% n-heptane/25% EA in 45 min, then 75% n-heptane/25% EA for 15 min). The pure compound containing fractions were combined and concentrated in vacuo to yield 995 mg of the title compound.

LC/MS: m/z=188.0 $[M+H]^+$; tR: 1.16 min (LC/MS-method A)

I-27 I-27a

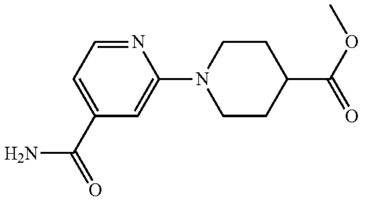

1-(4-Carbamoyl-2-pyridyl) piperidine-4-carboxylic acid TFA salt
Methyl 1-(4-Carbamoyl-2-pyridyl) piperidine-4-carboxylate HBr solution (8 ml, 45 wt % in acetic acid) was added to methyl 1-(4-cyano-2-pyridyl)piperidine-4-carboxylate (I-24a, 665 mg) and the mixture was stirred for 2 h. Then sat. $NaHCO_3$ solution was added until the mixture showed a neutral pH. The aqueous mixture was extracted with DCM (3×), the organic phases were combined, dried over sodium sulphate, filtered and concentrated in vacuo. The residue was purified by silica gel chromatography (40 g $SiO_2$, 100% DCM to 80% DCM/20% EtOH in 45 min). The pure compound containing fractions were combined, concentrated in vacuo, the residue dissolved in ACN/water and lyophilised overnight to yield 593 mg of the title compound.

LC/MS: m/z=264.3 $[M+H]^+$; tR: 0.76 min (LC/MS-method A)

I-27

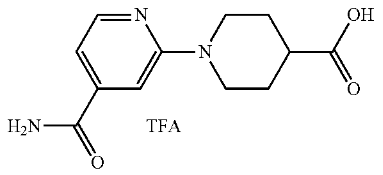

1-(4-Carbamoyl-2-pyridyl) piperidine-4-carboxylic acid TFA salt

Following the procedure described for I-24 636 mg of the title compound was obtained, starting from 590 mg methyl ester.

LC/MS: m/z=250.3 $[M+H]^+$; tR: 0.45 min (LC/MS-method A)

I-28: 5-[(3S)-2-(Piperidine-4-carbonyl)isoxazolidin-3-yl]pyridine-3-carbonitrile trifluoro acetic acid salt I-28a

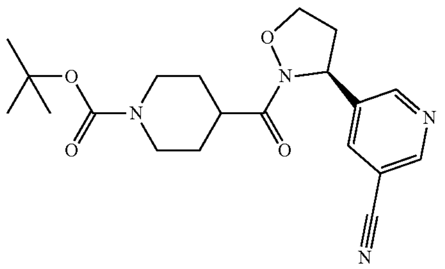

Tert-butyl 4-[(3S)-3-(5-Cyano-3-pyridyl)isoxazolidine-2-carbonyl]piperidine-1-carboxylate 1-Tert-butoxycarbonyl-piperidine-4-carboxylic acid (740 mg) was dissolved in dry DMF (10 ml) and DIPEA (1.17 ml) and HATU (2.17 g) were added with stirring. After 15 min (S)-5-(isoxazolidin-3-yl)nicotinonitrile (I 02-1, 0.49 g) dissolved in dry DMF (8 ml) was added with stirring. After 1 h sat. sodium bicarbonate solution was added and the aqueous phase was extracted with EA (3×). The combined organic phases were washed with brine, dried over sodium sulphate, filtered and concentrated in vacuo to yield 1.08 g of the title compound.

LC/MS: m/z=287.3 $[M-CO_2tBu+2H]^+$; tR: 1.91 min (LC/MS-method A).

I-28

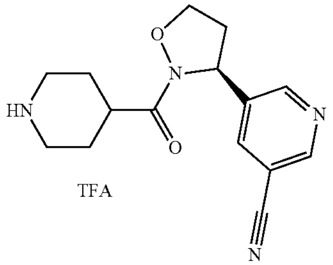

5-[(3S)-2-(Piperidine-4-carbonyl) isoxazolidin-3-yl]pyridine-3-carbonitrile trifluoro acetic acid salt TFA (7 ml) was added to a solution of tert-butyl (S)-4-(3-(5-cyanopyridin-3-yl)isoxazolidine-2-carbonyl)piperidine-1-carboxylate (1.08 g) in dry DCM (25 ml) under Ar with stirring. After 15 min the mixture was concentrated in vacuo, the residue dissolved in water+0.05% TFA/ACN and then purified by RP prep-HPLC (flow 25 ml/min; from 95% $H_2O$+0.05% TFA/5% ACN to 5% $H_2O$+0.05% TFA/95% ACN in 45 min.; Purosphere® STAR-RP18 25×250 mm, 10 μm). The pure product containing fractions were combined and the ACN was removed in vacuo. The aqueous solution was lyophilised to yield 677 mg of the title compound.

LC/MS: m/z=287.2 $[M+H]^+$; tR: 0.58 min (LC/MS-method A)

I-29

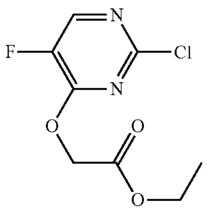

Ethyl 2-((2-chloro-5-fluoropyrimidin-4-yl) oxy)acetate

Ethyl glycolate (0.91 ml) was dissolved in THF (60 ml) and cooled to 0° C. Sodium hydride (430 mg, 60% in mineral oil) was added in portions with stirring and then the cooling bath was removed. After 15 min the mixture was again cooled to 0° C. and 2,4-dichloro-5-fluorpyrimidine (1.5 g) was added in portions. After removal of the cooling bath stirring was continued for 1 h. Then water (75 ml) was added, followed by 1 N HCl to adjust the pH of the mixture to 1. The aqueous phase was extracted with DCM (2×). The combined organic phases were dried over sodium sulphate, filtered and concentrated in vacuo. The residue was purified by silica gel chromatography (24 g $SiO_2$, 100% n-heptane for 5 min, 100% n-heptane to 50% n-heptane/50% EA in 30 min, then 50% n-heptane/50% EA for 10 min). The pure compound containing fractions were combined and concentrated in vacuo to yield 1.89 g of the title compound.

LC/MS: m/z=235.1 $[M+H]^+$; tR: 1.69 min (LC/MS-method A)

I-30: Ethyl 6-chloro-5-fluoro-pyrimidine-4-carboxylate

I-30a

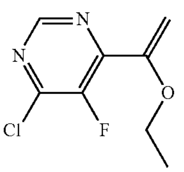

4-Chloro-6-(1-ethoxyvinyl) -5-fluoro-pyrimidine 4,6-Dichloro-5-fluoro-pyrimidine (2.5 g) and tributyl(1-ethoxyvinyl)tin were dissolved in dioxane and Ar was bubbled through the solution for 15 min. Then bis(triphenylphosphine) palladium(II) dichloride (1 g) was added and Ar was bubbled for a further 15 min though the mixture.

After heating the mixture for 3 h at 90° C. under Ar it was cooled and concentrated in vacuo. Water and diethyl ether were added. The aqueous phase was extracted with diethyl ether (3×). The combined organic phases were dried over sodium sulphate, filtered and concentrated in vacuo. The residue was purified by silica gel chromatography (40 g $SiO_2$, 100% n-heptane for 5 min, 100% n-heptane to 75% n-heptane/25% EA in 60 min, then 75% n-heptane/25% EA for 15 min). The pure compound containing fractions were combined and concentrated in vacuo. The residue was dissolved in ACN/water and lyophilised overnight to yield 2.06 g of the title compound.

LC/MS: m/z=203.2 $[M+H]^+$; tR: 1.92 min (LC/MS-method A)

I-30

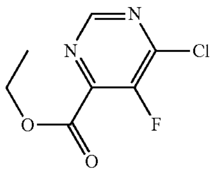

Ethyl 6-chloro-5-fluoro-pyrimidine-4-carboxylate

4-Chloro-6-(1-ethoxyvinyl)-5-fluoropyrimidine (2.06 g) was dissolved in a mixture of 1,4-dioxane (90 ml) and water (24 ml) with stirring. Then sodium periodate (5.44 g) was added and stirring was continued for 10 min. Potassium permanganate (0.96 g) was added and the mixture was vigorously stirred for 2 h. Then the mixture was filtered through Celite®. The filter cake was washed with a mixture of DCM (180 ml) and methanol (60 ml). Water was added to the combined filtrate which was extracted with DCM (3×). The combined DCM phases were dried over sodium sulphate, filtered and concentrated in vacuo to yield 1.71 g of the title compound.

$^1H$ NMR (400.23 MHz, DMSO-$d_6$) δ ppm 9.01 (1H), 4.41 (2H), 1.33 (3H)

I-31

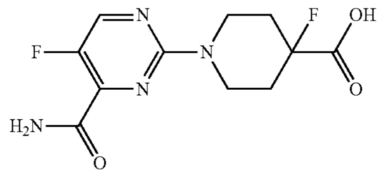

1-(4-Carbamoyl-5-fluoro-pyrimidin-2-yl) -4-fluoro-piperidine-4-carboxylic acid

I-31a

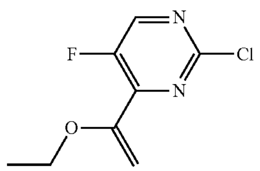

2-Chloro-4-(1-ethoxyvinyl) -5-fluoro-pyrimidine

To a solution of 2,4-dichloro-5-fluoro-pyrimidine (20 g) in DMF (170 ml) was added tributyl(1-ethoxyvinyl)tin (47.59 g) and $Pd(PPh_3)_2Cl_2$ (1.67 g). The mixture was stirred at 70° C. under $N_2$ for 1 h. Then reaction mixture was quenched with 10% aqueous KF solution (50 ml), stirred at 25° C. for 12 h, diluted with EA (120 ml) and filtered. The organic phases were washed with brine (50 ml), dried over $Na_2SO_4$, filtered and concentrated. The residue was purified by silica gel column chromatography (PE:EA=1:0 to 20:1) to yield 23.7 g of the title compound.

$^1$H NMR (400 MHz, DMSO-$d_6$): δ ppm 8.90 (1H), 5.20 (1H), 4.87 (1H), 3.94 (2H), 1.32 (3H)

I-31b

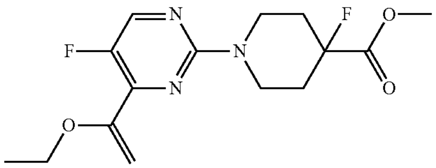

Methyl 1-[4-(1-ethoxyvinyl)-5-fluoro-pyrimidin-2-yl]-4-fluoro-piperidine-4-carboxylate A mixture of 2-chloro-4-(1-ethoxyvinyl)-5-fluoro-pyrimidine (1.95 g), methyl 4-fluoropiperidine-4-carboxylate HCl salt (2 g) and DIPEA (3.74 g) in DMSO (20 ml) was stirred at 80° C. for 2 h. The reaction mixture was diluted with water (20 ml), extracted with EA (30 ml×3). The combined organic layers were washed with brine (50 ml), dried over anhydrous $Na_2SO_4$, filtered and concentrated. The residue was purified by silica gel column chromatography (PE: EA=1:0 to 20:1) to give 1.8 g of the title compound.

I-31c

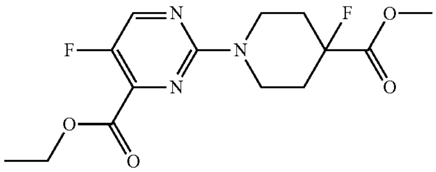

Ethyl 5-fluoro-2-(4-fluoro-4-methoxycarbonyl-1-piperidyl)pyrimidine-4-carboxylate To a solution of methyl 1-[4-(1-ethoxyvinyl)-5-fluoro-pyrimidin-2-yl]-4-fluoro-piperidine-4-carboxylate (1.6 g) in dioxane (60 ml) was added solution of $NaIO_4$ (4.18 g) in water (30 ml), then $KMnO_4$ (772 mg) was added. The mixture was stirred at 25° C. for 2 h. The reaction mixture was filtered, the filtrate was diluted with EA (50 ml), saturated $NaHCO_3$ solution (50 ml) and brine (50 ml). The aqueous layer was extracted with EA (50 ml×2), the combined organic layers were dried over $NaSO_4$, filtrated and concentrated. The residue was purified by silica gel column chromatography (PE:EA=20:1 to 0:1) to yield 980 mg of the title compound.

$^1$H NMR (400 MHz, $CDCl_3$): δ ppm 8.35 (1H), 4.68-4.59 (2H), 4.45 (2H), 3.81 (3H), 3.41-3.26 (2H), 2.15-2.00 (4H), 1.42 (3H)

I-31d

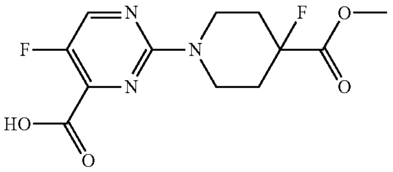

5-Fluoro-2-(4-fluoro-4-methoxycarbonyl-1-piperidyl)pyrimidine-4-carboxylic acid

To a solution of Novozyme 435 (750 mg) in buffer (25 ml, 100 mmol/l, pH=7, phosphate buffer) was added dropwise a solution of ethyl 5-fluoro-2-(4-fluoro-4-methoxycarbonyl-1-piperidyl)pyrimidine-4-carboxylate (980 mg) in DMSO (10 ml). The mixture was stirred at 37° C. for 6 h. The reaction mixture was adjusted to pH=2 with 1N HCl solution and extracted with EA (50 m×3). The combined organic layers were washed with brine (100 ml), dried over $Na_2SO_4$, filtered and concentrated to yield 1.1 g of the title compound, which was used in the next step without further purification.

I-31e

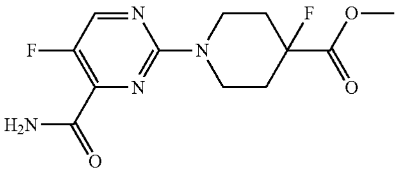

Methyl 1-(4-carbamoyl-5-fluoro-pyrimidin-2-yl)-4-fluoro-piperidine-4-carboxylate A mixture of 5-fluoro-2-(4-fluoro-4-methoxycarbonyl-1-piperidyl)pyrimidine-4-carboxylic acid (1.1 g), HATU (2.78 g), DIPEA (2.36 g) and $NH_4Cl$ (976.60 mg) in DMF (9 ml) was stirred at 25° C. for 2 h. Then the reaction mixture was diluted with water (5 ml) and extracted with EA (5 ml×5). The combined organic layers were washed with brine (10 ml), dried over $Na_2SO_4$, filtered and concentrated. The residue was purified by silica gel column chromatography (PE:EA=2:1 to 1:1) to yield 830 mg of the title compound.

$^1$H NMR (400 MHz, $CDCl_3$): δ ppm 8.32 (1H), 7.94 (1H), 7.18 (1H), 4.49 (2H), 3.73 (3H), 3.32-3.23 (2H), 2.01-1.93 (4H)

I-31

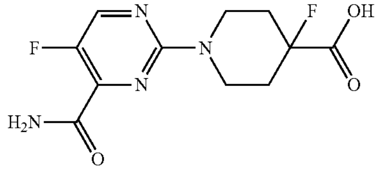

1-(4-Carbamoyl-5-fluoro-pyrimidin-2-yl)-4-fluoro-piperidine-4-carboxylic acid

To a mixture of methyl 1-(4-carbamoyl-5-fluoro-pyrimidin-2-yl)-4-fluoro-piperidine-4-carboxylate (880 mg) in THF (4 ml) and $H_2O$ (4 ml) was added $LiOH{\cdot}H_2O$ (122.99 mg), the mixture was stirred at 25° C. for 2 h. Then the reaction mixture was concentrated, the residue was purified by prep. RP-HPLC (column: Phenomenex luna C18, 150×25 mm, 10 um; mobile phase: [water (0.1% TFA)-ACN]; B %: 7%-37%, 10 min) to yield 147 mg of the title compound.

$^1$H NMR (400 MHz, DMSO-$d_6$): δ ppm 8.59 (1H), 8.16 (1H), 7.82 (1H), 4.52 (2H), 3.24-3.18 (2H), 2.03-1.78 (4H)

I-32: (4-Methyl-4-piperidyl)-[(3S)-3-pyrimidin-5-ylisoxazolidin-2-yl]methanone TFA salt I-32a

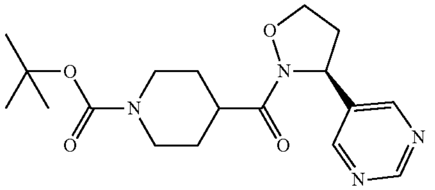

Tert-butyl 4-methyl-4-[(3S)-3-pyrimidin-5-ylisoxazolidine-2-carbonyl]piperidine-1-carboxylate 1-Tert-butoxycarbonyl-4-methyl-piperidine-4-carboxylic acid (300 mg) was dissolved in dry DCM (5 ml) under Ar. A catalytic amount of dry DMF (~2 drops) was added and the mixture cooled to 0° C. Then thionyl chloride (175 μl) was added with stirring. After 1.5 h further thionyl chloride (80 μl) was added. After 1 h the mixture was concentrated in vacuo and the residue was dissolved in dry DCM (5 ml). This solution was added to a mixture of (3S)-3-pyrimidin-5-ylisoxazolidine TFA salt (I-01, 320 mg) and DIPEA (55 μl) dissolved in dry DCM (1.5 ml) under Ar with stirring at 0° C. After the addition the ice bath was removed and stirring continued for 1 h. Then sat. $NaHCO_3$ solution was added and the aqueous phase was extracted with DCM (3×). The combined organic phases were dried over sodium sulphate, filtered and concentrated in vacuo. The residue was purified by silica gel chromatography (24 g $SiO_2$, 100% DCM to 80% DCM/20% EtOH in 35 min). The pure compound containing fractions were combined, concentrated in vacuo, the residue dissolved in ACN/water and lyophilised overnight to yield 224 mg of the title compound.

LC/MS: m/z=277.3 $[M-CO_2tBu+2H]^+$; tR: 1.87 min (LC/MS-method A).

I-32

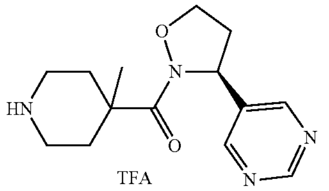

TFA (4-Methyl-4-piperidyl)-[(3S)-3-pyrimidin-5-ylisoxazolidin-2-yl]methanone TFA salt Tert-butyl 4-methyl-4-[(3S)-3-pyrimidin-5-ylisoxazolidine-2-carbonyl]piperidine-1-carboxylate (224 mg) was dissolved in DCM (6 ml). Then TFA (1.4 ml) was added with stirring. After 0.75 h the DCM was removed in vacuo, the residue was dissolved in water and lyophilised overnight to yield 332 mg of the title compound.

LC/MS: m/z=277.3 $[M+H]^+$; tR: 0.6 min (LC/MS-method A)

I-33

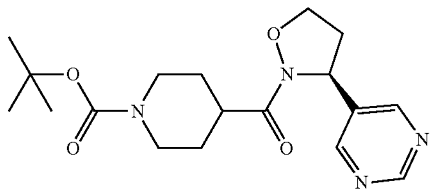

4-Piperidyl-[(3S)-3-pyrimidin-5-ylisoxazolidin-2-yl]methanone TFA salt
I-33a: Tert-butyl 4-[(3S)-3-pyrimidin-5-ylisoxazolidine-2-carbonyl]piperidine-1-carboxylate 1-Tert-butoxycarbonyl-piperidine-4-carboxylic acid (300 mg) was reacted as described in I-32a to yield 552 mg of crude product which was purified by silica gel chromatography (24 g $SiO_2$, 100% DCM to 85% DCM/15% ethanol in 40 min). The pure product containing fractions were combined and the solvent was removed in vacuo to yield 148 mg of the title compound.

LC/MS: m/z=263.3 $[M-CO_2tBu+2H]^+$; tR: 1.68 min (LC/MS-method A).

I-33

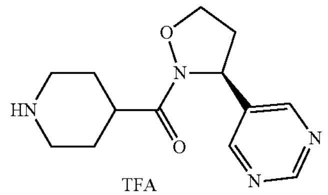

TFA

4-Piperidyl-[(3S)-3-pyrimidin-5-ylisoxazolidin-2-yl]methanone TFA salt

Tert-butyl 4-[(3S)-3-pyrimidin-5-ylisoxazolidine-2-carbonyl]piperidine-1-carboxylate (148 mg) was reacted as described in I-32 to yield 196 mg of the title compound.

LC/MS: m/z=263.3 $[M+H]^+$; tR: 0.31 min (LC/MS-method A)

I-34

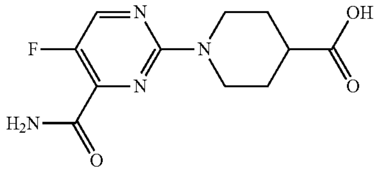

1-(4-Carbamoyl-5-fluoro-pyrimidin-2-yl)piperidine-4-carboxylic acid

I-34a

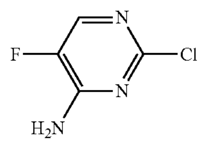

2-Chloro-5-fluoro-pyrimidin-4-amine

A mixture of 2,4-dichloro-5-fluoro-pyrimidine (100 g) in $NH_3 \cdot H_2O$ (200 ml) was stirred at 60° C. for 1 h. The reaction mixture was filtered to yield 78 g of the title compound.

$^1$H NMR (400 MHz, DMSO-$d_6$): δ ppm 8.09 (1H), 7.81 (2H)

I-34b

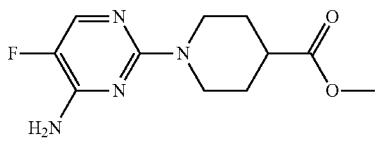

Methyl 1-(4-amino-5-fluoro-pyrimidin-2-yl)piperidine-4-carboxylate

A mixture of 2-chloro-5-fluoro-pyrimidin-4-amine (67 g), methyl piperidine-4-carboxylate hydrochloride salt (122.37 g) and DIPEA (205.42 g) in n-BuOH (670 ml) was stirred at 100° C. for 12 h under $N_2$ atmosphere. Then the reaction mixture was concentrated under reduced pressure to remove the solvent. The residue was diluted with water (500 ml) and extracted with EA (300 ml×3). The combined organic layers were washed with brine (500 ml), dried over $Na_2SO_4$, filtered and concentrated. The residue was purified by silica gel column chromatography (PE:EA=10:1 to 4:1) to yield 73 g of the title compound.

$^1$H NMR (400 MHz, $CDCl_3$): δ ppm 7.81 (1H), 4.82 (2H), 4.49 (2H), 3.69 (3H), 3.00-2.87 (2H), 2.52 (1H), 1.92 (2H), 1.76-1.57 (2H)

I-34c

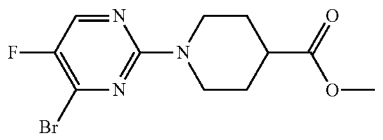

Methyl 1-(4-bromo-5-fluoro-pyrimidin-2-yl)piperidine-4-carboxylate

To a mixture of methyl 1-(4-amino-5-fluoro-pyrimidin-2-yl)piperidine-4-carboxylate (68.8 g) and $CuBr_2$ (120.87 g) in DCM (688 ml) was added isopentyl nitrite (63.40 g) at 0° C. The mixture was warmed to 25° C. smoothly and stirred for 12 h. Then the reaction mixture was filtered, the filtrate was diluted with water (500 ml) and extracted with DCM (500 ml×3). The combined organic layers were washed with brine (1000 ml), dried over $Na_2SO_4$, filtered and concentrated under reduced pressure to give a residue. The residue was purified by silica gel column chromatography (PE:EA=20:1 to 10:1) to yield 26 g of the title compound.

$^1$H NMR (400 MHz, $CDCl_3$): δ ppm 8.06 (1H), 4.53 (2H), 3.71 (3H), 3.14-2.98 (2H), 2.58 (1H), 2.03-1.93 (2H), 1.80-1.62 (2H)

I-34d

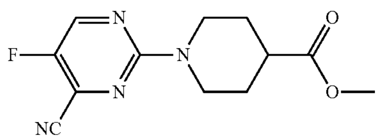

Methyl 1-(4-cyano-5-fluoro-pyrimidin-2-yl)piperidine-4-carboxylate

To a mixture of methyl 1-(4-bromo-5-fluoro-pyrimidin-2-yl)piperidine-4-carboxylate (26 g) and $Zn(CN)_2$ (57.58 g) in DMF (260 ml) was added $Pd(PPh_3)_4$ (9.44 g). The mixture was stirred at 120° C. for 12 h under $N_2$ atmosphere. Then the reaction mixture was filtered, the filtrate was diluted with water (200 ml) and extracted with EA (200 ml×3). The combined organic layers were washed with brine (500 ml), dried over $Na_2SO_4$, filtered and concentrated. The residue was purified by silica gel column chromatography (PE:EA=10:1 to 0:1) to yield 15 g of the title compound.

$^1$H NMR (400 MHz, $CDCl_3$): δ ppm 8.38 (1H), 4.52 (2H), 3.71 (3H), 3.20-3.04 (2H), 2.61 (1H), 2.04-1.92 (2H), 1.80-1.62 (2H)

I-34

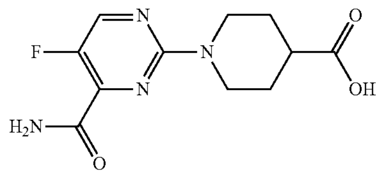

1-(4-Carbamoyl-5-fluoro-pyrimidin-2-yl)piperidine-4-carboxylic acid

To a solution of methyl 1-(4-cyano-5-fluoro-pyrimidin-2-yl)piperidine-4-carboxylate (13.7 g) in THF (640 ml) was added $H_2O_2$ (11.76 g, 30% purity) and an aqueous solution of $LiOH{\cdot}H_2O$ (1 M, 51.84 ml). The mixture was stirred at 25° C. for 12 h. Additional $LiOH{\cdot}H_2O$ (1 M, 25.92 ml) was added, the mixture was stirred at 25° C. for 8 h. Then the mixture was adjusted with 1 N HCl solution (30 ml) to pH=5~6 and quenched with saturated $Na_2SO_3$ solution (20 ml). The reaction mixture was concentrated under reduced pressure to remove most of the solvent and filtered. The filter cake was triturated with EA (80 ml) to yield 10.4 g of the title compound.

$^1$H NMR (400 MHz, DMSO-$d_6$): δ ppm 12.55-11.93 (1H), 8.52 (1H), 8.09 (1H), 7.78 (1H), 4.54-4.42 (2H), 3.13-2.95 (2H), 2.55-2.51 (1H), 1.86 (2H), 1.59-1.41 (2H)

I-35: 6-[(3S)-Isoxazolidin-3-yl]pyridine-3-carbonitrile hydrochloride salt

I-35a

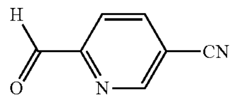

6-Formylpyridine-3-carbonitrile

To a solution of 6-methylpyridine-3-carbonitrile (40 g) in DMSO (400 ml) was added $I_2$ (77.34 g), then the mixture was stirred at 150° C. for 1 h. The reaction mixture was diluted with saturated $NaHCO_3$ solution (1 l), extracted with EA (1 l×3), dried over anhydrous $Na_2SO_4$, filtered and concentrated under reduced pressure to give a residue, which was purified by silica gel column chromatography (PE:EA=10:1~5:1) to yield 19 g of the title compound.

$^1$H NMR (400 MHz, $CDCl_3$): δ ppm 10.13 (1H), 9.06 (1H), 8.21-8.16 (1H), 8.08 (1H)

I-35b

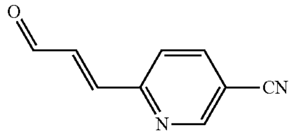

6-[(E)-3-Oxoprop-1-enyl]pyridine-3-carbonitrile

To a solution of 6-Formylpyridine-3-carbonitrile (19 g) in toluene (170 ml) was added (formylmethylene)triphenylphosphorane (43.76 g), the mixture was stirred at 25° C. under $N_2$ for 2 h. The reaction mixture was concentrated under reduced pressure to give a residue. The residue was purified by silica gel column chromatography (PE:EA=10:1~5:1) to yield 7.2 g of the title compound.

$^1$H NMR (400 MHz, $CDCl_3$): δ ppm 9.86 (1H), 8.95 (1H), 8.05 (1H), 7.66-7.61 (1H), 7.52 (1H), 7.20 (1H)

I-35c

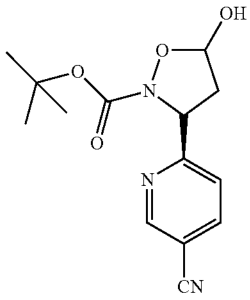

Tert-butyl (3S)-3-(5-cyano-2-pyridyl)-5-hydroxy-isoxazolidine-2-carboxylate

To a solution of [diphenyl-[(2S)-pyrrolidin-2-yl]methoxy]-trimethyl-silane (2.96 g) in $CHCl_3$ (70 ml) was added 6-[(E)-3-oxoprop-1-enyl]pyridine-3-carbonitrile (7.2 g) at 0° C. The mixture was stirred at 0° C. for 30 min, tert-butyl N-hydroxycarbamate (6.67 g) was added, the mixture was warmed to 20° C. smoothly and stirred for 12 h. The reaction mixture was concentrated under reduced pressure to give a residue which was purified by prep. RP LC (flow: 200 ml/min; gradient: from 100% $H_2O$ (0.1% FA)/0% ACN to 68% $H_2O$ (0.1% FA)/32% ACN in 12 min; 68% $H_2O$ (0.1% FA)/32% ACN for 17 min; column: Welch Ultimate XB_C18, 20-40 μm, 120 Å, 95 mm×365 mm) to yield 6.46 g of the title compound.

I-35d

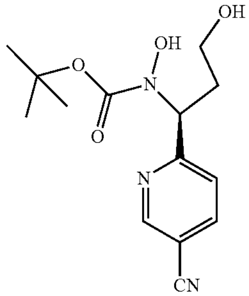

Tert-butyl N-[(1S)-1-(5-Cyano-2-pyridyl)-3-hydroxy-propyl]-N-hydroxy-carbamate

To a solution of tert-butyl (3S)-3-(5-cyano-2-pyridyl)-5-hydroxy-isoxazolidine-2-carboxylate (6.46 g) in MeOH (60 ml) was added $NaBH_4$ (838.98 mg) at 0° C. The mixture was stirred at 0° C. for 15 min. The reaction mixture was quenched by addition saturated $NH_4Cl$ solution (4 ml), diluted with brine (100 ml) and extracted with EA (150 ml×3). The combined organic layers were dried over anhydrous $Na_2SO_4$, filtered and concentrated under reduced pressure to give a residue, which was purified by preparative RP LC (flow: 200 ml/min; gradient: from 100% $H_2O$ (0.1% FA)/0% ACN to 68% $H_2O$ (0.1% FA)/32% ACN in 15.5 min; 68% $H_2O$ (0.1% FA)/32% ACN for 8 min; column: Welch Ultimate XB_C18, 20-40 μm, 120 Å, 95 mm×365 mm) to yield 5.4 g of the title compound.

$^1$H NMR (400 MHz, $CDCl_3$): δ ppm 8.81-8.78 (1H), 7.98 (1H), 7.53 (1H), 5.51 (1H), 3.89-3.84 (2H), 2.40-2.16 (2H), 1.47 (s, 9H)

I-35e

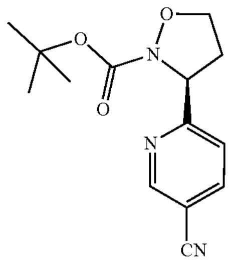

Tert-butyl (3S)-3-(5-Cyano-2-pyridyl) isoxazolidine-2-carboxylate

To a solution of tert-butyl N-[(1S)-1-(5-cyano-2-pyridyl)-3-hydroxy-propyl]-N-hydroxy-carbamate (4.3 g) in THF (40 ml) was added tributylphosphane (4.75 g) and DIAD (3.85 g) at 0° C. The mixture was warmed to 20° C. smoothly and stirred for 12 h under $N_2$ atmosphere. The mixture was concentrated under reduced pressure to give a residue, which was purified by silica gel chromatography (PE:EA=1:1~0:1) and preparative RP LC (flow: 100 ml/min; gradient: from 100% $H_2O$ (0.1% FA)/0% ACN to 50% $H_2O$ (0.1% FA)/50% ACN in 30 min; 50% $H_2O$ (0.1% FA)/50% ACN for 8 min; column: Agela C18, 20 μm, 100 Å, 60.6 mm×187 mm) to give 2 g product (91.1% e.e.), which was further purified by SFC (column: DAICEL CHIRALPAK AD (250 mm×30 mm, 10 um; mobile phase: A $CO_2$; B: MeOH (0.05% DEA); B %: 60%—no gradient, 4.2 min) to yield 1.71 g of the title compound.

$^1$H NMR (400 MHz, $CDCl_3$): δ ppm 8.83 (1H), 7.95 (1H), 7.67 (1H), 5.40 (1H), 4.14 (1H), 3.91 (1H), 2.91-2.78 (1H), 2.61-2.48 (1H), 1.50 (9H)

Chiral HPLC:

(chiralpak AD-3, 50×4.6 mm, 3 μm; phase A: $CO_2$, B: MeOH (0.05% DEA; A 50%/B 50% (0.05% DEA); flow 3 ml/min; T 35° C., p 100 bar)

Tert-butyl (3S)-3-(5-cyano-2-pyridyl)isoxazolidine-2-carboxylate: tR 0.86 min, 99.9%

Tert-butyl (3R)-3-(5-cyano-2-pyridyl)isoxazolidine-2-carboxylate: tR 0.36 min, 0.01

I-35

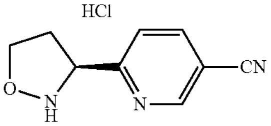

6-[(3S)-Isoxazolidin-3-yl] pyridine-3-carbonitrile hydrochloride salt

Tert-butyl (3S)-3-(5-cyano-2-pyridyl)isoxazolidine-2-carboxylate (500 mg) was dissolved in dioxane (4.5 ml) and HCl solution (4 M in dioxane, 4.5 ml) was added with stirring. After stirring for 4 h and standing overnight the mixture was concentrated in vacuo, the residue dissolved in water and lyophilised to yield 380 mg of the title compound.

LC/MS: m/z=176.2 [M+H]$^+$; tR: 0.75 min (LC/MS-method A)

I-36 I-36a

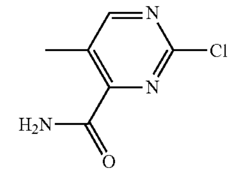

1-(4-Carbamoyl-5-methyl-pyrimidin-2-yl) piperidine-4-carboxylic acid TFA salt
2-Chloro-5-methyl-pyrimidine-4-carboxamide 2-Chloro-5-methylpyrimidine-4-carboxylic acid (300 mg) was dissolved in dry DCM (10 ml) with stirring under Ar. Then catalytic DMF (4 drops) was added and the mixture cooled to 0° C. Thionyl chloride (1.5 ml) was added, followed by a second portion (1.5 ml) after 45 min. After stirring for an additional hour the solvent was removed in vacuo, DIPEA (1.1 ml) added to the residue and the resulting mixture was dropped into an ammonia solution (7 N in MeOH, 5 ml) with stirring at 0° C. After 30 min saturated sodium bicarbonate solution was added and the aqueous phase was extracted with DCM (3×). The combined organic phases were dried over sodium sulphate, filtered and concentrated in vacuo. The residue was purified by silica gel chromatography (12 g $SiO_2$, 100% DCM to 90% DCM/10% ethanol in 30 min). The pure fractions were combined and concentrated. The pure product containing fractions were combined and the solvent was removed in vacuo to yield 174 mg of the title compound.

LC/MS: m/z=172.1 [M+H]$^+$; tR: 0.74 min (LC/MS-method A)

I-36b

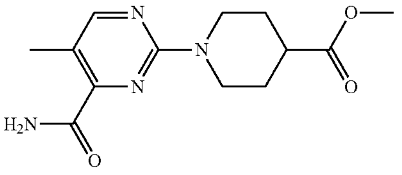

Methyl 1-(4-Carbamoyl-5-methyl-pyrimidin-2-yl) piperidine-4-carboxylate

2-Chloro-5-methyl-pyrimidine-4-carboxamide (170 mg) was dissolved in dry ACN (10 ml) in a microwave vessel (10-20 ml). After DIPEA (700 μl) and methyl piperidine-4-carboxylate (160 μl) were added the mixture was heated at 100° C. in a microwave oven for 1 h. After cooling the solvent was removed in vacuo and the residue was purified by RP HPLC (flow 40 ml/min, 97% $H_2O$/3% ACN to 10% $H_2O$/90% ACN in 15 min; Agilent Prep C18-5 μm, 30×100 mm). The product containing fractions were combined, the ACN was removed in vacuo and the aqueous phase was lyophilised to yield 236 mg of the title compound.

LC/MS: m/z=279.3 [M+H]$^+$; tR: 1.48 min (LC/MS-method A)

I-36

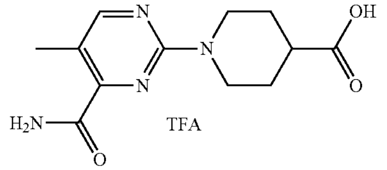

1-(4-Carbamoyl-5-methyl-pyrimidin-2-yl) piperidine-4-carboxylic acid TFA salt

Methyl 1-(4-carbamoyl-5-methyl-pyrimidin-2-yl)piperidine-4-carboxylate (234 mg) was dissolved in THF (8 ml). Then LiOH (41 mg) and water (0.8 ml) were added with stirring. After 45 min further water (0.5 ml) was added with stirring. After stirring for 1.5 h the THF was removed in vacuo and the mixture was acidified with HCl (1 N in water). After lyophilisation overnight the residue was dissolved in ACN/water and purified by RP prep-HPLC (flow 25 ml/min; 95% $H_2O$+0.05% TFA/5% ACN in 45 min to 95% ACN/5% $H_2O$+0.05% TFA; column: Purosphere® STAR-RP18 25×250 mm, 10 μm). The pure compound containing fractions were combined, the ACN was removed in vacuo and the residue lyophilised overnight to yield 166 mg of the title compound with minor impurities.

LC/MS: m/z=265.2 [M+H]$^+$; tR: 1.15 min (LC/MS-method A).

I-37: 5-[(3S)-2-[(3R,4R)-3-Fluoropiperidine-4-carbonyl]isoxazolidin-3-yl]pyridine-3-carbonitrile and 5-[(3S)-2-[(3S,4S)-3-fluoropiperidine-4-carbonyl] isoxazolidin-3-yl]pyridine-3-carbonitrile (~1:1 mixture, compound with 4-methylbenzenesulfonic acid)

I-37a

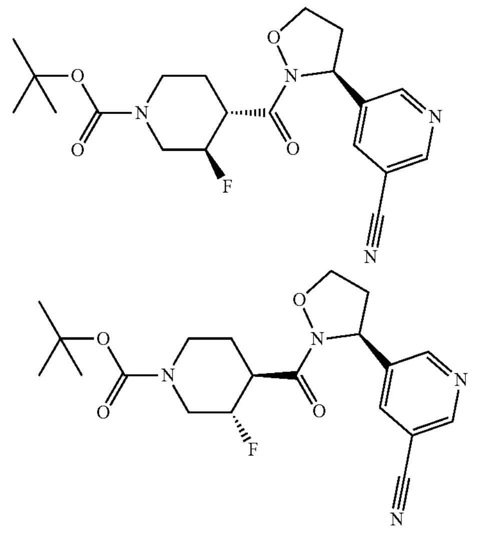

Tert-butyl (3R,4R)-4-[(3S)-3-(5-cyano-3-pyridyl) isoxazolidine-2-carbonyl]-3- fluoro-piperidine-1-Carboxylate and tert-butyl (3S,4S)-4-[(3S)-3-(5-Cyano-3- pyridyl) isoxazolidine-2-carbonyl]-3-fluoro-piperidins-1-Carboxylate (~1 :1 mixture)

A mixture of (3,4-trans)-1-tert-butoxycarbonyl-3-fluoro-piperidine-4-carboxylic acid (161 mg), DMF (0.5 ml) and DCM (1.5 ml) was added 3-(ethyliminomethyleneamino)-N,N-dimethyl-propan-1-amine (hydrochloride, 329 mg), sodium hydrogen carbonate (482 mg) and ethyl (2Z)-2-cyano-2-hydroxyimino-acetate (246 mg). After 15 minutes, a mixture of 5-[(3S)-isoxazolidin-3-yl]pyridine-3-carbonitrile (compound with 4-methylbenzenesulfonic acid, 100 mg, I-02-3) and DMF (0.5 ml) was added. After 30 minutes, the reaction mixture was partitioned between water (10 ml) and ethyl acetate (20 ml). The organic layer was washed with water (3×10 ml) and brine (10 ml) and was dried ($Na_2SO_4$), filtered and concentrated to provide 350 mg of the title compound. The crude was used directly in the next step. Purification of an aliquot by preparative RP HPLC (Column: Waters SunFire Prep C18 OBD, 5 μm, 50 mm×100 mm; mobile phase: water/ACN 95:5 (0.0 min) to 95:5 (2.0 min) to 8515 (2.5 min) to 15:85 (10.5 min) to 0:100 (11.0 min) to 0:100 (13.0 min) to 95:5 (13.5 min) to 95:5 (14.9 min); flow rate: 120 ml/min) provided an analytical sample:

LC/MS: m/z=305.27 $[M-BOC+2H]^+$; tR: 1.94 and 1.98 min (LC/MS-method A)

I-37

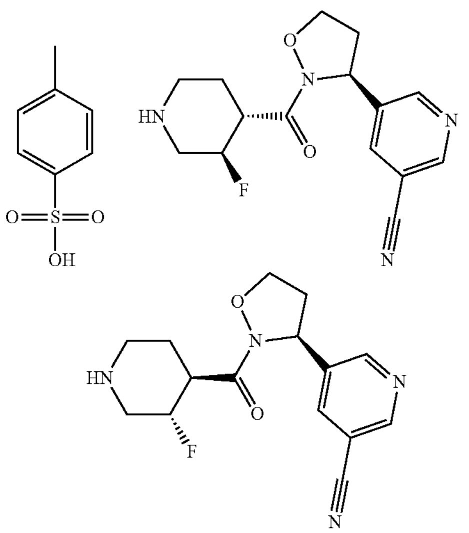

5-[(3S)-2-[(3R,4R)-3-Fluoropiperidine-4-carbonyl]isoxazolidin-3-yl]pyridine-3-carbonitrile and 5-[(3S)-2-[(3S,4S)-3-fluoropiperidine-4-carbonyl]isoxazolidin-3- yl]pyridine-3-carbonitrile (~1 :1 mixture, compound with 4-methylbenzenesulfonic acid)

A mixture of tert-butyl (3R,4R)-4-[(3S)-3-(5-cyano-3-pyridyl)isoxazolidine-2-carbonyl]-3-fluoro-piperidine-1-carboxylate and tert-butyl (3S,4S)-4-[(3S)-3-(5-cyano-3-pyridyl)isoxazolidine-2-carbonyl]-3-fluoro-piperidine-1-carboxylate (~1:1 mixture, 320 mg, crude), 4-methylbenzenesulfonic acid (hydrate, 200 mg) and 1,4-dioxane (3 ml) was heated at 50° C. for three hours. Volatiles were removed in vacuo to leave 500 mg of the crude title compound, which was used directly in the next step.

5-[(3S)-2-[(3R,4R)-3-Fluoropiperidine-4-carbonyl]isoxazolidin-3-yl]pyridine-3-carbonitrile and 5-[(3S)-2-[(3S,4S)-3-fluoropiperidine-4-carbonyl]isoxazolidin-3-yl]pyridine-3-carbonitrile (~1:1 mixture) were obtained after RP HPLC (Column: Waters SunFire Prep C18 OBD, 5 μm, 50 mm×100 mm; mobile phase: water/ACN 98:2 (0.0 min) to 98:2 (2.0 min) to 98:2 (2.5 min) to 48:52 (10.5 min) to 1:99 (11.0 min) to 1:99 (13.0 min) to 95:5 (13.5 min) to 95:5 (14.9 min); flow rate: 120 ml/min) of an aliquot of the above crude:

LC/MS: m/z=305.29 $[M+H]^+$; tR: 0.62 and 0.63 min (LC/MS-method A)

I-38 I-38a

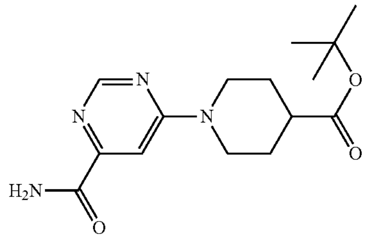

1-(6-Carbamoylpyrimidin-4-yl)piperidine-4-carboxylic acid TFA salt
Tert-butyl 1-(6-Carbamoylpyrimidin-4-yl)piperidine-4-carboxylate Tert-butyl piperidine-4-carboxylate hydrochloride (800 mg) was dissolved in dry ACN (5 ml). At RT DIPEA (3 ml) and 6-chloropyrimidine-4-carboxamide (682.2 mg) were added and the mixture was heated at 120° C. for 2.5 h under argon. After cooling the solvent was removed in vacuo. The residue thus obtained was dissolved in a mixture of water and DCM, the phases were separated and the aqueous phase was extracted with DCM (3×). The combined organic phases were dried over magnesium sulphate, filtered and concentrated in vacuo to yield 984 mg of the title compound.

LC/MS: m/z=307.3 $[M+H]^+$; tR: 0.97 min (LC/MS-method D)

I-38

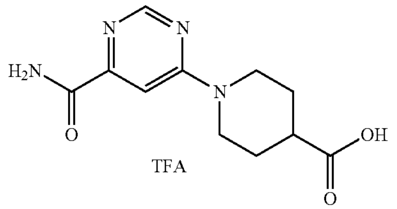

1-(6-Carbamoylpyrimidin-4-yl)piperidine-4-carboxylic acid TFA salt

Tert-butyl 1-(6-carbamoylpyrimidin-4-yl)piperidine-4-carboxylate (984 mg) was dissolved in DCM (10 ml) and TFA (5.3 ml) was added at RT with stirring. After 2.5 h the solvent was removed in vacuo and the residue co-evaporated twice with toluene. The solid thus obtained was dissolved in ACN/DCM/heptane. After standing overnight the precipitate was filtered, washed with heptane and dried in vacuo to yield 1.066 g of the title compound.

LC/MS: m/z=251.1 $[M+H]^+$; tR: 0.37 min (LC/MS-method D)

$^1H$ NMR (400 MHz, DMSO-$d_6$) δ ppm 8.69 (1H), 8.24 (1H), 7.95 (1H), 7.43 (1H), 4.35 (2H), 3.24 (2H), 2.63 (1H), 1.96 (1H), 1.55 (1H).

I-39: 1-(6-Cyanopyrimidin-4-yl)piperidine-4-carboxylic acid

I-39a

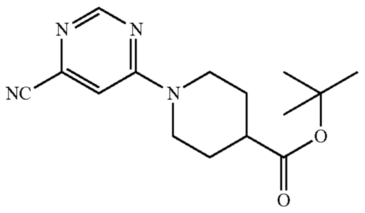

Tert-butyl 1-(6-cyanopyrimidin-4-yl)piperidine-4-carboxylate

Tert-butyl piperidine-4-carboxylate hydrochloride (1.000 g) was dissolved in dry ACN (10 ml). At RT DIPEA (3.7 ml) and 6-chloropyrimidine-4-carbonitrile (629.4 mg) were added and the mixture was heated at 120° C. for 2.5 h under argon. After cooling the solvent was removed in vacuo. The residue thus obtained was dissolved in a mixture of water and DCM, the phases were separated and the aqueous phase was extracted with DCM (3×). The combined organic phases were dried over magnesium sulphate, filtered and concentrated in vacuo. The residue was purified by flash chromatography on silica gel (25 g; 0% to 80% EA in heptane in 9 min). The compound containing fractions were combined and the solvent was removed in vacuo to yield 906 mg of the title compound.

LC/MS: m/z=289.2 [M+H]$^+$; tR: 1.46 min (LC/MS-method D)

I-39

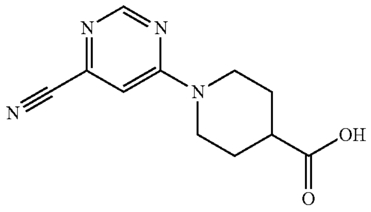

1-(6-Cyanopyrimidin-4-yl)piperidine-4-carboxylic acid

Tert-butyl 1-(6-cyanopyrimidin-4-yl)piperidine-4-carboxylate (906 mg) was dissolved in DCM (10 ml) and TFA (6.6 ml) was added at RT with stirring. After 2.5 h the solvent was removed in vacuo and the residue was co-evaporated twice with toluene. The residue was dissolved in ACN, the precipitate was filtered, washed with ACN/heptane and dried in vacuo to yield 683 mg of the title compound LC/MS: m/z=233.2 [M+H]$^+$; tR: 0.78 min (LC/MS-method D)

I-39-1

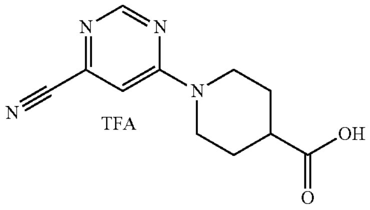

1-(6-Cyanopyrimidin-4-yl)piperidine-4-carboxylic acid TFA salt

Crude tert-butyl 1-(6-cyanopyrimidin-4-yl)piperidine-4-carboxylate (I-39a, 445 mg) was dissolved in DCM (12 ml) and TFA (1.22 ml) was added at RT with stirring. After standing overnight toluene (10 ml) was added and then the solvent was removed in vacuo. The residue was lyophilised to yield 390 mg of the title compound.

LC/MS: m/z=233.2 [M+H]$^+$; tR: 1.12 min (LC/MS-method A)

I-40 I-40a

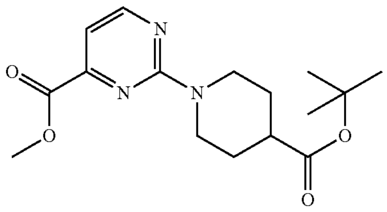

1-(4-Methoxycarbonylpyrimidin-2-yl)piperidine-4-carboxylic acid
Methyl 2-(4-tert-butoxycarbonyl-1-piperidyl)pyrimidine-4-carboxylate Tert-butyl piperidine-4-carboxylate hydrochloride (1.000 g) was dissolved in dry ACN (25 ml). At RT DIPEA (3.7 ml) and methyl 2-chloropyrimidine-4-carboxylate (924.2 mg) were added and the mixture was heated at 120° C. for 3 h under argon. After cooling the solvent was removed in vacuo. The residue thus obtained was dissolved in a mixture of water and DCM, the phases were separated and the aqueous phase was extracted with DCM (3×). The combined organic phases were dried over magnesium sulphate, filtered and concentrated in vacuo. The residue was purified by flash chromatography on silica gel (30 g; 10% to 22% EA in heptane over 37 min). The compound containing fractions were combined and the solvent was removed in vacuo to yield 1.2 g of the title compound.

LC/MS: m/z=322.3 [M+H]$^+$; tR: 1.57 min (LC/MS-method D)

I-40

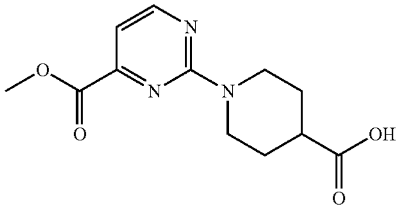

1-(4-Methoxycarbonylpyrimidin-2-yl) piperidine-4-carboxylic acid

Methyl 2-(4-tert-butoxycarbonyl-1-piperidyl)pyrimidine-4-carboxylate (1.2 g) was dissolved in DCM (20 ml) and TFA (5.7 ml) was added at RT with stirring. After 4 h the solvent was removed in vacuo and the residue was co-evaporated twice with toluene. The residue was dissolved in EA/heptane, the precipitate was filtered, washed with heptane and dried in vacuo to yield 870 mg of the title compound.

LC/MS: m/z=266.2 $[M+H]^+$; tR: 0.93 min (LC/MS-method D)

$^1H$ NMR (400 MHz, DMSO-$d_6$) δ ppm 8.59 (1H), 7.07 (1H), 4.54 (2H), 3.09 (2H), 2.54 (1H), 1.91 (2H), 1.48 (2H).

I-40-1

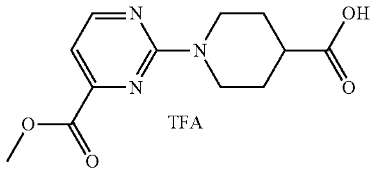

1-(4-Methoxycarbony|pyrimidin-2-y|)piperidine-4-carboxylic acid TFA salt

Crude methyl 2-(4-tert-butoxycarbonyl-1-piperidyl)pyrimidine-4-carboxylate (I-40a, 496 mg) was dissolved in DCM (12 ml) and TFA (1.22 ml) was added at RT with stirring. After standing overnight toluene (10 ml) was added and then the solvent was removed in vacuo. The residue was lyophilised to yield 450 mg of the title compound.

LC/MS: m/z=266.3 $[M+H]^+$; tR: 1.37 min (LC/MS-method A)

I-41

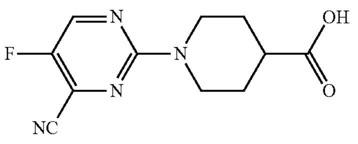

1-(4-Cyano-5-fluoro-pyrimidin-2-yl)piperidine -4-carboxylic acid

To a solution of methyl 1-(4-cyano-5-fluoro-pyrimidin-2-yl)piperidine-4-carboxylate (I-34d) (21.6 g) in THF (1000 ml) and water (172 ml) was added a solution of aqueous LiOH solution (1 M, 77.65 ml) at 0° C. The mixture was stirred at 0° C. for 6 h. The reaction mixture was adjusted with 1 N HCl solution to pH=5~6, concentrated under reduced pressure to remove most of the solvent and filtered. The filter cake was triturated with EA (100 ml) to yield 11.96 g of the title compound.

$^1H$ NMR ($CDCl_3$, 400 MHz): δ ppm 8.31 (1H), 4.45 (2H), 3.06 (2H), 2.57 (1H), 1.97-1.93 (2H), 1.68-1.63 (2H)

I-42

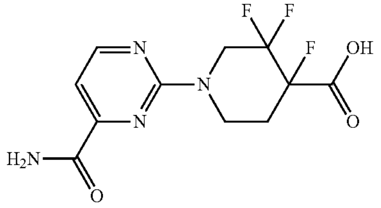

1-(4-Carbamoylpyrimidin-2-yl)-3,3,4-trifluoro-piperidine-4-carboxylic acid

I-42a

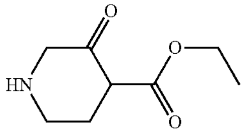

Ethyl 3-oxopiperidine-4-carboxylate

A mixture of 01-tert-butyl 04-ethyl 3-oxopiperidine-1,4-dicarboxylate (48 g, 176.92 mmol) in HCl/dioxane (4 M, 150 ml) was stirred at 20° C. for 1 h. The mixture was concentrated to give the title compound (38 g, crude, HCl) as yellow solid, which was used in next step without further purification.

I-42b

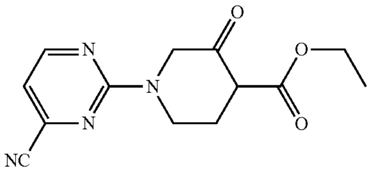

Ethyl 1-(4-Cyanopyrimidin-2-yl)-3-oxo-piperidine -4-carboxylate

To a solution of ethyl 3-oxopiperidine-4-carboxylate (38 g, 221.97 mmol) and 2-chloropyrimidine-4-carbonitrile (30.97 g, 221.97 mmol) in ACN (600 ml) was added DIPEA (86.06 g, 665.91 mmol, 115.99 ml). The mixture was stirred at 50° C. for 16 h. The mixture was concentrated, diluted with $H_2O$ (500 ml), extracted with EA (200 ml*2). The combined organic layers were washed with brine (300 ml), dried with anhydrous $Na_2SO_4$, filtered and concentrated under reduced pressure to give the title compound (56 g, crude) as yellow solid.

I-42c

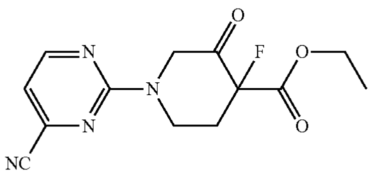

Ethyl 1-(4-cyanopyrimidin-2-y|)-4-fluoro-3-oxo-piperidine-4-carboxylate

To a solution of ethyl 1-(4-cyanopyrimidin-2-yl)-3-oxo-piperidine-4-carboxylate (56 g, 206.64 mmol) in ACN (3360 ml) was added Select F (72.3 g, 206.64 mmol) dropwise at 0° C. The mixture was warmed to 20° C. smoothly and stirred for 16 h. The reaction was poured into ice-water (2 l) and neutralized with saturated $NaHCO_3$ solution (100 ml), extracted with EA (1 l*3). The combined organic phases were washed with brine (1 l), dried with anhydrous $Na_2SO_4$, filtered and concentrated under reduced pressure to give a residue. The residue was purified by silica gel column chromatography (PE:EA=1:1) to give the title compound (44.2 g) as yellow solid. H-NMR showed a mixture of ketone and enol form.

I-42d

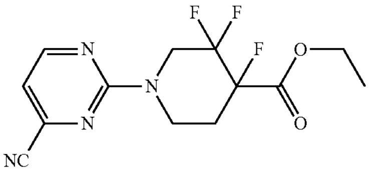

Ethyl 1-(4-cyanopyrimidin-2-yl)-3,3,4-trifluoro-piperidine-4-carboxylate

To a solution of ethyl 1-(4-cyanopyrimidin-2-yl)-4-fluoro-3-oxo-piperidine-4-carboxylate (44.2 g, 151.23 mmol) in DCM (220 ml) was added DAST (121.88 g, 756.15 mmol, 99.9 ml) dropwise at 20° C. under nitrogen atmosphere. The mixture was stirred at 60° C. for 22 h. The mixture was concentrated, poured into ice/water (400 ml), adjusted with saturated $NaHCO_3$ solution to pH=7, extracted with EA (400 ml*3). The combined organic layers were washed with brine (400 ml*2), dried over anhydrous $Na_2SO_4$, filtered and concentrated to give a residue. The residue was purified by silica gel column chromatography to give the title compound (17.4 g) as yellow solid.

$^1$H NMR ($CDCl_3$, 400 MHz): δ ppm 8.52 (1H), 6.89 (1H), 5.05-4.92 (1H), 4.64 (1H), 4.36 (2H), 3.87-3.69 (1H), 3.50 (1H), 2.55-2.35 (1H), 2.21 (1H), 1.35 (3H)

I-42

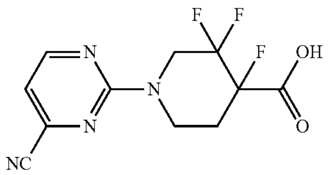

1-(4-Carbamoylpyrimidin-2-yl)-3,3,4-trifluoro-piperidine-4-carboxylic acid

To a solution of ethyl 1-(4-cyanopyrimidin-2-yl)-3,3,4-trifluoro-piperidine-4-carboxylate (8 g, 25.46 mmol) in THF (320 ml) and $H_2O$ (29 ml) was added aqueous LiOH solution (1 M, 50.91 ml) and $H_2O_2$ (5.77 g, 50.91 mmol, 4.89 mL, 30% purity) dropwise. The mixture was stirred at 25° C. for 4 h. The reaction mixture was quenched with saturated $Na_2SO_3$ solution (10 ml), adjusted with 1 N HCl solution (50 ml) to pH=6~7. The mixture was concentrated under reduced pressure to remove most of solvent, filtered and dried under vacuum to give 6.75 g of the title compound.

$^1$H NMR (400 MHz, DMSO-$d_6$) δ ppm 8.58 (1H), 8.31 (br, 1H), 7.74 (br, 1H), 7.15 (1H), 4.91-4.62 (1H), 4.56-4.30 (2H), 3.87-3.74 (1H), 2.07 (1H), 1.87-1.67 (1H)

I-43: 1-(5-Fluoro-4-methoxy-pyrimidin-2-yl)piperidine-4-carboxylic acid as lithium salt I-43a

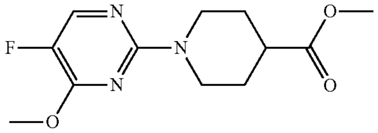

Methyl 1-(5-fluoro-4-methoxy-pyrimidin-2-yl) piperidine-4-carboxylate

2-Chloro-5-fluoro-4-methoxy-pyrimidine (275 mg) was dissolved in dry ACN (5 ml) in a microwave vessel (10 -20 ml). After DIPEA (890 μl) and methyl piperidine-4-carboxylate (200 μl) were added the mixture was heated at 140° C. in a microwave oven for 0.75 h. After cooling the solvent was removed in vacuo and the residue was purified by RP HPLC (flow 75 ml/min, 90% $H_2O$/10% ACN to 10% $H_2O$/90% ACN in 17.5 min; Agilent Prep C18-10 μm, 30×250 mm). The product containing fractions were combined, the ACN was removed in vacuo and the aqueous phase was lyophilised. The residue was further purified by silica gel chromatography (4 g $SiO_2$, 100% DCM to 80% DCM/20% EE in 20 min, then 80% DCM/20% EE for 10 min). The pure product containing fractions were combined and the solvent was removed in vacuo to yield 143 mg of the title compound.

LC/MS: m/z=270.3 $[M+H]^+$; tR: 1.95 min (LC/MS-method A)

I-43

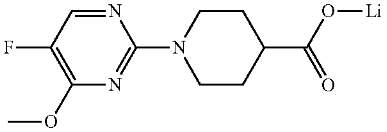

1-(5-Fluoro-4-methoxy-pyrimidin-2-yl) piperidine-4-carboxylic acid as lithium salt LiOH (19 mg) was added to a solution of methyl 1-(5-fluoro-4-methoxy-pyrimidin-2-yl)piperidine-4-carboxylate (142 mg) in THF (4 ml) and $H_2O$ (1 ml). The mixture was stirred at RT. After standing overnight additional LiOH (6 mg) was added. After stirring for 1 h at RT the reaction mixture was concentrated. The residue was lyophilised to yield 140 mg of the title compound, which was directly used in the next step without further purification.

LC/MS: m/z=256.3 [M+H]; tR: 1.49 min (LC/MS-method A)

I-44: 6-[(3S)-Isoxazolidin-3-yl]pyrazine-2-carbonitrile TFA Salt

I-44a

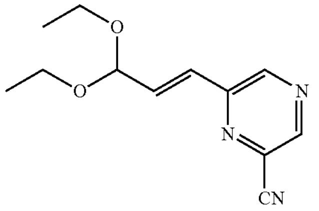

6-[(E)-3, 3-Diethoxyprop-1-enyl] pyrazine-2-carbonitrile

A mixture of 6-chloropyrazine-2-carbonitrile (25 g, 179.16 mmol), 3,3-diethoxyprop-1-ene (69.97 g, 537.47 mmol, 81.93 ml), TEA (54.39 g, 537.47 mmol, 74.81 ml), $Pd(t\text{-}Bu_3P)_2$ (4.58 g, 8.96 mmol) in DMF (250 ml) was degassed and purged with $N_2$ for 3 times, and then the mixture was stirred at 80° C. for 2 h under $N_2$ atmosphere. The mixture was concentrated, diluted with water (500 ml), extracted with EA (300 ml*3). The combined organic layers were washed with brine (200 ml*2), dried with $Na_2SO_4$, filtered and concentrated to give the title compound (45 g, crude) as brown oil.

I-44b

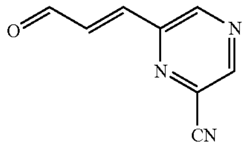

6-[(E)-3-Oxoprop-1-enyl] pyrazine-2-carbonitrile

A mixture of 6-[(E)-3,3-diethoxyprop-1-enyl]pyrazine-2-carbonitrile (45 g, crude) in HCl (1 M, 385.83 ml, 2 eq) and acetone (200 ml) was stirred at 20° C. for 1 h. The mixture was adjusted with saturated $NaHCO_3$ solution to pH=9, extracted with EA (300 ml*3), dried with $Na_2SO_4$, filtered and concentrated. The residue was purified by silica gel chromatography (PE:EA=1:0~4:1) to give the title compound (19.3 g) as yellow solid.

$^1$H NMR ($CDCl_3$, 400 MHz): δ ppm 9.88 (1H), 8.96 (1H), 8.91 (1H), 7.54 (1H), 7.32-7.23 (1H)

I-44c

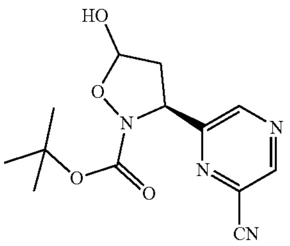

Tert-butyl (3S)-3-(6-cyanopyrazin-2-y|)-5-hydroxy-isoxazolidine-2-carboxylate

To a solution of 6-[(E)-3-oxoprop-1-enyl]pyrazine-2-carbonitrile (7.49 g, 23.00 mmol) in $CHCl_3$ (183 ml) was added [diphenyl-[(2S)-pyrrolidin-2-yl]methoxy]-trimethyl-silane (18.3 g, 114.99 mmol, 1 eq) at 0° C. The mixture was stirred at 0° C. for 0.5 h, tert-butyl N-hydroxycarbamate (16.84 g, 126.49 mmol) was added at 0° C. The mixture was warmed to 25° C. smoothly, stirred for 12 h under $N_2$ atmosphere. The reaction mixture was concentrated under reduced pressure to give a residue. The residue was purified by Prep. RP LC (flow: 400 ml/min; gradient: from 70% $H_2O$ (0.1% FA)/30% ACN to 60% $H_2O$ (0.1% FA)/40% ACN in 56 min, 60% $H_2O$ (0.1% FA)/40% ACN to 60% $H_2O$ (0.1% FA)/40% ACN in 21 min; column: Welch Ultimate XB C18, 15 μm, 100 Å, I.D. 15 0 mm*H400 mm) to give the title compound (18.7 g) as yellow oil.

I-44d

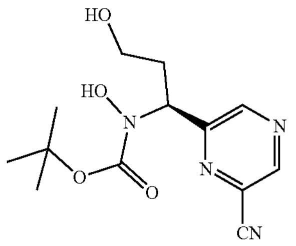

Tert-butyl N-[(1S)-1-(6-Cyanopyrazin-2-yl)-3-hydroxy-propyl]-N-hydroxy-carbamate To a solution of tert-butyl (3S)-3-(6-cyanopyrazin-2-yl)-5-hydroxy-isoxazolidine-2-carboxylate (5.85 g, 17.21 mmol) in MeOH (60 ml) was added $NaBH_4$ (195.34 mg, 5.16 mmol) at 0° C. The mixture was stirred at 0° C. for 2 h. The mixture was quenched with saturated $NH_4Cl$ solution (3 ml), diluted by water (300 ml), extracted with EA (300 ml*3), dried with $Na_2SO_4$, filtered and concentrated under reduced pressure to give a residue. The residue was combined with another batch on 6.85 g scale of the title compound, purified by Prep. RP LC (flow: 200 ml/min; gradient: from 80% $H_2O$ (0.1% FA)/20% ACN to 60% $H_2O$ (0.1% FA)/40% ACN in 35 min; 60% $H_2O$ (0.1% FA)/40% ACN to 60% $H_2O$ (0.1% FA)/40% ACN in 16 min; column: Phenomenex luna C18, 20-40 μm, 120 Å, I.D. 75 mm*H348 mm) to give the title compound (6.9 g, 74.1% e.e.) as yellow oil.

$^1$H NMR ($CDCl_3$, 400 MHz): δ ppm 8.96 (1H), 8.84 (1H), 5.56 (1H), 3.98-3.84 (m, 2H), 2.46-2.28 (2H), 1.51 (9H)

I-44e

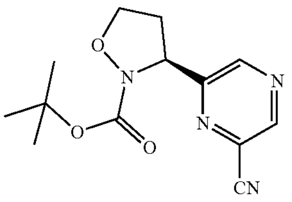

Tert-butyl (3S)-3-(6-cyanopyrazin-2-yl) isoxazolidine-2-carboxylate

To a solution of tert-butyl N-[(1 S)-1-(6-cyanopyrazin-2-yl)-3-hydroxy-propyl]-N-hydroxy-carbamate (500 mg, 1.70 mmol) in THF (5 ml) was added tributylphosphane (446.84 mg, 2.21 mmol, 544.93 ul) and DIAD (343.54 mg, 1.70 mmol, 330.32 ul) at 0° C., the mixture was stirred at 0° C. for 0.5 h. This reaction was carried in parallel in 14 batches. The reaction mixture was concentrated under reduced pressure to give a residue. The residue was purified by Prep. RP LC (flow: 200 ml/min; gradient: from 90% $H_2O$ (0.1% FA)/10% ACN to 60% $H_2O$ (0.1% FA)/40% ACN in 20 min; 60% $H_2O$ (0.1% FA)/40% ACN to 50% $H_2O$ (0.1% FA)/50% ACN in 10 min; 50% $H_2O$ (0.1% FA)/50% ACN to 50% $H_2O$ (0.1% FA)/50% ACN in 15 min; column: Phenomenex luna C18, 20-40 μm, 120 Å, I.D 0.95 mm*H365 mm) and silica gel column chromatography (PE:EA=9:1~1:3) to give 4.6 g of the title compound with 80.3% e.e. It was further purified by SFC (column: Daicel ChiralpakAD (250 mm*30 mm, 10 um); mobile phase: [A $CO_2$, B MeOH]; B %: 60%-60%, 4.7; 100 min), to yield the title compound (3.7 g, >99.9% e.e.) and its enantiomer (396 mg, >99.9% e.e).

$^1$H NMR ($CDCl_3$, 400 MHz): δ ppm 9.02 (1H), 8.84 (1H), 5.45 (1H), 4.20 (1H), 3.94 (1H), 2.84 (1H), 2.74-2.59 (1H), 1.53 (9H)

Chiral HPLC:

(chiralpak AD-3, 50×4.6 mm, 3 μm; phase A: $CO_2$, B: MeOH (0.05% DEA); B in A from 5 to 40%; flow 3 ml/min; T 35° C., p 100 bar)

Tert-butyl (3S)-3-(6-cyanopyrazin-2-yl)isoxazolidine-2-carboxylate: tR 1.82 min, 100%

Tert-butyl (3R)-3-(6-cyanopyrazin-2-yl)isoxazolidine-2-carboxylate: tR 0.83 min

I-44

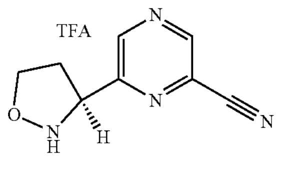

6-[(3S)-Isoxazolidin-3-yl] pyrazine-2-carbonitrile TFA salt

Tert-butyl (3S)-3-(6-cyanopyrazin-2-yl)isoxazolidine-2-carboxylate (110 mg) was dissolved in a mixture of TFA (0.98 ml) and water (250 μl). After 0.5 h the mixture was concentrated in vacuo. The residue was lyophilised (water/ACN) to yield 124 mg of the title compound as crude material, which was directly used in the next step.

I-45

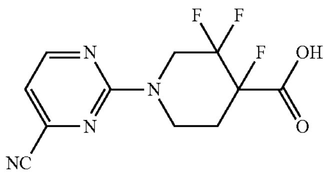

1-(4-Cyanopyrimidin-2-yl)-3,3,4-trifluoro-piperidine-4-carboxylic acid

To a solution of ethyl 1-(4-cyanopyrimidin-2-yl)-3,3,4-trifluoro-piperidine-4-carboxylate (7.8 g, 24.82 mmol) in THF (312 ml) and $H_2O$ (54.42 ml) was added $LiOH \cdot H_2O$ (1 M, 23.58 ml) dropwise at 25° C. The mixture was stirred at 25° C. for 3 h. The reaction mixture was adjusted with 1 N HCl solution to pH=6-7. The mixture was concentrated under reduced pressure to remove most of the solvent and filtered. The filter cake was triturated with EA (50 ml), filtered and dried under vacuum to yield the title compound (4.8 g) as off-white solid.

$^1$H NMR (400 MHz, DMSO-$d_6$) δ ppm 8.69 (1H), 7.24 (1H), 4.67-4.52 (1H), 4.45-4.24 (2H), 3.87-3.74 (1H), 2.09 (1H), 1.85-1.70 (1H)

I-46: 2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxylic acid I-46a

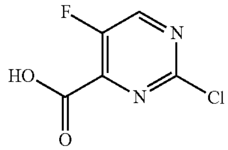

2-Chloro-5-fluoro-pyrimidine-4-carboxylic acid

Ethyl 2-chloro-5-fluoropyrimidine-4-carboxylate (800 mg) was dissolved in THF (12 ml). Lithium hydroxide (206 mg) and water (2 ml) were added. After 1 h the solvent was removed and water added to the residue followed by aqueous HCl solution (1 N). After lyophilisation 808 mg of the title compound containing LiCl were obtained. This crude material was directly used in the I-46.

I-46b

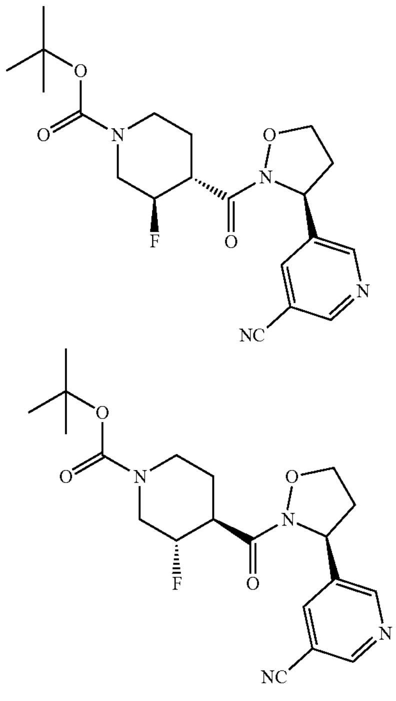

Tert-butyl (3R,4R or 3S,4S)-4-[(3S)-3-(5-cyano-3-pyridyl)isoxazolidine-2-carbonyl]-3-fluoro-piperidine-1-carboxylate (diastereomer 1) and tert-butyl (3S,4S or 3R,4R)-4-[(3S)-3-(5-cyano-3-pyridyl)isoxazolidine-2-carbonyl]-3-fluoro-piperidine-1-carboxylate (diastereomer 2)

(3,4)-Trans-1-tert-butoxycarbonyl-3-fluoro-piperidine-4-carboxylic acid (300 mg), (S)-5-(isoxazolidin-3-yl)nicotinonitrile (I-02-1, 320 mg) and DIPEA (700 μl) were dissolved in isopropanol (10 ml). After stirring for 10 min $T_3P$ (50% by wt. in EE, 1.03 ml) was added. After 2 h saturated ammonium chloride solution was added and the mixture was extracted with EA (2×). the combined organic layers were washed with HCl (0.1 n in water, 3×) and brine. The EA phase was dried, filtered and concentrated in vacuo. The residue was purified by preparative RP HPLC (flow 120 ml/min, 2 min 95% $H_2O$+0.1% TFA/5% ACN; 0.5 min 55% $H_2O$+0.1% TFA/45% ACN; 8 min 50% $H_2O$+0.1% TFA/50% ACN; 2.5 min 1% $H_2O$+0.1% TFA/99% ACN; Waters SunFire Prep OBD C18 (5 μm, 50×100 mm). The product containing fractions were combined, the ACN was removed in vacuo and the aqueous phase was lyophilised over night to yield 120 mg of diastereomer 1 and 154 mg of diastereomer 2.

Diastereomer 2 was further purified by silica gel chromatography (12 g $SiO_2$, 100% DCM for 5 min; from 100% DCM to 5% ethanol in 40 min; then 5% EtOH for 10 min). The pure product containing fractions were combined and concentrated in vacuo. The residue was dissolved in ACN/Water and lyophilised to yield 108 mg of diastereomer 2.

Firstly Eluating Product (Diastereomer 1):

LC/MS: m/z=349.2 [M+H-isobutylene]+; tR: 1.96 min (LC/MS-method A)

$^1$H NMR (400 MHz, DMSO-$d_6$) δ ppm 8.95 (1H), 8.78 (1H), 8.19 (1H), 5.45 (1H), 4.72-4.52 (1H), 4.33 (1H), 4.00 (2H), 3.75 (1H), 3.10 (1H), 2.94 (2H), 2.34 (1H), 1.85 (1H), 1.44 (1H), 1.40 (9H)

Secondly Eluating Product (Diastereomer 2):

LC/MS: m/z=349.2 [M+H-isobutylene]+; tR: 1.99 min (LC/MS-method A)

$^1$H NMR (400 MHz, DMSO-$d_6$) δ ppm 8.95 (1H), 8.79 (1H), 8.22 (1H), 5.49 (1H), 4.72-4.52 (1H), 4.33 (1H), 4.07 (1H), 3.89 (1H), 3.73 (1H), 3.05 (1H), 2.94 (2H), 2.32 (1H), 1.99 (1H), 1.48 (1H), 1.40 (9H)

I-46c

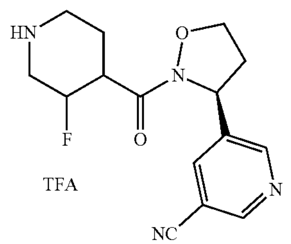

5-[(3S)-2-[(3R,4R or 3S,4S)-3-Fluoropiperidine-4-carbonyl]isoxazolidin-3-yl]pyridine-3-carbonitrile TFA salt Tert-butyl (3R,4R or 3S,4S)-4-((S)-3-(5-cyanopyridin-3-yl)isoxazolidine-2-carbonyl)-3-fluoropiperidine-1-carboxylate (diastereomer 1, 120 mg) was dissolved in DCM (7 ml) and TFA (340 μl) was added. After stirring for 2 h at RT the sovent was removed and the residue lyophilised from ACN/water to yield 131 mg of crude material.

LC/MS: m/z=305.2 [M+H]$^+$; tR: 0.64 min (LC/MS-method A)

I-46

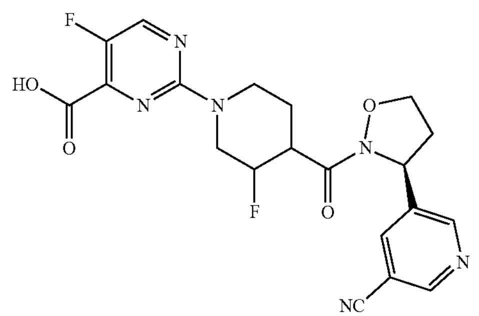

2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxylic acid 5-[(3S)-2-[(3R,4R or 3S,4S)-3-fluoropiperidine-4-carbonyl]isoxazolidin-3-yl]pyridine-3-carbonitrile TFA salt (100 mg) was dissolved in dry ACN (4.0 ml) in a microwave vessel (2-5 ml). After DIPEA (210 μl) and 2-chloro-5-fluoro-pyrimidine-4-carboxylic acid (I-46a, 76 mg) were added, the mixture was heated at 100° C. in a microwave oven for 6 h. After cooling the solvent was removed in vacuo. The residue was purified by preparative RP HPLC (flow 120 ml/min, 2 min 95% $H_2O$+0.1% TFA/5% ACN; 0.5 min 90% $H_2O$+0.1% TFA/10% ACN; 8 min 45% $H_2O$+0.1% TFA/55% ACN; 2.5 min 1% $H_2O$+0.1% TFA/99% ACN; Waters SunFire Prep OBD C18 (5 μm, 50×100 mm). The product containing fractions were combined, the ACN was removed in vacuo and the aqueous phase was lyophilised over night to yield 21 mg of the title compound.

LC/MS: m/z=445.2 [M+H]$^+$; tR: 1.46 min (LC/MS-method A)

I-46

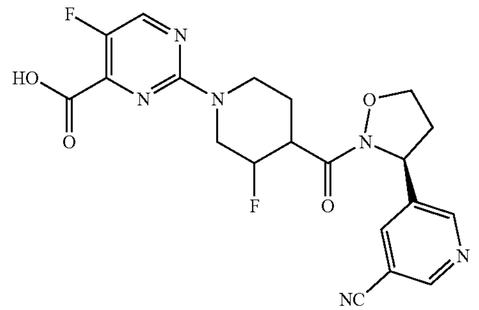

2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxylic acid Following the procedures described in I-46c 139 mg 5-[(3S)-2-[(3S,4S or 3R,4R)-3-fluoropiperidine-4-carbonyl]isoxazolidin-3-yl]pyridine-3-carbonitrile TFA salt was prepared from tert-butyl (3S,4S or 3R,4R)-4-[(3S)-3-(5-cyano-3-pyridyl)isoxazolidine-2-carbonyl]-3-fluoro-piperidine-1-carboxylate (diastereomer 2, I-46b, 108 mg). Following the procedure described in I-46 5-[(3S)-2-[(3S,4S or 3R,4R)-3-fluoropiperidine-4-carbonyl]isoxazolidin-3-yl]pyridine-3-carbonitrile TFA salt (135 mg) were reacted with 2-chloro-5-fluoro-pyrimidine-4-carboxylic acid (I-46a, 103 mg) to yield 43 mg (24%) of the title compound.

LC/MS: m/z=445.2 [M+H]$^+$; tR: 1.48 min (LC/MS-method A)

I-48

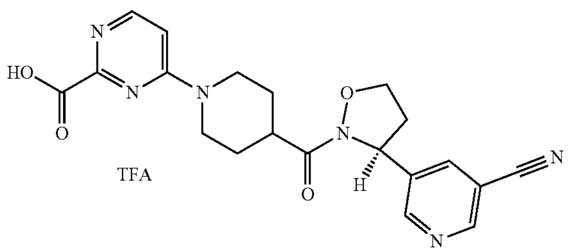

4-[4-[(3S)-3-(5-Cyano-3-pyridyl)isoxazolidine-2-carbonyl]-1-piperidyl]pyrimidine-2-carboxylic acid as TFA salt LiOH (2.3 mg) was added to a solution of ethyl 4-[4-[(3S)-3-(5-cyano-3-pyridyl)isoxazolidine-2-carbonyl]-1-piperidyl]pyrimidine-2-carboxylate (21 mg) in THF (2 ml) and $H_2O$ (0.5 ml). The mixture was stirred at RT. After 3 h additional LiOH (2 mg) was added. After stirring for 1 h at RT the reaction mixture was concentrated. The residue was purified by RP prep-HPLC (flow 25 ml/min; from 95% $H_2O$+0.05% TFA/5% ACN to 5% $H_2O$+0.05% TFA/95% ACN 45 min.; Purosphere® STAR-RP18, 25×250 mm, 10 μm). The product containing fractions were combined, the ACN was removed in vacuo and the aqueous phase was lyophilised over night to yield 16 mg of the title compound.

LC/MS: m/z=409.2 [M+H]+; tR: 0.91 min (LC/MS-method A)

I-49: 4-Piperidyl-[(3S)-3-pyrazin-2-ylisoxazolidin-2-yl]methanone trifluoro acetic acid salt I-49a

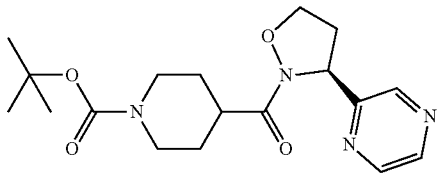

Tert-butyl 4-[(3S)-3-pyrazin-2-ylisoxazolidine-2-carbonyl]piperidine-1-carboxylate 1-Tert-butoxycarbonyl-piperidine-4-carboxylic acid (1.3 g) was dissolved in dry DMF (25 ml) and DIPEA (2.99 ml) and HATU (3.8 g) were added with stirring. After 15 min (3S)-3-pyrazin-2-ylisoxazolidine TFA salt (I-17 (as TFA salt), 1.3 g) dissolved in dry DMF (10 ml) was added with stirring. After 2 h sat. sodium bicarbonate solution was added and the aqueous phase was extracted with EA (3×). The combined organic phases were washed with brine, dried over sodium sulphate, filtered and concentrated in vacuo. The residue was purified by silica gel chromatography (80 g $SiO_2$, 100% n-heptane to 100% EA in 20 min). The product containing fractions were combined and the solvent was removed in vacuo. The residue was further purified by RP prep-HPLC (flow 50 ml/min; 90% $H_2O$/10% ACN to 10% $H_2O$/90% ACN in 15 min; Agilent Prep C18—10 μm, 30×250 mm). The product containing fractions were combined, the ACN was removed in vacuo and the aqueous phase was lyophilised over night to yield 1.07 g of the title compound.

LC/MS: m/z=363.3 $[M+H]^+$; tR: 1.76 min (LC/MS-method A).

I-49

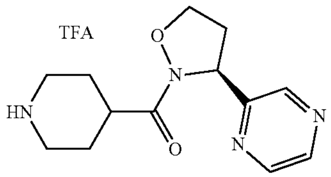

4-Piperidyl-[(3S)-3-pyrazin-2-ylisoxazolidin-2-yl]methanone trifluoro acetic acid salt TFA (3.42 ml) was added to a solution of tert-butyl 4-[(3S)-3-pyrazin-2-ylisoxazolidine-2-carbonyl]piperidine-1-carboxylate(1.07 g) in dry DCM (15 ml) under Ar with stirring. After 15 min the mixture was concentrated in vacuo and the residue was lyophilised from water/ACN to yield 1.75 g of the title compound.

LC/MS: m/z=263.2 $[M+H]1^+$; tR: 0.39 min (LC/MS-method A)

I-50: 4-[(3S)-Isoxazolidin-3-yl]thiophene-2-carbonitrile

I-50a

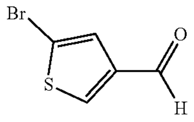

5-Bromothiophene-3-carbaldehyde

To a mixture of thiophene-3-carbaldehyde (20 g, 178.33 mmol, 16.26 ml) and $AlCl_3$ (40.42 g, 303.17 mmol, 16.57 mL) in DCM (100 ml) at 0° C., was added a solution of $Br_2$ (25.65 g, 160.50 mmol, 8.27 ml) in DCM (100 ml) dropwise at 0° C., and then the mixture was warmed smoothly to 40° C. for 4 h. The reaction mixture was quenched by addition $H_2O$ (200 ml) at 0° C., and then diluted with $H_2O$ (500 ml) and extracted with EA (200 ml). The combined organic layers were washed with brine 500 (ml), dried over $Na_2SO_4$, filtered and concentrated under reduced pressure to give a residue. The residue was purified by column chromatography ($SiO_2$, Petroleum ether/Ethyl acetate=1/0) to give the title compound (27 g, 141.33 mmol, 79.25% yield) as a yellow oil.

$^1H$ NMR ($CDCl_3$, 400 MHz): δ ppm 9.70 (1H), 7.93 (1H), 7.43 (1H).

I-50b

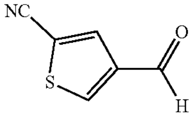

4-Formylthiophene-2-carbonitrile

A mixture of 5-bromothiophene-3-carbaldehyde (1 g, 5.23 mmol), CuCN (2.81 g, 31.41 mmol) in DMF (10 ml) was degassed and purged with $N_2$ for 3 times, and then the mixture was stirred at 160° C. for 1 h under $N_2$ atmosphere.

The reaction mixture was filtered and then diluted with $H_2O$ (100 ml) and extracted with EA (50 ml). The combined organic layers were washed with brine (100 ml), dried over $Na_2SO_4$, filtered and concentrated under reduced pressure to give a residue. The residue was purified by column chromatography ($SiO_2$, Petroleum ether/Ethyl acetate=2/1 to 4/1) to give the title compound (350 mg, 48.75% yield) as a yellow solid.

$^1H$ NMR ($CDCl_3$, 400 MHz): δ ppm 9.94 (1H), 8.34 (1H), 8.06 (1H)

I-50c

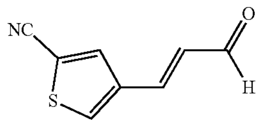

4-[(E)-3-Oxoprop-1-enyl]thiophene-2-carbonitrile

To a solution of 4-formylthiophene-2-carbonitrile (7 g, 51.04 mmol) in THF (70 ml) was added 2-(triphenyl-$\lambda^5$-phosphanylidene)acetaldehyde (15.53 g, 51.04 mmol). The mixture was stirred at 70° C. for 12 h. The reaction mixture was filtered and then diluted with $H_2O$ (100 ml) and extracted with EA (100 ml). The combined organic layers were washed with brine (50 ml), dried over $Na_2SO_4$, filtered and concentrated under reduced pressure to give a residue. The residue was purified by column chromatography ($SiO_2$, Petroleum ether/Ethyl acetate=3/1) to give the title compound (5 g, crude) as a yellow solid.

I-50d

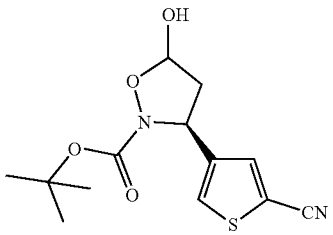

Tert-butyl (3S)-3-(5-cyano-3-thienyl)-5-hydroxy-isoxazolidine-2-carboxylate

To a solution of [diphenyl-[(2R)-pyrrolidin-2-yl]methoxy]-trimethyl-silane (1.80 g, 5.51 mmol) in $CHCl_3$ (45 ml) was added 4-[(E)-3-oxoprop-1-enyl]thiophene-2-carbonitrile (4.5 g, 27.57 mmol) and tert-butyl N-hydroxycarbamate (4.04 g, 30.33 mmol) at 0° C. The mixture was warmed smoothly to 25° C. for 12 h. The reaction mixture was filtered and concentrated under reduced pressure to give a residue. The crude product was purified by reversed-phase HP LC (flow: 120 ml/min; gradient: from 95% $H_2O$ (0.1% FA)/5% ACN to 70% $H_2O$ (0.1% FA)/30% ACN in 20 min; 70% $H_2O$ (0.1% FA)/30% ACN to 70% $H_2O$ (0.1% FA)/30% ACN in 30 min; column: 330 g Flash Column Welch Ultimate XB_C18 20-40 μm; 120 Å) to give the title compound (5.8 g, 19.57 mmol, 70.98% yield) as a white solid.

$^1H$ NMR ($CDCl_3$, 400 MHz): δ ppm 7.59 (1H), 7.46 (1H), 5.85 (1H), 5.38 (1H), 2.77 (1H), 2.28 (1H), 1.50 (9H)

I-50e

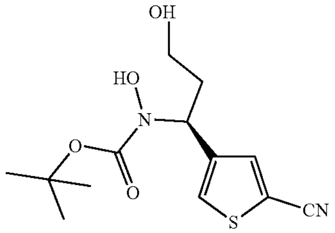

Tert-butyl N-hydroxy-N-[(1S)-1-(5-cyano-3-thienyl)-3-hydroxy-propyl]carbamate

To a solution of tert-butyl (3S)-3-(5-cyano-3-thienyl)-5-hydroxy-isoxazolidine-2-carboxylate (5.4 g, 18.22 mmol) in MeOH (50 ml) was added $NaBH_4$ (344.70 mg, 9.11 mmol) at 0° C. The mixture was warmed smoothly to 25° C. for 4 h. The reaction mixture was quenched by addition $NH_4Cl$ (20 ml) at 0° C., and then diluted with $H_2O$ (100 ml) and extracted with EA (100 ml*3). The combined organic layers were washed with brine (100 ml), dried over $Na_2SO_4$, filtered and concentrated under reduced pressure to give a residue. The residue was purified by column chromatography ($SiO_2$, Petroleum ether/Ethyl acetate=2/1 to 1/1) to give the title compound (4.81 g, 88.47% yield) as a yellow oil.

$^1H$ NMR ($CDCl_3$, 400 MHz): δ ppm 7.67 (1H), 7.54 (1H), 5.34 (1H), 3.89-3.73 (2H), 2.40-2.29 (1H), 2.09-2.04 (1H), 1.50 (9H)

I-50f

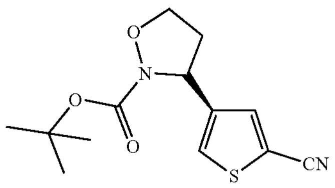

Tert-butyl (3S)-3-(5-cyano-3-thienyl)isoxazolidine-2-carboxylate

To a solution of tert-butyl N-hydroxy-N-[(1 S)-1-(5-cyano-3-thienyl)-3-hydroxy-propyl]carbamate (4.8 g, 16.09 mmol) in THF (48 ml) was added tributylphosphane (5.21 g, 25.74 mmol) and DIAD (4.23 g, 20.91 mmol) at 0° C. Then the mixture was warmed smoothly to 25° C. for 4 h. The reaction mixture was filtered and concentrated under reduced pressure to give a residue. The crude product was purified by preparative RP-LC (0.1% FA condition) and then by column chromatography ($SiO_2$, Petroleum ether/Ethyl acetate=4/1 to 3/1) to give the title compound (4.2 g, 93.12% yield) as a yellow solid.

$^1H$ NMR ($CDCl_3$, 400 MHz): δ ppm 7.51 (1H), 7.40 (1H), 5.21 (1H), 4.15-4.06 (1H), 3.86-3.76 (1H), 2.73-2.58 (1H), 2.26-2.12 (1H), 1.42 (9H)

SFC: tR 1.37 min (94%); enantiomer as impurity: tR: 0.98 min (6%)

(Column: Chiralpak AD-3, 50×4.6 mm, I.D., 3 μm, Mobile phase: A: $CO_2$, B: methanol (0.05% DEA), Gradient MeOH (0.05% DEA) in $CO_2$ from 5% to 40%, flow rate: 3.0 ml/min, Column temp.: 35° C., back pressure: 100 bar).

I-50

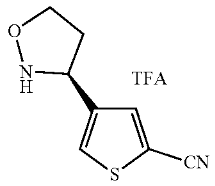

4-[(3S)-Isoxazolidin-3-yl]thiophene-2-carbonitrile TFA salt

Tert-butyl (3S)-3-(5-cyano-3-thienyl)isoxazolidine-2-carboxylate (50 mg) was dissolved in DCM (3 ml) and TFA (140 μl) was added. After stirring for 1 h at RT the solvent was removed and the residue lyophilised from ACN/water to yield 46 mg of crude material.

LC/MS: m/z=181.1 $[M+H]^+$; tR: 0.16 min (LC/MS-method C)

I-51: 4-[(3S)-Isoxazolidin-3-yl]furan-2-carbonitrile HCl Salt

I-51a

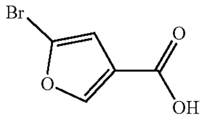

5-Bromofuran-3-carboxylic acid

To a mixture of pyridinium tribromide (138.39 g, 432.71 mmol) in AcOH (150 ml) was added furan-3-carboxylic acid (50 g, 446.10 mmol). The mixture was stirred at 40° C. for 12 h. The mixture was concentrated, diluted with water (500 ml), extracted with EA (400 ml*2), dried with $Na_2SO_4$, filtered and concentrated. The residue was purified by Prep. RP LC (flow: 400 ml/min; gradient: from 90% $H_2O$ (0.1% FA)/10% ACN to 69% $H_2O$ (0.1% FA)/31% ACN in 96 min; 69% $H_2O$ (0.1% FA)/31% ACN to 64% $H_2O$ (0.1% FA)/36% ACN in 21 min; column: Phenomenex luna C18, 15 μm, 100 Å, I.D. 150 mm*H400 mm) to give the title compound (13.5 g, 15.49% yield) as yellow solid.

$^1H$ NMR (MeOD, 400 MHz): δ ppm 8.14 (1H), 6.71 (1H)

I-51b

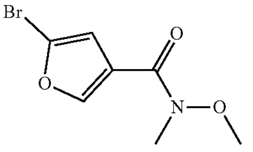

5-Bromo-N-methoxy-N-methyl-furan-3-carboxamide

A mixture of 5-bromofuran-3-carboxylic acid (13.5 g, 70.69 mmol), N-methoxymethanamine hydrochloride (6.90 g, 70.69 mmol), DIEA (27.41 g, 212.06 mmol, 36.94 ml) and HATU (32.25 g, 84.83 mmol) in DCM (135 ml) was stirred at 25° C. for 3 h under $N_2$ atmosphere. The reaction mixture was diluted with $H_2O$ (300 ml), extracted with DCM (200 ml*2). The combined organic layers were washed with brine (300 ml), dried over $Na_2SO_4$, filtered and concentrated under reduced pressure to give a residue. The residue was purified by silica gel column chromatography (PE:EA=5:1~3:1) to give the title compound (11.9 g, 72% yield) as yellow solid.

$^1H$ NMR ($CDCl_3$, 400 MHz): δ ppm 7.98 (1H), 6.79 (1H), 3.71 (3H), 3.31 (3H)

I-51c

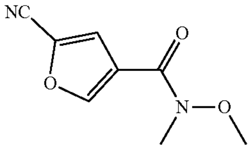

5-Cyano-N-methoxy-N-methyl-furan-3-carboxamide

A mixture of 5-Bromo-N-methoxy-N-methyl-furan-3-carboxamide (11.7 g, 49.99 mmol), DPPF (4.16 g, 7.50 mmol), $Zn(CN)_2$ (17.61 g, 149.97 mmol), $Pd_2(dba)_3$ (4.58 g, 5.00 mmol) and Zn (653.77 mg, 10.00 mmol) in DMF (120 ml) was degassed and purged with $N_2$ for 3 times, and then the mixture was stirred at 100° C. for 2 h under $N_2$ atmosphere. The reaction mixture was diluted with water (600 ml), extracted with methyl tert-butyl ether (300 ml*2). The combined organic layers were washed with brine (500 ml*2), dried over $Na_2SO_4$, filtered and concentrated under reduced pressure to give a residue. The residue was purified by silica gel column chromatography (PE:EA=1:0~3:1) to give the title compound (9.2 g, 97% yield) as brown solid.

$^1H$ NMR ($CDCl_3$, 400 MHz): δ ppm 8.13 (1H), 7.55 (1H), 3.74 (3H), 3.36 (3H)

I-51d

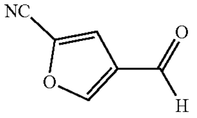

4-Formylfuran-2-carbonitrile

To a solution of 5-cyano-N-methoxy-N-methyl-furan-3-carboxamide (9.5 g, 52.73 mmol) in THF (95 ml) was added DIBAL-H (1 M, 52.73 ml). The mixture was stirred at −78° C. for 2 h. The reaction mixture was quenched by MeOH (0.5 ml), warmed to 25° C., filtered and concentrated under reduced pressure, purified by flash silica gel chromatography (PE:EA=1:0-1:1) to give the title compound (4.2 g, 65.78% yield) as yellow solid.

$^1H$ NMR ($CDCl_3$, 400 MHz): δ ppm 9.97 (1H), 8.20 (1H), 7.47 (1H)

I-51e

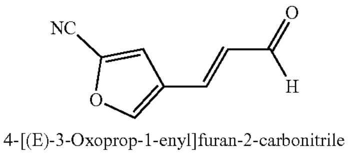

4-[(E)-3-Oxoprop-1-enyl]furan-2-carbonitrile

A mixture of 4-formylfuran-2-carbonitrile (5.5 g, 45.42 mmol), 2-(triphenyl-phosphanylidene)acetaldehyde (14.51 g, 47.69 mmol) in THF (50 ml) was degassed and purged with $N_2$ for (3×), and then the mixture was stirred at 70° C. for 12 h under $N_2$ atmosphere. The reaction mixture was concentrated under reduced pressure to give a residue. The residue was purified by silica gel column chromatography (PE:EA=4:1) to give the title compound (5.21 g, 77.96% yield) as yellow solid.

$^1$H NMR ($CDCl_3$, 400 MHz): δ ppm 9.67 (1H), 7.88 (1H), 7.37-7.29 (2H), 6.51 (1H)

I-51f

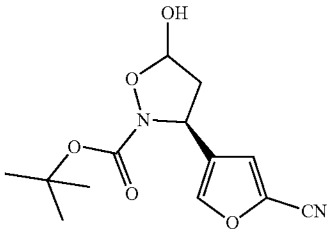

Tert-butyl (3S)-3-(5-cyano-3-furyl)-5-hydroxy-isoxazolidine-2-carboxylate

To a solution of 4-[(E)-3-oxoprop-1-enyl]furan-2-carbonitrile (2.08 g, 6.39 mmol) in $CHCl_3$ (47 ml) was added [diphenyl-[(2R)-pyrrolidin-2-yl]methoxy]-trimethyl-silane (4.7 g, 31.94 mmol) and tert-butyl N-hydroxycarbamate (4.68 g, 35.14 mmol) at 0° C. The mixture was warmed to 25° C. smoothly, stirred for 12 h. The reaction mixture was concentrated under reduced pressure to give a residue. The residue was purified by Prep. RP LC (flow: 200 mL/min, gradient: from 90% $H_2O$ (0.1% FA)/10% ACN to 60% $H_2O$ (0.1% FA)/40% ACN in 30 min; 60% $H_2O$ (0.1% FA)/40% ACN in 10 min; column: Agela C18, 20-40 μm, 120 Å, I.D.72 mm*H300 mm) to give the title compound (1.52 g, 38.42% yield) as brown oil.

$^1$H NMR ($CDCl_3$, 400 MHz): δ ppm 7.54 (1H), 7.09 (1H), 5.78 (1H), 5.29 (1H), 2.71 (1H), 2.24 (1H), 1.51 (9H)

I-51g

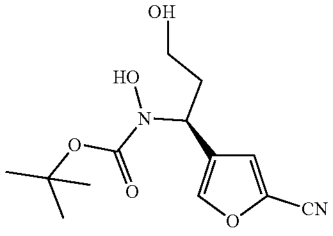

Tert-butyl N-hydroxy-N-[(1S)-1-(5-cyano-3-furyl)-3-hydroxy-propyl]carbamate

To a solution of tert-butyl (3S)-3-(5-cyano-3-furyl)-5-hydroxy-isoxazolidine-2-carboxylate (2.1 g, 5.62 mmol) in MeOH (21 ml) was added $NaBH_4$ (233.84 mg, 6.18 mmol) at 0° C. The mixture was warmed to 25° C. smoothly, stirred for 2 h. The reaction mixture was quenched with saturated $NH_4Cl$ solution (5 ml) at 0° C., diluted with water (30 ml), extracted with EA (50 ml*2). The combined organic layers were washed with brine (100 ml), dried over $Na_2SO_4$, filtered and concentrated under reduced pressure to give a residue. The residue was purified by silia gel column chromatography (PE:EA=2:1~1:1) to give the title compound (1.1 g, 63.82% yield, 51.08% e.e.) as yellow oil.

$^1$H NMR ($CDCl_3$, 400 MHz): δ ppm 7.58 (1H), 7.15 (1H), 6.75-6.31 (1H), 5.24 (1H), 3.88-3.69 (2H), 2.35-2.18 (1H), 2.04-1.87 (1H), 1.50 (9H)

I-51h

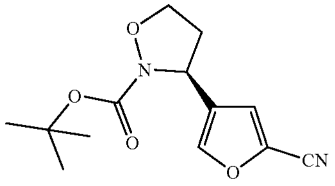

Tert-butyl (3S)-3-(5-cyano-3-furyl)isoxazolidine-2-carboxylate

To a solution of tert-butyl N-hydroxy-N-[(1 S)-1-(5-cyano-3-furyl)-3-hydroxy-propyl]carbamate (1.10 g, 3.90 mmol) in THF (11 ml) was added tributylphosphane (1.26 g, 6.23 mmol) and DIAD (1.02 g, 5.07 mmol) at 0° C., stirred for 2 h. The reaction mixture was concentrated under reduced pressure to give a residue. The residue was purified by preparative RP LC (flow: 100 ml/min; gradient: from 95% $H_2O$ (0.1% FA)/5% ACN to 40% $H_2O$ (0.1% FA)/60% ACN in 25 min; 40% $H_2O$ (0.1% FA)/60% ACN in 3 min; column: Welch Ultimate XB_C18, 20-40 μm, 120 Å, I.D.72 mm*H300 mm) and flash silica gel column chromatography (PE:EA=1:0~4:1) to give the title compound (850 mg, 83% yield, 52.9% e.e). The residue was further purified by SFC (column: Daicel ChiralPak-IG (250*30 mm, 10 μm); mobile phase A: $CO_2$, B: [isopropanol (0.1% sat. aqueous $NH_3$ solution]; B %: 30%-30%, 4.5; 30 min; flow rate: 60 ml/min; back pressure: 100 bar) to yield the pure title compound (483 mg, >99.9% e.e.) as a yellow oil.

$^1$H NMR ($CDCl_3$, 400 MHz): δ ppm 7.54 (1H), 7.10 (1H), 5.20 (1H), 4.17 (1H), 3.93-3.83 (1H), 2.69 (1H), 2.24 (1H), 1.51 (9H)

SFC: tR 1.52 min (>99.9%); tR of enantiomer: 0.83 min (Column: Chiralpak IG-3, 50×4.6 mm, I.D., 3 μm, Mobile phase: A: $CO_2$, B: methanol (0.05% DEA), Gradient: MeOH (0.05% DEA) in $CO_2$ from 5% to 40%, flow rate: 3.0 ml/min, column temp.: 35° C., back pressure: 100 bar).

I-51

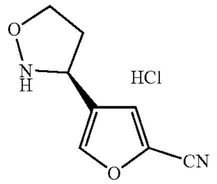

4-[(3S)-Isoxazolidin-3-yl]furan-2-carbonitrile HCl salt

Tert-butyl (3S)-3-(5-cyano-3-furyl)isoxazolidine-2-carboxylate (50 mg) was dissolved in dry dioxane (2 ml) and HCl (4 M in dioxane, 2 ml) was added. After stirring for 3 h at RT further HCl (0.5 ml) was added and stirring was continued for 1 h. Then the solvent was removed and the residue lyophilised from ACN/water to yield 48 mg of crude material.

LC/MS: m/z=165.1 $[M+H]^+$; tR: 0.09 min (LC/MS-method C)

I-52: 4-[(3S)-2-(Piperidine-4-carbonyl)isoxazolidin-3-yl]thiophene-2-carbonitrile trifluoro acetic acid salt I-52a

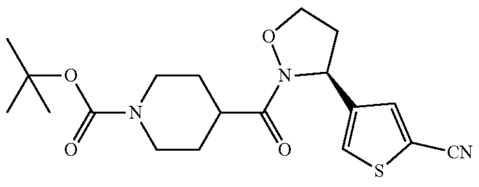

Tert-butyl 4-[(3S)-3-(5-cyano-3-thienyl)isoxazolidine-2-carbonyl]piperidine-1-carboxylate 1-Tert-butoxycarbonyl-piperidine-4-carboxylic acid (38 g) was dissolved in dry DMF (2 ml) and DIPEA (90 μl) and HATU (112 mg) were added with stirring. After 15 min 4-[(3S)-Isoxazolidin-3-yl]thiophene-2-carbonitrile TFA salt (I-50, 50 mg) dissolved in dry DMF (1 ml) was added with stirring. After 1 h sat. sodium bicarbonate solution was added and the aqueous phase was extracted with EA (3×). The combined organic phases were washed with brine, dried over sodium sulphate, filtered and concentrated in vacuo. The residue was purified by silica gel chromatography (4 g $SiO_2$, 100% n-heptane to 100% EA in 30 min). The product containing fractions were combined and the solvent was removed in vacuo to yield 47 mg of the title compound.

LC/MS: m/z=336.2 $[M+H\text{-isobutene}]^+$; tR: 2.17 min (LC/MS-method A).

I-52

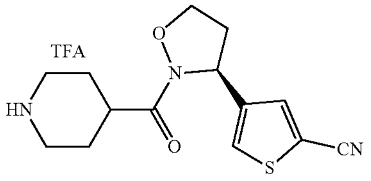

4-[(3S)-2-(Piperidine-4-carbonyl)isoxazolidin-3-yl]thiophene-2-carbonitrile trifluoro acetic acid salt TFA (90 μl) was added to a solution of tert-butyl 4-[(3S)-3-(5-cyano-3-thienyl)isoxazolidine-2-carbonyl]piperidine-1-carboxylate(45 mg) in dry DCM (3 ml) under Ar with stirring. After 3.5 h the mixture was concentrated in vacuo and the residue was lyophilised from water/ACN to yield 41 mg of the title compound.

LC/MS: m/z=292.1 $[M+H]^+$; tR: 0.80 min (LC/MS-method A)

I-53

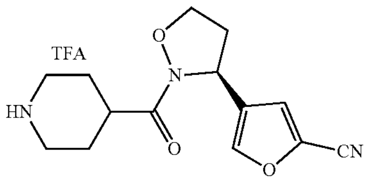

4 4-[(3S)-2-(Piperidine-4-carbonyl)isoxazolidin-3-yl]furan-2-carbonitrile trifluoro acetic acid salt Following the procedure described in I-52a/I-52 and starting with 4-[(3S)-Isoxazolidin-3-yl]furan-2-carbonitrile HCl salt (1-51, 190 mg) 181 mg of the title compound were obtained.

LC/MS: m/z=276.1 $[M+H]^+$; tR: 0.34 min (LC/MS-method C)

I-54: 5-[(3S)-Isoxazolidin-3-yl]pyridazine-3-carbonitrile

I-54a

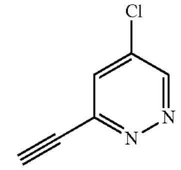

5-Chloropyridazine-3-carbonitrile

A mixture of 3,5-dichloropyridazine (25 g, 167.81 mmol) in DMF (250 ml) was added $Zn(CN)_2$ (19.71 g, 167.81 mmol), DPPF (9.30 g, 16.78 mmol), $Pd_2(dba)_3$ (7.68 g, 8.39 mmol), and then the mixture was stirred at 90° C. for 12 h. The reaction mixture was adjusted pH to 11, and filtered then diluted with $H_2O$ 500 ml and extracted with EA 500 ml. The combined organic layers were washed with brine 500 ml, dried over $Na_2SO_4$, filtered and concentrated under reduced pressure to give a residue. The residue was purified by column chromatography ($SiO_2$, Petroleum ether/Ethyl acetate=5/1 to 3/1) to give the title compound (7.7 g, 55.18 mmol) as a yellow solid.

$^1$H NMR ($CDCl_3$, 400 MHz): δ ppm 9.41 (1H), 7.91 (1H).

I-54b

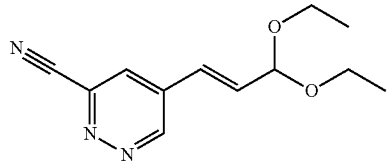

5-[(E)-3,3-Diethoxyprop-1-enyl]pyridazine-3-carbonitrile

To a solution of 5-chloropyridazine-3-carbonitrile (5.5 g, 39.41 mmol), 2-[(E)-3,3-diethoxyprop-1-enyl]-4,4,5,5-tetramethyl-1,3,2-dioxaborolane (11.19 g, 43.36 mmol) in dioxane (2.8 ml) and $H_2O$ (0.4 ml) was added $K_2CO_3$ (10.89 g, 78.83 mmol) and $Pd(dppf)Cl_2$ (2.88 g, 3.94 mmol). The mixture was stirred at 90° C. for 12 h. The reaction mixture was filtered and diluted with $H_2O$ (200 ml) and extracted with EA (200 ml), The combined organic layers were washed with brine (200 ml), dried over $Na_2SO_4$, filtered and concentrated under reduced pressure to give a residue. The residue (18 g, crude) as a black solid was directly used in the next step.

I-54c

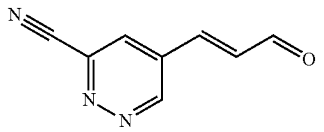

5-[(E)-3-Oxoprop-1-enyl]pyridazine-3-carbonitrile

To a solution of 5-[(E)-3,3-diethoxyprop-1-enyl] pyridazine-3-carbonitrile (18 g, 77.17 mmol) in acetone (180 ml) was added HCl (1 M, 77.17 ml). The mixture was stirred at 25° C. for 0.5 h. The reaction mixture was adjusted pH to 7 with $NaHCO_3$, and then diluted with $H_2O$ (200 ml) and extracted with EA 200 (ml). The combined organic layers were washed with brine 200 (ml), dried over $Na_2SO_4$, filtered and concentrated under reduced pressure to give a residue. The residue was purified by column chromatography ($SiO_2$, Petroleum ether/Ethyl acetate=2/1) to give the title compound (5.5 g, 34.56 mmol) as a white solid.

$^1H$ NMR ($CDCl_3$, 400 MHz): δ ppm 9.88 (1H), 9.51 (1H), 7.94 (1H), 7.46 (1H), 7.03 (1H)

I-54d

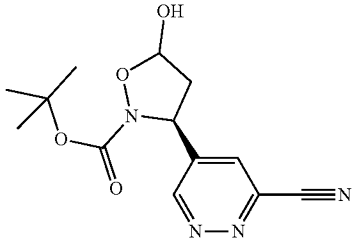

Tert-butyl (3S)-3-(6-cyanopyridazin-4-yl)-5-hydroxy-isoxazolidine-2-carboxylate

To a solution of 5-[(E)-3-oxoprop-1-enyl]pyridazine-3-carbonitrile (1.47 g, 4.52 mmol) in $CHCl_3$ (360 ml) was added [diphenyl-[(2R)-pyrrolidin-2-yl]methoxy]-trimethyl-silane (3.6 g, 22.62 mmol) and tert-butyl N-hydroxycarbamate (3.31 g, 24.88 mmol) at 0° C. The mixture was warmed smoothly to 25° C. for 12 h. The reaction mixture was concentrated under reduced pressure to give a residue. The crude product was purified by preparative RP-LC (0.1% FA condition), column: Phenomenex Gemini-NX C18 75*30 mm*3 μm; mobile phase: [water (0.225% FA)-ACN]: B %: 28%-38%, 7 min to give the title compound (2.6 g) as a yellow oil.

$^1H$ NMR ($CDCl_3$, 400 MHz): δ ppm 9.41 (1H), 7.91 (1H), 5.96 (1H), 5.48 (1H), 2.98 (1H), 2.27 (1H), 1.55-1.51 (9H)

I-54e

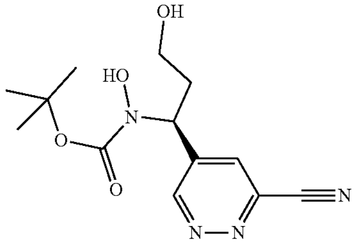

Tert-butyl-N-hydroxy-N-[(1S)-1-(6-cyanopyridazin-4-yl)-3-hydroxy-propyl]carbamate To a solution of tert-butyl (3S)-3-(6-cyanopyridazin-4-yl)-5-hydroxy-isoxazolidine-2-carboxylate (2.6 g, 8.90 mmol) in MeOH (20 ml) was added $NaBH_4$ (336.53 mg, 8.90 mmol). The mixture was stirred at 25° C. for 2 h. The reaction mixture was quenched by addition $NH_4Cl$ 5 (ml) at 0° C., and concentrated and then diluted with $H_2O$ (100 ml) and extracted with EA (100 ml). The combined organic layers were washed with brine 100 (ml), dried over $Na_2SO_4$, filtered and concentrated under reduced pressure to give a residue. The crude product was purified by preparative RP-LC (0.1% FA condition, see I-54d) to give the title compound (2 g) as yellow oil.

$^1H$ NMR ($CDCl_3$, 400 MHz): δ ppm 9.42 (1H), 7.98 (1H), 5.42 (1H), 4.01-3.75 (2H), 2.49-2.31 (1H), 2.19-2.08 (1H), 1.51 (9H)

I-54f

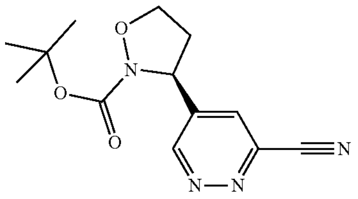

Tert-butyl (3S)-3-(6-cyanopyridazin-4-yl)isoxazolidine-2-carboxylate

To a solution of tert-butyl N-hydroxy-N-[(1 S)-1-(6-cyanopyridazin-4-yl)-3-hydroxy-propyl]carbamate (1.35 g, 4.59 mmol) in THF (10 ml) was added DIAD (1.04 g, 4.50 mmol) and tributylphosphane (1.39 g, 6.88 mmol, 1.70 ml) at 0° C. The mixture was stirred at 25° C. for 12 h. The reaction mixture was filtered and concentrated under reduced pressure to give a residue. The residue was purified by preparative RP-LC (column: 180 g flash column Welch Ultimate XB-C18; 20-45 μm; 100 Å; mobile phase: A: water (0.1% FA), B: methanol; gradient B %: 0-5% 10 min; 5% 10 min; flow rate: 80 ml/min) and column chromatography ($SiO_2$, Petroleum ether/Ethyl acetate=2/1 to 1/1) to give the title compound (750 mg, purity 72%) as a white solid which was further purified by SFC (column: Daicel Chiralpak (250 mm*30 mm, 10 um); mobile phase: [A $CO_2$, B 0.1% $NH_3/H_2O$ in MeOH]; B %: 40%-40%, 2.5 min; 40 min) to yield the title compound (595 mg, 79% yield, 99.9% e.e.) as a white solid.

$^1H$ NMR ($CDCl_3$, 400 MHz): δ ppm 9.38 (1H), 7.89 (1H), 5.38 (1H), 4.25 (1H), 3.92 (1H), 3.04-2.92 (1H), 2.34-2.23 (1H), 1.53 (9H)

Analytical SFC: tR 1.93 min (>99.9%); tR of R-enantiomer: 1.08 min (Column: Chiralpak AD-3, 50×4.6 mm, I.D., 3 μm, Mobile phase: A: $CO_2$, B: methanol (0.05% DEA), Gradient: MeOH (0.05% DEA) in $CO_2$ from 5% to 40%, flow rate: 3.0 ml/min, column temp.: 35° C., back pressure: 100 bar).

I-54

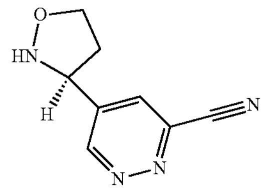

5-[(3S)-Isoxazolidin-3-yl]pyridazine-3-carbonitrile

Tert-butyl (3S)-3-(6-cyanopyridazin-4-yl)isoxazolidine-2-carboxylate (100 mg) was dissolved in DCM (5 ml) and TFA (500 μl) was added. After stirring for 0.5 h at RT the solvent was removed and the residue treated with DCM and saturated $NaHCO_3$. The organic layer was separated and the aqueous phase was extracted with DCM (2×). The combined organic layers were dried over $Na_2SO_4$, filtered and concentrated in vacuo to yield 58 mg of crude material.

LC/MS: m/z=177.0 $[M+H]^+$; tR: 0.58 min (LC/MS-method A)

I-55: 4-[(3S)-Isoxazolidin-3-yl]thiazole-2-carbonitrile

I-55a

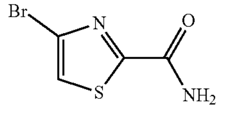

4-Bromothiazole-2-carboxamide

A mixture of 4-bromothiazole-2-carbaldehyde (500 mg, 2.60 mmol), aqueous $NH_3$ (9.13 g, 65.09 mmol, 10.03 ml, 25% purity), 12 (925.19 mg, 3.65 mmol) in THF (2.5 ml) was stirred at 25° C. for 2 h. The reaction mixture was quenched with sat. $Na_2SO_3$ (10 ml) solution, and extracted EA (20 ml*3). The combined organic layers were washed with brine (20 ml), dried over $Na_2SO_4$, filtered and concentrated under reduced pressure to give a residue. The residue was purified by silica gel column chromatography ($SiO_2$, PE:EA=1/0~0/1) to give the title compound (400 mg, 74% yield) as a yellow solid.

$^1H$ NMR ($CDCl_3$, 400 MHz): δ ppm 7.53 (1H), 7.07 (br, 1H), 5.77 (br, 1H)

I-55b

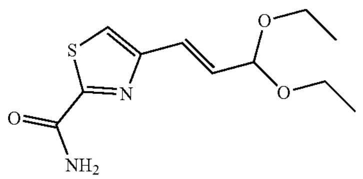

4-[(E)-3,3-Diethoxyprop-1-enyl]thiazole-2-carboxamide

A mixture of 4-bromothiazole-2-carboxamide (7.8 g, 37.67 mmol), 2-[(E)-3,3-diethoxyprop-1-enyl]-4,4,5,5-tetramethyl-1,3,2-dioxaborolane (11.58 g, 45.21 mmol), $Pd(dppf)Cl_2$ (4.13 g, 5.65 mmol), $Cs_2CO_3$ (30.69 g, 94.18 mmol) in dioxane (80 ml) and $H_2O$ (16 ml) was degassed and purged with $N_2$ for 3 times, and then the mixture was stirred at 110° C. for 12 h under $N_2$ atmosphere. The reaction mixture was water (100 ml) and extracted EA (100 ml*3). The combined organic layers were washed with brine (100 ml), dried over $Na_2SO_4$, filtered and concentrated under reduced pressure to give a residue. The crude product (10 g, crude) was used into the next step without further purification.

I-55c

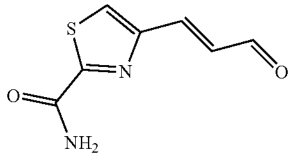

4-[(E)-3-Oxoprop-1-enyl]thiazole-2-carboxamide

To a solution of 4-[(E)-3,3-diethoxyprop-1-enyl]thiazole-2-carboxamide (10 g, 39.01 mmol) in THF (50 ml) was added HCl (1 M, 39.01 ml). The reaction was stirred at 25° C. for 10 min. The reaction mixture was adjusted sat $NaHCO_3$ with PH=7-8 and EA (100 ml*3). The combined organic layers were washed with brine (100 ml), dried over $Na_2SO_4$, filtered and concentrated under reduced pressure to give a residue. The residue was purified by silica gel column chromatography ($SiO_2$, PE:EA=10:1~1:1) to give the title compound (3.7 g, 20.31 mmol, 52% yield) as a yellow solid.

$^1H$ NMR ($CDCl_3$, 400 MHz): δ ppm 9.76 (1H), 7.81 (1H), 7.45 (1H), 7.13 (br, 1H), 7.00 (1H), 5.67 (br, 1H)

I-55d

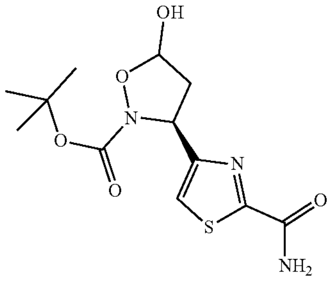

Tert-butyl (3S)-3-(2-carbamoylthiazol-4-yl)-5-hydroxy-isoxazolidine-2-carboxylate To a solution of 4-[(E)-3-oxoprop-1-enyl]thiazole-2-carboxamide (1.32 g, 4.06 mmol) in $CHCl_3$ (37 mL) was added [diphenyl-[(2R)-pyrrolidin-2-yl]methoxy]-trimethyl-silane (3.7 g, 20.31 mmol) at 0° C. under $N_2$. The reaction mixture was stirred at 0° C. for 0.5 h, tert-butyl N-hydroxycarbamate (2.97 g, 22.34 mmol) was added at 0° C. The reaction mixture was warmed to 25° C. smoothly, stirred for 36 h. The reaction mixture was concentrated. The crude product was purified by preparative RP-LC (column: 330 g flash column Welch Ultimate XB-C18; 20-40 μm; 120 Å; mobile phase: A: water (0.1% FA), B: ACN; gradient B %: 0-15% 8 min; 15% 15 min; flow rate: 80 ml/min) to give the title compound (3 g, 9.51 mmol, 47% yield) as a yellow solid.

$^1H$ NMR ($CDCl_3$, 400 MHz): δ ppm 7.52 (1H), 7.15 (br, 1H), 6.10 (1H), 5.85 (br, 1H), 5.50 (1H), 2.76 (1H), 2.56-2.65 (1H), 1.50 (9H)

I-55e

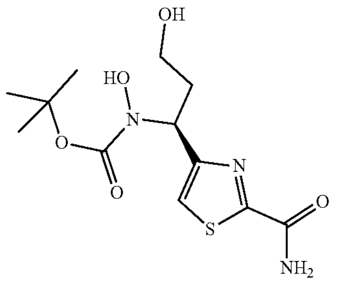

Tert-butyl N-hydroxy-N-[(1S)-1-(2-carbamoylthiazol-4-yl)-3-hydroxy-propyl]carbamate To a solution of tert-butyl (3S)-3-(2-carbamoylthiazol-4-yl)-5-hydroxy-isoxazolidine-2-carboxylate (3 g, 9.51 mmol) in MeOH (30 ml) was added $NaBH_4$ (359.91 mg, 9.51 mmol) at 0° C. The reaction mixture was stirred at 0° C. for 1 h. The reaction mixture was quenched with saturated $NH_4Cl$ solution and extracted EA (100 ml*3). The combined organic layers were washed with brine (50 ml), dried over $Na_2SO_4$, filtered and concentrated under reduced pressure to give a residue. The crude product was purified by preparative RP-LC (column: 330 g flash column Welch Ultimate XB-C18; 20-40 μm; 120 Å; mobile phase: A: water (0.1% FA), B: ACN; gradient B %: 0-10% 10 min; 10% 15 min; flow rate: 100 ml/min) to give the title compound (3 g, 99% yield) as a yellow solid.

$^1H$ NMR ($CDCl_3$, 400 MHz): δ ppm 7.51 (1H), 7.14 (br, 1H), 5.80 (br, 1H), 5.51 (1H), 3.85 (2H), 2.37 (1H), 2.21-2.30 (1H), 1.50 (9H)

I-55f

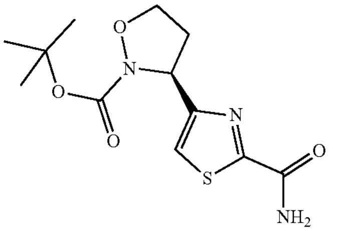

Tert-butyl (3S)-3-(2-carbamoylthiazol-4-yl)isoxazolidine-2-carboxylate

To a solution of tert-butyl N-hydroxy-N-[(1 S)-1-(2-carbamoylthiazol-4-yl)-3-hydroxy-propyl]carbamate (1.5 g, 4.73 mmol) in THF (15 ml) was added tributylphosphane (1.43 g, 7.09 mmol) and DIAD (955.74 mg, 4.73 mmol) at 0° C. The mixture was warmed to 25° C. smoothly, stirred for 12 h under $N_2$ atmosphere. The reaction mixture was concentrated. The crude product was purified by preparative RP-LC (column: 330 g flash column Welch Ultimate XB-C18; 20-40 μm; 120 Å; mobile phase: A: water (0.1% FA), B: ACN; gradient B %: 0-5% 10 min; 5% 15 min; flow rate: 80 ml/min) to give the title compound (1.6 g, crude) as yellow oil.

$^1H$ NMR ($CDCl_3$, 400 MHz): δ ppm 7.54 (1H), 7.09 (br, 1H), 5.64 (br, 1H), 5.42 (1H), 4.15-4.21 (1H), 3.95 (1H), 2.70-2.80 (1H), 2.52-2.62 (1H), 1.51 (9H)

I-55g

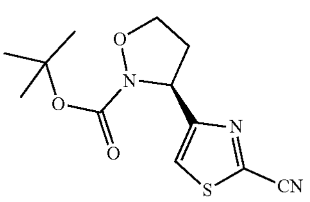

Tert-butyl (3S)-3-(2-cyanothiazol-4-yl)isoxazolidine-2-carboxylate

To a solution of tert-butyl (3S)-3-(2-carbamoylthiazol-4-yl)isoxazolidine-2-carboxylate (1.6 g, 5.34 mmol) in dioxane (16 ml) was added TFAA (5.61 g, 26.72 mmol, 3.72 ml) and pyridine (4.23 g, 53.45 mmol, 4.31 ml). The reaction mixture was stirred at 25° C. for 12 h. The reaction mixture was diluted water (20 ml) and extracted EA (20 ml*3). The combined organic layers were washed with brine (20 ml), dried over $Na_2SO_4$, filtered and concentrated under reduced pressure to give a residue. The residue was purified by silica gel column chromatography ($SiO_2$, PE:EA=1/0~1/2) to give the title compound (1.6 g, crude) as a yellow oil, which was further purified by preparative SFC (column: Daicel ChiralpakAD (250 mm*30 mm, 10 μm); mobile phase A: $CO_2$; B: 0.1% sat. aqueous $NH_3$ solution in methanol; B %: 20%-20%, 4.9; 65 min) to yield the title compound (966 mg, 60% yield, 99.9% e.e.) as a yellow oil.

$^1H$ NMR ($CDCl_3$, 400 MHz): δ ppm 7.66 (1H), 5.49 (1H), 4.15 (1H), 3.94 (1H), 2.79 (1H), 2.51-2.61 (1H), 1.52 (9H)

Analytical SFC: tR 1.08 min (>99.9%); tR of R-enantiomer: 0.75 min (Column: Chiralpak AD-3, 50×4.6 mm, I.D., 3 μm, Mobile phase: A: $CO_2$, B: methanol (0.05% DEA), Gradient: MeOH (0.05% DEA) in $CO_2$ from 5% to 40%, flow rate: 3.0 ml/min, column temp.: 35° C., back pressure: 100 bar).

I-55

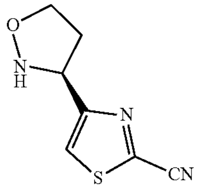

4-[(3S)-Isoxazolidin-3-yl]thiazole-2-carbonitrile

Tert-butyl (3S)-3-(2-cyanothiazol-4-yl)isoxazolidine-2-carboxylate (100 mg) was dissolved in DCM (5 ml) and TFA (500 μl) was added. After stirring for 3 h at RT the solvent was removed and the residue treated with DCM and saturated $NaHCO_3$. The organic layer was separated and the aqueous phase was extracted with DCM (2×). The combined organic layers were dried over $Na_2SO_4$, filtered and concentrated in vacuo to yield 74 mg of crude material.

LC/MS: m/z=182.0 $[M+H]^+$, tR: 0.78 min (LC/MS-method A)

I-56: (3S)-3-(2-Methylthiazol-4-yl)isoxazolidine trifluoroacetic acid salt

I-56a

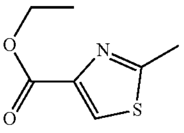

Ethyl 2-methylthiazole-4-carboxylate

To a solution of thioacetamide (7.86 g, 104.61 mmol) in EtOH (60 ml), and ethyl 3-bromo-2-oxo-propanoate (20 g, 102.56 mmol) was added dropwise in 10 min and stirred for 12 h at 25° C. The mixture was added to 300 ml 1N HCl, stirred 0.5 h, then the pH was adjust to 8, and the solution extracted with EA (200 ml*3), dried with $Na_2SO_4$ and concentrated. The crude product was triturated with PE:EA=5:1 (30 ml) to give the title compound (10.6 g, 58% yield) as a brown solid.

$^1H$ NMR ($CDCl_3$, 400 MHz): δ ppm 8.04 (1H), 4.43 (2H), 2.78 (3H), 1.41 (3H)

I-56b

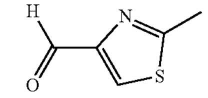

2-Methylthiazole-4-carbaldehyde

To a solution of ethyl 2-methylthiazole-4-carboxylate (9.6 g, 56.07 mmol, 1 eq) in DCM (96 ml) was added DIBAL-H (1 M, 84.10 ml). The mixture was stirred at −78° C. for 3 h. The reaction mixture was quenched by MeOH (5 ml), warmed to 25° C., filtered and concentrated under reduced pressure, purified by flash silica gel chromatography (PE: EA=1:0-5:1) to give the title compound (5.5 g, 76% yield) as yellow oil.

$^1$H NMR ($CDCl_3$, 400 MHz): δ ppm 9.99 (1H), 8.05 (1H), 2.79 (3H)

I-56c

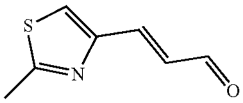

(E)-3-(2-Methylthiazol-4-yl)prop-2-enal

A mixture of 2-methylthiazole-4-carbaldehyde (5.5 g, 34.60 mmol), (formylmethylene)triphenylphosphorane (10.53 g, 34.60 mmol) in THF (55 ml) was degassed and purged with $N_2$ for 3 times, and then the mixture was stirred at 70° C. for 3 h under $N_2$ atmosphere. The reaction mixture was concentrated under reduced pressure to give a residue. The residue was purified by silice gel column chromatography (PE:EA=4:1) to give the title compound (4.5 g, 80% yield) as yellow oil.

$^1$H NMR ($CDCl_3$, 400 MHz): δ ppm 9.70 (1H), 7.45 (1H), 7.39 (1H), 6.93 (1H), 2.76 (3H)

I-56d

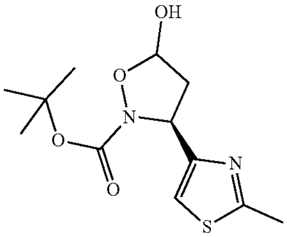

Tert-butyl (3S)-5-hydroxy-3-(2-methylthiazol-4-yl)isoxazolidine-2-carboxylate

To a solution of [diphenyl-[(2R)-pyrrolidin-2-yl] methoxy]-trimethyl-silane (1.78 g, 5.48 mmol) in $CHCl_3$ (42 ml) was added (E)-3-(2-methylthiazol-4-yl)prop-2-enal (4.2 g, 27.41 mmol) and tert-butyl N-hydroxycarbamate (4.02 g, 30.16 mmol) at 0° C. The mixture was warmed to 25° C. smoothly, stirred for 12 h. The reaction mixture was concentrated under reduced pressure to give a residue. The crude product was purified by preparative RP-LC (column: Agela C18, 20 μm; 120 Å; mobile phase: water/0.1% sat. aqueous $NH_3$ solution—ACN; B %: 5%-30%, 10 min; flow rate: 25 ml/min) to give the title compound (3.9 g, 50% yield) as yellow oil.

I-56e

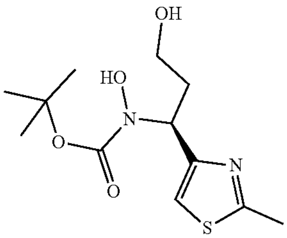

Tert-butyl N-hydroxy-N-[(1S)-3-hydroxy-1-(2-methylthiazol-4-yl) propyl]carbamate To a solution of tert-butyl (3S)-5-hydroxy-3-(2-methylthiazol-4-yl)isoxazolidine-2-carboxylate (3.4 g, 11.87 mmo) in MeOH (34 ml) was added $NaBH_4$ (494.10 mg, 13.06 mmol) at 0° C. The mixture was stirred for 2 h. The reaction mixture was quenched with saturated $NH_4Cl$ solution (2 ml) at 0° C., diluted with water (200 ml), extracted with EA (150 ml*3). The combined organic layers were washed with brine (100 ml), dried over $Na_2SO_4$, filtered and concentrated under reduced pressure to give a residue. The residue was purified by silia gel column chromatography (PE:EA=2: 1~1:1) to give the title compound (2.44 g, 70% yield) as a yellow oil.

$^1$H NMR ($CDCl_3$, 400 MHz): δ ppm 7.02 (1H), 5.46 (1H), 3.78 (2H), 2.71 (3H), 2.39-2.28 (1H), 2.17-2.09 (1H), 1.49 (9H)

I-56f

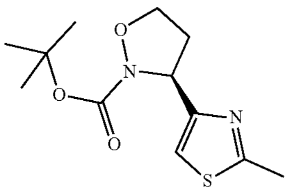

Tert-butyl (3S)-3-(2-methylthiazol-4-yl)isoxazolidine-2-carboxylate

To a solution of tert-butyl N-hydroxy-N-[(1S)-3-hydroxy-1-(2-methylthiazol-4-yl)propyl]carbamate (2.4 g, 8.32 mmol) in THF (24 ml) was added tributylphosphane (2.69 g, 13.32 mmol) and DIAD (2.19 g, 10.82 mmol) at 0° C., stirred for 1 h. The reaction mixture was concentrated under reduced pressure to give a residue. The residue was purified by prep. RP LC (flow: 100 ml/min; gradient: from 95% $H_2O$ (0.1% FA)/5% ACN to 40% $H_2O$ (0.1% FA)/60% ACN in 15 min; 40% $H_2O$ (0.1% FA)/60% ACN in 3 min; column: Welch Ultimate XB_C18, 20-40 μm, 120 Å, I.D.72 mm*H300 mm) and flash silica gel column chromatography (PE:EA=1:0~4:1) to give the title compound, which was further purified by SFC (column: Daicel Chiralpak AD (250 mm*30 mm, 10 μm); mobile phase A: $CO_2$, B: 0.1% aqueous $NH_3$ solution in methanol; B %: 15%-15%, 5.6; 60 min; flow rate: 50 ml/min; back pressure: 100 bar) to yield the title compound (483 mg, 99.6% e.e.) as an off white solid.

$^1$H NMR ($CDCl_3$, 400 MHz): δ ppm 7.07 (1H), 5.37 (1H), 4.18-4.11 (1H), 3.92 (1H), 2.71-2.69 (4H), 2.56-2.47 (1H), 1.50 (9H)

Analytical SFC: tR 0.93 min (99.8%); tR of R-enantiomer: 0.54 min (Column: Chiralpak AD-3, 50×4.6 mm, I.D., 3 μm, Mobile phase: A: $CO_2$, B: methanol (0.05% DEA), Gradient MeOH (0.05% DEA) in $CO_2$ from 5% to 40%, flow rate: 3.0 ml/min, column temp.: 35° C., back pressure: 100 bar).

I-56

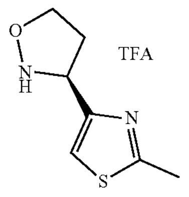

(3S)-3-(2-Methylthiazol-4-yl)isoxazolidine trifluoroacetic acid salt

Tert-butyl (3S)-3-(2-methylthiazol-4-yl)isoxazolidine-2-carboxylate (155 mg) was dissolved in DCM (8 ml) and TFA (442 μl) was added. After stirring for 3 h at RT the solvent was removed and the residue lyophilised from water/ACN to yield 179 mg of crude material.

LC/MS: m/z=171.1 $[M+H]^+$; tR: 0.46 min (LC/MS-method B)

I-57

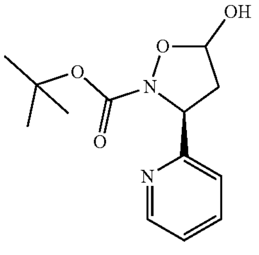

(3S)-3-(2-Pyridyl)isoxazolidine hydrochlorine salt
I-57a:Tert-butyl (3S)-5-hydroxy-3-(2-pyridyl)isoxazolidine-2-carboxylate To a solution of tert-butyl (3S)-3-(5-chloro-2-pyridyl)-5-hydroxy-isoxazolidine-2-carboxylate (I-19b, 3 g, 9.98 mmol) in EA (30 ml) was added Pd/C (300 mg, 9.98 mmol, 10% purity) and TEA (3.03 g, 29.93 mmol, 4.17 ml) under $N_2$. The suspension was degassed under vacuum and purged with $H_2$ several times. The mixture was stirred under $H_2$ (15 psi) at 25° C. for 3 h. The reaction mixture was filtered and concentrated to give the title compound (2.7 g, 73%) as yellow oil.

I-57b

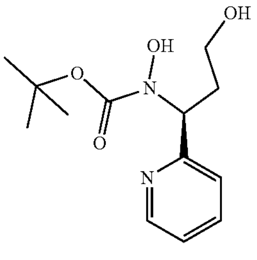

Tert-butyl N-hydroxy-N-[(1S)-3-hydroxy-1-(2-pyridyl)propyl]carbamate

To a solution of tert-butyl (3S)-5-hydroxy-3-(2-pyridyl) isoxazolidine-2-carboxylate (2.7 g, 8.72 mmol) in MeOH (30 ml) was added $NaBH_4$ (362.85 mg, 9.59 mmol) at 0° C. The mixture was stirred at 0° C. for 2 h. The reaction mixture was quenched with saturated $NH_4Cl$ solution (30 ml), diluted with water (200 ml), extracted with EA (200 ml*3). The combined organic layers were washed with brine (300 ml), dried over $Na_2SO_4$, filtered and concentrated. The residue was purified by Prep. RP LC (column: 330 g flash column Welch Ultimate XB-C18; 20-40 μm; 120 Å; mobile phase: A: water (0.1% FA), B: methanol; gradient B %: 0-10% 10 min; 10% 10 min; flow rate: 100 ml/min) to give the title compound (2.1 g, 86%) as yellow oil.

I-57c

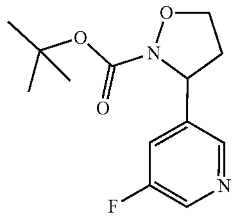

Tert-butyl (3S)-3-(2-pyridyl)isoxazolidine-2-carboxylate

To a solution of tert-butyl N-hydroxy-N-[(1S)-3-hydroxy-1-(2-pyridyl)propyl]carbamate (2.1 g, 7.20 mmol) in THF (21 ml) was added tributylphosphane (2.33 g, 11.52 mmol) and DIAD (1.89 g, 9.36 mmol) at 0° C. The mixture was warmed to 25° C. smoothly, stirred for 1.5 h under $N_2$. The reaction mixture was concentrated. The residue was purified by prep. RP LC (flow: 100 ml/min; gradient: from 90% $H_2O$ (0.1% FA)/10% ACN to 45% $H_2O$ (0.1% FA)/55% ACN in 15 min; 55% $H_2O$ (0.1% FA)/70% ACN in 3 min; column: Welch Ultimate XB-C18, 20-40 μm, 120 Å, I.D. 72 mm*H300 mm) and silica gel column chromatography (PE:EA=9/1~1/3) to give the title compound (1.1 g, 57%) as yellow oil, which was further separated by SFC (column: column: Daicel Chiralpak IG (250 mm*30 mm, 10 μm); mobile phase A: $CO_2$, B: 0.1% saturated $NH_3$ solution in methanol; B %: 40%-40%, 2.3; 130 min; flow rate: 70 ml/min; back pressure:100 bar) to yield the pure title compound (960 mg, >99.9% e.e.) as off white solid.

$^1H$ NMR (400 MHz, DMSO-$d_6$) δ ppm 8.57-8.47 (1H), 7.79 (1H), 7.39 (1H), 7.29 (1H), 5.21 (1H), 4.12 (1H), 3.84-3.67 (1H), 2.74 (1H), 2.47-2.33 (1H), 1.39 (9H)

Analytical SFC: tR 1.28 min (100%); tR of R-enantiomer: 0.95 min (Column: Chiralpak IG-3, 50×4.6 mm, I.D., 3 μm, Mobile phase: A: $CO_2$, B: methanol (0.05% DEA), Gradient: MeOH (0.05% DEA) in $CO_2$ from 5% to 40%, flow rate: 3.0 ml/min, column temp.: 35° C., back pressure: 100 bar).

I-57

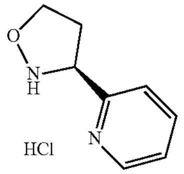

(3S)-3-(2-Pyridyl)isoxazolidine hydrochlorine salt

A mixture of tert-butyl (3S)-3-(2-pyridyl)isoxazolidine-2-carboxylate (900 mg) and hydrochloric acid (4 M in 1,4-dioxane, 20 ml) was stirred for 12 h. After evaporation of the volatiles, the residue was mixed with DCM and concentrated again to provide the crude title compound (760 mg), which was used in the next step without further purification.

LC/MS: m/z=151.1 $[M+H]^+$; tR: 0.12 min (LC/MS-method D)

I-58: (3S)-3-(6-Methoxypyrazin-2-yl)isoxazolidine trifluoroacetic acid

I-58a

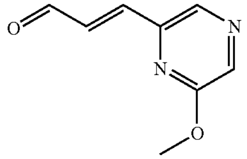

(E)-3-(6-Methoxypyrazin-2-yl)prop-2-enal

To a solution of 2-chloro-6-methoxy-pyrazine (10 g, 69.18 mmol) and 3,3-dimethoxyprop-1-ene (27.02 g, 207.53 mmol), $Pd(OAc)_2$ (1.55 g, 6.92 mmol), $K_2CO_3$ (14.34 g, 103.76 mmol) and KCl (5.16 g, 69.18 mmol), tris-o-tolylphosphane (4.21 g, 13.84 mmol), tetrabutylammonium acetate (41.71 g, 138.35 mmol) in DMF (100 ml) was degassed and purged with $N_2$ for 3 times, and then the mixture was stirred at 90° C. for 12 h under $N_2$ atmosphere. 2 N HCl (103 ml) was added to the reaction mixture and the mixture was stirred for 0.5 h. The mixture was diluted with water (500 ml) and extracted with EA (300 ml*3). The combined organic layers were washed with brine (500 ml), dried over $Na_2SO_4$, filtered and concentrated. The residue was purified by flash silica gel chromatography (ISCO®; Xg SepaFlash® SilicaFlash Column, Eluent of 0~20% Ethyl-acetate/Petroleumether gradient@75 mL/min) to give the title compound (2.3 g, 14.01 mmol, 20% yield) as a light yellow solid.

$^1$H NMR ($CDCl_3$, 400 MHz): δ ppm 9.85 (1H), 8.28 (2H), 7.47 (1H), 7.27-7.22 (1H), 4.04 (3H).

I-58b

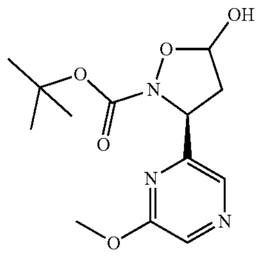

Tert-butyl (3S)-5-hydroxy-3-(6-methoxypyrazin-2-yl) isoxazolidine-2-carboxylate

To a solution of [diphenyl-[(2R)-pyrrolidin-2-yl] methoxy]-trimethyl-silane (2.62 g, 8.04 mmol) in $CHCl_3$ (60 ml) was added (E)-3-(6-methoxypyrazin-2-yl)prop-2-enal (6.6 g, 40.20 mmol) at 0° C. The mixture was stirred at 0° C. for 0.5 h, tert-butyl N-hydroxycarbamate (5.89 g, 44.22 mmol) was added at 0° C. The mixture was warmed to 25° C. smoothly, stirred for 16 h. The reaction mixture was concentrated under reduced pressure to give a residue. The crude product was purified by preparative RP-LC (column: Spherical C18, 20~45 μm, 120 Å; mobile phase: water (0.1% FA)—ACN; gradient B %: 0-5% 10 min; 5% 10 min; flow rate: 100 ml/min) to give the title compound (7.3 g, 24.55 mmol, 61% yield) as a light yellow oil.

I-58c

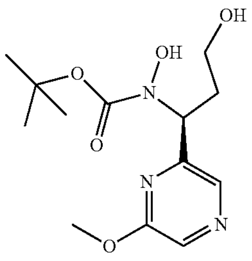

Tert-butyl N-hydroxy-N-[(1S)-3-hydroxy-1-(6-methoxypyrazin-2-yl)propyl]carbamate To a solution of tert-butyl (3S)-5-hydroxy-3-(6-methoxy-pyrazin-2-yl)isoxazolidine-2-carboxylate (8.0 g, 26.91 mmol) in MeOH (70 ml) was added $NaBH_4$ (1.12 g, 29.60 mmol) at 0° C. The mixture was stirred at 0° C. for 2 h. The mixture was quenched with saturated $NH_4Cl$ solution (50 ml), diluted by water (50 ml), extracted with EA (100 ml*2), dried with $Na_2SO_4$, filtered and concentrated under reduced pressure to give a residue. The crude product was purified by preparative RP-LC (column: 330 g flash column Welch Ultimate XB-C18, 20-40 μm; 120 Å; mobile phase: water (0.1% FA)—ACN; gradient B %: 0-10% 10 min; 10% 10 min; flow rate: 100 ml/min), then purified by flash silica gel chromatography (ISCO®; X g SepaFlash® Silica Flash Column, eluent of 0~100% Ethyl acetate/Petroleum ether-gradient@50 ml/min) to give the title compound (3.2 g, 10.69 mmol, 40%) as a yellow oil.

$^1$H NMR ($CDCl_3$, 400 MHz): δ ppm 8.20 (1H), 8.15 (1H), 7.59 (br, 1H), 5.41 (1H), 3.97 (3H), 3.85 (2H), 2.74 (br, 1H), 2.44-2.19 (2H), 1.49 (9H)

I-58d

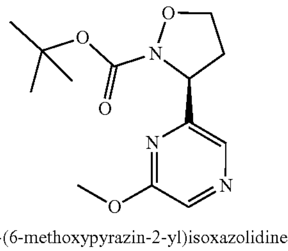

Tert-butyl (3S)-3-(6-methoxypyrazin-2-yl)isoxazolidine-2-carboxylate

To a solution of tert-butyl N-hydroxy-N-[(1 S)-3-hydroxy-1-(6-methoxypyrazin-2-yl)propyl]carbamate (3.2 g, 10.69 mmol) in THF (30 ml) was added dropwise tributylphosphane (3.46 g, 17.11 mmol) and DIAD (2.81 g, 13.90 mmol) at 0° C. The mixture was warmed to 25° C. smoothly, stirred for 2 h. The reaction mixture was concentrated under reduced pressure to give a residue. The crude product was purified by preparative RP-LC (column: 330 g Flash Column Welch Ultimate XB-C18, 20-40 μm; 120 Å;

mobile phase: water (0.1% FA)—ACN; gradient B %: 0-5% 8 min; 5% 15 min; flow rate: 100 ml/min), then the residue was purified by flash silica gel chromatography (ISCO®; X g SepaFlash® Silica Flash Column, Eluent of 0~100% ethyl acetate/petroleum ether gradient@60 ml/min) and the product was separated by SFC (column: Phenomenex-Cellulose-2 (250 mm*30 mm, 10 um); mobile phase: A $CO_2$; B 0.1% sat. aqueous $NH_3$ solution in isopropylalcohol; B %: 30%-30%, 4.4; 110 min) to give the title compound (2.3 g, 8.18 mmol, 76%, >99.9% e.e.) as as a light yellow oil.

$^1$H NMR ($CDCl_3$, 400 MHz): δ ppm 8.30 (1H), 8.15 (1H), 5.28 (1H), 4.21 (1H), 4.05-3.84 (4H), 2.75 (1H), 2.60 (1H), 1.50 (9H).

Analytical SFC: tR 1.08 min (100%); tR of R-enantiomer: 1.58 min (Column: Cellulose-2, 50×4.6 mm, I.D., 3 μm, Mobile phase: A: $CO_2$, B: isopropylalcohol (0.05% DEA), Gradient: isopropylalcohol (0.05% DEA) in $CO_2$ from 5% to 40%, flow rate: 3.0 ml/min, column temp.: 35° C., back pressure: 100 bar).

I-58

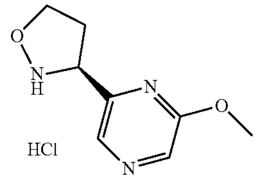

HCl (3S)-3-(6-Methoxypyrazin-2-yl)isoxazolidine trifluoric acid

Tert-butyl (3S)-3-(6-methoxypyrazin-2-yl)isoxazolidine-2-carboxylate (400 mg) was dissolved in DCM (15 ml) and TFA (1.1 ml) was added. After stirring for 2 h at RT the solvent was removed and the residue lyophilised from water/ACN to yield 501 mg of crude material.

LC/MS: m/z=182.1 [M+H]$^+$; tR: 0.87 min (LC/MS-method A)

I-59

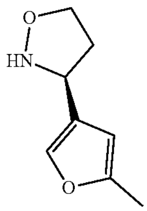

(3S)-3-(5-Methyl-3-furyl)isoxazolidine

Tert-butyl (S)-3-(5-methylfuran-3-yl)isoxazolidine-2-carboxylate (150 mg, 592.19 μmol, synthesised in the same manner as described for I-35 from 5-methylfuran-3-carbaldehyde) was dissolved in DCM (5 ml) and TFA (0.5 ml, 6.49 mmol) was added at RT with stirring. After standing overnight the solvent was removed in vacuo. The residue was lyophilised to yield 145 mg of the title compound.

LC/MS: m/z=154.1 [M+H]$^+$; tR: 0.74 min (LC/MS-method A)

I-60

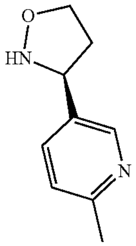

(3S)-3-(6-Methyl-3-pyridyl)isoxazolidine

Tert-butyl (S)-3-(6-methylpyridin-3-yl)isoxazolidine-2-carboxylate (500 mg, 1.89 mmol, synthesised in the same manner as described for 1-12 from 5-bromo-2-methyl-pyridine) was dissolved in DCM (15 ml) and TFA (1.5 ml, 19.47 mmol) was added at RT with stirring. After standing overnight the solvent was removed in vacuo. The residue was lyophilised to yield 693 mg of the title compound.

LC/MS: m/z=165.4 [M+H]$^+$; tR: 0.22 min (LC/MS-method A)

I-61

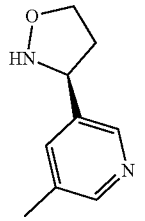

(3S)-3-(5-Methyl-3-pyridyl)isoxazolidine

Tert-butyl (S)-3-(5-methylpyridin-3-yl)isoxazolidine-2-carboxylate (500 mg, 1.89 mmol, synthesised in the same manner as described for 1-12 from 5-bromo-3-methyl-pyridine) was dissolved in DCM (15 ml) and TFA (1.5 ml, 19.47 mmol) was added at RT with stirring. After standing overnight the solvent was removed in vacuo. The residue was lyophilised to yield 761 mg of the title compound.

LC/MS: m/z=165.1 [M+H]$^+$; tR: 0.22 min (LC/MS-method A)

I-62

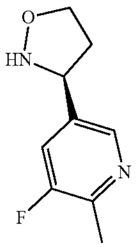

(3S)-3-(5-Fluoro-6-methyl-3-pyridyl)isoxazolidine

Tert-butyl (S)-3-(5-fluoro-6-methylpyridin-3-yl)isoxazolidine-2-carboxylate (500 mg, 1.77 mmol, synthesised in the same manner as described for I-21 from (E)-3-(5-fluoro-6-methyl-3-pyridyl)prop-2-enal) was dissolved in DCM (15 ml) and TFA (1.5 ml, 19.47 mmol) was added at RT with stirring. After standing overnight the solvent was removed in vacuo. The residue was lyophilised to yield 656 mg of the title compound.

LC/MS: m/z=183.1 [M+H]$^+$; tR: 0.79 min (LC/MS-method A)

I-63

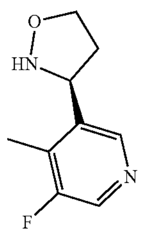

(3S)-3-(5-Fluoro-4-methyl-3-pyridyl)isoxazolidine

Tert-butyl (S)-3-(5-fluoro-4-methylpyridin-3-yl)isoxazolidine-2-carboxylate (500 mg, 1.77 mmol, synthesised in the same manner as described for 1-12 from 3-bromo-5-fluoro-4-methyl-pyridine) was dissolved in DCM (15 ml) and TFA (1.5 ml, 19.47 mmol) was added at RT with stirring. After standing overnight the solvent was removed in vacuo. The residue was lyophilised to yield 577 mg of the title compound.

LC/MS: m/z=183.1 [M+H]$^+$; tR: 0.71 min (LC/MS-method A)

I-64

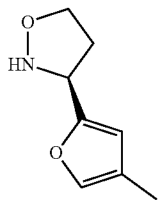

(3S)-3-(4-Methyl-2-furyl)isoxazolidine

Tert-butyl (S)-3-(4-methylfuran-2-yl)isoxazolidine-2-carboxylate (500 mg, 1.97 mmol, synthesised in the same manner as described for 1-6 from 4-methylfuran-2-carbaldehyde) was dissolved in DCM (15 ml) and TFA (1.5 ml, 19.47 mmol) was added at RT with stirring. After standing overnight the solvent was removed in vacuo. The residue was lyophilised to yield 514 mg of the title compound.

LC/MS: m/z=154.1 [M+H]$^+$; tR: 0.92 min (LC/MS-method A)

I-65

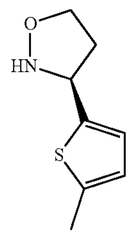

3-(S)-(5-Methyl-2-thienyl)isoxazolidine

-continued

I-65a

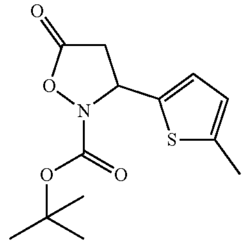

Tert-butyl 3-(5-methyl-2-thienyl)-5-oxo-isoxazolidine-2-carboxylate

To a solution of 5-methylthiophene-2-carbaldehyde (20.0 g, 158 mmol, 17.2 ml) in EA (200 ml) was added 2,2-dimethyl-1,3-dioxane-4,6-dione (22.8 g, 158 mmol), 1,4-diazabicyclo[2.2.2]octane (1.78 g, 15.8 mmol, 1.74 mL, 0.100 eq) and tert-butyl N-hydroxycarbamate (21.1 g, 158 mmol). The mixture was stirred at 15° C. for 16 h. The reaction mixture was diluted with $H_2O$ (200 ml) and extracted with EA (200 ml*3). The combined organic layers were dried over $Na_2SO_4$, filtered and concentrated under reduced pressure. The residue was purified by column chromatography ($SiO_2$, gradient: PE:EA=1:0 to 3:1) to give 20.0 g (70.6 mmol, 45% yield) of the title compound as a yellow solid.

I-65b

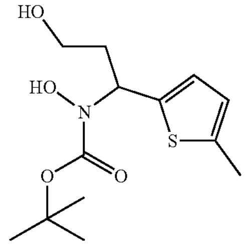

Tert-butyl N-hydroxy-N-[3-hydroxy-1-(5-methyl-2-thienyl)propyl]carbamate

To a solution of tert-butyl 3-(5-methyl-2-thienyl)-5-oxo-isoxazolidine-2-carboxylate (20.0 g, 70.6 mmol) in THF (100 ml) was added $LiBH_4$ (4.61 g, 211 mmol) at 0-10° C. and stirred at 10° C. for 20 min. The reaction mixture was quenched by addition of $H_2O$ 100 ml at 0-5° C., and then added drop-wise HCl (2N) to pH=6. The mixture was extracted with EA (100 ml*3). The combined organic layers were concentrated under reduced pressure to give 15 g of the title compound as a yellow oil.

I-65c

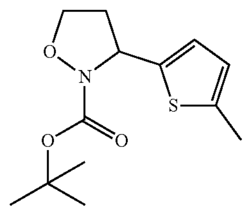

Tert-butyl 3-(5-methyl-2-thienyl)isoxazolidine-2-carboxylate

A mixture of tert-butyl N-hydroxy-N-[3-hydroxy-1-(5-methyl-2-thienyl)propyl]carbamate (15.7 g, 54.6 mmol) in THF (150 ml) was added $PPh_3$ (21.5 g, 81.9 mmol). DIAD (16.6 g, 81.9 mmol, 15.9 ml) was added drop-wise at 5-10° C. under $N_2$ and the mixture was stirred at 10° C. for 30 min. The reaction mixture was diluted with $H_2O$ (200 ml) and extracted with EA (200 ml*3). The combined organic layers were dried over $Na_2SO_4$, filtered and concentrated under reduced pressure. The residue was purified by column chromatography ($SiO_2$, gradient: PE:EA=1:0 to 5:1) to give 5.50 g (19.6 mmol, 40%) as a yellow oil.

LC/MS: m/z=170.1 $[M+H-COOtBu]^+$; tR: 0.92 min (LC/MS-method C)

$^1H$ NMR (MeOD, 400 MHz): δ ppm 6.79 (1H), 6.66-6.54 (1H), 5.38 (1H), 4.19 (1H), 3.87 (1H), 2.83-2.68 (1H), 2.45 (3H), 2.43-2.36 (1H), 1.48 (9H).

I-65d

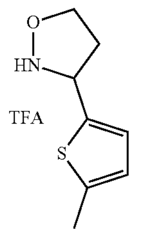

3-(5-Methyl-2-thienyl)isoxazolidine trifluoroacetate salt

Tert-butyl 3-(4-methylfuran-2-yl)isoxazolidine-2-carboxylate (200 mg, 0.74 mmol) was dissolved in DCM (10 ml) and TFA (1.0 ml, 12.98 mmol) was added at RT with stirring. After standing overnight the solvent was removed in vacuo. The residue was lyophilised to yield 203 mg of the title compound.

LC/MS: m/z=170.1 $[M+H]^+$; tR: 1.12 min (LC/MS-method A)

I-65

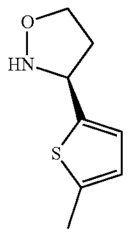

3-(S)-(5-Methyl-2-thienyl)isoxazolidine

Preparative separation of 3-(5-methyl-2-thienyl)isoxazolidine trifluoroacetate salt (791 mg, prepared in analogy to the description above, 2.79 mmol) on HPLC (column: Chiralcel OJ-H/66, 1 μm, 250×4.6 mm, eluent: heptane/ethanol/methanol=10/1/1, flow 1 ml/min) resulted in 193 mg (tR: 8.83 min) of the title compound and 179 mg (tR: 10.65 min) of its R-enantiomer.

LC/MS: m/z=170.1 $[M+H]^+$; tR: 1.14 min (LC/MS-method A)

I-66a

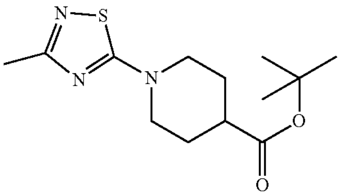

I-66: 1-(3-Methyl-1,2,4-thiadiazol-5-yl)piperidine-4-carboxylic acid

Tert-butyl 1-(3-methyl-1,2,4-thiadiazol-5-yl)piperidine-4-carboxylate

To a mixture of 5-chloro-3-methyl-1,2,4-thiadiazole (400 mg, 2.97 mmol) in DMF (5 ml) $Cs_2CO_3$ (879 mg, 2.70 mmol) was added at room temperature under argon atmosphere. Tert-butyl piperidine-4-carboxylate (500 mg, 2.70 mmol) was added and the reaction mixture was stirred at 80° C. for 18 h. The reaction mixture was filtered, purified by preparative HPLC (column: SunFire™ Prep C18 OBD, 100 mm*50 mm, 5 μm; flow: 120 ml/min; mobile phase: $H_2O$ (+0.1% TFA)/ACN; gradient: 95/5 for 2 min, from 95/5 to 55/45 in 0.5 min, from 55/45 to 5/95% in 8 min, from 5/95 to 1/99 in 1 min and 1/99 for 1.5 min) and the combined fractions lyophillised to give 495 mg of the title compound.

LC/MS: m/z=284.27 $[M+H]^+$; tR: 2.04 min (LC/MS-method A)

I-66

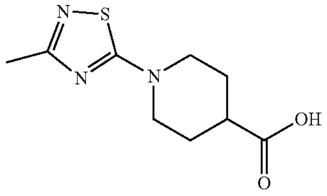

1-(3-methyl-1,2,4-thiadiazol-5-yl)piperidine-4-carboxylic acid

Tert-butyl 1-(3-methyl-1,2,4-thiadiazol-5-yl)piperidine-4-carboxylate (495 mg, 1.75 mmol) was dissolved in DCM (13.5 ml) and TFA (1.35 ml, 17.47 mmol) was added at RT with stirring. After standing overnight the solvent was removed in vacuo. The residue was lyophilised to yield 389 mg of the title compound.

LC/MS: m/z=228.1 $[M+H]^+$; tR: 0.81 min (LC/MS-method B)

I-67a

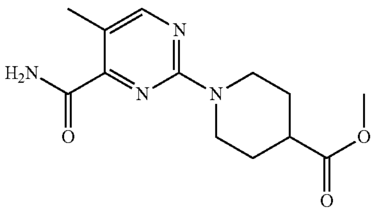

I-67: 1-(4-Carbamoyl-5-methyl-pyrimidin-2-yl)piperidine-4-carboxylic acid

Methyl 1-(4-carbamoyl-5-methyl-pyrimidin-2-yl)piperidine-4-carboxylate

A mixture of 2-chloro-5-methyl-pyrimidine-4-carbonitrile (1 g, 6.51 mmol), methyl piperidine-4-carboxylate (1.03 g, 7.16 mmol), DIEA (1.68 g, 13.02 mmol, 2.27 ml) was solved in DMSO (10 ml), and then the mixture was stirred at 80° C. for 2 h. The reaction mixture was diluted with $H_2O$ (100 ml) and extracted with EA (10 ml*3). The combined organic layers were washed with brine (10 ml*3), dried over $Na_2SO_4$, filtered and concentrated under reduced pressure to give a residue. The residue was purified by column chromatography ($SiO_2$, PE/EA=10/1) to give the title compound (1.8 g, crude) as a yellow solid.

LC/MS: m/z=261.1 $[M+H]^+$; tR: 0.91 min (LC/MS-method E)

$^1H$ NMR ($CDCl_3$, 400 MHz) δ ppm 8.34 (1H), 4.59 (2H), 3.72 (3H), 3.16-3.03 (2H), 2.61 (1H), 2.32 (3H), 2.05-1.93 (2H), 1.79-1.63 (2H).

I-67

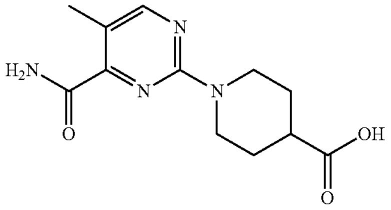

1-(4-Carbamoyl-5-methyl-pyrimidin-2-yl)piperidine-4-carboxylic acid

To a solution of methyl 1-(4-carbamoyl-5-methyl-pyrimidin-2-yl)piperidine-4-carboxylate (1.5 g, 5.76 mmol) in THF (15 ml) was added $H_2O_2$ (1.31 g, 11.53 mmol, 1.11 mL, 30% purity) and aqueous LiOH solution (1 M, 5.76 ml). After 13 h again aqueous LiOH solution (1 M, 2.88 ml was added and the mixture was stirred at 25° C. for 1 h. The reaction mixture was filtered and concentrated under reduced pressure. The crude product was adjusted pH to 3 and filtered to yield 1.02 g of the title compound as a yellow solid.

LCMS: m/z=265.1 $[M+H]^+$; tR: 0.31 min (LC/MS-method E)

$^1H$ NMR (400 MHz, DMSO-$d_6$) δ ppm 12.96-11.45 (1H), 8.32 (1H), 7.99 (1H), 7.57 (1H), 4.59-4.43 (2H), 3.09-2.93 (2H), 2.57-2.52 (1H), 2.25 (3H), 1.86 (2H), 1.57-1.37 (2H)

I-68: 1-(6-Fluoropyrimidin-4-yl)piperidine-4-carboxylic acid

I-68a

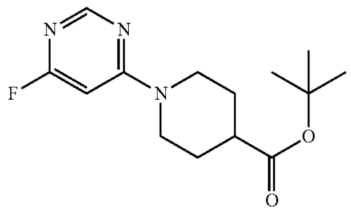

Tert-butyl 1-(6-fluoropyrimidin-4-yl)piperidine-4-carboxylate

To a solution of 4,6-difluoropyrimidine (500 mg, 4.31 mmol) in ethanol (30 ml) tert-butyl piperidine-4-carboxylate hydrochloride (640 mg, 2.89 mmol) and triethylamine (2.19 ml, 15.72 mmol) was added at room temperature under argon atmosphere. The reaction mixture was stirred at 100° C. for 18 h. The reaction mixture was evaporated under reduced pressure, purified by preparative HPLC (column: SunFire™ Prep C18 OBD, 100 mm*50 mm, 5 μm; flow: 120 ml/min; mobile phase: $H_2O$ (+0.1% TFA)/ACN; gradient: 95/5 for 2 min, from 95/5 to 55/45 in 0.5 min, from 55/45 to 15/85% in 8 min, from 15/85 to 1/99 in 1 min and 1/99 for 1.5 min) and the combined fractions lyophillised to give 531 mg of the title compound.

LC/MS: m/z=282.32 $[M+H]^+$; tR: 2.16 min (LC/MS-method A)

I-68

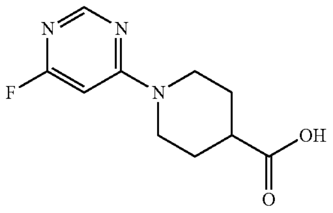

1-(6-fluoropyrimidin-4-yl)piperidine-4-carboxylic acid

Tert-butyl 1-(6-fluoropyrimidin-4-yl)piperidine-4-carboxylate (530 mg, 1.88 mmol) was dissolved in DCM (15 ml) and TFA (1.5 ml, 19.47 mmol) was added at RT with stirring. After standing overnight the solvent was removed in vacuo. The residue was lyophilised to yield 453 mg of the title compound.

LC/MS: m/z=226.2 $[M+H]^+$; tR: 1.14 min (LC/MS-method A)

I-69: 1-(6-Carbamoyl-5-fluoro-pyrimidin-4-yl)piperidine-4-carboxylic acid

I-69a

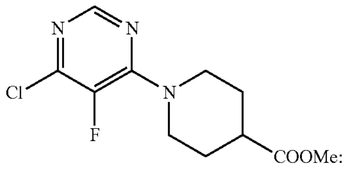

Methyl 1-(6-chloro-5-fluoro-pyrimidin-4-yl) piperidine-4-carboxylate

A mixture of 4,6-dichloro-5-fluoro-pyrimidine (50 g, 299.45 mmol) in DMSO (500 ml) was added methyl piperidine-4-carboxylate (48.4 g, 269.50 mmol), DIEA (58.05 g, 449.2 mmol), then the mixture was stirred at 80° C. for 2 h under $N_2$ atmosphere. The residue was diluted with $H_2O$ (1 l) and extracted with EA (200 ml*2). The combined organic layers were dried over $Na_2SO_4$, filtered and concentrated under reduced pressure. The residue was purified by flash silica gel chromatography (ISCO®; 100 g Sepa-Flash® Silica Flash Column, gradient: 0~50% EA/PE, flow 200 ml/min) to give 54.2 g of the title compound as a yellow oil.

LCMS: m/z=274.0 $[M+H]^+$; tR: 0.61 min (LC/MS-method E)

$^1H$ NMR ($CDCl_3$, 400 MHz) δ ppm 8.14 (1H), 4.41 (2H), 3.70 (3H), 3.21 (2H), 2.64 (1H), 2.04-1.98 (2H), 1.86-1.73 (2H).

I-69b

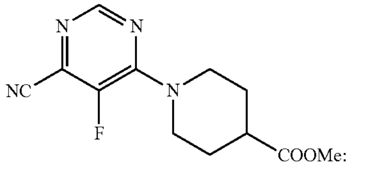

Methyl 1-(6-chloro-5-fluoro-pyrimidin-4-yl) piperidine-4-carboxylate

A mixture of methyl 1-(6-chloro-5-fluoro-pyrimidin-4-yl) piperidine-4-carboxylate (49 g, 179 mmol), $Zn(CN)_2$ (42.05 g, 358.07 mmol), DPPF (14.89 g, 26.86 mmol), $Pd_2(dba)_3$ (8.20 g, 8.95 mmol) in DMF (500 ml) was degassed and purged with $N_2$, and then the mixture was stirred at 100° C. for 5 h under $N_2$ atmosphere. The residue was diluted with $H_2O$ (1 l) and extracted with EA (500 ml*2). The combined organic layers were dried over $Na_2SO_4$, filtered and concentrated under reduced pressure. The crude product was purified by preparative RP LC (column; I.D.150 mm*400 mm Phenomenex Luna C18 15 μm; 100 Å; flow: 500 ml/min; mobile phase: $H_2O$ (+0.1% FA/ACN; gradient: 30-60% ACN in 55 min; 60% ACN for 15 min) to give 44 g of the title compound as a yellow solid.

LCMS: m/z=265.2 $[M+H]^+$; tR: 0.84 min (LC/MS-method E)

$^1H$ NMR ($CDCl_3$, 400 MHz) δ ppm 8.41 (1H), 4.42-4.26 (2H), 3.62 (3H), 3.31-3.23 (2H), 2.84-2.71 (1H), 2.01-1.89 (2H), 1.70-1.54 (2H).

I-69

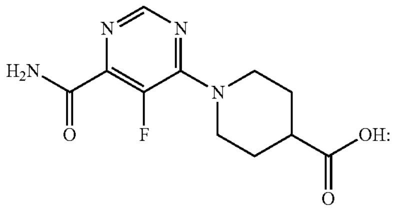

1-(6-Carbamoyl-5-fluoro-pyrimidin-4-yl) piperidine-4-carboxylic acid

To a mixture of methyl 1-(6-cyano-5-fluoro-pyrimidin-4-yl)piperidine-4-carboxylate (34.5 g, 131 mmol) in $H_2O$ (175 ml) and THF (175 ml) was added $LiOH{\cdot}H_2O$ (5.48 g, 131 mmol) and $H_2O_2$ (29.61 g, 261.11 mmol, 25.09 mL, 30%). After stirring at 25° C. for 2 h additional $LiOH{\cdot}H_2O$ (5.48 g, 130.56 mmol) was added and the mixture was stirred at 25° C. for another 2 h. The reaction mixture was adjusted with 1N HCl solution to pH=5~6, quenched with saturated $Na_2SO_3$ solution (100 ml) and concentrated under reduced pressure to remove most of the solvent. The residue was purified by purified by preparative RP LC (column; I.D.150 mm*400 mm Phenomenex Luna C18 15 μm; 100 Å; flow: 500 ml/min; mobile phase: $H_2O$ (+0.1% FA/ACN; gradient: 5-20% ACN in 35 min; 20% ACN for 35 min) to give 23.1 g of the title compound as a white solid.

LCMS: m/z=269.2 $[M+H]^+$; tR: 0.68 min (LC/MS-method F)

$^1H$ NMR (400 MHz, DMSO-$d_6$) δ ppm 12.42-12.17 (1H), 8.34 (1H), 8.08-7.91 (1H), 7.86-7.63 (1H), 4.34-4.23 (2H), 3.26-3.17 (2H), 2.65-2.56 (1H), 1.92 (2H), 1.65-1.51 (2H).

I-70: Trans-1-(4-carbamoyl-5-methyl-pyrimidin-2-yl)-3-fluoro-piperidine-4-carboxylic acid I-70a

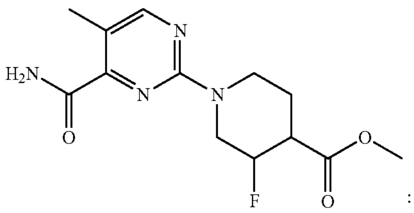

Trans methyl 1-(4-cyano-5-methyl-pyrimidin-2-yl)-3-fluoro-piperidine-4-carboxylate To a mixture of 2-chloro-5-methyl-pyrimidine-4-carbonitrile (1 g, 6.51 mmol) and trans methyl 3-fluoropiperidine-4-carboxylate (1.42 g, 7.16 mmol) in DMSO (20 ml) was added DIEA (3.37 g, 26.05 mmol, 4.54 ml) in one portion at 25° C. under $N_2$. The mixture was stirred at 80° C. for 2 h. The reaction mixture was poured into saturated $NaHCO_3$ aqueous solution (80 ml) and extracted with EA (50 ml*3). The combined organic layer was washed with brine (50 ml), dried over $Na_2SO_4$, filtered and concentrated in vacuo. The residue was purified by flash silica gel chromatography (gradient 10~30% EA/PE) to give 1.11 g of the title compound as a yellow oil.

LC/MS: m/z=279.2 $[M+H]^+$; tR: 0.89 min (LC/MS-method E)

$^1H$ NMR ($CDCl_3$, 400 MHz) δ ppm 8.36 (1H), 4.92-4.74 (1H), 4.65 (1H), 4.36-4.29 (1H), 3.77 (3H), 3.41 (1H), 3.29 (1H), 2.85 (1H), 2.33 (3H), 2.13-2.06 (1H), 1.79 (1H).

I-70

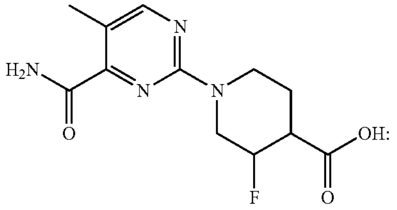

Trans methyl 1-(4-cyano-5-methyl-pyrimidin-2-yl)-3-fluoro-piperidine-4-carboxylic acid To a solution of trans methyl 1-(4-cyano-5-methyl-pyrimidin-2-yl)-3-fluoro-piperidine-4-carboxylate (1.11 g, 3.99 mmol) in THF (50 ml) was added an aqueous solution of $H_2O_2$ (904.39 mg, 7.98 mmol, 766.43 μL, 30%) and aqueous LiOH solution (1 M, 3.99 ml). The mixture was stirred at 20° C. for 3 h. The mixture was adjusted with 1N HCl solution to pH=5~6, quenched with saturated $Na_2SO_3$ solution (20 ml). The reaction mixture was concentrated under reduced pressure to remove most of the solvent and filtered, the filtrate was extracted with EA (10 ml*3). The combined organic layers were washed with brine (20 ml), dried over $Na_2SO_4$, filtered and concentrated in vacuo. The residue was purified by preparative RP LC (column: Phenomenex luna C18 150*40 mm, 15 μm; mobile phase: eluents: A: water (plus 0.225% FA), B: ACN], gradient: B % 12%-42% in 13 min) to give 410 mg of the title compound as a yellow solid.

LC/MS: m/z=283.1 $[M+H]^+$; tR: 0.71 min (LC/MS-method E)

$^1$H NMR (400 MHz, DMSO-$d_6$) δ ppm 13.08-12.25 (1H), 8.37 (1H), 8.08 (1H), 7.61 (1H), 4.81-4.60 (2H), 4.37-4.31 (1H), 3.29-3.15 (2H), 2.83-2.72 (1H), 2.27 (3H), 1.99 (1H), 1.65-1.52 (1H).

I-71: ([3S)-3-(3,5-Difluorophenyl)isoxazolidin-2-yl]-(4-piperidyl)methanone TFA salt I-71a

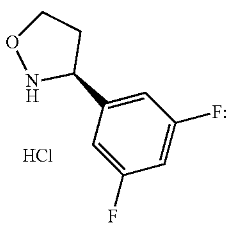

(3S)-3-(3,5-difluorophenyl) isoxazolidine HCl salt

Tert-butyl (3S)-3-(3,5-difluorophenyl)isoxazolidine-2-carboxylate (1.25 g) was dissolved in dioxane (9 ml) and 4 M HCl in dioxane (4.38 ml) was added at RT with stirring. After stirring overnight the solvent was removed in vacuo, the residue dissolved in ACN/water and lyophilised overnight. 920 mg of the title compound were obtained.

LC/MS: m/z=186.2 [M+H-isobutene]+; tR: 1.31 min (LC/MS-method A)

I-71b

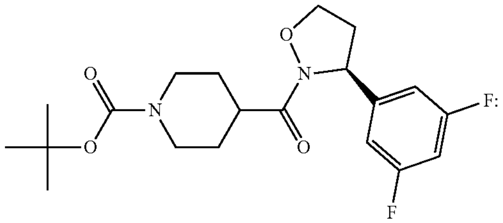

Tert-butyl 4-[(3S)-3-(3,5-difluorophenyl)isoxazolidine-2-carbonyl]piperidine-1-carboxylate To a solution of 1-tert-butoxycarbonylpiperidine-4-carboxylic acid (1.07 g, 4.57 mmol) in DMF (15 ml) diisopropylethylamine (2.54 ml, 14.53 mmol) and (3S)-3-(3,5-difluorophenyl)isoxazolidine HCl salt (920 mg, 4.15 mmol) dissolved in DMF (5 ml) were added. After stirring for 15 min at RT HATU (3.16 g, 8.3 mmol) was added and the reaction mixture was stirred for 4 h. The reaction mixture was quenched with saturated sodium bicarbonate solution and extracted three times with EA. The combined organic layers were dried with sodium sulfate, filtered, and evaporated under reduced pressure. The row material was purified by silica gel chromatography (40 g $SiO_2$, n-heptane/EA, 5 min 100% n-heptane, 100/0% to 80/20% in 30 min). The combined fractions gave 1.62 mg of the title compound.

LC/MS: m/z=341.2 [M+H-isobutene]+; tR: 2.44 min (LC/MS-method A)

I-71

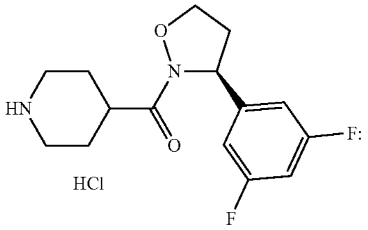

([3S)-3-(3,5-Difluorophenyl)isoxazolidin-2-yl]-(4-piperidyl)methanone HCl salt

Following the procedure described in I-71 tert-butyl 4-[(3S)-3-(3,5-difluorophenyl)isoxazolidine-2-carbonyl]piperidine-1-carboxylate (1.62 g) gave 1.68 g of the title compound as crude material.

LC/MS: m/z=297.2 $[M+H]^+$; tR: 1.05 min (LC/MS-method A)

I-72

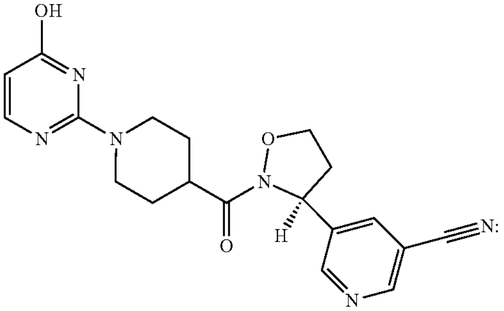

5-[(3S)-2-[1-(4-Hydroxypyrimidin-2-yl)piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoroacetic acid salt (I-28, 350 mg) and 2-chloropyrimidin-2-ol (127 mg) were treated at 140° C. and otherwise as described in ex. 157/158 to yield 234 mg (70%) of the title compound.

LC/MS: m/z=381.2 $[M+H]^+$; tR: 1.01 min (LC/MS-method A)

EXAMPLE COMPOUNDS

The example compounds 2, 6-8, 12-15, 23-25, 29-32, 36-38, 40-42, 46-52, 54 and 89 are marked with *, which denotes racemic mixtures which are regarded as comparison examples.

Example pairs 4/16 and 69/70 demonstrate that the S form (Ex. 4 and 70) is significantly more active in the ADP-Glo and U937 assays.

Ex. 001

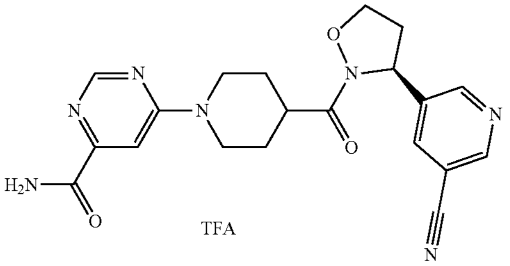

6-[4-[(3S)-3-(5-Cyano-3-pyridyl)isoxazolidine-2-carbonyl]-1-piperidyl]pyrimidine-4-carboxamide TFA salt 1-(6-Carbamoylpyrimidin-4-yl)piperidine-4-carboxylic acid TFA salt (I-38, 75 mg) was dissolved in DMF (0.5 ml) before DIPEA (174 μl) and HATU (91.1 mg) were added with stirring. After 5 min 5-[(3S)-isoxazolidin-3-yl]pyridine-3-carbonitrile trifluoroacetic acid salt (I-02-2, 75.1 mg) as solution in DMF (2.5 ml) was added and stirring was continued for 2 h. The solution was purified by preparative RP-HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 57 mg of the title compound.

LC/MS: m/z=408.4 $[M+H]^+$; tR: 1.20 min (LC/MS-method A)

Analytical chiral analysis (column: Chiralcel OD-H/126, 250×4.6 mm, eluent: Hep:EtOH:MeOH 5:1:1, flow: 1 ml/min, T: 30° C.): tR: 16.50 min $^1$H NMR (400 MHz, DMSO-$d_6$) δ ppm 8.94 (1H), 8.78 (1H), 8.59 (1H), 8.21 (2H), 7.91 (1H), 7.41 (1H), 5.43 (1H), 4.45 (2H), 4.33 (1H), 3.97 (1H), 3.20 (3H), 2.93 (1H), 2.32 (1H), 2.00 (1H), 1.83 (1H), 1.55 (2H).

Ex. 002*

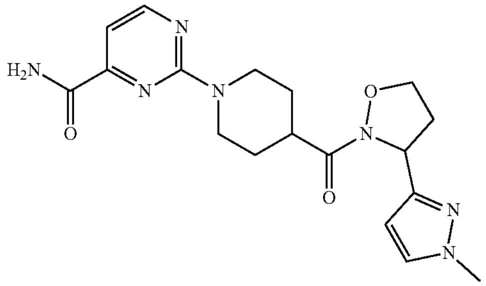

2-[4-[3-(1-Methylpyrazol-3-yl)isoxazolidine-2-carbonyl]-1-piperidyl]pyrimidine-4-carboxamide 1-(4-Carbamoylpyrimidin-2-yl)piperidine-4-carboxylic acid (I-22-1, 30 mg) was dissolved in DMF (1 ml) before DIPEA (105 μl) and HATU (54.7 mg) were added with stirring. After 5 min 3-(1-methylpyrazol-3-yl)isoxazolidine TFA salt (I-03, 38.4 mg) was added as solution in DMF (1.5 ml) and stirring was continued for 1.5 h. The solution was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 39 mg of the title compound.

LC/MS: m/z=386.3 $[M+H]^+$; tR: 1.34 min (LC/MS-method A)

$^1$H NMR (400 MHz, DMSO-$d_6$) δ ppm 8.54 (1H), 8.14 (1H), 7.70 (1H), 7.58 (1H), 7.07 (1H), 6.08 (1H), 5.35 (1H), 4.76 (2H), 4.24 (4H), 3.89 (2H), 3.78 (3H), 3.00 (3H), 2.67 (1H), 1.83 (1H), 1.69 (1H), 1.49 (2H).

Ex. 003

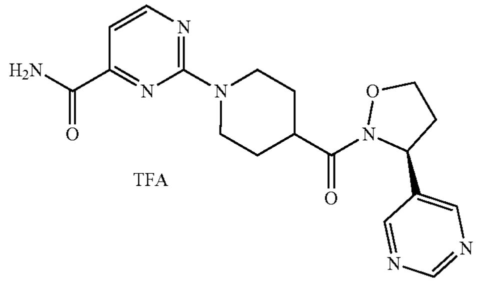

2-[4-[(3S)-3-Pyrimidin-5-ylisoxazolidine-2-carbonyl]-1-piperidyl]pyrimidine-4-carboxamide 1-(4-Carbamoylpyrimidin-2-yl)piperidine-4-carboxylic acid (I-22-1, 14.7 mg) was dissolved in DMF (1 ml). DIPEA (30 μl) and 3-pyrimidin-5-ylisoxazolidine hydrochloride salt (I-01, 10 mg) were added with stirring. Then HATU (40.5 mg) was added and stirring was continued for 6 h. After standing overnight the mixture was poured into saturated $NaHCO_3$ solution and the aqueous phase was extracted with EA (3×). The combined organic phases were washed with brine, dried over sodium sulphate, filtered and concentrated in vacuo. The residue was purified by preparative RP HPLC (flow: 25 ml/min; gradient: 95% $H_2O$+0.05% TFA/5% ACN in 45 min to 5% $H_2O$+0.05% TFA/95% ACN; column: Purosphere® STAR-RP18, 25×250 mm, 10 μm), the pure product containing fractions were combined and the ACN was removed in vacuo. The aqueous solution was lyophilised to yield 4 mg of the title compound.

LC/MS: m/z=384.4 $[M+H]^+$; tR: 1.23 min (LC/MS-method A)

Ex. 004

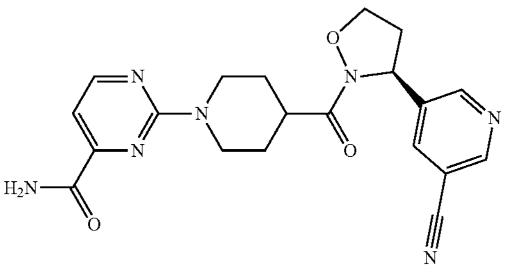

2-[4-[(3S)-3-(5-Cyano-3-pyridyl)isoxazolidine-2-carbonyl]-1-piperidyl]pyrimidine-4-carboxamide 1-(4-Carbamoylpyrimidin-2-yl)piperidine-4-carboxylic acid (I-22-1, 400 mg) was dissolved in DMF (10 ml) before DIPEA (1.40 ml) and HATU (729.3 mg) were added with stirring. After 5 min 5-[(3S)-isoxazolidin-3-yl]pyridine-3-carbonitrile trifluoroacetic acid salt (I-02-2, 554.7 mg) was added as solution in DMF (5 ml) and stirring was continued for 3 h. The mixture was poured into a mixture of EA and saturated $NaHCO_3$ solution, the phases were separated and the aqueous phase was extracted with EA (3×). The combined organic phases were washed with brine, dried over sodium sulphate, filtered and concentrated in vacuo. The residue was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 350 mg of the title compound.

LC/MS: m/z=408.4 [M+H]$^+$; tR: 1.44 min (LC/MS-method A)

$^1$H NMR (400 MHz, DMSO-$d_6$) δ ppm 8.94 (1H), 8.79 (1H), 8.54 (1H), 8.21 (1H), 8.15 (1H), 7.70 (1H), 7.07 (1H), 5.44 (1H), 4.78 (2H), 4.33 (1H), 3.97 (1H), 3.05 (3H), 2.93 (1H), 2.32 (1H), 1.93 (1H), 1.76 (1H), 1.50 (2H).

Ex. 005

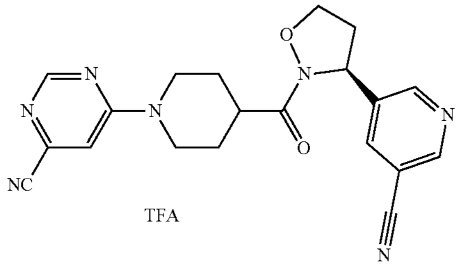

TFA

6-[4-[(3S)-3-(5-Cyano-3-pyridyl)isoxazolidine-2-carbonyl]-1-piperidyl]pyrimidine-4-carbonitrile TFA salt In analogy to the procedure described for example 001 by using 1-(6-cyanopyrimidin-4-yl)piperidine-4-carboxylic acid (I-39, 40 mg) 85 mg of the title compound were obtained.

LC/MS: m/z=390.3 [M+H]$^+$; tR: 1.57 min (LC/MS-method A)

$^1$H NMR (400 MHz, DMSO-$d_6$) δ ppm 8.94 (1H), 8.79 (1H), 8.54 (1H), 8.21 (1H), 7.56 (1H), 5.43 (1H), 4.32 (1H), 3.97 (1H), 3.13 (3H), 2.93 (1H), 2.67 (1H), 2.32 (1H), 1.96 (1H), 1.79 (1H), 1.51 (2H).

Analogously to example 002 were prepared:

| Ex. | Acid | Structure | LCMS m/z; tR; (yield) | Name |
|---|---|---|---|---|
| 006* | 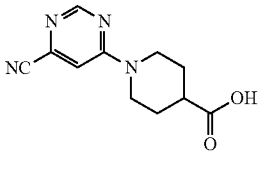 [SMILES: N#Cc1cc(N2CCC(C(=O)O)CC2)ncn1] I-39 | 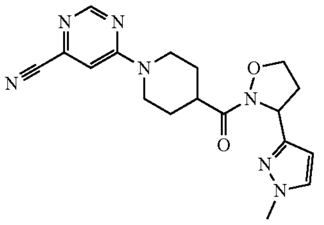 [SMILES: Cn1ccc(C2CCON2C(=O)C2CCN(c3cc(C#N)ncn3)CC2)n1] | 368.4 [M + H]$^+$ 1.45 min (41.5 mg, 47%) | 6-[4-[3-(1-methylpyrazol-3-yl)isoxazolidine-2-carbonyl]-1-piperidyl]pyrimidine 4-carbonitrile |
| 007* | 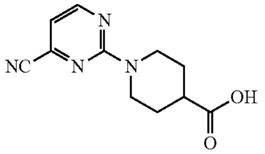 [SMILES: N#Cc1ccnc(N2CCC(C(=O)O)CC2)n1] I-23 | 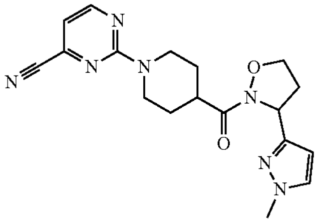 [SMILES: Cn1ccc(C2CCON2C(=O)C2CCN(c3nccc(C#N)n3)CC2)n1] | 368.4 [M + H]$^+$ 1.74 min (24 mg, 51%) | 2-[4-[3-(1-methylpyrazol-3-yl)isoxazolidine-2-carbonyl]-1-piperidyl] pyrimidine-4-carbonitrile |
| 008* | 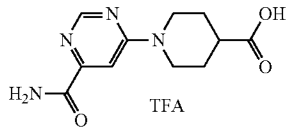 [SMILES: NC(=O)c1cc(N2CCC(C(=O)O)CC2)ncn1] TFA I-38 | 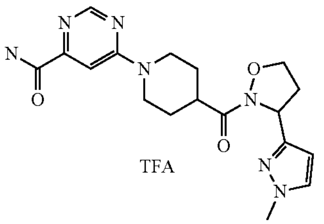 [SMILES: Cn1ccc(C2CCON2C(=O)C2CCN(c3cc(C(N)=O)ncn3)CC2)n1] TFA | 386.4 [M + H]$^+$ 1.11 (42 mg, 63%) | 6-[4-[3-(1-methylpyrazol-3-yl)isoxazolidine-2-carbonyl]-1-piperidyl] pyrimidine-4-carboxamide TFA salt |

Ex. 009

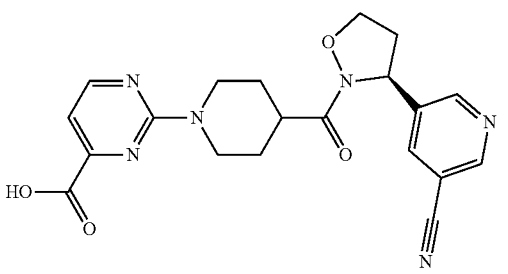

2-[4-[(3S)-3-(5-Cyano-3-pyridyl)isoxazolidine-2-carbonyl]-1-piperidyl]pyrimidine-4-carboxylic acid Methyl 2-[4-[(3S)-3-(5-cyano-3-pyridyl)isoxazolidine-2-carbonyl]-1-piperidyl]pyrimidine-4-carboxylate (Ex. 010) (28 mg) was dissolved in THE (2.5 ml) and water (0.5 ml) before LiOH (4.8 mg) was added at RT with stirring. After 1.5 h the mixture was acidified to pH 1 by using 6 M HCl and the solution was concentrated in vacuo. The residue thus obtained was purified by preparative RIP HPLC (120 ml/mmn, 95% $H_2O$+0.1% TFA/5% ACN to 5% $H_2O$+0.1% TFA/95% ACN in 13 min; Waters Sunfire Prep C18 OBD—5 μm, 50×100 mm). The pure compound containing fractions were combined, the ACN was removed in vacuo and the residue lyophilised overnight and 6.4 mg of the title compound were obtained.

LC/MS: m/z=409.4 $[M+H]^+$; tR: 1.41 min (LC/MS-method A)

$^1H$ NMR (400 MHz, DMSO-$d_6$) δ ppm 8.94 (1H), 8.79 (1H), 8.56 (1H), 8.21 (1H), 7.05 (1H), 5.44 (1H), 4.69 (2H), 4.33 (1H), 3.97 (1H), 3.05 (3H), 2.93 (1H), 2.32 (1H), 1.95 (1H), 1.78 (1H), 1.50 (m, 2H).

Ex. 010

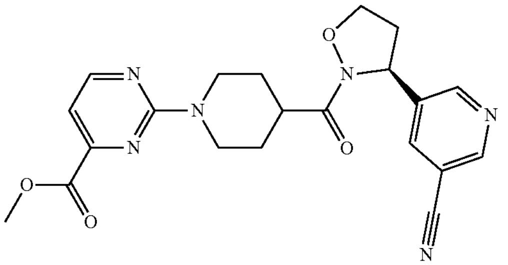

Methyl 2-[4-[(3S)-3-(5-Cyano-3-pyridyl)isoxazolidine-2-carbonyl]-1-piperidyl]pyrimidine-4-carboxylate In analogy to the procedure described for example 001 by using 1-(4-methoxycarbonylpyrimidin-2-yl)piperidine-4-carboxylic acid (I-40, 30 mg) 37 mg of the title compound was obtained.

LC/MS: m/z=423.4 $[M+H]^+$; tR: 1.76 min (LC/MS-method A)

$^1H$ NMR (400 MHz, DMSO-$d_6$) δ ppm 8.94 (1H), 8.79 (1H), 8.59 (1H), 8.21 (1H), 7.08 (1H), 5.43 (1H), 4.66 (2H), 4.33 (1H), 3.98 (2H), 3.86 (s, 3H), 3.06 (3H), 2.93 (1H), H), 2.32 (1H), 1.94 (1H), 1.78 (1H), 1.50 (2H).

Ex. 011

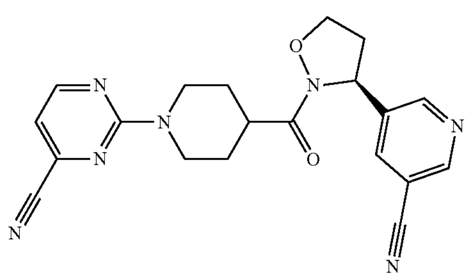

2-[4-[(3S)-3-(5-Cyano-3-pyridyl)isoxazolidine-2-carbonyl]-1-piperidyl]pyrimidine-4- carbonitrile In analogy to the procedure described for example 004 by using 1-(4-cyanopyrimidin-2-yl)piperidine-4-carboxylic acid (I-23, 29 mg) 27 mg of the title compound was obtained.

LC/MS: m/z=390.3 $[M+H]^+$; tR: 1.87 min (LC/MS-method A)

$^1H$ NMR (400 MHz, DMSO-$d_6$) δ ppm 8.94 (1H), 8.79 (1H), 8.62 (1H), 8.21 (1H), 7.12 (1H), 5.43 (1H), 4.56 (2H), 4.32 (1H), 3.97 (1H), 3.09 (3H), 2.92 (1H), 2.31 (1H), 1.96 (1H), 1.78 (1H), 1.50 (2H).

Ex. 012*

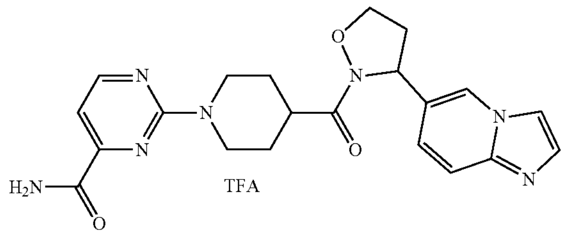

2-[4-[3-Imidazo[1,2-a]pyridin-6-ylisoxazolidine-2-carbonyl]-1-piperidyl]pyrimidine-4- carboxamide TFA salt 1-(4-Carbamoylpyrimidin-2-yl)piperidine-4-carboxylic acid (I-22-1, 27.6 mg) was dissolved in DMF (2 ml) before DIPEA (96 μl) and HATU (50.2 mg) were added with stirring. After 5 min 3-imidazo[1,2-a]pyridin-6-ylisoxazolidine TFA salt (I-04, 47.8 mg) was added as solution in DMF (1.5 ml) and stirring was continued for 24 h. The solution was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 25 mg of the title compound.

LC/MS: m/z=422.4 $[M+H]^+$; tR: 0.98 min (LC/MS-method A)

$^1H$ NMR (400 MHz, DMSO-$d_6$) δ ppm 8.82 (1H), 8.55 (1H), 8.32 (1H), 8.14 (2H), 7.95 (1H), 7.84 (1H), 7.72 (1H), 7.08 (1H), 5.52 (1H), 4.79 (2H), 4.36 (1H), 3.98 (1H), 3.02 (4H), 2.33 (1H), 1.94 (1H), 1.78 (1H), 1.52 (2H).

Analogously to example 012 were prepared:

| Ex. | Acid | structure | LCMS m/z; tR; (yield) | Name |
|---|---|---|---|---|
| 013* | 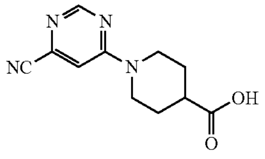 [SMILES: N#Cc1cc(N2CCC(C(=O)O)CC2)ncn1] I-39 | 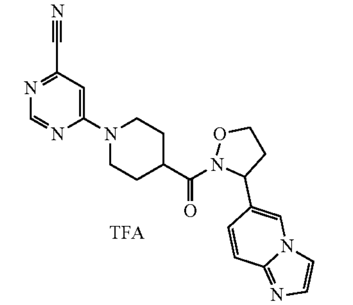 TFA | 404.4 $[M + H]^+$ 1.01 min (28 mg, 49%) | 2-[4-[3-imidazo[1,2-a]pyridin-6-ylisoxazolidine-2-carbonyl]-1-piperidyl] pyrimidine-4-carbonitrile TFA salt |
| 014* | 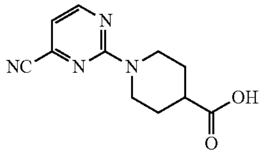 [SMILES: N#Cc1ccnc(N2CCC(C(=O)O)CC2)n1] I-23 | 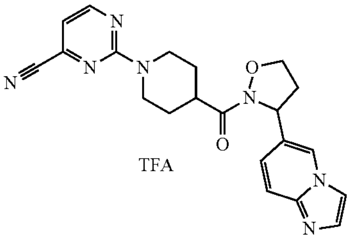 TFA | 404.4 $[M + H]^+$ 1.23 min (28 mg, 49%) | 2-[4-[3-imidazo[1,2-a]pyridin-6-ylisoxazolidine-2-carbonyl]-1-piperidyl] pyrimidine-4-carbonitrile TFA salt |
| 015* | 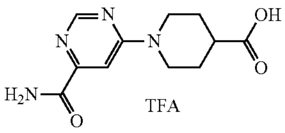 [SMILES: NC(=O)c1cc(N2CCC(C(=O)O)CC2)ncn1] TFA I-38 | 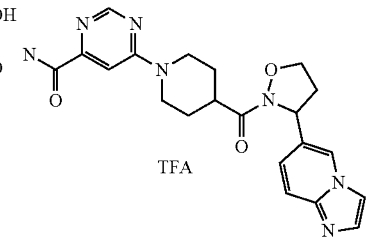 TFA | 422.4 $[M + H]^+$ 0.83 (35 mg, 59%) | 6-[4-[3-imidazo[1,2-a]pyridin-6-ylisoxazolidine-2-carbonyl]-1-piperidyl] pyrimidine-4-carboxamide TFA salt |

Ex. 016: (Comparison Example)

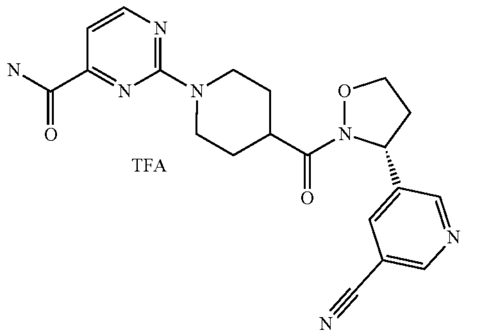

TFA

2-[4-[(3R)-3-(5-Cyano-3-pyridyl)isoxazolidine-2-carbonyl]-1-piperidyl]pyrimidine-4- carboxamide TFA salt In analogy to the procedure described for example 001 by using 1-(4-carbamoylpyrimidin-2-yl)piperidine-4-carboxylic acid (I-22-1, 75 mg) and 5-[(3R)-isoxazolidin-3-yl] pyridine-3-carbonitrile TFA salt (I-02-2(R)) 110.4 mg of the title compound was obtained.

LC/MS: m/z=408.4 $[M+H]^+$; tR: 1.44 min (LC/MS-method A)

$^1H$ NMR (400 MHz, DMSO-$d_6$) δ ppm 8.94 (1H), 8.79 (1H), 8.54 (1H), 8.21 (1H), 8.15 (1H), 7.70 (1H), 7.07 (1H), 5.44 (1H), 4.77 (2H), 4.33 (1H), 3.97 (1H), 3.06 (3H), 2.93 (1H), 2.32 (m, 1H), 1.93 (1H), 1.76 (1H), 1.50 (2H).

Ex. 017

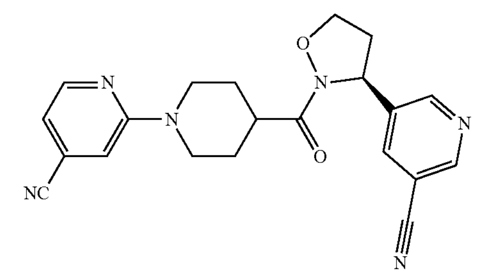

2-[4-[(3S)-3-(5-Cyano-3-pyridyl)isoxazolidine-2-carbonyl]-1-piperidyl]pyridine-4- carbonitrile 5-[(3S)-Isoxazolidin-3-yl]pyridine-3-carbonitrile TFA salt (I-02-2, 20 mg) was dissolved in DMF (3.5 ml). Then 1-(4-cyanopyridin-2-yl)piperidine-4-carboxylic acid TFA salt (I-24, 17 mg) and DIPEA (34 μl) were added. After stirring for 15 min under Ar HATU (40 mg) was added and after stirring for an additional 30 min sat. $NaHCO_3$ solution was added followed by water. The aqueous phase was extracted with EA (3×), the organic phases were combined and the solvent was removed in vacuo. The residue was dissolved in ACN/water and purified by preparative RP HPLC (flow 25 ml/min; 95% $H_2O$+0.05% TFA/5% ACN to 5% $H_2O$+0.05% TFA/95% ACN 45 min; column: Purosphere® STAR-RP18, 25×250 mm, 10 μm). The pure product containing fractions were combined and the ACN was removed in vacuo. The aqueous phase was set basic with sat. $NaHCO_3$ solution and the aqueous phase was extracted with DCM (3×). The organic phases were combined and the solvent was removed in vacuo. The residue was further purified by an additional RP HLPC separation (Column: X-Bridge TMBEH 130 PrepC18; 10 μm OBDTM 19×250 mm; flow 15 ml/min; 90% $H_2O$+0.05% TFA/10% ACN to 60% $H_2O$+0.05% TFA/40% ACN in 45 min). The pure product containing fractions were combined and the ACN was removed in vacuo. The aqueous phase was set basic with sat. NaHCO3 solution and the aqueous phase was extracted with DCM (3×). The organic phases were combined and the solvent was removed in vacuo. The residue was dissolved in ACN/water and lyophilised to yield 5.5 mg of the title compound.

LC/MS: m/z=389.4 $[M+H]^+$; tR: 1.79 min (LC/MS-method A)

Ex. 018

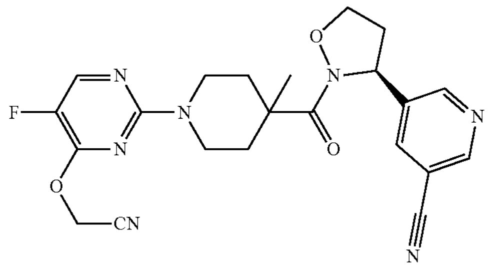

5-[(3S)-2-[1-[4-(Cyanomethoxy)-5-fluoro-2-pyridyl]-4-methyl-piperidine-4-carbonyl]isoxazolidin-3-yl|]pyridine-3-carbonitrile 5-[(3S)-2-(4-Methylpiperidine-4-carbonyl)isoxazolidin-3-yl]pyridine-3-carbonitrile trifluoroacetic acid salt (I-25, 20 mg) was dissolved in dry ACN (2.0 ml) in a microwave vessel. DIPEA (34 μl) and 2-(2-chloro-5-fluoro-pyrimidin-4-yl)oxyacetonitrile (I-26, 10 mg) were added and the mixture was heated at 80° C. for 90 min and then at 100° C. for 75 min in a microwave oven. After cooling the mixture was concentrated in vacuo and the residue was purified by silica gel chromatography (4 g $SiO_2$, 100% DCM to 90% DCM/10% ethanol in 35 min). The pure product containing fractions were combined and the solvent was removed in vacuo. The residue was dissolved in ACN/water and lyophilised overnight to yield 20 mg of the title compound.

LC/MS: m/z=452.4 $[M+H]^+$; tR: 2.07 min (LC/MS-method A)

Ex. 019

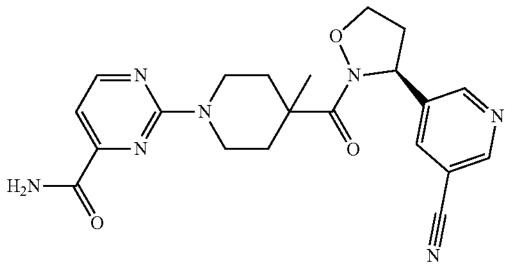

2-[4-[(3S)-3-(5-Cyano-3-pyridyl)isoxazolidine-2-carbonyl]-4-methyl-1-piperidyl]pyrimidine-4-carboxamide 5-[(3S)-2-(4-methylpiperidine-4-carbonyl)isoxazolidin-3-yl]pyridine-3-carbonitrile trifluoroacetic acid salt (I-25, 20 mg) was dissolved in dry ACN (2.0 ml) in a microwave vessel. DIPEA (34 μl) and 2-chloropyrimidine-4-carboxamide (9 mg) were added and the mixture was heated at 100° C. for 1 h in a microwave oven. After cooling the mixture was concentrated in vacuo and the residue was purified by silica gel chromatography (4 g $SiO_2$, 100% n-heptane to 100% EA in 40 min). The pure product containing fractions were combined and the solvent was removed in vacuo. The residue was dissolved in ACN/water and lyophilised overnight to yield 20 mg of the title compound.

LC/MS: m/z=422.4 $[M+H]^+$; tR: 1.60 min (LC/MS-method A)

Ex. 020

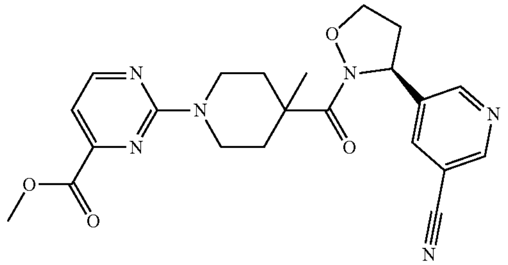

Methyl 2-[4-[(3S)-3-(5-cyano-3-pyridyl)isoxazolidine-2-carbonyl]-4-methyl-1-piperidyl]pyrimidine-4-carboxylate The title compound (30 mg) was prepared analogously to example 19 using methyl 2-chloropyrimidine-4-carboxylate (17 mg) as starting material.

LC/MS: m/z=437.4 $[M+H]^+$; tR: 1.95 min (LC/MS-method A)

Ex. 021

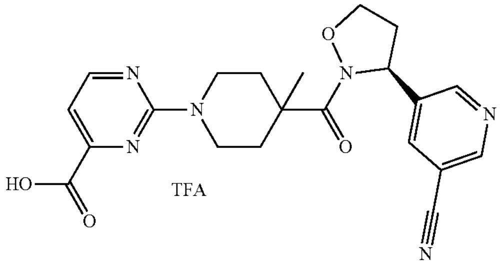

2-[4-[(3S)-3-(5-Cyano-3-pyridyl)isoxazolidine-2-carbonyl]-4-methyl-1-piperidyl]pyrimidine-4-carboxylic acid TFA salt Methyl 2-[4-[(3S)-3-(5-cyano-3-pyridyl)isoxazolidine-2-carbonyl]-4-methyl-1-piperidyl]pyrimidine-4-carboxylate (ex. 020, 25 mg) was dissolved in THF (2.5 ml). Then LiOH (3 mg) was added, followed by water until a clear solution was obtained. After stirring at 50° C. for 1 h the THF was removed in vacuo. Water was added followed by 1 N HCl to acidify the mixture which was lyophilised overnight. The crude product was purified by preparative RP HPLC (flow: 25 l/min; gradient: 95% $H_2O$+0.05% TFA/5% ACN in 45 min to 5% $H_2O$+0.05% TFA/95% ACN; column: Purosphere® STAR-RP18, 25×250 mm, 10 μm), the pure product containing fractions were combined and the ACN was removed in vacuo. The aqueous solution was lyophilised to yield 20 mg of the title compound.

LC/MS: m/z=423.4 $[M+H]^+$; tR: 1.59 min (LC/MS-method A)

Ex. 022: (Comparison Example)

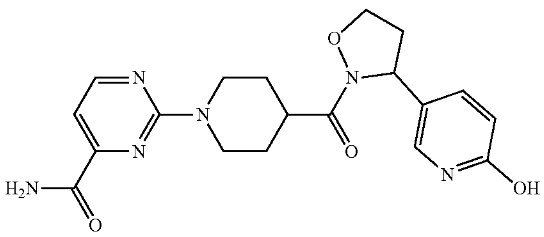

2-(4-(3-(6-Hydroxypyridin-3-yl)isoxazolidine-2-carbonyl) piperidin-1-yl)pyrimidine-4- car boxamide 1-(4-Carbamoylpyrimidin-2-yl)piperidine-4-carboxylic acid (I-22-1, 70 mg) was dissolved in DMF (2 ml) before DIPEA (244 μl) and HATU (127.6 mg) were added with stirring. After 5 min 5-(isoxazolidin-3-yl)pyridin-2-ol HCl salt (I-05, 111.6 mg) was added and stirring was continued for 24 h. The solution was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 2.2 mg of the title compound.

LC/MS: m/z=399.4 $[M+H]^+$; tR: 1.17 min (LC/MS-method A)

Ex. 023*: 6-[4-[3-Tetrahydropyran-3-ylisoxazolidine-2-carbonyl]-1-piperidyl]pyrimidine-4-carboxamide TFA salt

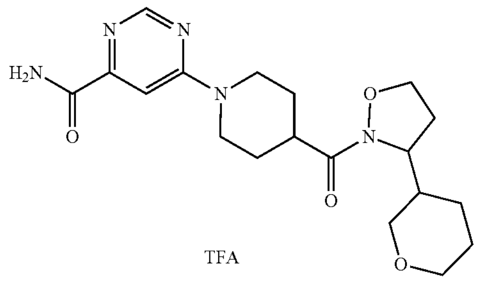 [SMILES: NC(=O)c1cc(N2CCC(C(=O)N3OCCC3C3CCCOC3)CC2)ncn1]

1-(6-Carbamoylpyrimidin-4-yl)piperidine-4-carboxylic acid TFA salt (I-38, 30 mg) was dissolved in DMF (2 ml) before DIPEA (86 μl) and HATU (37.6 mg) were added with stirring. After 5 min 3-tetrahydropyran-3-ylisoxazolidine TFA salt (I-06, 67 mg) was added and stirring was continued for 24 h. The solution was purified by preparative HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 16.8 mg of the title compound.

LC/MS: m/z=390.5 $[M+H]^+$; tR: 1.30 min (LC/MS-method A)

$^1H$ NMR (400 MHz, DMSO-$d_6$) δ ppm 8.60 (1H), 8.23 (1H), 7.94 (1H), 7.42 (1H), 4.47 (2H), 4.16 (1H), 2.34 (1H), 2.03 (2H), 1.73 (2H), 1.57 (4H), 1.43 (1H), 1.21 (1H). Signals below water not listed.

Ex 024*: 2-[4-[3-Tetrahydropyran-3-ylisoxazolidine-2-carbonyl]-1-piperidyl]pyrimidine-4-carboxamide

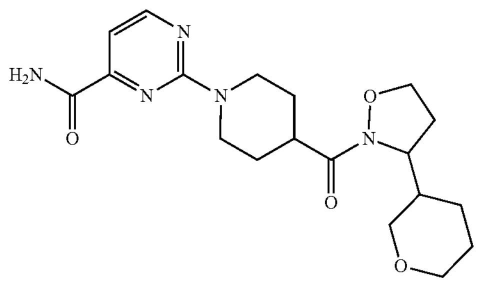 [SMILES: NC(=O)c1ccnc(N2CCC(C(=O)N3OCCC3C3CCCOC3)CC2)n1]

In analogy to the procedure described for example 023 by using 1-(4-carbamoylpyrimidin-2-yl)piperidine-4-carboxylic acid (I-22-1, 20 mg) 19.7 mg of the title compound was obtained.

LC/MS: m/z=390.5 $[M+H]^+$; tR: 1.55 min (LC/MS-method A)

$^1H$ NMR (400 MHz, DMSO-$d_6$) δ ppm 8.54 (1H), 8.14 (1H), 7.70 (1H), 7.07 (1H), 4.75 (2H), 4.17 (1H), 4.01 (1H), 3.67 (4H), 3.03 (3H), 2.35 (1H), 2.05 (1H), 1.88 (1H), 1.66 (1H), 1.53 (4H), 1.24 (2H). Signals below water not listed.

Ex. 025*: 2-[4-[3-[5-(Hydroxymethyl)-3-pyridyl] isoxazolidine-2-carbonyl]-1-piperidyl]pyrimidine-4-carboxamide

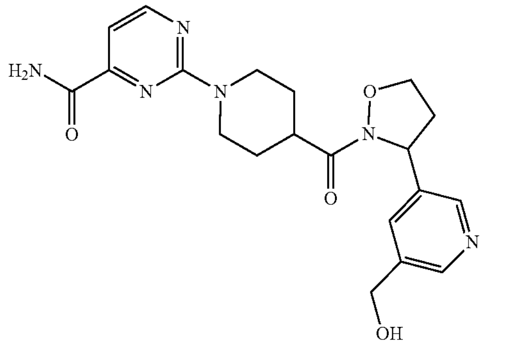 [SMILES: NC(=O)c1ccnc(N2CCC(C(=O)N3OCCC3c3cncc(CO)c3)CC2)n1]

1-(4-Carbamoylpyrimidin-2-yl)piperidine-4-carboxylic acid (I-22-1, 30 mg) was dissolved in DMF (1 ml) before DIPEA (105 μl) and HATU (54.7 mg) were added with stirring. After 5 min (5-isoxazolidin-3-yl-3-pyridyl)methanol TFA salt (I-07, 46.6 mg) was added as solution in DMF (1.5 ml) and stirring was continued for 24 h. The solution was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 5 mg of the title compound.

LC/MS: m/z=413.4 $[M+H]^+$; tR: 1.00 min (LC/MS-method A)

$^1H$ NMR (400 MHz, DMSO-$d_6$) δ ppm 8.53 (3H), 8.14 (1H), 7.87 (1H), 7.71 (1H), 7.07 (1H), 5.44 (1H), 4.78 (2H), 4.59 (s, 2H), 4.34 (1H), 3.96 (1H), 3.05 (m, 4H), 2.29 (1H), 1.92 (1H), 1.75 (1H), 1.50 (2H).

Ex. 026

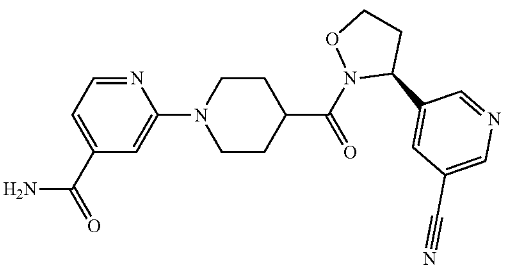

2-[4-[(3S)-3-(5-Cyano-3-pyridyl)isoxazolidine-2-carbonyl] -1-piperidyl]pyridine-4-carboxamide 5-[(3S)-Isoxazolidin-3-yl]pyridine-3-carbonitrile trifluoroacetic acid salt (I-02-2, 20 mg) was dissolved in dry DMF (2.5 ml). Then 1-(4-carbamoyl-2-pyridyl)piperidine-4-carboxylic acid TFA salt (I-27, 20 mg) and DIPEA (35 μl) were added with stirring. After 15 min HATU (40 mg) was added. After standing over the weekend the mixture was purified by preparative RP HPLC (flow 25 ml/min; 95% $H_2O$+0.05% TFA/5% ACN to 5% $H_2O$+0.05% TFA/95% ACN in 45 min; Purosphere® STAR-RP18, 25×250 mm, 10 μm). The product containing fractions were combined and the ACN was removed in vacuo. The aqueous solution was lyophilised overnight. For further purification a second RP HPLC was performed (flow 40 ml/min, 97% $H_2O$/3% ACN to 10% $H_2O$/90% ACN in 15 min; Agilent Prep C18—5 μm, 30×100 mm). The pure product containing fractions were combined and the ACN was removed in vacuo. The aqueous solution was lyophilised overnight to yield 7.3 mg of the title compound.

LC/MS: m/z=407.4 $[M+H]^+$; tR: 0.96 min (LC/MS-method A)

Ex. 027

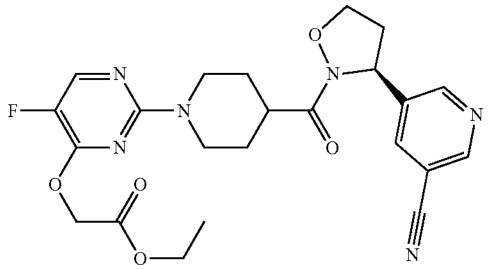

Ethyl 2-[2-[4-[(3S)-3-(5-Cyano-3-pyridyl)isoxazolidine-2-carbonyl]-1-piperidyl]-5- fluoro-pyrimidin-4-yl]oxyacetate (S)-5-(2-(Piperidine-4-carbonyl)isoxazolidin-3-yl)nicotinonitrile 2,2,2-trifluoroacetate (I-28, 50 mg) was dissolved in acetonitrile (2.5 ml) in a microwave vessel. Then ethyl 2-((2-chloro-5-fluoropyrimidin-4-yl)oxy)acetate (I-29, 32 mg) and DIPEA (87 μl) were added. The solution was heated in a microwave oven for 1 h followed by an additional hour at 100° C. After cooling the solution was concentrated in vacuo. The residue was purified by silica gel chromatography (40 g $SiO_2$, 100% n-heptane to 100% EA in 35 min). The pure compound containing fractions were combined and concentrated in vacuo. The residue was dissolved in ACN/water and lyophilised overnight to yield 36 mg of the title compound.

LC/MS: m/z=485.5 $[M+H]^+$; tR: 2.05 min (LC/MS-method A)

Ex. 028

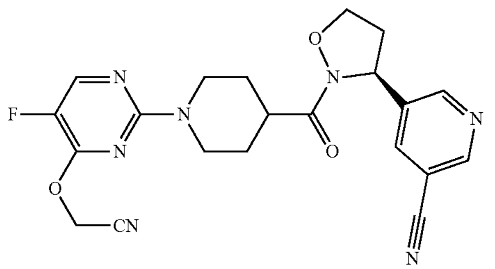

5-[(3S)-2-[1-[4-(Cyanomethoxy)-5-fluoro-pyrimidin-2-yl]piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoroacetic acid salt (I-28, 20 mg) was dissolved in dry ACN (2.0 ml) in a microwave vessel. DIPEA (34 μl) and 2-(2-chloro-5-fluoro-pyrimidin-4-yl)

oxyacetonitrile (I-26, 10 mg) were added and the mixture was heated in a microwave oven at 80° C. for 90 min and then at 100° C. for 75 min. After cooling the mixture was concentrated in vacuo and the residue was purified by silica gel chromatography (4 g $SiO_2$, 100% n-heptane to 100% EA in 35 min). The pure product containing fractions were combined and the solvent was removed in vacuo. The residue was dissolved in ACN/water and lyophilised overnight to yield 8.4 mg of the title compound.

LC/MS: m/z=438.4 $[M+H]^+$; tR: 1.89 min (LC/MS-method A)

Ex. 029*

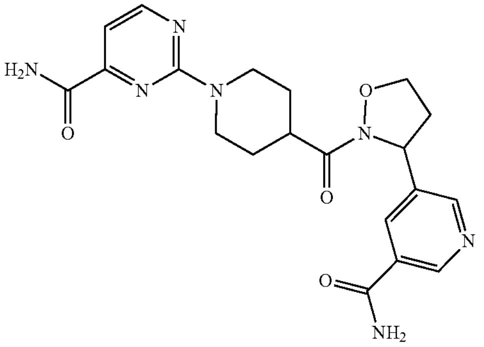

2-[3-(5-Carbamoyl-3-pyridyl)isoxazolidine-2-carbonyl]-1-piperidyl]pyrimidine-4-carboxamide 1-(4-Carbamoylpyrimidin-2-yl)piperidine-4-carboxylic acid (I-22-1, 30 mg) was dissolved in DMF (1 ml) before DIPEA (105 μl) and HATU (54.7 mg) were added with stirring. After 5 min 5-(isoxazolidin-3-yl)pyridine-3-carboxamide TFA salt (I-08, 46.5 mg) was added as solution in DMF (1.5 ml) and stirring was continued for 24 h. The solution was purified by preparative RP HPLC (120 ml/min, 95% $H_2O$+0.1% TFA/5% ACN to 5% $H_2O$+0.1% TFA/95% ACN in 13 min; Waters Sunfire Prep C18 OBD—5 μm, 50×100 mm). The pure product containing fractions were combined and the ACN was removed in vacuo. The aqueous solution was lyophilised to yield 51.5 mg of the title compound.

LC/MS: m/z=426.4 $[M+H]^+$; tR: 1.15 min (LC/MS-method A)

$^1H$ NMR (400 MHz, DMSO-$d_6$) δ ppm 8.94 (1H), 8.64 (1H), 8.54 (1H), 8.21 (1H), 8.12 (2H), 7.70 (1H), 7.62 (1H), 7.07 (1H), 5.44 (1H), 4.77 (2H), 4.34 (1H), 3.96 (1H), 3.00 (4H), 2.30 (1H), 1.92 (1H), 1.76 (1H), 1.50 (2H).

Ex. 030*

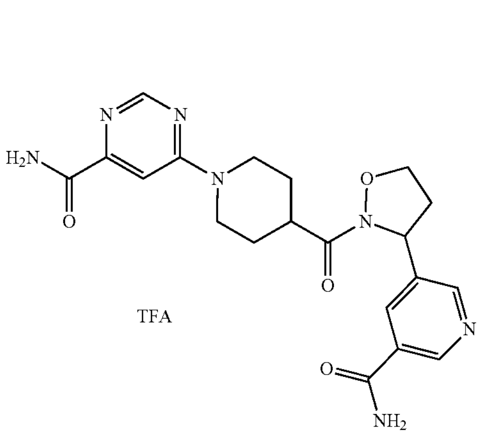

TFA

6-[4-[3-(5-Carbamoyl-3-pyridyl)isoxazolidine-2-carbonyl]-1-piperidyl]pyrimidine-4-carboxamide In analogy to the procedure described for example 029 by using 1-(6-carbamoylpyrimidin-4-yl)piperidine-4-carboxylic acid TFA salt (I-38, 50 mg) 20.8 mg of the title compound was obtained.

LC/MS: m/z=426.4 $[M+H]^+$; tR: 0.95 min (LC/MS-method A)

$^1H$ NMR (400 MHz, DMSO-$d_6$) δ ppm 8.94 (1H), 8.62 (m, 1H), 8.59 (1H), 8.24 (1H), 8.19 (1H), 8.10 (1H), 7.95 (1H), 7.62 (1H), 7.44 (1H), 5.43 (1H), 4.48 (2H), 4.34 (1H), 3.97 (1H), 3.22 (m, 3H), 2.94 (1H), 2.32 (1H), 1.99 (1H), 1.82 (1H), 1.56 (2H).

Ex. 031*

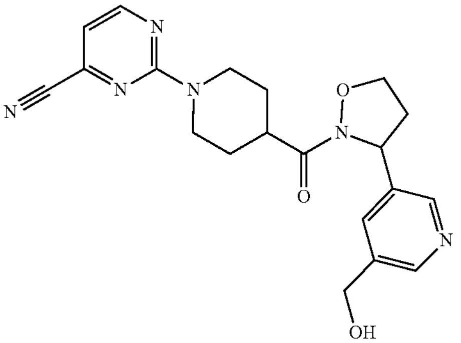

2-[4-[3-[5-(Hydroxymethyl)-3-pyridyl]isoxazolidine-2-carbonyl]-1-piperidyl]pyrimidine-4-carbonitrile In analogy to the procedure described for example 025 by using 1-(4-cyanopyrimidin-2-yl)piperidine-4-carboxylic acid (I-23, 30 mg) 19.5 mg of the title compound was obtained.

LC/MS: m/z=395.4 $[M+H]^+$; tR: 1.29 min (LC/MS-method A)

$^1H$ NMR (400 MHz, DMSO-$d_6$) δ ppm 8.62 (1H), 8.51 (2H), 7.86 (1H), 7.12 (1H), 5.43 (1H), 4.59 (4H), 4.33 (1H), 3.96 (m, 1H), 3.10 (3H), 2.94 (1H), 2.26 (1H), 1.94 (1H), 1.78 (1H), 1.50 (2H).

Ex. 032*: 6-[4-[3-[5-(Hydroxymethyl)-3-pyridyl]isoxazolidine-2-carbonyl]-1-piperidyl]pyrimidine-4-carboxamide TFA salt

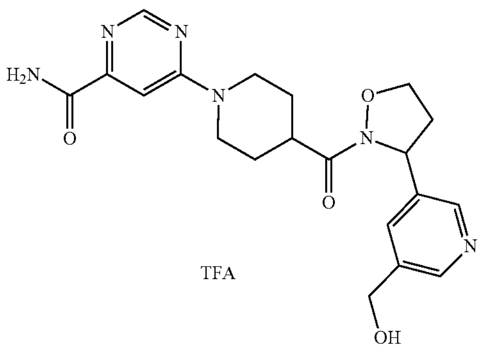 [SMILES: NC(=O)c1cc(N2CCC(C(=O)N3OCCC3c3cncc(CO)c3)CC2)ncn1]

In analogy to the procedure described for example 025 by using 1-(6-carbamoylpyrimidin-4-yl)piperidine-4-carboxylic acid TFA salt (I-38, 50 mg) 5.5 mg of the title compound was obtained.

LC/MS: m/z=413.4 [M+H]+; tR: 0.84 min (LC/MS-method A)

Ex. 033/034

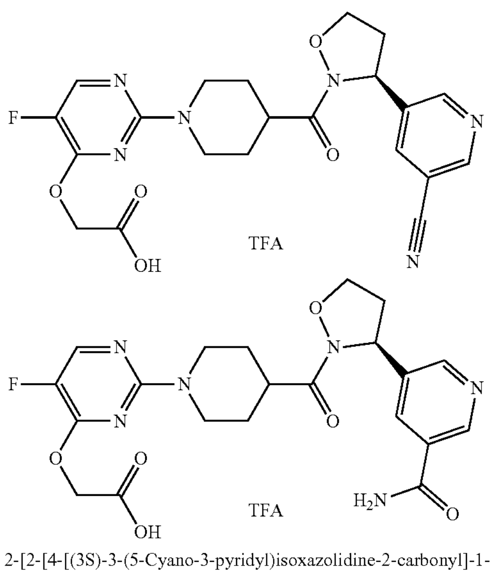

2-[2-[4-[(3S)-3-(5-Cyano-3-pyridyl)isoxazolidine-2-carbonyl]-1-piperidyl]-5-fluoro-pyrimidin-4-yl]oxyacetic acid and 2-[2-[4-[(3S)-3-(5-carbamoyl-3-pyridyl)isoxazolidine-2-carbonyl]-1-piperidyl]-5-fluoro-pyrimidin-4-yl]oxyacetic acid as their TFA salts Ethyl 2-[2-[4-[(3S)-3-(5-cyano-3-pyridyl)isoxazolidine-2-carbonyl]-1-piperidyl]-5-fluoro-pyrimidin-4-yl]oxyacetate (ex. 27, 32 mg) was dissolved in THF (3.5 ml). Then lithium hydroxide (3.2 mg) and water (0.5 ml) were added with stirring. After stirring for 1 h the solvent was removed. The residue was dissolved in a mixture of water and 1 N HCl and was purified by RP HPLC (flow 25 ml/min; from 95% $H_2O$+0.05% TFA/5% ACN to 5% $H_2O$+0.5% TFA/95% ACN in 45 min; Purosphere® STAR-RP18, 25×250 mm, 10 μm). The respective compound containing fractions were combined and the ACN was removed in vacuo. The aqueous solution was lyophilised to yield 10 mg of the nitrile.

LC/MS: m/z=457.4 [M+H]+; tR: 1.59 min (LC/MS-method A)

The amide required further purification after lyophilisation. Water and saturated sodium bicarbonate solution were added and the aqueous solution was extracted with DCM (3×). The aqueous phase was purified by RP HPLC (column: X-Bridge TMBEH 130 PrepC18; 10 μm OBDTM 19×250 mm; flow 15 ml/min; 90% $H_2O$+0.05% TFA/10% ACN to 60% $H_2O$+0.05% TFA/40% ACN in 45 min). The pure product containing fractions were combined, the ACN was removed in vacuo and the aqueous phase was lyophilised to yield 2.2 mg of the amide.

LC/MS: m/z=475.4 [M+H]+; tR: 1.28 min (LC/MS-method A)

Ex. 035

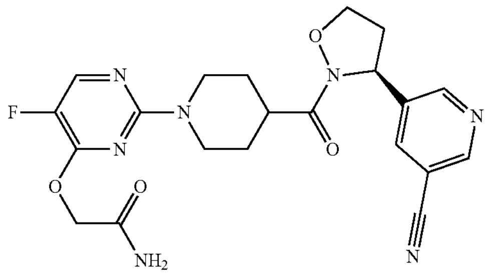

2-[2-[4-[(3S)-3-(5-Cyano-3-pyridyl)isoxazolidine-2-carbonyl]-1-piperidyl]-5-fluoro-pyrimidin-4-yl]oxyacetamide 2-[2-[4-[(3S)-3-(5-Cyano-3-pyridyl)isoxazolidine-2-carbonyl]-1-piperidyl]-5-fluoro-pyrimidin-4-yl]oxyacetic acid TFA salt (Ex. 033, 5.8 mg) was dissolved in DMF (1.5 ml) under Ar with stirring. DIPEA (7.1 μl) and HOBT ammonium salt (7 mg) were added. After 30 min 1-(3-dimethylaminopropyl)-3-ethylcarbodiimid hydrochloride (5.1 mg) was added. After 2 h further HOBT ammonium salt (7 mg) and 1-(3-dimethylaminopropyl)-3-ethylcarbodiimid hydrochloride (5.1 mg) were added. After standing overnight the solution was purified by RP-HPLC (flow 40 ml/min, 97% $H_2O$/3% ACN; 15 min; 90% ACN/10% $H_2O$; Agilent Prep C18, 5 μm, 30 mm×100 mm). The pure product containing fractions were combined, the ACN was removed in vacuo and the aqueous phase was lyophilised to yield 2.2 mg of the title compound.

LC/MS: m/z=456.4 [M+H]+; tR: 1.44 min (LC/MS-method A)

Ex. 036*

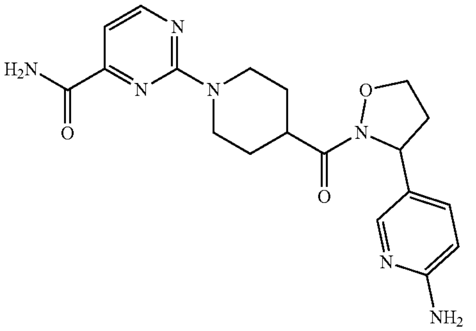

2-[4-[3-(6-Amino-3-pyridyl)isoxazolidine-2-carbonyl]-1-piperidyl]pyrimidine-4-carboxamide 1-(4-Carbamoylpyrimidin-2-yl)piperidine-4-carboxylic acid (I-22-1, 22.5 mg) was dissolved in DMF (1 ml) before DIPEA (63 μl) and HATU (41 mg) were added with stirring. After 5 min 5-(isoxazolidin-3-yl)pyridin-2-amine TFA salt (I-09, 35.4 mg) was added and stirring was continued for 24 h. The solution was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 17.7 mg of the title compound.

LC/MS: m/z=398.4 $[M+H]^+$; tR: 0.96 min (LC/MS-method A)

$^1H$ NMR (400 MHz, DMSO-$d_6$) δ ppm 8.54 (1H), 8.14 (1H), 7.83 (1H), 7.71 (2H), 7.52 (1H), 7.42 (1H), 7.07 (1H), 6.84 (1H), 5.24 (1H), 4.77 (2H), 4.30 (1H), 3.91 (1H), 3.03 (3H), 2.81 (1H), 2.23 (1H), 1.88 (1H), 1.73 (1H), 1.48 (2H).

Ex. 037*

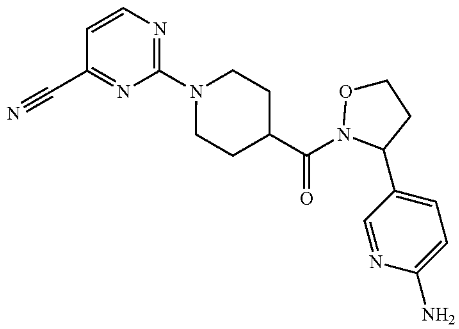

2-[4-[3-(6-Amino-3-pyridyl)isoxazolidine-2-carbonyl]-1-piperidyl]pyrimidine-4-carbonitrile In analogy to the procedure described for example 036 by using 1-(4-cyanopyrimidin-2-yl)piperidine-4-carboxylic acid (I-23, 21 mg) 12.9 mg of the title compound were obtained.

LC/MS: m/z=380.4 $[M+H]^+$, tR: 1.20 min (LC/MS-method A)

$^1H$ NMR (400 MHz, DMSO-$d_6$) δ ppm 8.62 (1H), 7.82 (1H), 7.62 (1H), 7.12 (3H), 6.76 (1H), 5.22 (1H), 4.57 (2H), 4.29 (1H), 3.91 (1H), 3.08 (3H), 2.81 (1H), 2.22 (1H), 1.89 (1H), 1.75 (1H), 1.47 (2H).

Ex. 038*

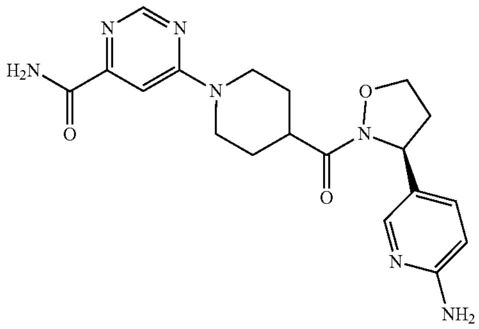

6-[4-[3-(6-Amino-3-pyridyl)isoxazolidine-2-carbonyl]-1-piperidyl]pyrimidine-4-carboxamide In analogy to the procedure described for example 036 by using 1-(6-carbamoylpyrimidin-4-yl)piperidine-4-carboxylic acid TFA salt (I-38, 33 mg) 23.2 mg of the title compound were obtained.

LC/MS: m/z=398.5 $[M+H]^+$; tR: 0.81 min (LC/MS-method A)

$^1H$ NMR (400 MHz, DMSO-$d_6$) δ ppm 8.54 (1H), 8.03 (1H), 7.82 (1H), 7.72 (1H), 7.49 (1H), 7.29 (1H), 6.63 (3H), 5.20 (1H), 4.43 (2H), 4.29 (1H), 3.90 (1H), 3.10 (3H), 2.79 (1H), 2.21 (1H), 1.90 (1H), 1.75 (1H), 1.49 (2H).

Ex. 039

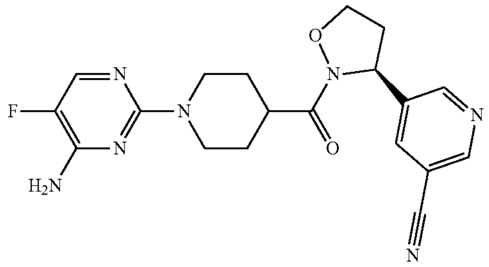

5-[(3S)-2-[1-(4-Amino-5-fluoro-pyrimidin-2-yl)piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoro acetic acid salt (I-28, 25 mg) was dissolved in ACN (2.5 ml) in a microwave vessel. Then DIPEA (34 μl) and 2-chloro-5-fluoro-pyrimidin-4-amine (I-34a, 8 mg) were added. Then the mixture was heated in a microwave oven for 10 h at 150° C. After cooling the mixture was directly separated by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 7.3 mg of the title compound.

LC/MS: m/z=475.4 $[M+H]^+$; tR: 1.28 min (LC/MS-method A)

Ex. 040*

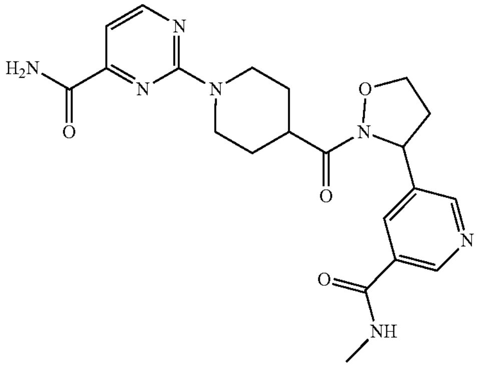

2-[4-[3-[5-(Methylcarbamoyl)-3-pyridyl]isoxazolidine-2-carbonyl]-1-piperidyl]pyrimidine-4-carboxamide 1-(4-Carbamoylpyrimidin-2-yl)piperidine-4-carboxylic acid (I-22-1, 23 mg) was dissolved in DMF (2 ml) before DIPEA (48 μl) and HATU (42 mg) were added with stirring. After 5 min 5-(isoxazolidin-3-yl)-N-methyl-pyridine-3-carboxamide TFA salt (I-10, 29.5 mg) was added and stirring was continued for 24 h. The solution was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 24.1 mg of the title compound.

LC/MS: m/z=440.5 $[M+H]^+$; tR: 1.21 min (LC/MS-method A)

$^1$H NMR (400 MHz, DMSO-$d_6$) δ ppm 8.88 (1H), 8.67 (1H), 8.63 (1H), 8.54 (1H), 8.15 (1H), 8.05 (1H), 7.70 (1H), 7.07 (1H), 5.43 (1H), 4.78 (2H), 4.34 (1H), 3.97 (1H), 3.00 (4H), 2.80 (3H), 2.29 (1H), 1.91 (1H), 1.75 (1H), 1.50 (2H).

Analogously to example 040 were prepared:

| Ex. | Acid | Structure | LCMS m/z; tR; (yield) | Name |
|---|---|---|---|---|
| 041* | 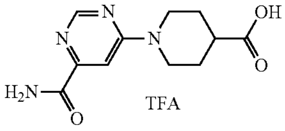 [SMILES: NC(=O)c1cc(N2CCC(C(=O)O)CC2)ncn1] TFA I-38 | 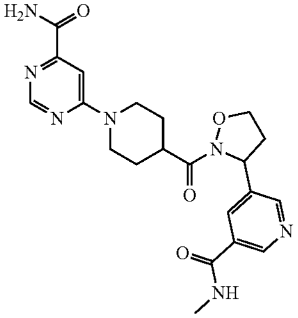 [SMILES: CNC(=O)c1cncc(C2CCON2C(=O)C2CCN(c3cc(C(N)=O)ncn3)CC2)c1] | 440.5 $[M + H]^+$ 1.01 min (26 mg, 63%) | 6-[4-[3-15-(methylcarbamoyl)-3-pyridyl] isoxazolidine-2-carbonyl]-1-piperidyl]pyrimidine-4-carboxamide |
| 042* | 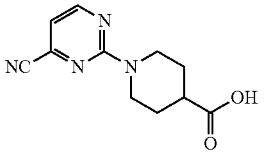 [SMILES: N#Cc1ccnc(N2CCC(C(=O)O)CC2)n1] I-23 | 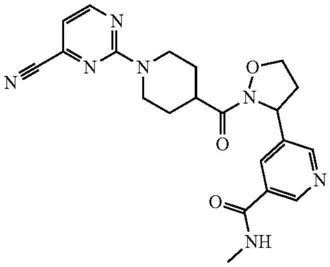 [SMILES: CNC(=O)c1cncc(C2CCON2C(=O)C2CCN(c3nccc(C#N)n3)CC2)c1] | 422.4 $[M + H]^+$ 1.57 min (21 mg, 53%) | 5-[2-[1-(4-cyanopyrimidin-2-yl)piperidine-4-carbonyl] isoxazolidin-3-yl]-N-methyl-pyridine-3-carboxamide |

Ex. 043

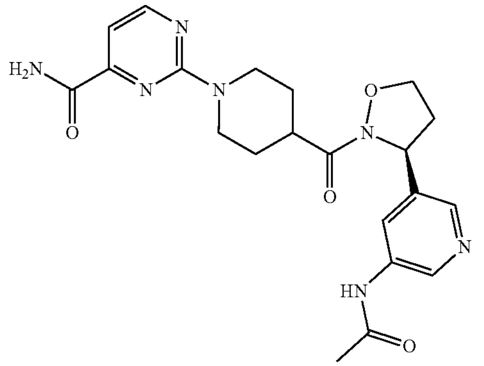

2-[4-[(3S)-3-(5-Acetamido-3-pyridyl)isoxazolidine-2-carbonyl]-1-piperidyl]pyrimidine-4-carboxamide 1-(4-Carbamoylpyrimidin-2-yl)piperidine-4-carboxylic acid (I-22-1, 16 mg) was dissolved in DMF (1 ml) before DIPEA (56 μl) and HATU (29.2 mg) were added with stirring. After 5 min N-[5-[(3S)-isoxazolidin-3-yl]-3-pyridyl]acetamide TFA salt (I-11, 29.5 mg) was added as solution in DMF (1.5 ml) and stirring was continued for 24 h. The solution was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 2.5 mg of the title compound.

LC/MS: m/z=440.4 $[M+H]^+$; tR: 1.14 min (LC/MS-method A)

$^1H$ NMR (400 MHz, DMSO-$d_6$) δ ppm 10.26 (1H), 8.69 (1H), 8.54 (1H), 8.24 (1H), 8.15 (1H), 7.99 (1H), 7.71 (1H), 7.07 (1H), 5.38 (1H), 4.78 (2H), 4.31 (1H), 3.94 (1H), 3.05 (3H), 2.94 (1H), 2.22 (1H), 2.07 (3H), 1.92 (1H), 1.74 (1H), 1.51 (2H).

Ex. 044

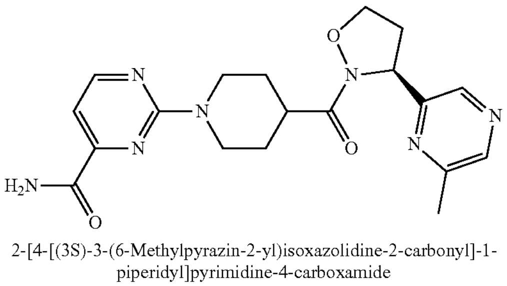 [SMILES: Cc1cncc([C@@H]2CCON2C(=O)C2CCN(c3nccc(C(N)=O)n3)CC2)n1]

2-[4-[(3S)-3-(6-Methylpyrazin-2-yl)isoxazolidine-2-carbonyl]-1-piperidyl]pyrimidine-4-carboxamide 1-(4-Carbamoylpyrimidin-2-yl)piperidine-4-carboxylic acid HCl salt (I-22, 125 mg) was dissolved in dry DMF (8 ml). DIPEA (380 μl) and (3S)-3-(6-methylpyrazin-2-yl) isoxazolidine HCl salt (I-12, 97 mg) were added with stirring. Then HATU (330 mg) was added and stirring was continued for 6 h. After standing overnight the mixture was poured onto saturated sodium bicarbonate solution and the aqueous phase was extracted with EA (3×). The combined organic phases were washed with brine, dried over sodium sulphate, filtered and concentrated in vacuo. The residue was dissolved in ACN/water and purified by RP HPLC (flow 75 ml/min, 90% $H_2O$/10% ACN to 10% $H_2O$/90% ACN in 15 min; Agilent Prep C18—5 μm, 30×250 mm). The pure product containing fractions were combined and the ACN was removed in vacuo and the aqueous phase was lyophilised to yield 65 mg of the title compound.

LC/MS: m/z=398.4 $[M+H]^+$; tR: 1.40 min (LC/MS-method A)

$^1H$ NMR (600.05 MHz, DMSO-$d_6$) ppm 8.54 (1H), 8.46 (1H), 8.38 (1H), 8.15 (1H), 7.70 (1H), 7.07 (1H), 5.39 (1H), 4.77 (2H), 4.34 (1H), 3.98 (1H), 3.29 (m, 1H), 3.04 (3H), 2.84 (1H), 1.90 (1H), 1.76 (1H), 1.50 (2H), signals below water and/or DMSO not listed Ex. 045

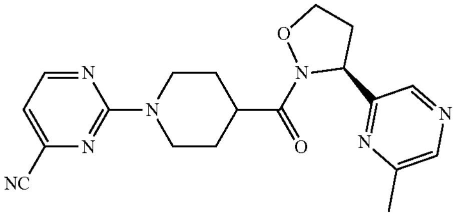

2-[4-[(3S)-3-(6-Methylpyrazin-2-yl)isoxazolidine-2-carbonyl]-1-piperidyl]pyrimidine-4-carbonitrile Following the procedure in example 44 using 1-(4-cyanopyrimidin-2-yl)piperidine-4-carboxylic acid (I-23, 30 mg) 28 mg of the title compound was obtained. RP HPLC conditions were as follows: flow 40 ml/min, 97% $H_2O$/3% ACN to 10% $H_2O$/90% ACN in 15 min; Agilent Prep C18—5 μm, 30×100 mm.

LC/MS: m/z=380.4 $[M+H]^+$; tR: 1.82 min (LC/MS-method A)

Ex. 046*

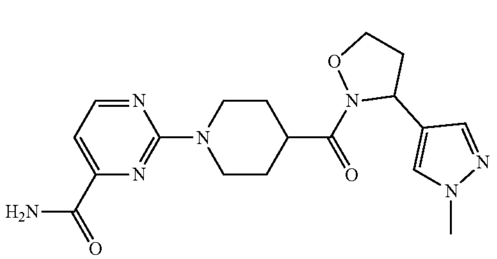

2-[4-[3-(1-Methylpyrazol-4-yl)isoxazolidine-1-carbonyl]-1-piperidyl]pyrimidine-4-carboxamide Following the procedure in example 44 using 3-(1-methyl-1H-pyrazol-4-yl)isoxazolidine hydrochloride salt (I-13, 25 mg) 14 mg of the title compound was obtained.

LC/MS: m/z=386.4 $[M+H]^+$; tR: 1.30 min (LC/MS-method A)

Ex. 047*

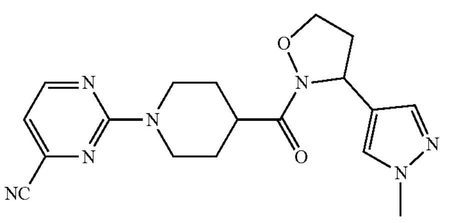

2-[4-[3-(1-Methylpyrazol-4-yl)isoxazolidine-2-carbonyl]-1-piperidyl]pyrimidine-4-carbonitrile Following the procedure in example 44 using 1-(4-cyanopyrimidin-2-yl)piperidine-4-carboxylic acid (I-23, 30 mg) 21 mg of the title compound was obtained. RP HPLC conditions were as follows: flow 40 ml/min, 97% $H_2O$/3% ACN to 90% ACN/10% $H_2O$ in 15 min; Agilent Prep C18—5 μm, 30×100 mm).

LC/MS: m/z=368.4 $[M+H]^+$; tR: 1.70 min (LC/MS-method A)

Ex. 048*

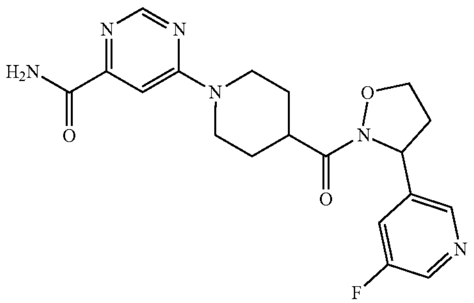

6-[4-[3-(5-Fluoro-3-pyridyl)isoxazolidine-2-carbonyl]-1-piperidyl]pyrimidine-4-carboxamide 1-(6-Carbamoylpyrimidin-4-yl)piperidine-4-carboxylic acid 2,2,2-trifluoroacetic acid (I-38, 47.8 mg), 3-(5-fluoropyridin-3-yl)isoxazolidine TFA salt (I-14-1, 31 mg) and HATU (55.5 mg) were solved in dimethylformamide (0.75 ml). DIPEA (85 μl) was added and the solution was stirred for 1 h. The reaction mixture was purified by RP prep-HPLC (Column: Agilent Prep-C18, 10 μm, 30×100 mm; flow rate: 50 ml/min; 1 min 90% $H_2O$, within 12 min up to 100% ACN, 2 min 100% ACN). The combined fractions were lyophilised and gave 30 mg of the title compound.

LC/MS: m/z=401.4 $[M+H]^+$; tR: 1.24 min (LC/MS-method A)

Ex. 049*

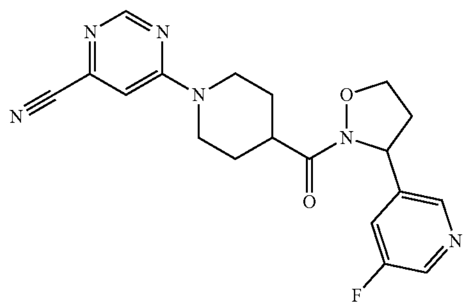

6-[4-[3-(5-Fluoro-3-pyridyl)isoxazolidine-2-carbonyl]-1-piperidyl]pyrimidine-4-carbonitrile The synthesis was done as described for example 048 using 1-(6-cyanopyrimidin-4-yl)piperidine-4-carboxylic acid TFA salt (I-39-1, 34.1 mg) to give 27 mg (70.6 μmol) of the title compound.

LC/MS: m/z=383.4 $[M+H]^+$; tR: 1.61 min (LC/MS-method A)

$^1H$ NMR (400.23 MHz, DMSO-$d_6$) δ ppm 8.54 (1H), 8.49 (1H), 8.41 (1H), 7.60 (1H), 7.56 (1H), 5.42 (1H), 4.32 (1H), 3.96 (1H), 3.13 (3H), 2.92 (1H), 2.32 (1H), 2.28 (1H), 1.96 (1H), 1.78 (1H), 1.52 (2H).

Ex. 050*

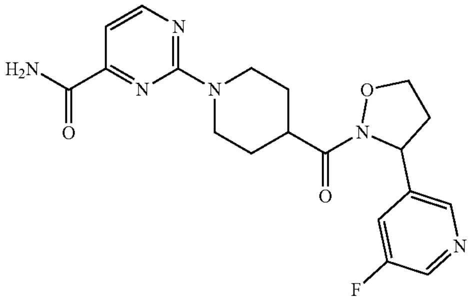

2-[4-[3-(5-Fluoro-3-pyridyl)isoxazolidine-2-carbonyl]-1-piperidyl]pyrimidine-4-carboxamide The synthesis was done as described for example 048 using 1-(4-carbamoylpyrimidin-2-yl)piperidine-4-carboxylic acid TFA salt (I-22-2, 35.0 mg) to give 31 mg of the title compound.

LC/MS: m/z=401.4 $[M+H]^+$; tR: 1.48 min (LC/MS-method A)

$^1H$ NMR (400.23 MHz, DMSO-$d_6$) δ ppm 8.54 (1H), 8.49 (1H), 8.41 (1H), 8.14 (1H), 7.70 (1H), 7.60 (1H), 7.07 (1H), 5.43 (1H), 4.77 (2H), 4.32 (1H), 3.95 (1H), 3.04 (3H), 2.93 (1H), 2.29 (1H), 1.93 (1H), 1.75 (1H), 1.50 (2H).

Ex. 051*

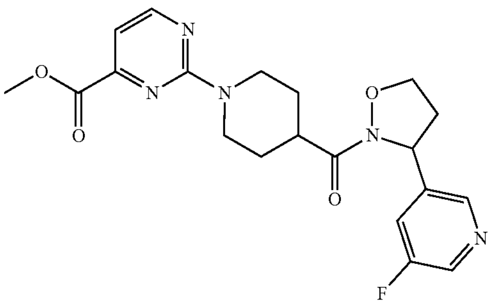

Methyl 2-[4-[3-(5-fluoro-3-pyridyl)isoxazolidine-2-carbonyl]-1-piperidyl]pyrimidine-4-carboxylate The synthesis was done as described for example 048 using 1-(4-(methoxycarbonyl)pyrimidin-2-yl)piperidine-4-carboxylic acid trifluoroacetic acid salt (I-40-1, 40.1 mg) to give 21 mg of the title compound.

LC/MS: m/z=416.4 $[M+H]^+$; tR: 1.80 min (LC/MS-method A)

Ex. 052*

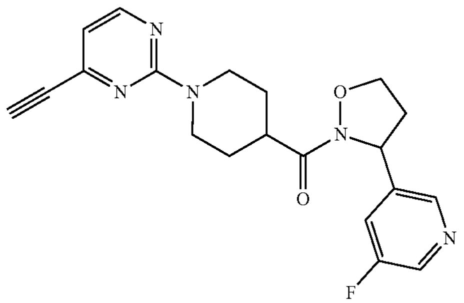

2-[4-[3-(5-Fluoro-3-pyridyl)isoxazolidine-2-carbonyl]-1-piperidyl]pyrimidine-4- carbonitrile The synthesis was done as described for example 048 using 1-(4-cyanopyrimidin-2-yl)piperidine-4-carboxylic acid trifluoroacetic acid salt (I-23-1, 32.6 mg) to give 26 mg of the title compound.

LC/MS: m/z=383.4 $[M+H]^+$; tR: 1.92 min (LC/MS-method A)

Ex. 053

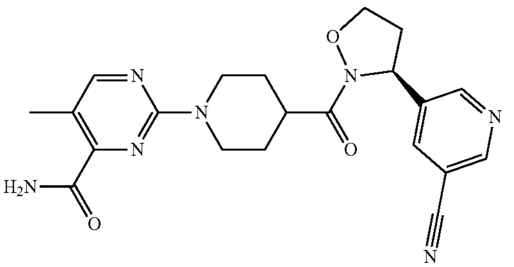

2-[4-[3S)-3-(5-Cyano-3-pyridyl)isoxazolidine-2-carbonyl]-1-piperidyl]-5-methyl-pyrimidine-4-carboxamide 2-Chloro-5-methylpyrimidine-4-carboxamide (I-36a, 10 mg) was dissolved in ACN (2.5 ml) in a microwave vessel. Then DIPEA (40 μl) and 5-[(3S)-2-(piperidine-4-carbonyl) isoxazolidin-3-yl]pyridine-3-carbonitrile trifluoro acetic acid salt (I-28, 33 mg) were added. The mixture was heated in a microwave oven for 2 h at 80° C., followed by 2 h at 120° C. After cooling sat. sodium bicarbonate solution was added and the aqueous phase was extracted with DCM (3×). The combined organic phases were dried over sodium sulphate, filtered and concentrated in vacuo. The residue was separated by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 16.3 mg of the title compound.

LC/MS: m/z=422.4 $[M+H]^+$; tR: 1.55 min (LC/MS-method A)

$^1$H NMR (400.23 MHz, DMSO-$d_6$) δ ppm 8.94 (1H), 8.78 (1H), 8.32 (1H), 8.21 (1H), 7.98 (1H), 7.56 (1H), 5.43 (1H), 4.66 (2H), 4.33 (1H), 3.97 (1H), 2.97 (4H), 2.31 (1H), 2.25 (3H), 1.91 (1H), 1.73 (1H), 1.48 (2H)

Ex. 054*

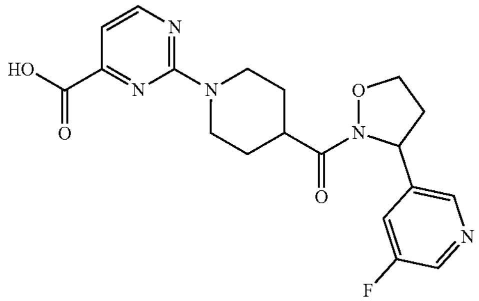

2-[4-[3-(5-Fluoro-3-pyridyl)isoxazolidine-2-carbonyl]-1-piperidyl]pyrimidine-4-carboxylic acid Methyl 2-[4-[3-(5-fluoro-3-pyridyl)isoxazolidine-2-carbonyl]-1-piperidyl]pyrimidine-4-carboxylate (example 51, 17 mg) was solved in methanol (200 μl), tetrahydrofurane (200 μl) and sodium hydroxide (aq. 2 N, 200 μl) and stirred for 5 h. Sulfuric acid (aq. 2 N, 200 μl) was added and the mixture was purified by RP prep-HPLC (Column: Agilent Prep-C18, 10 μm 30×100 mm; flow rate: 50 ml/min; 1 min 90% $H_2O$, within 12 min up to 100% ACN, 2 min 100% ACN). The combined fractions were lyophilised and gave 3.0 mg of the title compound.

LC/MS: m/z=402.4 $[M+H]^+$; tR: 1.45 min (LC/MS-method A)

Ex. 055

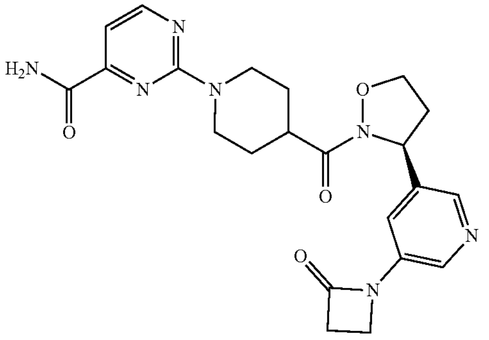

2-[4-[(3S)-3-[5-(2-Oxoazetidin-1-yl)-3-pyridyl]isoxazolidine-2-carbonyl]-1-piperidyl]pyrimidine-4-carboxamide 1-(4-Carbamoylpyrimidin-2-yl)piperidine-4-carboxylic acid (I-22-1, 30 mg) was dissolved in DMF (1 ml) before DIPEA (105 μl) and HATU (54.7 mg) were added with stirring. After 5 min 1-[5-[(3S)-isoxazolidin-3-yl]-3-pyridyl]azetidin-2-one TFA salt (I-15, 40 mg) was added as solution in DMF (1 ml) and stirring was continued for 24 h. The solution was purified by preparative RP HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 25 mg of the title compound.

LC/MS: m/z=452.5 $[M+H]^+$; tR: 1.30 min (LC/MS-method A)

$^1$H NMR (400 MHz, DMSO-$d_6$) δ ppm 8.54 (1H), 8.45 (1H), 8.25 (1H), 8.15 (1H), 7.69 (1H), 7.67 (1H), 7.07 (1H), 5.38 (1H), 4.77 (2H), 4.32 (1H), 3.95 (1H), 3.69 (2H), 3.13 (t, 5H), 3.05 (2H), 2.93 (1H), 2.23 (1H), 1.91 (1H), 1.74 (1H), 1.50 (2H).

Ex. 056: 2-[4-[(3S)-3-[5-(2-Oxoazetidin-1-yl)-3-pyridyl]isoxazolidine-2-carbonyl]-1-piperidyl]pyrimidine-4-carbonitrile

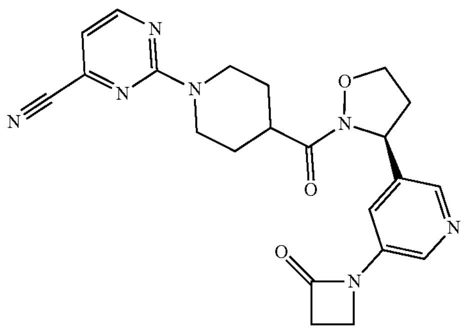 [SMILES: N#Cc1ccnc(N2CCC(C(=O)N3OCC[C@H]3c3cncc(N4CCC4=O)c3)CC2)n1]

In analogy to the procedure described for example 055 by using 1-(4-cyanopyrimidin-2-yl)piperidine-4-carboxylic acid (I-23, 27 mg) 14 mg of the title compound were obtained.

LC/MS: m/z=434.4 $[M+H]^+$; tR: 1.68 min (LC/MS-method A)

$^1$H NMR (400 MHz, DMSO-$d_6$) δ ppm 8.62 (1H), 8.45 (1H), 8.24 (1H), 7.66 (1H), 7.11 (1H), 5.38 (1H), 4.55 (2H), 4.31 (1H), 3.95 (1H), 3.69 (2H), 3.12 (H), 2.93 (1H), 2.23 (1H), 1.94 (1H), 1.77 (1H), 1.50 (2H).

Ex. 057

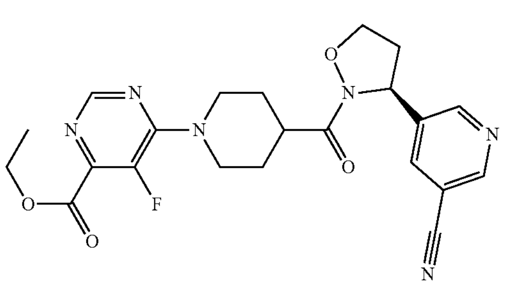

Ethyl 6-[4-[(3S)-3-(5-cyano-3-pyridyl)isoxazolidine-2-carbonyl]-1-piperidyl]-5-fluoro-pyrimidine-4-carboxylate 5-[(3S)-2-(Piperidine-4-carbonyl)isoxazolidin-3-yl]pyridine-3-carbonitrile trifluoro acetic acid salt (I-28, 35 mg) was dissolved in ACN (2.5 ml) in a microwave vessel. Then ethyl 6-chloro-5-fluoro-pyrimidine-4-carboxylate (I-30, 15 mg) and DIPEA (47 μl) were added and the mixture was heated in a microwave oven for 1 h at 80° C. Then additional ethyl 6-chloro-5-fluoro-pyrimidine-4-carboxylate (I-30, 15 mg) was added and heating was repeated at 80° C. for 1 h. After cooling the mixture was directly purified by RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilised to yield 48 mg of the title compound which was further purified by silica gel chromatography (4 g $SiO_2$, 100% DCM to 90% DCM/5% ethanol in 40 min, then from 5% EtOH to 10% EtOH in 10 min). The pure product containing fractions were combined and the solvent was removed in vacuo. The residue was dissolved in ACN/water and lyophilised overnight to yield 20 mg of the title compound.

LC/MS: m/z=455.4 $[M+H]^+$; tR: 1.76 min (LC/MS-method A)

Ex. 058

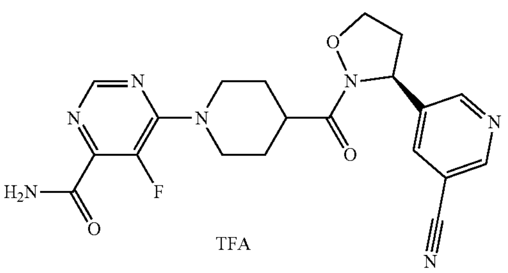

TFA

6-[4-[(3S)-3-(5-Cyano-3-pyridyl)isoxazolidine-2-carbonyl]-1-piperidyl]-5-fluoro-pyrimidine-4-carboxylic acid TFA salt Ethyl 6-[4-[(3S)-3-(5-cyano-3-pyridyl)isoxazolidine-2-carbonyl]-1-piperidyl]-5-fluoro-pyrimidine-4-carboxylate (ex. 057, 17 mg) was treated as described in ex. 21 to yield 9 mg of the title compound.

LC/MS: m/z=427.3 $[M+H]^+$; tR: 1.04 min (LC/MS-method A)

Ex. 059

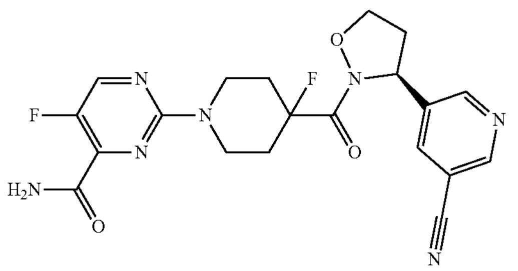

2-[4-[(3S)-3-(5-Cyano-3-pyridyl)isoxazolidine-2-carbonyl]-4-fluoro-1-piperidyl]-5-fluoro-pyrimidine-4-carboxamide 1-(4-Carbamoyl-5-fluoropyrimidin-2-yl)-4-fluoropiperidine-4-carboxylic acid (I-31, 17 mg) was dissolved in dry DMF (2 ml). DIPEA (30 µl) and 5-[(3S)-isoxazolidin-3-yl]pyridine-3-carbonitrile (I-02-1, 11 mg) were added with stirring. Then HATU (34 mg) was added and stirring was continued for 6 h. After standing over the weekend the mixture was poured onto saturated sodium bicarbonate solution and the aqueous phase was extracted with EA (3×). The combined organic phases were washed with brine, dried over sodium sulphate, filtered and concentrated in vacuo. The residue was lyophilised, treated with ACN in an ultra sound bath and sucked off to yield 9.1 mg of the title compound.

LC/MS: m/z=444.3 $[M+H]^+$; tR: 1.46 min (LC/MS-method A)

Ex. 060

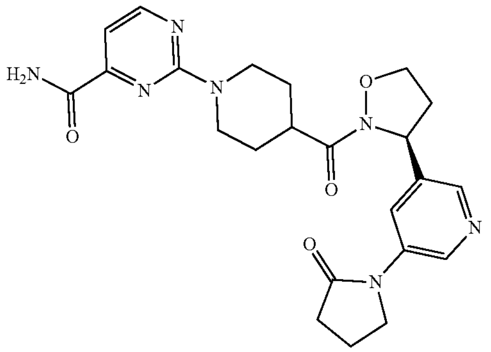

2-[4-[(3S)-3-[5-(2-Oxopyrrolidin-1-yl)-3-pyridyl]isoxazolidine-2-carbonyl]-1-piperidyl]pyrimidine-4-carboxamide 1-(4-Carbamoylpyrimidin-2-yl)piperidine-4-carboxylic acid (I-22-1, 15 mg) was dissolved in DMF (1 ml) before DIPEA (52 µl) and HATU (27.4 mg) were added with stirring. After 5 min 1-[5-[(3S)-isoxazolidin-3-yl]-3-pyridyl]pyrrolidin-2-one TFA salt (I-16, 20.8 mg) was added as solution in 1 ml DMF and stirring was continued for 1.5 h. The solution was purified by preparative RP HPLC (120 ml/min, 95% $H_2O$/5% ACN to 5% $H_2O$/95% ACN in 13 min; Waters Sunfire Prep C18 OBD—5 µm, 50×100 mm). The pure product containing fractions were combined and the ACN was removed in vacuo. The aqueous solution was lyophilised to yield 19 mg of the title compound.

LC/MS: m/z=466.5 $[M+H]^+$; tR: 1.27 min (LC/MS-method A)

$^1$H NMR (400 MHz, DMSO-$d_6$) δ ppm 8.68 (1H), 8.54 (1H), 8.28 (1H), 8.15 (1H), 8.10 (1H), 7.70 (1H), 7.07 (1H), 5.39 (1H), 4.77 (2H), 4.32 (1H), 3.95 (1H), 3.86 (2H), 3.05 (br t, 3H), 2.93 (1H), 2.33 (1H), 2.09 (2H), 1.91 (1H), 1.75 (1H), 1.50 (2H). Signals below water not listed.

Ex. 061

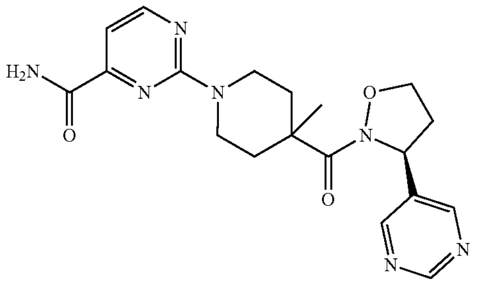

2-[4-Methyl-4-[(3S)-3-pyrimidin-5-ylisoxazolidine-2-carbonyl]-1-piperidyl]pyrimidine-4-carboxamide (4-Methyl-4-piperidyl)-[(3S)-3-pyrimidin-5-ylisoxazolidin-2-yl]methanone TFA salt (I-32, 30 mg) was dissolved in dry ACN (1.5 ml) in a microwave vessel. DIPEA (52 µl) and 2-chloropyrimidine-4-carboxamide (11 mg) were added and the mixture was heated in a microwave oven at 80° C. for 1 h. After cooling DMF (1.5 ml) was added to the mixture which was directly purified by RP HPLC (flow 40 ml/min, 97% $H_2O$/3% ACN to 10% $H_2O$/90% ACN in 15 min; Agilent Prep C18—5 µm, 30×150 mm). The pure product containing fractions were combined, the ACN was removed in vacuo and the residue was lyophilised overnight to yield 14 mg of the title compound.

LC/MS: m/z=398.4 $[M+H]^+$; tR: 1.39 min (LC/MS-method A)

Ex. 062

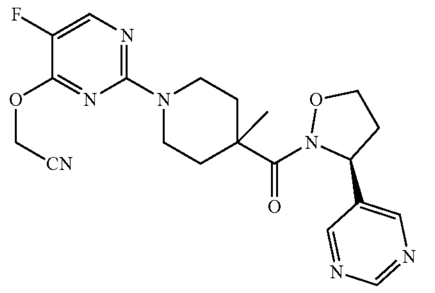

2-[5-Fluoro-2-[4-methyl-4-[(3S)-3-pyrimidin-5-ylisoxazolidine-2-carbonyl]-1-piperidyl]pyrimidin-4-yl]oxyacetonitrile (4-Methyl-4-piperidyl)-[(3S)-3-pyrimidin-5-ylisoxazolidin-2-yl]methanone TFA salt (I-32, 30 mg) was dissolved in dry ACN (1.5 ml) in a microwave vessel. DIPEA (52 µl) and 2-(2-chloro-5-fluoro-pyrimidin-4-yl)oxyacetonitrile (I-26, 13 mg) were added and the mixture was heated in a microwave oven at 80° C. for 1 h. After cooling DMF (1.5 ml) was added to the mixture which was directly purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the residue was lyophilised overnight to yield 11 mg of the title compound.

LC/MS: m/z=428.4 $[M+H]^+$; tR: 1.84 min (LC/MS-method A)

Ex. 063

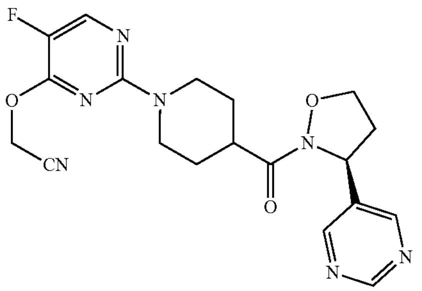

2-[5-Fluoro-2-[4-[(3S)-3-pyrimidin-5-ylisoxazolidine-2-carbonyl]-1-piperidyl]pyrimidin-4-yl]oxyacetonitrile 4-Piperidyl-[(3S)-3-pyrimidin-5-ylisoxazolidin-2-yl] methanone TFA salt (I-33, 30 mg) and 2-(2-chloro-5-fluoro-pyrimidin-4-yl)oxyacetonitrile (I-26, 13 mg) were reacted in a microwave oven for 2 h at 80° C. and otherwise analogously as described in example 62 to yield 8 mg of the title compound.

LC/MS: m/z=414.3 $[M+H]^+$; tR: 1.66 min (LC/MS-method A)

Ex. 064

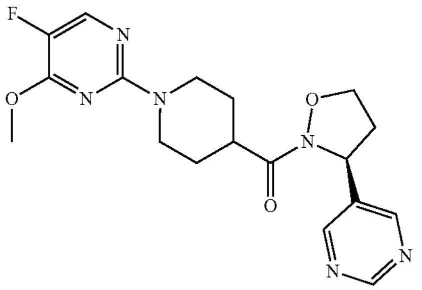

[1-(5-Fluoro-4-methoxy-pyrimidin-2-yl)-4-piperidyl]-[(3S-3-pyrimidin-5-ylisoxazolidin-2-yl]methanone 4-Piperidyl-[(3S)-3-pyrimidin-5-ylisoxazolidin-2-yl] methanone TFA salt (I-33, 30 mg) and 2-chloro-5-fluoro-4-methoxypyrimidine (12 mg) were reacted in a microwave oven for 1.5 h at 80° C., for 1 h at 100° C. and for 4 h at 120° C. and otherwise analogously as described in example 62 to yield 7 mg of the title compound.

LC/MS: m/z=389.3 $[M+H]^+$; tR: 1.66 min (LC/MS-method A)

$^1$H NMR (400.23 MHz, DMSO-$d_6$) δ ppm 9.11 (1H), 8.73 (2H), 8.14 (1H), 5.40 (1H), 4.53 (2H), 4.33 (1H), 3.98 (1H), 3.93 (3H), 2.97 (4H), 2.35 (1H), 1.89 (1H), 1.74 (1H), 1.49 (2H)

Ex. 065

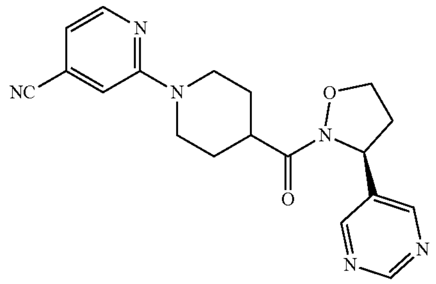

2-[4-[(3S)-3-Pyrimidin-5-ylisoxazolidine-2-carbonyl]-1-piperidyl]pyridine-4-carbonitrile 4-Piperidyl-[(3S)-3-pyrimidin-5-ylisoxazolidin-2-yl] methanone TFA salt (I-33, 30 mg) and 2-chloro-4-cyano-pyridine (10 mg) were reacted in a microwave oven for 1.5 h at 80° C., for 1 h at 100° C. and for 4 h at 140° C. and otherwise analogously as described in example 62 to yield 4 mg of the title compound.

LC/MS: m/z=365.3 $[M+H]^+$; tR: 1.52 min (LC/MS-method A)

Ex. 066

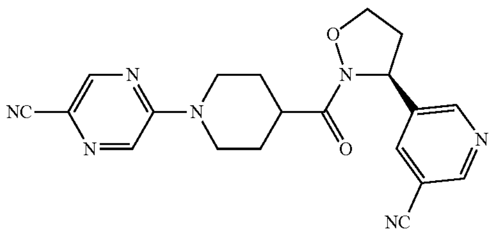

5-[4-[(3S)-3-(5-Cyano-3-pyridyl)isoxazolidine-2-carbonyl]-1-piperidyl]pyrazine-2-carbonitrile 5-[(3S)-2-(Piperidine-4-carbonyl)isoxazolidin-3-yl]pyridine-3-carbonitrile trifluoro acetic acid salt (I-28, 30 mg) and 5-chloropyrazine-2-carbonitrile (12 mg) were reacted analogously as described in example 62 to yield 16 mg of the title compound.

LC/MS: m/z=390.3 $[M+H]^+$; tR: 1.64 min (LC/MS-method A)

Ex. 067

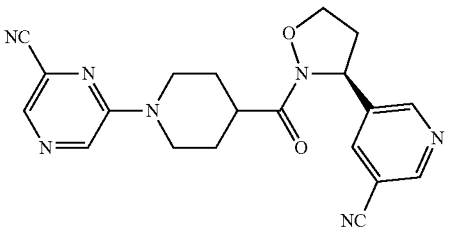

6-[4-[(3S)-3-(5-Cyano-3-pyridyl)isoxazolidine-2-carbonyl]-1-piperidyl]pyrazine-2-carbonitrile 5-[(3S)-2-(Piperidine-4-carbonyl)isoxazolidin-3-yl]pyridine-3-carbonitrile trifluoro acetic acid salt (I-28, 30 mg) and 6-chloropyrazine-2-carbonitrile (12 mg) were reacted for 1 h at 80° C. and for 0.5 h at 100° C. and otherwise analogously as described in example 62 to yield 15 mg of the title compound.

LC/MS: m/z=390.3 $[M+H]^+$; tR: 1.71 min (LC/MS-method A)

Ex. 068

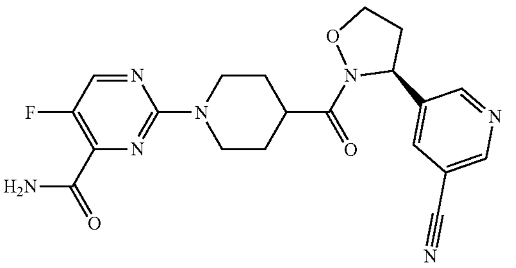

2-[4-[(3S)-3-(5-Cyano-3-pyridyl)isoxazolidine-2-carbonyl]-1-piperidyl]-5-fluoro-pyrimidine-4-carboxamide 1-(4-Carbamoyl-5-fluoropyrimidin-2-yl)piperidine-4-carboxylic acid (I-34, 110 mg) was dissolved in dry DMF (5 ml). DIPEA (210 μl) and 5-[(3S)-isoxazolidin-3-yl]pyridine-3-carbonitrile (I-02-1, 79 mg) dissolved in DMF (2 ml) were added with stirring. Then HATU (234 mg) was added and stirring was continued for 30 min. The mixture was poured onto saturated sodium bicarbonate solution and the aqueous phase was extracted with EA (2×). The combined organic phases were washed with brine, dried over sodium sulphate, filtered and concentrated in vacuo. The residue was purified by silica gel chromatography (12 g $SiO_2$, 100% DCM for 5 min; then from 100% DCM to 90% DCM/10% ethanol in 45 min followed by 90% DCM/10% ethanol for 10 min). The pure product containing fractions were combined and the solvent was removed in vacuo. The residue was dissolved in ACN/water and lyophilised overnight to yield 122 mg of the title compound.

LC/MS: m/z=426.3 $[M+H]^+$; tR: 1.47 min (LC/MS-method A)

$^1H$ NMR (600.05 MHz, DMSO-$d_6$) δ ppm 8.94 (1H), 8.79 (1H), 8.54 (1H), 8.21 (1H), 8.09 (1H), 7.78 (1H), 5.43 (1H), 4.61 (2H), 4.33 (1H), 3.97 (1H), 3.03 (3H), 2.92 (1H), 2.31 (1H), 1.92 (1H), 1.75 (1H), 1.50 (2H)

Ex. 069/070(Ex. 069 for Comparison)

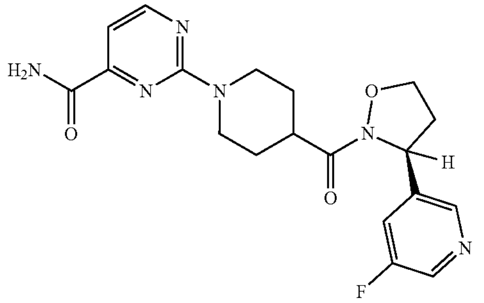

-continued

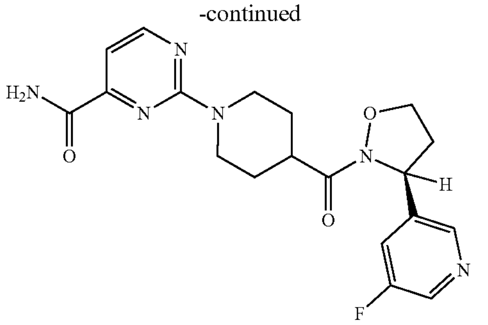

2-[4-[(3R)-3-(5-Fluoro-3-pyridyl)isoxazolidine-2-carbonyl]-1-piperidyl]pyrimidine-4-carboxamide and 2-[4-[(3S)-3-(5-Fluoro-3-pyridyl)isoxazolidine-2-carbonyl]-1-piperidyl]pyrimidine-4-carboxamide Chiral separation of the racemate synthesized in example 50:

The mixture was purified by chiral separation (Column: Chiralpak IA/32, 250×30 mm, 5 μm; flow rate: 30 ml/min; Eluent: EtOH/MeOH 1:1, duration 20 min, wavelength 240 nm and 254 nm. Two fractions were separately evaporated.

Ex. 069

Chiral analytic HPLC (Column Chiralpak IA/64, 250×4.6 mm, solvent

EtOH:MeOH 1:1, flow 1.0 ml/min) tR: =6.02 min $^1H$ NMR (400.13 MHz, DMSO-$d_6$) ppm 8.55 (1H), 8.50 (1H), 8.40 (1H), 8.15 (1H), 7.70 (1H), 7.60 (1H), 7.05 (1H), 5.45 (1H), 4.75 (2H), 4.35 (1H), 3.95 (1H), 3.15-2.85 (4H), 3.05 (3H), 2.30 (1H), 1.95 (1H), 1.75 (1H), 1.50 (2H).

Ex. 070

Chiral analytic HPLC (Column Chiralpak IA/64, 250×4.6 mm, solvent

EtOH:MeOH 1:1, flow 1.0 ml/min tR: =9.40 min $^1H$ NMR (400.13 MHz, DMSO-$d_6$) ppm 8.55 (1H), 8.50 (1H), 8.40 (1H), 8.15 (1H), 7.70 (1H), 7.60 (1H), 7.05 (1H), 5.45 (1H), 4.75 (2H), 4.35 (1H), 3.95 (1H), 3.15-2.85 (4H), 3.05 (3H), 2.30 (1H), 1.95 (1H), 1.76 (1H), 1.50 (2H).

Ex. 71

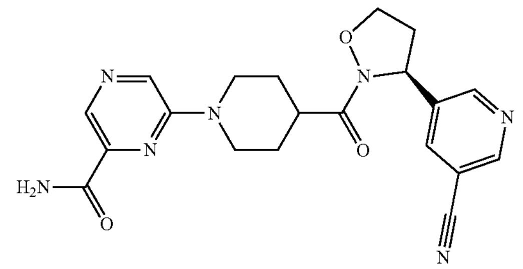

6-[4-[(3S)-3-(5-Cyano-3-pyridyl)isoxazolidine-2-carbonyl]-1-piperidyl]pyrazine-2-carboxamide 5-[(3S)-2-(Piperidine-4-carbonyl)isoxazolidin-3-yl]pyridine-3-carbonitrile trifluoro acetic acid salt (I-28, 30 mg) and 6-chloropyrazine-2-carboxamide (14 mg) were reacted in a microwave oven for 1 h at 100° C. and for 4 h at 120°

C. and otherwise analogously as described in example 62 to yield 18 mg of the title compound.

LC/MS: m/z=408.3 [M+H]$^+$; tR: 1.30 min (LC/MS-method A)

Ex. 072

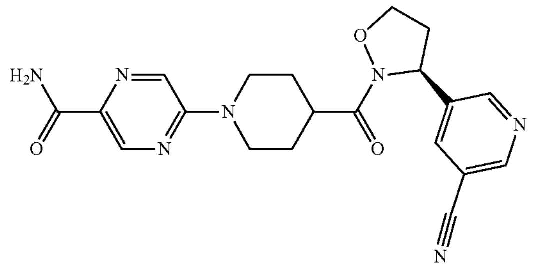

5-[4-[(3S)-3-(5-Cyano-3-pyridyl)isoxazolidine-2-carbonyl]-1-piperidyl] pyrazine-2-carboxamide 5-[(3S)-2-(Piperidine-4-carbonyl)isoxazolidin-3-yl]pyridine-3-carbonitrile trifluoro acetic acid salt (I-28, 30 mg) and 5-chloropyrazine-2-carboxamide (14 mg) were reacted in a microwave oven for 1 h at 100° C. and for 4 h at 120° C. and otherwise analogously as described in example 62 to yield 20 mg of the title compound.

LC/MS: m/z=408.3 [M+H]$^+$; tR: 1.30 min (LC/MS-method A)

Ex. 073

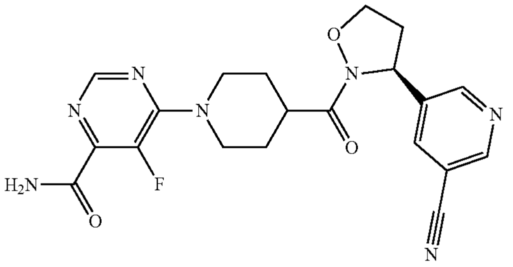

6-[4-[(3S)-3-(5-Cyano-3-pyridyl)isoxazolidine-2-carbonyl]-1-piperidyl]-5-fluoro-pyrimidine-4-carboxamide Ethyl 6-[4-[(3S)-3-(5-cyano-3-pyridyl)isoxazolidine-2-carbonyl]-1-piperidyl]-5-fluoro-pyrimidine-4-carboxylate (ex. 057, 15 mg) was mixed with $NH_3$ solution (7 N in MeOH, 1 ml) in a microwave vessel. After capping the vessel the mixture was stirred for 1 h at rt. Then water+0.05% TFA (2 ml) was added and the mixture was directly purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the residue was lyophilised overnight to yield 9 mg of the title compound.

LC/MS: m/z=426.3 [M+H]$^+$; tR: 1.31 min (LC/MS-method A)

Ex. 074

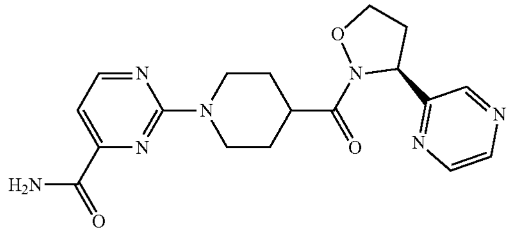

2-[4-[(3S)-3-Pyrazin-2-ylisoxazolidine-2-carbonyl]-1-piperidyl] pyrimidine-4-carboxamide 1-(4-Carbamoylpyrimidin-2-yl)piperidine-4-carboxylic acid hydrochloride salt (I-22, 42 mg) was dissolved in dry DMF (3 ml). DIPEA (80 μl) and (3S)-3-pyrazin-2-ylisoxazolidine HCl salt (I-17, 50 mg) were added with stirring. After 15 min HATU (103 mg) was added and stirring was continued for 30 min. Then saturated sodium bicarbonate solution was added and the aqueous phase was extracted with EA (3×). The combined organic phases were washed with brine, dried over sodium sulphate, filtered and concentrated in vacuo. The residue was dissolved in ACN/water and purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined and the ACN was removed in vacuo and the aqueous phase was lyophilised to yield 22 mg of the title compound.

LC/MS: m/z=384.3 [M+H]$^+$; tR: 1.28 min (LC/MS-method A)

$^1H$ NMR (600.05 MHz, DMSO-$d_6$) δ ppm 8.68-8.52 (4H), 8.14 (1H), 7.70 (1H), 7.07 (1H), 5.44 (1H), 4.76 (2H), 4.35 (1H), 4.01 (1H), 3.29 (1H), 3.04 (3H), 2.85 (1H), 1.89 (1H), 1.76 (1H), 1.49 (2H)

Ex. 075

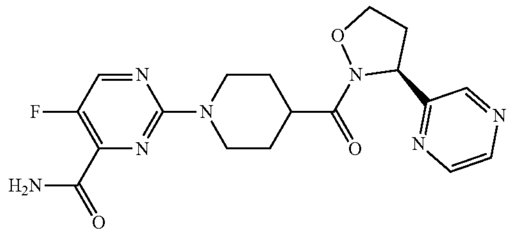

5-Fluoro-2-[4-[(3S)-3-pyrazin-2-ylisoxazolidine-2-carbonyl]-1-piperidyl]pyrimidine-4-carboxamide 1-(4-Carbamoyl-5-fluoro-pyrimidin-2-yl)piperidine-4-carboxylic acid (I-34, 39 mg) was dissolved in dry DMF (3 ml), DIPEA (80 μl) and HATU (103 mg) were added with stirring. After 15 min (3S)-3-pyrazin-2-ylisoxazolidine HCl salt (I-17, 50 mg) was added and stirring was continued for 30 min. The saturated sodium bicarbonate solution was added and the aqueous phase was extracted with EA (2×). The combined organic phases were washed with brine, dried over sodium sulphate, filtered and concentrated in vacuo.

The residue was dissolved in ACN/water and purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 27 mg of the title compound.

LC/MS: m/z=402.3 $[M+H]^+$; tR: 1.32 min (LC/MS-method A)

$^1$H NMR (600.05 MHz, DMSO-$d_6$) δ ppm 8.68-8.58 (3H), 8.53 (1H), 8.09 (1H), 7.78 (1H), 5.43 (1H), 4.60 (2H), 4.34 (1H), 4.01 (1H), 3.29 (1H), 3.02 (3H), 2.85 (1H), 1.88 (1H), 1.75 (1H), 1.49 (2H)

Ex. 076

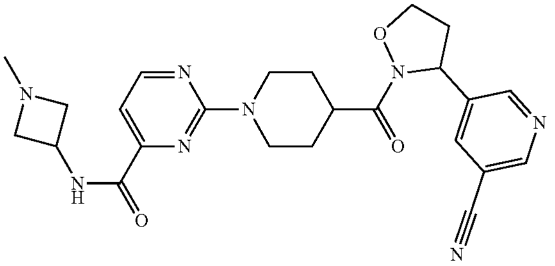

2-[4-[(3S)-3-(5-Cyano-3-pyridyl)isoxazolidine-2-carbonyl]-1-piperidyl]-N-(1-methylazetidin-3-yl)pyrimidine-4-carboxamide 2-[4-[(3S)-3-(5-Cyano-3-pyridyl)isoxazolidine-2-carbonyl]-1-piperidyl]pyrimidine-4-carboxylic acid (ex. 102, 20 mg) was dissolved in dry DMF (3 ml). DIPEA (40 μl) and (1-methylazetidin-3-yl)methanamine dihydrochlorid (9 mg) were added with stirring. After 15 min HATU (103 mg) was added and stirring was continued for 30 min. Then saturated sodium bicarbonate solution was added and the aqueous phase was extracted with EA (3×). The combined organic phases were washed with brine, dried over sodium sulphate, filtered and concentrated in vacuo. The residue was dissolved in ACN/water and purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 5 mg of the title compound.

LC/MS: m/z=491.4 $[M+H]^+$; tR: 1.13 min (LC/MS-method A)

Analogously to example 76 were prepared:

| Ex. | amine | structure | LCMS m/z; tR; (yield) | Name |
|---|---|---|---|---|
| 77 | 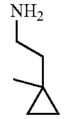 HCl | 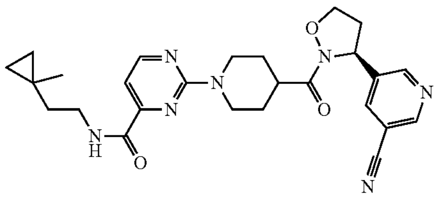 [SMILES: CC1(CCNC(=O)c2ccnc(N3CCC(C(=O)N4OCC[C@H]4c4cncc(C#N)c4)CC3)n2)CC1] | 490.4 $[M + H]^+$ 2.17 min (7 mg, 27%) | 2-[4-[(3S)-3-(5-cyano-3-pyridyl) isoxazolidine-2-carbonyl]-1-piperidyl]-N-[2-(1-methylcyclo-propyl)ethyl]pyrimidine-4-carboxamide |
| 78 | 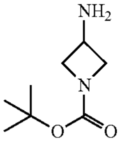 | 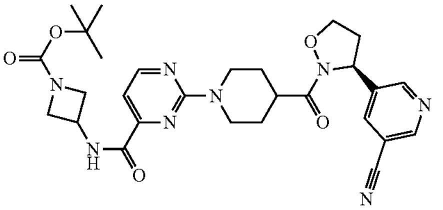 | 577.5 $[M + H]^+$ 2.06 min (23 mg, 33%) | tert-butyl 3-[2-[4-[(3S)-3-(5-cyano-3-pyridyl)isoxazolidine-2-carbonyl]-1-piperidyl] pyrimidine-4-carbonyllamino] azetidine-1-carboxylate |

Ex. 079

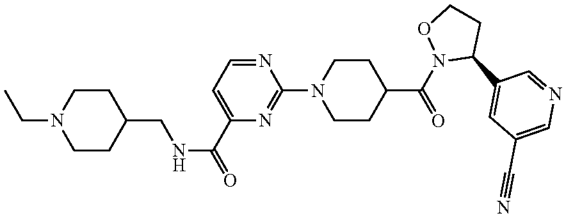

2-[4-[(3S)-3-(5-Cyano-3-pyridyl)isoxazolidine-2-carbonyl]-1-piperidyl]-N-[(1-ethyl-4-piperidyl)methyl]pyrimidine-4-carboxamide 2-[4-[(3S)-3-(5-Cyano-3-pyridyl)isoxazolidine-2-carbonyl]-1-piperidyl]pyrimidine-4-carboxylic acid (ex. 102, 20 mg) was dissolved in dry DCM (3 ml) under Ar. A catalytic amount of dry DMF (50 μl) was added and the mixture cooled to 0° C. Then thionyl chloride (10 μl) dissolved in dry DCM (0.5 ml) was added with stirring. After 1.5 h further thionyl chloride (25 μl in 0.3 ml dry DCM) was added, followed by additional thionyl chloride (15 μl in 0.3 ml dry DCM) 1.5 h later. After 1 h the mixture was concentrated in vacuo and the residue was dissolved in dry DCM (2 ml) and cooled to 0° C. To this solution was added to a mixture of (1-ethylpiperidin-4-yl)methanamine (7 mg) and DIPEA (30 μl) dissolved in dry DCM (3 ml) under Ar with stirring at 0° C. After the addition the ice bath was removed and stirring continued for 10 min. Then sat. $NaHCO_3$ solution was added and the aqueous phase was extracted with DCM (3×). The combined organic phases were dried over sodium sulphate, filtered and concentrated in vacuo. The residue was purified by preparative RP HPLC (flow: 25 ml/min; gradient: 95% $H_2O$+0.05% TFA/5% ACN in 45 min to 5% $H_2O$+0.05% TFA/95% ACN; column: Purosphere® STAR-RP18, 25×250 mm, 10 μm), the pure product containing fractions were combined and the ACN was removed in vacuo. The aqueous solution was lyophilised to yield 11 mg of the title compound.

LC/MS: m/z=533.5 $[M+H]^+$; tR: 1.26 min (LC/MS-method A)

Ex. 080

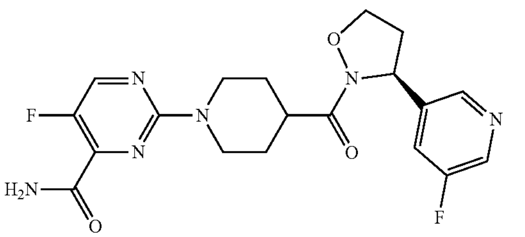

5-Fluoro-2-[4-[(3S)-3-(5-fluoro-3-pyridyl)isoxazolidine-2-carbonyl]-1- piperidyl]pyrimidine-4-carboxamide 1-(4-Carbamoyl-5-fluoro-pyrimidin-2-yl)piperidine-4-carboxylic acid (I-34, 21 mg) was dissolved in dry DMF (3 ml). DIPEA (70 μl) and HATU (45 mg) were added with stirring. After 10 min (3S)-3-(5-fluoro-3-pyridyl)isoxazolidine HCl salt (I-14-2, 21 mg) was added and stirring was continued for 1 h. Then saturated sodium bicarbonate solution was added and the aqueous phase was extracted with EA (2×). The combined organic phases were washed with brine, dried over sodium sulphate, filtered and concentrated in vacuo. The residue was purified by silica gel chromatography (12 g $SiO_2$, 100% DCM to 90% DCM/10% ethanol in 30 min). The pure product containing fractions were combined and the solvent was removed in vacuo. The residue was dissolved in ACN/water and lyophilised overnight. The residue was further purified by RP-HPLC (flow 40 ml/min, 97% $H_2O$/3% ACN to 10% $H_2O$/90% ACN in 15 min; Agilent Prep C18—μm, 30×100 mm). The pure product containing fractions were combined, the ACN was removed in vacuo and the aqueous phase was lyophilised to yield 14 mg of the title compound.

LC/MS: m/z=419.3 $[M+H]^+$; tR: 1.51 min (LC/MS-method A)

$^1$H NMR (600.05 MHz, DMSO-$d_6$) δ ppm 8.54 (1H), 8.49 (1H), 8.41 (1H), 8.09 (1H), 7.78 (1H), 7.60 (1H), 5.42 (1H), 4.61 (2H), 4.32 (1H), 3.95 (1H), 3.02 (3H), 2.92 (1H), 2.28 (1H), 1.92 (1H), 1.74 (1H), 1.51 (2H)

Ex. 081

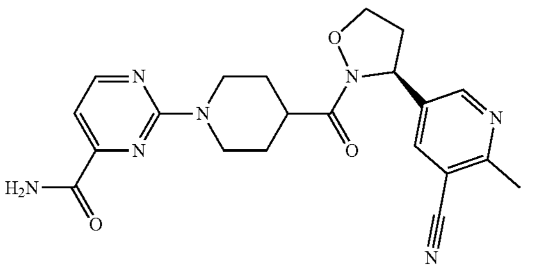

2-[4-[(3S)-3-(5-Cyano-6-methyl-3-pyridyl)isoxazolidine-2-carbonyl]-1-piperidyl]pyrimidine-4-carboxamide 1-(4-Carbamoylpyrimidin-2-yl)piperidine-4-carboxylic acid hydrochloride salt (I-22, 28 mg) was dissolved in dry DMF (3.5 ml). DIPEA (60 μl) and 5-[(3S)-isoxazolidin-3-yl]-2-methyl-pyridine-3-carbonitrile HCl salt (I-18, 20 mg) were added with stirring. After 10 min HATU (67 mg) was added with stirring. After standing overnight saturated sodium bicarbonate solution was added and the aqueous phase was extracted with EA (3×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 8 mg of the title compound.

LC/MS: m/z=422.3 $[M+H]^+$; tR: 1.53 min (LC/MS-method A)

$^1$H NMR (600.05 MHz, DMSO-$d_6$) δ ppm 8.64 (1H), 8.54 (1H), 8.14 (1H), 8.12 (1 H), 7.70 (1H), 7.07 (1H), 5.40 (1H), 4.77 (2H), 4.32 (1H), 3.96 (1H), 3.04 (3H), 2.90 (1H), 2.66 (3H), 2.30 (1H), 1.91 (1H), 1.75 (1H), 1.49 (2H)

Ex. 082

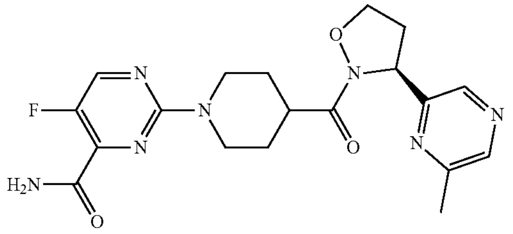

5-Fluoro-2-[4-[(3S)-3-(6-methylpyrazin-2-yl)isoxazolidine-2-carbonyl]-1-piperidyl]pyrimidine-4-carboxamide 1-(4-Carbamoyl-5-fluoro-pyrimidin-2-yl)piperidine-4-carboxylic acid (I-34, 20 mg) was dissolved in dry DMF (2 ml). DIPEA (70 μl) and (3S)-3-(6-methylpyrazin-2-yl)isoxazolidine hydrochloride salt (I-12, 17 mg) were added with stirring. After 10 min HATU (43 mg) was added and stirring was continued for 5 h. Saturated sodium bicarbonate solution was added and the aqueous phase was extracted with EA (3×). The combined organic phases were washed with brine, dried over sodium sulphate, filtered and concentrated in vacuo. The residue was purified by silica gel chromatography (12 g $SiO_2$, 100% DCM to 90% DCM/10% ethanol in 30 min). The pure product containing fractions were combined and the solvent was removed in vacuo. The residue was dissolved in ACN/water and lyophilised overnight. The residue was further purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 18 mg of the title compound.

LC/MS: m/z=416.3 $[M+H]^+$; tR: 1.43 min (LC/MS-method A)

$^1$H NMR (600.05 MHz, DMSO-$d_6$) δ ppm 8.54 (1H), 8.49 (1H), 8.41 (1H), 8.09 (1H), 7.78 (1H), 7.60 (1H), 5.42 (1H), 4.61 (2H), 4.32 (1H), 3.95 (1H), 3.02 (3H), 2.92 (1H), 2.28 (1H), 1.92 (1H), 1.74 (1H), 1.51 (2H)

Ex. 083

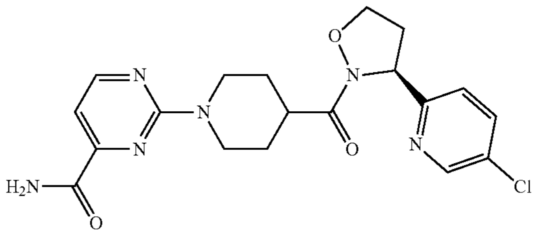

2-[4-[(3S)-3-(5-Chloro-2-pyridyl)isoxazolidine-2-carbonyl]-1-piperidyl]pyrimidine-4-carboxamide 1-(4-Carbamoylpyrimidin-2-yl)piperidine-4-carboxylic acid hydrochloride salt (I-22, 24 mg) was dissolved in dry DMF (1.5 ml). DIPEA (51 μl) and (3S)-3-(5-chloro-2-pyridyl)isoxazolidine TFA salt (I-19, 30 mg dissolved in DMF (1 ml)) were added with stirring. After 15 min HATU (56 mg) was added and stirring was continued. After standing overnight saturated sodium bicarbonate solution and water were added and the aqueous phase was extracted with EA (3×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined and the solvent was removed in vacuo. The residue was dissolved in ACN/water and lyophilised overnight. The pure product containing fractions were combined and the ACN was removed in vacuo and the aqueous phase was lyophilised to yield 20 mg of the title compound.

LC/MS: m/z=417.3 $[M+H]^+$; tR: 1.69 min (LC/MS-method A)

Ex. 084

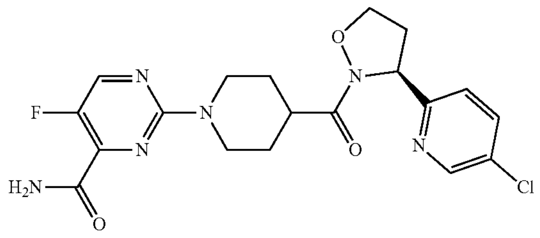

2-[4-[(3S)-3-(5-Chloro-2-pyridyl)isoxazolidine-2-carbonyl]-1- piperidyl]-5-fluoro-pyrimidine-4-carboxamide 1-(4-Carbamoyl-5-fluoro-pyrimidin-2-yl)piperidine-4-carboxylic acid (I-34, 24 mg) was dissolved in dry DMF (1.5 ml). DIPEA (51 μl) and (3S)-3-(5-chloro-2-pyridyl)isoxazolidine TFA salt (I-19, 30 mg dissolved in DMF (1 ml)) were added with stirring. After 15 min HATU (56 mg) was added and stirring was continued. After standing overnight saturated sodium bicarbonate solution and water were added and the aqueous phase was extracted with EA (3×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined and the solvent was removed in vacuo. The residue was dissolved in ACN/water and lyophilised overnight to yield 22 mg of the title compound.

LC/MS: m/z=435.3 $[M+H]^+$; tR: 1.73 min (LC/MS-method A)

Ex. 085

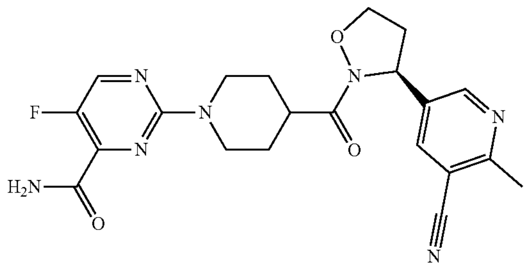

2-[4-[(3S)-3-(5-Cyano-6-methyl-3-pyridyl)isoxazolidine-2-carbonyl]-1-piperidyl]-5-fluoro-pyrimidine-4-carboxamide 1-(4-Carbamoyl-5-fluoro-pyrimidin-2-yl)piperidine-4-carboxylic acid (I-34, 20 mg) was dissolved in dry DMF (2 ml). DIPEA (70 μl) and 5-[(3S)-isoxazolidin-3-yl]-2-methyl-pyridine-3-carbonitrile HCl salt (I-18, 19 mg) were added with stirring. After 10 min HATU (43 mg) was added and stirring was continued. After standing overnight saturated sodium bicarbonate solution was added and the aqueous phase was extracted with EA (3×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined and the ACN was removed in vacuo and the aqueous phase was lyophilised to yield 24 mg of the title compound.

LC/MS: m/z=440.3 $[M+H]^+$; tR: 1.57 min (LC/MS-method A)

Ex. 086

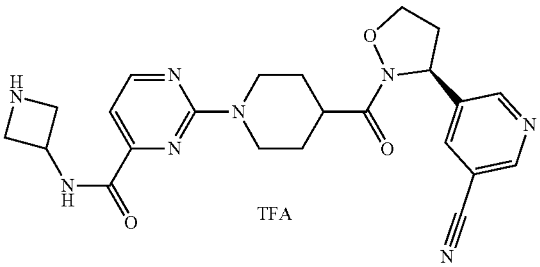

N-(Azetidin-3-yl)-2-[4-[(3S)-3-(5-cyano-3-pyridyl)isoxazolidine-2-carbonyl]-1-piperidyl]pyrimidine-4-carboxamide TFA salt Tert-butyl 3-[[2-[4-[(3S)-3-(5-cyano-3-pyridyl)isoxazolidine-2-carbonyl]-1-piperidyl]pyrimidine-4-carbonyl]amino]azetidine-1-carboxylate (ex. 78, 32 mg) was dissolved in TFA (1.9 ml) and water (100 μl) was added with stirring. After 1 h the mixture was concentrated in vacuo. The residue was purified by preparative RP HPLC (flow: 25 ml/min; gradient: 95% $H_2O$+0.05% TFA/5% ACN in 45 min to 5% $H_2O$+0.05% TFA/95% ACN; column: Purosphere® STAR-RP18, 25×250 mm, 10 μm), the pure product containing fractions were combined and the ACN was removed in vacuo. The aqueous solution was lyophilised to yield 27 mg of the title compound.

LC/MS: m/z=477.4 $[M+H]^+$; tR: 1.13 min (LC/MS-method A)

Ex. 087

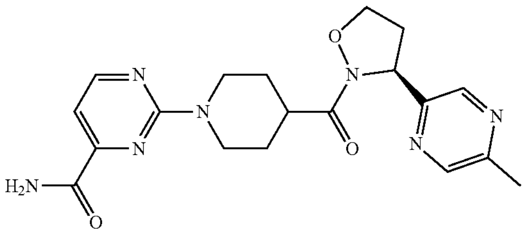

2-[4-[(3S)-3-(5-Methylpyrazin-2-yl)isoxazolidine-2-carbonyl]-1-piperidyl]pyrimidine-4-carboxamide 1-(4-Carbamoylpyrimidin-2-yl)piperidine-4-carboxylic acid hydrochloride salt (I-22, 23 mg) was dissolved in dry DMF (3 ml). DIPEA (51 μl) and (3S)-3-(5-methylpyrazin-2-yl)isoxazolidine HCl salt (I-20, 15 mg) were added with stirring. After 10 min HATU (57 mg) was added and stirring was continued. After standing overnight saturated sodium bicarbonate solution was added and the aqueous phase was extracted with EA (3×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined and the ACN was removed in vacuo and the aqueous phase was lyophilised to yield 12 mg of the title compound.

LC/MS: m/z=398.3 $[M+H]^+$; tR: 1.38 min (LC/MS-method A)

Ex. 088

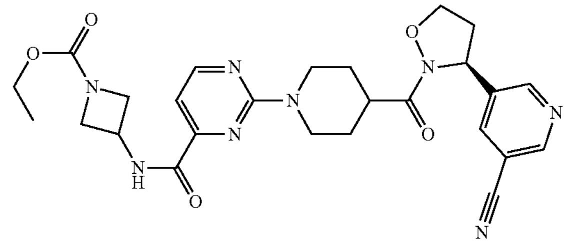

Ethyl 3-[[2-[4-[(3S)-3-(5-cyano-3-pyridyl)isoxazolidine-2-carbonyl]-1-piperidyl]pyrimidine-4-carbonyl]amino]azetidine-1-carboxylate N-(Azetidin-3-yl)-2-[4-[(3S)-3-(5-cyano-3-pyridyl) isoxazolidine-2-carbonyl]-1-piperidyl]pyrimidine-4-carboxamide TFA salt (ex. 86, 20 mg) was dissolved in THF (3 ml). DIPEA (30 μl) was added and the mixture was cooled to 0° C. Then ethyl chloroformate (3.9 mg) was added with stirring. After 15 min the mixture was poured onto saturated sodium bicarbonate solution and the aqueous phase was extracted with EA (2×). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure and impure product containing fractions were combined separately, the ACN was removed in vacuo and the aqueous phases were lyophilised. The impure product containing fractions were further purified by silica gel chromatography (4 g $SiO_2$, 100% DCM for 5 min; then from 100% DCM to 94% DCM/6% ethanol in 25 min followed by 94% DCM/6% ethanol for 10 min). The pure fractions were combined and concentrated. The residue was dissolved in ACN/water, combined with the pure residue from the HPLC separation and lyophilised to yield 7 mg of the title compound.

LC/MS: m/z=549.4 $[M+H]^+$; tR: 1.81 min (LC/MS-method A)

Ex. 089*

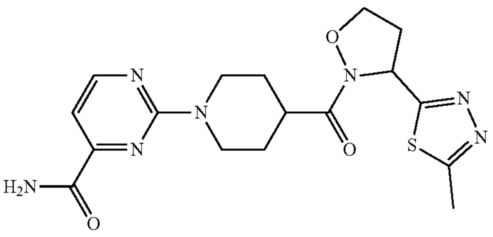

2-[4-[3-(5-Methyl-1,3,4-thiadiazol-2-yl)isoxazolidine-2-carbonyl]-1-piperidyl]pyrimidine-4-carboxamide 1-(4-Carbamoylpyrimidin-2-yl)piperidine-4-carboxylic acid (I-22-1, 22 mg) was dissolved in DMF (2 ml) before DIPEA (77 μl) and HATU (40 mg) were added with stirring. After 5 min 3-(5-methyl-1,3,4-thiadiazol-2-yl)isoxazolidine TFA salt (I-21, 34.5 mg) was added as solution in DMF (1 ml) and stirring was continued for 24 h. The solution was purified by preparative RP HPLC preparative HPLC (120 ml/min, 95% $H_2O$/5% ACN to 5% $H_2O$/95% ACN in 13 min; Waters Sunfire Prep C18 OBD—5 μm, 50×100 mm). The pure product containing fractions were combined and the ACN was removed in vacuo. The aqueous solution was lyophilised to yield 6.7 mg of the title compound (purity ca. 70%).

LC/MS: m/z=404.3 $[M+H]^+$; tR: 1.35 min (LC/MS-method A)

$^1H$ NMR (600.05 MHz, DMSO-$d_6$) δ ppm 8.55 (1H), 8.15 (1H), 7.71 (1H), 7.08 (1H), 5.73 (1H), 4.75 (1H), 4.72 (1H), 4.33 (1H), 3.99 (1H), 3.05 (3H), 2.89 (1H), 2.71 (1H), 2.68 (3H), 1.87 (1H), 1.75 (1H), 1.51 (2H), 1.49 (1H).

Analogously to example 87 were prepared:

| Ex. | acid | structure | LCMS m/z; tR; (yield) | Name |
|---|---|---|---|---|
| 90 | 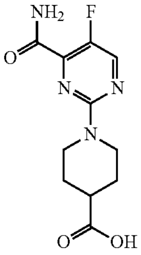 [SMILES: NC(=O)c1nc(N2CCC(C(=O)O)CC2)ncc1F] I-34 | 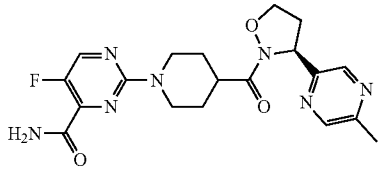 [SMILES: Cc1cnc([C@@H]2CCON2C(=O)C2CCN(c3ncc(F)c(C(N)=O)n3)CC2)cn1] | 416.3 [M + H]$^+$ 1.41 min (13 mg, 43%) | 5-fluoro-2-[4-[(3S)-3-(5-methylpyrazin-2-yl)isoxazolidine-2-carbonyl]-1-piperidyl]pyrimidine-4-carboxamide |
| 91 | 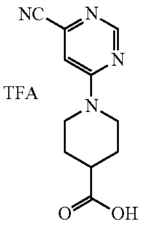 [SMILES: N#Cc1cc(N2CCC(C(=O)O)CC2)ncn1] TFA I-39-1 | 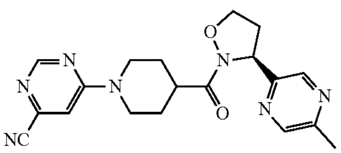 [SMILES: Cc1cnc([C@@H]2CCON2C(=O)C2CCN(c3cc(C#N)ncn3)CC2)cn1] | 380.3 [M + H]$^+$ 1.49 min (10 mg, 35%) | 6-[4-[(3S)-3-(5-methylpyrazin-2-yl)isoxazolidine-2-carbonyl]-1-piperidyl]pyrimidine-4-carbonitrile |

Ex. 092

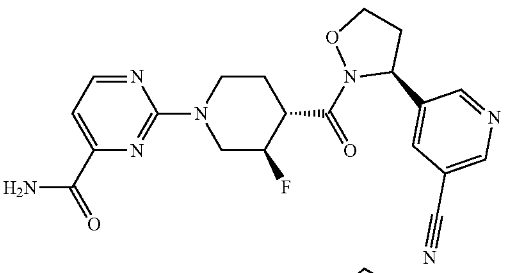

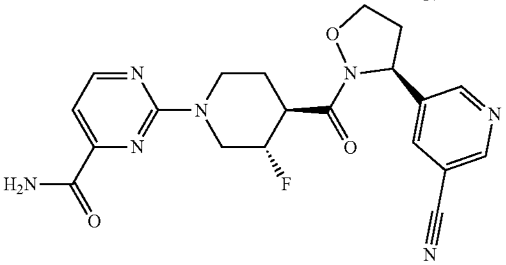

2-[(3R,4R)-4-[(3S)-3-(5-Cyano-3-pyridyl)isoxazolidine-2-carbonyl]-3-fluoro-1-piperidyl]pyrimidine-4-carboxamide and 2-[(3S,4S)-4-[(3S)-3-(5-cyano-3-pyridyl)isoxazolidine-2-carbonyl]-3-fluoro-1-piperidyl]pyrimidine-4-carboxamide (~1:1 mixture)

A mixture of 2-chloropyrimidine-4-carboxamide (92 mg), DIPEA (367 mg), 5-[(3S)-2-[(3R,4R)-3-fluoropiperidine-4-carbonyl]isoxazolidin-3-yl]pyridine-3-carbonitrile and 5-[(3S)-2-[(3S,4S)-3-fluoropiperidine-4-carbonyl]isoxazolidin-3-yl]pyridine-3-carbonitrile (I-37, ~1:1 mixture, compound with 4-methylbenzenesulfonic acid, 173 mg, crude), and DMF (2 ml) was heated at 80° C. for 2 h. The mixture was allowed to cool to room temperature and purified by preparative RP HPLC (Column: Waters SunFire Prep C18 OBD, 5 µm, 50 mm×100 mm; mobile phase: water/ACN 95:5 (0.0 min) to 95:5 (2.0 min) to 90:10 (2.5 min) to 5:95 (10.5 min) to 1:99 (11.5 min) to 1:99 (13.0 min) to 95:5 (13.5 min) to 95:5 (14.9 min); flow rate: 120 ml/min), the pure product containing fractions were combined and the ACN was removed in vacuo. The aqueous solution was lyophilised to yield 53 mg of the title compounds.

LC/MS: m/z=426.32 [M+H]$^+$; tR: 1.47 min (LC/MS-method A)

Ex. 093/94

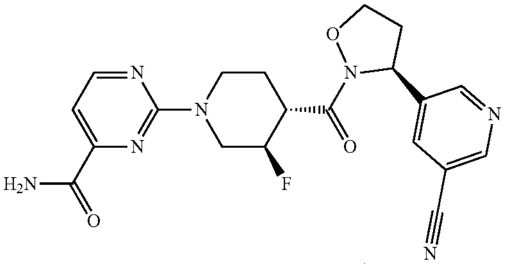

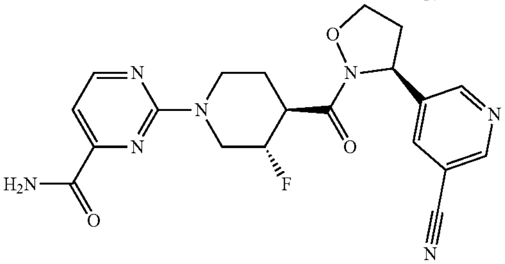

2-[(3R,4R)-4-[(3S)-3-(5-Cyano-3-pyridyl)isoxazolidine-2-carbonyl]-3-fluoro-1-piperidyl]pyrimidine-4-carboxamide (Isomer 1, 3R,4R stereochemistry arbitrarily assigned) and 2-[(3S,4S)-4-[(3S)-3-(5-Cyano-3-pyridyl)isoxazolidine-2-carbonyl]-3-fluoro-1-piperidyl]pyrimidine-4-carboxamide (Isomer 2, 3S,4S stereochemistry arbitrarily assigned)

A sample of 2-[(3R,4R)-4-[(3S)-3-(5-cyano-3-pyridyl)isoxazolidine-2-carbonyl]-3-fluoro-1-piperidyl]pyrimidine-4-carboxamide and 2-[(3S,4S)-4-[(3S)-3-(5-cyano-3-pyridyl)isoxazolidine-2-carbonyl]-3-fluoro-1-piperidyl]pyrimidine-4-carboxamide (ex. 92, ~1:1 mixture, 48 mg) was separated by preparative HPLC (flow rate 1.0 ml/min, temperature 30° C., column Chiralpak IC/130, 250×4.6 mm, eluent n-heptane:EtOH MeOH 1:33) to yield 24 mg of Isomer 1 and 18 mg of Isomer 2.

Isomer1

Chiral analytical HPLC (flow rate 1.0 ml/min, temperature 30° C., column Chiralpak IC/130, 250×4.6 mm, eluent n-heptane:EtOH:MeOH 1:33) tR: 10.6 min LC/MS: m/z=426.3 $[M+H]^+$, tR: 1.47 min (LC/MS-method A)

$^1$H NMR (600.05 MHz, DMSO-$d_6$) δ ppm 8.95 (1H), 8.80 (1H), 8.58 (1H), 8.27 (1H), 8.23 (1H), 7.73 (1H), 7.14 (1H), 5.51 (1H), 4.99 (1H), 4.70 (1H), 4.61 (1H), 4.36 (1H), 3.91 (1H), 3.16 (1H), 2.95 (1H), 2.35 (1H), 2.09 (1H), 1.56 (1H). Only signals not overlaying with solvent/water are reported.

Isomer2

Chiral analytical HPLC (flow rate 1.0 ml/min, temperature 30° C., column Chiralpak IC/130, 250×4.6 mm, eluent n-heptane:EtOH:MeOH 1:3:3) tR: 13.4 min LC/MS: m/z=426.3 $[M+H]^+$; tR: 1.46 min (LC/MS-method A)

$^1$H NMR (600.05 MHz, DMSO-$d_6$) δ ppm 8.96 (1H), 8.79 (1H), 8.58 (1H), 8.27 (1H), 8.20 (1H), 7.73 (1H), 7.15 (1H), 5.48 (1H), 4.95 (1H), 4.70 (1H), 4.62 (1H), 4.36 (1H), 4.03 (1H), 3.17 (1H), 2.95 (1H), 2.36 (1H), 1.96 (1H), 1.53 (1H). Only signals not overlaying with solvent/water are reported.

Ex. 095/96

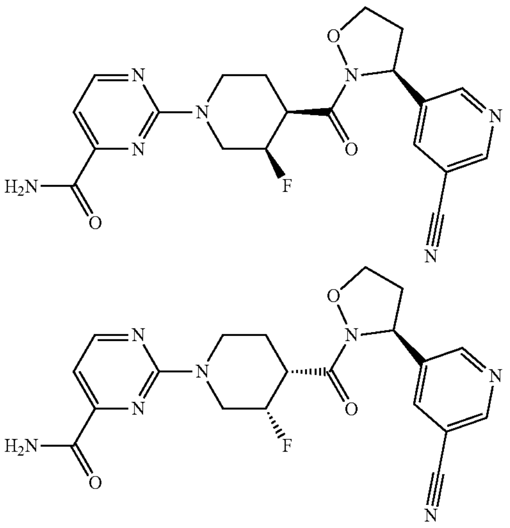

2-[(3R,4S)-4-[(3S)-3-(5-Cyano-3-pyridyl)isoxazolidine-2-carbonyl]-3-fluoro-1-piperidyl]pyrimidine-4-carboxamide (Isomer 1, 3R,4S stereochemistry arbitrarily assigned) and 2-[(3S,4R)-4-[(3S)-3-(5-cyano-3-pyridyl)isoxazolidine-2-carbonyl]-3-fluoro-1-piperidyl]pyrimidine-4-carboxamide (Isomer 2, 3S,4R stereochemistry arbitrarily assigned)

In analogy to the procedures described for examples 092/093/094 2-[(3R,4S)-4-[(3S)-3-(5-cyano-3-pyridyl)isoxazolidine-2-carbonyl]-3-fluoro-1-piperidyl]pyrimidine-4-carboxamide (Isomer 1, 3R,4S stereochemistry arbitrarily assigned) and 2-[(3S,4R)-4-[(3S)-3-(5-cyano-3-pyridyl)isoxazolidine-2-carbonyl]-3-fluoro-1-piperidyl]pyrimidine-4-carboxamide (Isomer 2, 3S,4R stereochemistry arbitrarily assigned) were synthesised starting with 5-[(3S)-isoxazolidin-3-yl]pyridine-3-carbonitrile (compound with 4-methylbenzenesulfonic acid) and (3,4-cis)-1-tert-butoxycarbonyl-3-fluoro-piperidine-4-carboxylic acid.

Final HPLC separation of isomers (flow rate 1.0 ml/min, temperature 30° C., column Chiralpak IC/130, 250×4.6 mm, eluent EtOH:MeOH 1:1) provided 3 mg of Isomer 1 and 6 mg of Isomer 2.

Isomer1:

Chiral analytical HPLC (flow rate 1.0 ml/min, temperature 30° C., column Chiralpak IC/130, 250×4.6 mm, eluent EtOH:MeOH 1:1) tR: 9.0 min LC/MS: m/z=426.32 $[M+H]^+$; tR: 1.34 min (LC/MS-method A)

$^1$H NMR (600.05 MHz, DMSO-$d_6$) δ ppm 8.95 (1H), 8.78 (1H), 8.55 (1H), 8.17 (2H), 7.73 (1H), 7.10 (1H), 5.48 (1H), 5.31 (1H), 5.19 (1H), 4.94 (1H), 4.33 (1H), 4.03 (1H), 3.22 (1H), 2.96 (2H), 2.32 (1H), 1.91 (1H), 1.64 (1H). Only signals not overlaying with solvent/water are reported.

Isomer2:

Chiral analytical HPLC (flow rate 1.0 ml/min, temperature 30° C., column Chiralpak IC/130, 250×4.6 mm, eluent EtOH MeOH 1:1) tR: 12.9 min LC/MS: m/z=426.32 $[M+H]^+$; tR: 1.35 min (LC/MS-method A)

$^1$H NMR (600.05 MHz, DMSO-$d_6$) δ ppm 8.95 (1H), 8.82 (1H), 8.55 (1H), 8.25 (1H), 8.19 (1H), 7.72 (1H), 7.10 (1H), 5.46 (1H), 5.21-5.09 (2H), 4.88 (1H), 4.36 (1H), 4.02 (1H), 3.23 (1H), 3.05 (1H), 2.96 (1H), 2.35 (1H), 1.94 (1H), 1.73 (1H).

Only signals not overlaying with solvent/water are reported.

Ex. 097

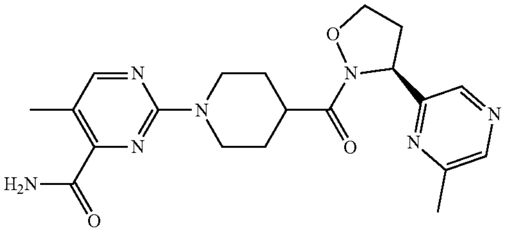

5-Methyl-2-[4-[(3S)-3-(6-methylpyrazin-2-yl)isoxazolidine-2-carbonyl]-1-piperidyl]pyrimidine-4-carboxamide 1-(4-Carbamoyl-5-methyl-pyrimidin-2-yl)piperidine-4-carboxylic acid TFA salt (I-36, 30 mg) was dissolved in dry DMF (2 ml). DIPEA (33 μl) and (3S)-3-(6-methylpyrazin-2-yl)isoxazolidine hydrochloride salt (I-12, 33 mg) were added with stirring. After 15 min HATU (60 mg) was added and stirring was continued for 45 min. Then the mixture was directly purified by RP prep-HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilised. The residue was further purified by silica gel chromatography (4 g $SiO_2$, 100% DCM to 90% DCM/10% ethanol in 35 min). The pure product containing fractions were combined and the solvent was removed in vacuo. The residue was dissolved in ACN/water and lyophilised overnight to yield 16 mg of the title compound.

LC/MS: m/z=412.4 $[M+H]^+$; tR: 1.50 min (LC/MS-method A)

$^1H$ NMR (600.05 MHz, DMSO-$d_6$) δ ppm 8.46 (1H), 8.37 (1H), 8.32 (1H), 7.98 (1 H), 7.56 (1H), 5.38 (1H), 4.65 (2H), 4.33 (1H), 3.98 (1H), 3.29 (1H), 3.03 (1H), 2.98 (2H), 2.83 (1H), 2.50 (3H+DMSO), 2.25 (3H), 1.87 (1H), 1.73 (1H), 1.48 (2H)

Ex. 098

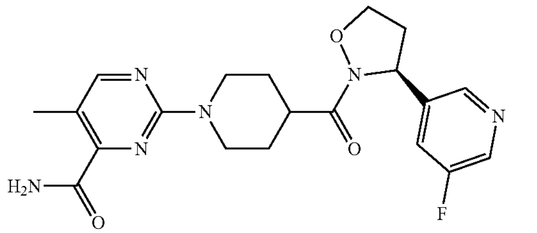

2-[4-[(3S)-3-(5-Fluoro-3-pyridyl)isoxazolidine-2-carbonyl]-1-piperidyl]-5-methyl-pyrimidine-4-carboxamide 1-(4-Carbamoyl-5-methyl-pyrimidin-2-yl)piperidine-4-carboxylic acid TFA salt (I-36, 28 mg) was dissolved in dry DMF (1.5 ml). DIPEA (52 μl) and (3S)-3-(5-fluoro-3-pyridyl)isoxazolidine HCl salt (I-14-2, 15 mg) were added with stirring. After 15 min HATU (57 mg) was added and stirring was continued for 2 h. After standing overnight saturated sodium bicarbonate solution was added and the aqueous phase was extracted with EA (3x). The combined organic phases were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The pure product containing fractions were combined, the ACN was removed in vacuo and the aqueous phase was lyophilised to yield 13 mg of the title compound.

LC/MS: m/z=415.4 $[M+H]^+$; tR: 1.58 min (LC/MS-method A)

$^1H$ NMR (600.05 MHz, DMSO-$d_6$) δ ppm 8.49 (1H), 8.41 (1H), 8.32 (1H), 7.98 (1H), 7.60 (1H), 7.56 (1H), 5.42 (1H), 4.66 (2H), 4.32 (1H), 3.95 (1H), 3.05 (1H), 3.02-2.90 (3H), 2.29 (1H), 2.25 (3H), 1.90 (1H), 1.73 (1H), 1.49 (2H)

Ex. 99

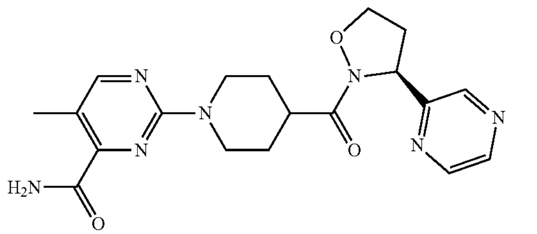

5-Methyl-2-[4-[(3S)-3-pyrazin-2-ylisoxazolidine-2-carbonyl]-1-piperidyl]pyrimidine-4-carboxamide 1-(4-Carbamoyl-5-methyl-pyrimidin-2-yl)piperidine-4-carboxylic acid TFA salt (I-36, 30 mg) was dissolved in dry DMF (2 ml). DIPEA (33 μl) and (3S)-3-pyrazin-2-ylisoxazolidine hydrochloride salt (I-17, 32 mg) were added with stirring. After 15 min HATU (60 mg) was added and stirring was continued for 45 min. Then the mixture was directly purified by RP HPLC (flow 40 ml/min, 97% $H_2O$/3% ACN to 10% $H_2O$/90% ACN in 15 min; Agilent Prep C18—5 μm, 30×100 mm). The product containing fractions were combined and the ACN was removed in vacuo and the aqueous phase was lyophilised. The residue was further purified by silica gel chromatography (4 g $SiO_2$, 100% DCM to 90% DCM/10% ethanol in 35 min). The pure product containing fractions were combined and the solvent was removed in vacuo. The residue was dissolved in ACN/water and lyophilised overnight to yield 11 mg of the title compound.

LC/MS: m/z=398.4 $[M+H]^+$; tR: 1.38 min (LC/MS-method A)

Ex. 100

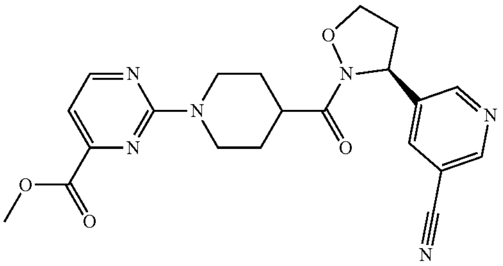

Methyl 2-[4-[(3S)-3-(5-cyano-3-pyridyl)isoxazolidine-2-carbonyl]-1-piperidyl]pyrimidine-4-carboxylate 5-[(3S)-2-(Piperidine-4-carbonyl)isoxazolidin-3-yl]pyridine-3-carbonitrile trifluoro acetic acid salt (I-28, 273 mg) was dissolved in acetonitrile (4.5 ml) in a microwave vessel. Then methyl 2-chloropyrimidine-4-carboxylate (107 mg) and DIPEA (430 μl) were added. The solution was heated in a microwave oven for 30 min at 80° C. After cooling the solution was concentrated in vacuo. The residue was purified by silica gel chromatography (12 g $SiO_2$, 100% DCM for 5 min; then 100% DCM to 90% DCM/10% EtOH in 40 min; 90% DCM/10% EtOH continued for 10 min). The pure compound containing fractions were combined and concentrated in vacuo to yield 243 mg of the title compound.

LC/MS: m/z=423.4 $[M+H]^+$; tR: 1.76 min (LC/MS-method A)

Ex. 101

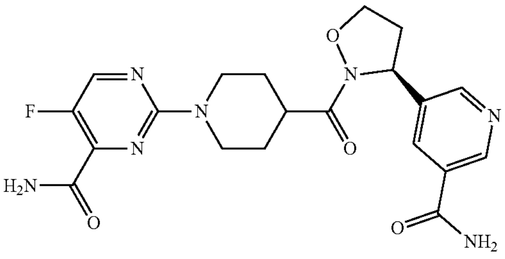

2-[4-[(3S)-3-(5-Carbamoyl-3-pyridyl)isoxazolidine-2-carbonyl]-1-piperidyl]-5-fluoro-pyrimidine-4-carboxamide (S)-2-(4-(3-(5-Cyanopyridin-3-yl)isoxazolidine-2-carbonyl)piperidin-1-yl)-5-fluoropyrimidine-4-carboxamide (example 068, 17 mg) was dissolved in dry THF (2.5 ml). Lithium hydroxide (2 mg) was added and then water was added until the lithium hydroxide was dissolved completely. The mixture was stirred at RT for 45 min. After stirring for 1.5 h at 50° C. the mixture was concentrated in vacuo. The residue was mixed with water and 1 N HCl and then purified by preparative RP HPLC (flow 25 ml/min; from 95% $H_2O$+0.05% TFA/5% ACN to 5% $H_2O$+0.05% TFA/95% ACN 45 min.; Purosphere® STAR-RP18, 25×250 mm, 10 μm). The product containing fractions were combined and the ACN was removed in vacuo. The aqueous solution was lyophilised overnight. The residue was further purified by silica gel chromatography (4 g $SiO_2$, 100% DCM to 40% DCM/60% ethanol in 40 min). The pure product containing fractions were combined and concentrated. The residue was dissolved in ACN/Water and lyophilized to yield 5 mg of the title compound.

LC/MS: m/z=444.3 $[M+H]^+$; tR: 1.17 min (LC/MS-method A)

Ex. 102

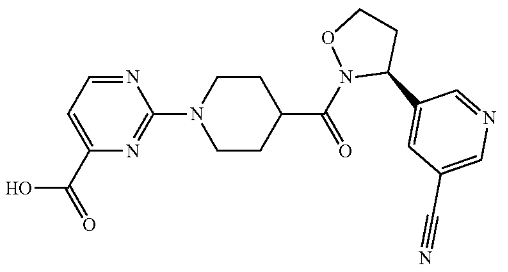

2-[4-[(3S)-3-(5-Cyano-3-pyridyl)isoxazolidine-2-carbonyl]-1-piperidyl]pyrimidine-4-carboxylic acid Methyl 2-[4-[(3S)-3-(5-cyano-3-pyridyl)isoxazolidine-2-carbonyl]-1-piperidyl]pyrimidine-4-carboxylate (ex. 100, 241 mg) was dissolved in a mixture of THF/water (4:1, 5 ml) and LiOH (16 mg) was added with stirring. After 5 h further LiOH (0.5 eq.) was added. After standing overnight HCl solution (2 M, 0.34 ml) was added and the aqueous phase was extracted with EA (3×). The combined organic layers were dried over sodium sulphate, filtered and concentrated in vacuo to yield 227 mg of the crude product that was directly used without further purification.

LC/MS: m/z=409.3 $[M+H]^+$; tR: 1.41 min (LC/MS-method A)

Ex. 103

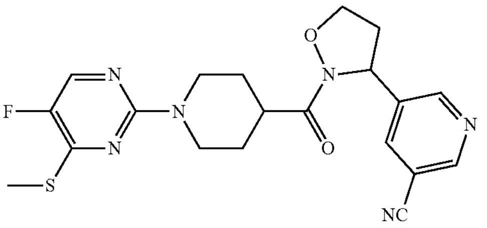

5-[(3S)-2-[1-(5-Fluoro-4-methylsulfanyl-pyrimidin-2-yl)piperidine-4-carbonyl]isoxazolidin-3-yl]pyridine-3-

(S)-5-(2-(Piperidine-4-carbonyl)isoxazolidin-3-yl)nicotinonitrile TFA salt (I-28, 100 mg) was dissolved in dry ACN (2.5 ml) in a microwave vessel (2-5 ml). After DIPEA (174 μl) and 2-chloro-5-fluoro-4-(methylsulfanyl)pyrimidine (49 mg) were added, the mixture was heated at 100° C. in a microwave oven for 2 h. After cooling the solvent was removed in vacuo. The residue was purified by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilised over night to yield 69 mg of the title compound.

LC/MS: m/z=429.3 $[M+H]^+$; tR: 2.23 min (LC/MS-method A)

Ex. 104

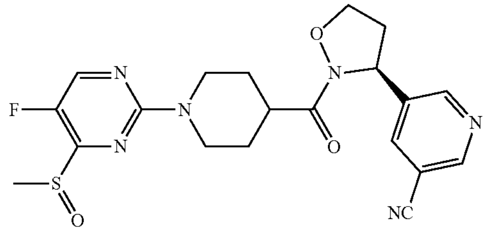

5-[(3S)-2-[1-(5-Fluoro-4-methylsulfinyl-pyrimidin-2-yl)piperidine-4-carbonyl]isoxazolidin-3-yl]pyridine-3-carbonitrile 5-[(3S)-2-[1-(5-Fluoro-4-methylsulfanyl-pyrimidin-2-yl)piperidine-4-carbonyl]isoxazolidin-3-yl]pyridine-3-carbonitrile (example 103, 20 mg) was dissolved under argon in dry DCM (1 ml). The mixture was cooled to 0° C. and 3-chloroperoxybenzoic acid (12 mg) was added in portions. The cooling bath was removed so that the mixture slowly reached RT. After stirring at RT for 1.5 h the reaction mixture was diluted with saturated $NaHCO_3$ solution and extracted with DCM (3×). The combined DCM layers were dried with $Na_2SO_4$, filtered and concentrated. The residue was purified by silica gel chromatography (4 g $SiO_2$, 100% DCM to 90% DCM/10% ethanol in 45 min). The pure product containing fractions were combined and concentrated in vacuo to yield 16 mg of the title compound.

LC/MS: m/z=445.3 $[M+H]^+$; tR: 1.52 min (LC/MS-method A)

Ex. 105

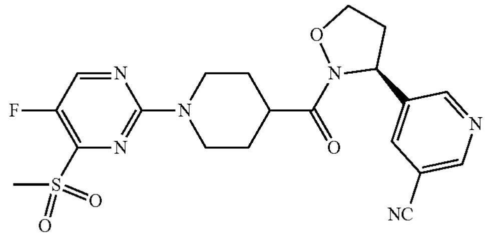

5-[(3S)-2-[1-(5-Fluoro-4-methylsulfonyl-pyrimidin-2-yl)piperidine-4-carbonyl[isoxazolidin-3-yl]pyridine-3-carbonitrile 5-[(3S)-2-[1-(5-Fluoro-4-methylsulfanyl-pyrimidin-2-yl)piperidine-4-carbonyl]isoxazolidin-3-yl]pyridine-3-carbonitrile (example 104, 45 mg) was dissolved under argon in dry DCM (3.5 ml). The mixture was cooled to 0° C. and 3-chloroperoxybenzoic acid (36 mg) was added in portions. The cooling bath was removed so that the mixture slowly reached RT. After stirring at RT for 3 h 3-chloroperoxybenzoic acid (36 mg) was added again at RT. After another hour of stirring at RT the reaction mixture was diluted with saturated $NaHCO_3$ solution and extracted with DCM (3×). The combined DCM layers were dried with $Na_2SO_4$, filtered and concentrated. The residue was purified by silica gel chromatography (4 g $SiO_2$, 100% DCM to 95% DCM/5% ethanol in 45 min). The pure product containing fractions were combined and concentrated to yield 24 mg of the title compound.

LC/MS: m/z=461.3 $[M+H]^+$; tR: 1.71 min (LC/MS-method A)

Ex. 106

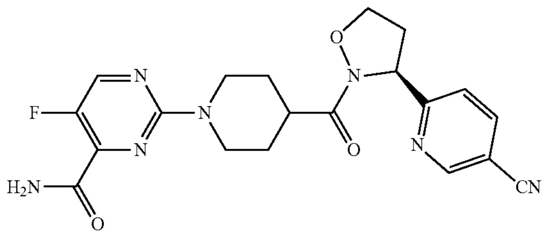

2-[4-[(3S)-3-(5-Cyano-2-pyridyl)isoxazolidine-2-carbonyl]-1-piperidyl]-5-fluoro-pyrimidine-4-carboxamide 1-(4-Carbamoyl-5-fluoro-pyrimidin-2-yl)piperidine-4-carboxylic acid (I-34, 20 mg) was dissolved in DMF (2 ml). DIPEA (50 µl) and 6-[(3S)-Isoxazolidin-3-yl]pyridine-3-carbonitrile hydrochloride salt (I-35, 17 mg) were added. After 10-15 min of stirring, HATU (43 mg) was added and stirring was continued for 30 min. The reaction mixture was diluted with half-saturated $NaHCO_3$ solution and extracted with EA (2×). The combined EA phases were washed with brine, dried with $Na_2SO_4$, filtered and concentrated. The residue was purified by preparative RP HPLC (flow 40 ml/min, 97% $H_2O$/3% ACN to 10% $H_2O$/90% ACN in 15 min; Agilent Prep C18—5 µm, 30×100 mm). The product containing fractions were combined, the ACN was removed in vacuo and the aqueous phase was lyophilised. The residue was further purified by silica gel chromatography (4 g $SiO_2$, 100% DCM for 5 min; from 100% DCM to 5% ethanol in 30 min; then 5% EtOH for 15 min). The pure product containing fractions were combined and concentrated in vacuo. The residue was dissolved in ACN/Water and lyophilised to yield 7 mg of the title compound.

LC/MS: m/z=426.4 $[M+H]^+$; tR: 1.52 min (LC/MS-method A)

Ex. 107

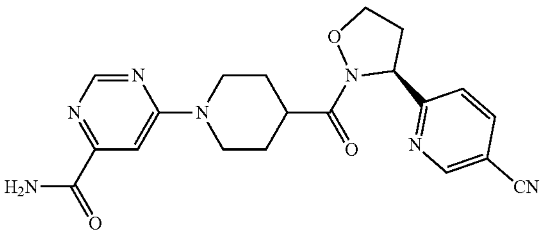

6-[4-[(3S)-3-(5-Cyano-2-pyridyl)isoxazolidine-2-carbonyl]-1-piperidyl]pyrimidine-4-carboxamide 1-(6-Carbamoylpyrimidin-4-yl)piperidine-4-carboxylic acid (I-38, 20 mg) was dissolved in DMF (2 ml). DIPEA (60 µl) and 6-[(3S)-Isoxazolidin-3-yl]pyridine-3-carbonitrile hydrochloride salt (I-35, 17 mg) were added. After 10-15 min of stirring, HATU (46 mg) was added and stirring was continued for 30 min. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 40 ml/min, 97% $H_2O$/3% ACN to 10% $H_2O$/90% ACN in 15 min; Agilent Prep C18—5 µm, 30×100 mm). The product containing fractions were combined, the ACN was removed in vacuo and the aqueous phase was lyophilised. The residue was further purified by silica gel chromatography (4 g $SiO_2$, 100% DCM for 5 min; from 100% DCM to 5% ethanol in 30 min; then 5% EtOH for 15 min). The pure product containing fractions were combined and concentrated in vacuo. The residue was dissolved in ACN/Water and lyophilised to yield 9 mg of the title compound.

LC/MS: m/z=408.4 $[M+H]^+$; tR: 1.24 min (LC/MS-method A)

Ex. 108

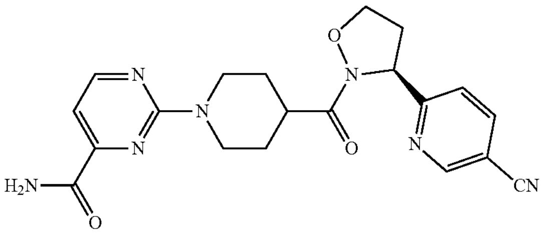

2-[4-[(3S)-3-(5-Cyano-2-pyridyl)isoxazolidine-2-carbonyl]-1-piperidyl]pyrimidine-4-carboxamide 1-(4-Carbamoylpyrimidin-2-yl)piperidine-4-carboxylic acid hydrochloride salt (I-22, 20 mg) was dissolved in DMF (2 ml). DIPEA (50 µl) and 6-[(3S)-Isoxazolidin-3-yl]pyridine-3-carbonitrile hydrochloride salt (I-35, 16 mg) were added with stirring. After 10-15 min of stirring HATU (40 mg) was added and stirring was continued for 30 min. The reaction mixture was diluted with half-saturated $NaHCO_3$ solution and extracted with EA (2×). The combined organic phases were washed with brine, dried with $Na_2SO_4$, filtered and concentrated. The residue was purified by preparative RP HPLC (flow 40 ml/min, 97% $H_2O$/3% ACN to 10%

$H_2O$/90% ACN in 15 min; Agilent Prep C18—5 μm, 30×100 mm). The product containing fractions were combined, the ACN was removed in vacuo and the aqueous phase was lyophilized. The residue was further purified by silica gel chromatography (4 g $SiO_2$, 100% DCM for 5 min; from 100% DCM to 5% ethanol in 30 min; then 5% EtOH for 15 min). The product containing fractions were combined and concentrated. The residue was dissolved in ACN/Water and lyophilized. The residue was purified again by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilized. The residue was purified again by silica gel chromatography (4 g $SiO_2$, 100% DCM for 5 min; from 100% DCM to 10% ethanol in 30 min; then 10% EtOH for 15 min). The pure product containing fractions were combined and concentrated in vacuo. The residue was dissolved in ACN/Water and lyophilized to yield 4 mg of the title compound.

LC/MS: m/z=408.4 [M+H]+; tR: 1.47 min (LC/MS-method A)

Ex. 109

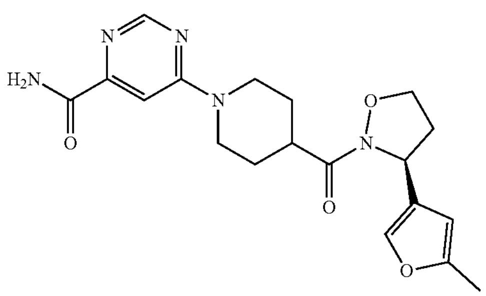

(S)-6-(4-(3-(5-Methylfuran-3-yl)isoxazolidine-2-carbonyl)piperidin-1-yl)pyrimidine-4-carboxamide (S)-3-(5-Methylfuran-3-yl)isoxazolidine 2,2,2-trifluoroacetate salt (I-59, 29.6 mg, 130 μmol), 1-(6-carbamoylpyrimidin-4-yl)piperidine-4-carboxylic acid 2,2,2-trifluoroacetic acid salt (I-38, 51.1 mg, 143.00 μmol) and HATU (59.3 mg, 156.00 μmol) were dissolved in DMF (1 ml), DIPEA (90.8 μl, 520.00 μmol) was added and the reaction mixture was stirred at room temperature for 1 hour. The solution was purified by preparative RP HPLC (50 ml/min, 90% $H_2O$/10% ACN to 0% $H_2O$/100% ACN in 12 min; Agilent Prep C18—10 μm, 30×100 mm). The pure product containing fractions were combined and the ACN was removed in vacuo. The aqueous solution was lyophilized to yield 22 mg of the title compound.

LC/MS: m/z=386.36 [M+H]+; tR: 1.5 min (LC/MS-method A)

Analogously to example 109 was prepared:

| Ex. | Acid | isoxazolidine | structure | LCMS (method A) m/z; tR [min]; (yield) | Name |
|---|---|---|---|---|---|
| 110 | 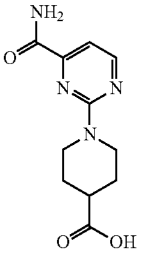 I-22 | 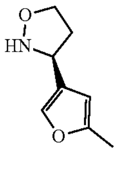 I-59 | 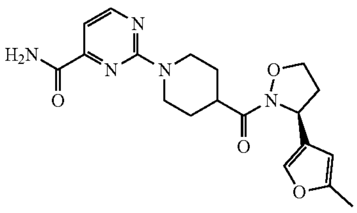 [SMILES: Cc1cc([C@@H]2CCON2C(=O)C2CCN(c3nccc(C(N)=O)n3)CC2)co1] | 386.3 1.72 (22 mg, 44%) | (S)-2-(4-(3-(5-methylfuran-3-yl)isoxazolidine-2-carbonyl)piperidin-1-yl)pyrimidine-4-carboxamide |

Ex. 111

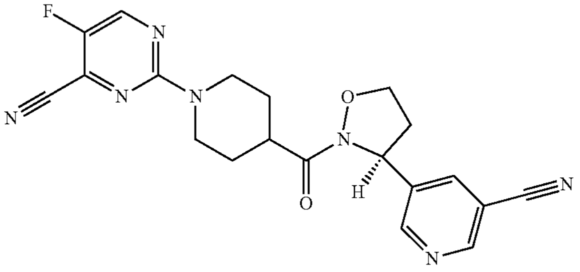

2-[4-[(3S)-3-(5-Cyano-3-pyridyl)isoxazolidine-2-carbonyl]-1-piperidyl]-5-fluoro-pyrimidine-4-carbonitrile 1-(4-Cyano-5-fluoro-pyrimidin-2-yl)piperidine-4-carboxylic acid (I-41, 15 mg) was dissolved in DMF (2 ml). DIPEA (50 μl) and 5-[(3S)-isoxazolidin-3-yl]pyridine-3-carbonitrile (I-02-1, 11 mg) were added. After 10-15 min of stirring, HATU (34 mg) was added and stirring was continued for 30 min. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilized to yield 15 mg of the title compound.

LC/MS: m/z=408.3 [M+H]+; tR: 2.02 min (LC/MS-method A)

Analogously to example 111 was prepared:

| Ex. | amine | structure | LCMS m/z; tR; (yield) | Name |
|---|---|---|---|---|
| 112 | 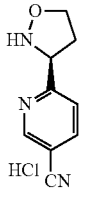 I-35 | 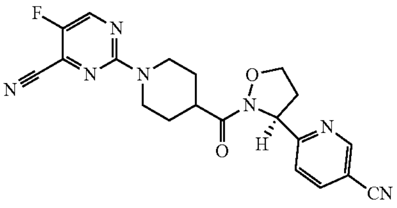 [SMILES: N#Cc1ccc([C@@H]2CCON2C(=O)C2CCN(c3ncc(F)c(C#N)n3)CC2)nc1] | 408.3 (method A) 2.06 min (7 mg, 29%) | 2-[4-[(3S)-3-(5-cyano-2-pyridyl)isoxazolidine-2-carbonyl]-1-piperidyl]-5-fluoro-pyrimidine-4-carbonitrile |

Ex. 113

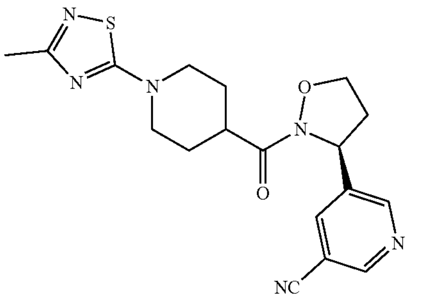

5-[(3S)-2-[1-(3-Methyl-1,2,4-thiadiazol-5-yl)piperidine-4-carbonyl]isoxaolidin-3-yl]pyridine-3-carbonitrile 1-(3-Methyl-1,2,4-thiadiazol-5-yl)piperidine-4-carboxylic acid (I-66, 25.0 mg, 0.11 mmol) was solved in a solution of DIPEA (105 µl, 0.60 mmol) in DMF (0.5 ml) and a solution of HBTU (75.9 mg, 0.2 mmol) in DMF (0.5 molar) was added. (3S)-3-pyrimidin-5-ylisoxazolidine HCl salt (I-01, 21.2 mg, 0.10 mmol) in DMF (1 ml) was added and the reaction was stirred at room temperature for 16 h. The solution was filtered (Captiva cartridge) and purified by preparative RP HPLC (50 ml/min, 90% $H_2O$/10% ACN to 0% $H_2O$/100% ACN in 12 min; Agilent Prep C18—10 µm, 30×100 mm). The pure product containing fractions were combined and the ACN was removed in vacuo. The aqueous solution was lyophilised to yield 22.5 mg of the title compound.

LC/MS: m/z=387.3 $[M+H]^+$; tR: 1.50 min (LC/MS-method A)

Ex. 114

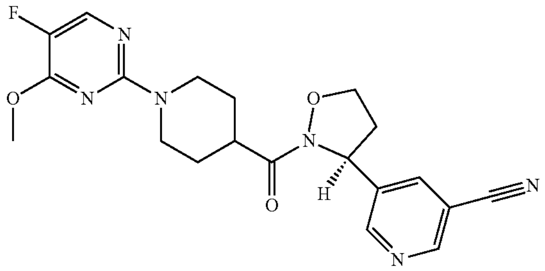

5-[(3S)-2-[1-(5-Fluoro-4-methoxy-pyrimidin-2-yl)piperidine-4-carbonyl]isoxazolidin-3-yl]pyridine-3-carbonitrile (S)-5-(2-(Piperidine-4-carbonyl)isoxazolidin-3-yl)nicotinonitrile TFA salt (I-28, 30 mg) was dissolved in dry ACN (3.0 ml) in a microwave vessel (2-5 ml). After DIPEA (50 µl) and 2-chloro-5-fluoro-4-methoxypyrimidine (14 mg) were added, the mixture was heated at 80° C. in a microwave oven for 0.5 h. To drive the reaction to completion the mixture was further heated to 120° C. for 0.5 h and 1.5 h, to 140° C. for 0.25 and 1 h. After cooling the solvent was removed in vacuo. The residue was purified by preparative RP HPLC (flow 40 ml/min, 97% $H_2O$/3% ACN to 10% $H_2O$/90% ACN in 15 min; Agilent Prep C18—5 µm, 30×100 mm). The product containing fractions were combined, the ACN was removed in vacuo and the aqueous phase was lyophilised over night to yield 9 mg of the title compound.

LC/MS: m/z=413.4 $[M+H]^+$; tR: 1.93 min (LC/MS-method A)

$^1H$ NMR (600 MHz, DMSO-$d_6$) δ ppm 8.94 (1H), 8.78 (1H), 8.21 (1H), 8.15 (1H), 5.43 (1H), 4.53 (2H), 4.32 (1H), 3.96 (1H), 3.93 (3H), 3.01 (3H), 2.93 (1H), 2.31 (1H), 1.91 (1H), 1.74 (1H), 1.49 (2H)

Ex. 115

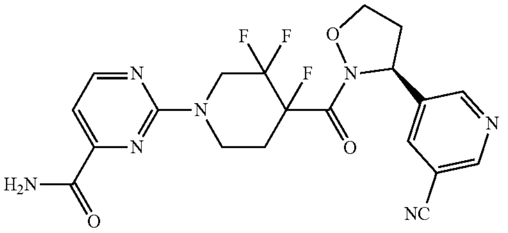

2-[4-[(3S)-3-(5-Cyano-3-pyridyl)isoxazolidine-2-carbonyl]-3,3,4-trifluoro-1-piperidyl]pyrimidine-4-carboxamide DMF (2 ml). DIPEA (70 μl) and (3S)-3-(6-methylpyrazin-2-yl)isoxazolidine hydrochloride salt (I-12, 17 mg) were added. After 10-15 min of stirring, HATU (45 mg) was added and stirring was continued for 1.5 h. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilized to yield 14 mg of the title compound.

LC/MS: m/z=403.4 $[M+H]^+$; tR: 1.86 min (LC/MS-method A)

Analogously to example 116 was prepared:

| Ex. | amine | structure | LCMS m/z; tR; (yield) | Name |
|---|---|---|---|---|
| 117 | 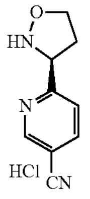 I-35 | 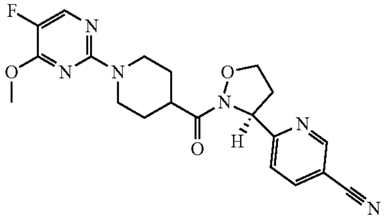 [SMILES: COc1nc(N2CCC(C(=O)N3OCC[C@H]3c3ccc(C#N)cn3)CC2)ncc1F] | 413.4 (method A) 1.96 min (9 mg, 27%) | 6-[(3S)-2-[1-(5-fluoro-4-methoxy-pyrimidin-2-yl)piperidine-4-carbonyl]isoxazolidin-3-yl]pyridine-3-carbonitrile |

5-[(3S)-Isoxazolidin-3-yl]pyridine-3-carbonitrile (I-02-1, 11 mg) was dissolved in dry DMF (1.5 ml). DIPEA (120 μl) and 1-(4-Carbamoylpyrimidin-2-yl)-3,3,4-trifluoro-piperidine-4-carboxylic acid (I-42, 57 mg) were added with stirring. After 15 min HATU (130 mg) was added and stirring was continued for 4 h. Then the mixture was directly purified by RP HPLC (flow 40 ml/min, 97% $H_2O$/3% ACN to 10% $H_2O$/90% ACN in 15 min; Agilent Prep C18—5 μm, 30×100 mm). The product containing fractions were combined and the ACN was removed in vacuo and the aqueous phase was lyophilised overnight to yield 16 mg of the title compound.

LC/MS: m/z=462.3 $[M+H]^+$; tR: 1.55 min (LC/MS-method A)

Ex. 116

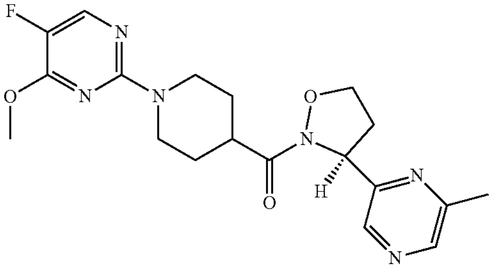

[1-(5-Fluoro-4-methoxy-pyrimidin-2-yl)-4-piperidyl]-[(3S)-3-(6-methylpyrazin-2-yl)isoxazolidin-2-yl]methanone 1-(5-Fluoro-4-methoxy-pyrimidin-2-yl)piperidine-4-carboxylic acid as lithium salt (I-43, 20 mg) was dissolved in Ex. 118

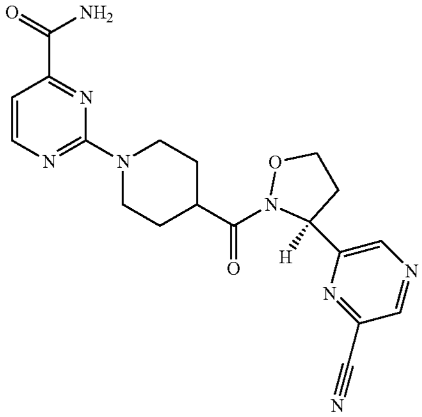

2-[4-[(3S)-3-(6-Cyanopyrazin-2-yl)isoxazolidine-2-carbonyl]-1-piperidyl]pyrimidine-4-carboxamide 1-(4-Carbamoylpyrimidin-2-yl)piperidine-4-carboxylic acid hydrochloride salt (I-22, 20 mg) was dissolved in DMF (2 ml). DIPEA (50 μl) and 6-[(3S)-Isoxazolidin-3-yl]pyrazine-2-carbonitrile TFA salt (I-44, 22 mg) were added. After 10-15 min of stirring, HATU (40 mg) was added and stirring was continued for 30 min. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 40 ml/min, 97%

$H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilized. The residue was further purified by silica gel chromatography (4 g $SiO_2$, 100% DCM for 5 min; from 100% DCM to 5% ethanol in 30 min; then 5% EtOH for 15 min). The pure product containing fractions were combined and concentrated in vacuo. The residue was dissolved in ACN/Water and lyophilised to yield 6 mg of the title compound.

LC/MS: m/z=409.4 $[M+H]^+$; tR: 1.49 min (LC/MS-method A)

$^1H$ NMR (600 MHz, DMSO-$d_6$) δ ppm 9.16 (1H), 8.92 (1H), 8.54 (1H), 8.15 (br, 1H), 7.70 (br, 1H), 7.07 (1H), 5.51 (1H), 4.78 (2H), 4.36 (1H), 4.03 (1H), 3.29 (m, 1H), 3.05 (3H), 2.88 (1H), 1.90 (1H), 1.78 (1H), 1.49 (2H)

Analogously to example 118 were prepared:

| Ex. | acid + amine | structure | LCMS (method A) m/z; tR; (yield) | Name |
|---|---|---|---|---|
| 119 | 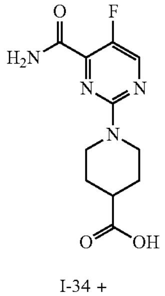 I-34 + I-44 | 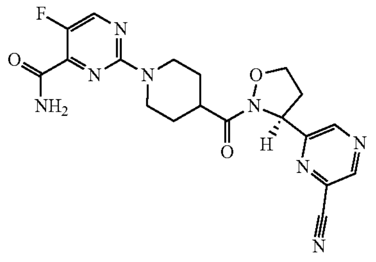 [SMILES: N#Cc1cncc([C@@H]2CCON2C(=O)C2CCN(c3ncc(F)c(C(N)=O)n3)CC2)n1] | 427.4 1.53 min (9 mg, 27%) | 6-[(3S)-2-[1-(5-fluoro-4-methoxy-pyrimidin-2-yl)piperidine-4-carbonyl]isoxazolidin-3-yl]pyridine-3-carbonitrile |
| 120 | 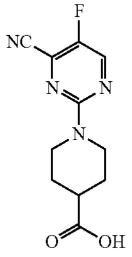 [SMILES: N#Cc1nc(N2CCC(C(=O)O)CC2)ncc1F] I-41 + I-17 | 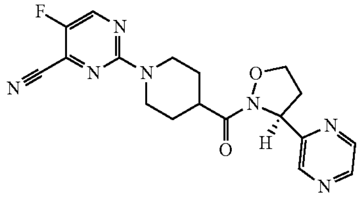 [SMILES: N#Cc1nc(N2CCC(C(=O)N3OCC[C@H]3c3cnccn3)CC2)ncc1F] | 384.4 1.87 min (10 mg, 42%) | 5-fluoro-2-[4-[(3S)-3-pyrazin-2-ylisoxazolidine-2-carbonyl]-1-piperidyl]pyrimidine-4-carbonitrile |

Ex. 121

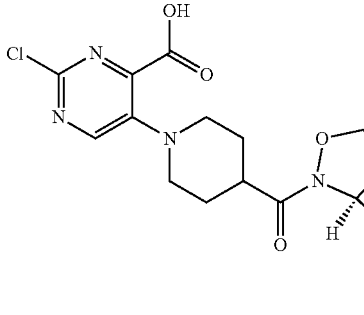

TFA

2-Chloro-5-[4-[(3S)-3-(5-cyano-3-pyridyl)isoxazolidine-2-carbonyl]-1-piperidyl]pyrimidine-4-carboxylic acid as TFA salt (S)-5-(2-(Piperidine-4-carbonyl)isoxazolidin-3-yl)nicotinonitrile TFA salt (I-28, 227 mg) was dissolved in dry DMF (4.5 ml) in a microwave vessel (2-5 ml). After TEA (320 μl) and 2-chloro-5-fluoropyrimidine-4-carboxylic acid (100 mg) were added, the mixture was heated at 100° C. in a microwave oven for 1 h. After cooling the solvent was removed in vacuo. The residue was purified by preparative RP HPLC. The product containing fractions were combined, the ACN was removed in vacuo and the aqueous phase was lyophilised over night to yield 45 mg of the title compound.

LC/MS: m/z=443.1 $[M+H]^+$; tR: 1.28 min (LC/MS-method A)

Analogously to example 115 was prepared:

| Ex. | amine | structure | LCMS m/z; tR; (yield) | Name |
|---|---|---|---|---|
| 122 | 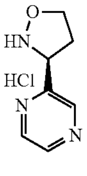 I-17 | 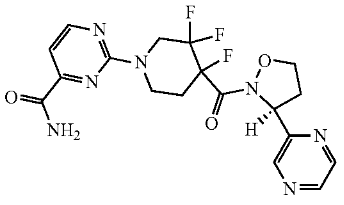 [SMILES: NC(=O)c1ccnc(N2CCC(F)(C(=O)N3OCC[C@H]3c3cnccn3)C(F)(F)C2)n1] | 438.1 (method A) 1.41/1.43 min (30 mg, 34%) | 2-[3,3,4-trifluoro-4-[(3S)-3-pyrazin-2-ylisoxazolidine-2-carbonyl]-1-piperidyl]pyrimidine-4-carboxamide (mixture of diasteromers) |

Ex. 123

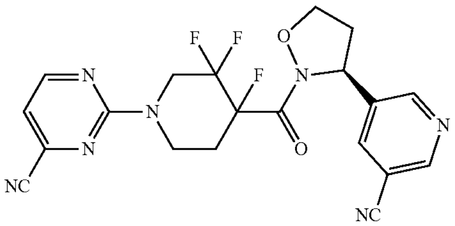

2-[4-[(3S)-3-(5-Cyano-3-pyridyl)isoxazolidine-2-carbonyl]-3,3,4-trifluoro-1-piperidyl]pyrimidine-4-carbonitrile 1-(4-Cyanopyrimidin-2-yl)-3,3,4-trifluoropiperidine-4-carboxylic acid (I-45, 25 mg) was dissolved in dry DCM (2.5 ml), DMF (100 μl) was added and the mixture was cooled to 0° C. Thionyl chloride (32 μl) was added dropwise and the cooling bath was removed. After 0.5 h the mixture was cooled again and additional thionyl chloride (32 μl) was added followed by the removal of the cooling bath. This procedure was repeated after 2 h (addition of 65 μl thionyl chloride) and 1 h later (addition of 65 μl thionyl chloride) to enforce acid chloride formation. 0.5 h after the last addition of thionyl chloride the mixture was cocentrated in vacuo and the residue was dissoved in DCM (1.5 ml). At 0° C. this solution was added to a mixture of 5-[(3S)-isoxazolidin-3-yl]pyridine-3-carbonitrile (I-02-1, 15 mg), DIPEA (61 μl) and DCM (1.0 ml) and the cooling bath was removed. After 0.5 h sodium bicarbonate solution was added and the aqueous phase was extracted with DCM (3×). The combined organic layers were dried over sodium sulphate, filtered and concentrated in vacuo. The residue was purified by RP HPLC (flow 40 ml/min, 97% $H_2O$/3% ACN to 10% $H_2O$/90% ACN in 15 min; Agilent Prep C18—5 μm, 30×100 mm). The product containing fractions were combined and the ACN was removed in vacuo and the aqueous phase was lyophilised overnight. The residue was further purified by silica gel chromatography (4 g $SiO_2$, 100% DCM for 5 min; from 100% DCM to 10% ethanol in 40 min). The pure product containing fractions were combined and concentrated in vacuo. The residue was dissolved in ACN/Water and lyophilised to yield 17 mg of the title compound.

LC/MS: m/z=444.2.1 $[M+H]^+$; tR: 1.95/1.96 min; mixture of diastereomers (LC/MS-method A)

Analogously to example 123 was prepared:

| Ex. | amine | structure | LCMS m/z; tR; (yield) | Name |
|---|---|---|---|---|
| 124 | 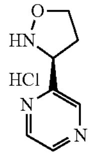 HCl I-17 | 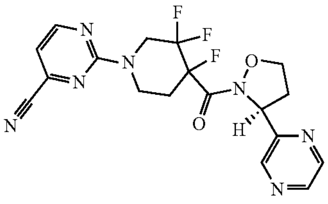 [SMILES: N#Cc1ccnc(N2CCC(F)(C(=O)N3OCC[C@H]3c3cnccn3)C(F)(F)C2)n1] | 420.2 (method A) 1.80/1.82 min (20 mg, 55%) | 2-[3,3,4-trifluoro-4-[(3S)-3-pyrazin-2-ylisoxazolidine-2-carbonyl]-1-piperidyl]pyrimidine-4-carbonitrile (mixture of diasteromers) |

Analogously to example 114 was prepared:

| Ex. | chloride | structure | LCMS m/z; tR; (yield) | Name |
|---|---|---|---|---|
| 125 | 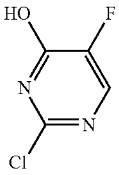 | 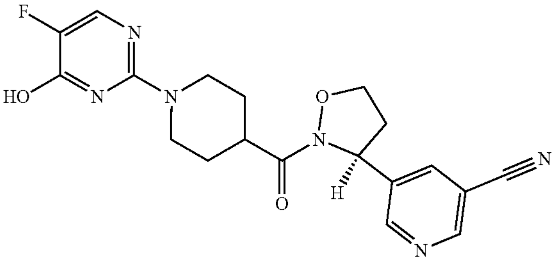 [SMILES: N#Cc1cncc([C@@H]2CCON2C(=O)C2CCN(c3ncc(F)c(O)n3)CC2)c1] | 399.2 (method A) 1.14 min (3 mg, 16 %) | 5-[(3S)-2-[1-(5-fluoro-4-hydroxy-pyrimidin-2-yl)piperidine-4-carbonyl]isoxazolidin-3-yl]pyridine-3-carbonitrile |

Analogously to example 109 was prepared:

| Ex. | Acid | isoxazolidine | structure |
|---|---|---|---|
| 126 | 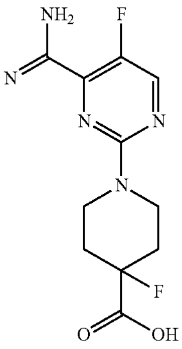 | 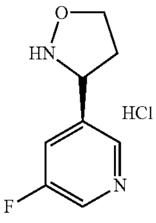 HCl | 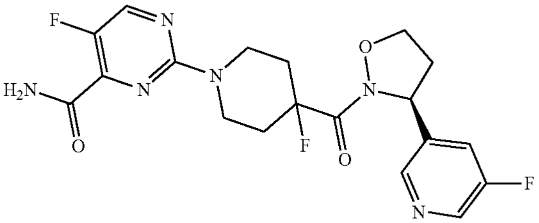 [SMILES: NC(=O)c1nc(N2CCC(F)(C(=O)N3OCC[C@H]3c3cncc(F)c3)CC2)ncc1F] |
| 127 | 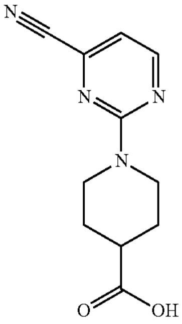 | 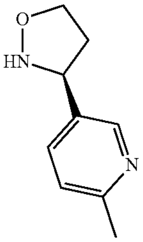 | 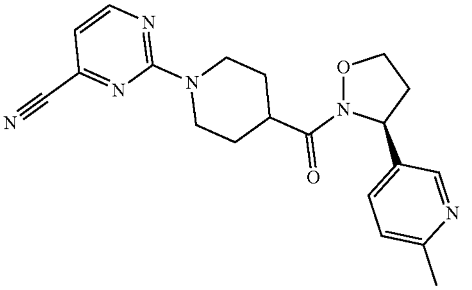 [SMILES: Cc1ccc([C@@H]2CCON2C(=O)C2CCN(c3nccc(C#N)n3)CC2)cn1] |

-continued

| | | | |
|---|---|---|---|
| 128 | 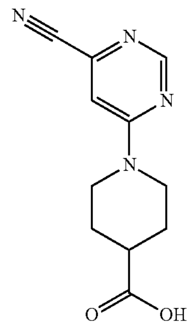 | 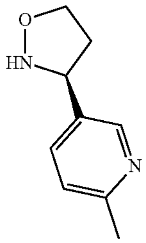 | 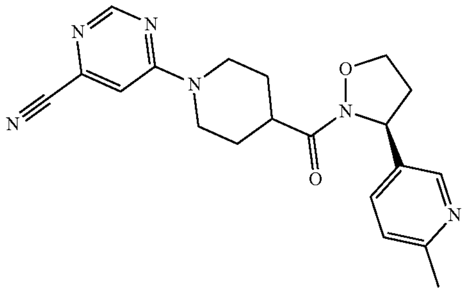 [SMILES: Cc1ccc([C@@H]2CCON2C(=O)C2CCN(c3cc(C#N)ncn3)CC2)cn1] |
| 129 | 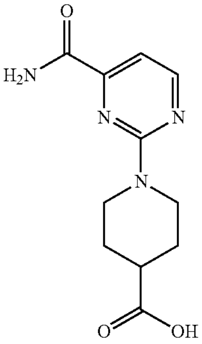 [SMILES: NC(=O)c1ccnc(N2CCC(C(=O)O)CC2)n1] | 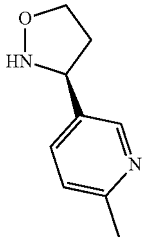 | 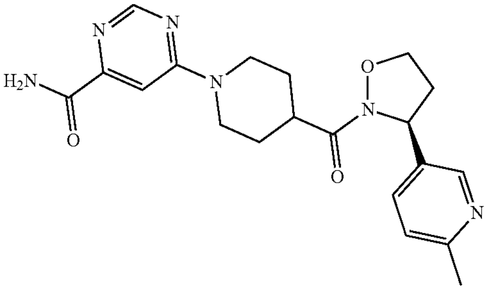 [SMILES: Cc1ccc([C@@H]2CCON2C(=O)C2CCN(c3cc(C(N)=O)ncn3)CC2)cn1] |

| Ex. | LCMS (method A) m/z; tR; (yield) | Name |
|---|---|---|
| 126 | 437.2 1.53 min (32 mg, 49%) | (S)-5-fluoro-2-(4-fluoro-4-(3-(5-fluoropyridin-3-yl)isoxazolidine-2-carbonyl)piperidin-1-yl)pyrimidine-4-carboxamide |
| 127 | 379.2 1.31 min (33 mg, 64%) | (S)-2-(4-(3-(6-methylpyridin-3-yl)isoxazolidine-2-carbonyl)piperidin-1-yl)pyrimidine-4-carbonitrile |
| 128 | 379.2 1.07 min (35 mg, 68%) | (S)-6-(4-(3-(6-methylpyridin-3-yl)isoxazolidine-2-carbonyl)piperidin-1-yl)pyrimidine-4-carbonitrile |
| 129 | 397.2 1.02 min (38 mg, 71%) | (S)-2-(4-(3-(6-methylpyridin-3-yl)isoxazolidine-2-carbonyl)piperidin-1-yl)pyrimidine-4-carboxamide |

Analogously to example 103 was prepared:
| Ex. | chloride | structure | LCMS (method A) m/z; tR; (yield) | Name |
|---|---|---|---|---|
| 130 | 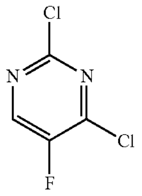 | 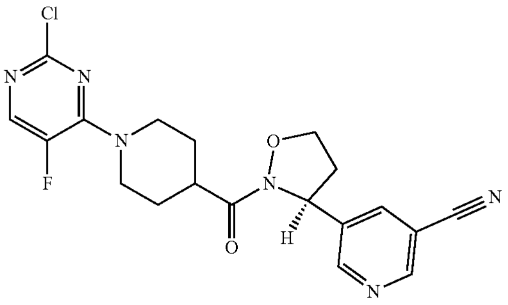 [SMILES: N#Cc1cncc([C@@H]2CCON2C(=O)C2CCN(c3nc(Cl)ncc3F)CC2)c1] | 417.2 1.85 min (32 mg, 78 %) | 5-[(3S)-2-[1-(2-chloro-5-fluoro-pyrimidin-4-yl)piperidine-4-carbonyl]isoxazolidin-3-yl]pyridine-3-carbonitrile |
Analogously to example 109 was prepared:
| Ex. | Acid | isoxazolidine | structure |
|---|---|---|---|
| 131 | 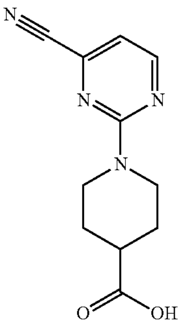 I-23 | 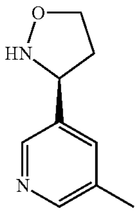 I-61 | 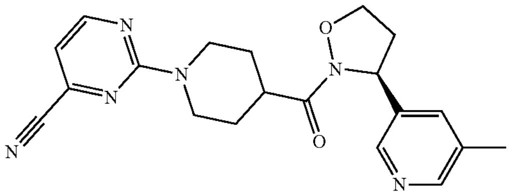 [SMILES: Cc1cncc([C@@H]2CCON2C(=O)C2CCN(c3nccc(C#N)n3)CC2)c1] |
| 132 | 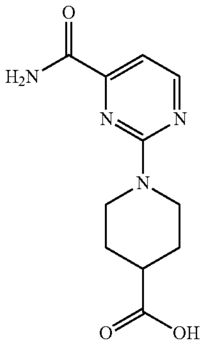 [SMILES: NC(=O)c1ccnc(N2CCC(C(=O)O)CC2)n1] I-22-1 | 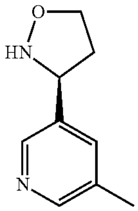 I-61 | 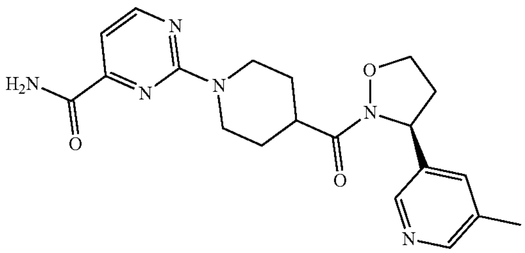 [SMILES: Cc1cncc([C@@H]2CCON2C(=O)C2CCN(c3nccc(C(N)=O)n3)CC2)c1] |

-continued
133
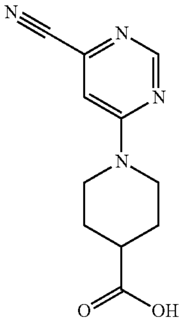 [SMILES: N#Cc1cc(N2CCC(C(=O)O)CC2)ncn1]
I-39
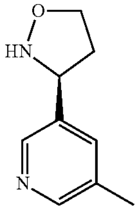
I-61
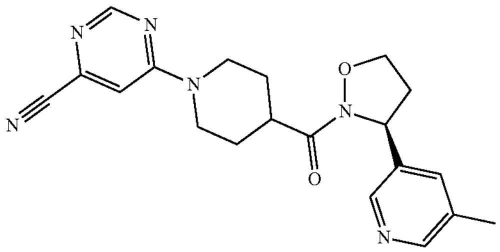 [SMILES: Cc1cncc([C@@H]2CCON2C(=O)C2CCN(c3cc(C#N)ncn3)CC2)c1]
134
TFA
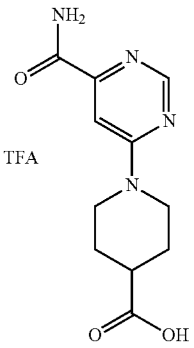 [SMILES: NC(=O)c1cc(N2CCC(C(=O)O)CC2)ncn1]
I-38
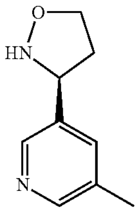
I-61
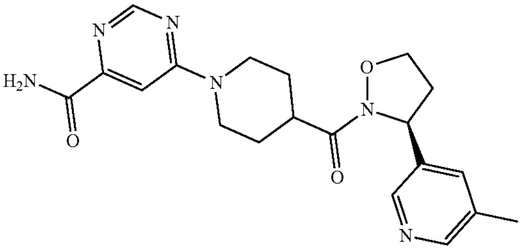 [SMILES: Cc1cncc([C@@H]2CCON2C(=O)C2CCN(c3cc(C(N)=O)ncn3)CC2)c1]
135
TFA
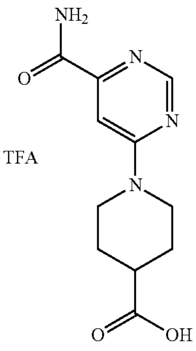
I-38
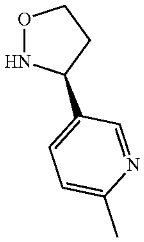
I-60
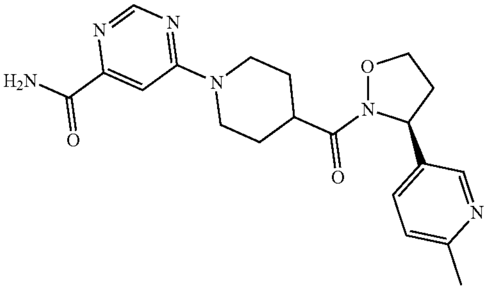 [SMILES: Cc1ccc([C@@H]2CCON2C(=O)C2CCN(c3cc(C(N)=O)ncn3)CC2)cn1]
136
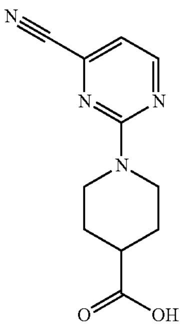
I-23
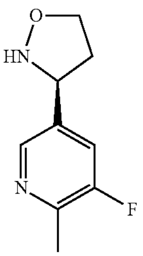
I-62
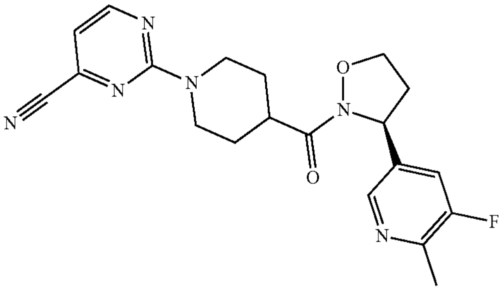 [SMILES: Cc1ncc([C@@H]2CCON2C(=O)C2CCN(c3nccc(C#N)n3)CC2)cc1F]

-continued
137 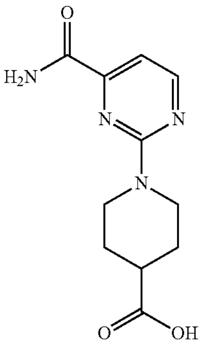 [SMILES: NC(=O)c1ccnc(N2CCC(C(=O)O)CC2)n1] 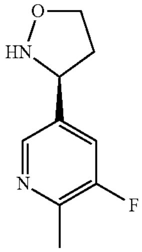 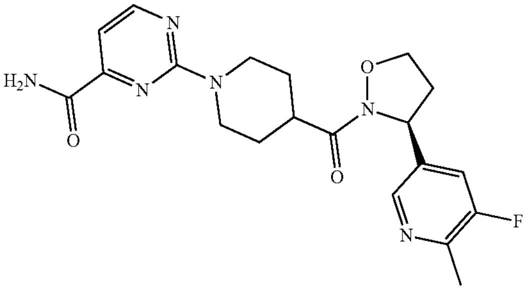 [SMILES: Cc1ncc([C@@H]2CCON2C(=O)C2CCN(c3nccc(C(N)=O)n3)CC2)cc1F]
I-62
I-22
138 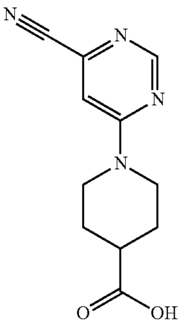 [SMILES: N#Cc1cc(N2CCC(C(=O)O)CC2)ncn1] 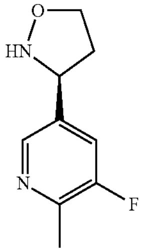 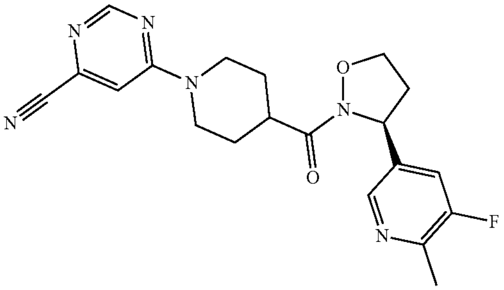 [SMILES: Cc1ncc([C@@H]2CCON2C(=O)C2CCN(c3cc(C#N)ncn3)CC2)cc1F]
I-62
I-39
139 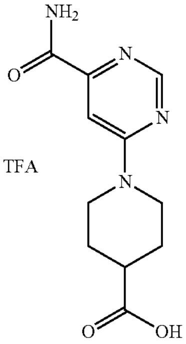 [SMILES: NC(=O)c1cc(N2CCC(C(=O)O)CC2)ncn1] 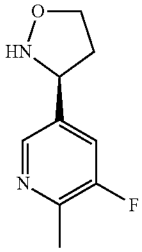 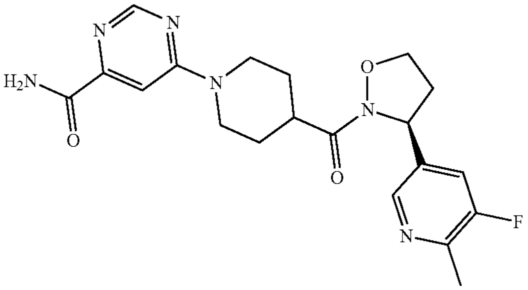 [SMILES: Cc1ncc([C@@H]2CCON2C(=O)C2CCN(c3cc(C(N)=O)ncn3)CC2)cc1F]
TFA
I-62
I-38
140 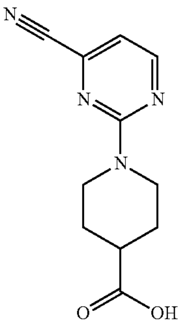 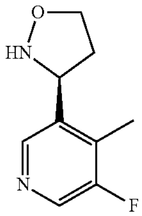 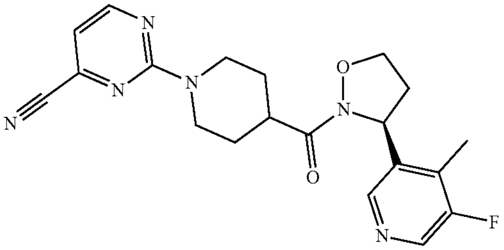 [SMILES: Cc1c(F)cncc1[C@@H]1CCON1C(=O)C1CCN(c2nccc(C#N)n2)CC1]
I-63
I-23

-continued
| | | | |
|---|---|---|---|
| 141 | 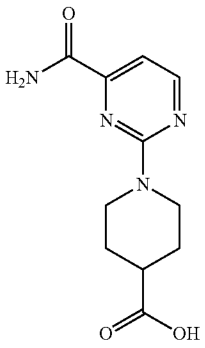 [SMILES: NC(=O)c1ccnc(N2CCC(C(=O)O)CC2)n1] I-22-1 | 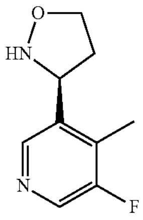 I-63 | 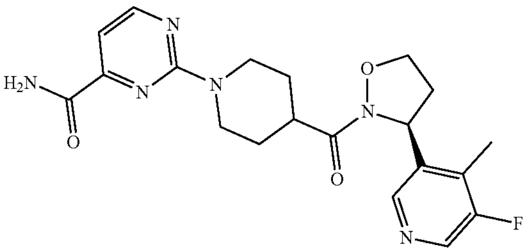 [SMILES: Cc1c(F)cncc1[C@@H]1CCON1C(=O)C1CCN(c2nccc(C(N)=O)n2)CC1] |
| 142 | TFA 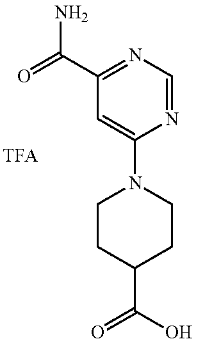 I-38 | 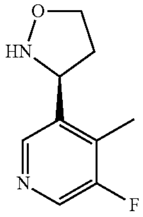 I-63 | 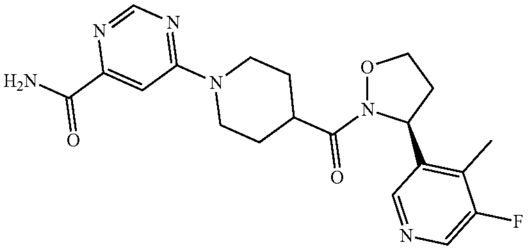 [SMILES: Cc1c(F)cncc1[C@@H]1CCON1C(=O)C1CCN(c2cc(C(N)=O)ncn2)CC1] |
| 143 | 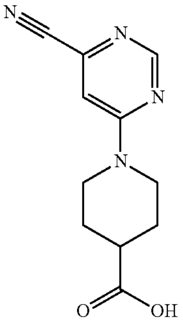 [SMILES: N#Cc1cc(N2CCC(C(=O)O)CC2)ncn1] I-39 | 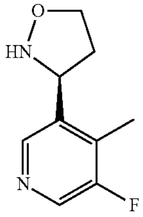 I-63 | 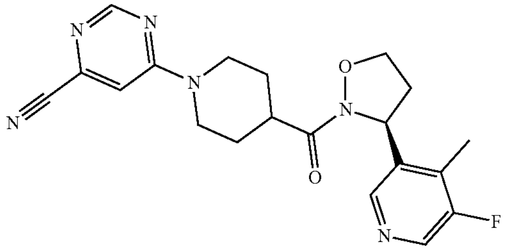 [SMILES: Cc1c(F)cncc1[C@@H]1CCON1C(=O)C1CCN(c2cc(C#N)ncn2)CC1] |
| Ex. | LCMS (method A) m/z; tR; (yield) | Name |
|---|---|---|
| 131 | 379.2 1.42 min (25 mg, 53%) | (S)-2-(4-(3-(5-methylpyridin-3-yl)isoxazolidine-2-carbonyl)piperidin-1-yl)pyrimidine-4-carbonitrile |

-continued

| | | |
|---|---|---|
| 132 | 397.2<br>1.1 min<br>(30 mg,<br>61%) | (S)-2-(4-(3-(5-methylpyridin-3-yl)isoxazolidine-2-carbonyl)piperidin-1-yl)pyrimidine-4-carboxamide |
| 133 | 379.2<br>1.16 min<br>(29 mg,<br>62%) | (S)-6-(4-(3-(5-methylpyridin-3-yl)isoxazolidine-2-carbonyl)piperidin-1-yl)pyrimidine-4-carbonitrile |
| 134 | 397.2<br>0.93 min<br>(34 mg,<br>69%) | (S)-6-(4-(3-(5-methylpyridin-3-yl)isoxazolidine-2-carbonyl)piperidin-1-yl)pyrimidine-4-carboxamide |
| 135 | 397.2<br>0.87 min<br>(41 mg,<br>76%) | (S)-6-(4-(3-(6-methylpyridin-3-yl)isoxazolidine-2-carbonyl)piperidin-1-yl)pyrimidine-4-carboxamide |
| 136 | 397.2<br>2.02 min<br>(33 mg,<br>62%) | (S)-2-(4-(3-(5-fluoro-6-methylpyridin-3-yl)isoxazolidine-2-carbonyl)piperidin-1-yl)pyrimidine-4-carbonitrile |
| 137 | 415.2<br>1.59 min<br>(34 mg,<br>61%) | 2-[4-[(3S)-3-(5-fluoro-6-methyl-3-pyridyl)isoxazolidine-2-carbonyl]-1-piperidyl]pyrimidine-4-carboxamide |
| 138 | 397.2<br>1.73 min<br>(35 mg,<br>65%) | (S)-6-(4-(3-(5-fluoro-6-methylpyridin-3-yl)isoxazolidine-2-carbonyl)piperidin-1-yl)pyrimidine-4-carbonitrile |
| 139 | 415.2<br>1.36 min<br>(37 mg,<br>66%) | 6-[4-[(3S)-3-(5-fluoro-6-methyl-3-pyridyl)isoxazolidine-2-carbonyl]-1-piperidyl]pyrimidine-4-carboxamide |
| 140 | 397.2<br>1.94 min<br>(27 mg,<br>50%) | (S)-2-(4-(3-(5-fluoro-4-methylpyridin-3-yl)isoxazolidine-2-carbonyl)piperidin-1-yl)pyrimidine-4-carbonitrile |
| 141 | 415.2<br>1.51 min<br>(27 mg,<br>48%) | (S)-2-(4-(3-(5-fluoro-4-methylpyridin-3-yl)isoxazolidine-2-carbonyl)piperidin-1-yl)pyrimidine-4-carboxamide |
| 142 | 415.2<br>1.28 min<br>(27 mg,<br>48%) | (S)-6-(4-(3-(5-fluoro-4-methylpyridin-3-yl)isoxazolidine-2-carbonyl)piperidin-1-yl)pyrimidine-4-carboxamide |
| 143 | 397.2<br>1.65 min<br>(27 mg,<br>50%) | (S)-6-(4-(3-(5-fluoro-4-methylpyridin-3-yl)isoxazolidine-2-carbonyl)piperidin-1-yl)pyrimidine-4-carbonitrile |

Analogously to example 103 was prepared:

| Ex. | chloride | structure | LCMS [method] m/z; tR; (yield) | Name |
|---|---|---|---|---|
| 144 | 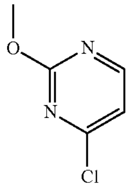 | 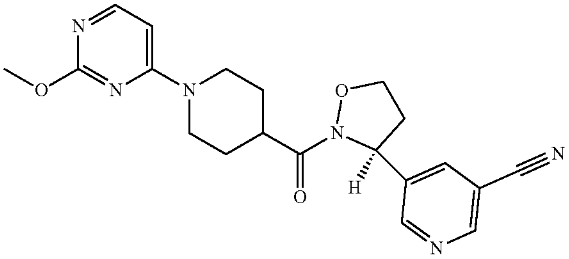 [SMILES: COc1nccc(N2CCC(C(=O)N3OCC[C@H]3c3cncc(C#N)c3)CC2)n1] | [A] 395.2 1.01 min (8 mg, 33%) | 5-[(3S)-2-[1-(2-methoxypyrimidin-4-yl)piperidine-4-carbonyl]isoxazolidin-3-yl]pyridine-3-carbonitrile |
| 145 | 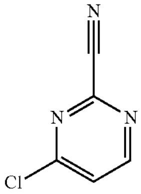 | 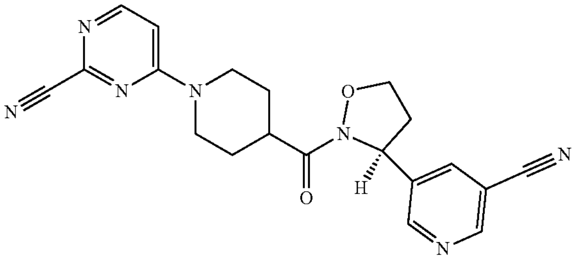 [SMILES: N#Cc1cncc([C@@H]2CCON2C(=O)C2CCN(c3ccnc(C#N)n3)CC2)c1] | [A] 390.2 1.66 min (18 mg, 74%) | 4-[4-[(3S)-3-(5-cyano-3-pyridyl)isoxazolidine-2-carbonyl]-1-piperidyl]pyrimidine-2-carbonitrile |
| 146 | 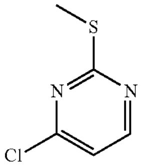 | 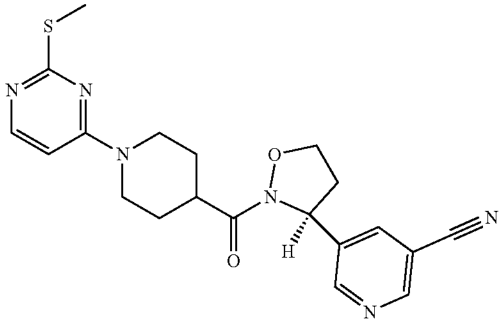 [SMILES: CSc1nccc(N2CCC(C(=O)N3OCC[C@H]3c3cncc(C#N)c3)CC2)n1] | [A] 411.2 1.15 min (20 mg, 77%) | 5-[(3S)-2-[1-(2-methylsulfanylpyrimidin-4-yl)piperidine-4-carbonyl]isoxazolidin-3-yl]pyridine-3-carbonitrile |
| 147 | 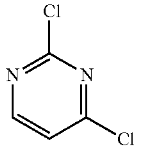 | 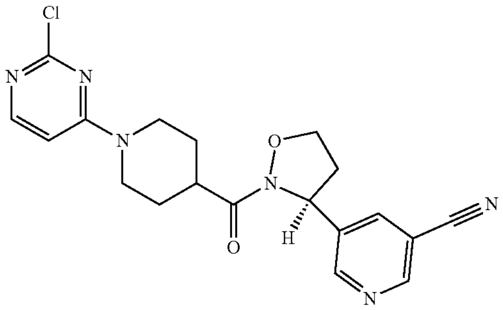 [SMILES: N#Cc1cncc([C@@H]2CCON2C(=O)C2CCN(c3ccnc(Cl)n3)CC2)c1] | [C] 399.2 0.79 min (47 mg, 67%) | 5-[(3S)-2-[1-(2-chloropyrimidin-4-yl)piperidine-4-carbonyl]isoxazolidin-3-yl]pyridine-3-carbonitrile |
| 148 | 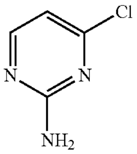 | 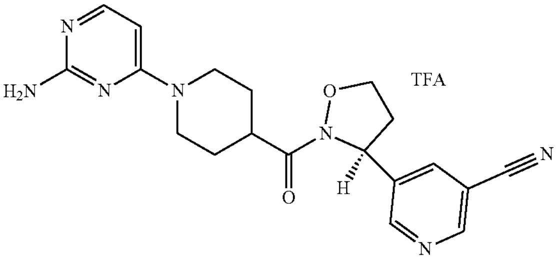 [SMILES: N#Cc1cncc([C@@H]2CCON2C(=O)C2CCN(c3ccnc(N)n3)CC2)c1] TFA | [A] 380.2 0.93 min (6 mg, 19%) | 5-[(3S)-2-[1-(2-aminopyrimidin-4-yl)piperidine-4-carbonyl]isoxazolidin-3-yl]pyridine-3-carbonitrile |

-continued
| Ex. | chloride | structure | LCMS [method] m/z; tR; (yield) | Name |
|---|---|---|---|---|
| 149 | 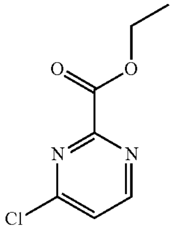 | 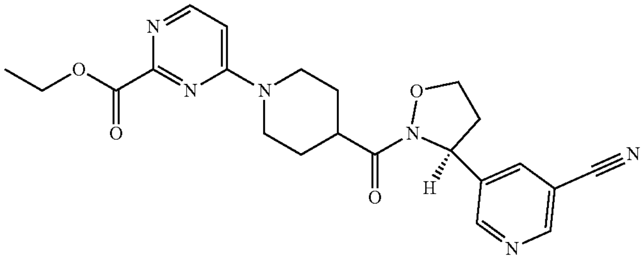 [SMILES: CCOC(=O)c1nccc(N2CCC(C(=O)N3OCC[C@H]3c3cncc(C#N)c3)CC2)n1] | [A] 437.2 1.31 min (25 mg, 47%) | ethyl 4-[4-[(3S)-3-(5-cyano-3-pyridyl)isoxazolidine-2-carbonyl]-1-piperidyl]pyrimidine-2-carboxylate |
Analogously to example 109 was prepared:
| Ex. | Acid | isoxazolidine | structure |
|---|---|---|---|
| 150 | 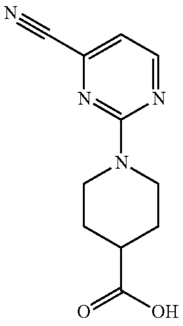 I-23 | 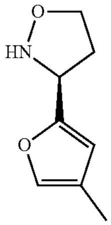 I-64 | 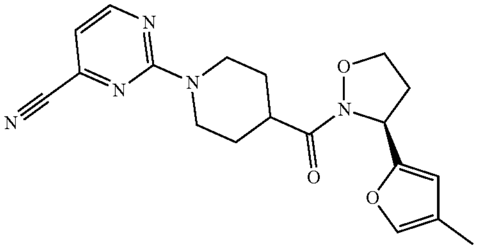 [SMILES: Cc1coc([C@@H]2CCON2C(=O)C2CCN(c3nccc(C#N)n3)CC2)c1] |
| 151 | 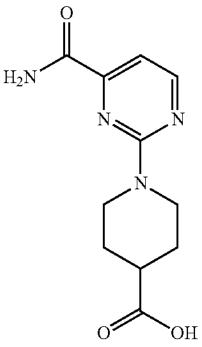 [SMILES: NC(=O)c1ccnc(N2CCC(C(=O)O)CC2)n1] I-22-1 | 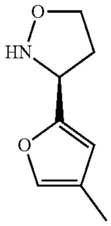 I-64 | 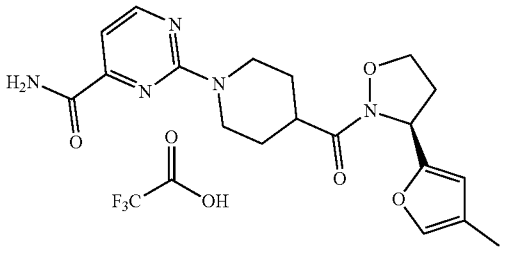 |
| 152 | 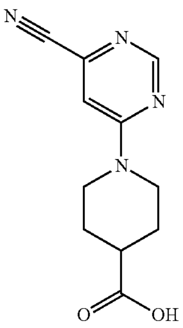 [SMILES: N#Cc1cc(N2CCC(C(=O)O)CC2)ncn1] I-39 | 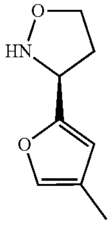 I-64 | 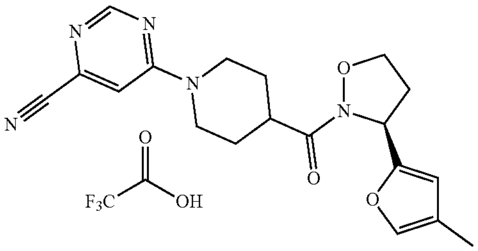 |

-continued

153

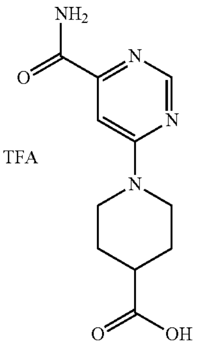 [SMILES: NC(=O)c1cc(N2CCC(C(=O)O)CC2)ncn1]

TFA

I-38

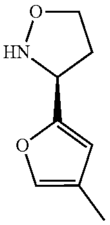

I-64

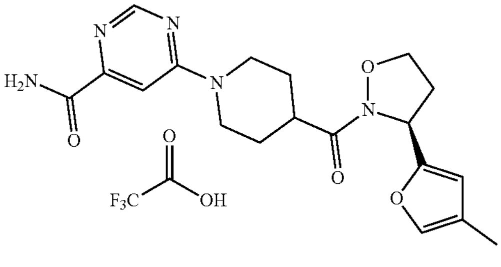

| Ex. | LCMS (method A) m/z; tR; (yield) | Name |
|---|---|---|
| 150 | 368.2 2.23 min (14 mg, 26 %) | (S)-2-(4-(3-(4-methylfuran-2-yl)isoxazolidine-2-carbonyl)piperidin-1-yl)pyrimidine-4-carbonitrile |
| 151 | 386.2 1.78 min (27 mg, 42 %) | (S)-2-(4-(3-(4-methylfuran-2-yl)isoxazolidine-2-carbonyl)piperidin-1-yl)pyrimidine-4-carboxamide 2,2,2-trifluoroacetate salt |
| 152 | 368.2 1.94 min (23 mg, 41 %) | (S)-6-(4-(3-(4-methylfuran-2-yl)isoxazolidine-2-carbonyl)piperidin-1-yl)pyrimidine-4-carbonitrile 2,2,2-trifluoroacetate salt |
| 153 | 386.2 1.54 min (30 mg, 41 %) | (S)-6-(4-(3-(4-methylfuran-2-yl)isoxazolidine-2-carbonyl)piperidin-1-yl)pyrimidine-4-carboxamide 2,2,2-trifluoroacetate salt |

Ex. 154

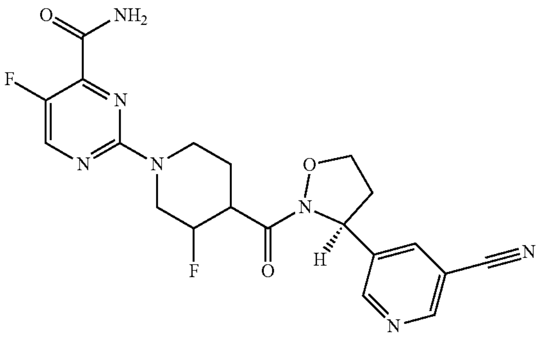

2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxamide 2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxylic acid (I-46, 24 mg) was treated as described in ex. 35 to yield 12 mg (62%) of the title compound.

LC/MS: m/z=444.2 $[M+H]^+$; tR: 1.50 min (LC/MS-method A)

$^1H$ NMR (400 MHz, DMSO-$d_6$) δ ppm 8.96 (1H), 8.79 (1H), 8.58 (1H), 8.20 (br, 2H), 7.80 (br, 1H), 5.47 (1H), 4.77 (1.5H), 4.66 (0.5H), 4.45 (1H), 4.35 (1H), 4.02 (1H), 3.3 ($H_2O$, br), 3.17 (1H), 2.95 (1H), 2.35 (1H), 1.94 (1H), 1.53 (1H)

Ex. 155

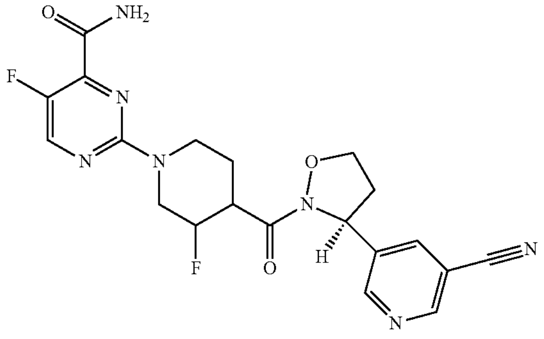

2-[(3S,4S or 3R,4R)-4-[(3S)-3-(5-Cyano-3-pyridyl)isoxazolidine-2-carbonyl]-3-fluoro-1-piperidyl]-5-fluoro-pyrimidine-4-carboxamide 2-[(3S,4S or 3R,4R)-4-[(3S)-3-(5-Cyano-3-pyridyl)isoxazolidine-2-carbonyl]-3-fluoro-1-piperidyl]-5-fluoro-pyrimidine-4-carboxylic acid (I-47, 38 mg) was treated as described in ex. 35 to yield 26 mg (86%) of the title compound.

LC/MS: m/z=444.2 $[M+H]^+$; tR: 1.51 min (LC/MS-method A)

$^1H$ NMR (400 MHz, DMSO-$d_6$) δ ppm 8.95 (1H), 8.80 (1H), 8.58 (1H), 8.22 (1H), 8.18 (br, 1H), 7.80 (br, 1H), 5.51 (1H), 4.80 (1.5H), 4.66 (0.5H), 4.45 (1H), 4.36 (1H), 3.91 (1H), 3.3 ($H_2O$, br), 3.16 (1H), 2.95 (1H), 2.33 (1H), 2.09 (1H), 1.57 (1H)

Ex. 156

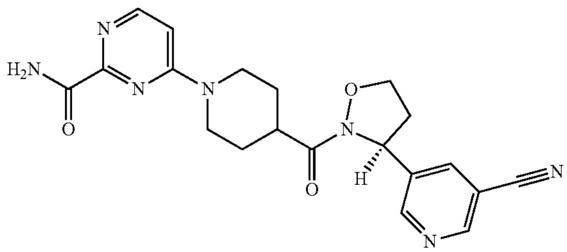

4-[4-[(3S)-3-(5-Cyano-3-pyridyl)isoxazolidine-2-carbonyl]-1-piperidyl]pyrimidine-2-carboxamide 4-[4-[(3S)-3-(5-Cyano-3-pyridyl)isoxazolidine-2-carbonyl]-1-piperidyl]pyrimidine-2-carboxylic acid (I-48, 12 mg) was treated as described in ex. 35 to yield 5 mg (57%) of the title compound.

LC/MS: m/z=408.2 $[M+H]^+$; tR: 0.88 min (LC/MS-method A)

Ex. 157 and 158

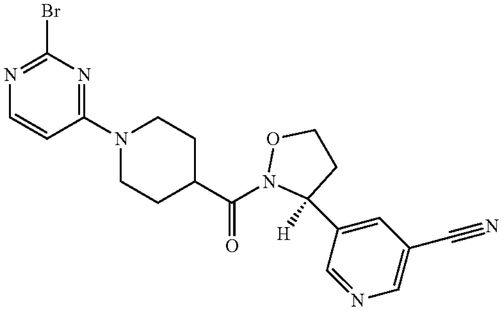

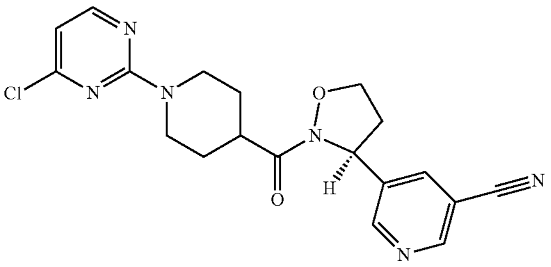

5-[(3S)-2-[1-(2-Bromopyrimidin-4-yl)piperidine-4-carbonyl]isoxazolidin-3-yl]pyridine-3-carbonitrile and 5-[(3S)-2-[1-(4-chloropyrimidin-2-yl)piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoroacetic acid salt (I-28, 180 mg) was dissolved in dry ACN (4.0 ml) in a microwave vessel (2-5 ml). After DIPEA (270 μl) and 2-bromo-4-chloro-pyrimidine (101 mg) were added, the mixture was heated at 100° C. in a microwave oven for 1 h. After cooling the solvent was removed in vacuo. The residue was purified by preparative RP HPLC (flow 70 ml/min, 90% v/10% ACN to 10% $H_2O$/90% ACN in 17.5 min; Agilent Prep C18—10 μm, 30×250 mm). The product containing fractions were combined, the ACN was removed in vacuo and the aqueous phase was lyophilised over night to yield 133 mg of the bromo and 29 mg of the chloro derivative.

Ex. 157

LC/MS: m/z=443.1 $[M+H]^+$; tR: 1.67 min (LC/MS-method A)

Ex. 158

LC/MS: m/z=399.2 $[M+H]^+$; tR: 2.03 min (LC/MS-method A)

Ex. 159

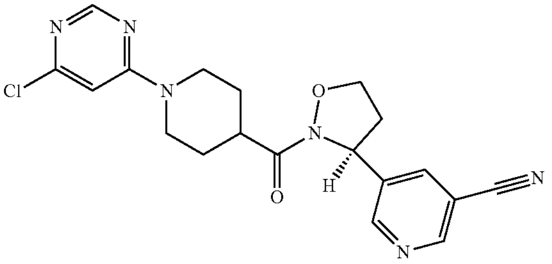

5-[(3S)-2-[1-(6-Chloropyrimidin-4-yl)piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoroacetic acid salt (I-28, 100 mg) was dissolved in dry ACN (10 ml) in a microwave vessel (10-20 ml). After DIPEA (130 μl) and 4,6-dichloro-pyrimidine (42 mg) were added, the mixture was heated at 80° C. in a microwave oven for 1 h. After cooling the solvent was removed in vacuo. The residue was purified by silica gel chromatography (24 g $SiO_2$, 100% n-heptane to 100% EA in 45 min). The product containing fractions were combined, the solvent was removed in vacuo and the residue was lyophilised over night to yield 86 mg of the title compound.

LC/MS: m/z=399.2 $[M+H]^+$; tR: 1.66 min (LC/MS-method A)

Ex. 161

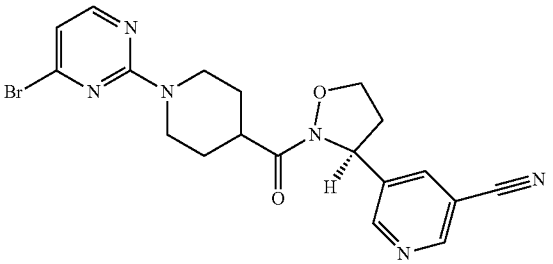

5-[(3S)-2-[1-(4-Bromopyrimidin-2-yl)piperidine-4-carbonyl]isoxazolidin-3-yl]pyridine-3-carbonitrile 5-[(3S)-2-[1-(4-Hydroxypyrimidin-2-yl)piperidine-4-carbonyl]isoxazolidin-3-yl]pyridine-3-carbonitrile (I-72, 220 mg) and phosphorus oxybromide (510 mg) were suspended in ACN (4.5 ml) and DMF (0.5 ml) and heated in the microwave oven at 90° C. for 15 min (attention, strong temperature increase!). After cooling the mixture was poured into ice water, neutralised with saturated sodium bicarbonate solution and extracted with DCM (3×). The combined organic layers were washed with brine, dries over sodium sulfate, filtered and concentrated in vacuo. The residue was purified by silica gel chromatography (12 g $SiO_2$, 100% DCM for 5 min, 100% DCM to 95% DCM/5% ethanol in 30 min, 95% DCM/5% ethanol for 15 min). The product containing fractions were combined, the solvent was removed in vacuo to yield 26 mg of the title compound.

LC/MS: m/z=443.1 $[M+H]^+$; tR: 2.10 min (LC/MS-method A)

Analogously to example 109 was prepared:

| Ex. | Acid | isoxazolidine | structure |
|---|---|---|---|
| 162 | 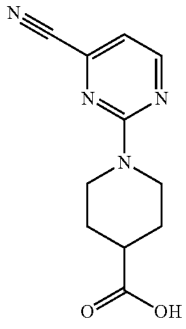 [SMILES: N#Cc1ccnc(N2CCC(C(=O)O)CC2)n1] I-23 | 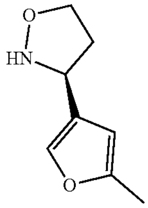 I-59 | 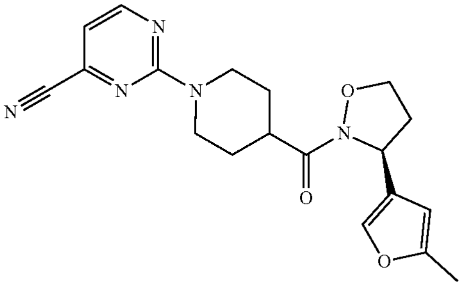 [SMILES: Cc1cc([C@@H]2CCON2C(=O)C2CCN(c3nccc(C#N)n3)CC2)co1] |
| 163 | 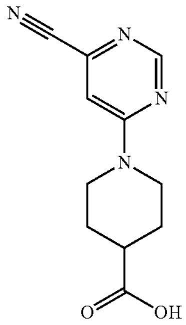 [SMILES: N#Cc1cc(N2CCC(C(=O)O)CC2)ncn1] I-39 | 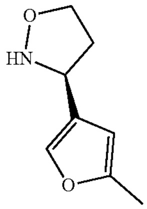 I-59 | 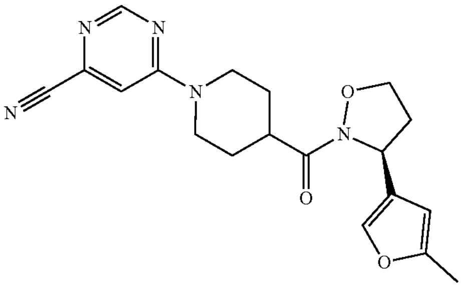 [SMILES: Cc1cc([C@@H]2CCON2C(=O)C2CCN(c3cc(C#N)ncn3)CC2)co1] |

-continued

| Ex. | LCMS (method A) m/z; tR; (yield) | Name |
|---|---|---|
| 162 | 368.2 2.2 min (24 mg, 47 %) | (S)-2-(4-(3-(5-methylfuran-3-yl)isoxazolidine-2-carbonyl)piperidin-1-yl)pyrimidine-4-carbonitrile |
| 163 | 368.2 1.91 min (26 mg, 51 %) | (S)-6-(4-(3-(5-methylfuran-3-yl)isoxazolidine-2-carbonyl)piperidin-1-yl)pyrimidine-4-carbonitrile |

Ex. 164

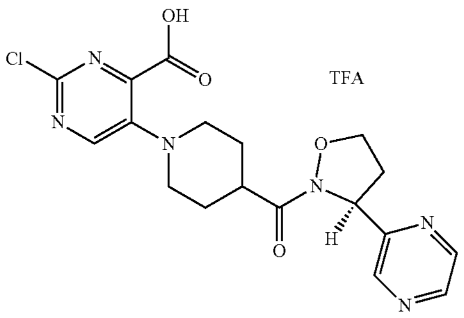

TFA

2-Chloro-5-[4-[(3S)-3-pyrazin-2-ylisoxazolidine-2-carbonyl]-1-piperidyl]pyrimidine-4-carboxylic acid TFA salt 4-Piperidyl-[(3S)-3-pyrazin-2-ylisoxazolidin-2-yl]methanone trifluoro acetic acid salt (I-49, 150 mg) was dissolved in dry ACN (10 ml) in a microwave vessel (10-20 ml). After DIPEA (190 μl) and 2-chloro-5-fluoro-pyrimidine-4-carboxylic acid (I-46a, 97 mg) were added, the mixture was heated at 100° C. in a microwave oven for 6 h. After cooling the solvent was removed in vacuo. The residue was purified by preparative RP-HPLC (120 ml/min, 95% $H_2O$+0.1% TFA/5% ACN to 25% $H_2O$+0.1% TFA/75% ACN in 10.5 min; Waters Sunfire Prep C18 OBD—5 μm, 30×100 mm). The product containing fractions were combined, the solvent was removed in vacuo and the residue was lyophilised over night to yield 36 mg of the title compound.

LC/MS: m/z=419.2 $[M+H]^+$; tR: 1.12 min (LC/MS-method A)

Ex. 165

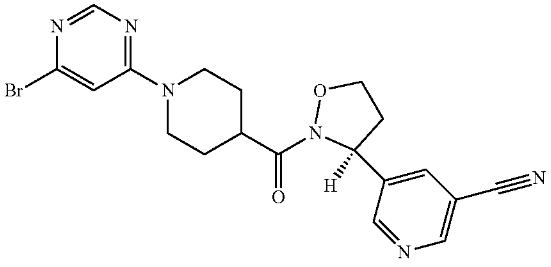

5-[(3S)-2-[1-(6-Bromopyrimidin-4-yl)piperidine-4-carbonyl]isoxazolidin-3-yl]pyridine-3-carbonitrile 5-[(3S)-2-(Piperidine-4-carbonyl)isoxazolidin-3-yl]pyridine-3-carbonitrile trifluoro acetic acid salt (I-28, 200 mg) was dissolved in dry ACN (4.5 ml) in a microwave vessel (2-5 ml). After DIPEA (310 μl) and 4,6-dibromo-pyrimidine (144 mg) were added, the mixture was heated at 100° C. in a microwave oven for 1 h. After cooling the solvent was removed in vacuo. The residue was purified by preparative RP HPLC (flow 50 ml/min, 90% $H_2O$/10% ACN to 10% $H_2O$/90% ACN in 15 min; Agilent Prep C18—10 μm, 30×250 mm). The product containing fractions were combined, the ACN was removed in vacuo and the aqueous phase was lyophilised over night to yield 176 mg of the title compound.

LC/MS: m/z=443.2 $[M+H]^+$; tR: 1.71 min (LC/MS-method A)

Ex. 166

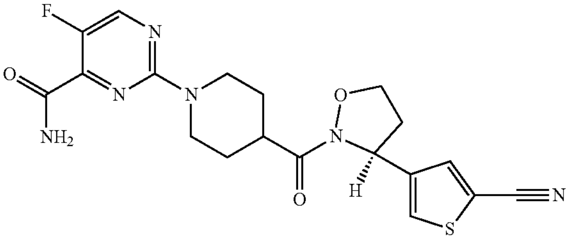

2-[4-[(3S)-3-(5-Cyano-3-thienyl)isoxazolidine-2-carbonyl]-1-piperidyl]-5-fluoro-pyrimidine-4-carboxamide 4-[(3S)-Isoxazolidin-3-yl]thiophene-2-carbonitrile TFA salt (I-50, 41 mg) was dissolved in dry DMF (2.0 ml). DIPEA (90 μl) and 1-(4-carbamoyl-5-fluoro-pyrimidin-2-yl)piperidine-4-carboxylic acid (I-34, 34 mg) were added with stirring. After 15 min HATU (98 mg) was added and stirring was continued for 1 h. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 50 ml/min, 90% $H_2O$/10% ACN to 10% $H_2O$/90% ACN in 15 min; Agilent Prep C18—10 μm, 21.5×250 mm). The product containing fractions were combined and the ACN was removed in vacuo and the aqueous phase was lyophilised overnight to yield 39 mg of the title compound.

LC/MS: m/z=431.2 $[M+H]^+$; tR: 1.72 min (LC/MS-method A)

Ex. 167

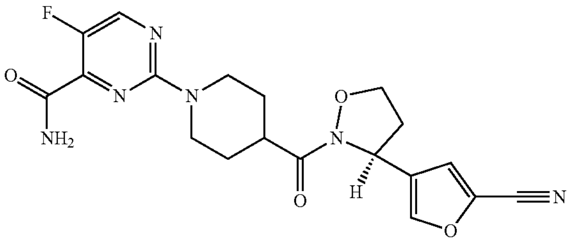

2-[4-[(3S)-3-(5-Cyano-3-furyl)isoxazolidine-2-carbonyl]-1-piperidyl]-5-fluoro-pyrimidine-4-carboxamide 4-[(3S)-Isoxazolidin-3-yl]furan-2-carbonitrile HCl salt (I-51, 24 mg) was dissolved in dry DMF (2.0 ml). DIPEA (80 μl) and 1-(4-carbamoyl-5-fluoro-pyrimidin-2-yl)piperidine-4-carboxylic acid (I-34, 29 mg) were added with stirring. After 15 min HATU (84 mg) was added and stirring was continued for 1 h. The reaction mixture was diluted with half-saturated $NaHCO_3$ solution and extracted with EA (3×). The combined EA phases were washed with brine, dried with $Na_2SO_4$, filtered and concentrated. The residue was purified by silica gel chromatography (4 g $SiO_2$, 100% DCM for 8 min, 100% DCM to 90% DCM/10% ethanol in 60 min, 90% DCM/10% ethanol for 15 min). The product containing fractions were combined and the solvent was removed in vacuo. For further purification the residue was purified by preparative RP HPLC (flow 50 ml/min, 90% $H_2O$/10% ACN to 10% $H_2O$/90% ACN in 15 min; Agilent Prep C18—10 μm, 21.5×250 mm). The product containing fractions were combined and the ACN was removed in vacuo and the aqueous phase was lyophilised overnight to yield 7 mg of the title compound.

LC/MS: m/z=415.2 $[M+H]^+$; tR: 1.69 min (LC/MS-method A)

Ex. 168

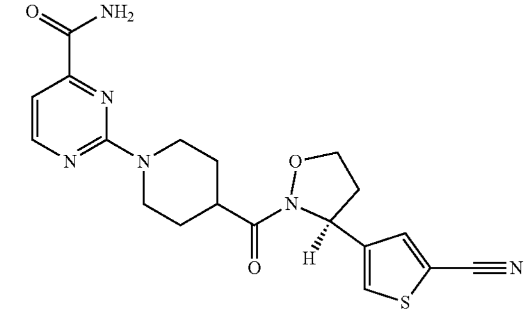

2-[4-[(3S)-3-(5-Cyano-3-thienyl)isoxazolidine-2-carbonyl]-1-piperidyl]pyrimidine-4-carboxamide 4-[(3S)-2-(Piperidine-4-carbonyl)isoxazolidin-3-yl]thiophene-2-carbonitrile trifluoroacetic acid salt (1-52, 20 mg) was dissolved in dry ACN (0.5 ml) in a microwave vessel (2-5 ml). After DIPEA (30 μl) and 2-chloropyrimidine-4-carboxamide (9 mg) were added, the mixture was heated at 100° C. in a microwave oven for 1 h. After cooling the solvent was removed in vacuo. The residue was purified by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilised over night. The residue was further purified by silica gel chromatography (4 g $SiO_2$, 100% DCM for 5 min, 100% DCM to 95% DCM/5% ethanol in 30 min, 95% DCM/5% ethanol for 10 min). The product containing fractions were combined, the solvent was removed in vacuo and the residue lyophilised from water/ACN to yield 18 mg of the title compound.

LC/MS: m/z=413.2 $[M+H]^+$; tR: 1.68 min (LC/MS-method A)

Analogously to example 109 was prepared:

| Ex. | Acid | isoxazolidine | structure | LCMS (method A) m/z; tR; (yield) | Name |
|---|---|---|---|---|---|
| 169 | 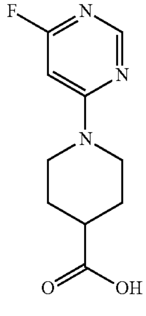 I-68 | 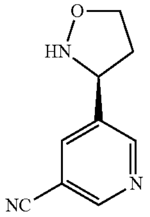 I-02-1 | 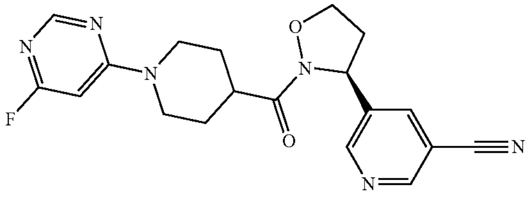 [SMILES: N#Cc1cncc([C@@H]2CCON2C(=O)C2CCN(c3cc(F)ncn3)CC2)c1] | 383.2 1.59 min (27 mg, 71 %) | (S)-5-(2-(1-(6-fluoropyrimidin-4-yl)piperidine-4-carbonyl) isoxazolidin-3-yl)nicotinonitrile |

Ex. 170

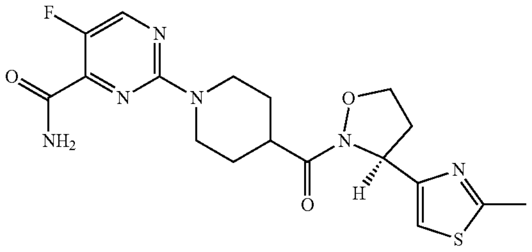

5-Fluoro-2-[4-[(3S)-3-(2-methylthiazol-4-yl)isoxazolidine-2-carbonyl]-1-piperidyl]pyrimidine-4-carboxamide To a mixture of 1-(4-carbamoyl-5-fluoro-pyrimidin-2-yl) piperidine-4-carboxylic acid (I-34, 80 mg) and DMF (6 ml) under argon was added ethyl (hydroxyimino)cyanoacetate (130 mg), EDC (170 mg) and $NaHCO_3$ (250 mg). After stirring for 45 min at RT, a mixture of (3S)-3-(2-methylthiazol-4-yl)isoxazolidine trifluoroacetic acid salt (I-56, 80 mg) and DMF (3 ml) was added. After stirring for 2 h at RT, the reaction mixture was diluted with EA and washed with water. The organic layer was washed with saturated solutions of $NH_4Cl$, $NaHCO_3$ and NaCl, respectively, and concentrated. The residue was purified by preparative RP HPLC (flow 120 ml/min, $H_2O$/0.1% TFA:ACN 75:25 to 45:55 in 8 min; Waters Sunfire Prep C18 OBD—5 μm, 50×100 mm). The product containing fractions were combined, the ACN was removed in vacuo and the aqueous phase was lyophilised to obtain the title compound (94 mg).

LC/MS: m/z=421.2 $[M+H]^+$; tR: 1.54 min (LC/MS-method A)

Ex. 171

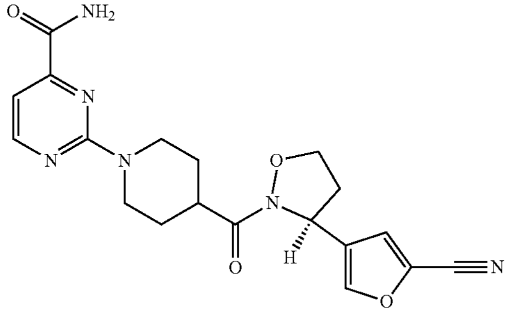

2-[4-[(3S)-3-(5-Cyano-3-furyl)isoxazolidine-2-carbonyl]-1-piperidyl]pyrimidine-4-carboxamide 4-[(3S)-2-(Piperidine-4-carbonyl)isoxazolidin-3-yl]furan-2-carbonitrile trifluoroacetic acid salt (1-53, 25 mg) was dissolved in dry ACN (0.5 ml) in a microwave vessel (2-5 ml). After DIPEA (40 μl) and 2-chloropyrimidine-4-carboxamide (12 mg) were added, the mixture was heated at 100° C. in a microwave oven for 1 h. After cooling the solvent was removed in vacuo. The residue was purified by preparative RP HPLC (flow 40 ml/min, 97% $H_2O$/3% ACN to 10% $H_2O$/90% ACN in 15 min; Agilent Prep C18—5 μm, 30×100 mm). The product containing fractions were combined, the ACN was removed in vacuo and the aqueous phase was lyophilised over night to yield 13 mg of the title compound.

LC/MS: m/z=397.2 $[M+H]^+$; tR: 1.66 min (LC/MS-method A)

Analogously to example 165 was prepared:

| Ex | building blocks | structure | LCMS (method A) m/z; tR; (yield) | Name |
|---|---|---|---|---|
| 174 | 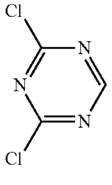 + I-17 | 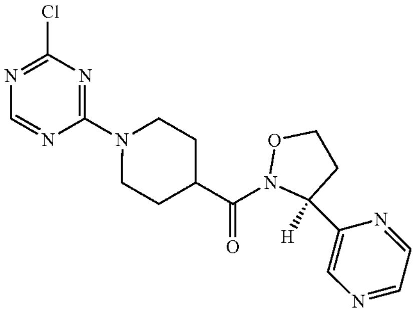 [SMILES: O=C(C1CCN(c2ncnc(Cl)n2)CC1)N1OCC[C@H]1c1cnccn1] | 376.1 1.52 min (11 mg, 42 %) | [1-(4-chloro-1,3,5-triazin-2-yl)-4-piperidyl]-[(3S)-3-pyrazin-2-ylisoxazolidin-2-yl]methanone |

Ex. 175

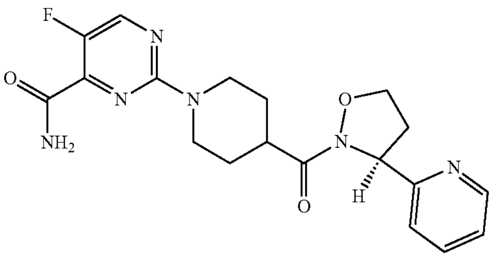

5-Fluoro-2-[4-[(3S)-3-(2-pyridyl)isoxazolidine-2-carbonyl]-1-piperidyl]pyrimidine-4-carboxamide To a mixture of 1-(4-carbamoyl-5-fluoro-pyrimidin-2-yl) piperidine-4-carboxylic acid (I-34, 75 mg) and DMF (3 ml) under argon was added ethyl (hydroxyimino)cyanoacetate (145 mg), EDC (200 mg) and $NaHCO_3$ (300 mg). After stirring for 1 h at RT, a mixture of (3S)-3-(2-pyridyl) isoxazolidine hydrochloride salt (I-57, 60 mg) and DMF (3 ml) was added. After stirring for 2 h at RT, the reaction mixture was diluted with EA and washed with water. The organic layer was washed with saturated solutions of $NH_4Cl$, $NaHCO_3$ and NaCl, respectively, and concentrated. The residue was purified by preparative RP HPLC (flow 120 ml/min, $H_2O$/0.1% TFA:ACN 85:15 to 45:55 in 8 min; Waters Sunfire Prep C18 OBD—5 μm, 50×100 mm). The product containing fractions were combined, the ACN was removed in vacuo and the aqueous phase was lyophilised to obtain the title compound (85 mg).

LC/MS: m/z=401.2 $[M+H]^+$; tR: 1.36 min (LC/MS-method A)

Ex. 176

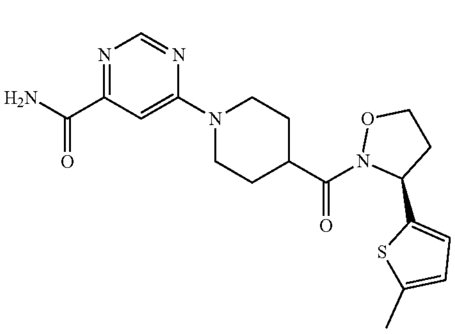

6-[4-[(3S)-3-(5-Methyl-2-thienyl)isoxazolidine-2-carbonyl]-1-piperidyl]pyrimidine-4-carboxamide 3-(5-Methylthiophen-2-yl)isoxazolidine 2,2,2-trifluoroacetate salt (I-65d, 27.8 mg, 100.0 μmol), 1-(6-carbamoylpyrimidin-4-yl)piperidine-4-carboxylic acid (I-38, 26.3 mg, 105.0 μmol) and HATU (45.6 mg, 120.0 μmol) were dissolved in DMF (1 ml), DIPEA (78.6 μl, 450.0 μmol) was added and the reaction mixture was stirred at room temperature for 1 hour. The solution was purified by preparative RP HPLC (50 mL/min, 90% $H_2O$/10% ACN to 0% $H_2O$/100% ACN in 12 min; Agilent Prep C18—10 μm, 30×100 mm). The pure product containing fractions were combined and the ACN was removed in vacuo. The aqueous solution was lyophilized to yield 22 mg (55%) of the racemate of the title compound.

LC/MS: m/z=402.2 $[M+H]^+$; tR: 1.68 min (LC/MS-method A)

Preparative separation of the racemate (50 mg, prepared in analogy to the description above, 0.125 μmol) on HPLC (column: Chiralpak IE/179, 250×4.6 mm, eluent: ethanol/methonal=1/1+0.1% DEA, flow 1 ml/min) resulted in 18.5 mg (37% peak 1, retention time 9.74 minutes) of the title compound and 14.0 mg (28%, peak 2, retention time 11.88 minutes) of the R-enantiomer.

Peak 1: LC/MS: m/z=402.2 $[M+H]^+$; tR: 1.67 min (LC/MS-method A)

Peak 2: LC/MS: m/z=402.2 $[M+H]^+$; tR: 1.67 min (LC/MS-method A)

Ex. 177 Comparison Example

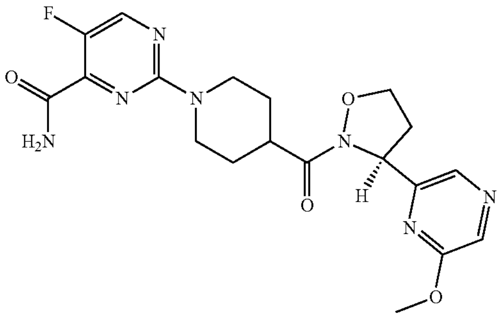

5-Fluoro-2-[4-[(33)-3-(6-methoxypyrazin-2-yl)isoxazolidine-2-carbonyl]-1-piperidyl]pyrimidine-4-carboxamide To a mixture of 1-(4-carbamoyl-5-fluoro-pyrimidin-2-yl) piperidine-4-carboxylic acid (I-34, 75 mg) and DMF (3 ml) under argon was added ethyl (hydroxyimino)cyanoacetate (125 mg), EDC (165 mg) and $NaHCO_3$ (250 mg). After stirring for 1 h at RT, a mixture of (3S)-3-(6-methoxy-pyrazin-2-yl)isoxazolidine trifluoroacetic acid (I-58, 60 mg) and DMF (3 ml) was added. After stirring for 2 h at RT, the reaction mixture was diluted with EA and washed with water. The organic layer was washed with saturated solutions of $NH_4Cl$, $NaHCO_3$ and NaCl, respectively, and concentrated. The residue was purified by preparative RP HPLC (flow 120 ml/min, $H_2O$/0.1% TFA:ACN 90:10 to 10:90 in 8 min; Waters Sunfire Prep C18 OBD—5 μm, 50×100 mm). The product containing fractions were combined, the ACN was removed in vacuo and the aqueous phase was lyophilised to obtain the title compound (102 mg).

LC/MS: m/z=432.2 $[M+H]^+$; tR: 1.60 min (LC/MS-method A)

Ex. 178

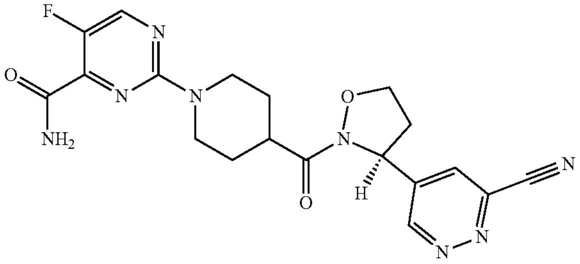

2-[4-[(3S)-3-(6-Cyanopyridazin-4-yl)isoxazolidine-2-carbonyl]-1-piperidyl]-5-fluoro-pyrimidine-4-carboxamide 5-[(3S)-Isoxazolidin-3-yl]pyridazine-3-carbonitrile (I-54, 13 mg) was dissolved in dry DMF (2.0 ml). DIPEA (50 μl) and 1-(4-carbamoyl-5-fluoro-pyrimidin-2-yl)piperidine-4-carboxylic acid (I-34, 21 mg) were added with stirring. After 15 min HATU (58 mg) was added and stirring was continued for 0.5 h. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 25 ml/min, 95% $H_2O$/5% ACN to 10% $H_2O$/90% ACN in 40 min; Purospher® STAR-RP (10 μm, 25×100 mm)). The product containing fractions were combined and the ACN was removed in vacuo and the aqueous phase was lyophilised overnight to yield 6 mg of the title compound.

LC/MS: m/z=427.2 $[M+H]^+$; tR: 1.43 min (LC/MS-method A)

$^1H$ NMR (400 MHz, DMSO-$d_6$) δ ppm 9.45 (1H), 8.54 (1H), 8.28 (1H), 8.09 (br, 1H), 7.78 (br, 1H), 5.47 (1H), 4.62 (2H), 4.31 (1H), 3.99 (1H), 3.00 (4H), 2.33 (1H), 1.97 (1H), 1.77 (1H), 1.52 (2H)

Analogously to example 178 was prepared:

Ex. 180

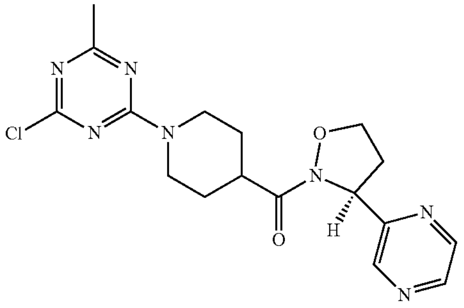

[1-(4-Chloro-6-methyl-1,3,5-triazin-2-yl)-4-piperidyl]-[(3S)-3-pyrazin-2- ylisoxazolidin-2-yl]methanone 4-Piperidyl-[(3S)-3-pyrazin-2-ylisoxazolidin-2-yl]methanone trifluoroacetic acid salt (I-49, 60 mg) was dissolved in dry ACN (3.5 ml) in a microwave vessel (2-5 ml). After DIPEA (111 μl) and 2,4-dichloro-6-methyl-1,3,5-triazine (29 mg) were added, the mixture was heated at 10000 in a microwave oven for 0.5 h. After cooling the solvent was removed in vacuo. The residue was purified by preparative RP HPLC (flow 40 ml/min, 97% $H_2O$/3% ACN to 10% $H_2O$/90% ACN in 15 min; Agilent Prep C18—5 μm, 30×100 m). The product containing fractions were combined, the ACN was removed in vacuo and the aqueous phase was lyophilised over night to yield 20 mg of the title compound.

LC/MS: m/z=390.1 $[M+H]^+$; tR 1.65 min (LC/MS-method A)

| Ex. | acid | structure | LCMS m/z; tR; (yield) | Name |
|---|---|---|---|---|
| 179 | 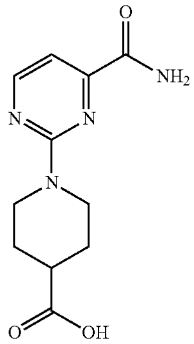 [SMILES: NC(=O)c1ccnc(N2CCC(C(=O)O)CC2)n1] I-22-1 | 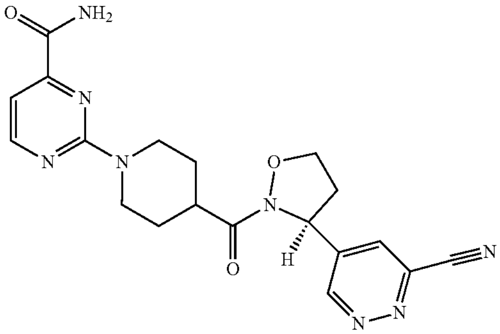 [SMILES: N#Cc1cc([C@@H]2CCON2C(=O)C2CCN(c3nccc(C(N)=O)n3)CC2)cnn1] | 409.2 (method A) 1.39 min (14 mg, 31 %) | 2-[4-[(3S)-3-(6-cyanopyridazin-4-yl)isoxazolidine-2-carbonyl]-1-piperidyl]pyrimidine-4-carboxamide |

Analogously to example 180 was prepared:

| Ex. | Chloro moiety | structure | LCMS [A] m/z; tR; (yield) | Name |
|---|---|---|---|---|
| 181 | 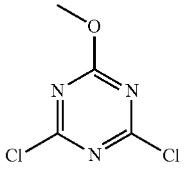 | 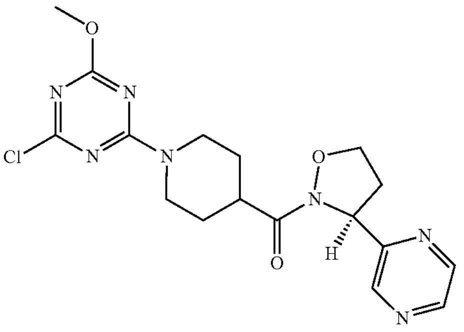 [SMILES: COc1nc(Cl)nc(N2CCC(C(=O)N3OCC[C@H]3c3cnccn3)CC2)n1] | 406.2 (method A) 1.72 min (27 mg, 41 %) | [1-(4-chloro-6-methoxy-1,3,5-triazin-2-yl)-4-piperidyl]-[(3S)-3-pyrazin-2-ylisoxazolidin-2-yl]methanone |

Analogously to example 109 was prepared:

| Ex. | Acid | isoxazolidine | structure | LCMS (method A) m/z; tR; (yield) | Name |
|---|---|---|---|---|---|
| 182 | 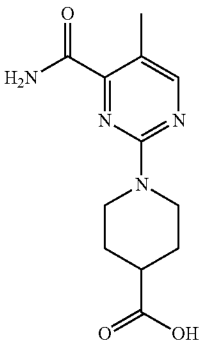 [SMILES: Cc1cnc(N2CCC(C(=O)O)CC2)nc1C(N)=O] I-67 | 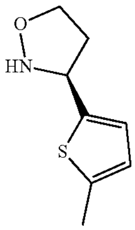 I-65 | 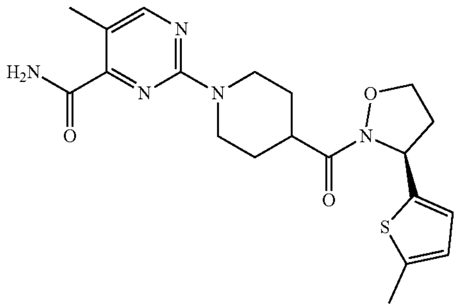 [SMILES: Cc1ccc([C@@H]2CCON2C(=O)C2CCN(c3ncc(C)c(C(N)=O)n3)CC2)s1] | 416.2 2.03 min (26 mg, 63 %) | 5-methyl-2-[4-[(3S)-3-(5-methyl-2-thienyl) isoxazolidine-2-carbonyl]-1-piperidyl] pyrimidine-4-carboxamide |
| 183 | 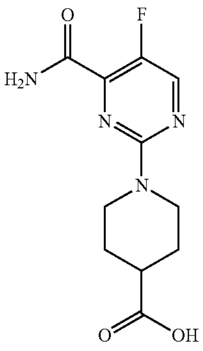 I-34 | 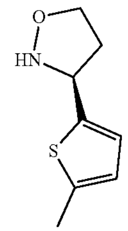 I-65 | 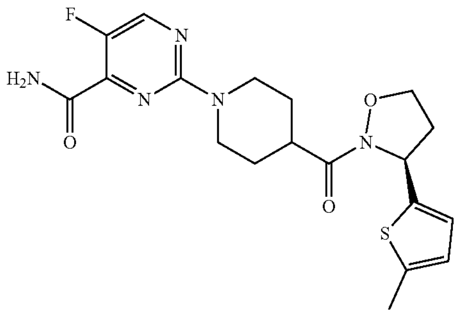 [SMILES: Cc1ccc([C@@H]2CCON2C(=O)C2CCN(c3ncc(F)c(C(N)=O)n3)CC2)s1] | 420.2 1.96 min (25 mg, 60 %) | 5-fluoro-2-[4-[(3S)-3-(5-methyl-2-thienyl) isoxazolidine-4-carboxamide piperidyl] pyrimidine-2-carbonyl]-1- |

Ex. 184

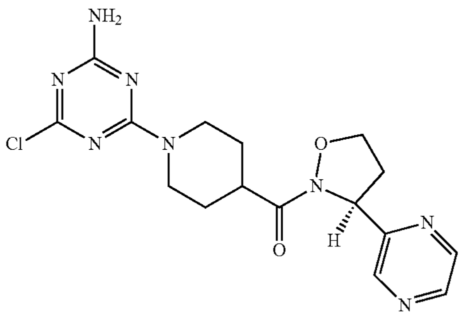

[1-(4-Amino-6-chloro-1,3,5-triazin-2-yl)-4-piperidyl]-[(3S)-3-pyrazin-2- ylisoxazolidin-2-yl]methanone 4-Piperidyl-[(3S)-3-pyrazin-2-ylisoxazolidin-2-yl]methanone trifluoro acetic acid salt (I-49, 60 mg) was dissolved in dry ACN (3.5 ml) in a microwave vessel (2-5 ml). After DIPEA (111 µl) and 4,6-dichloro-1,3,5-triazin-2-amine (29 mg) were added, the mixture was heated at 100° C. in a microwave oven for 0.5 h. After cooling the solvent was removed in vacuo. The residue was purified by preparative RP HPLC (flow 25 ml/min, 95% $H_2O$/5% ACN to 10% $H_2O$/90% ACN in 45 min; Purosphere® STAR-RP (10 µm, 25×100 mm)). The product containing fractions were combined, the ACN was removed in vacuo and the aqueous phase was lyophilised over night to yield 27 mg of the title compound.

LC/MS: m/z=391.1 $[M+H]^+$; tR: 1.39 min (LC/MS-method A)

$^1$H NMR (400 MHz, DMSO-$d_6$) δ ppm 8.60 (3H), 7.32 (br, 1H), 7.27 (br, 1H), 5.43 (1H), 4.48 (2H), 4.33 (1H), 4.00 (1H), 3.02 (3H), 2.84 (1H), 2.50 (DMSO+1H?), 1.87 (1H), 1.75 (1H), 1.45 (2H)

Ex. 185 and 186

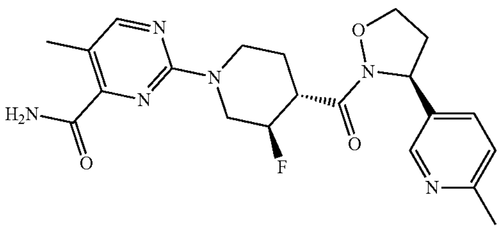

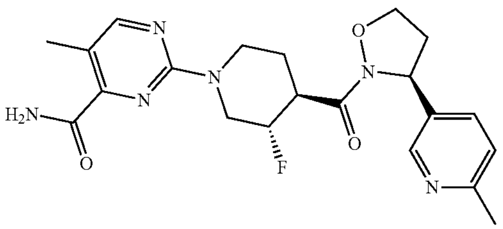

2-[(3R,4R or 3S,4S)-3-fluoro-4-[(3S)-3-(6-methyl-3-pyridyl)isoxazolidine-2-carbonyl]-1-piperidyl]-5-methyl-pyrimidine-4-carboxamide and 2-[(3S,4S or 3R,4R)-3-fluoro-4-[(3S)-3-(6-methyl-3-pyridyl)isoxazolidine-2-carbonyl]-1-piperidyl]-5-methyl-pyrimidine-4-carboxamide (3S)-3-(6-methyl-3-pyridyl)isoxazolidine trifluoroacetic acid salt (I-60, 27.8 mg, 100.0 µmol), 1-(4-carbamoyl-5-methyl-pyrimidin-2-yl)-3-fluoro-piperidine-4-carboxylic acid (I-70, equimolar mixture of RR and SS enantiomer, 31.0 mg, 110.0 µmol) and HATU (57.0 mg, 150.0 µmol) were dissolved in DMF (0.5 ml), DIPEA (61 µl, 350.0 µmol) was added and the reaction mixture was stirred at room temperature for 1 hour. The reaction suspension was filtered and purified by preparative RP HPLC (50 ml/min, 95% $H_2O$/5% ACN to 0% $H_2O$/100% ACN in 20 min; Luna® C18—5 µm, 30×100 mm). The pure product containing fractions were combined and the ACN was removed in vacuo. The aqueous solution was lyophilised to yield 5 mg (12%) of peak 1 and 6.5 mg (15%) of peak 2.

Peak 1:

LC/MS: m/z=429.2 $[M+H]^+$; tR: 1.15 min (LC/MS-method A)

Peak 2:

LC/MS: m/z=429.2 $[M+H]^+$; tR: 1.16 min (LC/MS-method A)

Analogously to example 109 was prepared:

| Ex. | Acid | isoxazolidine | structure | LCMS (method A) m/z; tR; (yield) | Name |
|---|---|---|---|---|---|
| 187 | 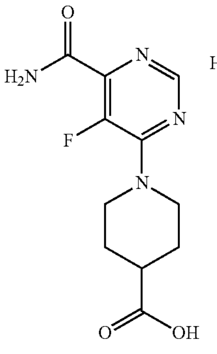 I-69 | 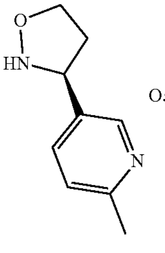 I-60 | 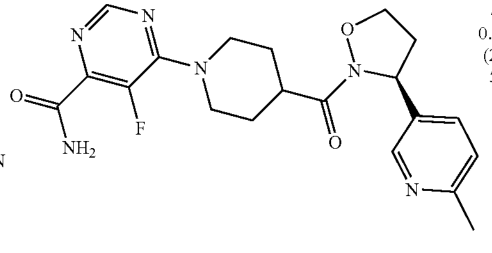 | 415.2 0.94 min (22 mg, 53 %) | 5-fluoro-6-[4-[(3S)-3-(6-methyl-3-pyridyl) isoxazolidine-2-carbonyl]-1-piperidyl] pyrimidine-4-carboxamide; trifluoroacetic acid |

Ex. 188

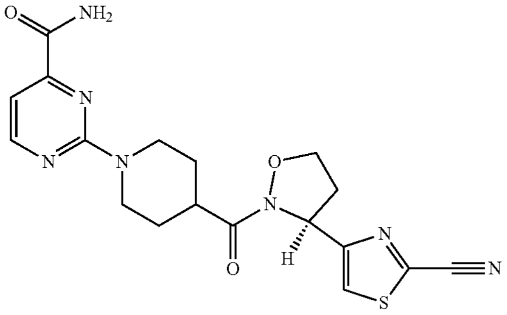

2-[4-[(3S)-3-(2-Cyanothiazol-4-yl)isoxazolidine-2-carbonyl]-1-piperidyl]pyrimidine-4-carboxamide 4-[(3S)-Isoxazolidin-3-yl]thiazole-2-carbonitrile (1-55, 14 mg) was dissolved in dry DMF (2.0 ml). DIPEA (40 μl) and 1-(4-carbamoylpyrimidin-2-yl)piperidine-4-carboxylic acid hydrochloride salt (I-22, 18 mg) were added with stirring. After 15 min HATU (46 mg) was added and stirring was continued for 0.5 h. The reaction mixture was diluted with half-saturated $NaHCO_3$ solution and extracted with EA (3×). The combined EA phases were washed with brine, dried with $Na_2SO_4$, filtered and concentrated. The residue was purified by preparative RP HPLC (flow 25 ml/min, 95% $H_2O$/5% ACN to 10% $H_2O$/90% ACN in 40 min; Purospher® STAR-RP (10 μm, 25×100 mm)). The product containing fractions were combined and the ACN was removed in vacuo and the aqueous phase was lyophilised overnight to yield 6 mg of the title compound.

LC/MS: m/z=414.1 $[M+H]^+$; tR: 1.58 min (LC/MS-method A)

Ex. 189

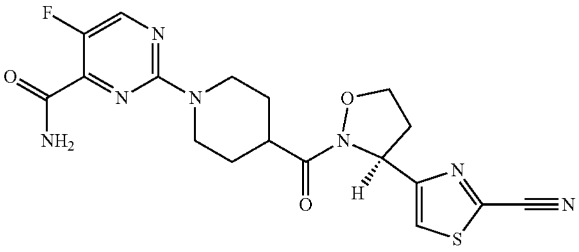

2-[4-[(3S)-3-(2-Cyanothiazol-4-yl)isoxazolidine-2-carbonyl]-1-piperidyl]-5-fluoro- pyrimidine-4-carboxamide 1-(4-Carbamoyl-5-fluoro-pyrimidin-2-yl)piperidine-4-carboxylic acid (I-34, 28 mg) was treated as described in ex. 188 to yield 10 mg (25%) of the title compound.

LC/MS: m/z=432.1 $[M+H]^+$; tR: 1.62 min (LC/MS-method A)

$^1H$ NMR (400 MHz, DMSO-$d_6$) δ ppm 8.54 (1H), 8.09 (br, 1H), 8.03 (1H), 7.78 (br, 1H), 5.54 (1H), 4.61 (2H), 4.30 (1H), 3.96 (1H), 3.02 (3H), 2.83 (1H), 2.44 (1H), 1.87 (1H), 1.74 (1H), 1.50 (2H)

Reference Compound K

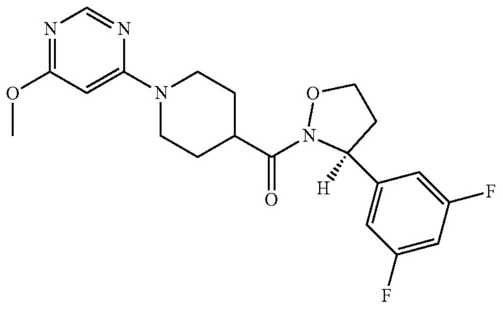

[1-(6-Methoxypyrimidin-4-yl)-4-piperidyl]-[(3S)-3-(3,5-difluorophenyl)isoxazolidin-2-yl]methanone (S)-(3-(3,5-Difluorophenyl)isoxazolidin-2-yl)(piperidin-4-yl)methanone HCl salt (I-71, 200 mg) and 4-chloro-6-methoxypyrimidine (133 mg) were mixed in dry ACN (4 ml) in a microwave vessel (2-5 ml). After DIPEA (525 µl) was added, the mixture was heated at 120° C. in a microwave oven for 1 h. After cooling water was added to the mixture which was purified in 3 runs by preparative RP HPLC (flow 50 ml/min, A: $H_2O$, B: ACN, B: 10% for 1 min, to 100% in 12 min, 100% for 2 min; Agilent Prep C18—10 µm, 30×100 mm). The product containing fractions were combined, the ACN was removed in vacuo and the aqueous phase was lyophilised over night to yield 154 mg of the title compound.

LC/MS: m/z=405.3 $[M+H]^+$; tR: 1.88 min (LC/MS-method A)

$^1H$ NMR (400 MHz, DMSO-$d_6$) δ ppm 8.23 (1H), 7.13 (1H), 6.98 (2H), 6.08 (1H), 5.35 (1H), 4.28 (3H), 3.90 (1H), 3.81 (3H), 3.10-1.82 (4H), 2.20 (1H), 1.90 (1H), 1.71 (1H), 1.48 (2H)

Evaluation of Receptor-Interacting Protein Kinase 1 Inhibition.

The catalytic activity of RIPK1 was measured by monitoring the conversion of Adenosine triphosphate (ATP) to Adenosine diphosphate (ADP) due to autophosphorylation using an ADP-Glo kinase kit (Promega, catalog no. V9104).

In detail, 2 µl recombinantly produced hRIPK1 (aa 1-375) fusion protein (end concentration 3.6 µg/ml) and 2 µl compound (end concentration 33300—1.69 nM, DMSO end concentration 1%) were incubated for 30 minutes at RT and then 2 µl ATP (ADP Glo kit, end concentration 50 µM) were added. After another 240 minutes incubation at room temperature, 5 µl Promega ADP-Glo reagent I were added to quench the reaction and deplete unconsumed ATP. After an incubation period of 30 minutes, 10 µl Promega ADP-Glo detection reagent II were added resulting in conversion of ADP to ATP, which generates a light-reaction between luciferase and luciferin. Luminescence was quantified after 30 minutes with a Pherastar FS (BMG LABTECH, Ortenberg).

For the dose response experiments an $IC_{50}$ value with 95% confidence interval was calculated using the 4-parameter logistic model according to Ratkowsky and Reedy with constraints for lower and upper asymptotes at 0% and 100%. The adjustment was obtained by nonlinear regression using the Levenberg Marquardt algorithm.

Results are shown in Table 1 (ADP-Glo IC50 (µM))

| example | ADP-Glo IC50 (µM) |
|---|---|
| 1 | 0.03256 |
| 2* | 0.132 |
| 3 | 0.0704 |
| 4 | 0.0238 |
| 5 | 0.0353 |
| 6* | 0.567 |
| 7* | 0.0649 |
| 8* | 0.306 |
| 9 | 4.69 |
| 10 | 0.012 |
| 11 | 0.0245 |
| 12* | 0.305 |
| 13* | 3.01 |
| 14* | 0.729 |
| 15* | 13.1 |
| 16 | 18.8 |
| 17 | 0.056 |
| 18 | 0.0116 |
| 19 | 0.0235 |
| 20 | 0.0107 |
| 21 | 0.0704 |
| 22 | >33 |
| 23* | 0.797 |
| 24* | 0.156 |
| 25* | 0.0516 |
| 26 | 0.0627 |
| 27 | 0.0239 |
| 28 | 0.0173 |
| 29* | 0.0812 |
| 30* | 0.247 |
| 31* | 0.0515 |
| 32* | 0.18 |
| 33 | 0.511 |
| 34 | 6.04 |
| 35 | 0.0661 |
| 36* | 0.0489 |
| 37* | 0.0315 |
| 38* | 0.0899 |
| 39 | 0.0501 |
| 40* | 0.864 |
| 41* | 2.8 |
| 42* | 0.193 |
| 43 | 0.0384 |
| 44 | 0.009313 |
| 45 | 0.0172 |
| 46* | 0.0651 |
| 47* | 0.0649 |
| 48* | 0.0332 |
| 49* | 0.00999 |
| 50* | 0.0267 |
| 51* | 0.134 |
| 52* | 0.043 |
| 53 | 0.0117 |
| 54* | 0.767 |
| 55 | 0.101 |
| 56 | 0.0425 |
| 57 | 0.0309 |
| 58 | 0.935 |
| 59 | 0.0208 |
| 60 | 0.43 |
| 61 | 0.03907 |
| 62 | 0.0141 |
| 63 | 0.0134 |
| 64 | 0.0204 |
| 65 | 0.0656 |
| 66 | 0.0351 |
| 67 | 0.0848 |
| 68 | 0.01471 |
| 69 | >33 |
| 70 | 0.00676 |
| 71 | 0.0256 |
| 72 | 0.025 |
| 73 | 0.011 |
| 74 | 0.00828 |

-continued

| example | ADP-Glo IC50 (μM) |
|---|---|
| 75 | 0.008461 |
| 76 | 0.331 |
| 77 | 0.0281 |
| 78 | 0.0529 |
| 79 | 0.627 |
| 80 | 0.01034 |
| 81 | 0.0157 |
| 82 | 0.00887 |
| 83 | 0.0161 |
| 84 | 0.0121 |
| 85 | 0.0153 |
| 86 | 0.0947 |
| 87 | 0.00955 |
| 88 | 0.0336 |
| 89* | 0.396 |
| 90 | 0.0126 |
| 91 | 0.0149 |
| 92 | 0.0122 |
| 93 | 0.00416 |
| 94 | 0.0102 |
| 95 | 0.0305 |
| 96 | 0.026 |
| 97 | 0.02398 |
| 98 | 0.01375 |
| 99 | 0.0223 |
| 100 | 0.0245 |
| 101 | 0.036 |
| 102 | 0.443 |
| 103 | 0.0175 |
| 104 | 0.0134 |
| 104,1 | 0.0214 |
| 105 | 0.0112 |
| 106 | 0.0429 |
| 107 | 0.364 |
| 108 | 0.0816 |
| 109 | 0.0193 |
| 110 | 0.0173 |
| 111 | 0.0282 |
| 112 | 0.0488 |
| 113 | 0.122 |
| 114 | 0.014 |
| 115 | 0.0247 |
| 116 | 0.0214 |
| 117 | 0.0374 |
| 118 | 0.0246 |
| 119 | 0.0211 |
| 120 | 0.0188 |
| 121 | >33 |
| 122 | 0.0293 |
| 123 | 0.0263 |
| 124 | 0.0392 |
| 125 | 0.161 |
| 126 | 0.025 |
| 127 | 0.0241 |
| 128 | 0.0698 |
| 129 | 0.0386 |
| 130 | 0.0223 |
| 131 | 0.0239 |
| 132 | 0.0251 |
| 133 | 0.0198 |
| 134 | 0.0416 |
| 135 | 0.0813 |
| 136 | 0.0217 |
| 137 | 0.02162 |
| 138 | 0.0281 |
| 139 | 0.0336 |
| 140 | 0.0713 |
| 141 | 0.0819 |
| 142 | 0.407 |
| 143 | 0.323 |
| 144 | 0.0752 |
| 145 | 0.0466 |
| 146 | 0.0458 |
| 147 | 0.0306 |
| 148 | 0.321 |

-continued

| example | ADP-Glo IC50 (μM) |
|---|---|
| 149 | 0.37 |
| 150 | 0.069 |
| 151 | 0.1 |
| 152 | 0.132 |
| 153 | 0.102 |
| 154 | 0.0219 |
| 155 | 0.0165 |
| 156 | 0.297 |
| 157 | 0.0439 |
| 158 | 0.0197 |
| 159 | 0.0318 |
| 161 | 0.0202 |
| 162 | 0.0201 |
| 163 | 0.0208 |
| 164 | 17.5 |
| 165 | 0.025 |
| 166 | 0.0372 |
| 167 | 0.0311 |
| 168 | 0.0454 |
| 169 | 0.0234 |
| 170 | 0.0217 |
| 171 | 0.0519 |
| 174 | 0.021 |
| 175 | 0.0223 |
| 176 | 0.022 |
| 177* | 0.0143 |
| 178 | 0.112 |
| 179 | 0.173 |
| 180 | 0.032 |
| 181 | 0.0165 |
| 182 | 0.0156 |
| 183 | 0.0153 |
| 184 | 0.00326 |
| 185 | 0.297 |
| 186 | 0.0384 |
| 187 | 0.0659 |
| 188 | 0.0592 |
| 189 | 0.0303 |

Cellular Assay in U937 Cells to Measure the Activity of RIPK1-Inhibitors on Cell Death (Necroptosis).

Upon TNF-Receptor I ligation, Ser/Thr kinase RIPK1 is recruited to a transient receptor complex I. Upon modification of RIPK1 which promotes activation of RIPK1, complex IIb can form, that involves recruitment of RIPK3 and MLKL (mixed lineage-kinase domain-like protein) which then translocates from the cytosol to the plasma membrane to execute cell death (Cai, Z. et al, Nat. Cell Biol. (2014) 16:55-65).

Cell death was quantified in 96 well plates by determination of the amount of live cell using a CellTiter 96 AQueous reagent (Promega), a calorimetric method to measure the amount of live cells by reducing tetrazolium compound [3-(4,5-dimethylthiazol-2-yl)-5-(3-carboxymethoxyphenyl)-2-(4-sulfophenyl)-2H-tetrazolium, inner salt; MTS] into formazan. Absorbance of formazan was read at 490 nm. The inhibitory activity of the test compound was quantified in a concentration response curve (CRC) experiment. Compounds were obtained as 10 mM stock solutions and were diluted 1 to 10 volumes with DMSO to yield a 1 mM solution. From this solution 2 μl were diluted with 998 μl growth medium. 100 μl of 2 μM compound solution was further diluted sequentially with a dilution factor of 2.5 by adding 150 μl growth medium. A total of 10 concentrations were tested ranging from 10 μM to 0.26 nM or from 1 μM to 0.07 nM.

U937 cells were cultured in RPMI1640 Glutamax and 10% heat inactivated FBS. 50 μl cell suspension containing 1×106 cells/ml supplemented with 50 μM zVAD.fmk (Benzyloxycarbonyl-Val-Ala-Asp (OMe) fluoromethylketone) and 100 ng/ml recombinant human TNFα were dispensed in each well of a 96-well plate. 50 μl of compound dilutions (see above) were added and the cell suspension incubated overnight (18 to 24 hours) at 37° C., 5% $CO_2$ in a humidified atmosphere (95% rH). High (no compound) and low control (no TNFα, zVAD.fmk) were tested with 7 replicates; all compound concentrations were tested in duplicates on each experimental plate.

CellTiter 96 Aqueous reagent was mixed (100 μl PMS (phenazine methosulfate) solution/2 ml MTS (3-(4,5-dimethyldiazol-2-yl)-5-(3-carboxymethoxyphenyl)-2-(4-sulfophenyl)-2H-tetrazolium, inner salt) solution) and 20 μl were added per well. After 4 hours incubation at 37° C. (5% $CO_2$ 95% rH) optical density was measured at 490 nm on a microplate reader (Tecan Infinite M1000).

The % inhibition is expressed as percentage of the maximal inhibition value obtained in the absence of TNFα/zVAD.fmc. For each dose response experiment an $IC_{50}$ value with 95% confidence interval was calculated using the 4-parameter logistic model according to Ratkowsky and Reedy without constraints using an internal application (Biost@t-Speed LTS V2.3).

Results are shown in Table 2 (U937 IC50 (μM))

| example | U937 IC50 (μM) |
|---|---|
| 1 | 0.1334 |
| 2* | 1.829 |
| 3 | 0.2899 |
| 4 | 0.02212 |
| 5 | 0.1154 |
| 6* | 5.597 |
| 7* | 2.418 |
| 8* | 5.218 |
| 9 | >10 |
| 10 | 0.2096 |
| 11 | 0.0126 |
| 12* | 7.257 |
| 13* | >10 |
| 14* | >10 |
| 15* | nt |
| 16 | nt |
| 17 | 0.343 |
| 18 | 0.0103 |
| 19 | 0.0573 |
| 20 | 0.118 |
| 21 | >10 |
| 22 | >10 |
| 23* | 4.67 |
| 24* | 0.834 |
| 25* | 0.498 |
| 26 | 1.9 |
| 27 | 0.528 |
| 28 | 0.00105 |
| 29* | 2.2 |
| 30* | 4.17 |
| 31* | 0.395 |
| 32* | 2.44 |
| 33 | >10 |
| 34 | >10 |
| 35 | 0.183 |
| 36* | 0.198 |
| 37* | 0.177 |
| 38* | 1.71 |
| 39 | 0.18 |
| 40* | >10 |
| 41* | >10 |
| 42* | 6.01 |
| 43 | 2.7 |
| 44 | 0.008475 |

-continued

| example | U937 IC50 (μM) |
|---|---|
| 45 | 0.0664 |
| 46* | 0.605 |
| 47* | 0.549 |
| 48* | 0.133 |
| 49* | 0.0411 |
| 50* | 0.0329 |
| 51* | 0.678 |
| 52* | 0.0449 |
| 53 | 0.0561 |
| 54* | >10 |
| 55 | 0.844 |
| 56 | 2.2 |
| 57 | 0.11 |
| 58 | 0.3587 |
| 59 | 0.05071 |
| 60 | 7.31 |
| 61 | 0.256 |
| 62 | 0.0124 |
| 63 | 0.0151 |
| 64 | 0.0642 |
| 65 | 0.612 |
| 66 | 0.205 |
| 67 | 0.553 |
| 68 | 0.003249 |
| 69 | >10 |
| 70 | 0.00611 |
| 71 | 0.964 |
| 72 | 0.554 |
| 73 | 0.103 |
| 74 | 0.00975 |
| 75 | 0.002734 |
| 76 | 1.47 |
| 77 | 0.0385 |
| 78 | 0.316 |
| 79 | 1.67 |
| 80 | 0.00337 |
| 81 | 0.0297 |
| 82 | 0.00325 |
| 83 | 0.0495 |
| 84 | 0.0178 |
| 85 | 0.0206 |
| 86 | 8.68 |
| 87 | 0.0505 |
| 88 | 0.158 |
| 89* | 2.16 |
| 90 | 0.0381 |
| 91 | 0.183 |
| 92 | 0.0502 |
| 93 | 0.0193 |
| 94 | 0.185 |
| 95 | 0.12 |
| 96 | 0.204 |
| 97 | 0.04148 |
| 98 | 0.03247 |
| 99 | 0.054 |
| 100 | 0.471 |
| 101 | 0.442 |
| 102 | >10 |
| 103 | 0.00144 |
| 104 | 0.736 |
| 104,1 | 0.00367 |
| 105 | 7.94 |
| 106 | 0.548 |
| 107 | 7.52 |
| 108 | 1.01 |
| 109 | 0.00531 |
| 110 | 0.00169 |
| 111 | 0.0116 |
| 112 | 0.0755 |
| 113 | 0.773 |
| 114 | 0.00785 |
| 115 | 0.0627 |
| 116 | 0.0045 |
| 117 | 0.0684 |
| 118 | 0.00761 |

-continued

| example | U937 IC50 (μM) |
|---|---|
| 119 | 0.00555 |
| 120 | 0.00169 |
| 121 | 4.44 |
| 122 | 0.0442 |
| 123 | 0.0442 |
| 124 | 0.0313 |
| 125 | 8.65 |
| 126 | 0.0396 |
| 127 | 0.0533 |
| 128 | 0.224 |
| 129 | 0.0376 |
| 130 | 0.0222 |
| 131 | 0.034 |
| 132 | 0.0319 |
| 133 | 0.0494 |
| 134 | 0.148 |
| 135 | 0.491 |
| 136 | 0.0204 |
| 137 | 0.01651 |
| 138 | 0.0972 |
| 139 | 0.0447 |
| 140 | 0.55 |
| 141 | 0.254 |
| 142 | 3 |
| 143 | 1.76 |
| 144 | 0.536 |
| 145 | 0.149 |
| 146 | 0.229 |
| 147 | 0.0569 |
| 148 | 2.21 |
| 149 | 6.17 |
| 150 | 0.0235 |
| 151 | 0.025 |
| 152 | 0.128 |
| 153 | 0.0998 |
| 154 | 0.0388 |
| 155 | 0.00406 |
| 156 | 0.927 |
| 157 | 0.114 |
| 158 | 0.0197 |
| 159 | 0.0771 |
| 161 | 0.02 |
| 162 | 0.00541 |
| 163 | 0.00604 |
| 164 | 1.97 |
| 165 | 0.0527 |
| 166 | 0.0597 |
| 167 | 0.048 |
| 168 | 0.0792 |
| 169 | 0.119 |
| 170 | 0.0165 |
| 171 | 0.0858 |
| 174 | 3.03 |
| 175 | 0.0446 |
| 176 | 0.00371 |
| 177* | 0.00586 |
| 178 | 1.3 |
| 179 | 2.03 |
| 180 | 1.05 |
| 181 | 0.0301 |
| 182 | 0.00701 |
| 183 | 0.000675 |
| 184 | 0.00179 |
| 185 | 1.15 |
| 186 | 0.148 |
| 187 | 0.321 |
| 188 | 0.204 |
| 189 | 0.102 |

nt: not tested

It is understood that the examples and embodiments described herein are for illustrative purposes only and that various modifications or changes in light thereof will be suggested to persons skilled in the art and are to be included within the spirit and purview of this application and scope of the appended claims.

Calculation of TPSA Using Optibrium's Stardrop Version 6.5.0

Topological polar surface area (TPSA) is calculated based on the method described by Ertl and co-workers (Ertl, Rhodes & Selzer, J. Med. Chem. 2000, 43, 3714-3717) as implemented in the StarDrop Version 6.5.0 using only N and O containing fragments for the summation to compute TPSA. Results are shown in table 3, (TPSA (Å$^2$)).

| example | TPSA (Å2) |
|---|---|
| 1 | 138.3 |
| 2* | 119.5 |
| 3 | 127.4 |
| 4 | 138.3 |
| 5 | 119 |
| 6* | 100.2 |
| 7* | 100.2 |
| 8* | 119.5 |
| 9 | 132.5 |
| 10 | 121.5 |
| 11 | 119 |
| 12* | 118.9 |
| 13* | 99.65 |
| 14* | 99.65 |
| 15* | 118.9 |
| 16 | 138.3 |
| 17 | 106.1 |
| 18 | 128.3 |
| 19 | 138.3 |
| 20 | 121.5 |
| 21 | 132.5 |
| 22 | 134.8 |
| 23* | 110.9 |
| 24* | 110.9 |
| 25* | 134.8 |
| 26 | 125.4 |
| 27 | 130.8 |
| 28 | 128.3 |
| 29* | 157.6 |
| 30* | 157.6 |
| 31* | 115.5 |
| 32* | 134.8 |
| 33 | 141.8 |
| 34 | 161.1 |
| 35 | 147.6 |
| 36* | 140.6 |
| 37* | 121.3 |
| 38* | 140.6 |
| 39 | 121.3 |
| 40* | 143.6 |
| 41* | 143.6 |
| 42* | 124.3 |
| 43 | 143.6 |
| 44 | 127.4 |
| 45 | 108.1 |
| 46* | 119.5 |
| 47* | 100.2 |
| 48* | 114.5 |
| 49* | 95.24 |
| 50* | 114.5 |
| 51* | 97.75 |
| 52* | 95.24 |
| 53 | 138.3 |
| 54* | 108.8 |
| 55 | 134.9 |
| 56 | 115.6 |
| 57 | 121.5 |
| 58 | 132.5 |
| 59 | 138.3 |
| 60 | 134.9 |
| 61 | 127.4 |
| 62 | 117.4 |
| 63 | 117.4 |

-continued

| example | TPSA (Å2) |
|---|---|
| 64 | 93.57 |
| 65 | 95.24 |
| 66 | 119 |
| 67 | 119 |
| 68 | 138.3 |
| 69 | 114.5 |
| 70 | 114.5 |
| 71 | 138.3 |
| 72 | 138.3 |
| 73 | 138.3 |
| 74 | 127.4 |
| 75 | 127.4 |
| 76 | 127.6 |
| 77 | 153.9 |
| 78 | 153.9 |
| 79 | 127.6 |
| 80 | 114.5 |
| 81 | 138.3 |
| 82 | 127.4 |
| 83 | 114.5 |
| 84 | 114.5 |
| 85 | 138.3 |
| 86 | 136.4 |
| 87 | 127.4 |
| 88 | 153.9 |
| 89* | 127.4 |
| 90 | 127.4 |
| 91 | 108.1 |
| 92 | 138.3 |
| 93 | 138.3 |
| 94 | 138.3 |
| 95 | 138.3 |
| 96 | 138.3 |
| 97 | 127.4 |
| 98 | 114.5 |
| 99 | 127.4 |
| 100 | 121.5 |
| 101 | 157.6 |
| 102 | 132.5 |
| 103 | 95.24 |
| 104 | 112.3 |
| 104.1 | 95.24 |
| 105 | 129.4 |
| 106 | 138.3 |
| 107 | 138.3 |
| 108 | 138.3 |
| 109 | 114.8 |
| 110 | 114.8 |
| 111 | 119 |
| 112 | 119 |
| 113 | 95.24 |
| 114 | 104.5 |
| 115 | 138.3 |
| 116 | 93.57 |
| 117 | 104.5 |
| 118 | 151.2 |
| 119 | 151.2 |
| 120 | 108.1 |
| 121 | 132.5 |
| 122 | 127.4 |
| 123 | 119 |
| 124 | 108.1 |
| 125 | 115.5 |
| 126 | 114.5 |
| 127 | 95.24 |
| 128 | 95.24 |
| 129 | 114.5 |
| 130 | 95.24 |
| 131 | 95.24 |
| 132 | 114.5 |
| 133 | 95.24 |
| 134 | 114.5 |
| 135 | 114.5 |
| 136 | 95.24 |
| 137 | 114.5 |
| 138 | 95.24 |

-continued

| example | TPSA (Å2) |
|---|---|
| 139 | 114.5 |
| 140 | 95.24 |
| 141 | 114.5 |
| 142 | 114.5 |
| 143 | 95.24 |
| 144 | 104.5 |
| 145 | 119 |
| 146 | 95.24 |
| 147 | 95.24 |
| 148 | 121.3 |
| 149 | 121.5 |
| 150 | 95.49 |
| 151 | 114.8 |
| 152 | 95.49 |
| 153 | 114.8 |
| 154 | 138.3 |
| 155 | 138.3 |
| 156 | 138.3 |
| 157 | 95.24 |
| 158 | 95.24 |
| 159 | 95.24 |
| 161 | 95.24 |
| 162 | 95.49 |
| 163 | 95.49 |
| 164 | 121.6 |
| 165 | 95.24 |
| 166 | 125.4 |
| 167 | 138.6 |
| 168 | 125.4 |
| 169 | 95.24 |
| 170 | 114.5 |
| 171 | 138.6 |
| 174 | 97.23 |
| 175 | 114.5 |
| 176 | 101.6 |
| 177* | 136.7 |
| 178 | 151.2 |
| 179 | 151.2 |
| 180 | 97.23 |
| 181 | 106.5 |
| 182 | 101.6 |
| 183 | 101.6 |
| 184 | 123.3 |
| 185 | 114.5 |
| 186 | 114.5 |
| 187 | 114.5 |
| 188 | 138.3 |
| 189 | 138.3 |

Pharmacokinetic Studies in Rats

Ex. 004, 068, 075

A suspension of the test article (18 mg/kg, 6 ml/kg, 3 mg/ml) was made in 0.6% methyl cellulose (MC) by thorough mixing of the fine solid with a freshly prepared and filtered MC solution and administered to 6 non-fasted male Sprague-Dawley rats (350-400 g) by gavage. Serial sampling of blood (with the addition of K3-EDTA) was performed at 0.25, 0.5, 1, 2, 4, 6, 8 and 24 h post admin. Plasma was generated by centrifugation and deep-frozen (−20° C.). After 2 h, 3 of the 6 animals were sacrificed and brain and liver excised. Additional plasma was generated from terminal blood. The organs were homogenized and the homogenate extracted with an acetonitrile-water mixture prior to measurement by HPLC-MS/MS. The brain/plasma ratio was determined at 2 h by dividing the brain concentration at 2 h through the respective value for the plasma concentration at 2 h.

Pharmacokinetic Studies in Mice

Oral Application Ex. 004, 044, G, K

A suspension of the respective test articles (30 mg/kg, 10 ml/kg, 3 mg/ml) was prepared in 0.6% methyl cellulose (MC) by thorough mixing of the fine solid with the freshly made and filtered MC solution and administered to 24 non-fasted male C57BL/6 mice (20-25 g) by gavage. Terminal blood sampling (with the addition of K2-EDTA) was performed at 0.25, 0.5, 1, 2, 4, 6, 8 and 24 h post admin. Plasma was generated by centrifugation and deep-frozen (−20° C.). In addition, after 2 h, brain and liver were removed from the respective 3 mice. Additional plasma was collected from terminal blood. The organs were pooled, homogenized and the homogenate extracted with an acetonitrile-water mixture prior to measurement by HPLC-MS/MS. The brain/plasma ratio was determined at 2 h by dividing the brain concentration at 2 h through the respective value for the plasma concentration at 2 h.

Ex. 004: 21 mice were used in the study, without the 6 h sampling time. The same study design was applied.

A, D, E

A suspension of the respective test articles (30 mg/kg, 10 ml/kg, 3 mg/ml) was prepared in freshly prepared and filtered 0.6% methyl cellulose solution by wet-milling using Retsch MM 301 mixer mill (10 min, room temperature) and administered to 6 non-fasted male C57BL/6 mice (20-25 g) by gavage. Serial sampling of blood (with the addition of K3-EDTA) was performed at 0.25, 0.5, 1, 2, 4, 6, 8 and 24 h post admin. The blood samples were diluted (10 μl blood were added to a mixture of 90 μl 25% acetonitrile in water) and deep-frozen (−20° C.). After 2 h, 3 of the 6 animals were sacrificed and brain and liver taken off. Additional plasma was prepared from terminal blood. The organs were homogenized and the homogenate extracted with an acetonitrile-water mixture prior to measurement by HPLC-MS/MS. The brain/plasma ratio was determined at 2 h by dividing the brain concentration at 2 h through the respective value for the plasma concentration at 2 h.

Intravenous Application with Non-Serial Sampling Compound K

A solution of the respective test articles (3 mg/kg, 5 mL/kg, 0.6 mg/mL) was prepared by dissolving the solids in 7.5% N-Methyl pyrrolidon followed by addition of 60% PEG200 and 32.5% water for injection. Intravenous administration to 24 (3×8, groups per time) non-fasted male C57BL/6 mice (20-25 g) followed immediately after preparation. Terminal blood sampling (with the addition of K2-EDTA) was performed at 0.083, 0.25, 0.5, 1, 2, 4, 8 and 24 h post admin. Plasma was generated by centrifugation and deep-frozen (−20° C.). In addition, brain and liver were removed from all animals. The organs were pooled per time group, homogenized and the homogenate extracted with an acetonitrile-water mixture prior to measurement by HPLC-MS/MS. The brain/plasma ratio was determined by dividing the brain concentration through the respective value for the plasma concentration at the same sampling time.

Pharmacokinetic Studies in Cynomolgus Monkeys

Intra Venous Application

Ex. 004, Ex. 068

A solution of the respective test article (1 mg/kg, 0.2 ml/kg, 5 mg/ml) was prepared by dissolving the solid in 7.5% N-Methyl pyrrolidon followed by addition of 50% PEG200 and 42.5% water for injection (in case of example 068) or by dissolving in 5% NMP followed by addition of 20% PEG200 and 75% water for injection in case of example 004.

Intravenous administration was done immediately after preparation of the formulation to 3 non-fasted male cynomolgus monkeys (approx. 4.5 kg). Blood sampling (with the addition of K3-EDTA) was performed at 0.083, 0.25, 0.5, 1, 2, 4, 8 and 24 h post admin. Plasma was generated by centrifugation and deep-frozen (−20° C.) followed by addition of acetonitrile and standard workup of the extract prior to measurement by HPLC-MS/MS. Urine samples were taken from 0-8 and 8-24 h sampling intervals, acetonitrile extracts generated and test article concentration determined by HPLC-MSMS.

Compound K

A solution of the respective test article (1 mg/kg, 0.2 ml/kg, 5 mg/ml) was prepared by dissolving the solid in 7.5% N-Methyl pyrrolidone, 60% PEG200 and 32.5% water for injection. Intravenous administration followed immediately after preparation to 3 non-fasted male cynomolgus monkeys (approx. 3.5 kg). Blood sampling (with the addition of K3-EDTA) was performed at 0.083, 0.25, 0.5, 1, 2, 4, 8 and 24 h post admin. Plasma was generated by centrifugation and deep-frozen (−20° C.) followed by addition of acetonitrile and standard workup of the extract prior to measurement by HPLC-MS/MS.

When the brain permeable comparator compound K, a close analogue of the isoxazolidine derivatives claimed in WO2019130230 and WO2020043173, was applied to cynomolgus monkeys (1 mg/kg, i.v.) severe side effects were observed (hypoactivity followed by decubitus, hyporeactivity, limb stiffness and hypotonic with phases of prostration). Histopathological examination revealed bilateral and symmetrical lesions of brain necrosis (i.e., malacia) located in the basal ganglia (globus pallidus) and the hypothalamic area, consisting of neuronal necrosis, spongiosis, cellular infiltration dominated by a population of macrophages, and reactive neocapillaries.

The isoxazolidine derivative, comparator compound K, possessing severe CNS related side effects in the monkey as described above shows a TPSA of 68 $Å^2$. In the mouse 15 min after i.v. application of 3 mg/kg a brain/blood ratio of 2.1 and brain levels of 1.58 μg/ml were observed confirming the good brain permeability of this kind of compounds. 2 h after oral application of 30 mg/kg to the mouse a brain/plasma ratio of 1.6 was determined.

Table 4 summarizes the results of selected compounds of the invention. High in vitro activity in combination with high TPSA (>120 $A^2$) values show a low concentration ratio of brain/blood in the animal indicating a low blood/brain barrier penetration.

The comparator compounds of Table 5 were resynthesized according to the given reference and in vitro data measured as described above (for compounds H and I literature data are shown). In vivo data were collected for selected compounds as shown in the table.

In general the structural similar comparator compounds show also good in vitro activity data (for A, D, E G I and K), but the corresponding calculated TPSA values are much lower (<102 $A^2$) resulting in brain/blood concentration ratios around 10 to 20 fold higher than the ones in table 4. A value of 1 means equal concentration in brain and blood, thus a high penetration of the blood/brain barrier.

Key compound table 4:
| # | structure | ADP-Glo IC50 (uM) | U937 IC50 (uM) Mean | TPSA | Mouse/rat PK brain/ blood ratio |
|---|---|---|---|---|---|
| Ex. 004 | 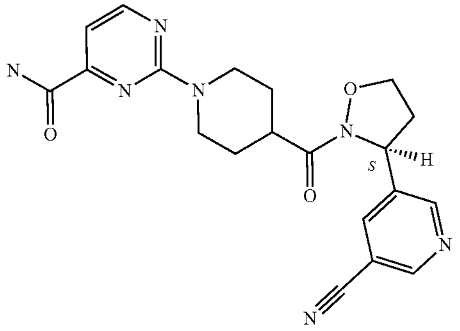 | 0.016 | 0.022 | 138.3 | mouse: 0.1(2 h) rat: 0.05 (2 h) |
| Ex. 044 | 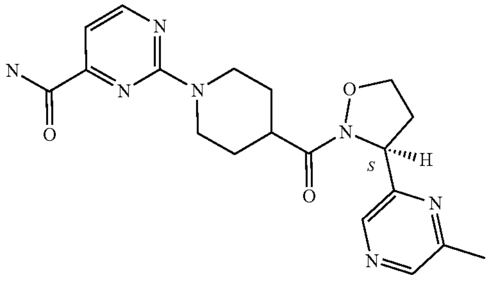 | 0.009 | 0.009 | 127.4 | mouse: 0.12 (2 h) |
| Ex. 068 | 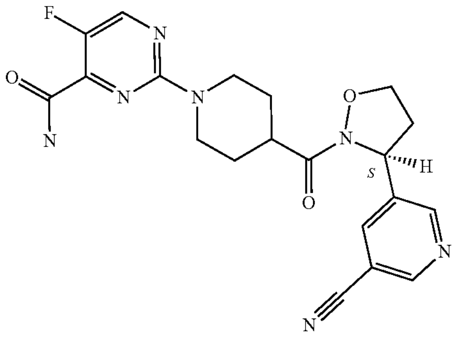 | 0.011 | 0.003 | 138.3 | rat: 0.06 (2 h) |
| Ex. 075 | 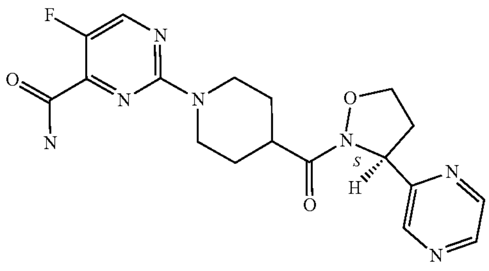 | 0.008 | 0.003 | 127.4 | rat: 0.09 (2 h) |

Comparator table 5:
| # | structure | ADP-Glo IC50 (uM) | U937 IC50 (uM) Mean | TPSA | Mouse PK brain/blood ratio | Reference |
|---|---|---|---|---|---|---|
| A | 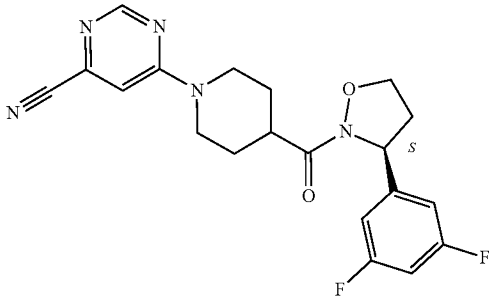 | 0.012 | 0.003 | 82.35 | 0.82 (2 h) | WO2019130230; ex. 8 WO2020043173, ex. 2 |
| B | 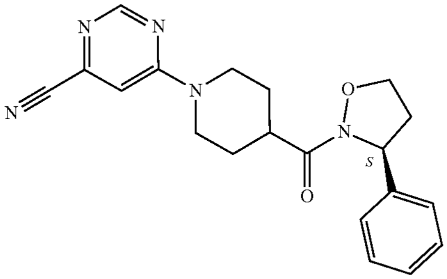 | | | 82.35 | | WO2020043173, ex. 1 |
| C | 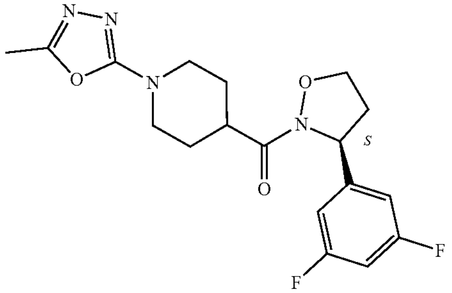 | | | 71.7 | | WO2019130230; ex 5 WO2020043173, ex. 3 |
| D | 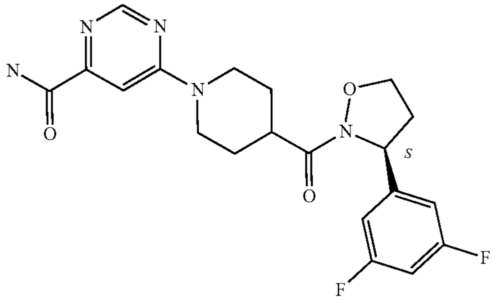 | 0.010 | 0.004 | 101.6 | 1.1 (2 h) | WO2019130230; ex 4 |
| E | 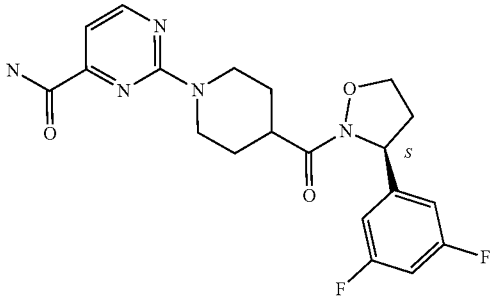 | 0.011 | 0.002 | 101.6 | 1.1 (2 h) | |

-continued
Comparator table 5:
| # | structure | ADP-Glo IC50 (uM) | U937 IC50 (uM) Mean | TPSA | Mouse PK brain/blood ratio | Reference |
|---|---|---|---|---|---|---|
| F | 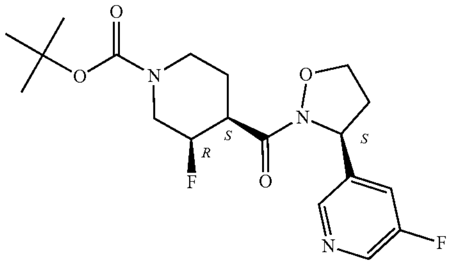 | | >10 | 71.97 | | WO2019130230; ex 51 |
| G | 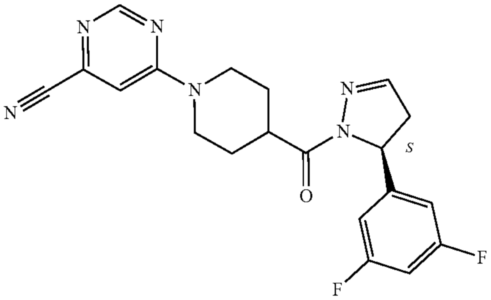 | 0.010 | 0.002 | 85.48 | 1.5 (2 h) | WO2018092089; ex 78<br>J Med Chem (2019) 62, 5096 (#76) |
| H | 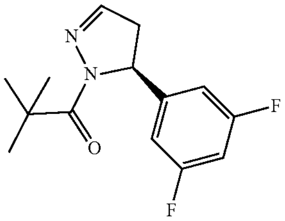 [SMILES: CC(C)(C)C(=O)N1N=CC[C@H]1c1cc(F)cc(F)c1] | 0.001* | 0.006* | 32.7 | | J Med Chem (2019) 62, 5096 (#23) |
| I | 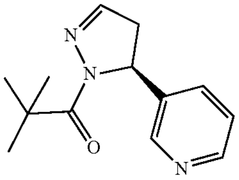 [SMILES: CC(C)(C)C(=O)N1N=CC[C@H]1c1cccnc1] | 0.159* | 0.126* | 45.6 | | J Med Chem (2019) 62, 5096 (#30) |
| K | 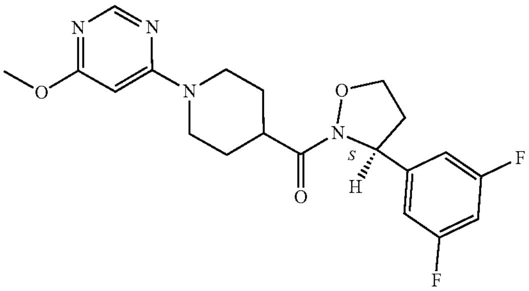 | 0.018 | 0.010 | 68 | 2.1 (15 min i.v. 3 mg/kg) | |
*data from P.A. Harris et al. J Med Chem 2019, 62, 5096

The invention is further characterized by the following items:

Item 1. Compounds of the formula I

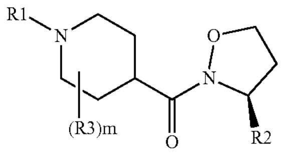

(I)

wherein

R1 represents a 5-6 membered heteroaryl in which 1 to 4 ringatoms are independently selected from —N—, —O— or —S— and wherein R1 is optionally substituted by 1 to 4 substituents independently selected from halogen,
—(C1-C4)alkyl,
—O(C1-C4)alkyl,
—S(C1-C4)alkyl,
—S(O)(C1-C4)alkyl,
—$S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra and Rb are independently from each other H or (C1-C4)alkyl; and
wherein Rc is H or (C1-C4)alkyl; and
wherein Rd is —$(CH_2)_x$—(C3-C7)cycloalkyl or —$(CH_2)_x$—(C3-C7)heterocyclyl,
wherein cycloalkyl or heterocyclyl is optionally substituted with 1 to 3 substituents selected from (C1-C4)alkyl, (CO)OH or (CO)O(C1-C4)alkyl;
x is an integer 0, 1, 2 or 3;

R2
is a 5-10 membered heteroaryl or 5 to 6 membered heterocycle, wherein 1 to 4 ring atoms are independently selected from —N—, —O— or —S—, and wherein heteroaryl or heterocycle is optionally substituted by 1 to 4 substituents selected from halogen, CN, —(C1-C4)alkyl, —(C1-C4)alkyl-OH, —(CO)NReRf and —NReRf, wherein Re and Rf are independently selected from H, (C1-C4)alkyl or —CO(C1-C4)alkyl; or
wherein Re and Rf form together with the nitrogen atom to which they are attached a 4 to 6 membered ring, which is optionally substituted with oxo;
R3 is Halogen or (C1-C2)alkyl;
m is an integer 0, 1, 2, 3 or 4;
R4 is OH, CN, —(CO)OH, —(CO)NRgRh or —(CO)O(C1-C4)alkyl;
wherein Rg and Rh are independently selected from H or (C1-C4)alkyl;
or a pharmaceutically acceptable salt, solvate, or stereoisomer thereof.

Item 2. Compounds of item 1, in which
R1 represents a 5-6 membered heteroaryl in which 1 to 2 ringatoms are —N-atoms and wherein R1 is optionally substituted by 1 to 3 substituents independently selected from
halogen,
—(C1-C4)alkyl,
—O(C1-C4)alkyl,
—S(C1-C4)alkyl,
—S(O)(C1-C4)alkyl,
—$S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra, Rb are independently from each other H or (C1-C4)alkyl; and
wherein Rc is H or (C1-C4)alkyl; and
wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, COOH or COO(C1-C4)alkyl;
x is an integer 0, 1, 2 or 3;
or a pharmaceutically acceptable salt, solvate, or stereoisomer thereof.

Item 3. Compounds of item 1, in which
R1 is pyridyl, pyrazinyl or pyrimidinyl and wherein R1 is optionally substituted by 1 to 2 substituents independently selected from
halogen,
—(C1-C4)alkyl,
—O(C1-C4)alkyl,
—S(C1-C4)alkyl,
—S(O)(C1-C4)alkyl,
—$S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra, Rb are independently from each other H or (C1-C4)alkyl; and
wherein Rc is H or (C1-C4)alkyl; and
wherein Rd is —$(CH_2)_x$-cycloalkyl or —$(CH_2)_x$-heterocyclyl, wherein cycloalkyl or heterocyclyl is optionally substituted with 1 to 3 substituents selected from (C1-C4)alkyl, (CO)OH or (CO)O(C1-C4)alkyl;
x is an integer 0, 1, 2 or 3;
or a pharmaceutically acceptable salt, solvate, or stereoisomer thereof.

Item 4. Compounds of item 1, in which
R1 is pyridyl, pyrazinyl or pyrimidinyl and wherein R1 is optionally substituted by 1 to 2 substituents independently selected from
F, Cl,
methyl,
—O-methyl,
—S methyl,
—S(O) methyl,
—$S(O)_2$ methyl,
—O—$CH_2$—R4,
—(CO)OH,
—CN,
—(CO)O—$CH_3$, —(CO)O—$CH_2$—$CH_3$,
—$NH_2$,
—(CO)$NH_2$, (CO)$NHCH_3$, and
—(CO)NRcRd;

wherein Rc is H or methyl; and wherein Rd is —($CH_2$)-cycloalkyl or —($CH_2$)-heterocyclyl, wherein cycloalkyl or heterocyclyl is optionally substituted with methyl, ethyl, (CO)OH or (CO)O(C1-C4)alkyl;

or a pharmaceutically acceptable salt, solvate, or stereoisomer thereof.

Item 5. Compounds of item 1, in which

R1 is pyridyl, pyrazinyl or pyrimidinyl and wherein R1 is substituted by

—(CO)NRcRd;

wherein Rc is H or methyl; and wherein Rd is —($CH_2$)-cycloalkyl or —($CH_2$)-heterocyclyl, wherein cycloalkyl is selected from cycloprpopyl, cyclobutyl, cyclopentyl and cyclohexyl, and wherein heterocyclyl is selected from azirine, azetidine, pyrrolidine and piperidine, and wherein cycloalkyl or heterocyclyl, is optionally substituted with methyl, ethyl, (CO)OH or (CO)O(C1-C4)alkyl;

or a pharmaceutically acceptable salt, solvate, or stereoisomer thereof.

Item 6. Compounds of item 1, in which

R1 is pyridyl, pyrazinyl or pyrimidinyl and wherein R1 is substituted by

—(CO)NRcRd wherein Rc is H; and wherein Rd is —($CH_2$)-cyclopropyl, —($CH_2$)-azetidine or —($CH_2$)-piperidine, wherein the cyclic group, is optionally substituted with methyl, ethyl, (CO)OH or (CO)O(C1-C4)alkyl;

or a pharmaceutically acceptable salt, solvate, or stereoisomer thereof.

Item 7. Compounds of any of item 1 to 6, in which

R2 is a 5-10 membered heteroaryl or 5 to 6 membered heterocycle, wherein 1 to 3 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo;

or a pharmaceutically acceptable salt, solvate, or stereoisomer thereof.

Item 8. Compounds of any of item 1 to 6, in which

R2 is a 5-10 membered heteroaryl wherein 1 to 3 ring atoms are independently selected from —N—, or —S—, or a 5 to 6 membered heterocycle, wherein 1 to 2 ring atoms are independently selected from —N—, —O— or —S—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

Item 9. Compounds of any of item 1 to 6, in which

R2 is a 5-10 membered heteroaryl, wherein 1 to 2 ring atoms are —N—, and additionally up to 1 ring atom is —S—; or a 5 to 6 membered heterocycle, wherein 1 to 2 ring atoms are —O—, and wherein heteroaryl or heterocycle is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

Item 10. Compounds of any of item 1 to 6, in which

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is optionally substituted with oxo at the position adjacent to the nitrogen atom;

or a pharmaceutically acceptable salt, solvate, or stereoisomer thereof.

Item 11. Compounds of any of item 1 to 6, in which

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from F, Cl, Br, CN, -methyl, —$(CH)_2$—OH, $NH_2$, NH(C1-C4)alkyl, NH(CO)—(C1-C4)alkyl, (CO)$NH_2$, —(CO)NH(C1-C4)alkyl, —(CO)NH(CO)—(C1-C4)alkyl, 1-oxo-azirinyl, 1-oxo-azetidinyl, 1-oxo-pyrrolidinyl and 1-oxo-piperidinyl;

or a pharmaceutically acceptable salt, solvate, or stereoisomer thereof.

Item 12. Compounds of any of item 1 to 6, in which

R2 is selected from pyrazolyl, thiadiazolyl, pyridyl, pyrimidinyl, pyrazinyl, imidazo[1,2a]pyridinyl or tetrahydropyranyl, and is optionally substituted by 1 to 2 substituents selected from F, Cl, Br, CN, -methyl, —$(CH)_2$—OH, $NH_2$, $NHCH_3$, —(CO)$NH_2$, —(CO)$NHCH_3$, —(CO)NH(CO)$CH_3$, 1-oxo-azirinyl, 1-oxo-azetidinyl, 1-oxo-pyrrolidinyl and 1-oxo-piperidinyl;

or a pharmaceutically acceptable salt, solvate, or stereoisomer thereof.

Item 13. Compounds of any of item 1 to 12, in which

R3 is F, Cl, methyl or ethyl;

m is an integer 0, 1 or 2.

Item 14. Compounds of any of item 1 to 12, in which R3 is F or methyl;
m is an integer 0 or 1.
Item 15. Compounds of any of item 1 to 12, in which R3 is F or methyl.
Item 16. Compounds of any of item 1 to 12, in which m is an integer 0, 1, 2 or 3.
Item 17. Compounds of any of item 1 to 12, in which m is an integer 0.
Item 18. Compounds of any of item 1 to 12, in which m is an integer 1.
Item 19. Compounds of any of item 1 to 12, in which R3 is F or methyl;
m is an integer 1.
Item 20. Compounds of any of item 1 to 19, in which R4 is OH, CN, —(CO)OH, —(CO)$NH_2$, —(CO)$NHCH_3$ or —(CO)O(C1-C4)alkyl;
or a pharmaceutically acceptable salt, solvate, or stereoisomer thereof.
Item 21. Compounds of any of item 1 to 19, in which R4 is OH, CN, —(CO)OH, —(CO)$NH_2$, —(CO)$NHCH_3$, —(CO)O—$CH_3$ or —(CO)O—$CH_2$—$CH_3$;
or a pharmaceutically acceptable salt, solvate, or stereoisomer thereof.
Item 22. Compounds of any of item 1 to 21, which show in the ADP Glo assay as described in the examples an $IC_{50}$ value of 200 nM or less;
or a pharmaceutically acceptable salt, solvate, or stereoisomer thereof.
Item 23. Compounds of any of item 1 to 21, which show in the ADP Glo assay as described in the examples an $IC_{50}$ value of 50 nM or less;
or a pharmaceutically acceptable salt, solvate, or stereoisomer thereof.
Item 24. Compounds of any of item 1 to 21, which show in the ADP Glo assay as described in the examples an $IC_{50}$ value of 20 nM or less;
or a pharmaceutically acceptable salt, solvate, or stereoisomer thereof.
Item 25. Compounds of any of item 1 to 24, which have a TPSA value as described in the examples of 90 $Å^2$ or more;
or a pharmaceutically acceptable salt, solvate, or stereoisomer thereof.
Item 26. Compounds of any of item 1 to 24, which have a TPSA value as described in the examples of 105 $Å^2$ or more;
or a pharmaceutically acceptable salt, solvate, or stereoisomer thereof.
Item 27. Compounds of any of item 1 to 24, which have a TPSA value as described in the examples of 120 $Å^2$ or more;
or a pharmaceutically acceptable salt, solvate, or stereoisomer thereof.

The invention claimed is:

1. A compound of formula I:

(I)

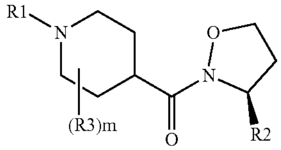

wherein

R1 represents a 5-6 membered heteroaryl in which 1 to 3 ring atoms are independently selected from —N— or —S— and wherein R1 is substituted by 1 or 2 substituents independently selected from
halogen,
—(C1-C4)alkyl,
—O(C1-C4)alkyl,
—S(C1-C4)alkyl,
—S(O)(C1-C4)alkyl,
—$S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra and Rb are H; and
wherein Rc is H; and
wherein Rd is —$(CH_2)_x$—(C3-C7)cycloalkyl or —$(CH_2)_x$—(C3-C7)heterocyclyl, wherein cycloalkyl or heterocyclyl is unsubstituted or substituted with 1 substituent selected from (C1-C4)alkyl or (CO)O(C1-C4)alkyl;
x is an integer 0, 1 or 2;
R2
is a 5-10 membered heteroaryl or 5 to 6 membered heterocycle, wherein 1 to 3 ring atoms are independently selected from —N—, —O— or —S—, and wherein heteroaryl or heterocycle is unsubstituted or substituted by 1 or 2 substituents selected from halogen, CN, —(C1-C4)alkyl, —(C1-C4)alkyl-OH, —(CO)NReRf and —NReRf, wherein Re and Rf are independently selected from H, (C1-C4)alkyl or —CO(C1-C4)alkyl; or
wherein Re and Rf form together with the nitrogen atom to which they are attached a 4 to 6 membered ring, which is unsubstituted or substituted with oxo;
R3 is Halogen or (C1-C2)alkyl;
m is an integer 0, 1 or 3;
R4 is CN, —(CO)OH, —(CO)NRgRh or —(CO)O(C1-C4)alkyl;
wherein Rg and Rh are H;
or a pharmaceutically acceptable salt, solvate, or stereoisomer thereof.

2. The compound of the formula I according to claim 1, with a TPSA (topological polar surface area) value of 90 $Å^2$ or more;
or a pharmaceutically acceptable salt, solvate, or stereoisomer thereof.

3. The compound of the formula I according to claim 1, with a TPSA (topological polar surface area) value of 105 $Å^2$ or more;
or a pharmaceutically acceptable salt, solvate, or stereoisomer thereof.

4. The compound of the formula I according to claim 1, wherein
R1 represents a 5-6 membered heteroaryl in which 1 or 2 ring atoms are —N-atoms and wherein R1 is substituted by 1 or 2 substituents independently selected from
halogen,
—(C1-C4)alkyl,
—O(C1-C4)alkyl,
—S(C1-C4)alkyl,
—S(O)(C1-C4)alkyl,
—$S(O)_2$(C1-C4)alkyl,
—O(C1-C4)alkyl-R4,
—(CO)OH, —CN,
—(CO)O(C1-C4)alkyl,
—NRaRb,
—(CO)NRaRb, and
—(CO)NRcRd;
wherein Ra, Rb are H; and
wherein Rc is H; and
wherein Rd is $—(CH_2)_x$—(C3-C7)cycloalkyl or $—(CH_2)_x$—(C3-C7)heterocyclyl, wherein cycloalkyl or heterocyclyl is unsubstituted or substituted with 1 substituent selected from (C1-C4)alkyl or COO(C1-C4)alkyl;
x is an integer 0, 1 or 2;
R2
is a 5-10 membered heteroaryl or 5 to 6 membered heterocycle, wherein 1 to 3 ring atoms are independently selected from —N—, —O— or —S—, and wherein heteroaryl or heterocycle is unsubstituted or substituted by 1 or 2 substituents selected from halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is unsubstituted or substituted with oxo;
R3 is F, Cl, methyl or ethyl;
m is an integer 0 or 1,
R4 is CN, —(CO)OH, $—(CO)NH_2$ or —(CO)O(C1-C4)alkyl;
or a pharmaceutically acceptable salt, solvate, or stereoisomer thereof.

5. The compound of the formula I according to claim 1, wherein
R1 is pyridyl, pyrazinyl or pyrimidinyl and wherein R1 is substituted by 1 or 2 substituents independently selected from
halogen,
—(C1-C4)alkyl,
—O(C1-C4)alkyl,
—S(C1-C4)alkyl,
—S(O)(C1-C4)alkyl,
$—S(O)_2$(C1-C4)alkyl,
—O(C1-C4)alkyl-R4,
—(CO)OH,
—CN,
—(CO)O(C1-C4)alkyl,
—NRaRb,
—(CO)NRaRb, and
—(CO)NRcRd;
wherein Ra, Rb are H; and
wherein Rc is H; and
wherein Rd is $—(CH_2)_x$—(C3-C7)cycloalkyl or $—(CH_2)_x$—(C3-C7)heterocyclyl, wherein cycloalkyl or heterocyclyl is unsubstituted or substituted with 1 to 3 substituents selected from (C1-C4)alkyl or (CO)O(C1-C4)alkyl;
x is an integer 0, 1 or 2;
R2
is a 5-10 membered heteroaryl wherein 1 to 3 ring atoms are independently selected from —N—, or —S—, or a 5 to 6 membered heterocycle, wherein 1 or 2 ring atoms are independently selected from —N—, —O— or —S—,
and wherein heteroaryl or heterocycle is unsubstituted or substituted by 1 or 2 substituents selected from
halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is unsubstituted or substituted with oxo at the position adjacent to the nitrogen atom;
R3 is F or methyl;
m is an integer 0 or 1;
R4 is CN, —(CO)OH, $—(CO)NH_2$ or —(CO)O(C1-C4)alkyl;
or a pharmaceutically acceptable salt, solvate, or stereoisomer thereof.

6. The compound of the formula I according to claim 1, wherein
R1 is pyridyl, pyrazinyl or pyrimidinyl and wherein R1 is substituted by 1 or 2 substituents independently selected from
F, Cl,
methyl,
—O-methyl,
—S methyl,
—S(O) methyl,
$—S(O)_2$ methyl,
$—O—CH_2—R4$,
—(CO)OH,
—CN,
$—(CO)O—CH_3$, $—(CO)O—CH_2—CH_3$,
$—NH_2$,
$—(CO)NH_2$, and
—(CO)NRcRd;
wherein Rc is H; and
wherein Rd is $—(CH_2)$—(C3-C7)cycloalkyl or $—(CH_2)$—(C3-C7)heterocyclyl, wherein cycloalkyl or heterocyclyl is unsubstituted or substituted with methyl, ethyl, or (CO)O(C1-C4)alkyl;
R2
is a 5-10 membered heteroaryl, wherein 1 or 2 ring atoms are —N—, and additionally up to 1 ring atom is —S—; or
a 5 to 6 membered heterocycle, wherein 1 or 2 ring atoms are —O—,
and wherein heteroaryl or heterocycle is unsubstituted or substituted by 1 or 2 substituents selected from
halogen, CN, —(C1-C4)alkyl, —(C1-C4)alkyl-OH, (CO)NReRf and —NReRf, wherein Re and Rf are independently selected from H, (C1-C4)alkyl or —CO(C1-C4)alkyl; or wherein Re and Rf form together with the nitrogen atom to which they are attached a 4 to 6 membered ring, which is unsubstituted or substituted with oxo at the position adjacent to the nitrogen atom;
R3 is F or methyl;
m is an integer 0 or 1;
R4 is CN, —(CO)OH, $—(CO)NH_2$ or —(CO)O(C1-C4)alkyl;
or a pharmaceutically acceptable salt, solvate, or stereoisomer thereof.

7. The compound of the formula I according to claim 1, wherein
R1 is pyridyl, pyrazinyl or pyrimidinyl and wherein R1 is substituted by
—(CO)NRaRb, wherein Ra and Rb are H, or
—(CO)NRcRd;
wherein Rc is H; and
wherein Rd is $—(CH_2)$—(C3-C7)cycloalkyl or $—(CH_2)$—(C3-C7)heterocyclyl,
wherein cycloalkyl is selected from cyclopropyl, cyclobutyl, cyclopentyl and cyclohexyl, and wherein heterocyclyl is selected from azirine, azetidine, pyrrolidine and piperidine, and wherein cycloalkyl or heterocyclyl, is optionally substituted with methyl, ethyl or (CO)O(C1-C4)alkyl;

or a pharmaceutically acceptable salt, solvate, or stereoisomer thereof.

8. The compound of the formula I according to claim 1, wherein

R1 is pyrimidinyl and wherein R1 is either substituted by —(CO)$NH_2$, or substituted by —(CO)$NH_2$ and additionally by F;

R2 is selected from pyridyl and pyrazinyl, and is unsubstituted or substituted by -methyl or —CN, m is an integer 0;

or a pharmaceutically acceptable salt, solvate, or stereoisomer thereof.

9. The compound of the formula I according to claim 1, wherein

R1 is pyridyl, pyrazinyl or pyrimidinyl and wherein R1 is substituted by

—(CO)NRaRb, wherein Ra and Rb are H, or

—(CO)NRcRd wherein Rc is H; and wherein Rd is —($CH_2$)-cyclopropyl, —($CH_2$)-azetidine or —($CH_2$)-piperidine, wherein the cyclic group, is unsubstituted or substituted with methyl, ethyl or (CO)O(C1-C4)alkyl;

or a pharmaceutically acceptable salt, solvate, or stereoisomer thereof.

10. The compound of the formula I according to claim 1, wherein

R2 is selected from pyrazolyl, thiadiazolyl, pyridyl, pyrimidinyl, pyrazinyl, imidazo[1,2a]pyridinyl or tetrahydropyranyl, and is unsubstituted or substituted by 1 or 2 substituents selected from F, Cl, Br, CN, -methyl, —($CH_2$)—OH, $NH_2$, NH(C1-C4) alkyl, NH(CO)—(C1-C4)alkyl, (CO)$NH_2$, —(CO)NH (C1-C4)alkyl, —(CO)NH(CO)—(C1-C4)alkyl, 1-oxo-azirinyl, 1-oxo-azetidinyl, 1-oxo-pyrrolidinyl and 1-oxo-piperidinyl;

R3 is F or methyl;

m is an integer 0 or 1;

R4 is CN, —(CO)OH, —(CO)$NH_2$, —(CO)O—$CH_3$ or —(CO)O—$CH_2$—$CH_3$;

or a pharmaceutically acceptable salt, solvate, or stereoisomer thereof.

11. The compound of the formula I according to claim 1 wherein the compound of formula I is selected from 6-[4-[(3S)-3-(5-Cyano-3-pyridyl)isoxazolidine-2-carbonyl]-1-piperidyl]pyrimidine-4-carboxamide 2-[4-[(3S)-3-Pyrimidin-5-ylisoxazolidine-2-carbonyl]-1-piperidyl]pyrimidine-4-carboxamide 2-[4-[(3S)-3-(5-Cyano-3-pyridyl)isoxazolidine-2-carbonyl]-1-piperidyl]pyrimidine-4-carboxamide 6-[4-[(3S)-3-(5-Cyano-3-pyridyl)isoxazolidine-2-carbonyl]-1-piperidyl]pyrimidine-4-carbonitrile 2-[4-[(3S)-3-(5-Cyano-3-pyridyl)isoxazolidine-2-carbonyl]-1-piperidyl]pyrimidine-4-carboxylic acid Methyl 2-[4-[(3S)-3-(5-cyano-3-pyridyl)isoxazolidine-2-carbonyl]-1-piperidyl]pyrimidine-4-carboxylate 2-[4-[(3S)-3-(5-Cyano-3-pyridyl)isoxazolidine-2-carbonyl]-1-piperidyl]pyrimidine-4-carbonitrile 2-[4-[(3S)-3-(5-Cyano-3-pyridyl)isoxazolidine-2-carbonyl]-1-piperidyl]pyridine-4-carbonitrile 5-[(3S)-2-[1-[4-(Cyanomethoxy)-5-fluoro-2-pyridyl]-4-methyl-piperidine-4-carbonyl]isoxazolidin-3-yl]pyridine-3-carbonitrile 2-[4-[(3S)-3-(5-Cyano-3-pyridyl)isoxazolidine-2-carbonyl]-4-methyl-1-piperidyl]pyrimidine-4-carboxamide Methyl 2-[4-[(3S)-3-(5-cyano-3-pyridyl)isoxazolidine-2-carbonyl]-4-methyl-1-piperidyl]pyrimidine-4-carboxylate 2-[4-[(3S)-3-(5-Cyano-3-pyridyl)isoxazolidine-2-carbonyl]-4-methyl-1-piperidyl]pyrimidine-4-carboxylic acid 2-[4-[(3S)-3-(5-Cyano-3-pyridyl)isoxazolidine-2-carbonyl]-1-piperidyl]pyridine-4-carboxamide Ethyl 2-[2-[4-[(3S)-3-(5-Cyano-3-pyridyl)isoxazolidine-2-carbonyl]-4-methyl-1-piperidyl]-5-fluoro-pyrimidin-4-yl]oxyacetate 5-[(3S)-2-[1-[4-(Cyanomethoxy)-5-fluoro-pyrimidin-2-yl]piperidine-4-carbonyl]isoxazolidin-3-yl]pyridine-3-carbonitrile 2-[2-[4-[(3S)-3-(5-Cyano-3-pyridyl)isoxazolidine-2-carbonyl]-1-piperidyl]-5-fluoro-pyrimidin-4-yl]oxyacetic acid 2-[2-[4-[(3S)-3-(5-Carbamoyl-3-pyridyl)isoxazolidine-2-carbonyl]-1-piperidyl]-5-fluoro-pyrimidin-4-yl]oxyacetic acid 2-[2-[4-[(3S)-3-(5-Cyano-3-pyridyl)isoxazolidine-2-carbonyl]-1-piperidyl]-5-fluoro-pyrimidin-4-yl]oxyacetamide 5-[(3S)-2-[1-(4-Amino-5-fluoro-pyrimidin-2-yl)piperidine-4-carbonyl]isoxazolidin-3-yl]pyridine-3-carbonitrile 2-[4-[(3S)-3-(5-Acetamido-3-pyridyl)isoxazolidine-2-carbonyl]-1-piperidyl]pyrimidine-4-carboxamide 2-[4-[(3S)-3-(6-Methylpyrazin-2-yl)isoxazolidine-2-carbonyl]-1-piperidyl]pyrimidine-4-carboxamide 2-[4-[(3S)-3-(6-Methylpyrazin-2-yl)isoxazolidine-2-carbonyl]-1-piperidyl]pyrimidine-4-carbonitrile 2-[4-[(3S)-3-(5-Cyano-3-pyridyl)isoxazolidine-2-carbonyl]-1-piperidyl]-5-methyl-pyrimidine-4-carboxamide 2-[4-[(3S)-3-[5-(2-Oxoazetidin-1-yl)-3-pyridyl]isoxazolidine-2-carbonyl]-1-piperidyl]pyrimidine-4-carboxamide 2-[4-[(3S)-3-[5-(2-Oxoazetidin-1-yl)-3-pyridyl]isoxazolidine-2-carbonyl]-1-piperidyl]pyrimidine-4-carbonitrile Ethyl 6-[4-[(3S)-3-(5-cyano-3-pyridyl)isoxazolidine-2-carbonyl]-1-piperidyl]-5-fluoro-pyrimidine-4-carboxylate 6-[4-[(3S)-3-(5-Cyano-3-pyridyl)isoxazolidine-2-carbonyl]-1-piperidyl]-5-fluoro-pyrimidine-4-carboxylic acid 2-[4-[(3S)-3-(5-Cyano-3-pyridyl)isoxazolidine-2-carbonyl]-4-fluoro-1-piperidyl]-5-fluoro-pyrimidine-4-carboxamide 2-[4-[(3S)-3-[5-(2-Oxopyrrolidin-1-yl)-3-pyridyl]isoxazolidine-2-carbonyl]-1-piperidyl]pyrimidine-4-carboxamide 2-[4-Methyl-4-[(3S)-3-pyrimidin-5-ylisoxazolidine-2-carbonyl]-1-piperidyl]pyrimidine-4-carboxamide 2-[5-Fluoro-2-[4-methyl-4-[(3S)-3-pyrimidin-5-ylisoxazolidine-2-carbonyl]-1-piperidyl]pyrimidin-4-yl]oxyacetonitrile 2-[5-Fluoro-2-[4-[(3S)-3-pyrimidin-5-ylisoxazolidine-2-carbonyl]-1-piperidyl]pyrimidin-4-yl]oxyacetonitrile

[1-(5-Fluoro-4-methoxy-pyrimidin-2-yl)-4-piperidyl]-[(3S)-3-pyrimidin-5-ylisoxazolidin-2-yl]methanone 2-[4-[(3S)-3-Pyrimidin-5-ylisoxazolidine-2-carbonyl]-1-piperidyl]pyridine-4-carbonitrile 5-[4-[(3S)-3-(5-Cyano-3-pyridyl)isoxazolidine-2-carbonyl]-1-piperidyl]pyrazine-2-carbonitrile 6-[4-[(3S)-3-(5-Cyano-3-pyridyl)isoxazolidine-2-carbonyl]-1-piperidyl]pyrazine-2-carbonitrile 2-[4-[(3S)-3-(5-Cyano-3-pyridyl)isoxazolidine-2-carbonyl]-1-piperidyl]-5-fluoro-pyrimidine-4-carboxamide 2-[4-[(3S)-3-(5-Fluoro-3-pyridyl)isoxazolidine-2-carbonyl]-1-piperidyl]pyrimidine-4-carboxamide 6-[4-[(3S)-3-(5-Cyano-3-pyridyl)isoxazolidine-2-carbonyl]-1-piperidyl]pyrazine-2-carboxamide 5-[4-[(3S)-3-(5-Cyano-3-pyridyl)isoxazolidine-2-carbonyl]-1-piperidyl]pyrazine-2-carboxamide 6-[4-[(3S)-3-(5-Cyano-3-pyridyl)isoxazolidine-2-carbonyl]-1-piperidyl]-5-fluoro-pyrimidine-4-carboxamide 2-[4-[(3S)-3-Pyrazin-2-ylisoxazolidine-2-carbonyl]-1-piperidyl]pyrimidine-4-carboxamide 5-Fluoro-2-[4-[(3S)-3-pyrazin-2-ylisoxazolidine-2-carbonyl]-1-piperidyl]pyrimidine-4-carboxamide 2-[4-[(3S)-3-(5-Cyano-3-pyridyl)isoxazolidine-2-carbonyl]-1-piperidyl]-N-(1-methylazetidin-3-yl)pyrimidine-4-carboxamide 2-[4-[(3S)-3-(5-Cyano-3-pyridyl) isoxazolidine-2-carbonyl]-1-piperidyl]-N-[2-(1-methylcyclo-propyl)ethyl] pyrimidine-4-carboxamide Tert-butyl 3-[[2-[4-[(3S)-3-(5-cyano-3-pyridyl)isoxazolidine-2-carbonyl]-1-piperidyl]pyrimidine-4-carbonyl] amino]azetidine-1-carboxylate 2-[4-[(3S)-3-(5-Cyano-3-pyridyl)isoxazolidine-2-carbonyl]-1-piperidyl]-N-[(1-ethyl-4-piperidyl)methyl]pyrimidine-4-carboxamide 5-Fluoro-2-[4-[(3S)-3-(5-fluoro-3-pyridyl)isoxazolidine-2-carbonyl]-1-piperidyl]pyrimidine-4-carboxamide 2-[4-[(3S)-3-(5-Cyano-6-methyl-3-pyridyl)isoxazolidine-2-carbonyl]-1-piperidyl]pyrimidine-4-carboxamide 5-Fluoro-2-[4-[(3S)-3-(6-methylpyrazin-2-yl)isoxazolidine-2-carbonyl]-1-piperidyl]pyrimidine-4-carboxamide 2-[4-[(3S)-3-(5-Chloro-2-pyridyl)isoxazolidine-2-carbonyl]-1-piperidyl]pyrimidine-4-carboxamide 2-[4-[(3S)-3-(5-Chloro-2-pyridyl)isoxazolidine-2-carbonyl]-1-piperidyl]-5-fluoro-pyrimidine-4-carboxamide 2-[4-[(3S)-3-(5-Cyano-6-methyl-3-pyridyl)isoxazolidine-2-carbonyl]-1-piperidyl]-5-fluoro-pyrimidine-4-carboxamide N-(Azetidin-3-yl)-2-[4-[(3S)-3-(5-cyano-3-pyridyl) isoxazolidine-2-carbonyl]-1-piperidyl]pyrimidine-4-carboxamide 2-[4-[(3S)-3-(5-Methylpyrazin-2-yl)isoxazolidine-2-carbonyl]-1-piperidyl]pyrimidine-4-carboxamide Ethyl 3-[[2-[4-[(3S)-3-(5-cyano-3-pyridyl)isoxazolidine-2-carbonyl]-1-piperidyl]pyrimidine-4-carbonyl]amino] azetidine-1-carboxylate 5-Fluoro-2-[4-[(3S)-3-(5-methylpyrazin-2-yl)isoxazolidine-2-carbonyl]-1-piperidyl]pyrimidine-4-carboxamide 6-[4-[(3S)-3-(5-Methylpyrazin-2-yl)isoxazolidine-2-carbonyl]-1-piperidyl]pyrimidine-4-carbonitrile 2-[(3R,4R)-4-[(3S)-3-(5-Cyano-3-pyridyl)isoxazolidine-2-carbonyl]-3-fluoro-1-piperidyl]pyrimidine-4-carboxamide 2-[(3S,4S)-4-[(3S)-3-(5-Cyano-3-pyridyl)isoxazolidine-2-carbonyl]-3-fluoro-1-piperidyl]pyrimidine-4-carboxamide 2-[(3R,4S)-4-[(3S)-3-(5-Cyano-3-pyridyl)isoxazolidine-2-carbonyl]-3-fluoro-1-piperidyl]pyrimidine-4-carboxamide 2-[(3S,4R)-4-[(3S)-3-(5-Cyano-3-pyridyl)isoxazolidine-2-carbonyl]-3-fluoro-1-piperidyl]pyrimidine-4-carboxamide 5-Methyl-2-[4-[(3S)-3-(6-methylpyrazin-2-yl)isoxazolidine-2-carbonyl]-1-piperidyl]pyrimidine-4-carboxamide 2-[4-[(3S)-3-(5-Fluoro-3-pyridyl)isoxazolidine-2-carbonyl]-1-piperidyl]-5-methyl-pyrimidine-4-carboxamide 5-Methyl-2-[4-[(3S)-3-pyrazin-2-ylisoxazolidine-2-carbonyl]-1-piperidyl]pyrimidine-4-carboxamide 5-[(3S)-2-[1-(5-Fluoro-4-methylsulfanyl-pyrimidin-2-yl) piperidine-4-carbonyl]isoxazolidin-3-yl]pyridine-3-carbonitrile 5-[(3S)-2-[1-(5-Fluoro-4-methylsulfinyl-pyrimidin-2-yl) piperidine-4-carbonyl]isoxazolidin-3-yl]pyridine-3-carbonitrile 5-[(3S)-2-[1-(5-Fluoro-4-methylsulfonyl-pyrimidin-2-yl) piperidine-4-carbonyl]isoxazolidin-3-yl]pyridine-3-carbonitrile 2-[4-[(3S)-3-(5-Cyano-2-pyridyl)isoxazolidine-2-carbonyl]-1-piperidyl]-5-fluoro-pyrimidine-4-carboxamide 6-[4-[(3S)-3-(5-Cyano-2-pyridyl)isoxazolidine-2-carbonyl]-1-piperidyl]pyrimidine-4-carboxamide 2-[4-[(3S)-3-(5-Cyano-2-pyridyl)isoxazolidine-2-carbonyl]-1-piperidyl]pyrimidine-4-carboxamide (S)-6-(4-(3-(5-Methylfuran-3-yl)isoxazolidine-2-carbonyl)piperidin-1-yl)pyrimidine-4-carboxamide (S)-2-(4-(3-(5-Methylfuran-3-yl)isoxazolidine-2-carbonyl)piperidin-1-yl)pyrimidine-4-carboxamide 2-[4-[(3S)-3-(5-Cyano-3-pyridyl)isoxazolidine-2-carbonyl]-1-piperidyl]-5-fluoro-pyrimidine-4-carbonitrile 2-[4-[(3S)-3-(5-Cyano-2-pyridyl)isoxazolidine-2-carbonyl]-1-piperidyl]-5-fluoro-pyrimidine-4-carbonitrile 5-[(3S)-2-[1-(3-Methyl-1,2,4-thiadiazol-5-yl)piperidine-4-carbonyl]isoxazolidin-3-yl]pyridine-3-carbonitrile 5-[(3S)-2-[1-(5-Fluoro-4-methoxy-pyrimidin-2-yl)piperidine-4-carbonyl]isoxazolidin-3-yl]pyridine-3-carbonitrile 2-[4-[(3S)-3-(5-Cyano-3-pyridyl)isoxazolidine-2-carbonyl]-3,3,4-trifluoro-1-piperidyl]pyrimidine-4-carboxamide

[1-(5-Fluoro-4-methoxy-pyrimidin-2-yl)-4-piperidyl]-[(3S)-3-(6-methylpyrazin-2-yl)isoxazolidin-2-yl] methanone 6-[(3S)-2-[1-(5-Fluoro-4-methoxy-pyrimidin-2-yl)piperidine-4-carbonyl]isoxazolidin-3-yl]pyridine-3-carbonitrile 2-[4-[(3S)-3-(6-Cyanopyrazin-2-yl)isoxazolidine-2-carbonyl]-1-piperidyl]pyrimidine-4-carboxamide 5-Fluoro-2-[4-[(3S)-3-pyrazin-2-ylisoxazolidine-2-carbonyl]-1-piperidyl]pyrimidine-4-carbonitrile 2-Chloro-5-[4-[(3S)-3-(5-cyano-3-pyridyl)isoxazolidine-2-carbonyl]-1-piperidyl]pyrimidine-4-carboxylic acid 2-[3,3,4-Trifluoro-4-[(3S)-3-pyrazin-2-ylisoxazolidine-2-carbonyl]-1-piperidyl]pyrimidine-4-carboxamide 2-[4-[(3S)-3-(5-Cyano-3-pyridyl)isoxazolidine-2-carbonyl]-3,3,4-trifluoro-1-piperidyl]pyrimidine-4-carbonitrile 2-[3,3,4-Trifluoro-4-[(3S)-3-pyrazin-2-ylisoxazolidine-2-carbonyl]-1-piperidyl]pyrimidine-4-carbonitrile (S)-5-Fluoro-2-(4-fluoro-4-(3-(5-fluoropyridin-3-yl) isoxazolidine-2-carbonyl)piperidin-1-yl)pyrimidine-4-carboxamide (S)-2-(4-(3-(6-Methylpyridin-3-yl)isoxazolidine-2-carbonyl)piperidin-1-yl)pyrimidine-4-carbonitrile
(S)-6-(4-(3-(6-Methylpyridin-3-yl)isoxazolidine-2-carbonyl)piperidin-1-yl)pyrimidine-4-carbonitrile
(S)-2-(4-(3-(6-Methylpyridin-3-yl)isoxazolidine-2-carbonyl)piperidin-1-yl)pyrimidine-4-carboxamide
5-[(3S)-2-[1-(2-Chloro-5-fluoro-pyrimidin-4-yl)piperidine-4-carbonyl]isoxazolidin-3-yl]pyridine-3-carbonitrile
(S)-2-(4-(3-(5-Methylpyridin-3-yl)isoxazolidine-2-carbonyl)piperidin-1-yl)pyrimidine-4-carbonitrile
(S)-2-(4-(3-(5-Methylpyridin-3-yl)isoxazolidine-2-carbonyl)piperidin-1-yl)pyrimidine-4-carboxamide
(S)-6-(4-(3-(5-Methylpyridin-3-yl)isoxazolidine-2-carbonyl)piperidin-1-yl)pyrimidine-4-carbonitrile
(S)-6-(4-(3-(5-Methylpyridin-3-yl)isoxazolidine-2-carbonyl)piperidin-1-yl)pyrimidine-4-carboxamide
(S)-6-(4-(3-(6-Methylpyridin-3-yl)isoxazolidine-2-carbonyl)piperidin-1-yl)pyrimidine-4-carboxamide
(S)-2-(4-(3-(5-Fluoro-6-methylpyridin-3-yl)isoxazolidine-2-carbonyl)piperidin-1-yl)pyrimidine-4-carbonitrile
2-[4-[(3S)-3-(5-Fluoro-6-methyl-3-pyridyl)isoxazolidine-2-carbonyl]-1-piperidyl]pyrimidine-4-carboxamide
(S)-6-(4-(3-(5-Fluoro-6-methylpyridin-3-yl)isoxazolidine-2-carbonyl)piperidin-1-yl)pyrimidine-4-carbonitrile
6-[4-[(3S)-3-(5-Fluoro-6-methyl-3-pyridyl)isoxazolidine-2-carbonyl]-1-piperidyl]pyrimidine-4-carboxamide
(S)-2-(4-(3-(5-Fluoro-4-methylpyridin-3-yl)isoxazolidine-2-carbonyl)piperidin-1-yl)pyrimidine-4-carbonitrile
(S)-2-(4-(3-(5-Fluoro-4-methylpyridin-3-yl)isoxazolidine-2-carbonyl)piperidin-1-yl)pyrimidine-4-carboxamide
(S)-6-(4-(3-(5-Fluoro-4-methylpyridin-3-yl)isoxazolidine-2-carbonyl)piperidin-1-yl)pyrimidine-4-carboxamide
(S)-6-(4-(3-(5-Fluoro-4-methylpyridin-3-yl)isoxazolidine-2-carbonyl)piperidin-1-yl)pyrimidine-4-carbonitrile
5-[(3S)-2-[1-(2-Methoxypyrimidin-4-yl)piperidine-4-carbonyl]isoxazolidin-3-yl]pyridine-3-carbonitrile
4-[4-[(3S)-3-(5-Cyano-3-pyridyl)isoxazolidine-2-carbonyl]-1-piperidyl]pyrimidine-2-carbonitrile
5-[(3S)-2-[1-(2-Methylsulfanylpyrimidin-4-yl)piperidine-4-carbonyl]isoxazolidin-3-yl]pyridine-3-carbonitrile
5-[(3S)-2-[1-(2-Chloropyrimidin-4-yl)piperidine-4-carbonyl]isoxazolidin-3-yl]pyridine-3-carbonitrile
5-[(3S)-2-[1-(2-Aminopyrimidin-4-yl)piperidine-4-carbonyl]isoxazolidin-3-yl]pyridine-3-carbonitrile
Ethyl 4-[4-[(3S)-3-(5-cyano-3-pyridyl)isoxazolidine-2-carbonyl]-1-piperidyl]pyrimidine-2-carboxylate
(S)-2-(4-(3-(4-Methylfuran-2-yl)isoxazolidine-2-carbonyl)piperidin-1-yl)pyrimidine-4-carbonitrile
(S)-2-(4-(3-(4-Methylfuran-2-yl)isoxazolidine-2-carbonyl)piperidin-1-yl)pyrimidine-4-carboxamide
(S)-6-(4-(3-(4-Methylfuran-2-yl)isoxazolidine-2-carbonyl)piperidin-1-yl)pyrimidine-4-carbonitrile
(S)-6-(4-(3-(4-Methylfuran-2-yl)isoxazolidine-2-carbonyl)piperidin-1-yl)pyrimidine-4-carboxamide
2-[(3R,4R or 3S,4S)-4-[(3S)-3-(5-Cyano-3-pyridyl)isoxazolidine-2-carbonyl]-3-fluoro-1-piperidyl]-5-fluoro-pyrimidine-4-carboxamide
2-[(3S,4S or 3R,4R)-4-[(3S)-3-(5-Cyano-3-pyridyl)isoxazolidine-2-carbonyl]-3-fluoro-1-piperidyl]-5-fluoro-pyrimidine-4-carboxamide
4-[4-[(3S)-3-(5-Cyano-3-pyridyl)isoxazolidine-2-carbonyl]-1-piperidyl]pyrimidine-2-carboxamide
5-[(3S)-2-[1-(2-Bromopyrimidin-4-yl)piperidine-4-carbonyl]isoxazolidin-3-yl]pyridine-3-carbonitrile
5-[(3S)-2-[1-(4-Chloropyrimidin-2-yl)piperidine-4-carbonyl]isoxazolidin-3-yl]pyridine-3-carbonitrile
5-[(3S)-2-[1-(6-Chloropyrimidin-4-yl)piperidine-4-carbonyl]isoxazolidin-3-yl]pyridine-3-carbonitrile
5-[(3S)-2-[1-(4-Bromopyrimidin-2-yl)piperidine-4-carbonyl]isoxazolidin-3-yl]pyridine-3-carbonitrile
(S)-2-(4-(3-(5-Methylfuran-3-yl)isoxazolidine-2-carbonyl)piperidin-1-yl)pyrimidine-4-carbonitrile
(S)-6-(4-(3-(5-Methylfuran-3-yl)isoxazolidine-2-carbonyl)piperidin-1-yl)pyrimidine-4-carbonitrile
2-Chloro-5-[4-[(3S)-3-pyrazin-2-ylisoxazolidine-2-carbonyl]-1-piperidyl]pyrimidine-4-carboxylic acid
5-[(3S)-2-[1-(6-Bromopyrimidin-4-yl)piperidine-4-carbonyl]isoxazolidin-3-yl]pyridine-3-carbonitrile
2-[4-[(3S)-3-(5-Cyano-3-thienyl)isoxazolidine-2-carbonyl]-1-piperidyl]-5-fluoro-pyrimidine-4-carboxamide
2-[4-[(3S)-3-(5-Cyano-3-furyl)isoxazolidine-2-carbonyl]-1-piperidyl]-5-fluoro-pyrimidine-4-carboxamide
2-[4-[(3S)-3-(5-Cyano-3-thienyl)isoxazolidine-2-carbonyl]-1-piperidyl]pyrimidine-4-carboxamide
(S)-5-(2-(1-(6-Fluoropyrimidin-4-yl)piperidine-4-carbonyl)isoxazolidin-3-yl)nicotinonitrile
5-Fluoro-2-[4-[(3S)-3-(2-methylthiazol-4-yl)isoxazolidine-2-carbonyl]-1-piperidyl]pyrimidine-4-carboxamide
2-[4-[(3S)-3-(5-Cyano-3-furyl)isoxazolidine-2-carbonyl]-1-piperidyl]pyrimidine-4-carboxamide
[1-(4-Chloro-1,3,5-triazin-2-yl)-4-piperidyl]-[(3S)-3-pyrazin-2-ylisoxazolidin-2-yl]methanone
5-Fluoro-2-[4-[(3S)-3-(2-pyridyl)isoxazolidine-2-carbonyl]-1-piperidyl]pyrimidine-4-carboxamide
6-[4-[(3S)-3-(5-Methyl-2-thienyl)isoxazolidine-2-carbonyl]-1-piperidyl]pyrimidine-4-carboxamide
2-[4-[(3S)-3-(6-Cyanopyridazin-4-yl)isoxazolidine-2-carbonyl]-1-piperidyl]-5-fluoro-pyrimidine-4-carboxamide
2-[4-[(3S)-3-(6-Cyanopyridazin-4-yl)isoxazolidine-2-carbonyl]-1-piperidyl]pyrimidine-4-carboxamide
[1-(4-Chloro-6-methyl-1,3,5-triazin-2-yl)-4-piperidyl]-[(3S)-3-pyrazin-2-ylisoxazolidin-2-yl]methanone
[1-(4-Chloro-6-methoxy-1,3,5-triazin-2-yl)-4-piperidyl]-[(3S)-3-pyrazin-2-ylisoxazolidin-2-yl]methanone
5-Methyl-2-[4-[(3S)-3-(5-methyl-2-thienyl)isoxazolidine-2-carbonyl]-1-piperidyl]pyrimidine-4-carboxamide
5-Fluoro-2-[4-[(3S)-3-(5-methyl-2-thienyl)isoxazolidine-2-carbonyl]-1-piperidyl]pyrimidine-4-carboxamide
[1-(4-Amino-6-chloro-1,3,5-triazin-2-yl)-4-piperidyl]-[(3S)-3-pyrazin-2-ylisoxazolidin-2-yl]methanone
2-[(3R,4R or 3S,4S)-3-Fluoro-4-[(3S)-3-(6-methyl-3-pyridyl)isoxazolidine-2-carbonyl]-1-piperidyl]-5-methyl-pyrimidine-4-carboxamide
2-[(3S,4S or 3R,4R)-3-Fluoro-4-[(3S)-3-(6-methyl-3-pyridyl)isoxazolidine-2-carbonyl]-1-piperidyl]-5-methyl-pyrimidine-4-carboxamide
5-Fluoro-6-[4-[(3S)-3-(6-methyl-3-pyridyl)isoxazolidine-2-carbonyl]-1-piperidyl]pyrimidine-4-carboxamide; trifluoroacetic acid
2-[4-[(3S)-3-(2-Cyanothiazol-4-yl)isoxazolidine-2-carbonyl]-1-piperidyl]pyrimidine-4-carboxamide and 2-[4-[(3S)-3-(2-Cyanothiazol-4-yl)isoxazolidine-2-carbonyl]-1-piperidyl]-5-fluoro-pyrimidine-4-carboxamide or a pharmaceutically acceptable salt, solvate or stereoisomer thereof.

12. The compound of the formula I as claimed in claim 1, wherein the compound of formula I is selected from 2-[4-[(3S)-3-(5-Cyano-3-pyridyl)isoxazolidine-2-carbonyl]-1-piperidyl]pyrimidine-4-carboxamide, 2-[4-[(3S)-3-(5-Cyano-3-pyridyl)isoxazolidine-2-carbonyl]-1-piperidyl]-5-fluoro-pyrimidine-4-carboxamide, 2-[4-[(3S)-3-(6-Methylpyrazin-2-yl)isoxazolidine-2-carbonyl]-1-piperidyl]pyrimidine-4-carboxamide and 5-Fluoro-2-[4-[(3S)-3-pyrazin-2-ylisoxazolidine-2-carbonyl]-1-piperidyl]pyrimidine-4-carboxamide;

or a pharmaceutically acceptable salt, solvate, or stereoisomer thereof.

13. The compound of the formula I as claimed in claim 1, wherein the compound of formula I is selected from 2-[4-[(3S)-3-(5-Cyano-3-pyridyl)isoxazolidine-2-carbonyl]-1-piperidyl]pyrimidine-4-carboxamide, 2-[4-[(3S)-3-(5-Cyano-3-pyridyl)isoxazolidine-2-carbonyl]-1-piperidyl]-5-fluoro-pyrimidine-4-carboxamide, 2-[4-[(3S)-3-(6-Methylpyrazin-2-yl)isoxazolidine-2-carbonyl]-1-piperidyl]pyrimidine-4-carboxamide and 5-Fluoro-2-[4-[(3S)-3-pyrazin-2-ylisoxazolidine-2-carbonyl]-1-piperidyl]pyrimidine-4-carboxamide with a TPSA (topological polar surface area) value of >120 Å2 or more;

or a pharmaceutically acceptable salt, solvate, or stereoisomer thereof.

14. A pharmaceutical composition comprising a compound according to claim 1, or a pharmaceutically acceptable salt, solvate, or stereoisomer thereof, together with at least one pharmaceutically acceptable carrier.

15. The pharmaceutical composition according to claim 14, further comprising one or more additional active pharmaceutical agents selected from a thrombolytic agent, a tissue plasminogen activator, an anticoagulant, a platelet aggregation B inhibitor, an antimicrobial agent, a beta agonist, a corticosteroid a leukotriene modifier, an anti-IgE, a methylxanthine bronchodilator, a mast cell inhibitor, a protein tyrosine kinase inhibitor, a CRTH2/D prostanoid receptor antagonist, epinephrine, a phosphodiesterase inhibitor, a phosphodiesterase-3 inhibitor, a phosphodiesterase-4 inhibitor, an anticholinergic, a muscarinic antagonist, a steroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor, a cystic fibrosis transmembrane conductance regulator potentiator, a mucolytic agent, pancreatic enzymes, a bronchodilator, an anti-vascular endothelial growth factor inhibitor, a ciliary neurotrophic growth factor agent, a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, inactivated influenza vaccine, a ciliary neurotrophic growth factor, a gene transfer agent, an immunomodulator, calcineurin inhibitor, an interferon gamma, an antihistamine, a monoclonal antibody, a polyclonal anti-Tcell antibody, an anti-thymocyte gamma globulin-equine antibody, an antithymocyte globulin-rabbit antibody, an anti-CD40 antagonist, a JAK inhibitor, and an anti-TCR murine mAb.

16. A method of treating a RIP kinase 1 mediated disease or disorder comprising administering a therapeutically effective amount of the compound according to claim 1, or a pharmaceutically acceptable salt, solvate, or stereoisomer thereof, to a subject in need thereof.

17. The method of treating a disease or disorder comprising administering a therapeutically effective amount of the compound according to claim 1, or a pharmaceutically acceptable salt, solvate, or stereoisomer thereof, to a subject in need thereof, wherein the disease or disorder is selected from the group consisting of: necrotizing enterocolitis, tuberous sclerosis, Tangier's Disease, Wohlman's Syndrome, inflammatory bowel disease (IBD), Crohn's disease, ulcerative colitis, psoriasis, retinal detachment, retinitis pigmentosa, macular degeneration, pancreatitis, atopic dermatitis, rheumatoid arthritis (RA), spondyloarthritis, gout, SoJIA, systemic lupus erythematosus, Sjogren's syndrome, systemic scleroderma, antiphospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome (SIRS), cerebrovascular accident, myocardial infarction, allergic diseases, asthma, atopic dermatitis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, bacterial infection, staphylococcus infection, mycobacterium infection, retinitis pigmentosa, influenza, transplant rejection, burns, hypoxia, cutaneous lupus erythematosus (CLE), Lichen planus (LP), toxic epidermal necrolysis (TEN), Stevens-Johnson syndrome (SJS), acute respiratory distress syndrome (ARDS), severe acute respiratory syndrome (SARS), Middle East Respiratory Syndrome (MERS), Respiratory-Syncytial-Virus (RSV), and bronchiolitis.

* * * * *